US012630611B2

(12) United States Patent (10) Patent No.: US 12,630,611 B2
Walker (45) Date of Patent: *May 19, 2026

(54) ANTI-RESPIRATORY SYNCYTIAL VIRUS ANTIBODIES, METHODS OF THEIR GENERATION AND USE

(71) Applicant: Mapp Biopharmaceutical, Inc., San Diego, CA (US)

(72) Inventor: Laura M. Walker, Lebanon, NH (US)

(73) Assignee: Mapp Biopharmaceutical, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/337,918

(22) Filed: Jun. 20, 2023

(65) Prior Publication Data

US 2024/0228597 A1    Jul. 11, 2024

Related U.S. Application Data

(62) Division of application No. 16/754,848, filed as application No. PCT/US2018/055750 on Oct. 12, 2018, now Pat. No. 11,725,045.

(60) Provisional application No. 62/572,400, filed on Oct. 13, 2017.

(51) Int. Cl.
*A61K 39/395* (2006.01)
*C07K 16/10* (2006.01)

(52) U.S. Cl.
CPC ...... *C07K 16/1027* (2013.01); *C07K 2317/21* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 11,725,045 B2 * | 8/2023 | Walker | ............... | C07K 16/1027 424/211.1 |
| 2005/0002926 A1 | 1/2005 | Young et al. | | |
| 2014/0141044 A1 | 5/2014 | Bhatt et al. | | |
| 2014/0271653 A1 | 9/2014 | Gurnett-Bander et al. | | |
| 2015/0118233 A1 | 4/2015 | Depla et al. | | |
| 2019/0075433 A1 | 3/2019 | Shan et al. | | |
| 2020/0239550 A1 | 7/2020 | Walker | | |

FOREIGN PATENT DOCUMENTS

| | | |
|---|---|---|
| WO | WO-01/98361 A2 | 12/2001 |
| WO | WO-2017/075124 A1 | 5/2017 |
| WO | WO-2017/172890 A1 | 10/2017 |

OTHER PUBLICATIONS

Caldas, C. Humanization of the anti-CD18 antibody 6.7: an unexpected effect of a framework residue in binding to antigen, Molecular Immunology, 39:941-652 (2003).

Dondelinger, M. et al., Understanding the Significance and Implications of Antibody Numbering and Antigen-Binding Surface/Residue Definition, Frontiers in Immunology, 9(Article 2278):1-15 (2018).

Du, J. et al., Molecular Basis of Recognition of Human Osteopontin by 23C3, a Potential Therapeutic Antibody for Treatment of Rheumatoid Arthritis, J. Mol. Biol., 382:835-842 (2008).

Panka, D. et al., Variable region framework differences result in decreased or increased affinity of variant anti-digoxin antibodies, Immunology, 85:3080-3084 (1988).

Xiang, J. et al., Modification in Framework Region I Results in a Decreased Affinity of Chimeric Anti-TAG72 Antibody, Molecular Immunology, 28(1/2):141-148 (1991).

Acosta, P. L. et al., Brief History and Characterization of Enhanced Respiratory Syncytial Virus Disease, Clin Vaccine Immunol, 23:189-195 (2015).

Adams, P. D. et al., PHENIX: building new software for automated crystallographic structure determination, Acta Crystallogr D Biol Crystallogr, 58:1948-1954 (2002).

Anderson, L. J. et al., Identification of epitopes on respiratory syncytial virus proteins by competitive binding immunoassay, J Clin Microbiol, 23:475-480 (1986).

Anderson, L. J. et al., Strategic priorities for respiratory syncytial virus (RSV) vaccine development, Vaccine, 31 (Suppl 2):B209-215 (2013).

Bailey, J. R. et al., Broadly neutralizing antibodies with few somatic mutations and hepatitis C virus clearance, JCI Insight, 2(9):e92872 (2017).

Battles, M. B. et al., Molecular mechanism of respiratory syncytial virus fusion inhibitors, Nat Chem Biol, 12:87-93 (2016).

Battye, T. G. et al., iMOSFLM: a new graphical interface for diffraction-image processing with MOSFLM, Acta Crystallogr D Biol Crystallogr, 67:271-281 (2011).

Beeler, J. A. and Van Wyck Coelingh, K., Neutralization epitopes of the F glycoprotein of respiratory syncytial virus: effect of mutation upon fusion function, J Virol, 63:2941-2950 (1989).

Bornholdt, Z. A. et al., Isolation of potent neutralizing antibodies from a survivor of the 2014 Ebola virus outbreak, Science, 351:1078-1083 (2016).

Chin, J. et al., Field evaluation of a respiratory syncytial virus vaccine and a trivalent parainfluenza virus vaccine in a pediatric population, Am J Epidemiol, 89:449-463 (1969).

Collaborative Computational Project, No. 4, The CCP4 suite: programs for protein crystallography, Acta Crystallogr D Biol Crystallogr, 50(Pt 5):760-3 (1994).

Corti, D., Bianchi, S., Vanzetta, F., Minola, A., Perez, L., Agatic, G., Guarino, B., Silacci, C., Marcandalli, J., Marsland, B.J., et al. (2013). Cross-neutralization of four paramyxoviruses by a human monoclonal antibody. Nature 501, 439-443.

(Continued)

*Primary Examiner* — Michael Szperka

(74) *Attorney, Agent, or Firm* — Choate, Hall & Stewart LLP; Brenda Herschbach Jarrell; Meaghan E. Bychowski

(57) ABSTRACT

Provided are antibodies or antigen binding polypeptides characterized by the ability to neutralize respiratory syncytial virus (RSV). Specifically, the antibodies or antigen binding polypeptides are characterized by high affinity binding to RSV fusion glycoprotein (RSVF). Further provided are methods for their identification, isolation, generation, preparation, and use, as well as the heavy chain and light chain sequences of the antibodies provided.

44 Claims, 37 Drawing Sheets

Specification includes a Sequence Listing.

(56) References Cited

OTHER PUBLICATIONS

Crooks, G.E., Hon, G., Chandonia, J.M., and Brenner, S.E. (2004). WebLogo: a sequence logo generator. Genome Res 14, 1188-1190.

D'Angelo, S. et al., Many Routes to an Antibody Heavy-Chain CDR3: Necessary, Yet Insufficient, for Specific Binding, Frontiers in Immunology, 9:3965, 13 pages (2018).

DeKosky, B.J., Ippolito, G.C., Deschner, R.P., Lavinder, J.J., Wine, Y., Rawlings, B.M., Varadarajan, N., Giesecke, C., Dorner, T., Andrews, S.F., et al. (2013). High-throughput sequencing of the paired human immunoglobulin heavy and light chain repertoire. Nat Biotechnol 31, 166-169.

Doria-Rose, N.A., Klein, R.M., Daniels, M.G., O'Dell, S., Nason, M., Lapedes, A., Bhattacharya, T., Migueles, S.A., Wyatt, R.T., Korber, B.T., et al. (2010). Breadth of human immunodeficiency virus-specific neutralizing activity in sera: clustering analysis and association with clinical variables. J Virol 84, 1631-1636.

Edwards, B. et al., The Remarkable Flexibility of the Human Antibody Repertoire; Isolation of Over One Thousand Different Antibodies to a Single Protein, BLyS, J. Mol. Biol., 334:103-118 (2003).

Ekiert, D.C., Bhabha, G., Elsliger, M.A., Friesen, R.H., Jongeneelen, M., Throsby, M., Goudsmit, J., and Wilson, I.A. (2009). Antibody recognition of a highly conserved influenza virus epitope. Science 324, 246-251.

Emsley, P., and Cowtan, K. (2004). Coot: model-building tools for molecular graphics. Acta Crystallogr D Biol Crystallogr 60, 2126-2132.

Esposito, S., Scarselli, E., Lelii, M., Scala, A., Vitelli, A., Capone, S., Fornili, M., Biganzoli, E., Orenti, A., Nicosia, A., et al. (2016). Antibody response to respiratory syncytial virus infection in children <18 months old. Hum Vaccin Immunother 12, 1700-1706.

Evans, P.R., and Murshudov, G.N. (2013). How good are my data and what is the resolution? Acta Crystallogr D Biol Crystallogr 69, 1204-1214.

Fuentes, S., Coyle, E.M., Beeler, J., Golding, H., and Khurana, S. (2016). Antigenic Fingerprinting following Primary RSV Infection in Young Children Identifies Novel Antigenic Sites and Reveals Unlinked Evolution of Human Antibody Repertoires to Fusion and Attachment Glycoproteins. PLoS Pathog 12, e1005554.

Fulginiti, V.A., Eller, J.J., Sieber, O.F., Joyner, J.W., Minamitani, M., and Meiklejohn, G. (1969). Respiratory virus immunization. I. A field trial of two inactivated respiratory virus vaccines; an aqueous trivalent parainfluenza virus vaccine and an alum-precipitated respiratory syncytial virus vaccine. Am J Epidemiol 89, 435-448.

Gans, H., Yasukawa, L., Rinki, M., DeHovitz, R., Forghani, B., Beeler, J., Audet, S., Maldonado, Y., and Arvin, A.M. (2001). Immune responses to measles and mumps vaccination of infants at 6, 9, and 12 months. J Infect Dis 184, 817-826.

Garcia-Barreno, B., Palomo, C., Penas, C., Delgado, T., Perez-Brena, P., and Melero, J.A. (1989). Marked differences in the antigenic structure of human respiratory syncytial virus F and G glycoproteins. J Virol 63, 925-932.

GenPept_S31669, Ig heavy chain V region—human (fragment), online Jul. 23, 1999, https://www.ncbi.nlm.nih.gov/protein/S31669>Definition, and Origin, retrieved on Dec. 6, 2018 (2 pages).

Gietz, R.D., and Schiestl, R.H. (2007). High-efficiency yeast transformation using the LiAc/SS carrier DNA/PEG method. Nat Protoc 2, 31-34.

Gilman, M.S., Castellanos, C.A., Chen, M., Ngwuta, J.O., Goodwin, E., Moin, S.M., Mas, V., Melero, J.A., Wright, P.F., Graham, B.S., et al. (2016). Rapid profiling of RSV antibody repertoires from the memory B cells of naturally infected adult donors. Sci Immunol 1.

Gilman, M.S., Moin, S.M., Mas, V., Chen, M., Patel, N.K., Kramer, K., Zhu, Q., Kabeche, S.C., Kumar, A., Palomo, C., et al. (2015). Characterization of a Prefusion-Specific Antibody That Recognizes a Quaternary, Cleavage-Dependent Epitope on the RSV Fusion Glycoprotein. PLoS Pathog 11, e1005035.

Glezen, W. P. et al., Risk of primary infection and reinfection with respiratory syncytial virus, Am J Dis Child, 140:543-546 (1986).

Goel, M. et al., Plasticity within the Antigen-Combining Site May Manifest as Molecular Mimicry in the Humoral Immune Response, The Journal of Immunology, 7358-7367 (2004).

Graham, B.S., Vaccine development for respiratory syncytial virus, Curr Opin Virol, 23:107-112 (2017).

Gray, E.S., Madiga, M.C., Hermanus, T., Moore, P.L., Wibmer, C.K., Tumba, N.L., Werner, L., Mlisana, K., Sibeko, S., Williamson, C., et al. (2011). The neutralization breadth of HIV-1 develops incrementally over four years and is associated with CD4+ T cell decline and high viral load during acute infection. J Virol 85, 4828-4840.

Griffin, M.P., Khan, A.A., Esser, M.T., Jensen, K., Takas, T., Kankam, M.K., Villafana, T., and Dubovsky, F. (2017). Safety, Tolerability, and Pharmacokinetics of MEDI8897, the Respiratory Syncytial Virus Prefusion F-Targeting Monoclonal Antibody with an Extended Half-Life, in Healthy Adults. Antimicrob Agents Chemother 61.

Group, T.I.-R.S. (1998). Palivizumab, a humanized respiratory syncytial virus monoclonal antibody, reduces hospitalization from respiratory syncytial virus infection in high-risk infants. Pediatrics 102, 531-537.

Hall, C.B., Walsh, E.E., Long, C.E., and Schnabel, K.C. (1991). Immunity to and frequency of reinfection with respiratory syncytial virus. J Infect Dis 163, 693-698.

Harkensee, C. et al., Passive immunisation of preterm infants with palivizumab against RSV infection, Journal of Infection, 52:2-8 (2006).

Henderson, F.W., Collier, A.M., Clyde, W.A., Jr., and Denny, F.W. (1979). Respiratory-syncytial-virus infections, reinfections and immunity. A prospective, longitudinal study in young children. N Engl J Med 300, 530-534.

Homaira, N., Rawlinson, W., Snelling, T.L., and Jaffe, A. (2014). Effectiveness of Palivizumab in Preventing RSV Hospitalization in High Risk Children: A Real-World Perspective. Int J Pediatr 2014, 571609.

Huang, K., Incognito, L., Cheng, X., Ulbrandt, N.D., and Wu, H. (2010). Respiratory syncytial virus-neutralizing monoclonal antibodies motavizumab and palivizumab inhibit fusion. J Virol 84, 8132-8140.

IJspeert, H., van Schouwenburg, P.A., van Zessen, D., Pico-Knijnenburg, I., Driessen, G.J., Stubbs, A.P., and van der Burg, M. (2016). Evaluation of the Antigen-Experienced B-Cell Receptor Repertoire in Healthy Children and Adults. Front Immunol 7, 410.

International Search Report for PCT/US2018/55750 (Anti-Respiratory Syncytial Virus Antibodies, Methods of Their Generation and Use, filed Oct. 12, 2018), issued by ISA/US, 7 pages (Feb. 11, 2019).

Jain, T., Sun, T., Durand, S., Hall, A., Houston, N.R., Nett, J.H., Sharkey, B., Bobrowicz, B., Caffry, I., Yu, Y., et al. (2017). Biophysical properties of the clinical-stage antibody landscape. Proc Natl Acad Sci U S A 114, 944-949.

Janet, S. et al., Respiratory syncytial virus seasonality and its implications on prevention strategies, Human Vaccines & Immunotherapeutics, 14(1):234-244 (2018).

Janeway, C. et al., ImmunoBiology, 3rd Edition, The Immune System in Health and Disease, Garland Publishing Inc., 3-1-3-11 (1997).

Jans, J., Pettengill, M., Kim, D., van der Made, C., de Groot, R., Henriet, S., de Jonge, M.I., Ferwerda, G., and Levy, O. (2016). Human newborn B cells mount an interferon-alpha/beta receptor-dependent humoral response to respiratory syncytial virus. J Allergy Clin Immunol.

Jardine, J.G., Kulp, D.W., Havenar-Daughton, C., Sarkar, A., Briney, B., Sok, D., Sesterhenn, F., Ereno-Orbea, J., Kalyuzhniy, O., Deresa, I., et al. (2016). HIV-1 broadly neutralizing antibody precursor B cells revealed by germline-targeting immunogen. Science 351, 1458-1463.

Kamal-Bahl, S., Doshi, J., and Campbell, J. (2002). Economic analyses of respiratory syncytial virus immunoprophylaxis in high-risk infants: a systematic review. Arch Pediatr Adolesc Med 156, 1034-1041.

Kanyavuz, A. et al., Breaking the law: unconventional strategies for antibody diversification, Nature Reviews, 19:355-368 (2019).

(56)                    References Cited

OTHER PUBLICATIONS

Kapikian, A.Z., Mitchell, R.H., Chanock, R.M., Shvedoff, R.A., and Stewart, C.E. (1969). An epidemiologic study of altered clinical reactivity to respiratory syncytial (RS) virus infection in children previously vaccinated with an inactivated RS virus vaccine. Am J Epidemiol 89, 405-421.

Kashyap, A.K., Steel, J., Oner, A.F., Dillon, M.A., Swale, R.E., Wall, K.M., Perry, K.J., Faynboym, A., Ilhan, M., Horowitz, M., et al. (2008). Combinatorial antibody libraries from survivors of the Turkish H5N1 avian influenza outbreak reveal virus neutralization strategies. Proc Natl Acad Sci U S A 105, 5986-5991.

Kelly, R.L., Sun, T., Jain, T., Caffry, I., Yu, Y., Cao, Y., Lynaugh, H., Brown, M., Vasquez, M., Wittrup, K.D., et al. (2015). High through-put cross-interaction measures for human IgG1 antibodies correlate with clearance rates in mice. MAbs, 0.

Killikelly, A.M., Kanekiyo, M., and Graham, B.S. (2016). Pre-fusion F is absent on the surface of formalin-inactivated respiratory syncytial virus. Sci Rep 6, 34108.

Kim, H.W., Canchola, J.G., Brandt, C.D., Pyles, G., Chanock, R.M., Jensen, K., and Parrott, R.H. (1969). Respiratory syncytial virus disease in infants despite prior administration of antigenic inacti-vated vaccine. Am J Epidemiol 89, 422-434.

Krarup, A., Truan, D., Furmanova-Hollenstein, P., Bogaert, L., Bouchier, P., Bisschop, I.J., Widjojoatmodjo, M.N., Zahn, R., Schuitemaker, H., Mclellan, J.S., et al. (2015). A highly stable prefusion RSV F vaccine derived from structural analysis of the fusion mechanism. Nat Commun 6, 8143.

Kristjansson, S., Bjarnarson, S.P., Wennergren, G., Palsdottir, A.H., Arnadottir, T., Haraldsson, A., and Jonsdottir, I. (2005). Respiratory syncytial virus and other respiratory viruses during the first 3 months of life promote a local TH2-like response. J Allergy Clin Immunol 116, 805-811.

Lambert, D.M., Barney, S., Lambert, A.L., Guthrie, K., Medinas, R., Davis, D.E., Bucy, T., Erickson, J., Merutka, G., and Petteway, S.R., Jr. (1996). Peptides from conserved regions of paramyxovirus fusion (F) proteins are potent inhibitors of viral fusion. Proc Natl Acad Sci U S A 93, 2186-2191.

Lambert, L., Sagfors, A.M., Openshaw, P.J., and Culley, F.J. (2014). Immunity to RSV in Early-Life. Front Immunol 5, 466.

Legg, J.P., Hussain, I.R., Warner, J.A., Johnston, S.L., and Warner, J.O. (2003). Type 1 and type 2 cytokine imbalance in acute respiratory syncytial virus bronchiolitis. Am J Respir Crit Care Med 168, 633-639.

Lerner, R.A. (2011). Rare antibodies from combinatorial libraries suggests an S.O.S. component of the human immunological reper-toire. Mol Biosyst 7, 1004-1012.

Lloyd, C. et al., Modelling the human immune response: perfor-mance of a 1011 human antibody repertoire against a broad panel of therapeuticallyl relevant antigens, Protein Engineering, Design & Selection, 22(3):159-168 (2009).

Magro, M., Mas, V., Chappell, K., Vazquez, M., Cano, O., Luque, D., Terron, M.C., Melero, J.A., and Palomo, C. (2012). Neutralizing antibodies against the preactive form of respiratory syncytial virus fusion protein offer unique possibilities for clinical intervention. Proc Natl Acad Sci U S A 109, 3089-3094.

McCoy, A.J., Grosse-Kunstleve, R.W., Adams, P.D., Winn, M.D., Storoni, L.C., and Read, R.J. (2007). Phaser crystallographic soft-ware. J Appl Crystallogr 40, 658-674.

Mclellan, J. et al., Structure of Respiratory Syncytial Virus Fusion Glycoprotein in the Postfusion Conformation Reveals Preservation of Neutralizing Epitopes, Journal of Virology, 85(15):7788-7796 (2011).

McLellan, J.S., Chen, M., Chang, J.S., Yang, Y., Kim, A., Graham, B.S., and Kwong, P.D. (2010a). Structure of a major antigenic site on the respiratory syncytial virus fusion glycoprotein in complex with neutralizing antibody 101F. J Virol 84, 12236-12244.

McLellan, J.S., Chen, M., Kim, A., Yang, Y., Graham, B.S., and Kwong, P.D. (2010b). Structural basis of respiratory syncytial virus neutralization by motavizumab. Nat Struct Mol Biol 17, 248-250.

McLellan, J.S., Chen, M., Leung, S., Graepel, K.W., Du, X., Yang, Y., Zhou, T., Baxa, U., Yasuda, E., Beaumont, T., et al. (2013). Structure of RSV fusion glycoprotein trimer bound to a prefusion-specific neutralizing antibody. Science 340, 1113-1117.

McLellan, J.S., Yang, Y., Graham, B.S., and Kwong, P.D. (2011). Structure of respiratory syncytial virus fusion glycoprotein in the postfusion conformation reveals preservation of neutralizing epitopes. J Virol 85, 7788-7796.

Morin, A., Eisenbraun, B., Key, J., Sanschagrin, P.C., Timony, M.A., Ottaviano, M., and Sliz, P. (2013). Collaboration gets the most out of software. Elife 2, e01465.

Mousa, J.J., Kose, N., Matta, P., Gilchuk, P., and Crowe, J.E., Jr. (2017). A novel pre-fusion conformation-specific neutralizing epitope on the respiratory syncytial virus fusion protein. Nat Microbiol 2, 16271.

Murphy, B.R., Alling, D.W., Snyder, M.H., Walsh, E.E., Prince, G.A., Chanock, R.M., Hemming, V.G., Rodriguez, W.J., Kim, H.W., Graham, B.S., et al. (1986). Effect of age and preexisting antibody on serum antibody response of infants and children to the F and G glycoproteins during respiratory syncytial virus infection. J Clin Microbiol 24, 894-898.

Murphy, B.R., and Walsh, E.E. (1988). Formalin-inactivated respi-ratory syncytial virus vaccine induces antibodies to the fusion glycoprotein that are deficient in fusion-inhibiting activity. J Clin Microbiol 26, 1595-1597.

Ngwuta, J.O., Chen, M., Modjarrad, K., Joyce, M.G., Kanekiyo, M., Kumar, A., Yassine, H.M., Moin, S.M., Killikelly, A.M., Chuang, G.Y., et al. (2015). Prefusion F-specific antibodies determine the magnitude of RSV neutralizing activity in human sera. Sci Transl Med 7, 309ra162.

Panda, S., and Ding, J.L. (2015). Natural antibodies bridge innate and adaptive immunity. J Immunol 194, 13-20.

Path, RSV Vaccine and mAb Snapshot. Updated Sep. 28, 2021. URL: https://www.path.org/resources/rsv-vaccine-and-mab-snapshot/.

Polack, F.P., Teng, M.N., Collins, P.L., Prince, G.A., Exner, M., Regele, H., Lirman, D.D., Rabold, R., Hoffman, S.J., Karp, C.L., et al. (2002). A role for immune complexes in enhanced respiratory syncytial virus disease. J Exp Med 196, 859-865.

Pons, JMV et al., Meta-analysis of passive immunoprophylaxis in paediatric patients at risk of severe RSV infection, Acta Paediatr., 100(3):324-329 (2011).

Potterton, E., Briggs, P., Turkenburg, M., and Dodson, E. (2003). A graphical user interface to the CCP4 program suite. Acta Crystallogr D Biol Crystallogr 59, 1131-1137.

Rechavi, E., Lev, A., Lee, Y.N., Simon, A.J., Yinon, Y., Lipitz, S., Amariglio, N., Weisz, B., Notarangelo, L.D., and Somech, R. (2015). Timely and spatially regulated maturation of B and T cell repertoire during human fetal development. Sci Transl Med 7, 276ra225.

Reed, J.H., Jackson, J., Christ, D., and Goodnow, C.C. (2016). Clonal redemption of autoantibodies by somatic hypermutation away from self-reactivity during human immunization. J Exp Med 213, 1255-1265.

Reichert, J.M. (2016). Antibodies to watch in 2016. MAbs 8, 197-204.

Ridings, J., Dinan, L., Williams, R., Roberton, D., and Zola, H. (1998). Somatic mutation of immunoglobulin V(H)6 genes in human infants. Clin Exp Immunol 114, 33-39.

Rossey, I., Gilman, M.S., Kabeche, S.C., Sedeyn, K., Wrapp, D., Kanekiyo, M., Chen, M., Mas, V., Spitaels, J., Melero, J.A., et al. (2017). Potent single-domain antibodies that arrest respiratory syn-cytial virus fusion protein in its prefusion state. Nat Commun 8, 14158.

Rudikoff, S. et al., Single amino acid substitution altering antigen-binding specificity, Proc. Natl. Acad. Sci. USA, 79:1979-1983 (1982).

Sande, C.J., Cane, P.A., and Nokes, D.J. (2014). The association between age and the development of respiratory syncytial virus neutralising antibody responses following natural infection in infants. Vaccine 32, 4726-4729.

Saravia, J., You, D., Shrestha, B., Jaligama, S., Siefker, D., Lee, G.I., Harding, J.N., Jones, T.L., Rovnaghi, C., Bagga, B., et al. (2015).

(56)     References Cited

OTHER PUBLICATIONS

Respiratory Syncytial Virus Disease Is Mediated by Age-Variable IL-33. PLoS Pathog 11, e1005217.

Sastre, P., Melero, J.A., Garcia-Barreno, B., and Palomo, C. (2005). Comparison of affinity chromatography and adsorption to vaccinia virus recombinant infected cells for depletion of antibodies directed against respiratory syncytial virus glycoproteins present in a human immunoglobulin preparation. J Med Virol 76, 248-255.

Sather, D.N., Armann, J., Ching, L.K., Mavrantoni, A., Sellhorn, G., Caldwell, Z., Yu, X., Wood, B., Self, S., Kalams, S., et al. (2009). Factors associated with the development of cross-reactive neutralizing antibodies during human immunodeficiency virus type 1 infection. J Virol 83, 757-769.

Shi, T., McAllister, D.A., O'Brien, K.L., Simoes, E.A.F., Madhi, S.A., Gessner, B.D., Polack, F.P., Balsells, E., Acacio, S., Aguayo, C., et al. (2017). Global, regional, and national disease burden estimates of acute lower respiratory infections due to respiratory syncytial virus in young children in 2015: a systematic review and modelling study. Lancet.

Shinoff, J.J., O'Brien, K.L., Thumar, B., Shaw, J.B., Reid, R., Hua, W., Santosham, M., and Karron, R.A. (2008). Young infants can develop protective levels of neutralizing antibody after infection with respiratory syncytial virus. J Infect Dis 198, 1007-1015.

Siegrist, C.A., and Aspinall, R. (2009). B-cell responses to vaccination at the extremes of age. Nat Rev Immunol 9, 185-194.

Simek, M.D., Rida, W., Priddy, F.H., Pung, P., Carrow, E., Laufer, D.S., Lehrman, J.K., Boaz, M., Tarragona-Fiol, T., Miiro, G., et al. (2009). Human immunodeficiency virus type 1 elite neutralizers: individuals with broad and potent neutralizing activity identified by using a high-throughput neutralization assay together with an analytical selection algorithm. J Virol 83, 7337-7348.

Sok, D., Briney, B., Jardine, J.G., Kulp, D.W., Menis, S., Pauthner, M., Wood, A., Lee, E.C., Le, K.M., Jones, M., et al. (2016). Priming HIV-1 broadly neutralizing antibody precursors in human Ig loci transgenic mice. Science 353, 1557-1560.

Sui, J., Hwang, W.C., Perez, S., Wei, G., Aird, D., Chen, L.M., Santelli, E., Stec, B., Cadwell, G., Ali, M., et al. (2009). Structural and functional bases for broad-spectrum neutralization of avian and human influenza A viruses. Nat Struct Mol Biol 16, 265-273.

Swanson, K.A., Settembre, E.C., Shaw, C.A., Dey, A.K., Rappuoli, R., Mandl, C.W., Dormitzer, P.R., and Carfi, A. (2011). Structural basis for immunization with postfusion respiratory syncytial virus fusion F glycoprotein (RSV F) to elicit high neutralizing antibody titers. Proc Natl Acad Sci U S A 108, 9619-9624.

Swers, J.S., Kellogg, B.A., and Wittrup, K.D. (2004). Shuffled antibody libraries created by in vivo homologous recombination and yeast surface display. Nucleic Acids Res 32, e36.

Thomson, C.A., Bryson, S., McLean, G.R., Creagh, A.L., Pai, E.F., and Schrader, J.W. (2008). Germline V-genes sculpt the binding site of a family of antibodies neutralizing human cytomegalovirus. EMBO J 27, 2592-2602.

Throsby, M., van den Brink, E., Jongeneelen, M., Poon, L.L., Alard, P., Cornelissen, L., Bakker, A., Cox, F., van Deventer, E., Guan, Y., et al. (2008). Heterosubtypic neutralizing monoclonal antibodies cross-protective against H5N1 and H1N1 recovered from human IgM+ memory B cells. PLoS One 3, e3942.

Tiller, T., Meffre, E., Yurasov, S., Tsuiji, M., Nussenzweig, M.C., and Wardemann, H. (2008). Efficient generation of monoclonal antibodies from single human B cells by single cell RT-PCR and expression vector cloning. J Immunol Methods 329, 112-124.

Trang, N.V., Braeckman, T., Lernout, T., Hau, V.T., Anh Ie, T.K., Luan Ie, T., Van Damme, P., and Anh, D.D. (2014). Prevalence of rotavirus antibodies in breast milk and inhibitory effects to rotavirus vaccines. Hum Vaccin Immunother 10, 3681-3687.

Troisi, C.L., Hollinger, F.B., Krause, D.S., and Pickering, L.K. (1997). Immunization of seronegative infants with hepatitis A vaccine (HAVRIX; SKB): a comparative study of two dosing schedules. Vaccine 15, 1613-1617.

Villafana, T. et al., Passive and active immunization against respiratory syncytial virus for the young and old, Expert Review of Vaccines, 16(7):737-749 (2017).

Wang, J., He, Y., Jin, D., Liu, J., Zheng, J., Yuan, N., Bai, Y., Yan, T., Yang, Y., Liu, Y., et al. (2017). No response to hepatitis B vaccine in infants born to HBsAg(+) mothers is associated to the transplacental transfer of HBsAg. Infect Dis (Lond), 1-8.

Wen, X., Mousa, J.J., Bates, J.T., Lamb, R.A., Crowe, J.E., Jr., and Jardetzky, T.S. (2017). Structural basis for antibody crossneutralization of respiratory syncytial virus and human metapneumovirus. Nat Microbiol 2, 16272.

Williams, J.V., Weitkamp, J.H., Blum, D.L., LaFleur, B.J., and Crowe, J.E., Jr. (2009). The human neonatal B cell response to respiratory syncytial virus uses a biased antibody variable gene repertoire that lacks somatic mutations. Mol Immunol 47, 407-414.

Written Opinion for PCT/US2018/55750 (Anti-Respiratory Syncytial Virus Antibodies, Methods of Their Generation and Use, filed Oct. 12, 2018), issued by ISA/US, 16 pages (Feb. 11, 2019).

Wu, S.J., Schmidt, A., Beil, E.J., Day, N.D., Branigan, P.J., Liu, C., Gutshall, L.L., Palomo, C., Furze, J., Taylor, G., et al. (2007). Characterization of the epitope for anti-human respiratory syncytial virus F protein monoclonal antibody 101F using synthetic peptides and genetic approaches. J Gen Virol 88, 2719-2723.

Xu, Y., Roach, W., Sun, T., Jain, T., Prinz, B., Yu, T.Y., Torrey, J., Thomas, J., Bobrowicz, P., Vasquez, M., et al. (2013). Addressing polyspecificity of antibodies selected from an in vitro yeast presentation system: a FACS-based, high-throughput selection and analytical tool. Protein Eng Des Sel 26, 663-670.

Yacoob, C., Pancera, M., Vigdorovich, V., Oliver, B.G., Glenn, J.A., Feng, J., Sather, D.N., McGuire, A.T., and Stamatatos, L. (2016). Differences in Allelic Frequency and CDRH3 Region Limit the Engagement of HIV Env Immunogens by Putative VRC01 Neutralizing Antibody Precursors. Cell Rep 17, 1560-1570.

Yeung, Y.A., Foletti, D., Deng, X., Abdiche, Y., Strop, P., Glanville, J., Pitts, S., Lindquist, K., Sundar, P.D., Sirota, M., et al. (2016). Germline-encoded neutralization of a *Staphylococcus aureus* virulence factor by the human antibody repertoire. Nat Commun 7, 13376.

Zhang, X., Zhivaki, D., and Lo-Man, R. (2017). Unique aspects of the perinatal immune system. Nat Rev Immunol.

Zhu, Q., Mclellan, J.S., Kallewaard, N.L., Ulbrandt, N.D., Palaszynski, S., Zhang, J., Moldt, B., Khan, A., Svabek, C., McAuliffe, J.M., et al. (2017). A highly potent extended half-life antibody as a potential RSV vaccine surrogate for all infants. Sci Transl Med 9.

* cited by examiner

Fig. 3A                                   Fig. 3B
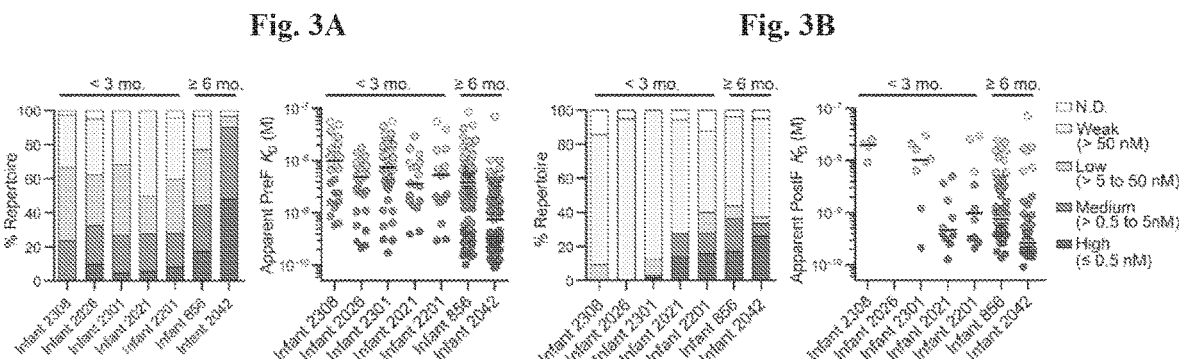
Fig. 3C                                   Fig. 3D
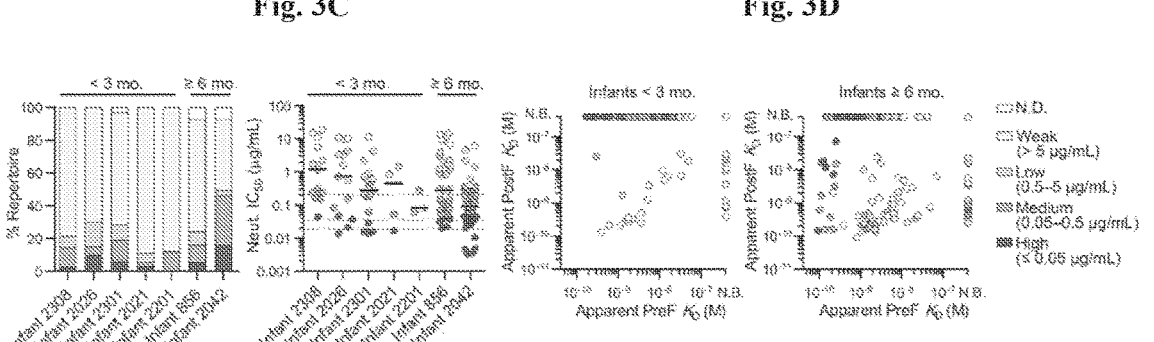

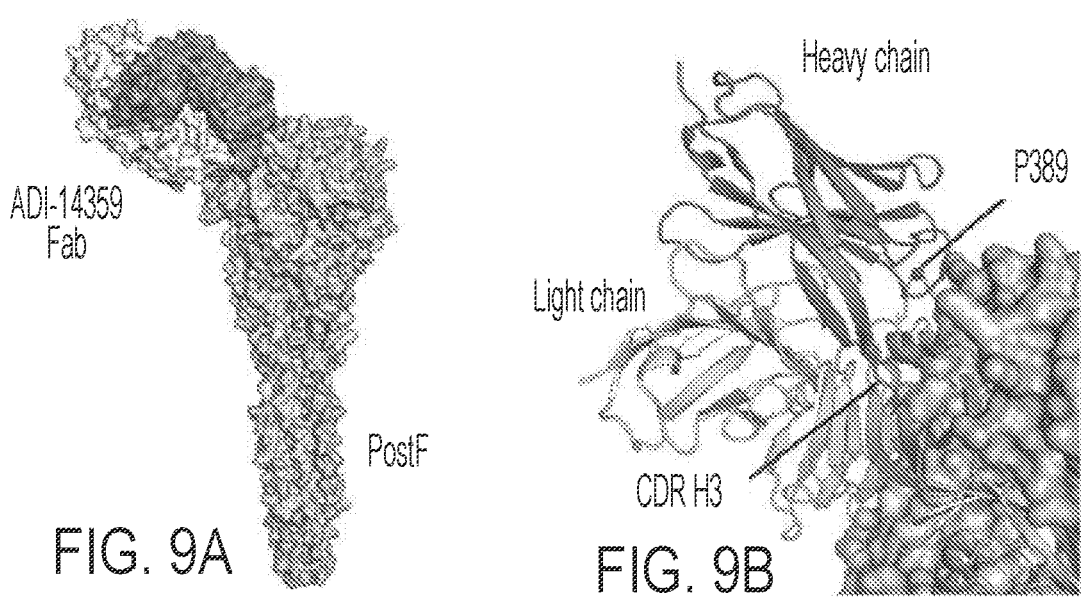
FIG. 9A
FIG. 9B
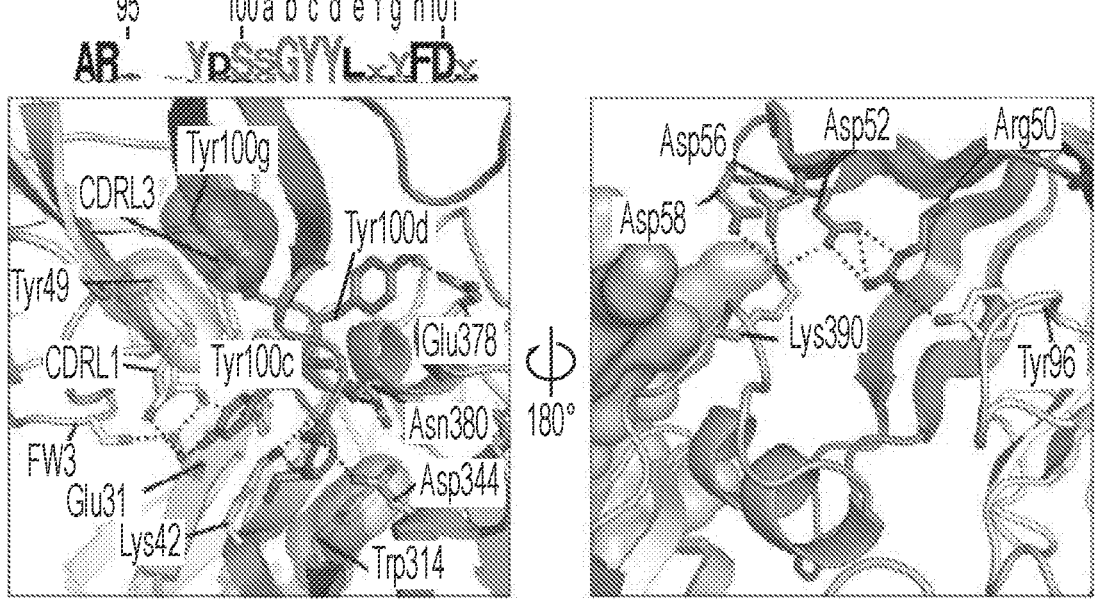
FIG. 9C

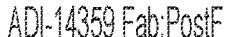
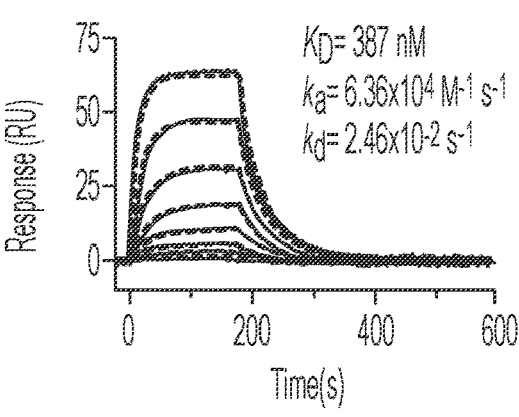
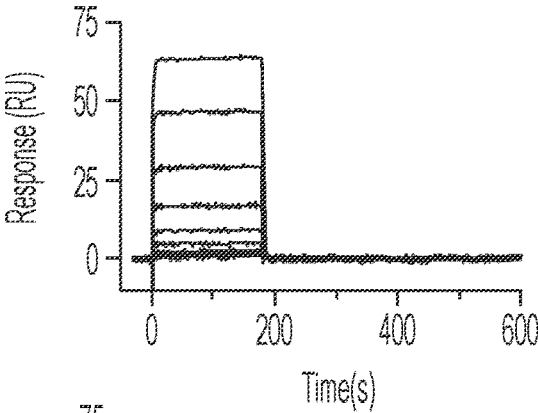
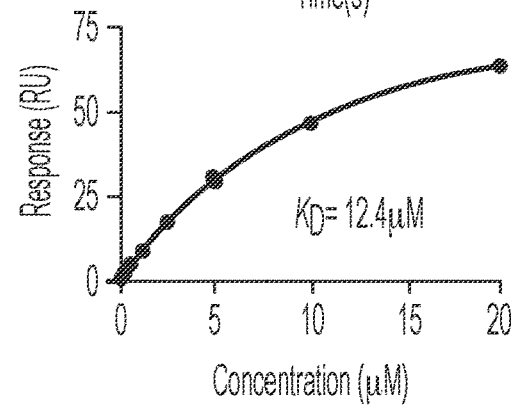
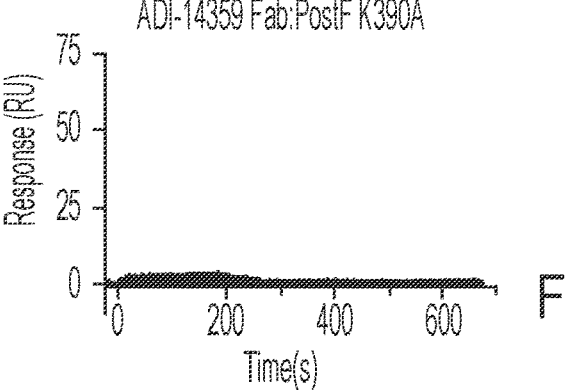
FIG. 9D

Fused membranes

PostF

ADI-14359
Fab

PreF

ADI-14359
Fab

Viral membrane

Glu31
Tyr33 FW3
CDRL1

Heavy
chain

D

Glu31
β22
Tyr33 FW3
CDRL1

Heavy
chain

Fig. 12A
Fig. 12B
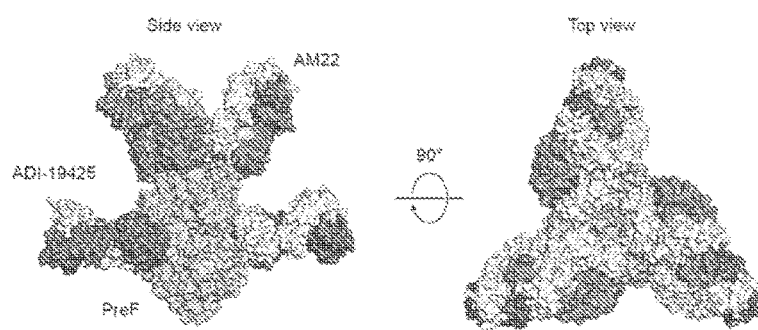
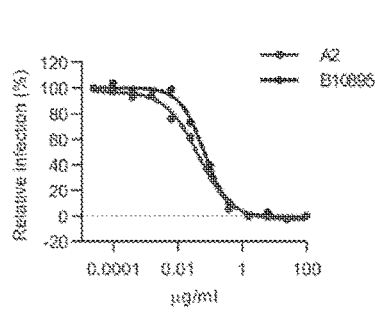
Fig. 12C
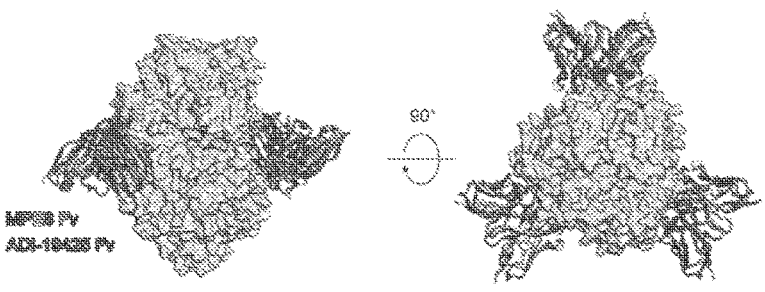
Fig. 12D
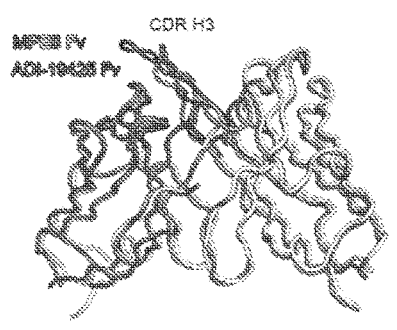
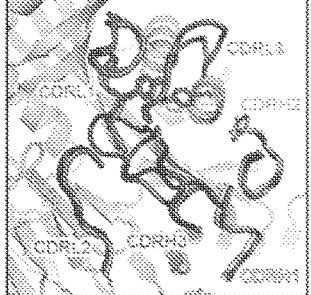

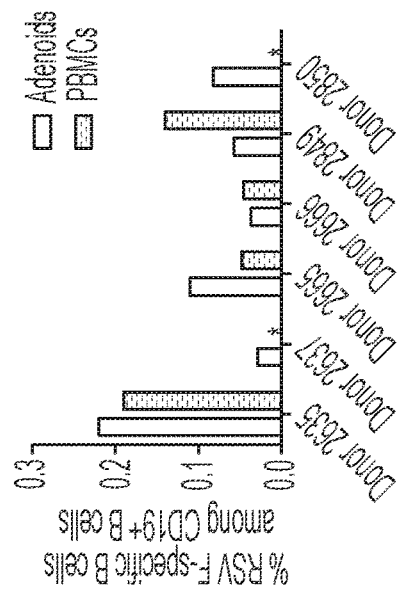
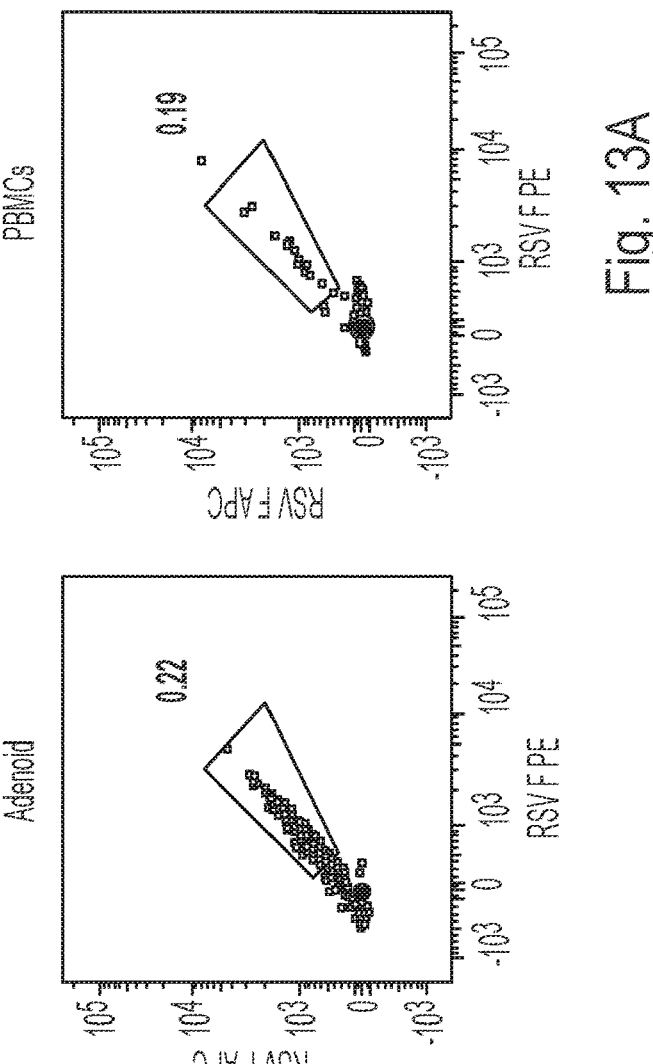
Fig. 13A

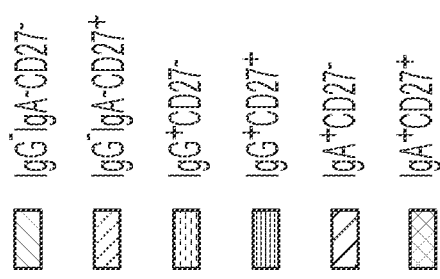
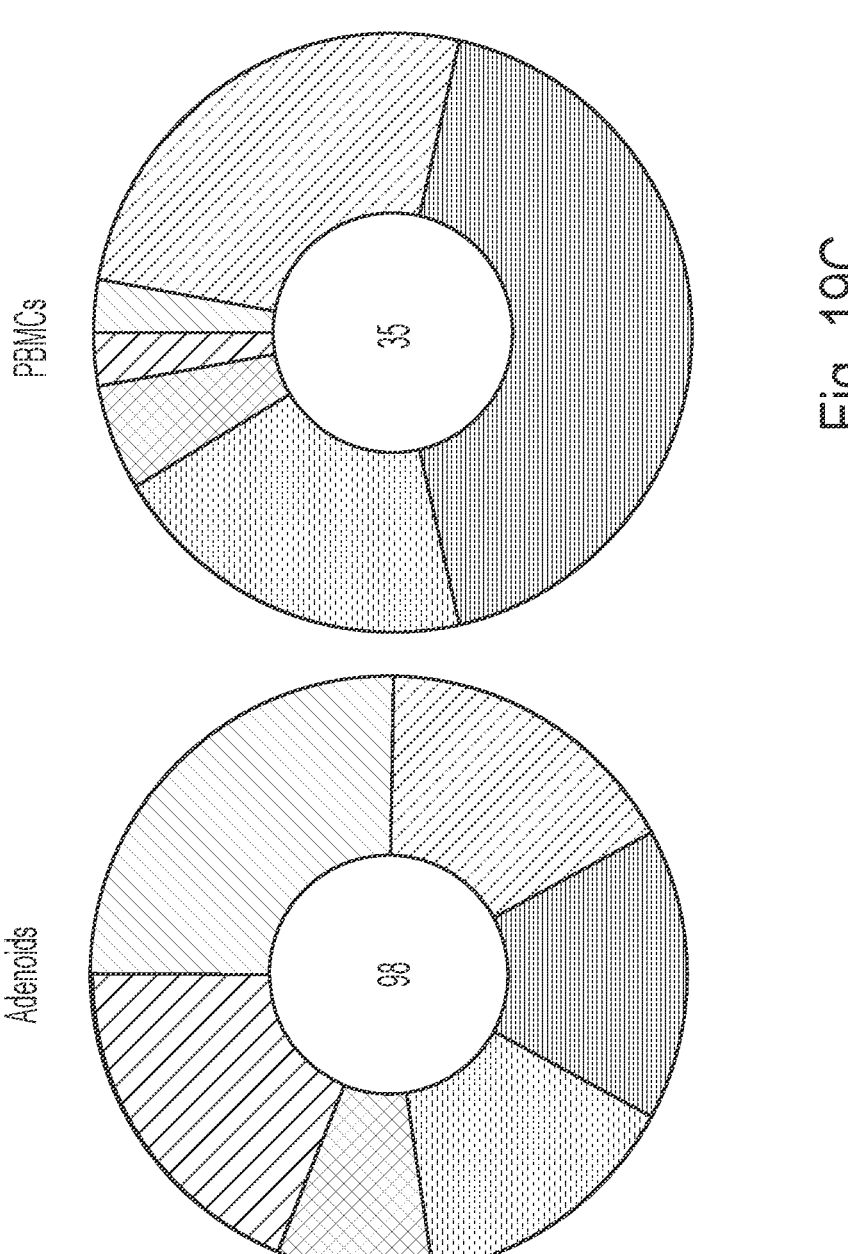
Fig. 19C

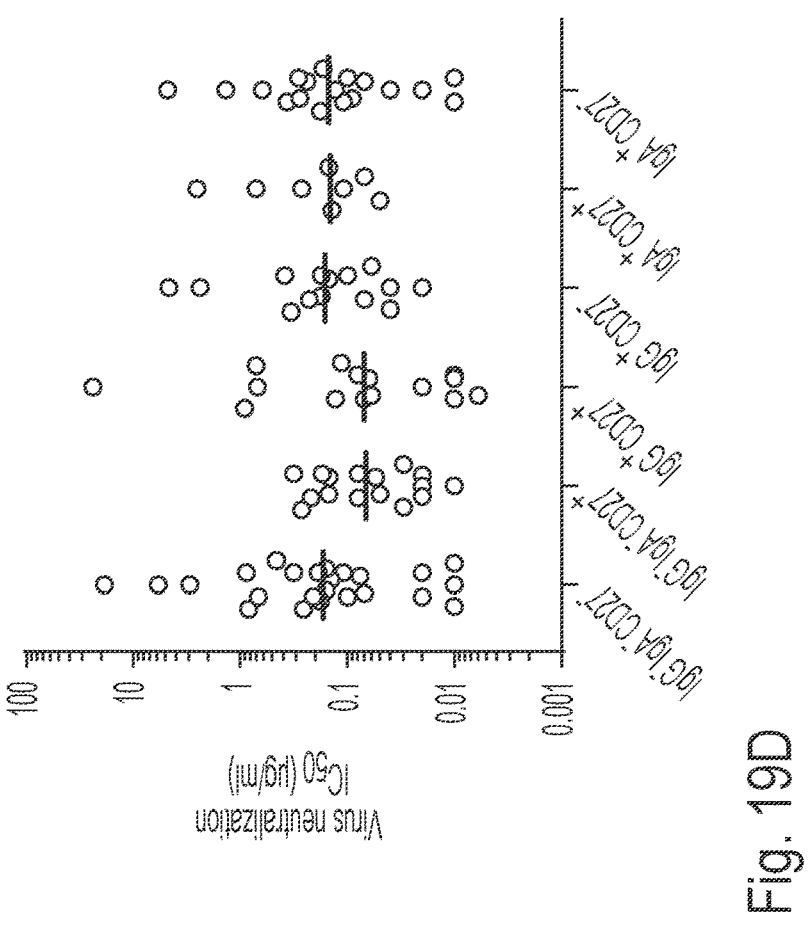
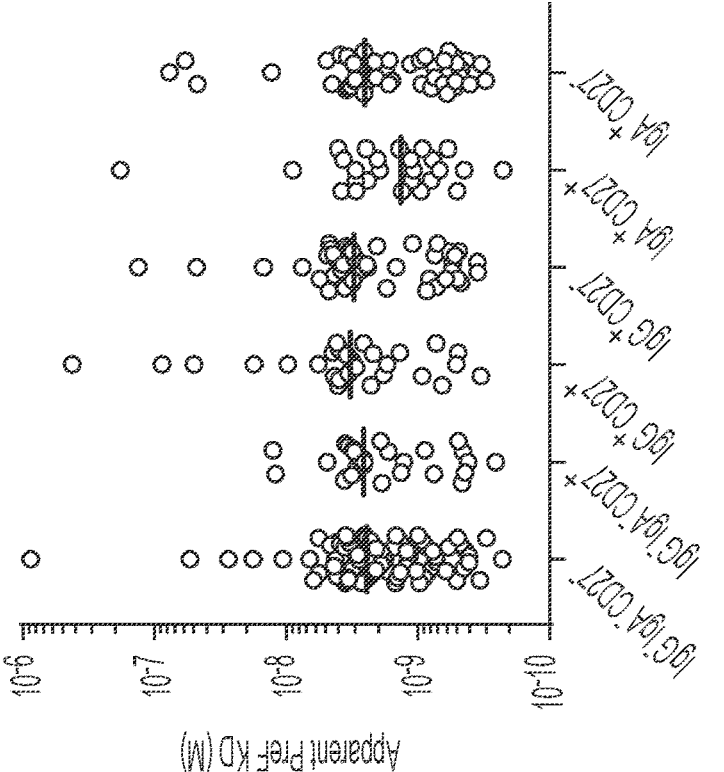
Fig. 19D

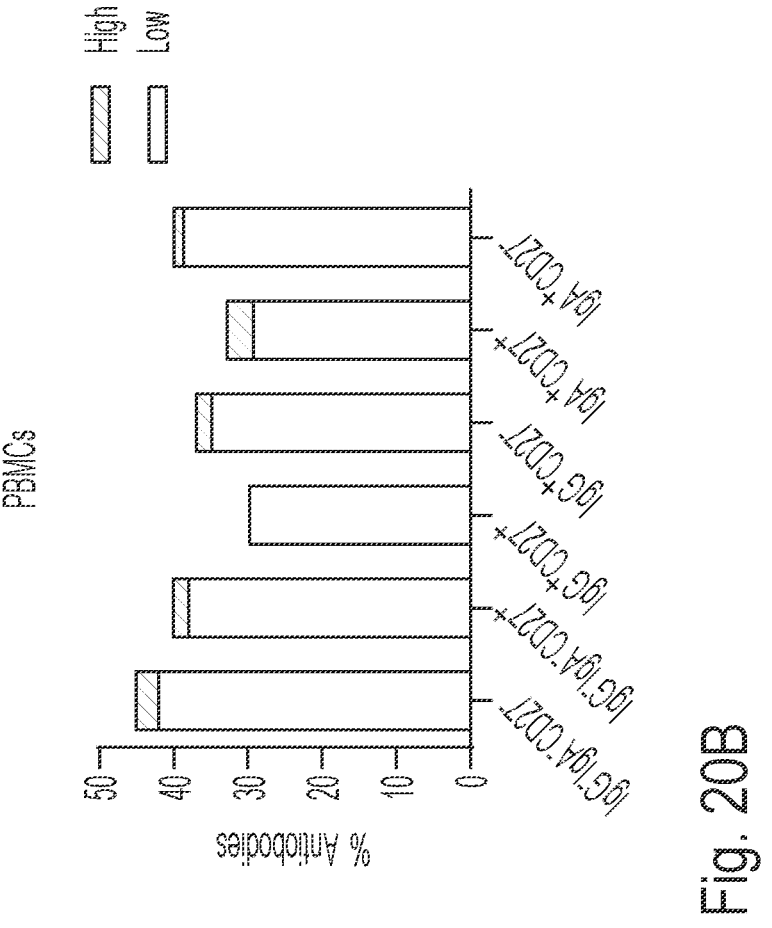
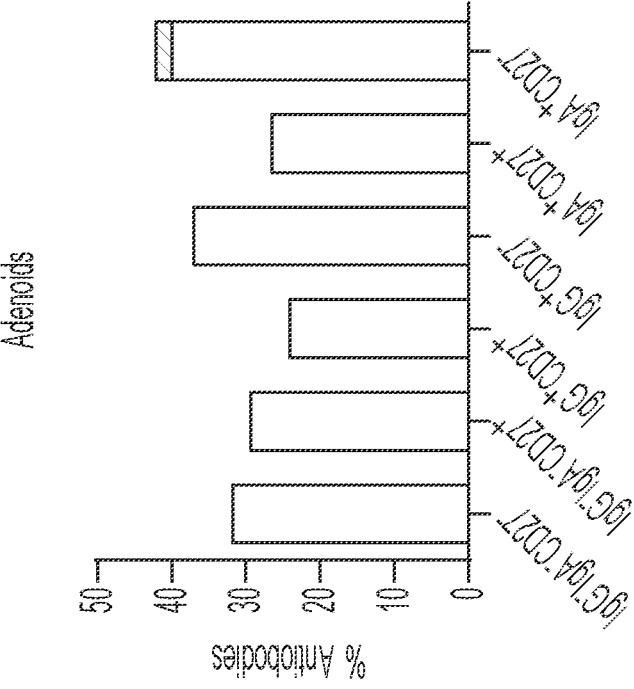
Fig. 20B

ANTI-RESPIRATORY SYNCYTIAL VIRUS ANTIBODIES, METHODS OF THEIR GENERATION AND USE

CROSS REFERENCE TO RELATED APPLICATIONS

This application claims priority to U.S. application Ser. No. 16/754,848 (now U.S. Pat. No. 11,725,045), filed Apr. 9, 2020, which is a national stage filing under 35 U.S.C. § 371 of International PCT Application No. PCT/US2018/055750 filed Oct. 12, 2018, which claims the benefit of U.S. Provisional Application No. 62/572,400 filed Oct. 13, 2017, the content of all of which are herein incorporated by reference their entirety.

SEQUENCE LISTING

This application contains a Sequence Listing which has been submitted electronically in XML file format and is hereby incorporated by reference in its entirety. Said XML copy, created Oct. 5, 2023, is named 2014218-0007_SL.xml and is 3,296,340 bytes in size.

FIELD OF THE INVENTION

The invention is related to human antibodies and antigen-binding fragments thereof that specifically bind to Respiratory Syncytial Virus fusion glycoprotein (RSV F) ("anti-RSV F antibodies"), in particular infant anti-RSV F antibodies, compositions comprising these antibodies, and methods for the preparation and use of these antibodies.

BACKGROUND OF THE INVENTION

Respiratory syncytial virus (RSV) is a ubiquitous pathogen that causes bronchiolitis and pneumonia in infants and the elderly and substantial morbidity and mortality in infants, the elderly, and immunocompromised individuals. Recent estimates indicate that RSV causes nearly 60,000 deaths annually in children under the age of five (Shi et al., 2017). Currently, the only preventive measure available for RSV is passive prophylaxis with the monoclonal antibody Synagis® (Group, 1998). Unfortunately, prophylaxis with Synagis® is costly, requires multiple doses per RSV season, and is only modestly efficacious (Group, 1998; Homaira et al., 2014; Kamal-Bahl et al., 2002). These factors restrict its use to high-risk infants and limit its availability in developing countries where the greatest burden of RSV-associated mortality exists. Therefore, the development of an effective RSV vaccine and next-generation monoclonal antibodies is of great importance and ongoing clinical trials are evaluating numerous candidates (Griffin et al., 2017; PATH, 2017; Reichert, 2016; Zhu et al., 2017).

The development of an RSV vaccine has proven to be particularly challenging, due in part to the young age at which primary infection occurs (Glezen et al., 1986), a history of vaccine-enhanced disease in infants (Chin et al., 1969; Fulginiti et al., 1969; Kapikian et al., 1969; Kim et al., 1969), and a lack of long-lived immunity in response to natural infection, resulting in frequent reinfections (Hall et al., 1991; Henderson et al., 1979). Although there are no clinically approved RSV vaccines, there are 43 vaccine candidates in development, of which 19 are in clinical stage development (Center for Vaccine Innovation and Access, PATH available on the world wide web at path.org/programs/center-for-vaccine-innovation-and-access/). Most of these vaccines seek to induce neutralizing antibodies that recognize the RSV fusion (F) glycoprotein, which is targeted by the prophylactic antibody palivizumab and the majority of RSV-specific neutralizing antibodies in human sera.

The goal of most vaccination efforts against RSV is not to prevent infection, but to reduce the risk of RSV-related complications in high-risk populations, such as infants and the elderly. Five target age groups for vaccination have been proposed-infants under six months of age, infants over six months of age, school-aged children, pregnant women, and adults over 65 years old—with the goal of either directly or indirectly protecting at-risk populations (Anderson et al., 2013). These target age groups have different immunological characteristics that may require different vaccination strategies for optimal protection. Although multiple modalities for an RSV vaccine are currently being pursued, most vaccination strategies share a common goal: to elicit neutralizing antibodies that recognize the RSV fusion glycoprotein (RSV F), which is targeted by the majority of RSV-neutralizing activity in human sera (Magro et al., 2012; Sastre et al., 2005).

RSV F is a class I fusion protein that mediates viral entry into host cells by converting from a metastable prefusion conformation (preF) to a highly stable postfusion (postF) conformation. On the surface of the virus, RSV F exists in a metastable trimeric prefusion conformation (preF) before undergoing a dramatic structural rearrangement that results in the insertion of a hydrophobic fusion peptide into the host-cell membrane. This intermediate state of RSV F tethers the viral and host-cell membranes before collapsing to form the stable six-helix bundle that is characteristic of the postfusion conformation (postF). Fusion of the viral and host-cell membranes is driven by these conformational changes, and the antigenic topology of RSV F is substantially altered during this transition. Over the past several years, epitope mapping studies using both human and murine monoclonal antibodies have defined at least 6 major antigenic sites on the RSV F protein. Some groups of epitopes, referred to as antigenic sites, are generally conserved on both the preF and postF, whereas others antigenic sites are preferentially or exclusively expressed on only one conformation (Graham, 2017; Mclellan et al., 2013; Mclellan et al., 2011; Swanson et al., 2011). Molecules that prevent these structural changes can prevent viral fusion and have potential as therapeutics for RSV (Battles et al., 2016; Huang et al., 2010; Lambert et al., 1996; McLellan et al., 2013). Recent studies have shown that the vast majority of highly potent neutralizing antibodies target epitopes that are exclusively expressed on preF. Hence, vaccines that specifically induce preF-specific antibodies may have great clinical potential.

The first characterized RSV F-reactive antibodies bound to structural elements shared by both preF and postF and were F-conformation-independent. These include Synagis®, which recognizes a helix-turn-helix motif called antigenic site II (Beeler and van Wyke Coclingh, 1989; Mclellan et al., 2010b), and 101F, which recognizes the $\beta$-strand-rich antigenic site IV (McLellan et al., 2010a; Wu ct al., 2007). Antibodies that preferentially bind to postF at antigenic site I were also among the first to be isolated, but were only weakly neutralizing (Anderson et al., 1986; Garcia-Barreno et al., 1989). The first preF-specific antibodies to be described recognized antigenic site Ø, present at the apex of the preF trimer, and were shown to be extremely potent (McLellan et al., 2013). A second class of potently neutralizing antibodies, epitomized by MPE8, was later described and shown to recognize antigenic site III (Corti et al., 2013).

Although the secondary structure elements that form site III are present on both preF and postF, they adopt a different spatial arrangement in postF that dramatically decreases the affinity of site III-directed antibodies for this conformation and results in preferential binding to preF (Corti et al., 2013; Rossey et al., 2017; Wen et al., 2017). Antigenic site V, located between sites Ø and III, was recently identified and shown to be the target of additional preF-specific antibodies that are also potently neutralizing (Gilman et al., 2016; Mousa et al., 2017). The isolation and characterization of preF-specific antibodies spurred the development of second-generation prophylactics, such as MEDI8897, which recognizes site Ø (Griffin et al., 2017; Zhu et al., 2017) and is currently in late-phase clinical trials as a potential replacement for Synagis®.

An effective RSV vaccine will likely require the elicitation of potent neutralizing antibodies and balanced cellular responses (Kristjansson et al., 2005; Lambert et al., 2014; Legg et al., 2003; Saravia et al., 2015; Zhang et al., 2017). Infants present a number of unique challenges for vaccine development, including suppression of B cell responses by maternally derived antibody (Gans et al., 2001; Sande et al., 2014; Trang et al., 2014; Troisi et al., 1997; Wang et al., 2017) and immunological immaturity that results in reduced levels of T cell help, antibody class-switching, and somatic hypermutation (SHM) (Siegrist and Aspinall, 2009). Studies of convalescent infant sera have demonstrated that infants generally produce low titers of RSV-neutralizing antibodies after natural infection (Esposito et al., 2016; Murphy et al., 1986; Sande et al., 2014) but that these titers are higher when levels of maternal antibody are low (Shinoff et al., 2008), suggesting that infants are capable of mounting neutralizing antibody responses to RSV under certain circumstances. Serum studies have also suggested that different epitopes may be targeted as children age into adulthood (Fuentes et al., 2016), but little is known about how these changes are associated with antibody sequence or neutralization potency. In addition, sequencing studies have demonstrated that the antibody variable genes cloned from RSV-specific B cells in infants under three months of age contain little to no SHM, but the corresponding antibodies were not produced and characterized (Williams et al., 2009).

RSV replicates exclusively in respiratory epithelial cells, initiating infection in the upper respiratory tract and in some cases progressing to the lower respiratory tract. Therefore, an effective RSV vaccine may induce systemic and mucosal immune responses that protect both the upper and lower respiratory tracts (Varga, Current Opinion in Virology, 2014). A substantial body of literature suggests that RSV-specific mucosal antibody levels correlate more strongly with protection against RSV infection than serum antibody titers (Mills J T J Immnology 1971; Singleton R et al, JVI, 2003; walsh E E et al, JID, 2004; Habibi, AJRCCM 2015; Bagga JID, 2015; Vissers, CVI 2016; Watt P J Vaccine 1990). For example, experimental RSV challenge studies in adult donors have shown that nasal antibody strongly predicts protection from RSV infection (Habibi, AJRCCM 2015). In addition, a recent study in a clinical pediatric cohort showed that high levels of RSV-specific mucosal IgG correlated with reduced viral load and inflammation, whereas plasma IgG levels were not predictive of cither (Vissers, CVI 2016). Finally, preclinical immunogenicity and efficacy studies utilizing a live-attenuated vaccine candidate, RGAM2-2, showed that the protective efficacy of this vaccine was significantly higher when delivered by the intrasanal route compared to the intramuscular route, despite both vaccines inducing comparable serum antibody titers.

These studies provide compelling evidence that mucosal immunity may be required for efficient protection against RSV. However, relatively little is known about the anatomic location(s) of RSV-specific memory B cells within mucosa-associated lymphoid tissues, the specificities and functional properties of these antibodies, and if/how the RSV-specific mucosal antibody response differs from the systemic antibody response. A better understanding of these aspects of RSV infection and immune responses may provide useful information for the development of effective RSV vaccines.

SUMMARY OF THE INVENTION

An improved understanding of the specificities and functional activities of antibodies induced by natural RSV infection in young infants could facilitate the design of vaccine antigens that are less susceptible to interference by maternal antibodies and that focus the response on epitopes associated with neutralizing activity. RSV is a leading cause of infant mortality, and there are currently no licensed vaccines to protect this vulnerable population. A comprehensive understanding of infant antibody responses to natural RSV infection will facilitate vaccine development.

Applicant has discovered, isolated, and characterized an extensive panel of RSV F-specific monoclonal antibodies from several RSV-infected infants, some of which antibodies recognize antigenic sites distinct from those sites that dominate adult responses. In particular, over 450 RSV F-specific antibodies from the peripheral B cells of seven RSV-infected infants were isolated and characterized and, additionally, over 800 RSV F-specific antibodies from paired peripheral blood and adenoid tissues of 6 young children were isolated and characterized.

Binding and functional studies of the isolated anti-RSV F infant antibodies generally demonstrate binding to 2 primary antigenic sites and different neutralization potentials, i.e., non-neutralizing antibodies that bind to site I on postfusion F and neutralizing antibodies that bind to site III or site V on postfusion F. Structural studies provide a molecular basis for the conserved features of antibodies recognizing these sites. A subset of antibodies targeting one of the sites displayed potent neutralizing activity despite lacking somatic mutations, suggesting such antibodies can be induced in young infants with suitably designed vaccine antigens. Accordingly, Applicant provides fundamental insights into infant antibody responses in different immune compartments (e.g., mucosal and systemic) and, thus, provides a blueprint for the rational design of infant vaccine immunogens that selectively elicit desired B cell responses in infants.

In some embodiments, the present disclosure provides isolated antibodies or antigen-binding polypeptides comprising a VH CDR3 having an amino acid sequence according to an antibody number in Table 9B.

In some embodiments, the present disclosure provides isolated antibodies or antigen-binding polypeptides comprising a VH CDR3 having an amino acid sequence according to an ADI listed in Table 8.

In some embodiments, the present disclosure provides isolated antibodies or antigen binding polypeptides characterized by ability to neutralize respiratory syncytial virus (RSV).

In some embodiments, antibodies or antigen binding polypeptides are characterized by high affinity binding to RSV F.

In some embodiments, antibodies or antigen binding polypeptides are characterized by high affinity binding to RSV prefusion F (preF).

In some embodiments, isolated antibodies have an amino acid sequence according to:

(i) Antibody Number 2, 71, 112, 217, 227, 228, 249, 466, 467, 469, 470, 832, 471, 516, 527, 532, 543, 544, 551, 554, 571, 578, 581, 592, 615, 641, 843, 868, or 870;

(ii) an Antibody Number of (i) with no more than 3 amino acid substitutions, additions, or deletions;

(iii) an Antibody Number of (i) with no more than 3, 2, or 1 amino acid substitution(s), addition(s), or deletion(s) in a CDR; or (iv) an Antibody Number of (i) with no more than 3, 2, or 1 amino acid substitution(s), addition(s), or deletion(s) in CDRH3.

In some embodiments, antibodies or antigen-binding polypeptides have an IC50 of less than 300 pM, less than 200 pM, or less than 100 pM for neutralization of RSV.

In some embodiments, antibodies or antigen-binding polypeptides are characterized by binding affinity to pre-F with a kD of less than 10 nM.

In some embodiments, antibodies or antigen-binding polypeptides characterized by a binding affinity to pre-F that is at least 10, 100, or 1000 fold greater than binding affinity to post-F.

In some embodiments, antibodies or antigen-binding polypeptides are characterized by high affinity binding to RSV F site III.

In some embodiments, the present disclosure provides an antibody or antigen-binding fragment thereof that cross-competes for binding or specifically binds to the same epitope(s) of a Respiratory Syncytial Virus (RSV) fusion glycoprotein (F) ("an anti-RSV F antibody") as an antibody or antigen-binding fragment thereof comprising a CDRH3 amino acid sequence that is at least 80%, 85%, 90%, 95%, 96%, 97%, 98%, or 99% identical to a CDRH3 amino acid sequence of an antibody selected from Antibody Number 1 through Antibody Number 947 as disclosed in Table 5.

The present disclosure also provides an antibody or antigen-binding fragment thereof that cross-competes for binding or specifically binds to the same epitope(s) of a Respiratory Syncytial Virus (RSV) fusion glycoprotein (F) ("an anti-RSV F antibody") as an antibody or antigen-binding fragment thereof comprising a CDRH2 amino acid sequence that is at least 80%, 85%, 90%, 95%, 96%, 97%, 98%, or 99% identical to a CDRH2 amino acid sequence of an antibody selected from Antibody Number 1 through Antibody Number 947 as disclosed in Table 5.

The present disclosure further provides an antibody or antigen-binding fragment thereof that cross-competes for binding or specifically binds to the same epitope(s) of a Respiratory Syncytial Virus (RSV) fusion glycoprotein (F) ("an anti-RSV F antibody") as an antibody or antigen-binding fragment thereof comprising a CDRH1 amino acid sequence that is at least 80%, 85%, 90%, 95%, 96%, 97%, 98%, or 99% identical to a CDRH1 amino acid sequence of an antibody selected from Antibody Number 1 through Antibody Number 947 as disclosed in Table 5.

The present disclosure also provides an antibody or antigen-binding fragment thereof that cross-competes for binding or specifically binds to the same epitope(s) of a Respiratory Syncytial Virus (RSV) fusion glycoprotein (F) ("an anti-RSV F antibody") as an antibody or antigen-binding fragment thereof comprising a CDRL3 amino acid sequence that is at least 80%, 85%, 90%, 95%, 96%, 97%, 98%, or 99% identical to a CDRL3 amino acid sequence of an antibody selected from Antibody Number 1 through Antibody Number 947 as disclosed in Table 5.

The present disclosure further provides an antibody or antigen-binding fragment thereof that cross-competes for binding or specifically binds to the same epitope(s) of a Respiratory Syncytial Virus (RSV) fusion glycoprotein (F) ("an anti-RSV F antibody") as an antibody or antigen-binding fragment thereof comprising a CDRL2 amino acid sequence that is at least 80%, 85%, 90%, 95%, 96%, 97%, 98%, or 99% identical to a CDRL2 amino acid sequence of an antibody selected from Antibody Number 1 through Antibody Number 947 as disclosed in Table 5.

The present disclosure also provides an antibody or antigen-binding fragment thereof that cross-competes for binding or specifically binds to the same epitope(s) of a Respiratory Syncytial Virus (RSV) fusion glycoprotein (F) ("an anti-RSV F antibody") as an antibody or antigen-binding fragment thereof comprising a CDRL1 amino acid sequence that is at least 80%, 85%, 90%, 95%, 96%, 97%, 98%, or 99% identical to a CDRL1 amino acid sequence of an antibody selected from Antibody Number 1 through Antibody Number 947 as disclosed in Table 5.

In some embodiments, the anti-RSV F antibody comprises (i) the CDRH3 amino acid sequence of an antibody selected from Antibody Number 1 through Antibody Number 947 as disclosed in Table 5; (ii) the CDRH2 amino acid sequence of an antibody selected from Antibody Number 1 through Antibody Number 947 as disclosed in Table 5; (iii) the CDRH1 amino acid sequence of an antibody selected from Antibody Number 1 through Antibody Number 947 as disclosed in Table 5; (iv) the CDRL3 amino acid sequence of an antibody selected from Antibody Number 1 through Antibody Number 947 as disclosed in Table 5; (v) the CDRL2 amino acid sequence of an antibody selected from Antibody Number 1 through Antibody Number 947 as disclosed in Table 5; (vi) the CDRL1 amino acid sequence of an antibody selected from Antibody Number 1 through Antibody Number 947 as disclosed in Table 5; or (vii) any combination of two or more of (i), (ii), (iii), (iv), (v), and (vi).

In other embodiments, the antibody or antigen-binding fragment thereof that cross-competes for binding or specifically binds to the same epitope(s) of a Respiratory Syncytial Virus (RSV) fusion glycoprotein (F) ("an anti-RSV F antibody") as an antibody or antigen-binding fragment thereof comprising (i) a heavy chain variable region ($V_H$) that is at least 80%, 85%, 90%, 95%, 96%, 97%, 98%, or 99% identical to a $V_H$ amino acid sequence of an antibody selected from Antibody Number 1 through Antibody Number 947 as disclosed in Table 5, and/or (ii) a light chain variable region ($V_L$) that is at least 80%, 85%, 90%, 95%, 96%, 97%, 98%, or 99% identical to a $V_L$ amino acid sequence of an antibody selected from Antibody Number 1 through Antibody Number 947 as disclosed in Table 5.

In yet other embodiments, the anti-RSV F antibody comprises (i) the $V_H$ amino acid sequence of an antibody selected from Antibody Number 1 through Antibody Number 947 as disclosed in Table 5; and/or (ii) the $V_L$ amino acid sequence of an antibody selected from Antibody Number 1 through Antibody Number 947 as disclosed in Table 5.

In certain embodiments, the anti-RSV F antibody is selected from the group consisting of Antibody Number 1 through Antibody Number 947 as disclosed in Table 5.

In some embodiments, the anti-RSV F antibody binds to an epitope comprising site Ø, site I, site II, site III, site IV, or site V of RSV F. In one embodiment, the anti-RSV F antibody binds to an epitope on prefusion F (preF), preferably antigenic site III. In other embodiments, the anti-RSV F antibody binds to an epitope on postfusion F (post F), preferably antigenic site I.

In some embodiments, the anti-RSV F antibody binds to prefusion F (preF) with high affinity but does not bind to or binds with low affinity to postfusion F (postF).

In some embodiments, the anti-RSV F antibody does not compete with D25 for binding to RSV F. In some embodiments, the anti-RSV F antibody competes with MPE8 and/or motavizumab for binding to RSV F.

In some embodiments, the anti-RSV F antibody is a neutralizing antibody. In a certain embodiment, the anti-RSV F antibody has a neutralizing activity (IC50) of less than 100 $\mu$g/ml, 50 $\mu$g/ml, 25 $\mu$g/ml, 10 $\mu$g/ml, 5 $\mu$g/ml, 1 $\mu$g/ml, 0.5 $\mu$g/ml, 0.1 $\mu$g/ml, or 0.05 $\mu$g/ml.

In some embodiments, the anti-RSV F antibody binds to RSV prefusion F with a $K_D$ value of less than 50 nM, 25 nM, 10 nM, 5 nM, 1 nM, 0.5 nM, or 0.1 nM as measured by surface plasmon resonance.

In some embodiments, the anti-RSV F antibody binds to RSV prefusion F through one or both of the following interactions: a) Tyr33 in CDRL1 and Tyr93 in CDRL3 both contact the $\alpha$6-$\alpha$7 loop of RSV prefusion F; and b) five consecutive serine residues, preferably followed by a tyrosine residue (Tyr56), in CDRH2 form a network of hydrogen bonds with Asp310 on $\beta$6 of RSV prefusion F. In some embodiments, the anti-RSV F antibody has a clean or low polyreactivity profile.

In some embodiments, the anti-RSV F antibody is a full-length IgG1 monoclonal antibody.

In some embodiments, the anti-RSV F antibody is a human antibody.

In some embodiments, the anti-RSV F antibody comprises a Fc region that has been modified to alter effector function, half-life, proteolysis, and/or glycosylation.

In some embodiments, the anti-RSV F antibody is derivatized.

The present disclosure further encompasses a nucleic acid sequence or nucleic acid sequences encoding the anti-RSV F antibodies described herein; expression vectors comprising the isolated nucleic acid sequence(s); and host cell(s) comprising the isolated nucleic acid sequence(s) or the expression vector(s). In some embodiments, the host cell is a mammalian cell, a bacterial cell, a fungal cell, a yeast cell, or an insect cell.

Additionally, the present disclosure encompasses a method for producing an isolated human antibody or antigen-binding fragment thereof that specifically binds to Respiratory Syncytial Virus (RSV) fusion glycoprotein (F) ("an anti-RSV F antibody") comprising expressing the nucleic acid sequence(s) described herein or culturing the host cell(s) described herein (e.g., a yeast cell ora mammalian cell) under conditions that provide for expression of the anti-RSV F antibody and optionally recovering the anti-RSV F antibody from the host cell and/or culture medium.

The present disclosure also contemplates a pharmaceutical composition comprising (i) an anti-RSV F antibody (ies) described herein, the nucleic acid sequence(s) described herein, the expression vector(s) described herein, or the host cell(s) described herein; and (ii) a pharmaceutically acceptable carrier and/or excipient. The pharmaceutical composition can be used for preventing or treating a RSV infection in a subject. In one embodiment, the subject is a human, preferably an infant.

Furthermore, the present disclosure encompasses a method of preventing or treating a Respiratory Syncytial Virus (RSV) infection in a subject (e.g., a human or a non-human), comprising administering to the subject in need thereof an effective amount of the anti-RSV F antibody (ies) described herein, the isolated nucleic acid sequence(s) described herein, the expression vector(s) described herein, or the host cell(s) described herein, optionally in association with a further prophylactic and/or therapeutic agent. In one embodiment, the further prophylactic and/or therapeutic agent is selected from an antiviral agent; a vaccine specific for RSV; a vaccine specific for influenza virus; a vaccine specific for metapneumovirus (MPV); an siRNA specific for a RSV antigen; an siRNA specific for a MPV antigen; a second anti-RSV antibody; an anti-MPV antibody; an anti-IL4R antibody; an anti-influenza antibody; and a NSAID. In some embodiments, the subject is a human, preferably an infant.

Also provided herein is a method of preventing or treating a Respiratory Syncytial Virus (RSV) infection in a human subject (e.g., an infant) comprising administering to the subject in need thereof an effective amount of the pharmaceutical composition described herein.

Additionally provided herein is a method for detecting a Respiratory Syncytial Virus (RSV) infection in a subject (e.g., a human or a non-human) comprising obtaining a sample from the subject; contacting the sample with the anti-RSV F antibody (ies) described herein; and detecting the presence of a complex between the anti-RSV F antibody and the RSV fusion glycoprotein (F), wherein detection of the complex indicates the presence of RSV. In one embodiment, the subject is a human subject, preferably an infant.

Other features and advantages of the instant invention will be apparent from the following detailed description and examples which should not be construed as limiting. The contents of all cited references, including scientific articles, patents and patent applications cited throughout this application, are expressly incorporated herein by reference.

BRIEF DESCRIPTION OF THE FIGURES

FIG. 1A shows the gating strategy for a representative infant≥6 months (Infant 2042), and FIG. 1B shows the gating strategy for a representative infant<3 months (Infant 2026). Lymphocytes were gated based on forward and side scatter, followed by a live/dead gate and selection of CD3$^-$ CD8$^-$ CD14$^-$ cells. B cells were identified by gating on CD19$^+$/ CD20$^+$ cells. IgG$^+$ or IgA$^+$ B cells or CD19$^+$/CD20$^+$ B cells that showed reactivity with RSV F were single-cell sorted for antibody cloning. B cell reactivity with subtype A and subtype B is shown in the top and middle rows, respectively. The index sorting analysis is shown in the bottom panel. SSC-A, side scatter area; FSC-A, forward scatter area. FIG. 1C shows the percentage of RSV F-specific, class-switched B cells for each infant (FIG. 1C). Values were calculated based on flow cytometry data.

FIG. 2C shows the results of index sort analysis of the surface markers expressed on B cells from which RSV F-reactive antibodies were isolated. FIG. 2D shows the number of $V_H$ nucleotide substitutions for antibodies isolated from RSV F-specific class-switched B cells (the red bars indicate medians). In both FIG. 2C and FIG. 2D, infants are ordered from youngest to oldest, left to right. FIG. 2E shows a heat map of $V_H$ and $V_L$ germline gene usage for all infants (left panel), showing only genes for which at least one $V_H/V_L$ pairing was utilized in ≥0.5% of all antibodies isolated. The percent total of antibodies with the designated $V_H/V_L$ pairing is provided (right panel).

FIGS. 3A-3D show that a subset of RSV F-specific infant antibodies binds with high affinity to RSV F and neutralizes RSV. The fraction of isolated antibodies from each infant that binds with weak, low, medium, or high apparent affinity for preF (FIG. 3A) or postF (FIG. 3B) is shown for each antibody that displayed detectable binding in this assay. Infants are ordered from youngest to oldest, left to right. Apparent binding affinities are shown for each antibody. Black bars indicate medians. N.D., not determined. The percentage of antibodies isolated from each infant that shows weak, low, medium, or high neutralization potency is shown (FIG. 3C). Neutralization $IC_{50}$ values are shown for each antibody with measurable neutralization activity. Top, middle, and bottom dotted lines show $IC_{50}$ values for motavizumab, MPE8, and D25, respectively. Black bars indicate medians. FIG. 3D shows the apparent affinities for postF plotted against apparent affinities for preF for infants<3 months (left panel) and ≥6 months (right panel).

In FIGS. 4B and 4C, antibodies for which preF and postF binding affinities were measured are grouped according to preF or postF specificity.

FIG. 6A shows the preF structure with two protomers as grey molecular surfaces and one protomer as ribbons colored according to the antigenic site. FIG. 6B shows the percentage of isolated antibodies that recognize each antigenic site, plotted for each donor. Infants are ordered from youngest to oldest, left to right. FIG. 6C shows antibodies isolated from infants<3 months (left panel) and ≥6 months (right panel) grouped according to neutralization potency and antigenic site. N.N., non-neutralizing.

FIG. 8A shows the neutalization potency ($IC_{50}$) of antibodies lacking $V_H$ or $V_L$ nucleotide substitutions, grouped according to antigenic site. Top, middle, and bottom dotted lines show the $IC_{50}$ value for motavizumab, MPE8, and D25, respectively. N.N., non-neutralizing. No antibodies against site Ø lacking substitutions were obtained. FIG. 8B shows the results of index sort analysis of the surface markers expressed on cells from which RSV-reactive antibodies were isolated in infants<3 months. The percentage of B cells in each group is shown for all antibodies, neutralizing antibodies that lack somatic mutations (germline neut.), and neutralizing antibodies that contain somatic mutations (mutated neut.). FIG. 8C contains pie charts showing the fraction of RSV F-reactive naïve B cells isolated from the cord blood of four donors (top panel) and peripheral blood from two donors (bottom panel) that utilized VH3-21/VL1-40 or VH3-11/VL1-40 germline gene pairing. Naïve B cells were defined as $CD3^-CD14^-CD19^+$ $CD20^+IgM^+IgG^-$ $CD27^-$ cells. The number in the center of the pie (top and bottom) indicates the total number of antibodies with detectible binding to RSV F when produced as full-length IgG. FIG. 8D shows the apparent affinity for preF for each of these antibodies and colored according to germline usage. Black bars indicate medians. $IC_{50}$ values for antibodies that displayed detectible neutralizing activity.

FIGS. 9A-9D shows the non-neutralizing antibody ADI-14359 uses a convergent CDR H3 motif and germline features of the VK1-39 light chain for binding to antigenic site I on postF. FIG. 9A shows a crystal structure of infant antibody ADI-14359 ($V_H2$-70/VK1-39) in complex with postF. FIG. 9B shows a magnified view of the CDRH3 of ADI-14359 inserted into a groove on the surface of postF. The variable region of ADI-14359 and one RSV F protomer are shown as ribbons and the C-α atom of Pro389, a residue associated with viral escape from site I-directed antibodies, is shown as a sphere. FIG. 9C shows a magnified view of the antibody interface, highlighting the features of the convergent CDR H3 motif that mediate recognition of site I (left panel), whereas a 180° rotation highlights the CDR H2 contacts made with postF (right panel). The sequence logo for the convergent CDR H3 motif is shown (generated using WebLogo, described by Crooks et al., 2004). FIG. 9D shows the binding of ADI-14359 to postF as measured by surface plasmon resonance (top panel). Rate constants for the germline-reverted variant (R50L) binding to postF were too fast to be accurately determined (top middle panel) and, therefore, the equilibrium responses were plotted against the concentration of Fab and fit to a steady-state affinity model (bottom middle panel). Binding of ADI-14359 to the K390A variant of postF was too weak to determine an affinity (bottom panel).

FIG. 11A shows a crystal structure of ADI-19425 in complex with preF viewed along (left panel) and above (right panel) the viral membrane. FIG. 11B shows a magnified view of the interface with the variable region of ADI-19425 and one RSV F protomer shown in ribbon (left panel) and a 90-degree rotation showing the interactions between the light chain of ADI-19425 and the α6-α7 loop of antigenic site II (right panel). FIG. 11C shows the binding of ADI-19425 and the Y33A, Y93A and Y56A variants to preF as measured by surface plasmon resonance.

FIGS. 12A-12D show ADI-19425 and MPE8 utilize similar germline-encoded features to recognize preF. A ternary crystal structure of preF, 3 AM22 Fabs, and 3 ADI-19425 Fabs was generated (FIG. 12A, left and right panels). The right panel shows the same complex in the left panel, but rotated by 90° to show the view looking toward the viral membrane. Neutralization of two strains of RSV (A2 and B10895) by ADI-19425 IgG was measured using the fluorescence plate reader assay (FIG. 12B). The preF-bound MPE8 Fv was aligned to preF bound by ADI-19425 (FIG. 12C, left and right panels). The right panel is rotated by 90° relative to the left panel to show the top view. The MPE8 Fv is aligned to that of ADI-19425 (FIG. 12D, left and right panels). The right panel shows the binding interface between preF and ADI-19425, with the same orientation shown in FIG. 11B. The CDR loops are shown for both ADI-19425 and MPE8.

FIGS. 13A-C show analysis of RSV F-specific B cell responses in the adenoids and peripheral blood of young children. RSV F-specific B cells were measured in adenoid and peripheral blood by flow cytometry (FIG. 13A, left, middle, and right panels). The left panel shows the frequency of RSV F-specific B cells among CD19$^+$ B cells in adenoid for a representative donor. The middle panel shows the frequency of RSV F-specific B cells among CD19$^+$ B cells in PBMCs for a representative donor. The frequency of RSV F-reactive B cells within the CD14$^-$ CD3$^-$ CD8$^-$ CD19$^+$ CD20$^+$ population is shown next to the gate. The right panel shows a summary for all 6 donors analyzed. Index sort analysis of surface markers expressed on B cells from which RSV F-reactive antibodies were isolated (FIG. 13B). Percentage of RSV F-reactive B cells within each memory B cell subset that express FCRL4 (FIG. 13C). Asterisks indicate B cell responses that were below the limit of detection.

FIG. 14A shows the percentage of RSV F-specific B cells among CD19$^+$ B cells in the adenoids and PBMCs for a representative donor. FIG. 14B shows the percentage of RSV F-specific B cells among CD19$^+$ B cells in the adenoids (left panel) and in the PBMCs (right panel) for a representative donor.

FIG. 15A shows that the RSV F-specific antibody repertoires were highly diverse in both compartments (adenoids and PBMCs) in all donors, each containing few to no expanded clonal lineages. FIG. 15B shows the CDRH3 length distribution of the antibodies isolated from PBMCs and adenoids. FIG. 15C shows a comparable $V_H$ germline gene usage between the two compartments, though there was an enrichment for $V_H5$-51 and $V_H1$-69 in the adenoid-derived antibodies and an enrichment for $V_H4$-34 and $V_H3$-30 in the PBMC-derived antibodies.

FIG. 16A shows the the median number of $V_H$ nucleotide substitutions ranged from 8-11 in the adenoid-derived antibodies and 7-9 in the PBMC-derived antibodies. **** indicates that the difference in number of substitutions in the adenoid-derived antibodies relative to the PBMC-derived antibodies reached statistical significance in Donor 2665. FIG. 16B compares the levels of SHM within each individual B cell subset in adenoids (left panel) and PBMCs (right panel). FIG. 16C shows the the percentage of antibodies derived from IgG-IgA-CD27-peripheral blood B cells containing SHM. FIG. 16D shows a subset of somatically mutated antibodies derived from IgG-IgA-CD27-peripheral blood B cells that contained lower levels of SHM compared to antibodies derived from IgG-IgA-CD27-adenoid B cells. FIG. 16E shows the IgM and IgD expression profiles of RSV F-specific IgG-IgA-CD27-adenoid B cells.

FIG. 17A shows the number of $V_H$ nucleotide substitutions for Donor 2635. FIG. 17B shows the number of $V_H$ nucleotide substitutions for Donor 2665. **** indicates that the difference in number of substitutions in the adenoid-derived antibodies relative to the PBMC-derived antibodies reached statistical significance in Donor 2665. FIG. 17C shows the number of $V_H$ nucleotide substitutions for Donor 2666. FIG. 17D shows the number of $V_H$ nucleotide substitutions for Donor 2849.

FIG. 18A shows the percentage of antibodies that bind RSV preF, postF, and preF & postF using biolayer interferometry. FIG. 18B shows the percentage of antibodies that bind preF with weak (>50 nm), low (>5 to 50 nM), medium (>0.5 to 5 nM), and high (<0.5 nM) binding affinities.

FIGS. 19A-D show the neutralizing activity of the adenoid and PBMC-derived antibodies against RSV-A2. FIG. 19A shows the amount of detectable neutralizing activity (IC50<25 μg/mL) for adenoid and PBMC-derived antibodies using a luciferase-based assay. FIG. 19B shows the neutralization activity of preF-specific antibodies, postF-specific antibodies, and preF and PostF reactive antibodies isolated from both adenoids and PBMCs. FIG. 19C shows the memory B cell subsets for the adenoid-derived and PBMC-derived neutralizing antibodies. FIG. 19D shows the apparent preF $K_D$ (left panel) and the virus neutralization IC50 for each memory B cell subset.

FIGS. 20A-C shows the levels of polyreactivity and binding affinities of the antibodies derived from the adenoid and PBMC samples. FIG. 20A shows the percentage of antibodies having low and high levels of polyreactivity. FIG. 20B shows the percentage of low and high polyreactive clones across different B cell subsets within each compartment (left panel shows adenoid-derived antibodies and right panel shows PBMC-derived antibodies). FIG. 20C shows the percentage of antibodies having no binding or low, medium, or high affinity to RSV F.

DETAILED DESCRIPTION OF THE INVENTION

Figure 1A:
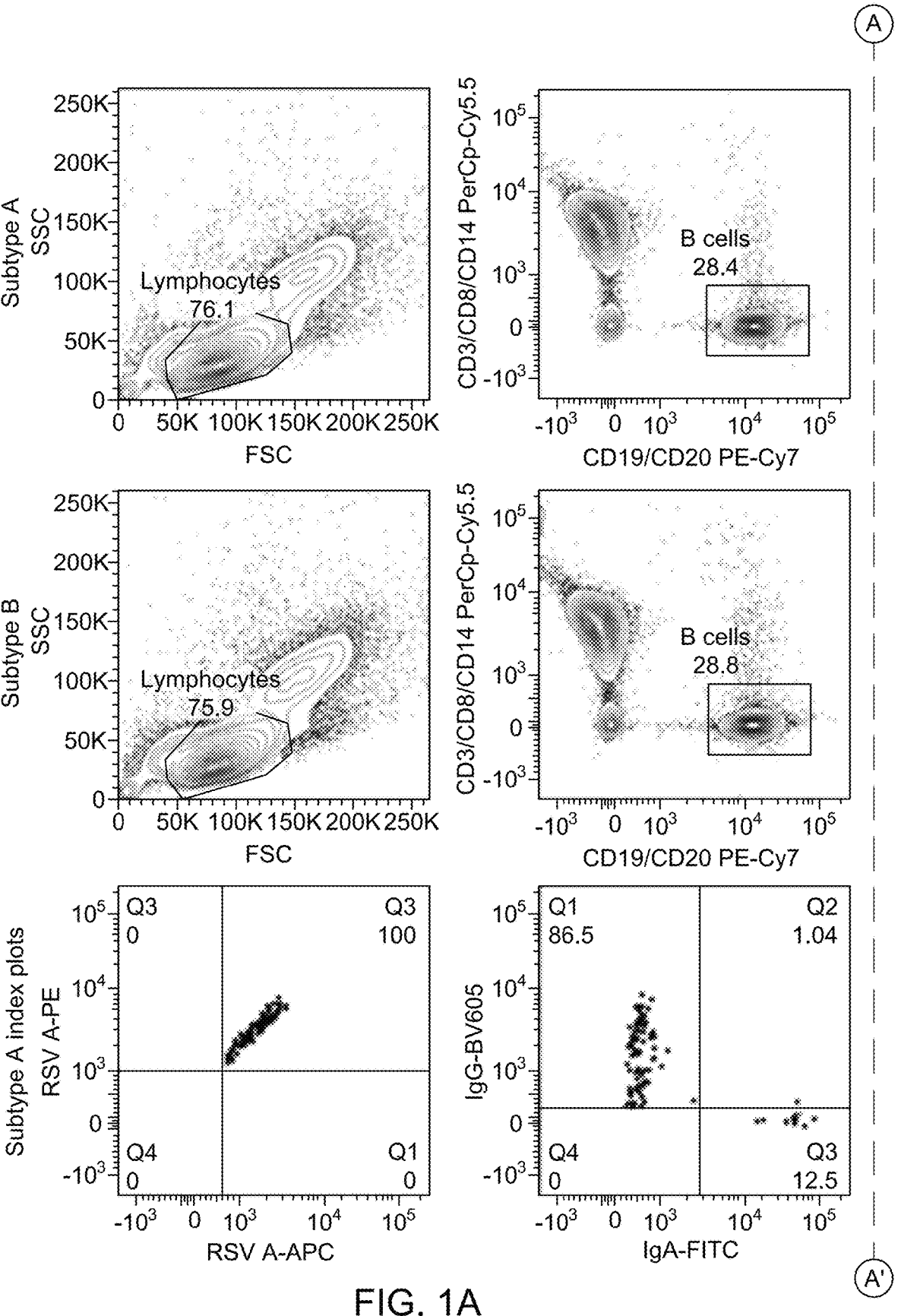
FIGS. 1A-1C show the single B cell sorting strategy.
Figure 1A:
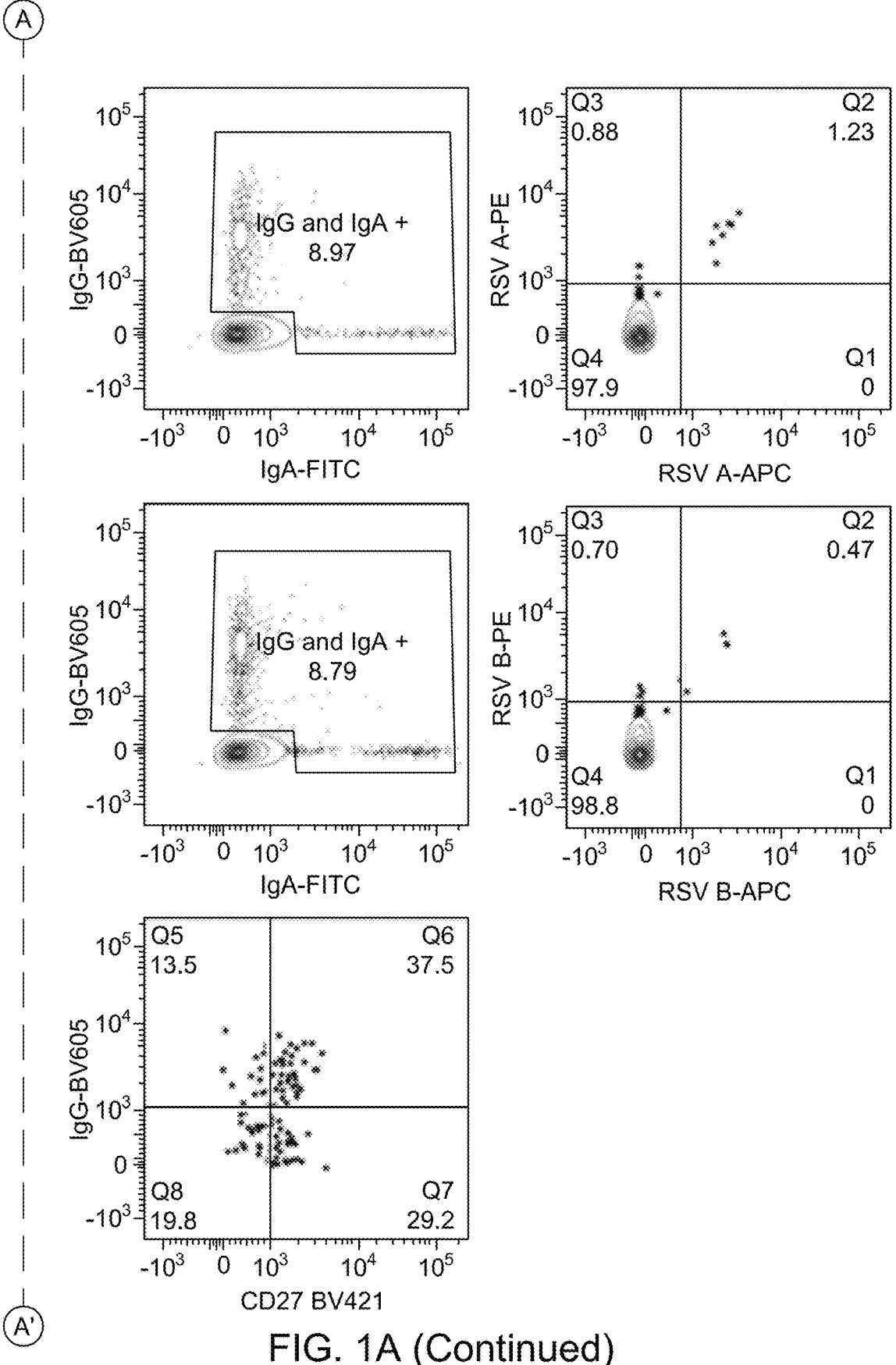

The present disclosure relates anti-RSV F infant antibodies, compositions comprising such antibodies, and methods for obtaining and using such antibodies. In some embodiments, the antibodies are neutralizing antibodies and, thus, the anti-RSV F neutralizing antibodies and compositions comprising such antibodies can be used as a vaccine. For infants, in particular, the subject anti-RSV F antibodies may provide advantageous protection.

Definitions

In order that the present disclosure may be more readily understood, certain terms are first defined. As used in this application, except as otherwise expressly provided herein, each of the following terms shall have the meaning set forth below. Additional definitions are set forth throughout the application. Unless defined otherwise, all technical and scientific terms used herein have the same meaning as commonly understood by one of ordinary skill in the art to which this invention belongs.

As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

"Respiratory Syncytial Virus fusion glycoprotein", also referred to as "RSV F", is a type I transmembrane surface protein that has an N terminal cleaved signal peptide and a membrane anchor near the C terminus (Collins, P. L. et al., (1984), PNAS (USA) 81:7683-7687). The RSV F protein is synthesized as an inactive 67 KDa precursor denoted as F0 (Calder, L. J.; et al., Virology (2000), 277, 122-131. The F0 protein is activated proteolytically in the Golgi complex by a furin-like protease at two sites, yielding two disulfide linked polypeptides, F2 and F1, from the N and C terminal, respectively. There is a 27 amino acid peptide released called "pep27". There are furin cleavage sites (FCS) on either side of the pep27 (Collins, P. L.; Mottet, G. (1991), J. Gen. Virol., 72:3095-3101; Sugrue, R. J, et al. (2001), J. Gen. Virol., 82, 1375-1386). The F2 subunit consists of the Heptad repeat C (HRC), while the F1 contains the fusion polypeptide (FP), heptad repeat A (HRA), domain I, domain II, heptad repeat B (HRB), transmembrane (TM), and cytoplasmic domain (CP) (Sec Sun, Z. et al. Viruses (2013), 5:21

1-225). The RSV F protein plays a role in fusion of the virus particle to the host cell membrane by irreversible protein refolding from the labile prefusion conformation (herein referred to as "prefusion F" or "preF") to the stable postfusion conformation (herein referred to as "postfusion F" or "postF"). RSV F is expressed on the surface of infected cells. Accordingly, it plays a role in cell to cell transmission of the virus and syncytia formation. The amino acid sequence of the RSV F protein is provided in GenBank as accession number AAX23994.

A stabilized variant of the PreF trimeric conformation of RSV F, termed "RSV-DS-Cav1" or "DS-Cav1" disclosed in, inter alia, Stewart-Jones et al., PLos One, Vol. 10(6)): e0128779. doi: 10.1371/journal.pone.0128779 and WO 2011/050168 was used in the identification, isolation, and characterization of the disclosed antibodies.

The term "laboratory strain" as used herein refers to a strain of RSV (subtype A or subtype B) that has been passaged extensively in in vitro cell culture. A "laboratory strain" can acquire adaptive mutations that may affect their biological properties. The term "clinical strain" as used herein refers to an RSV isolate (subtype A or subtype B), which is obtained from an infected individual and has been isolated and grown in tissue culture at low passage.

The term "$IC_{50}$" refers to the "half maximal inhibitory concentration", which value measures the effectiveness of compound (e.g., anti-RSV F antibody) inhibition towards a biological or biochemical utility. This quantitative measure indicates the quantity required for a particular inhibitor to inhibit a given biological process by half. In certain embodiments, RSV virus neutralization potencies for anti-RSV neutralizing antibodies disclosed herein are expressed as neutralization $IC_{50}$ values.

The term "infant", as used herein, generally refers to a young child between one month and one year (12 months) of age; however, it can also apply to a child older than 1 year (12 months). In one embodiment, the infant is at least ($\geq$) 6 months of age. In another embodiment, the infant is under 3 months of age.

The term "subject", as used herein, refers to a human or a nonhuman. The term "nonhuman" includes, but is not limited to, domestic animals (such as horses, dogs and cats) and livestock (such as cattle, sheep, swine, and poultry). In some embodiments, the subject is a human (and, more preferably, a human infant). The term "subject" may be interchangeably used with the term "patient" in the context of the present disclosure.

"Motavizumab", also referred to as "NUMAX™", is an enhanced potency RSV F-specific humanized monoclonal antibody derived by in vitro affinity maturation of the CDRs of the heavy and light chains of palivizumab. For reference purposes, the amino acid sequence of the NUMAXIM antibody is disclosed in U.S. Patent Publication 2003/0091584; U.S. Pat. No. 6,818,216; Wu et al., (2005) J. Mol. Bio. 350 (1): 126-144; and Wu, et al. (2007) J. Mol. Biol. 368:652-665.

"Palivizumab", also referred to as "SYNAGIS®", is a humanized anti-RSV F antibody with heavy and light chain variable domains having the amino acid sequences as set forth in U.S. Pat. Nos. 7,635,568 and 5,824,307. Palivizumab immunospecifically binds to the RSV F protein, and is currently FDA-approved for the passive immunoprophylaxis of serious RSV disease in high-risk children. It is administered intramuscularly at recommended monthly doses of 15 mg/kg of body weight throughout the RSV season (November through April in the northern hemisphere). SYNAGIS® is composed of 95% human and 5% murine antibody sequences. See also Johnson et al., (1997), J. Infect. Diseases 176:1215-1224.

"MPE8" is a human monoclonal antibody (MPE8), generated by Humabs BioMed SA, that binds to antigenic site III of RSV F and potently cross-neutralizes RSV and HMPV. For reference purposes, the amino acid sequence of the MPE8 antibody is disclosed in Corti et al., 2013.

"D25" is a human IgG1 kappa monoclonal antibody, developed by AIMM Therapeutics B.V. in partnership with MedImmune, which binds to antigenic site Ø on RSV F and neutralizes RSV with high efficiency. For reference purposes, the amino acid sequence of the D25 antibody is disclosed in U.S. Pat. No. 8,562,996.

As used herein, the terms "treat," "treatment," and "treating" refer to the reduction, alleviation, or amelioration of the progression, development, recurrence, severity, and/or duration of an upper and/or lower respiratory tract RSV infection or a symptom, complication, respiratory condition related thereto (such as pneumonia or bronchiolitis) resulting from the administration of one or more therapies (including, but not limited to, the administration of one or more prophylactic or therapeutic agents alone or in combination). In certain embodiments, such terms refer to the reduction or inhibition of the replication of RSV, the inhibition or reduction in the spread of RSV to other tissues or subjects (e.g., the spread to the lower respiratory tract), the inhibition or reduction of infection of a cell with a RSV, or the amelioration of one or more symptoms associated with an upper and/or lower respiratory tract RSV infection.

As used herein, the terms "prevent," "preventing," and "prevention" refer to the prevention or inhibition of the development or onset of an upper and/or lower respiratory tract RSV infection or a respiratory condition related thereto resulting from the administration of one or more therapies (including, but not limited to, the administration of one or more prophylactic or therapeutic agents alone or in combination).

The term "antibody" ("Ab"), as used herein, refers to an immunoglobulin molecule that binds specifically to an antigen and comprises four polypeptide chains, two heavy (H) chains and two light (L) chains interconnected by disulfide bonds (i.e., "full antibody molecules") or an antigen-binding fragment thereof. Each heavy chain is comprised of a heavy chain variable region ("HCVR" or "$V_H$") and a heavy chain constant region (comprised of domains $C_H1$, $C_H2$, and $C_H3$). Each light chain is comprised of a light chain variable region ("LCVR" or "$V_L$") and a light chain constant region ($C_L$). The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The $V_H$ and $V_L$ regions can be further subdivided into regions of hypervariability, termed complementarity determining regions (CDRs), interspersed with regions that are more conserved, termed framework regions (FRs). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs. Accordingly, the CDRs in a heavy chain are designated "CHRH1", "CDRH2", and "CDRH3", respectively, and the CDRs in a light chain are designated "CDRL1", "CDRL2", and "CDRL3".

Substitution of one or more CDR residues or omission of one or more CDRs is also possible. Antibodies have been described in the scientific literature in which one or two CDRs can be dispensed with for binding. Analysis of the contact regions between antibodies and their antigens, based on published crystal structures, concluded that only about one fifth to one third of CDR residues actually contact the antigen (Padlan et al. (1995 FASEB J. 9:133-139). Also, it has been shown that in many antibodies one or two CDRs had no amino acids in contact with an antigen (see also, Vajdos et al. 2002 J Mol Biol 320:415-428).

CDR residues not contacting antigen can be identified based on previous studies (for example, residues H60-H65 in CDRH2 are often not required), from regions of Kabat CDRs lying outside Chothia CDRs, by molecular modeling and/or empirically. If a CDR or residue(s) thereof is/are omitted, it is usually substituted with an amino acid occupying the corresponding position in another human antibody sequence or a consensus of such sequences. Positions for substitution within CDRs and amino acids to substitute can also be selected empirically.

The fully human monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, that are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

An immunoglobulin may derive from any of the commonly known isotypes, including but not limited to IgA, secretory IgA, IgG, and IgM. IgG subclasses are well known to those in the art and include, but are not limited to, human IgG1, IgG2, IgG3, and IgG4. "Isotype" refers to the antibody class or subclass (e.g., IgG1) that is encoded by the heavy chain constant region genes. The term "antibody" includes, by way of example, both naturally occurring and non-naturally occurring antibodies; monoclonal antibodies ("mAb") and polyclonal antibodies; chimeric and humanized antibodies; human or non-human antibodies; wholly synthetic antibodies; and single chain antibodies. Where not expressly stated, and unless the context indicates otherwise, the term "antibody" includes an antigen-binding fragment or an antigen-binding portion of any of the aforementioned immunoglobulins, a monovalent and a divalent fragment or portion, and a single chain antibody.

The term "human antibody", as used herein, is intended to include antibodies having variable and constant regions derived from human germline immunoglobulin sequences (and, thus, does not include antibodies in which CDRs derived from the germline of another mammalian species (e.g., mouse) have been grafted onto human FR sequences). The human antibodies of the invention may include amino acid residues not encoded by human germline immunoglobulin sequences (e.g., mutations introduced by random or site-specific mutagenesis in vitro or by somatic mutation in vivo), for example in the CDRs, in particular CDR3.

The term "humanized antibody", as used herein, refers to a human antibody in which one or more CDRs have been replaced with one or more corresponding CDRs obtained a non-human derived (e.g., mouse, rat, rabbit, primate) antibody. Humanized antibodies may also include certain non-CDR sequences or residues derived from such non-human antibodies as well as the one or more non-human CDR sequence. Such antibodies may also be referred to as "chimeric antibodies".

The term "recombinant" generally refers to any protein, polypeptide, or cell expressing a gene of interest that is produced by genetic engineering methods. The term "recombinant" as used herein with respect to a protein or polypeptide, means a polypeptide produced by expression of a recombinant polynucleotide. The proteins used in the immunogenic compositions of the invention may be isolated from a natural source or produced by genetic engineering methods.

The antibodies of the invention may, in some embodiments, be recombinant human antibodies. The term "recombinant human antibody", as used herein, is intended to include all antibodies (including human or humanized antibodies) that are prepared, expressed, created, or isolated by recombinant means, such as antibodies expressed using a recombinant expression vector transfected into a host cell (described further below); antibodies isolated from a recombinant, combinatorial human antibody library (described further below); antibodies isolated from an animal (e.g., a mouse) that is transgenic for human immunoglobulin genes (see, e.g., Taylor et al. (1992) Nucl. Acids Res. 20:6287-6295); or antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The terms "specifically binds" or "binds specifically to" are used interchangeably and mean that an antibody or antigen-binding fragment thereof forms a complex with an antigen that is relatively stable under physiologic conditions. Specific binding can be characterized by an equilibrium dissociation constant of at least about $1\times10^{-6}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, biolayer interferometry measurements using, e.g., a ForteBio Octet HTX instrument (Pall Life Sciences), which bind specifically to RSV F. Moreover, multi-specific antibodies that bind to RSV F protein and one or more additional antigens, or a bi-specific that binds to two different regions of RSV F, are nonetheless considered antibodies that "specifically bind". In certain embodiments, the antibodies disclosed herein display equilibrium dissociation constants (and hence specificities) of about $1\times100$ M; about $1\times10^{-7}$ M; about $1\times10^{-8}$ M; about $1\times10^{-9}$ M; about $1\times10^{-10}$ M; about $1\times10^{-11}$ M; about $1\times10^{-12}$ M; between about $1\times10^{-7}$ M and about $1\times10^{-11}$ M; or between about $1\times10^{-8}$ M and about $1\times10^{-10}$ M.

The term "high affinity antibody" refers to those antibodies having a binding affinity to RSV F (preF or postF) of about ≤0.5 nM as measured by surface plasmon resonance, e.g., BIACORE™, biolayer interferometry measurements using, e.g., a ForteBio Octet HTX instrument (Pall Life Sciences).

The term "medium affinity antibody" refers to those antibodies having a binding affinity to RSV F of about >0.5 to 5 nM as measured by surface plasmon resonance, e.g., BIACORE™ biolayer interferometry measurements using, e.g., a ForteBio Octet HTX instrument (Pall Life Sciences).

The term "low affinity antibody" refers to those antibodies having a binding affinity to RSV F of about >5 to 50 nM as measured by surface plasmon resonance, e.g., BIACORE™, biolayer interferometry measurements using, e.g., a ForteBio Octet HTX instrument (Pall Life Sciences).

The term "weak affinity antibody" refers to those antibodies having a binding affinity to RSV F of about >50 nM as measured by surface plasmon resonance, e.g., BIACORE™, biolayer interferometry measurements using, e.g., a ForteBio Octet HTX instrument (Pall Life Sciences).

The terms "antigen-binding portion" and "antigen-binding fragment" are used interchangeably and refer to any naturally occurring, enzymatically obtainable, synthetic, or genetically engineered polypeptide or glycoprotein that specifically binds an antigen to form a complex. In certain embodiments, the terms "antigen-binding portion" and "antibody fragment" refer to one or more fragments of an antibody that retains the ability to bind to RSV F.

An antibody fragment may include a Fab fragment, a F(ab')$_2$ fragment, a Fv fragment, a dAb fragment, a fragment containing a CDR, or an isolated CDR. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add, or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed by "antigen-binding fragment" and "antigen-binding portion".

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$-$V_L$, or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_h$1-$C_h$2; (v) $V_H$-$C_h$1-$C_h$2-$C_h$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody typically comprises at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

In certain embodiments, the antibody or antibody fragment is mono-specific, bi-specific, or multi-specific. Multi-specific antibodies may be specific for different epitopes of one target polypeptide or may contain antigen-binding domains specific for epitopes of more than one target polypeptide. An exemplary bi-specific antibody format that can be used in the context of the present invention involves the use of a first immunoglobulin (Ig) $C_H$3 domain and a second Ig $C_H$3 domain, wherein the first and second Ig $C_H$3 domains differ from one another by at least one amino acid, and wherein at least one amino acid difference reduces binding of the bi-specific antibody to Protein A as compared to a bi-specific antibody lacking the amino acid difference. In one embodiment, the first Ig $C_H$3 domain binds Protein A and the second Ig $C_H$3 domain contains a mutation that reduces or abolishes Protein A binding such as an H95R modification (by IMGT exon numbering; H435R by EU numbering). The second $C_H$3 may further comprise an Y96F modification (by IMGT; Y436F by EU). Further modifications that may be found within the second $C_H$3 include: D16E, L18M, N44S, K52N, V57M, and V82I (by IMGT; D356E, L358M, N384S, K392N, V397M, and V422I by EU) in the case of IgG1 monoclonal antibodies; N44S, K52N, and V82I (IMGT; N384S, K392N, and V422I by EU) in the case of IgG2 monoclonal antibodies; and Q15R, N44S, K52N, V57M, R69K, E79Q, and V82I (by IMGT; Q355R, N384S, K392N, V397M, R409K, E419Q, and V422I by EU) in the case of IgG4 monoclonal anitbodies. Variations of these bi-specific antibody formats are also encompassed within the scope of the present invention.

The antibodies provided herein can be derivatized or linked to another functional molecule (e.g., another peptide or protein). Accordingly, the antibodies of the invention are intended to include derivatized and otherwise modified forms of the anti-RSV F antibodies described herein. For example, an antibody can be functionally linked (e.g., by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by cross-linking two or more antibodies (of the same type or of different types, e.g., to create bispecific antibodies, which is also discussed below).

Exemplary detectable agents with which an antibody of the invention may be derivatized include fluorescent compounds (such as, but not limited to, fluorescein, fluorescein isothiocyanate, rhodamine, 5-dimethylamine-1-napthalene-sulfonyl chloride, phycoerythrin and the like). An antibody may also be derivatized with detectable enzymes (such as, but not limited to, alkaline phosphatase, horseradish peroxidase, glucose oxidase and the like). When an antibody is derivatized with a detectable enzyme, it can be detected by adding additional reagents that the enzyme uses to produce a detectable reaction product (e.g., when the detectable agent horseradish peroxidase is present, the addition of hydrogen peroxide and diaminobenzidine leads to a colored reaction product, which is detectable). An antibody may also be derivatized with biotin, and detected through indirect measurement of avidin or streptavidin binding. Such derivatized anti-RSV F antibodies may be useful for the detection and/or diagnosis of RSV in a subject.

The specific embodiments, antibodies, or antibody fragments of the invention may be conjugated to a therapeutic moiety ("immunoconjugate"), such as an antibiotic, a second anti-RSV F antibody, a vaccine, a toxoid, or any other therapeutic moiety useful for treating an RSV infection.

The antibodies of the invention can also be modified by pegylation. An antibody can be pegylated to, for example, increase the biological (e.g., serum) half-life of the antibody. To pegylate, an antibody typically is reacted with a polyethylene glycol (PEG) reagent, such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies described herein. See for example, EP 0154316 by Nishimura et al. and EP 0401384 by Ishikawa et al.

The term an "isolated antibody", as used herein, is intended to refer to an antibody that is substantially free of other antibodies having different antigenic specificities (e.g., an isolated antibody that specifically binds RSV F, or a fragment thereof, is substantially free of antibodies that specifically bind antigens other than RSV F).

The term a "blocking antibody" or a "neutralizing antibody", as used herein (or an "antibody that neutralizes RSV F"), is intended to refer to an antibody whose binding to RSV F results in inhibition of at least one biological activity of RSV F. For example, such an antibody may aid in blocking the fusion of RSV to a host cell, prevent syncytia formation, and/or prevent the primary disease caused by RSV. Alternatively, or in addition, such an antibody may demonstrate the ability to ameliorate at least one symptom of the RSV infection. This inhibition of the biological activity of RSV F can be assessed by measuring one or more indicators of RSV F biological activity using standard in vitro assays (such as a neutralization assay) or in vivo assays known in the art (such as animal models to look at protection from challenge with RSV following administration of one or more of the antibodies described herein).

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope", as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The terms "substantial identity" and "substantially identical" are used interchangeably herein and, when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98%, or 99% of the nucleotide bases, as measured by any well-known algorithm of sequence identity, such as FASTA, BLAST, or GAP, as discussed below. Accordingly, nucleic acid sequences that display a certain percentage identity share that percentage identity and/or are that percentage identical to one another. A nucleic acid molecule having substantial identity to a reference nucleic acid molecule may, in certain instances, encode a polypeptide having the same or substantially similar amino acid sequence as the polypeptide encoded by the reference nucleic acid molecule.

In certain embodiments, the disclosed antibody nucleic acid sequences are, e.g., at least 70% identical; at least 75% identical; 80% identical; at least 85% identical; at least 90% identical; at least 95% identical; at least 96% identical; at least 97% identical; at least 98% identical; at least 99%; and/or all percentages of identity in between, to other sequences and/or share such percentage identities with one another (or with certain subsets of the herein-disclosed antibody sequences).

As applied to polypeptides, the term "substantial identity" or "substantially identical" means that two peptide sequences, when optimally aligned, such as by the programs GAP or BESTFIT using default gap weights, share at least 90% sequence identity, even more preferably at least 95%, 96%, 97%, 98%, or 99% sequence identity. Accordingly, amino acid sequences that display a certain percentage identity share that percentage identity and/or are that percentage identical to one another. Accordingly, amino acid sequences that display a certain percentage identity share that percentage identity and/or are that percentage identical to one another.

In certain embodiments, the disclosed antibody amino acid sequences are, e.g., at least 70% identical; at least 75% identical; 80% identical; at least 85% identical; at least 90% identical; at least 95% identical; at least 96% identical; at least 97% identical; at least 98% identical; at least 99%; and/or all percentages of identity in between, to other sequences and/or share such percentage identities with one another (or with certain subsets of the herein-disclosed antibody sequences).

Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. (Sec, e.g., Pearson (1994) Methods Mol. Biol. 24:307-331). Examples of groups of amino acids that have side chains with similar chemical properties include: 1) aliphatic side chains: glycine, alanine, valine, leucine and isoleucine; 2) aliphatic-hydroxyl side chains: serine and threonine; 3) amide-containing side chains: asparagine and glutaminc; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparaginc-glutaminc. Alternatively, a conservative replacement is any change having a positive value in the PAM250 log-likelihood matrix disclosed in Gonnet et al. (1992) Science 256:1443 45. A "moderately conservative" replacement is any change having a non-negative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. (See, e.g., Altschul et al. (1990) J. Mol. Biol. 215:403 410 and (1997) Nucleic Acids Res. 25:3389 402).

The phrase "therapeutically effective amount" refers to an amount of a therapeutic agent (e.g., an anti-RSV F antibody disclosed herein) that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays. The exact amount will depend on the purpose of the treatment, and will be ascertainable by one skilled in the art using known techniques (see, for example, Lloyd (1999) The Art, Science and Technology of Pharmaceutical Compounding).

The term "immunogenic composition" refers to a composition containing an antigen/immunogen, e.g., a microorganism (such as a virus or a bacterium) or a component thereof, a protein, a polypeptide, a fragment of a protein or polypeptide, a whole cell inactivated, subunit or attenuated virus, a polysaccharide, or combination thereof, that is administered to stimulate the recipient's humoral and/or cellular immune systems to one or more of the antigens/immunogens present in the immunogenic composition. The immunogenic compositions of the present invention can be used to treat a human susceptible to RSV infection, or suspected of having or being susceptible to RSV infection, by means of administering the immunogenic compositions via a systemic route. These administrations can include injection via the intramuscular (i.m.), intradermal (i.d.), intranasal, inhalation, or subcutaneous (s.c.) routes; application by a patch or other transdermal delivery device. In one embodiment, the immunogenic composition may be used in the manufacture of a vaccine or in the elicitation of polyclonal or monoclonal antibodies that could be used to passively protect or treat a subject.

The terms "vaccine" or "vaccine composition", which are used interchangeably, refer to a composition comprising at least one immunogenic composition that induces an immune response in a subject (e.g., a mammal, e.g., a human).

In certain embodiments, a protein of interest comprises an antigen. The terms "antigen," "immunogen," "antigenic," "immunogenic," "antigenically active," and "immunologically active", when made in reference to a molecule, refer to any substance that is capable of inducing a specific humoral and/or cell-mediated immune response. In one embodiment, the antigen comprises an epitope.

"Immunologically protective amount", as used herein, is an amount of an antigen effective to induce an immunogenic response in the recipient that is adequate to prevent or ameliorate signs or symptoms of disease, including adverse health effects or complications thereof. Either humoral immunity or cell-mediated immunity or both can be induced. The immunogenic response of an animal to a composition can be evaluated, e.g., indirectly through measurement of antibody titers, lymphocyte proliferation assays, or directly through monitoring signs and symptoms after challenge with the microorganism. The protective immunity conferred by an immunogenic composition or vaccine can be evaluated by measuring, e.g., reduction of shed of challenge organisms, reduction in clinical signs such as mortality, morbidity, temperature, and overall physical condition, health and performance of the subject. The immune response can comprise, without limitation, induction of cellular and/or humoral immunity. The amount of a composition or vaccine that is therapeutically effective can vary, depending on the particular organism used, or the condition of the animal being treated or vaccinated.

The terms "immune response" or "immunological response", as used herein, referto the development of a humoral immune response, a cellular-immune response, or a humoral and a cellular immune response to an antigen/immunogen. A "humoral immune response" refers to one that is, at least in part, mediated by antibodies. A "cellular immune response" is one mediated by T-lymphocytes and/or other white blood cells and includes the production of cytokines, chemokines, and similar molecules produced by activated T-cells and/or white blood cells. Immune responses can be determined using standard immunoassays and neutralization assays, which are known in the art.

The term "immunogenicity", as used herein, refers to the capability of a protein or polypeptide to elicit an immune response directed specifically against a bacteria or virus that causes the identified disease.

Preparation of Human Antibodies

As disclosed herein, anti-RSV F infant antibodies may be obtained through B cell sorting techniques available to the artisan as well as those methods exemplified in the EXAMPLES below. Methods for generating human antibodies in transgenic mice are also known in the art and may also be employed to derive antibodies in accordance with the present disclosure. Any such known methods can be used in the context of the present invention to make human antibodies that specifically bind to RSV F (see, for example, U.S. Pat. No. 6,596,541).

The antibodies of the instant invention can possess affinities ($K_D$) ranging from about $1.0 \times 10^{-7}$ M to about $1.0 \times 10^{-12}$ M, when measured by binding to antigen either immobilized on solid phase or in solution phase. In some embodiments, the antibodies of the invention possess affinities ($K_D$) ranging from about $1 \times 10^{-7}$ M to about $1 \times 10^{-10}$ M, when measured by binding to antigen either immobilized on solid phase or in solution phase. In other embodiments, the antibodies of the invention possess a $K_D$ of less than 50 nM, 25 nM, 10 nM, 5 nM, 1 nM, 0.5 nM, or 0.1 nM, as measured by surface plasmon resonance.

The anti-RSV F antibodies and antibody fragments of the instant invention encompass proteins having amino acid sequences that may vary from the sequences of the described antibodies but, nonetheless, retain the ability to bind (and, in some cases, neutralize) RSV F. Such variant antibodies and antibody fragments comprise one or more additions, deletions, or substitutions of amino acids when compared to a parent sequence (i.e., amino acid sequence of a described antibody), but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment described herein.

Two antigen-binding proteins (e.g., antibodies) are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins (e.g., antibodies) are bioequivalent if there are no clinically meaningful differences in their safety, purity, and/or potency.

In another embodiment, two antigen-binding proteins (e.g., antibodies) are bioequivalent if a patient can be switched one or more times between the proteins (e.g., antibodies) without an expected increase in the risk of adverse effects, including a clinically significant change in immunogenicity, or diminished effectiveness, as compared to continued therapy without such switching.

In yet another embodiment, two antigen-binding proteins (e.g., antibodies) are bioequivalent if both proteins (e.g., antibodies) act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) a well-controlled clinical trial that establishes safety, efficacy, bioavailability, and/or bioequivalence of an antibody.

Bioequivalent variants of the antibodies of the invention may be constructed by, for example, making various substitutions of residues or sequences or deleting terminal or internal residues or sequences (which may occur in the variable or binding regions as well as framework regions) not needed for biological activity. In some embodiments, it is contemplated that the anti-RSV F antibodies may contain inter alia one or more additional amino acid residue substitutions, mutations and/or modifications in the constant region (i.e., the Fc region) which result in preferred characteristics including, but not limited to: altered pharmacokinetics, increased serum half life, increase binding affinity, reduced immunogenicity, increased production, altered Fc ligand binding to an Fc receptor (FcR), enhanced or reduced ADCC (antibody-dependent cell mediated cytotoxicity) or CDC (complement-dependent cytotoxicity) activity, altered glycosylation and/or disulfide bonds and modified binding specificity. In this regard it will be appreciated that these Fc variants may advantageously be used to enhance the effective anti-neoplastic properties of the disclosed modulators. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes that modify the glycosylation characteristics of the antibodies, e.g., mutations that eliminate or remove glycosylation. In still other contexts, bioequivalent antibodies may include antibody variants comprising amino acid changes that modify the Fc region. Such Fc variant may have increased half-life, improved stability, and/or modified effector function(s).

Biological and Biophysical Characteristics of the Antibodies

In certain embodiments, the antibodies and antigen-binding fragments thereof specifically bind to RSV F, wherein at least one of the CDRH1, CDRH2, CDRH3, CDRL1, CDRL2, and/or CDRL3 amino acid sequences of such antibody or the antigen-binding fragment thereof is at least 70% identical; at least 75% identical; 80% identical; at least 85% identical; at least 90% identical; at least 95% identical; at least 96% identical; at least 97% identical; at least 98% identical; at least 99%; and/or all percentages of identity in between, to at least one of the CDRH1, a CDRH2, aCDRH3, a CDRL1, a CDRL2, and/or a CDRL3 amino acid sequence of an antibody selected from Antibody Number 1 through Antibody Number 947 as disclosed in Table 5.

Without wishing to be bound by any theory, it is believed that the inventive antibodies and antigen-binding fragments thereof may function by binding to RSV F, preferably in the PreF conformation, and in so doing act to block the fusion of the viral membrane with the host cell membrane. The antibodies of the present invention may also function by binding to RSV F and in so doing block the cell to cell spread of the virus and block syncytia formation associated with RSV infection of cells. Subtype A is responsible for the majority of hospitalizations for RSV and RSV-related complications. Advantageously, RSV subtype A or both RSV subtype A and RSV subtype B are effectively blocked, or neutralized, by the majority of the anti-RSV antibodies disclosed herein.

In certain embodiments, the inventive antibodies and antigen-binding fragment thereof display better binding affinity for the prefusion (PreF) form of RSV F relative to the postfusion (PostF) form of RSV F. Indeed, in some embodiments, the anti-RSV F antibodies disclosed herein bind to PreF (e.g., with high affinity) but do not bind to PostF or bind to PostF with low affinity. In other embodiments, the antibodies and antigen-binding fragments thereof disclosed herein display better binding affinity for PostF than PreF.

Antibodies with a range of polyreactivity (high, medium, low, or undetectable) are disclosed. In some embodiments, the inventive antibodies and antigen-binding fragments thereof advantageously display a clean or low polyreactivity profile (see, e.g., WO 2014/179363 and Xu et al., *Protein Eng Des Sel*, October; 26 (10): 663-70. doi: 10.1093/protein/gzt047), and are thus particularly amenable to development as safe, efficacious, and developable therapeutic and/or prophylactic anti-RSV treatments.

In certain embodiments, the inventive antibodies and antigen-binding fragments thereof, without wishing to be bound by any theory, may function by blocking or inhibiting RSV fusion to the cell membrane by binding to any one or more of antigenic Sites Ø, I, II, III, IV, and/or Site V of the F protein. In certain embodiments, the antibodies disclosed herein display antigenic site specificity for Site III of (preF) RSV F and, generally, such antibodies are neutralizing antibodies (in some instances, e.g., ADI-19425, potently neutralizing). In other embodiments, the antibodies disclosed herein display antigenic site specificity for Site I of (postF) RSV F and, generally, such antibodies are non-neutralizing antibodies.

In certain embodiments, at least a portion of the epitope with which the inventive antibodies and antigen-binding fragments thereof interacts comprises the loop connecting α6 to α7 of PreF and/or β6 of PreF. In certain embodiments, the heavy chain (e.g., CDRL3) and the light chain (e.g., CDRH2) of the inventive antibodies interact with the epitope of PreF. In a particular embodiment, Tyr33 in CDRL1 and Tyr93 in CDRL3 both contact the α6-α7 loop of RSV preF and/or five consecutive serine residues, preferably followed by a tyrosine residue (Tyr56), in CDRH2 form a network of hydrogen bonds with Asp310 on β6 of RSV preF. In still further embodiments, the CDRH3 of the inventive antibodies have relatively few sequence (composition and/or length) restrictions.

In certain embodiments, the inventive antibodies and antigen-binding fragments thereof display an in vitro neutralization potency ($IC_{50}$) of greater than 0.5 ug/ml (referred to as "weak neutralization potency"); between about 0.5

µg/ml to about 5 µg/ml (referred to as "low neutralization potency"); between about 0.05 ug/ml to about 0.5 ug/ml (referred to as "medium neutralization potency"); or less than about 0.05 mg/ml (referred to as "high neutralization potency"). Neutralization potency can be measured using standard assays well known in the field, including, but not limited to, a high-throughput fluorescence plate reader neutralization assay (as described herein, see EXAMPLES).

In certain embodiments, the inventive antibodies and antigen-binding fragments thereof display at least about 2-fold; at least about 3-fold; at least about 4-fold; at least about 5-fold; at least about 6-fold; at least about 7-fold; at least about 8-fold; at least about 9-fold; at least about 10-fold; at least about 15-fold; at least about 20-fold; at least about 25-fold; at least about 30-fold; at least about 35-fold; at least about 40-fold; at least about 50-fold; at least about 55-fold; at least about 60-fold; at least about 70-fold; at least about 80-fold; at least about 90-fold; at least about 100-fold; greater than about 100-fold; and folds in between any of the foregoing; greater neutralization potency ($IC_{50}$) than motavizumab, MPE8, and D25.

In certain embodiments, the inventive antibodies and antigen-binding fragments thereof comprise the CDRH3 amino acid sequence of any one of the antibodies designated Antibody Number 1 through Antibody Number 947 as disclosed in Table 5.

In certain embodiments, the inventive antibodies and antigen-binding fragments thereof comprise the CDRH2 amino acid sequence of any one of the antibodies designated Antibody Number 1 through Antibody Number 947 as disclosed in Table 5.

In certain embodiments, the inventive antibodies and antigen-binding fragments thereof comprise the CDRH1 amino acid sequence of any one of the antibodies designated Antibody Number 1 through Antibody Number 947 as disclosed in Table 5.

In certain embodiments, the inventive antibodies and antigen-binding fragments thereof comprise the CDRL3 amino acid sequence of any one of the antibodies designated Antibody Number 1 through Antibody Number 947 as disclosed in Table 5.

In certain embodiments, the inventive antibodies and antigen-binding fragments thereof comprise the CDRL2 amino acid sequence of any one of the antibodies designated Antibody Number 1 through Antibody Number 947 as disclosed in Table 5.

In certain embodiments, the inventive antibodies and antigen-binding fragments thereof comprise the CDRL1 amino acid sequence of any one of the antibodies designated Antibody Number 1 through Antibody Number 947 as disclosed in Table 5.

In certain embodiments, the inventive antibodies and antigen-binding fragments thereof comprise any combination of two or more of the CDRH3, CDRH2, CDRH1, CDRL3, CDRL2, and CDRL1 amino acid sequences of any one of the antibodies designated Antibody Number 1 through Antibody Number 947 as disclosed in Table 5. By way of example only, the inventive antibodies and antigen-binding fragments thereof comprise the CDRL3 and the CDRH2 of any one of the antibodies designated Antibody Number 1 through Antibody Number 947 as disclosed in Table 5.

In certain embodiments, the inventive antibodies and antigen-binding fragments thereof comprise a heavy chain (HC) amino acid sequence of any one of the antibodies designated Antibody Number 1 through Antibody Number 947 as disclosed in Table 5. In certain embodiments, the inventive antibodies and antigen-binding fragments thereof comprise a light chain (LC) amino acid sequence of any one of the antibodies designated Antibody Number 1 through Antibody Number 947 as disclosed in Table 5. In certain embodiments, the inventive antibodies and antigen-binding fragments thereof comprise a heavy chain (HC) amino acid sequence and a light chain (LC) amino acid sequence of any one of the antibodies designated Antibody Number 1 through Antibody Number 947 as disclosed in Table 5.

In certain embodiments, the inventive antibodies and antigen-binding fragments thereof are each selected from the group consisting antibodies that are at least 70% identical; at least 75% identical; 80% identical; at least 85% identical; at least 90% identical; at least 95% identical; at least 96% identical; at least 97% identical; at least 98% identical; at least 99%; and/or all percentages of identity in between; to any one of the antibodies designated as Antibody Number 1 through Antibody Number 947 as disclosed in Table 5.

In certain embodiments, the inventive antibodies and antigen-binding fragments thereof comprise are each selected from the group consisting of the antibodies designated as Antibody Number 1 through Antibody Number 947 as disclosed in Table 5.

In certain embodiments, isolated nucleic acid sequences are provided that encode antibodies (or antigen-binding fragments thereof) that specifically bind to RSV F, wherein at least one of the CDRH1, CDRH2, CDRH3, CDRL1, CDRL2, and/or CDRL3 amino acid sequences of the antibody or the antigen-binding fragment thereof is at least 70% identical; at least 75% identical; 80% identical; at least 85% identical; at least 90% identical; at least 95% identical; at least 96% identical; at least 97% identical; at least 98% identical; at least 99%; and/or all percentages of identity in between; to at least one of the CDRH1, CDRH2, CDRH3, CDRL1, CDRL2, and/or CDRL3 amino acid sequences of an antibody selected from Antibody Number 1 through Antibody Number 947 as disclosed in Table 5. In certain embodiments, such nucleic acid sequences are selected from those nucleic acid sequences that are disclosed in Table 5 and compliments thereof.

In certain embodiments, isolated nucleic acid sequences are provided that encode the inventive antibodies and antigen-binding fragments thereof, wherein such nucleic acid sequences comprise sequences that encode the CDRH3 amino acid sequence of the antibodies designated Antibody Number 1 through Antibody Number 947 as disclosed in Table 5. In certain embodiments, such nucleic acid sequences are selected from those nucleic acid sequences that are disclosed in Table 5 and compliments thereof.

In certain embodiments, isolated nucleic acid sequences are provided that encode the inventive antibodies and antigen-binding fragments thereof, wherein such nucleic acid sequences comprise sequences that encode the CDRH2 amino acid sequences of the antibodies designated Antibody Number 1 through Antibody Number 947 as disclosed in Table 5. In certain embodiments, such nucleic acid sequences are selected from those nucleic acid sequences that are disclosed in Table 5 and compliments thereof.

In certain embodiments, isolated nucleic acid sequences are provided that encode the inventive antibodies and antigen-binding fragments thereof, wherein such nucleic acid sequences comprise sequences that encode the CDRH1 amino acid sequences of the antibodies designated Antibody Number 1 through Antibody Number 947 as disclosed in Table 5. In certain embodiments, such nucleic acid sequences are selected from those nucleic acid sequences that are disclosed in Table 5 and compliments thereof.

In certain embodiments, isolated nucleic acid sequences are provided that encode the inventive antibodies and antigen-binding fragments thereof, wherein such nucleic acid sequences comprise sequences that encode the CDRL3 amino acid sequences of the antibodies designated Antibody Number 1 through Antibody Number 947 as disclosed in Table 5. In certain embodiments, such nucleic acid sequences are selected from those nucleic acid sequences that are disclosed in Table 5 and compliments thereof.

In certain embodiments, isolated nucleic acid sequences are provided that encode the inventive antibodies and antigen-binding fragments thereof, wherein such nucleic acid sequences comprise sequences that encode the CDRL2 amino acid sequences of the antibodies designated Antibody Number 1 through Antibody Number 947 as disclosed in Table 5. In certain embodiments, such nucleic acid sequences are selected from those nucleic acid sequences that are disclosed in Table 5 and compliments thereof.

In certain embodiments, isolated nucleic acid sequences are provided that encode the inventive antibodies and antigen-binding fragments thereof, wherein such nucleic acid sequences comprise sequences that encode the CDRL1 amino acid sequences of the antibodies designated Antibody Number 1 through Antibody Number 947 as disclosed in Table 5. In certain embodiments, such nucleic acid sequences are selected from those nucleic acid sequences that are disclosed in Table 5 and compliments thereof.

In certain embodiments, isolated nucleic acid sequences are provided that encode the inventive antibodies and antigen-binding fragments thereof, wherein such nucleic acid sequences comprise sequences that encode the heavy chain (HC) amino acid sequences of the antibodies designated Antibody Number 1 through Antibody Number 947 as disclosed in Table 5. In certain embodiments, such nucleic acid sequences are selected from those nucleic acid sequences that are disclosed in Table 5 and compliments thereof.

In certain embodiments, isolated nucleic acid sequences are provided that encode the inventive antibodies and antigen-binding fragments thereof, wherein such nucleic acid sequences comprise sequences that encode the light chain (LC) amino acid sequences of the antibodies designated Antibody Number 1 through Antibody Number 947 as disclosed in Table 5. In certain embodiments, such nucleic acid sequences are selected from those nucleic acid sequences that are disclosed in Table 5 and compliments thereof.

In certain embodiments, isolated nucleic acid sequences are provided that encode the inventive antibodies and antigen-binding fragments thereof, wherein such nucleic acid sequences comprise sequences that are each selected from the group consisting of sequences that are at least 70% identical; at least 75% identical; 80% identical; at least 85% identical; at least 90% identical; at least 95% identical; at least 96% identical; at least 97% identical; at least 98% identical; at least 99%; and/or all percentages of identity in between; to any one of the nucleic acid sequences that are disclosed in Table 5 and compliments thereof.

In certain embodiments, isolated nucleic acid sequences are provided that encode the inventive antibodies and antigen-binding fragments thereof, wherein such nucleic acid sequences comprise sequences selected from the nucleic acid sequences that are disclosed in Table 5 and compliments thereof.

In certain embodiments, expression vectors are provided comprising the isolated nucleic acid sequences disclosed herein. In some embodiments, a single expression vector comprises the isolated nucleic acid sequences (e.g., $V_H$ and $V_L$ or HC and LC, are contained in the same vector). In this case, host cells are transfected, transformed, or transduced with a single expression vector. However, in other embodiments, more than one expression vector comprises the isolated nucleic acid sequences (e.g., Vu and $V_L$, or HC and LC, are each contained in a different vector). In this case, host cells are transfected, transformed, or transduced with more than one expression vector.

Host cells transfected, transformed, or transduced with the nucleic acid sequences and/or the expression vectors themselves are also encompassed by the subject invention.
Epitope Mapping and Related Technologies As described above and as demonstrated in the EXAMPLES, Applicant has characterized inter alia the epitope binding of the inventive antibodies and antigen-binding fragments thereof. In addition to the methods utilized by Applicant, various other techniques are available to the skilled artisan that can be used to carry out such characterization or to otherwise ascertain whether an antibody "interacts with one or more amino acids" within a polypeptide or protein. Exemplary techniques include, for example, a routine cross-blocking assay such as that described Antibodies, Harlow and Lane (Cold Spring Harbor Press, Cold Spring Harb., NY) can be performed. Other methods include alanine scanning mutational analysis, peptide blot analysis (Reincke (2004) Methods Mol Biol 248: 443-63), peptide cleavage analysis crystallographic studies and NMR analysis. In addition, methods such as epitope excision, epitope extraction and chemical modification of antigens can be employed (Tomer (2000) Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues that correspond to the specific amino acids with which the antibody interacts. See, e.g., Ehring (1999) Analytical Biochemistry 267 (2): 252-259; Engen and Smith (2001) Anal. Chem. 73: 256A-265A.

As the artisan will understand, an epitope can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or $8^{-10}$ amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see, e.g., US 2004/0101920). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

As the artisan understands, one can easily determine whether an antibody binds to the same epitope as, or competes for binding with, a reference anti-RSV F antibody by using routine methods available in the art. For example, to determine if a test antibody binds to the same epitope as a reference RSV F antibody of the invention, the reference antibody is allowed to bind to a RSV F protein or peptide under saturating conditions. Next, the ability of a test antibody to bind to the RSV F molecule is assessed. If the test antibody is able to bind to RSV F following saturation binding with the reference anti-RSV F antibody, it can be concluded that the test antibody binds to a different epitope than the reference anti-RSV F antibody. On the other hand, if the test antibody is not able to bind to the RSV F molecule following saturation binding with the reference anti-RSV F antibody, then the test antibody may bind to the same epitope as the epitope bound by the reference anti-RSV F antibody of the invention.

To determine if an antibody competes for binding with a reference anti-RSV F antibody, the above-described binding methodology is performed in two orientations. In a first orientation, the reference antibody is allowed to bind to a RSV F molecule under saturating conditions followed by assessment of binding of the test antibody to the RSV F molecule. In a second orientation, the test antibody is allowed to bind to a RSV F molecule under saturating conditions followed by assessment of binding of the reference antibody to the RSV F molecule. If, in both orientations, only the first (saturating) antibody is capable of binding to the RSV F molecule, then it is concluded that the test antibody and the reference antibody compete for binding to RSV F. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20-, or 100-fold excess of one antibody inhibits binding of the other by at least 50% but preferably 75%, 90% or even 99% as measured in a competitive binding assay (see, e.g., Junghans et al., Cancer Res. (1990) 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a RSV F antibody conjugated to a therapeutic moiety ("immunoconjugate"), such as an agent that is capable of reducing the severity of primary infection with RSV, or ameliorating at least one symptom associated with RSV infection, including coughing, fever, pneumonia, or the severity thereof. Such an agent may be a second different antibody to RSVF or a vaccine. The type of therapeutic moiety that may be conjugated to the anti-RSV F antibody and will take into account the condition to be treated and the desired therapeutic effect to be achieved. Alternatively, if the desired therapeutic effect is to treat the sequelae or symptoms associated with RSV infection, or any other condition resulting from such infection, such as, but not limited to, pneumonia, it may be advantageous to conjugate an agent appropriate to treat the sequelae or symptoms of the condition, or to alleviate any side effects of the antibodies of the invention. Examples of suitable agents for forming immunoconjugates are known in the art, see for example, WO 05/103081.

Multi-Specific Antibodies

The antibodies of the present invention may be mono-specific, bi-specific, or multi-specific. Multi-specific antibodies may be specific for different epitopes of one target polypeptide or may contain antigen-binding domains specific for more than one target polypeptide. Sec, e.g., Tutt ct al., 1991, J. Immunol. 147:60-69; Kufer et al., 2004, Trends Biotechnol. 22:238-244. As discussed above, the antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multi-specific antibody with a second binding specificity.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second Cus include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Therapeutic Administration and Formulations

The invention provides therapeutic compositions comprising the inventive anti-RSV F antibodies or antigen-binding fragments thereof. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of each of the antibodies of the invention may vary depending upon the age and the size of a subject to be administered, target disease, conditions, route of administration, and the like. When the antibodies of the present invention are used for treating a RSV infection in a patient, or for treating one or more symptoms associated with a RSV infection infection, such as the cough or pneumonia associated with a RSV infection in a patient, or for lessening the severity of the disease, it is advantageous to administer each of the antibodies of the present invention intravenously or subcutaneously normally at a single dose of about 0.01 to about 30 mg/kg body weight, more preferably about 0.1 to about 20 mg/kg body weight, or about 0.1 to about 15 mg/kg body weight, or about 0.02 to about 7 mg/kg body weight, about 0.03 to about 5 mg/kg body weight, or about 0.05 to about 3 mg/kg body weight, or about 1 mg/kg body weight, or about 3.0 mg/kg body weight, or about 10 mg/kg body weight, or about 20 mg/kg body weight. Multiple doses may be administered as necessary. Depending on the severity of the condition, the frequency and the duration of the treatment can be adjusted. In certain embodiments, the antibodies or antigen-binding fragments thereof of the invention can be administered as an initial dose of at least about 0.1 mg to about 800 mg, about 1 to about 600 mg, about 5 to about 300 mg, or about 10 to about 150 mg, to about 100 mg, or to about 50 mg. In certain embodiments, the initial dose may be followed by administration of a second or a plurality of subsequent doses of the antibodies or antigen-binding fragments thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings {e.g., oral mucosa, nasal mucosa, rectal and intestinal mucosa, etc.) and may be administered together with other biologically active agents. Administration can be systemic or local. It may be delivered as an aerosolized formulation (See U.S. Publication No. 2011/0311515 and U.S. Publication No. 2012/0128669). The delivery of agents useful for treating respiratory diseases by inhalation is becoming more widely accepted (See A. J. Bitonti and J. A. Dumont, (2006), Adv. Drug Deliv. Rev, 58:1 106-1 1 18). In addition to being effective at treating local pulmonary disease, such a delivery mechanism may also be useful for systemic delivery of antibodies (See Maillet et al. (2008), Pharmaceutical Research, Vol. 25, No. 6, 2008).

The pharmaceutical composition can be also delivered in a vesicle, in particular a liposome (see, for example, Langer (1990) Science 249:1527-1533).

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousands Oaks, CA), the PENLET™ (Haselmeier, Stuttgart, Germany), the EPIPEN (Dey, L. P.) and the HUMIRA™ Pen (Abbott Labs, Abbott Park, IL), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Administration Regimens

According to certain embodiments, multiple doses of an antibody to RSV F may be administered to a subject over a defined time course. The methods according to this aspect of the invention comprise sequentially administering to a subject multiple doses of an antibody to RSV F. As used herein, "sequentially administering" means that each dose of antibody to RSV F is administered to the subject at a different point in time, e.g., on different days separated by a predetermined interval (e.g., hours, days, weeks or months). The present invention includes methods which comprise sequentially administering to the patient a single initial dose of an antibody to RSV F, followed by one or more secondary doses of the antibody to RSV F and, optionally, followed by one or more tertiary doses of the antibody to RSV F.

The terms "initial dose," "secondary doses," and "tertiary doses," refer to the temporal sequence of administration of the antibody to RSV F. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of antibody to RSV F, but generally may differ from one another in terms of frequency of administration. In certain embodiments, however, the amount of antibody to RSV F contained in the initial, secondary and/or tertiary doses vary from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means that in a sequence of multiple administrations, the dose of antibody to RSV F, which is administered to a patient prior to the administration of the very next dose in the sequence with no intervening doses.

The methods according to this aspect of the invention may comprise administering to a patient any number of secondary and/or tertiary doses of an antibody to RSV F. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Accordingly, in certain embodiments are provided pharmaceutical compositions comprising: one or more of the inventive antibodies or antigen-binding fragments thereof disclosed herein and throughout and a pharmaceutically acceptable carrier and/or one or more excipients. In certain other embodiments are provided pharmaceutical compositions comprising: one or more nucleic acid sequences encoding one or more inventive antibodies or antigen-binding fragments thereof; or one or more the expression vectors harbouring such nucleic acid sequences; and a pharmaceutically acceptable carrier and/or one or more excipients.

Therapeutic Uses of the Antibodies

Due to their binding to and interaction with RSV F, it is believed that the inventive antibodies and antigen-binding fragments thereof are useful for preventing fusion of the virus with the host cell membrane, preventing cell to cell virus spread, and/or inhibiting syncytia formation. Additionally, a subset of the inventive anti-RSV antibodies and antigen-binding fragments thereof display specificity for RSV (i.e., epitopic specificity) that is unique from the specificity of adult anti-RSV antibodies. Therefore, the inventive antibodies and antigen-binding fragments thereof may be advantageous for preventing and/or treating an RSV infection in an infant. As such, the antibodies of the invention are contemplated for prophylactic use in infant, particularly pre-term infants and full-term infants born during RSV season (late fall to early spring). It is contemplated that the antibodies of the invention may be used alone, or in conjunction with one or more additional agents, for treating or preventing RSV infection or at least one symptom or complication associated with RSV infection. The second or third agents may be delivered concurrently with or separately (before or after) from the antibodies of the invention. The one or more additional agents may be an anti-viral (e.g., ribavirin), an NSAID or other agents to reduce fever or pain, another antibody that specifically binds RSV-F, an agent (e.g. an antibody) that binds to another RSV antigen (e.g., RSV G), a vaccine against RSV, and/or an siRNA specific for an RSV antigen.

In yet a further embodiment of the invention, the present antibodies are used for the preparation of a pharmaceutical composition for treating patients suffering from a RSV infection. The pharmaceutical composition can reduce the severity of a primary infection with RSV, reduce the duration of the infection, and/or reduce at least one symptom associated with the RSV infection. In a further embodiment, the anti-RSV F antibodies disclosed herein are used as adjunct therapy with any other agent useful for treating an RSV infection, including an antiviral, a toxoid, a vaccine, a second RSV-F antibody, or another antibody specific for an RSV antigen, including an RSV-G antibody, or any other palliative therapy known to those skilled in the art.

Accordingly, the disclosure provides methods of treating or preventing RSV infection, or at least one symptom associated with RSV infection, comprising administering to a patient in need thereof (or suspected of being in need thereof) one or more of the inventive antibodies or antigen-binding fragments thereof, e.g., one or more of the anti-RSV F antibodies disclosed in Table 5, such that the RSV infection is treated or prevented, or the at least on symptom associated with RSV infection is treated, alleviated, or reduced in severity.

Other embodiments provide methods of treating or preventing a RSV infection, or at least one symptom associated with RSV infection, comprising administering to a patient in need thereof (or suspected of being in need thereof) a nucleic acid sequence encoding one or more of the inventive antibodies or antigen-binding fragments thereof, such nucleic acid sequenced disclosed in Table 5 and compliments thereof, such that the RSV infection is treated or prevented, or the at least on symptom associated with RSV infection is treated, alleviated, or reduced in severity.

Additional embodiments provide methods of treating or preventing a RSV infection, or at least one symptom associated with RSV infection, comprising administering to a patient in need thereof (or suspected of being in need thereof) a host cell harboring a nucleic acid sequence or an expression vector comprising such a nucleic acid sequence, wherein such nucleic acid sequences is selected from the group consisting of sequences disclosed in Table 5 and compliments thereof, such that the RSV infection is treated or prevented, or the at least one symptom associated with RSV infection is treated, alleviated, or reduced in severity.

Further embodiments provide methods of treating or preventing a RSV infection, or at least one symptom associated with RSV infection, comprising administering to a patient in need thereof (or suspected of being in need thereof) a pharmaceutical composition comprising one or more of the inventive antibodies or antigen-binding fragments thereof as disclosed in Table 5, or one or more nucleic acid sequences or an expression vectors comprising such a nucleic acid sequence, wherein such nucleic acid sequences are selected from the group consisting of sequences disclosed in Table 5 and compliments thereof; one or more host cells harboring one or more nucleic acid sequences or an expression vectors comprising such one or more nucleic acid sequences, wherein such nucleic acid sequences are selected from the group consisting of sequences disclosed in Table 5 and compliments thereof; and a pharmaceutically acceptable carrier and/or one or more excipients, such that the RSV infection is treated or prevented, or the at least on symptom associated with RSV infection is treated, alleviated, or reduced in severity.

The anti-RSV F antibodies disclosed herein may also be suitable for therapeutic and/or prophylactic use in non-humans, e.g., cattle, swine, sheep, or poultry.

Combination Therapies

As noted above, according to certain embodiments, the disclosed methods comprise administering to the subject one or more additional therapeutic agents in combination with an antibody to RSV F. As used herein, the expression "in combination with" means that the additional therapeutic agents are administered before, after, or concurrent with the pharmaceutical composition comprising the anti-RSV F antibody. The term "in combination with" also includes sequential or concomitant administration of the anti-RSV F antibody and a second therapeutic agent.

For example, when administered "before" the pharmaceutical composition comprising the anti-RSV F antibody, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the anti-RSV F antibody. When administered "after" the pharmaceutical composition comprising the anti-RSV-F antibody, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the anti-RSV F antibodies. Administration "concurrent" or with the pharmaceutical composition comprising the anti-RSV F antibody means that the additional therapeutic agent is administered to the subject in a separate dosage form within less than 5 minutes (before, after, or at the same time) of administration of the pharmaceutical composition comprising the anti-RSV F antibody, or administered to the subject as a single combined dosage formulation comprising both the additional therapeutic agent and the anti-RSV F antibody.

Combination therapies may include an anti-RSV F antibody of the invention and any additional therapeutic agent that may be advantageously combined with an antibody of the invention, or with a biologically active fragment of an antibody of the invention.

For example, a second or third therapeutic agent may be employed to aid in reducing the viral load in the lungs, such as an antiviral, for example, ribavirin. The antibodies may also be used in conjunction with other therapies, as noted above, including a toxoid, a vaccine specific for RSV, a second antibody specific for RSV F, or an antibody specific for another RSV antigen, such as RSVG.

Diagnostic Uses of the Antibodies

The inventive anti-RSV antibodies and antigen-binding fragments thereof may also be used to detect and/or measure RSV in a sample, e.g., for diagnostic purposes. It is envisioned that confirmation of an infection thought to be caused by RSV may be made by measuring the presence of the virus through use of any one or more of the antibodies of the invention. Exemplary diagnostic assays for RSV may comprise, e.g., contacting a sample, obtained from a patient, with an anti-RSV F antibody of the invention, wherein the anti-RSV F antibody is labeled with a detectable label or reporter molecule or used as a capture ligand to selectively isolate the virus containing the F protein from patient samples. Alternatively, an unlabeled anti-RSV F antibody can be used in diagnostic applications in combination with a secondary antibody which is itself detectably labeled. The detectable label or reporter molecule can be a radioisotope, such as 3H, 14C, 32p, 35S, or 125I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure RSV containing the F protein in a sample include enzyme-linked immunosorbent assay (ELISA), radioimmunoassay (RIA), and fluorescence-activated cell sorting (FACS).

Samples that can be used in RSV diagnostic assays according to the present invention include any tissue or fluid sample obtainable from a patient, which contains detectable quantities of RSV F protein, or fragments thereof, under normal or pathological conditions. Generally, levels of RSV F in a particular sample obtained from a healthy patient (e.g., a patient not afflicted with a disease or condition associated with the presence of RSV F) will be measured to initially establish a baseline, or standard, level of the F protein from RSV. This baseline level of RSV F can then be compared against the levels of RSV F measured in samples obtained from individuals suspected of having an RSV infection or symptoms associated with such infection.

EXAMPLES

Example 1. Isolation and Characterization of Anti-RSV F-Specific Human Infant Antibodies from Memory B Cells Applicant has comprehensively profiled the human infant antibody response to RSV F by isolating and characterizing over 450 RSV F-specific monoclonal antibodies from the memory B cells of RSV-infected infants, and used these antibodies to characterize the infant antibody response as well as develop a framework for the rational design of age-specific RSV vaccines. The antibody responses were highly biased, with half of the antibodies recognizing only two antigenic sites. Antibodies targeting both sites showed convergent sequence features, the molecular determinants of which were revealed by X-ray crystallographic studies. A subset of antibodies targeting one of the sites displayed potent neutralizing activity despite lacking somatic mutations, suggesting suitably designed vaccines may be used to induce such antibodies in young infants.

RSV F-Specific Antibodies Isolated from Young Infants have Low Levels of SHM and Biased $V_H$ and VL Germline Gene Usage To analyze infant B cell responses to RSV F, blood samples from seven infants that were hospitalized due to complications associated with RSV infection were obtained. Of the seven infants, five were less than three months (<3 mo.) and two were at least six months (≥6 mo.) of age at the time of hospitalization (Table 1). Blood was drawn from seven infants hospitalized with bronchiolitis and confirmed RSV infection.

TABLE 1

| | | | | | | | |
|---|---|---|---|---|---|---|---|
| ID | Estimated gestational age (weeks) | Birth weight (kg) | Hospital stay (days) | Intensity of care[a] | Intubation | Age at admission (months) | Age at blood draw (months) |
| 2308 | 39 | 3.29 | 5 | R | N | 0.35 | 1.35 |
| 2026 | 37 | 2.41 | 7 | I | N | 0.96 | 2.75 |
| 2301 | 40 | 4.5 | 4 | R | CPAP | 1.48 | 3.00 |
| 2021 | 33 | 2.21 | 15 | I | N | 1.61 | 4.46 |
| 2201 | 39 | 4.39 | 3 | I | N | 2.54 | 12.35 |
| 856 | 32.5 | 2.07 | 3 | I | N | 6.00 | 10.61 |
| 2042 | 38 | 3.29 | 1 | I | Y | 26.64 | 29.57 |

[a]R, routine; I, intensive, all patients were administered $O_2$.

Figure 1B:
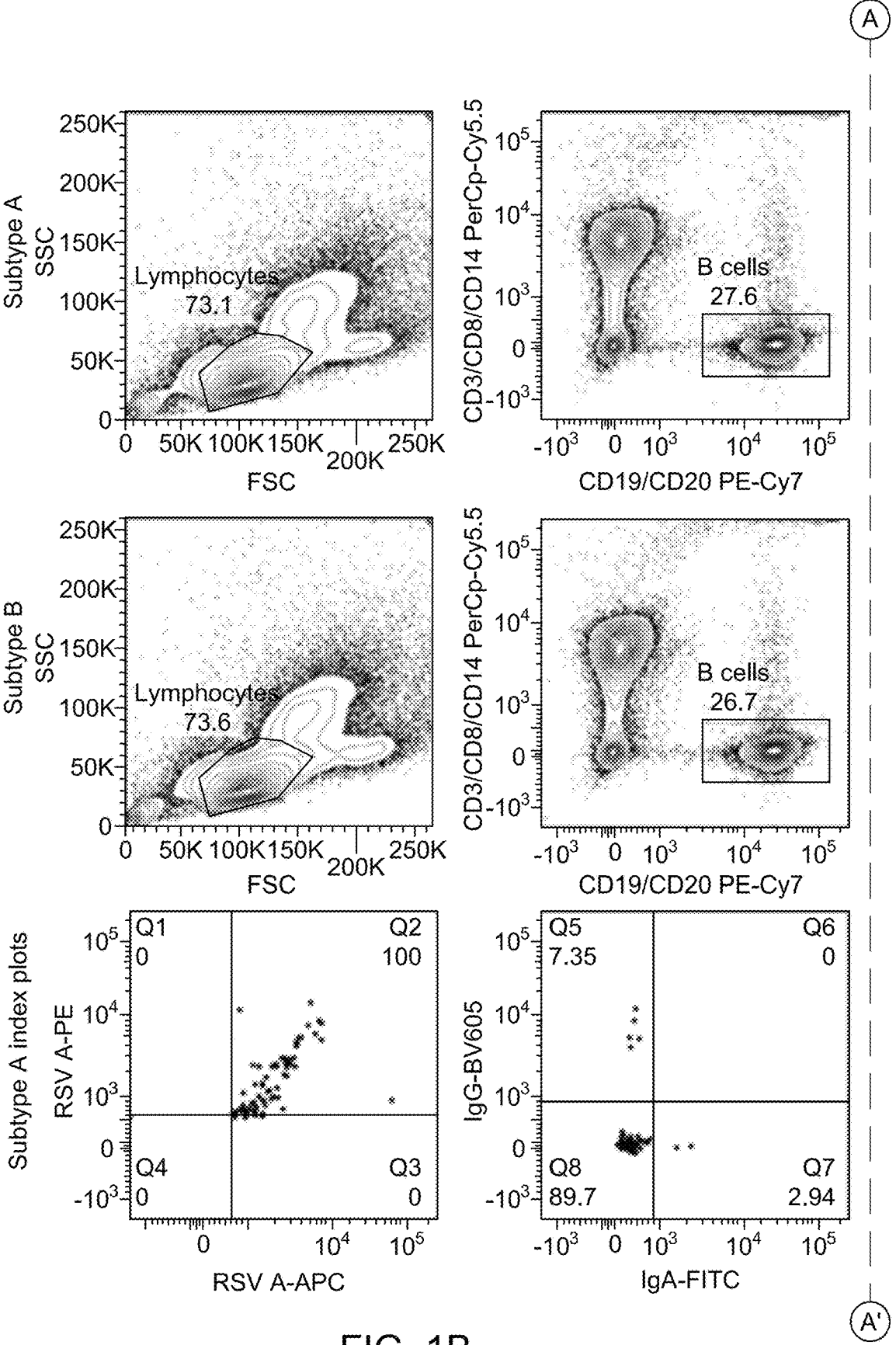
Figure 1B:
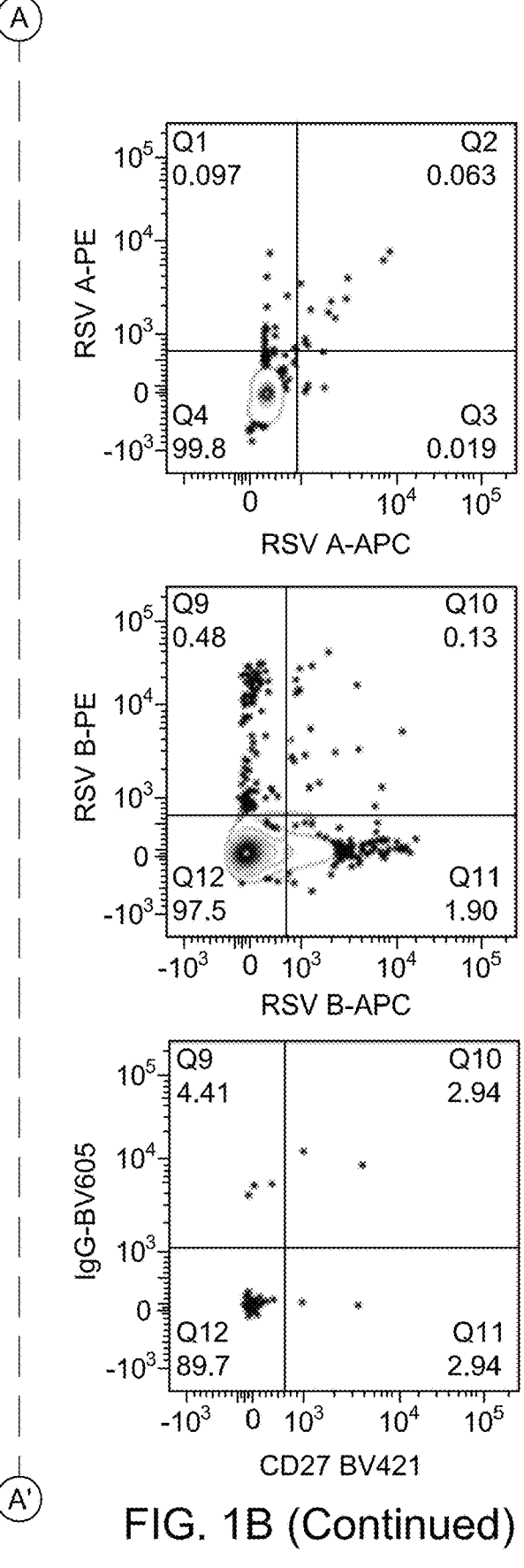
Figure 1C:
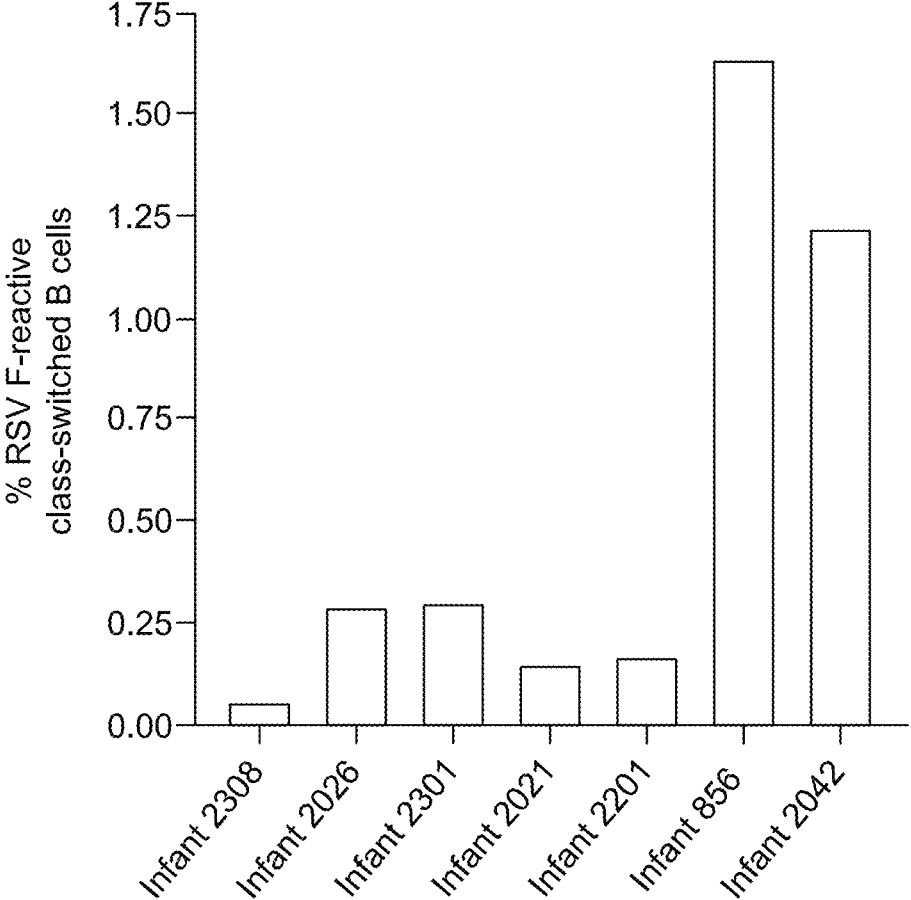
Figures 2A, 2B, 2C:
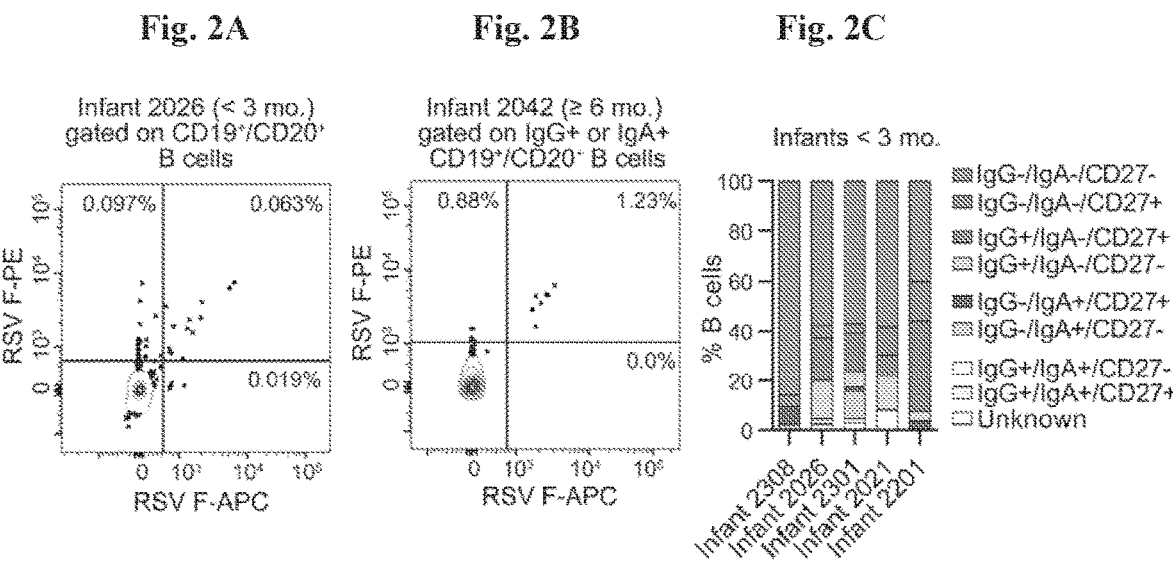
FIGS. 2A-2E show that anti-RSV F antibodies isolated from infant B cells display limited somatic hypermutation (SHM) and biased $V_H$ and $V_L$ gene usage. A representative flow plot is shown for the RSV F-specific B cell response in an infant<3 months of age (FIG. 2A) and an infant>6 months of age (FIG. 2B). Prior to sorting on double positive staining with dual labeled RSV F probes, the plot was gated on CD3$^+$ CD19$^+$ CD20$^+$ B cells (FIG. 1A) or CD3$^+$ CD19$^+$ CD20$^+$ IgG/IgA$^+$ B cells (FIG. 2B). RSV F-specific B cells are in the upper right quadrant of the plots.

Six out of the seven infants were infected during the first RSV season of their life and were therefore likely experiencing a primary infection. The remaining donor, who was 29.5 months old at the time of blood draw, was also likely experiencing a primary infection because secondary RSV infections generally do not result in hospitalization (Glezen et al., 1986). To assess the magnitude of the B cell response to RSV F, peripheral blood mononuclear cells (PBMCs) were stained with fluorescently labeled tetramers of preF and postF trimers and analyzed by flow cytometry (FIGS. 1A and 1B). The frequency of class-switched B cells that were RSV F-specific was substantially lower in infants<3 mo. compared with infants≥6 mo. (FIG. 1C). In infants<3 mo., the frequency of RSV F-specific class-switched B cells ranged from 0.05-0.3%, whereas in infants≥6 mo. the frequency ranged from 1.2-1.6%. To dissect the RSV F-specific B cell response, between 100 and 300 RSV F-reactive B cells from each donor were single-cell sorted and the antibody variable heavy (VH)- and variable light (VL)-chain sequences were rescued by single-cell PCR (Tiller et al., 2008). Due to the low frequency of RSV F-specific class-switched B cells in the five younger infants, all B cells that reacted with RSV F were single-cell sorted (FIG. 2A). For the two infants that were >6 mo., only class-switched B cells were sorted (FIG. 2B). Although all B cells that reacted with RSV F were sorted from infants<3 mo., index sorting was performed in order to analyze the B cell surface markers expressed on each sorted cell. This analysis revealed that 14-60% of the RSV F-specific B cells sorted from infants<3 mo. were class-switched and/or CD27+, with the remaining B cells lacking classical memory markers (FIG. 2C), suggesting that RSV infection induces more robust B cell responses in infants≥6 mo. compared with infants<3 mo.

Figures 2D, 2E:
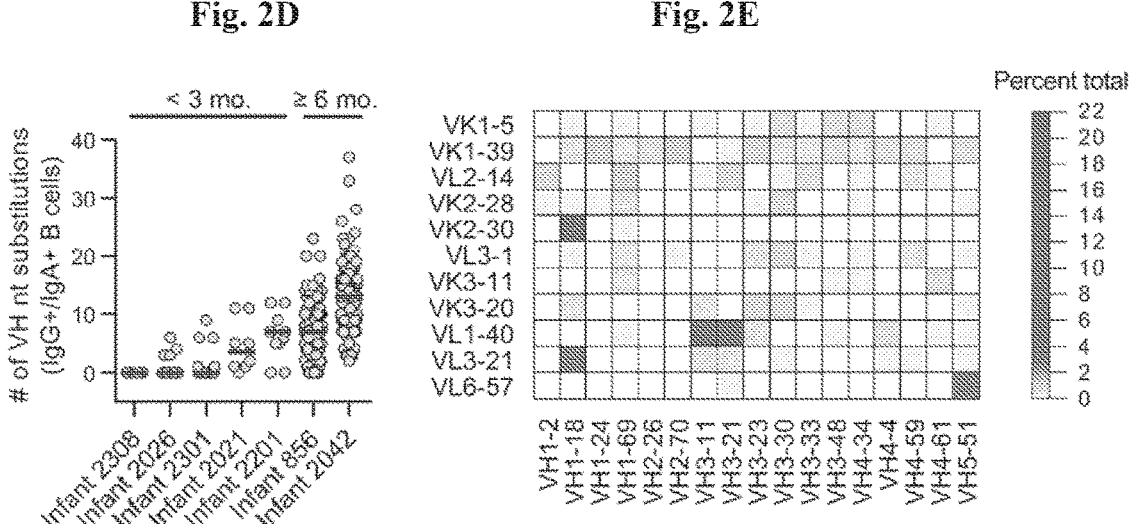
Figures 4A, 4B, 4C:
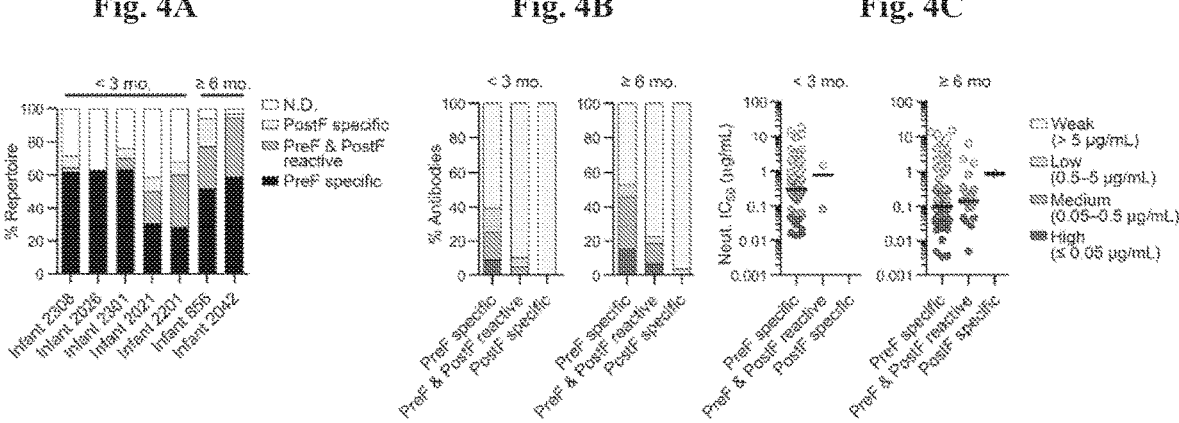
FIGS. 4A-4C show that RSV-neutralizing, F-conformation-independent antibodies are rare in young infants. The percentage of antibodies that are preF-specific (black), preF- and postF-reactive (grey), or postF-specific (light grey) is shown for each infant (FIG. 4A). N.D., not-determined (white). Infants are ordered from youngest to oldest, left to right. The percentage of antibodies with high, medium, low, or weak neutralization potency is plotted for each group in infants<3 mo. (left panel) and ≥6 mo. (right panel) (FIG. 4B). Neutralization $IC_{50}$s are shown for antibodies in each group that displayed measurable neutralization activity (FIG. 4C). Black bars indicate medians.

In total, over 450 cognate VH and VL pairs were cloned and expressed as full-length IgGs in an engineered strain of *Saccharomyces cerevisiae* (Bornholdt et al., 2016; Swers et al., 2004). As expected, sequence analysis showed that the median level of SHM in class-switched B cells increased as a function of age (FIG. 2D). Also, the majority of antibodies isolated from infants<3 mo. lacked SHM, similar to what was observed previously in postF-reactive B cells (Williams et al., 2009). However, nearly 5% of antibodies isolated from these infants had VH genes containing at least five nucleotide substitutions, consistent with previous studies showing that SHM does occur in young infants, albeit at relatively low frequency (Rechavi et al., 2015; Ridings et al., 1998). The level of SHM in antibodies isolated from the two infants≥6 mo. was relatively high, with a median of 7 and 13 $V_H$ nucleotide substitutions resulting in a median of 6 and 11 amino acid substitutions, respectively (FIG. 2D). Analysis of VH and VL germline gene usage showed that RSV F-reactive infant antibody responses were strongly biased toward either VH3-21/VL1-40 or the highly related VH3-11/VL1-40 gene pairing (FIG. 2E). There was also a more modest preference for the VH1-18/VK2-30, VH1-18/VL3-21, and VH5-51/VL6-57 gene pairs (FIG. 2E). The VH1-18/VK2-30 gene pair was present in 8.5% of RSV F-reactive antibodies isolated from adults and is associated with recognition of site V on profusion F (Gilman et al., 2016; Mousa et al., 2017). Overall, the results demonstrate that RSV infection induced B cell responses with higher levels of SHM in infants≥6 mo. compared to <3 mo., and that the responses in both age groups exhibit biased germline gene usage.

a Subset of Infant Antibodies Binds with High Affinity to RSV F and Potently Neutralizes RSV To further characterize the infant antibodies, the apparent binding affinity of each antibody for preF and postF was determined. For each of the infants<3 mo., 24-34% of the isolated antibodies bound to preF with an apparent affinity of ≤5 nM, compared with 45% and 91% for the two infants≥6 mo. (FIG. 3A). Although a total of 40 such antibodies were isolated from the youngest three infants, only two antibodies with ≤5 nM affinity for postF were isolated from the same three infants (FIG. 3B). In addition, for every infant the number of antibodies with ≤5 nM affinity for postF was lower than those with ≤5 nM affinity for preF (FIG. 3B). Consistent with this result, the percentage of preF-specific antibodies ranged from 28-63%, whereas substantially smaller percentages (2-17%) were postF-specific (FIG. 4A). Antibodies recognizing both preF and postF comprised about 19-36% of the antibody responses in the four oldest infants, but less than 10% of the response in the three youngest infants. Collectively, these results suggest that young infants generate a preF-biased antibody response that expands to include recognition of postF by six months of age.

Next, the antibodies were tested for neutralizing activity using ahigh-throughput assay. This analysis revealed that 12-49% of the antibodies isolated from each infant showed neutralizing activity, and a subset of antibodies isolated from six out of the seven infants showed highly potent neutralizing activity ($IC_{50}s<0.05$ µg/ml) (FIG. 3C). Interestingly, nearly 20% of the neutralizing antibodies lacked VH and VL gene mutations (Table 2), suggesting that extensive affinity maturation is not required for potent neutralization of RSV. The name, donor ID number, sequence information, binding affinity, neutralization $IC_{50}$, epitope and index sort information for each antibody is shown in the table.

TABLE 2

| | | Summary of antibody characteristics | | | | | |
|---|---|---|---|---|---|---|---|
| Name | Donor | Prefusion subtype A K$_d$ (M)* | Postfusion subtype A K$_d$ (M)* | Prefusion subtype B K$_d$ (M)* | Postfusion subtype B K$_d$ (M)* | Neut IC$_{50}$ (ug/ml) subtype A* | Neut IC$_{50}$ (ug/ml) subtype B* |
| ADI-25462 | Infant 2308 | 6.42E−10 | N.B. | 1.71E−09 | N.B. | 0.15 | 0.11 |
| ADI-25467 | Infant 2308 | N.B. | 2.53E−08 | N.B. | 2.62E−08 | N.N. | N.N. |
| ADI-25468 | Infant 2308 | 2.89E−08 | N.B. | N.B. | N.B. | N.N. | N.N. |
| ADI-25472 | Infant 2308 | 1.19E−08 | N.B. | 3.77E−08 | N.B. | N.N. | N.N. |
| ADI-25478 | Infant 2308 | 2.43E−09 | N.B. | 6.43E−09 | N.B. | 2.18 | 3.52 |
| ADI-25479 | Infant 2308 | 1.57E−09 | N.B. | 4.29E−09 | N.B. | 0.24 | 0.29 |
| ADI-25480 | Infant 2308 | 1.27E−09 | N.B. | 4.27E−09 | N.B. | 0.17 | 0.17 |
| ADI-25484 | Infant 2308 | 3.79E−09 | N.B. | 1.84E−08 | N.B. | 15.28 | 8.58 |
| ADI-25491 | Infant 2308 | 3.74E−08 | P.F. | 2.19E−08 | N.B. | N.N. | N.N. |
| ADI-25495 | Infant 2308 | 8.70E−10 | N.B. | 6.41E−09 | N.B. | 0.24 | 5.60 |
| ADI-25496 | Infant 2308 | 2.08E−08 | N.B. | N.B. | N.B. | N.N. | N.N. |
| ADI-25497 | Infant 2308 | 5.00E−08 | 1.84E−08 | 1.41E−08 | 1.48E−08 | N.N. | N.N. |
| ADI-25502 | Infant 2308 | 2.93E−08 | P.F. | N.B. | N.B. | N.N. | N.N. |
| ADI-25503 | Infant 2308 | 7.02E−09 | N.B. | N.B. | N.B. | N.N. | N.N. |
| ADI-25505 | Infant 2308 | P.F. | N.B. | N.B. | N.B. | N.N. | N.N. |
| ADI-25514 | Infant 2308 | 4.45E−09 | N.B. | N.B. | N.B. | N.N. | N.N. |
| ADI-25517 | Infant 2308 | N.B. | P.F. | N.B. | N.B. | N.N. | N.N. |
| ADI-25518 | Infant 2308 | 5.57E−08 | P.F. | 3.95E−08 | N.B. | N.N. | N.N. |
| ADI-25524 | Infant 2308 | 8.38E−09 | N.B. | 2.34E−08 | N.B. | 1.77 | 2.09 |
| ADI-25532 | Infant 2308 | 5.87E−10 | N.B. | 1.56E−09 | N.B. | 0.04 | 0.05 |
| ADI-25533 | Infant 2308 | N.B. | P.F. | N.B. | N.B. | N.N. | N.N. |
| ADI-25542 | Infant 2308 | 9.05E−09 | N.B. | N.B. | N.B. | N.N. | N.N. |
| ADI-25547 | Infant 2308 | N.B. | 2.15E−08 | 2.03E−08 | 2.31E−08 | N.N. | N.N. |
| ADI-25548 | Infant 2308 | 1.71E−08 | N.B. | N.B. | N.B. | N.N. | N.N. |
| ADI-25549 | Infant 2308 | 6.72E−09 | N.B. | 2.88E−08 | N.B. | 11.47 | 6.02 |
| ADI-25555 | Infant 2308 | 1.11E−08 | N.B. | 4.47E−08 | N.B. | 18.59 | 12.08 |
| ADI-25556 | Infant 2308 | 1.19E−08 | N.B. | 4.20E−08 | N.B. | N.N. | N.N. |
| ADI-25557 | Infant 2308 | 8.29E−09 | N.B. | 3.33E−08 | N.B. | N.N. | N.N. |
| ADI-25559 | Infant 2308 | 1.27E−08 | N.B. | 3.33E−08 | N.B. | N.N. | N.N. |
| ADI-25562 | Infant 2308 | 1.69E−09 | N.B. | 3.32E−09 | N.B. | 1.18 | 1.14 |
| ADI-25565 | Infant 2308 | 1.54E−08 | N.B. | 3.57E−08 | N.B. | N.N. | N.N. |
| ADI-25567 | Infant 2308 | 2.40E−08 | N.B. | 3.83E−09 | N.B. | 0.33 | 1.94 |
| ADI-25569 | Infant 2308 | N.B. | P.F. | P.F. | P.F. | N.N. | N.N. |
| ADI-25572 | Infant 2308 | N.B. | N.B. | P.F. | P.F. | N.N. | N.N. |
| ADI-25573 | Infant 2308 | N.B. | N.B. | N.B. | 4.86E−08 | N.N. | N.N. |
| ADI-25575 | Infant 2308 | N.B. | N.B. | N.B. | 3.96E−08 | 5.64 | N.N. |
| ADI-25576 | Infant 2308 | N.B. | N.B. | N.B. | 2.39E−08 | N.N. | N.N. |
| ADI-25577 | Infant 2308 | 1.40E−08 | N.B. | 4.42E−08 | N.B. | N.N. | N.N. |
| ADI-25587 | Infant 2308 | N.B. | 9.23E−09 | N.B. | 7.93E−09 | N.N. | N.N. |
| ADI-25588 | Infant 2308 | 1.73E−08 | N.B. | N.B. | N.B. | N.N. | N.N. |
| ADI-25595 | Infant 2308 | 1.27E−08 | N.B. | N.B. | N.B. | N.N. | N.N. |
| ADI-25598 | Infant 2308 | N.B. | N.B. | N.B. | P.F. | N.N. | N.N. |
| ADI-19420 | Infant 2026 | 5.70E−10 | N.B. | 2.47E−09 | N.B. | 0.55 | 0.64 |
| ADI-19421 | Infant 2026 | 7.22E−09 | N.B. | 5.42E−09 | N.B. | 10.00 | 3.30 |
| ADI-19422 | Infant 2026 | 2.23E−09 | N.B. | 1.08E−08 | N.B. | 0.73 | 1.90 |
| ADI-19424 | Infant 2026 | 1.07E−09 | N.B. | 1.71E−09 | N.B. | 0.08 | 0.21 |
| ADI-19425 | Infant 2026 | 4.56E−10 | N.B. | 1.37E−09 | N.B. | 0.02 | 0.04 |
| ADI-19426 | Infant 2026 | 2.87E−09 | N.B. | 1.29E−08 | N.B. | N.N. | N.N. |
| ADI-19427 | Infant 2026 | 2.78E−10 | N.B. | 5.00E−10 | N.B. | 0.01 | 0.03 |
| ADI-19428 | Infant 2026 | 4.96E−09 | N.B. | 1.67E−08 | N.B. | 3.25 | N.N. |
| ADI-19429 | Infant 2026 | 1.23E−08 | N.B. | N.B. | N.B. | N.N. | N.N. |
| ADI-19430 | Infant 2026 | 5.02E−09 | N.B. | 1.68E−08 | N.B. | N.N. | N.N. |
| ADI-19431 | Infant 2026 | 8.18E−09 | N.B. | 3.16E−09 | N.B. | 4.35 | 0.17 |
| ADI-19432 | Infant 2026 | P.F. | N.B. | N.B. | N.B. | 10.98 | N.N. |
| ADI-19433 | Infant 2026 | 3.60E−09 | N.B. | N.B. | N.B. | 1.56 | N.N. |
| ADI-19435 | Infant 2026 | N.B. | N.B. | N.B. | N.B. | N.N. | N.N. |
| ADI-19436 | Infant 2026 | N.B. | N.B. | N.B. | N.B. | N.N. | N.N. |
| ADI-19437 | Infant 2026 | N.B. | P.F. | N.B. | N.B. | N.N. | N.N. |
| ADI-19439 | Infant 2026 | N.B. | N.B. | N.B. | N.B. | N.N. | N.N. |
| ADI-19440 | Infant 2026 | 5.41E−09 | N.B. | 1.43E−08 | N.B. | N.N. | N.N. |
| ADI-19441 | Infant 2026 | N.B. | N.B. | N.B. | N.B. | N.N. | N.N. |
| ADI-19444 | Infant 2026 | N.B. | N.B. | N.B. | N.B. | N.N. | N.N. |
| ADI-19445 | Infant 2026 | N.B. | N.B. | N.B. | P.F. | N.N. | N.N. |
| ADI-19447 | Infant 2026 | P.F. | N.B. | N.B. | N.B. | N.N. | N.N. |
| ADI-19448 | Infant 2026 | 6.08E−09 | N.B. | 5.58E−09 | N.B. | 9.64 | N.N. |
| ADI-19449 | Infant 2026 | 1.48E−08 | N.B. | 2.60E−08 | N.B. | N.N. | N.N. |
| ADI-19450 | Infant 2026 | N.B. | N.B. | 3.86E−08 | N.B. | N.N. | N.N. |
| ADI-19454 | Infant 2026 | 2.52E−09 | N.B. | 1.57E−08 | N.B. | N.N. | N.N. |
| ADI-19455 | Infant 2026 | 1.80E−08 | N.B. | N.B. | N.B. | N.N. | N.N. |
| ADI-19457 | Infant 2026 | 8.29E−09 | N.B. | 1.67E−08 | N.B. | N.N. | N.N. |
| ADI-19458 | Infant 2026 | 2.15E−10 | N.B. | 2.43E−10 | N.B. | 0.04 | 0.07 |
| ADI-19459 | Infant 2026 | 1.09E−09 | N.B. | 1.45E−09 | N.B. | 0.05 | 0.10 |
| ADI-19460 | Infant 2026 | 7.50E−09 | N.B. | 6.01E−09 | N.B. | N.N. | N.N. |
| ADI-19461 | Infant 2026 | N.B. | N.B. | P.F. | N.B. | N.N. | N.N. |

TABLE 2-continued

| | | | | | | | Summary of antibody characteristics | |
|---|---|---|---|---|---|---|
| ADI-19462 | Infant 2026 | N.B. | P.F. | N.B. | N.B. | N.N. | N.N. |
| ADI-19463 | Infant 2026 | N.B. | N.B. | N.B. | N.B. | N.N. | N.N. |
| ADI-19465 | Infant 2026 | 2.74E−09 | N.B. | 1.94E−08 | N.B. | N.N. | N.N. |
| ADI-19506 | Infant 2026 | N.B. | N.B. | N.B. | N.B. | N.N. | N.N. |
| ADI-19507 | Infant 2026 | 1.09E−08 | N.B. | 1.01E−08 | N.B. | N.N. | N.N. |
| ADI-19509 | Infant 2026 | 9.33E−09 | N.B. | 1.58E−09 | N.B. | 3.42 | 1.56 |
| ADI-19510 | Infant 2026 | 2.38E−10 | N.B. | 2.39E−10 | N.B. | 0.16 | 0.83 |
| ADI-19511 | Infant 2026 | N.B. | N.B. | N.B. | 1.53E−08 | N.N. | N.N. |
| ADI-24792 | Infant 2301 | 6.52E−10 | N.B. | 1.83E−09 | N.B. | 0.27 | 0.19 |
| ADI-24793 | Infant 2301 | N.B. | N.B. | N.B. | 2.68E−08 | N.N. | N.N. |
| ADI-24795 | Infant 2301 | 2.39E−08 | N.B. | 3.42E−08 | N.B. | N.N. | N.N. |
| ADI-24796 | Infant 2301 | N.B. | N.B. | 8.22E−08 | N.B. | N.N. | N.N. |
| ADI-24798 | Infant 2301 | 9.92E−09 | N.B. | 5.27E−09 | N.B. | N.N. | N.N. |
| ADI-24799 | Infant 2301 | 1.22E−08 | N.B. | 1.90E−08 | N.B. | 11.53 | N.N. |
| ADI-24800 | Infant 2301 | 2.83E−08 | N.B. | 5.14E−08 | N.B. | N.N. | N.N. |
| ADI-24801 | Infant 2301 | 5.89E−08 | N.B. | N.B. | N.B. | N.N. | N.N. |
| ADI-24803 | Infant 2301 | N.B. | 1.20E−09 | N.B. | 4.42E−10 | N.N. | N.N. |
| ADI-24805 | Infant 2301 | 3.79E−09 | N.B. | 4.88E−09 | N.B. | 0.21 | 0.71 |
| ADI-24807 | Infant 2301 | N.B. | 1.64E−08 | N.B. | N.B. | N.N. | N.N. |
| ADI-24808 | Infant 2301 | N.B. | 1.08E−08 | N.B. | N.B. | N.N. | N.N. |
| ADI-24811 | Infant 2301 | 8.10E−09 | N.B. | 4.29E−09 | N.B. | N.N. | N.N. |
| ADI-24812 | Infant 2301 | 3.51E−09 | N.B. | 7.58E−09 | N.B. | 0.18 | N.N. |
| ADI-24813 | Infant 2301 | N.B. | N.B. | N.B. | N.B. | N.N. | N.N. |
| ADI-24814 | Infant 2301 | 8.11E−09 | N.B. | 2.39E−09 | N.B. | 0.73 | 0.32 |
| ADI-24815 | Infant 2301 | 1.84E−08 | N.B. | 2.91E−08 | N.B. | N.N. | N.N. |
| ADI-24816 | Infant 2301 | N.B. | N.B. | N.B. | N.B. | N.N. | N.N. |
| ADI-24817 | Infant 2301 | 6.80E−09 | N.B. | 9.23E−09 | N.B. | 2.20 | 4.40 |
| ADI-24818 | Infant 2301 | 3.36E−08 | 6.47E−09 | N.B. | N.B. | N.N. | N.N. |
| ADI-24819 | Infant 2301 | 6.52E−09 | N.B. | 9.44E−09 | N.B. | 4.33 | 6.28 |
| ADI-24820 | Infant 2301 | 3.06E−08 | N.B. | 3.85E−08 | N.B. | N.N. | N.N. |
| ADI-24821 | Infant 2301 | N.B. | N.B. | N.B. | N.B. | N.N. | N.N. |
| ADI-24822 | Infant 2301 | 4.65E−08 | N.B. | N.B. | N.B. | N.N. | N.N. |
| ADI-24823 | Infant 2301 | 4.16E−09 | N.B. | 6.03E−09 | N.B. | ND | ND |
| ADI-24824 | Infant 2301 | 1.51E−08 | N.B. | 4.75E−08 | N.B. | N.N. | N.N. |
| ADI-24825 | Infant 2301 | 3.31E−08 | 3.01E−08 | N.B. | 2.60E−08 | N.N. | N.N. |
| ADI-24826 | Infant 2301 | 6.88E−09 | N.B. | 9.03E−09 | N.B. | N.N. | N.N. |
| ADI-24827 | Infant 2301 | 7.42E−09 | N.B. | 6.62E−09 | N.B. | 0.02 | N.N. |
| ADI-24828 | Infant 2301 | 3.06E−10 | N.B. | 3.91E−10 | N.B. | 0.02 | 0.04 |
| ADI-24829 | Infant 2301 | N.B. | N.B. | N.B. | N.B. | N.N. | N.N. |
| ADI-24830 | Infant 2301 | N.B. | N.B. | N.B. | N.B. | N.N. | N.N. |
| ADI-24831 | Infant 2301 | 4.88E−09 | N.B. | 6.23E−09 | N.B. | 0.21 | 3.29 |
| ADI-24832 | Infant 2301 | 1.80E−09 | N.B. | 1.95E−09 | N.B. | 0.49 | 0.24 |
| ADI-24833 | Infant 2301 | 1.93E−08 | N.B. | 1.14E−08 | N.B. | N.N. | N.N. |
| ADI-24834 | Infant 2301 | 1.12E−09 | 2.11E−10 | 7.32E−10 | 2.60E−10 | N.N. | N.N. |
| ADI-24835 | Infant 2301 | 4.93E−09 | N.B. | 5.55E−09 | N.B. | 0.63 | 1.06 |
| ADI-24836 | Infant 2301 | 2.87E−09 | N.B. | 3.44E−09 | N.B. | N.N. | N.N. |
| ADI-24837 | Infant 2301 | 2.75E−08 | N.B. | N.B. | N.B. | N.N. | N.N. |
| ADI-24838 | Infant 2301 | N.B. | N.B. | N.B. | N.B. | N.N. | N.N. |
| ADI-24839 | Infant 2301 | 5.83E−09 | N.B. | 9.63E−09 | N.B. | 0.44 | 4.10 |
| ADI-24840 | Infant 2301 | 7.32E−09 | N.B. | 7.80E−09 | N.B. | N.N. | N.N. |
| ADI-24841 | Infant 2301 | N.B. | N.B. | 2.66E−08 | N.B. | N.N. | N.N. |
| ADI-24842 | Infant 2301 | 5.59E−10 | N.B. | 2.76E−09 | N.B. | 0.03 | 0.03 |
| ADI-24843 | Infant 2301 | N.B. | N.B. | N.B. | N.B. | N.N. | N.N. |
| ADI-24845 | Infant 2301 | 1.19E−08 | N.B. | 3.67E−08 | N.B. | N.N. | N.N. |
| ADI-24846 | Infant 2301 | N.B. | N.B. | N.B. | 2.91E−08 | N.N. | N.N. |
| ADI-24847 | Infant 2301 | N.B. | N.B. | 4.00E−08 | N.B. | N.N. | N.N. |
| ADI-24848 | Infant 2301 | 2.08E−08 | N.B. | 3.56E−08 | N.B. | N.N. | N.N. |
| ADI-24849 | Infant 2301 | 1.71E−10 | N.B. | 1.17E−09 | N.B. | 0.01 | 0.03 |
| ADI-24850 | Infant 2301 | 3.84E−09 | N.B. | 5.56E−09 | N.B. | 0.94 | 4.17 |
| ADI-24851 | Infant 2301 | N.B. | 2.09E−08 | N.B. | N.B. | N.N. | N.N. |
| ADI-24852 | Infant 2301 | 1.18E−08 | 9.57E−09 | 1.90E−08 | 9.17E−09 | N.N. | N.N. |
| ADI-24854 | Infant 2301 | N.B. | N.B. | 3.03E−08 | N.B. | N.N. | N.N. |
| ADI-24855 | Infant 2301 | 1.79E−08 | N.B. | 2.80E−08 | N.B. | N.N. | N.N. |
| ADI-24856 | Infant 2301 | 1.35E−08 | N.B. | 4.91E−09 | N.B. | N.N. | N.N. |
| ADI-24857 | Infant 2301 | 3.20E−09 | N.B. | 3.71E−09 | N.B. | 0.18 | 1.40 |
| ADI-24858 | Infant 2301 | 2.16E−08 | N.B. | 2.63E−08 | N.B. | N.N. | N.N. |
| ADI-24859 | Infant 2301 | 4.31E−09 | N.B. | 4.95E−09 | N.B. | 0.58 | N.N. |
| ADI-24860 | Infant 2301 | 1.08E−09 | N.B. | 1.56E−09 | N.B. | 0.06 | 0.09 |
| ADI-24861 | Infant 2301 | 3.01E−10 | N.B. | 4.61E−10 | N.B. | N.N. | N.N. |
| ADI-24862 | Infant 2301 | N.B. | N.B. | N.B. | N.B. | N.N. | N.N. |
| ADI-24863 | Infant 2301 | N.B. | N.B. | N.B. | N.B. | N.N. | N.N. |
| ADI-19467 | Infant 2021 | 9.13E−09 | N.B. | 3.77E−08 | N.B. | N.N. | N.N. |
| ADI-19468 | Infant 2021 | 2.22E−09 | N.B. | N.B. | N.B. | N.N. | N.N. |
| ADI-19469 | Infant 2021 | 1.74E−08 | N.B. | N.B. | N.B. | N.N. | N.N. |
| ADI-19470 | Infant 2021 | 2.97E−08 | N.B. | 1.97E−08 | N.B. | N.N. | N.N. |
| ADI-19471 | Infant 2021 | 3.23E−09 | N.B. | N.B. | N.B. | N.N. | N.N. |
| ADI-19473 | Infant 2021 | N.B. | N.B. | N.B. | N.B. | N.N. | N.N. |
| ADI-19474 | Infant 2021 | N.B. | N.B. | N.B. | N.B. | N.N. | N.N. |

TABLE 2-continued

Summary of antibody characteristics

| ADI-19475 | Infant 2021 | 1.43E−09 | N.B. | 4.25E−09 | N.B. | 0.05 | 0.04 |
|---|---|---|---|---|---|---|---|
| ADI-19476 | Infant 2021 | N.B. | 8.01E−10 | N.B. | 8.38E−10 | N.N. | N.N. |
| ADI-19478 | Infant 2021 | N.B. | 3.86E−10 | N.B. | 7.13E−10 | N.N. | N.N. |
| ADI-19479 | Infant 2021 | N.B. | 3.69E−09 | N.B. | 2.69E−09 | N.N. | N.N. |
| ADI-19480 | Infant 2021 | 3.95E−10 | 1.29E−10 | 3.83E−10 | 1.19E−10 | N.N. | 6.25 |
| ADI-19481 | Infant 2021 | 7.60E−09 | N.B. | N.B. | N.B. | N.N. | N.N. |
| ADI-19482 | Infant 2021 | 1.28E−09 | 1.71E−09 | 1.89E−09 | 5.55E−10 | 1.49 | 2.24 |
| ADI-19483 | Infant 2021 | 1.72E−09 | 3.21E−10 | 1.77E−09 | 1.53E−10 | N.N. | N.N. |
| ADI-19484 | Infant 2021 | 1.75E−09 | 3.69E−10 | 8.92E−09 | 3.55E−10 | N.N. | N.N. |
| ADI-19485 | Infant 2021 | 3.56E−09 | 2.51E−10 | N.B. | P.F. | N.N. | N.N. |
| ADI-19486 | Infant 2021 | 3.71E−09 | 5.25E−10 | N.B. | 7.55E−09 | N.N. | N.N. |
| ADI-19487 | Infant 2021 | N.B. | N.B. | N.B. | N.B. | N.N. | 7.96 |
| ADI-19488 | Infant 2021 | 9.02E−09 | N.B. | 1.07E−08 | N.B. | N.N. | 3.38 |
| ADI-19489 | Infant 2021 | N.B. | N.B. | N.B. | N.B. | N.N. | N.N. |
| ADI-19490 | Infant 2021 | N.B. | N.B. | N.B. | N.B. | N.N. | N.N. |
| ADI-19491 | Infant 2021 | N.B. | N.B. | N.B. | N.B. | N.N. | N.N. |
| ADI-19492 | Infant 2021 | N.B. | N.B. | N.B. | N.B. | N.N. | N.N. |
| ADI-19493 | Infant 2021 | 7.93E−09 | N.B. | 2.26E−08 | N.B. | N.N. | N.N. |
| ADI-19494 | Infant 2021 | 5.48E−09 | N.B. | N.B. | N.B. | 0.86 | N.N. |
| ADI-19495 | Infant 2021 | N.B. | N.B. | N.B. | N.B. | N.N. | N.N. |
| ADI-19496 | Infant 2021 | N.B. | N.B. | N.B. | N.B. | N.N. | N.N. |
| ADI-19497 | Infant 2021 | N.B. | P.F. | N.B. | 1.34E−08 | N.N. | N.N. |
| ADI-19498 | Infant 2021 | N.B. | P.F. | N.B. | P.F. | N.N. | N.N. |
| ADI-19499 | Infant 2021 | N.B. | N.B. | N.B. | N.B. | N.N. | N.N. |
| ADI-19500 | Infant 2021 | N.B. | N.B. | N.B. | N.B. | N.N. | N.N. |
| ADI-19501 | Infant 2021 | 4.46E−10 | N.B. | 1.59E−09 | N.B. | 0.02 | 0.02 |
| ADI-19502 | Infant 2021 | N.B. | N.B. | N.B. | N.B. | N.N. | N.N. |
| ADI-19503 | Infant 2021 | N.B. | N.B. | N.B. | 1.16E−08 | N.N. | N.N. |
| ADI-19505 | Infant 2021 | 1.33E−08 | 4.94E−09 | 4.44E−08 | 5.01E−09 | N.N. | N.N. |
| ADI-22756 | Infant 2201 | 7.85E−09 | N.B. | 5.58E−08 | N.B. | N.N. | N.N. |
| ADI-22757 | Infant 2201 | 3.10E−10 | N.B. | 5.38E−10 | N.B. | 0.06 | 0.07 |
| ADI-22758 | Infant 2201 | 6.32E−09 | N.B. | P.F. | N.B. | N.N. | N.N. |
| ADI-22759 | Infant 2201 | 2.97E−10 | 2.53E−08 | 3.53E−10 | 1.01E−08 | 0.08 | 0.20 |
| ADI-22760 | Infant 2201 | 5.21E−09 | 1.19E−09 | 3.07E−09 | 1.25E−09 | N.N. | N.N. |
| ADI-22762 | Infant 2201 | 5.76E−08 | P.F. | N.B. | N.B. | N.N. | N.N. |
| ADI-22763 | Infant 2201 | 1.58E−09 | 3.19E−10 | 1.08E−08 | 5.33E−09 | N.N. | N.N. |
| ADI-22764 | Infant 2201 | 2.27E−09 | 3.34E−10 | 1.42E−09 | 1.44E−09 | N.N. | N.N. |
| ADI-22765 | Infant 2201 | 4.04E−08 | N.B. | P.F. | N.B. | N.N. | N.N. |
| ADI-22766 | Infant 2201 | N.B. | N.B. | N.B. | N.B. | N.N. | N.N. |
| ADI-22767 | Infant 2201 | 1.71E−08 | N.B. | P.F. | N.B. | N.N. | N.N. |
| ADI-22768 | Infant 2201 | 5.61E−09 | 3.41E−09 | 4.57E−09 | N.B. | N.N. | N.N. |
| ADI-22769 | Infant 2201 | N.B. | N.B. | N.B. | P.F. | N.N. | N.N. |
| ADI-22770 | Infant 2201 | N.B. | P.F. | N.B. | P.F. | N.N. | N.N. |
| ADI-22771 | Infant 2201 | 7.06E−09 | N.B. | 9.41E−09 | N.B. | N.N. | N.N. |
| ADI-22772 | Infant 2201 | N.B. | N.B. | N.B. | 5.02E−08 | N.N. | N.N. |
| ADI-22773 | Infant 2201 | P.F. | N.B. | N.B. | N.B. | N.N. | N.N. |
| ADI-22774 | Infant 2201 | 2.06E−09 | N.B. | 4.28E−09 | N.B. | 0.29 | 7.53 |
| ADI-22775 | Infant 2201 | N.B. | 3.00E−08 | N.B. | P.F. | N.N. | N.N. |
| ADI-22776 | Infant 2201 | N.B. | N.B. | P.F. | N.B. | N.N. | N.N. |
| ADI-22777 | Infant 2201 | 1.80E−09 | 2.68E−10 | 7.62E−10 | 2.24E−10 | N.N. | N.N. |
| ADI-22778 | Infant 2201 | 6.22E−10 | 2.09E−10 | 4.02E−09 | 2.77E−09 | N.N. | N.N. |
| ADI-22779 | Infant 2201 | 1.60E−08 | 6.20E−09 | N.B. | N.B. | N.N. | N.N. |
| ADI-22780 | Infant 2201 | N.B. | 7.39E−10 | 2.38E−08 | 6.00E−10 | N.N. | N.N. |
| ADI-22781 | Infant 2201 | N.B. | P.F. | P.F. | P.F. | N.N. | N.N. |
| ADI-14333 | Infant 856 | 3.53E−10 | N.B. | 9.04E−10 | N.B. | 0.07 | 0.09 |
| ADI-14334 | Infant 856 | 3.16E−10 | N.B. | 6.22E−10 | N.B. | 0.05 | 0.11 |
| ADI-14335 | Infant 856 | 1.96E−10 | N.B. | 8.89E−10 | N.B. | 0.32 | 0.10 |
| ADI-14336 | Infant 856 | 3.12E−10 | N.B. | 2.65E−09 | N.B. | 0.07 | 0.09 |
| ADI-14337 | Infant 856 | 1.39E−09 | N.B. | 2.11E−09 | N.B. | 0.10 | 0.07 |
| ADI-14338 | Infant 856 | 8.41E−09 | 5.98E−09 | 7.04E−09 | 3.14E−09 | N.N. | 10.16 |
| ADI-14339 | Infant 856 | 2.45E−08 | 4.39E−10 | 1.77E−09 | 3.76E−10 | N.N. | N.N. |
| ADI-14340 | Infant 856 | 4.11E−10 | N.B. | 9.80E−08 | N.B. | 6.63 | 1.94 |
| ADI-14341 | Infant 856 | N.B. | 7.13E−10 | N.B. | 6.12E−10 | N.N. | 17.46 |
| ADI-14342 | Infant 856 | 1.57E−09 | 4.95E−10 | 2.61E−08 | P.F. | 1.75 | 8.27 |
| ADI-14343 | Infant 856 | 1.85E−08 | 2.94E−09 | 3.81E−08 | P.F. | N.N. | N.N. |
| ADI-14344 | Infant 856 | 1.81E−10 | N.B. | 5.86E−10 | N.B. | 8.68 | 1.20 |
| ADI-14345 | Infant 856 | 6.32E−09 | N.B. | 5.26E−09 | N.B. | 2.30 | 0.87 |
| ADI-14346 | Infant 856 | 3.09E−10 | N.B. | 9.25E−10 | N.B. | 0.05 | 0.07 |
| ADI-14347 | Infant 856 | 4.99E−10 | N.B. | 2.54E−09 | N.B. | 0.11 | 0.05 |
| ADI-14348 | Infant 856 | 1.96E−09 | 5.66E−09 | 1.10E−07 | N.B. | N.N. | N.N. |
| ADI-14349 | Infant 856 | 5.33E−09 | N.B. | 4.07E−09 | N.B. | N.N. | 1.84 |
| ADI-14350 | Infant 856 | 3.73E−09 | 2.64E−10 | 5.74E−10 | 1.48E−10 | N.N. | 4.82 |
| ADI-14351 | Infant 856 | 2.21E−08 | 3.61E−10 | 7.89E−10 | 2.15E−10 | N.N. | N.N. |
| ADI-14352 | Infant 856 | N.B. | 4.48E−10 | 5.54E−09 | 3.83E−10 | N.N. | N.N. |
| ADI-14353 | Infant 856 | 1.40E−08 | 2.60E−10 | 1.26E−08 | P.F. | N.N. | 14.62 |
| ADI-14354 | Infant 856 | 9.98E−09 | 1.04E−09 | 2.53E−08 | 6.63E−09 | N.N. | N.N. |
| ADI-14355 | Infant 856 | 6.60E−09 | 4.80E−10 | 1.25E−09 | 3.70E−10 | N.N. | 4.72 |
| ADI-14356 | Infant 856 | N.B. | 3.90E−09 | 1.30E−08 | 4.98E−09 | N.N. | N.N. |

TABLE 2-continued

| | | | Summary of antibody characteristics | | | | |
|---|---|---|---|---|---|---|---|
| ADI-14357 | Infant 856 | 1.76E−10 | N.B. | 3.06E−10 | N.B. | 1.24 | 0.88 |
| ADI-14358 | Infant 856 | 5.91E−09 | 6.56E−10 | 6.03E−08 | 2.75E−08 | N.N. | N.N. |
| ADI-14359 | Infant 856 | N.B. | 4.11E−09 | 3.46E−08 | P.F. | N.N. | N.N. |
| ADI-14360 | Infant 856 | N.B. | 5.88E−09 | 2.68E−08 | 9.03E−09 | N.N. | N.N. |
| ADI-14361 | Infant 856 | N.B. | 4.37E−10 | 5.28E−08 | 2.93E−10 | N.N. | N.N. |
| ADI-14362 | Infant 856 | 3.15E−09 | 1.57E−08 | 1.19E−07 | N.B. | N.N. | N.N. |
| ADI-14363 | Infant 856 | 3.54E−09 | N.B. | 5.35E−09 | N.B. | N.N. | N.N. |
| ADI-14364 | Infant 856 | 6.30E−10 | N.B. | 6.16E−08 | N.B. | 0.03 | 2.39 |
| ADI-14365 | Infant 856 | 1.19E−09 | 1.03E−08 | 9.62E−10 | 2.23E−08 | 0.80 | 0.49 |
| ADI-14366 | Infant 856 | 6.14E−09 | N.B. | 1.80E−08 | N.B. | N.N. | N.N. |
| ADI-14367 | Infant 856 | 1.57E−10 | N.B. | 2.69E−10 | N.B. | 3.94 | 0.33 |
| ADI-14368 | Infant 856 | 2.60E−09 | 2.45E−08 | 1.21E−09 | 1.77E−08 | N.N. | 1.10 |
| ADI-14369 | Infant 856 | N.B. | 1.22E−09 | 3.38E−09 | 9.00E−10 | N.N. | N.N. |
| ADI-14370 | Infant 856 | 8.12E−09 | N.B. | 4.18E−09 | N.B. | N.N. | 1.38 |
| ADI-14371 | Infant 856 | N.B. | 1.23E−09 | 8.43E−09 | 1.07E−09 | N.N. | N.N. |
| ADI-14372 | Infant 856 | N.B. | 6.59E−10 | N.B. | 4.43E−09 | N.N. | N.N. |
| ADI-14373 | Infant 856 | 1.96E−09 | 1.06E−09 | 1.59E−08 | N.B. | N.N. | N.N. |
| ADI-14374 | Infant 856 | 4.61E−09 | N.B. | 2.09E−09 | N.B. | N.N. | 0.86 |
| ADI-14375 | Infant 856 | N.B. | 4.77E−10 | 3.21E−09 | 3.31E−09 | N.N. | N.N. |
| ADI-14376 | Infant 856 | P.F. | P.F. | P.F. | P.F. | N.N. | N.N. |
| ADI-14377 | Infant 856 | 6.64E−09 | N.B. | 5.28E−09 | N.B. | N.N. | 2.13 |
| ADI-14378 | Infant 856 | 5.87E−09 | N.B. | 6.10E−09 | N.B. | N.N. | 21.58 |
| ADI-14379 | Infant 856 | N.B. | 3.29E−09 | N.B. | 2.35E−09 | N.N. | N.N. |
| ADI-14380 | Infant 856 | 6.04E−09 | N.B. | 1.08E−08 | N.B. | N.N. | N.N. |
| ADI-14381 | Infant 856 | 2.20E−09 | 7.54E−10 | 3.67E−08 | P.F. | ND | ND |
| ADI-14382 | Infant 856 | N.B. | 8.46E−10 | N.B. | N.B. | N.N. | N.N. |
| ADI-14383 | Infant 856 | N.B. | 4.34E−10 | 1.75E−09 | 2.51E−10 | N.N. | N.N. |
| ADI-14384 | Infant 856 | 3.71E−09 | 4.69E−10 | 4.78E−09 | N.B. | N.N. | N.N. |
| ADI-14385 | Infant 856 | 8.72E−08 | P.F. | P.F. | P.F. | N.N. | N.N. |
| ADI-14386 | Infant 856 | 6.29E−09 | 1.32E−09 | 3.04E−09 | P.F. | N.N. | N.N. |
| ADI-14388 | Infant 856 | 5.58E−09 | N.B. | 5.50E−08 | N.B. | N.N. | 3.07 |
| ADI-14389 | Infant 856 | N.B. | 2.29E−08 | 8.15E−08 | P.F. | N.N. | N.N. |
| ADI-14390 | Infant 856 | N.B. | N.B. | N.B. | N.B. | N.N. | N.N. |
| ADI-14391 | Infant 856 | 6.95E−09 | N.B. | 5.36E−09 | N.B. | N.N. | 22.25 |
| ADI-14392 | Infant 856 | 7.56E−09 | N.B. | 7.25E−08 | N.B. | N.N. | N.N. |
| ADI-14393 | Infant 856 | 3.11E−10 | N.B. | 4.74E−10 | 1.17E−08 | ND | ND |
| ADI-14394 | Infant 856 | 1.15E−08 | N.B. | P.F. | N.B. | N.N. | N.N. |
| ADI-14395 | Infant 856 | 2.49E−08 | N.B. | P.F. | N.B. | N.N. | N.N. |
| ADI-14396 | Infant 856 | N.B. | N.B. | 1.55E−08 | N.B. | N.N. | N.N. |
| ADI-14397 | Infant 856 | 2.85E−08 | N.B. | P.F. | N.B. | N.N. | N.N. |
| ADI-14399 | Infant 856 | 1.89E−10 | N.B. | 3.65E−10 | N.B. | 0.97 | 0.46 |
| ADI-14400 | Infant 856 | 2.90E−10 | N.B. | 4.51E−10 | N.B. | ND | 3.71 |
| ADI-14401 | Infant 856 | 1.19E−09 | N.B. | 2.17E−09 | N.B. | 0.05 | 0.06 |
| ADI-14402 | Infant 856 | 2.79E−10 | N.B. | 4.16E−10 | N.B. | 0.02 | 0.03 |
| ADI-14403 | Infant 856 | 5.09E−10 | N.B. | 6.99E−10 | N.B. | 0.08 | 0.N.N.1 |
| ADI-14404 | Infant 856 | N.B. | 6.27E−10 | N.B. | 4.98E−10 | N.N. | N.N. |
| ADI-14405 | Infant 856 | 1.42E−10 | 1.17E−08 | 2.27E−10 | 3.80E−08 | 0.04 | 0.04 |
| ADI-14406 | Infant 856 | 6.85E−09 | 3.39E−10 | 9.06E−10 | 4.73E−10 | N.N. | N.N. |
| ADI-14407 | Infant 856 | 6.28E−09 | 3.78E−10 | 1.14E−08 | P.F. | N.N. | N.N. |
| ADI-14408 | Infant 856 | 8.53E−09 | 2.14E−09 | 1.28E−08 | P.F. | N.N. | N.N. |
| ADI-14409 | Infant 856 | 1.50E−10 | N.B. | 2.89E−10 | N.B. | 0.29 | 0.23 |
| ADI-14410 | Infant 856 | 3.77E−10 | N.B. | 1.71E−08 | N.B. | 1.22 | 2.64 |
| ADI-14411 | Infant 856 | 6.12E−09 | N.B. | 3.92E−09 | N.B. | 9.27 | 1.96 |
| ADI-14412 | Infant 856 | 5.60E−09 | N.B. | 1.34E−08 | N.B. | N.N. | N.N. |
| ADI-14413 | Infant 856 | 5.45E−09 | N.B. | 2.71E−09 | N.B. | 15.13 | 1.69 |
| ADI-14414 | Infant 856 | 5.00E−09 | N.B. | 3.07E−09 | N.B. | N.N. | N.N. |
| ADI-14415 | Infant 856 | 4.20E−09 | N.B. | 3.51E−09 | N.B. | N.N. | N.N. |
| ADI-14416 | Infant 856 | 2.39E−09 | 1.82E−10 | 3.69E−10 | 1.06E−10 | N.N. | N.N. |
| ADI-14417 | Infant 856 | N.B. | 1.63E−09 | N.B. | 3.99E−09 | ND | ND |
| ADI-14418 | Infant 856 | 1.25E−09 | 4.41E−10 | 1.58E−09 | 2.58E−10 | 0.30 | 0.66 |
| ADI-14419 | Infant 856 | 2.69E−09 | N.B. | N.B. | N.B. | N.N. | N.N. |
| ADI-14420 | Infant 856 | 6.35E−09 | N.B. | 4.32E−09 | N.B. | N.N. | N.N. |
| ADI-14421 | Infant 856 | N.B. | 1.07E−09 | 2.82E−09 | 7.40E−10 | N.N. | N.N. |
| ADI-14422 | Infant 856 | 1.14E−08 | 4.76E−09 | 3.39E−08 | N.B. | N.N. | N.N. |
| ADI-14423 | Infant 856 | 9.65E−09 | N.B. | 3.40E−09 | N.B. | N.N. | N.N. |
| ADI-14424 | Infant 856 | 3.43E−09 | N.B. | 1.90E−09 | N.B. | N.N. | 2.48 |
| ADI-14425 | Infant 856 | 4.81E−08 | 7.42E−10 | 2.03E−08 | 9.34E−09 | N.N. | N.N. |
| ADI-14426 | Infant 856 | 2.38E−08 | 3.96E−10 | 1.92E−08 | P.F. | N.N. | N.N. |
| ADI-14427 | Infant 856 | 2.34E−10 | 3.33E−09 | 1.08E−08 | N.B. | 0.25 | N.N. |
| ADI-14428 | Infant 856 | 4.22E−08 | N.B. | 1.41E−08 | N.B. | N.N. | N.N. |
| ADI-14654 | Infant 856 | 2.04E−09 | N.B. | 7.64E−09 | N.B. | N.N. | N.N. |
| ADI-14655 | Infant 856 | 1.69E−08 | P.F. | 1.40E−08 | P.F. | N.N. | N.N. |
| ADI-14656 | Infant 856 | P.F. | 3.70E−10 | 2.51E−08 | P.F. | N.N. | N.N. |
| ADI-14657 | Infant 856 | 2.84E−09 | N.B. | N.B. | N.B. | N.N. | N.N. |
| ADI-14658 | Infant 856 | N.B. | 1.58E−08 | N.B. | 1.79E−08 | N.N. | N.N. |
| ADI-14659 | Infant 856 | 4.86E−09 | N.B. | 3.71E−09 | N.B. | N.N. | 5.56 |
| ADI-14571 | Infant 856 | 2.91E−09 | N.B. | N.B. | N.B. | N.N. | 3.06 |
| ADI-14572 | Infant 856 | N.B. | 1.70E−08 | P.F. | N.B. | N.N. | N.N. |

TABLE 2-continued

Summary of antibody characteristics

| ADI-14573 | Infant 856 | N.B. | 3.73E−10 | 2.10E−08 | 3.55E−09 | N.N. | N.N. |
|---|---|---|---|---|---|---|---|
| ADI-14575 | Infant 856 | 1.12E−08 | P.F. | N.B. | N.B. | N.N. | N.N. |
| ADI-14576 | Infant 856 | 6.97E−09 | N.B. | 1.93E−08 | N.B. | 3.11 | 0.77 |
| ADI-14577 | Infant 856 | 4.39E−10 | N.B. | 2.19E−09 | N.B. | 0.04 | 0.05 |
| ADI-14578 | Infant 856 | 3.29E−09 | N.B. | 4.02E−09 | N.B. | N.N. | N.N. |
| ADI-14579 | Infant 856 | 7.54E−09 | P.F. | 3.73E−09 | N.B. | N.N. | N.N. |
| ADI-14580 | Infant 856 | 6.70E−09 | N.B. | 4.54E−09 | N.B. | N.N. | 3.75 |
| ADI-14581 | Infant 856 | N.B. | N.B. | 2.88E−09 | N.B. | N.N. | 6.25 |
| ADI-14582 | Infant 856 | 5.82E−09 | N.B. | 1.81E−09 | N.B. | ND | ND |
| ADI-14583 | Infant 856 | 4.74E−10 | N.B. | 1.59E−09 | N.B. | 0.05 | 0.06 |
| ADI-14584 | Infant 856 | P.F. | N.B. | 4.76E−10 | N.B. | 1.53 | 0.65 |
| ADI-14585 | Infant 856 | 2.72E−10 | N.B. | 4.49E−10 | N.B. | 0.02 | 0.03 |
| ADI-14586 | Infant 856 | 4.52E−10 | N.B. | 6.70E−09 | N.B. | 0.05 | 0.50 |
| ADI-14587 | Infant 856 | 6.09E−10 | N.B. | 8.33E−10 | N.B. | 0.15 | 0.11 |
| ADI-14588 | Infant 856 | 3.24E−09 | N.B. | 1.48E−09 | N.B. | 13.60 | 0.59 |
| ADI-14589 | Infant 856 | 6.48E−09 | 5.96E−10 | 2.82E−08 | 1.54E−08 | N.N. | N.N. |
| ADI-14590 | Infant 856 | 1.32E−08 | 2.68E−09 | 5.99E−09 | 9.67E−10 | N.N. | N.N. |
| ADI-14591 | Infant 856 | 1.87E−10 | N.B. | 5.54E−10 | N.B. | N.N. | 9.36 |
| ADI-14592 | Infant 856 | 2.40E−10 | 1.36E−10 | 3.01E−10 | 9.32E−11 | N.N. | N.N. |
| ADI-14593 | Infant 856 | 2.33E−09 | 1.61E−10 | 3.58E−10 | 1.08E−10 | 2.28 | 4.03 |
| ADI-14594 | Infant 856 | N.B. | 2.57E−10 | 1.82E−08 | 2.14E−10 | N.N. | N.N. |
| ADI-14595 | Infant 856 | 2.19E−09 | 1.30E−09 | 1.60E−08 | 1.44E−08 | ND | ND |
| ADI-14596 | Infant 856 | 1.86E−10 | N.B. | 1.86E−09 | N.B. | N.N. | N.N. |
| ADI-14597 | Infant 856 | 5.26E−09 | N.B. | 1.67E−09 | N.B. | N.N. | 3.05 |
| ADI-14598 | Infant 856 | P.F. | 4.52E−10 | 7.07E−09 | 4.81E−09 | N.N. | N.N. |
| ADI-14599 | Infant 856 | 1.02E−10 | 6.36E−10 | 6.22E−10 | 3.58E−10 | 0.14 | 1.11 |
| ADI-14600 | Infant 856 | 7.58E−10 | N.B. | 9.86E−10 | N.B. | 0.12 | 0.08 |
| ADI-14601 | Infant 856 | 3.79E−09 | N.B. | 1.96E−09 | N.B. | 12.19 | 3.10 |
| ADI-14602 | Infant 856 | 4.73E−09 | N.B. | 8.94E−09 | N.B. | N.N. | 6.53 |
| ADI-14603 | Infant 856 | 8.40E−09 | N.B. | 3.05E−08 | N.B. | N.N. | 2.03 |
| ADI-14604 | Infant 856 | 2.44E−09 | N.B. | 1.53E−09 | N.B. | N.N. | N.N. |
| ADI-14605 | Infant 856 | N.B. | 9.24E−10 | 2.72E−09 | 3.99E−10 | N.N. | N.N. |
| ADI-14606 | Infant 856 | N.B. | 1.28E−09 | N.B. | 6.59E−10 | 0.85 | 0.29 |
| ADI-14607 | Infant 856 | 1.70E−09 | 3.81E−10 | 6.40E−10 | 2.27E−10 | N.N. | 0.13 |
| ADI-20959 | Infant 2042 | 3.37E−10 | N.B. | 4.30E−10 | N.B. | 0.06 | 0.28 |
| ADI-20960 | Infant 2042 | 2.20E−10 | 1.63E−10 | 2.30E−10 | 1.63E−10 | 0.35 | 0.71 |
| ADI-20961 | Infant 2042 | 3.74E−10 | N.B. | 5.04E−10 | N.B. | 0.09 | 0.32 |
| ADI-20962 | Infant 2042 | 2.89E−10 | N.B. | 4.63E−10 | N.B. | 0.07 | 0.15 |
| ADI-20963 | Infant 2042 | 7.91E−10 | 9.09E−11 | 3.14E−09 | 6.14E−10 | N.N. | N.N. |
| ADI-20964 | Infant 2042 | 3.60E−10 | N.B. | 2.49E−09 | N.B. | 0.06 | 0.14 |
| ADI-20965 | Infant 2042 | 1.21E−10 | P.F. | 5.33E−10 | P.F. | 0.32 | 0.64 |
| ADI-20966 | Infant 2042 | 3.06E−10 | N.B. | 8.62E−10 | N.B. | 0.00 | 0.13 |
| ADI-20967 | Infant 2042 | 2.23E−09 | 2.57E−10 | 4.08E−09 | 3.45E−09 | N.N. | N.N. |
| ADI-20968 | Infant 2042 | 1.35E−10 | 1.57E−10 | 1.27E−10 | 1.50E−10 | 0.14 | 0.44 |
| ADI-20969 | Infant 2042 | 3.01E−10 | N.B. | 4.09E−10 | N.B. | 0.12 | 0.27 |
| ADI-20970 | Infant 2042 | 1.83E−09 | N.B. | 2.55E−09 | N.B. | 2.14 | 2.92 |
| ADI-20971 | Infant 2042 | 3.33E−10 | N.B. | 5.44E−10 | N.B. | N.N. | N.N. |
| ADI-20972 | Infant 2042 | 8.88E−10 | 4.01E−10 | 6.06E−09 | 3.48E−09 | N.N. | N.N. |
| ADI-20973 | Infant 2042 | 3.08E−10 | N.B. | 4.17E−10 | N.B. | 0.03 | 0.19 |
| ADI-20974 | Infant 2042 | 2.91E−10 | N.B. | 3.60E−10 | N.B. | 0.00 | 0.09 |
| ADI-20975 | Infant 2042 | 9.20E−11 | 1.46E−10 | 9.58E−11 | 1.29E−10 | 0.05 | 0.49 |
| ADI-20976 | Infant 2042 | 1.86E−09 | 2.63E−10 | 9.55E−10 | 3.04E−10 | N.N. | N.N. |
| ADI-20977 | Infant 2042 | 1.51E−10 | N.B. | P.F. | N.B. | N.N. | N.N. |
| ADI-20978 | Infant 2042 | 2.90E−10 | N.B. | 3.19E−10 | N.B. | 0.01 | 0.17 |
| ADI-20979 | Infant 2042 | 9.79E−10 | N.B. | 4.00E−09 | N.B. | 0.29 | 0.21 |
| ADI-20980 | Infant 2042 | 2.00E−10 | N.B. | 5.42E−10 | N.B. | N.N. | N.N. |
| ADI-20981 | Infant 2042 | 2.34E−09 | 2.33E−10 | 2.14E−09 | 2.95E−10 | N.N. | N.N. |
| ADI-20982 | Infant 2042 | 4.88E−09 | N.B. | 5.45E−09 | N.B. | N.N. | N.N. |
| ADI-20983 | Infant 2042 | 2.13E−10 | 2.05E−09 | 1.17E−09 | P.F. | N.N. | N.N. |
| ADI-20984 | Infant 2042 | 3.29E−09 | N.B. | 2.02E−08 | N.B. | N.N. | N.N. |
| ADI-20986 | Infant 2042 | 4.14E−10 | N.B. | 1.25E−09 | N.B. | 0.02 | 0.19 |
| ADI-20987 | Infant 2042 | 4.63E−09 | N.B. | 3.56E−08 | N.B. | N.N. | N.N. |
| ADI-20988 | Infant 2042 | 2.94E−10 | N.B. | 1.29E−09 | N.B. | 0.06 | 0.27 |
| ADI-20989 | Infant 2042 | 4.80E−09 | 4.28E−10 | 6.29E−09 | 8.09E−10 | N.N. | N.N. |
| ADI-20990 | Infant 2042 | 1.58E−09 | 1.78E−10 | 9.04E−10 | 3.12E−10 | N.N. | N.N. |
| ADI-20991 | Infant 2042 | 2.34E−10 | N.B. | 2.58E−10 | N.B. | 0.14 | 0.19 |
| ADI-20992 | Infant 2042 | 9.56E−10 | N.B. | 1.22E−09 | N.B. | 0.04 | 0.64 |
| ADI-20993 | Infant 2042 | 1.38E−09 | 1.68E−10 | 7.42E−10 | 2.73E−10 | N.N. | N.N. |
| ADI-20994 | Infant 2042 | 8.94E−11 | P.F. | 1.09E−10 | P.F. | 0.06 | 0.18 |
| ADI-20995 | Infant 2042 | 2.60E−09 | N.B | 1.36E−08 | N.B | ND | ND |
| ADI-20996 | Infant 2042 | 1.03E−09 | 2.04E−10 | 1.06E−09 | 1.12E−09 | N.N. | N.N. |
| ADI-20997 | Infant 2042 | 1.78E−09 | 1.97E−10 | 3.09E−09 | 6.09E−10 | N.N. | N.N. |
| ADI-20998 | Infant 2042 | 2.57E−10 | N.B. | 1.35E−09 | N.B. | 0.03 | N.N. |
| ADI-20999 | Infant 2042 | 4.16E−09 | N.B. | 2.41E−08 | N.B. | N.N. | N.N. |
| ADI-21000 | Infant 2042 | 1.49E−09 | 2.95E−10 | 1.30E−09 | 6.02E−10 | N.N. | N.N. |
| ADI-21001 | Infant 2042 | 2.12E−09 | 2.77E−10 | 1.85E−09 | 3.02E−10 | N.N. | N.N. |
| ADI-21002 | Infant 2042 | 2.36E−09 | 2.14E−10 | 8.60E−09 | 6.39E−09 | N.N. | N.N. |
| ADI-21003 | Infant 2042 | 4.75E−09 | 4.40E−10 | 9.87E−10 | 4.21E−10 | N.N. | N.N. |

TABLE 2-continued

Summary of antibody characteristics

| | | | | | | | |
|---|---|---|---|---|---|---|---|
| ADI-21004 | Infant 2042 | 4.59E−09 | 5.40E−10 | 1.02E−08 | 7.98E−10 | N.N. | 4.78 |
| ADI-21005 | Infant 2042 | 3.37E−09 | N.B. | 7.70E−09 | N.B. | N.N. | N.N. |
| ADI-21006 | Infant 2042 | 1.04E−08 | N.B. | N.B. | N.B. | N.N. | N.N. |
| ADI-21007 | Infant 2042 | 1.48E−09 | 1.71E−10 | 1.72E−09 | 1.71E−10 | N.N. | N.N. |
| ADI-21008 | Infant 2042 | 5.68E−09 | 9.18E−10 | 4.14E−09 | 1.45E−09 | N.N. | N.N. |
| ADI-21009 | Infant 2042 | 4.88E−09 | N.B. | 1.95E−08 | N.B. | N.N. | N.N. |
| ADI-21010 | Infant 2042 | 3.58E−09 | N.B. | N.B. | N.B. | N.N. | N.N. |
| ADI-21011 | Infant 2042 | 1.41E−09 | 1.62E−10 | 9.82E−10 | 3.56E−10 | N.N. | N.N. |
| ADI-21012 | Infant 2042 | 3.71E−10 | 2.14E−10 | 1.92E−09 | 2.80E−10 | N.N. | N.N. |
| ADI-21013 | Infant 2042 | 2.29E−09 | N.B. | 1.79E−09 | N.B. | 0.08 | 0.14 |
| ADI-21014 | Infant 2042 | 4.08E−10 | N.B. | 3.78E−10 | N.B. | 0.05 | 0.17 |
| ADI-21015 | Infant 2042 | 4.41E−09 | N.B. | 3.24E−08 | N.B. | 1.46 | 1.15 |
| ADI-21017 | Infant 2042 | 3.05E−10 | N.B. | 1.56E−09 | N.B. | N.N. | N.N. |
| ADI-21018 | Infant 2042 | 3.50E−10 | N.B. | 3.66E−10 | N.B. | 0.24 | 0.34 |
| ADI-21019 | Infant 2042 | 1.82E−10 | 1.54E−10 | 9.62E−10 | 1.68E−10 | 6.25 | 6.25 |
| ADI-21021 | Infant 2042 | 2.55E−09 | N.B. | 4.50E−09 | N.B. | N.N. | N.N. |
| ADI-21022 | Infant 2042 | N.B. | 2.56E−10 | 1.74E−08 | 3.57E−10 | N.N. | N.N. |
| ADI-21023 | Infant 2042 | 2.64E−10 | N.B. | 3.16E−10 | N.B. | 0.12 | 0.26 |
| ADI-21025 | Infant 2042 | 2.42E−10 | N.B. | 2.95E−10 | N.B. | 0.09 | 0.19 |
| ADI-21026 | Infant 2042 | 6.35E−09 | 9.45E−10 | 3.99E−09 | 1.43E−09 | N.N. | N.N. |
| ADI-21027 | Infant 2042 | 2.96E−10 | N.B. | 3.40E−10 | N.B. | 0.13 | 0.27 |
| ADI-21028 | Infant 2042 | 5.45E−09 | N.B. | 3.33E−09 | N.B. | N.N. | 9.09 |
| ADI-21029 | Infant 2042 | 3.77E−09 | N.B. | 8.38E−10 | N.B. | N.N. | 0.96 |
| ADI-21030 | Infant 2042 | 2.57E−10 | N.B. | 3.01E−10 | N.B. | 0.16 | 0.26 |
| ADI-21031 | Infant 2042 | 1.07E−09 | N.B. | 1.50E−09 | N.B. | 0.31 | 3.36 |
| ADI-21032 | Infant 2042 | 2.96E−10 | N.B. | 3.44E−10 | N.B. | 0.10 | 0.30 |
| ADI-21033 | Infant 2042 | 1.93E−10 | N.B. | 1.40E−09 | N.B. | 4.64 | 9.20 |
| ADI-21034 | Infant 2042 | 1.45E−10 | N.B. | 1.74E−10 | N.B. | N.N. | 7.30 |
| ADI-21035 | Infant 2042 | 1.03E−08 | N.B. | N.B. | N.B. | N.N. | N.N. |
| ADI-21036 | Infant 2042 | 5.52E−09 | N.B. | N.B. | N.B. | N.N. | N.N. |
| ADI-21037 | Infant 2042 | 1.95E−10 | 2.48E−10 | 4.81E−09 | 3.17E−09 | N.N. | N.N. |
| ADI-21038 | Infant 2042 | 2.93E−09 | 1.45E−09 | 1.60E−08 | N.B. | N.N. | N.N. |
| ADI-21039 | Infant 2042 | 1.71E−09 | 2.40E−10 | 1.27E−08 | 6.31E−09 | N.N. | N.N. |
| ADI-21040 | Infant 2042 | N.B. | 7.77E−10 | N.B. | 1.03E−09 | N.N. | N.N. |
| ADI-21041 | Infant 2042 | 7.30E−09 | N.B. | N.B. | N.B. | N.N. | N.N. |
| ADI-21042 | Infant 2042 | 2.96E−09 | 2.87E−10 | 1.18E−09 | 3.98E−10 | N.N. | N.N. |
| ADI-21043 | Infant 2042 | 1.11E−10 | 1.65E−09 | 1.54E−10 | 1.93E−09 | 0.19 | 0.08 |
| ADI-21044 | Infant 2042 | 4.51E−09 | N.B. | 5.85E−09 | N.B. | N.N. | 2.13 |
| ADI-21045 | Infant 2042 | 4.56E−10 | N.B. | 5.96E−10 | N.B. | 0.04 | 0.09 |
| ADI-21046 | Infant 2042 | 1.66E−09 | 1.87E−10 | 6.94E−10 | 2.24E−10 | N.N. | N.N. |
| ADI-21047 | Infant 2042 | 2.11E−09 | 2.90E−10 | 7.56E−10 | 2.62E−10 | N.N. | N.N. |
| ADI-21048 | Infant 2042 | 1.11E−10 | P.F. | P.F. | P.F. | 0.08 | 0.16 |
| ADI-21049 | Infant 2042 | 3.97E−10 | N.B. | 1.27E−09 | N.B. | 0.62 | 0.56 |
| ADI-21050 | Infant 2042 | 3.62E−10 | N.B. | 3.23E−10 | N.B. | 0.08 | 0.12 |
| ADI-21051 | Infant 2042 | 2.92E−10 | N.B. | 3.35E−10 | N.B. | N.N. | N.N. |
| ADI-21052 | Infant 2042 | 1.26E−10 | 1.84E−08 | 1.10E−10 | P.F. | 0.05 | 0.11 |
| ADI-21053 | Infant 2042 | 7.10E−08 | 6.37E−09 | N.B. | 1.18E−07 | N.N. | N.N. |
| ADI-21054 | Infant 2042 | 1.85E−10 | 3.72E−10 | 1.39E−10 | 3.06E−10 | 0.09 | 0.49 |
| ADI-21055 | Infant 2042 | 1.10E−09 | 1.85E−10 | 2.98E−09 | 4.35E−09 | ND | ND |
| ADI-21056 | Infant 2042 | 2.51E−10 | 7.22E−08 | 2.23E−10 | 6.34E−08 | 0.00 | 0.02 |
| ADI-21057 | Infant 2042 | 9.36E−10 | N.B. | 8.60E−10 | N.B. | 0.00 | 0.00 |
| ADI-21058 | Infant 2042 | 9.72E−10 | N.B. | 5.15E−10 | N.B. | 0.04 | 0.48 |
| ADI-21059 | Infant 2042 | 3.05E−09 | N.B. | 9.43E−09 | N.B. | N.N. | 0.30 |
| ADI-21060 | Infant 2042 | 4.26E−10 | N.B. | 3.49E−10 | N.B. | 0.06 | 0.14 |
| ADI-21061 | Infant 2042 | 1.10E−09 | 1.42E−10 | 2.76E−09 | 2.48E−09 | N.N. | N.N. |
| ADI-21062 | Infant 2042 | 1.24E−09 | 2.36E−10 | 8.27E−10 | 4.17E−10 | N.N. | N.N. |
| ADI-21063 | Infant 2042 | 8.34E−10 | N.B. | 7.77E−10 | N.B. | 0.04 | 0.11 |
| ADI-21064 | Infant 2042 | 3.20E−10 | N.B. | 2.80E−10 | N.B. | 0.03 | 0.12 |
| ADI-21065 | Infant 2042 | 1.71E−10 | N.B. | P.F. | N.B. | N.N. | N.N. |
| ADI-21067 | Infant 2042 | 3.98E−09 | N.B | 5.90E−09 | N.B | ND | ND |
| ADI-21068 | Infant 2042 | 2.55E−10 | 1.55E−08 | 2.38E−10 | 7.85E−09 | 0.10 | N.N. |
| ADI-21069 | Infant 2042 | 1.23E−10 | P.F. | 1.19E−10 | P.F. | 0.11 | 0.26 |
| ADI-21070 | Infant 2042 | 5.37E−09 | N.B. | 7.59E−09 | N.B. | N.N. | 2.38 |
| ADI-21071 | Infant 2042 | 1.17E−09 | 2.16E−10 | 1.88E−09 | 1.38E−09 | N.N. | N.N. |
| ADI-21072 | Infant 2042 | 3.41E−10 | N.B. | 3.32E−10 | N.B. | 0.04 | 0.33 |
| ADI-21073 | Infant 2042 | 4.06E−09 | 5.80E−10 | 1.78E−09 | 6.75E−10 | ND | 11.15 |
| ADI-21075 | Infant 2042 | 4.07E−10 | N.B. | 5.15E−10 | N.B. | 0.03 | 0.48 |
| ADI-21076 | Infant 2042 | 2.19E−10 | 7.34E−09 | 1.96E−10 | 6.28E−09 | 0.03 | 0.30 |
| ADI-21077 | Infant 2042 | 4.28E−10 | N.B. | 3.83E−10 | N.B. | 0.06 | 0.06 |
| ADI-21078 | Infant 2042 | 3.11E−10 | N.B. | 3.07E−10 | N.B. | 0.03 | 0.20 |
| ADI-21079 | Infant 2042 | 3.13E−10 | N.B. | 3.08E−10 | N.B. | 0.20 | 0.29 |
| ADI-21080 | Infant 2042 | 3.60E−10 | N.B. | 3.72E−10 | N.B. | 0.10 | 0.17 |
| ADI-21081 | Infant 2042 | 2.84E−10 | N.B. | 2.77E−10 | N.B. | 0.10 | 0.32 |
| ADI-21082 | Infant 2042 | 2.85E−10 | N.B. | 2.81E−10 | 6.17E−09 | 0.09 | 0.25 |
| ADI-21083 | Infant 2042 | 2.25E−09 | N.B. | 2.65E−09 | N.B. | 0.36 | 0.79 |
| ADI-21084 | Infant 2042 | 1.09E−10 | 1.73E−08 | 1.04E−10 | 2.29E−08 | 0.14 | 0.46 |
| ADI-21085 | Infant 2042 | 3.07E−10 | N.B. | 3.09E−10 | 6.24E−09 | 0.10 | 0.48 |
| ADI-21086 | Infant 2042 | 2.90E−10 | N.B. | 2.76E−10 | N.B. | 0.11 | 0.47 |

| | | | Summary of antibody characteristics | | | | |
|---|---|---|---|---|---|---|---|
| ADI-21087 | Infant 2042 | N.B. | 5.45E–10 | N.B. | 4.76E–10 | N.N. | N.N. |
| ADI-21089 | Infant 2042 | 2.82E–10 | N.B. | 2.62E–10 | 3.34E–09 | 0.27 | 0.17 |
| ADI-21090 | Infant 2042 | 1.17E–09 | 1.76E–10 | 4.89E–10 | 1.75E–10 | ND | ND |
| ADI-21091 | Infant 2042 | 7.49E–10 | N.B. | 1.39E–09 | N.B. | 0.29 | 0.92 |

| Name | Antigenic Site Assignment | PSR Score | VH germline gene usage | LC germline gene usage | Number of nucleotide substitutions in VH | Number of nucleotide substitutions in VL |
|---|---|---|---|---|---|---|
| ADI-25462 | Site III | 0.001 | VH3-21 | VL1-40 | 1 | 0 |
| ADI-25467 | Unknown | 0.000 | VH4-59 | VK1-39 | 0 | 0 |
| ADI-25468 | Unknown | 0.402 | VH5-51 | VL3-1 | 0 | 0 |
| ADI-25472 | Site III | 0.000 | VH3-21 | VL1-40 | 0 | 0 |
| ADI-25478 | Site III | 0.817 | VH3-21 | VL1-40 | 0 | 0 |
| ADI-25479 | Site III | 0.373 | VH3-21 | VL1-40 | 0 | 0 |
| ADI-25480 | Site III | 0.340 | VH3-21 | VL1-40 | 0 | 0 |
| ADI-25484 | Site III | 0.000 | VH3-21 | VL1-40 | 0 | 0 |
| ADI-25491 | Site I | 0.000 | VH4-31 | VL3-1 | 0 | 0 |
| ADI-25495 | Site III | 0.000 | VH3-21 | VL2-14 | 0 | 1 |
| ADI-25496 | Unknown | 0.000 | VH3-21 | VL1-40 | 0 | 0 |
| ADI-25497 | Site III | 0.000 | VH3-7 | VK1D-16 | 0 | 0 |
| ADI-25502 | Site III | 0.043 | VH1-69 | VL3-27 | 0 | 1 |
| ADI-25503 | Site III | 0.277 | VH1-69 | VL3-1 | 0 | 0 |
| ADI-25505 | Site III | 0.000 | VH3-21 | VL1-40 | 0 | 0 |
| ADI-25514 | Site II | 0.493 | VH1-69 | VL3-1 | 0 | 0 |
| ADI-25517 | Site I | 0.107 | VH1-2 | VL2-14 | 0 | 1 |
| ADI-25518 | Site I | 0.116 | VH1-2 | VL2-14 | 0 | 1 |
| ADI-25524 | Site III | 0.000 | VH3-21 | VL1-40 | 0 | 0 |
| ADI-25532 | Site III | 0.000 | VH3-21 | VL1-40 | 0 | 0 |
| ADI-25533 | Site I | 0.006 | VH1-2 | VL2-14 | 0 | 1 |
| ADI-25542 | Site I | 0.000 | VH3-23 | VL8-61 | 0 | 0 |
| ADI-25547 | Unknown | 0.000 | VH3-53 | VK1-12 | 0 | 0 |
| ADI-25548 | Unknown | 0.010 | VH3-53 | VL2-11 | 0 | 0 |
| ADI-25549 | Site III | 0.702 | VH3-21 | VL1-40 | 0 | 0 |
| ADI-25555 | Site III | 0.029 | VH3-21 | VL1-40 | 0 | 0 |
| ADI-25556 | Site III | 0.000 | VH3-21 | VL1-40 | 0 | 0 |
| ADI-25557 | Site III | 0.000 | VH3-21 | VL1-40 | 0 | 0 |
| ADI-25559 | Site III | 0.000 | VH3-21 | VL1-40 | 0 | 0 |
| ADI-25562 | Site III | 0.105 | VH3-11 | VL1-40 | 0 | 0 |
| ADI-25565 | Site III | 0.108 | VH3-21 | VL1-40 | 0 | 0 |
| ADI-25567 | Site I | 0.000 | VH4-34 | VK4-1 | 0 | 0 |
| ADI-25569 | Site I | 0.000 | VH3-74 | VL3-25 | 0 | 1 |
| ADI-25572 | Site IV | 0.184 | VH1-2 | VK2-28 | 0 | 0 |
| ADI-25573 | Unknown | 0.000 | VH1-46 | VL3-21 | 0 | 1 |
| ADI-25575 | Unknown | 0.000 | VH1-46 | VL3-21 | 0 | 0 |
| ADI-25576 | Site I | 0.000 | VH3-74 | VL6-57 | 0 | 0 |
| ADI-25577 | Site III | 0.028 | VH3-21 | VL1-40 | 0 | 0 |
| ADI-25587 | Unknown | 0.000 | VH3-33 | VL2-14 | 0 | 1 |
| ADI-25588 | Site III | 0.100 | VH3-21 | VL1-40 | 0 | 0 |
| ADI-25595 | Site III | 0.012 | VH3-21 | VL1-40 | 0 | 0 |
| ADI-25598 | Site I | 0.106 | VH4-39 | VL3-25 | 5 | 1 |
| ADI-19420 | Site III | 0.709 | VH3-21 | VL1-40 | 0 | 0 |
| ADI-19421 | Site III | 0.120 | VH3-30 | VL2-14 | 0 | 1 |
| ADI-19422 | Site IV | 0.102 | VH3-30 | VL3-21 | 0 | 0 |
| ADI-19424 | Site IV | 0.020 | VH3-66 | VL3-21 | 4 | 0 |
| ADI-19425 | Site III | 0.007 | VH3-21 | VL1-40 | 0 | 0 |
| ADI-19426 | Site IV | 0.023 | VH4-59 | VL3-1 | 0 | 0 |
| ADI-19427 | Site III | 0.022 | VH3-21 | VL1-40 | 3 | 4 |
| ADI-19428 | Site III | 0.058 | VH3-21 | VL1-40 | 0 | 0 |
| ADI-19429 | Site I | 0.616 | VH4-39 | VL1-40 | 0 | 0 |
| ADI-19430 | Site I | 0.744 | VH1-69 | VK2-28 | 0 | 0 |
| ADI-19431 | Site III | 0.068 | VH3-21 | VL1-40 | 0 | 0 |
| ADI-19432 | Site IV | 0.000 | VH1-46 | VK1-05 | 0 | 0 |
| ADI-19433 | Site III | 0.000 | VH3-21 | VL1-40 | 0 | 0 |
| ADI-19435 | Site I | 0.000 | VH4-61 | VL3-01 | 0 | 1 |
| ADI-19436 | Site I | 0.073 | VH4-39 | VL3-1 | 0 | 0 |
| ADI-19437 | Unknown | 0.000 | VH1-18 | VK1-12 | 0 | 0 |
| ADI-19439 | Site III | 0.000 | VH3-23 | VK1-05 | 0 | 0 |
| ADI-19440 | Site III | 0.000 | VH3-48 | VL1-40 | 0 | 0 |
| ADI-19441 | Site I | 0.417 | VH1-69 | VK1-39 | 0 | 0 |
| ADI-19444 | Site V | 0.000 | VH1-18 | VK4-01 | 0 | 0 |
| ADI-19445 | Unknown | 0.002 | VH4-4 | VL3-21 | 0 | 1 |
| ADI-19447 | Site III | 0.029 | VH4-39 | VL3-01 | 0 | 0 |
| ADI-19448 | Site III | 0.000 | VH3-21 | VL1-40 | 0 | 0 |
| ADI-19449 | Site III | 0.142 | VH3-21 | VL1-40 | 0 | 0 |
| ADI-19450 | Unknown | 0.000 | VH3-23 | VK1-05 | 0 | 0 |
| ADI-19454 | Site III | 0.012 | VH3-21 | VL2-14 | 0 | 1 |

TABLE 2-continued

| | | | Summary of antibody characteristics | | |
|---|---|---|---|---|---|
| ADI-19455 | Site III | 0.007 VH3-21 | VL1-40 | 0 | 0 |
| ADI-19457 | Site III | 0.000 VH3-21 | VL1-40 | 0 | 0 |
| ADI-19458 | Site III | 0.101 VH3-21 | VL1-40 | 3 | 0 |
| ADI-19459 | Site IV | 0.026 VH3-66 | VL3-21 | 0 | 0 |
| ADI-19460 | Site I | 0.076 VH4-34 | VK1-39 | 0 | 0 |
| ADI-19461 | Site II | 0.000 VH3-11 | VL3-21 | 0 | 0 |
| ADI-19462 | Site IV | 0.000 VH2-5 | VK1-5 | 0 | 0 |
| ADI-19463 | Unknown | 0.065 VH4-304 | VK4-1 | 0 | 0 |
| ADI-19465 | Site III | 0.000 VH3-21 | VL1-40 | 0 | 0 |
| ADI-19506 | Unknown | 0.424 VH1-18 | VK2-28 | 0 | 0 |
| ADI-19507 | Site III | 0.000 VH3-21 | VL1-40 | 0 | 0 |
| ADI-19509 | Site III | 0.000 VH3-21 | VL1-40 | 0 | 0 |
| ADI-19510 | Site III | 0.108 VH3-21 | N/A | 6 | 2 |
| ADI-19511 | Unknown | 0.444 VH2-5 | VK1-17 | 0 | 0 |
| ADI-24792 | Site III | 0.000 VH3-11 | VL1-40 | 5 | 2 |
| ADI-24793 | Site I | 0.000 VH5-51 | VL6-57 | 1 | 2 |
| ADI-24795 | Site III | 0.000 VH3-21 | VL1-40 | 0 | 2 |
| ADI-24796 | Unknown | 0.000 VH3-33 | VL3-1 | 0 | 0 |
| ADI-24798 | Site I | 0.000 VH4-59 | VL3-1 | 0 | 0 |
| ADI-24799 | Site III | 0.000 VH3-21 | VL1-40 | 0 | 0 |
| ADI-24800 | Site III | 0.843 VH3-21 | VL1-40 | 0 | 2 |
| ADI-24801 | Site III | 0.158 VH1-18 | VL3-1 | 0 | 1 |
| ADI-24803 | Unknown | 0.077 VH3-23 | VK3-20 | 6 | 3 |
| ADI-24805 | Site III | 0.000 VH3-21 | VL1-40 | 0 | 0 |
| ADI-24807 | Site I | 0.083 VH4-39 | VL3-1 | 0 | 0 |
| ADI-24808 | Site I | 0.000 VH1-2 | VL2-8 | 0 | 0 |
| ADI-24811 | Site IV | 0.112 VH1-8 | VL3-21 | 0 | 0 |
| ADI-24812 | Site V | 0.000 VH3-23 | VL3-25 | 4 | 1 |
| ADI-24813 | Site IV | 0.000 VH3-9 | VL1-40 | 0 | 0 |
| ADI-24814 | Site IV | 0.117 VH3-30 | VK3-20 | 2 | 3 |
| ADI-24815 | Site III | 0.000 VH3-21 | VL1-40 | 0 | 0 |
| ADI-24816 | Site I | 0.102 VH1-8 | VL3-1 | 0 | 0 |
| ADI-24817 | Site III | 0.000 VH3-21 | VL1-40 | 0 | 0 |
| ADI-24818 | Site I | 0.000 VH1-2 | VL2-14 | 0 | 1 |
| ADI-24819 | Site III | 0.000 VH3-21 | VL1-40 | 0 | 0 |
| ADI-24820 | Unknown | 0.248 VH1-69 | VK1-39 | 0 | 0 |
| ADI-24821 | Site II | 0.000 VH3-9 | VL1-44 | 0 | 0 |
| ADI-24822 | Site III | 0.000 VH3-21 | VL1-40 | 0 | 0 |
| ADI-24823 | Site III | 0.000 VH3-21 | VL1-40 | 0 | 0 |
| ADI-24824 | Site III | 0.000 VH4-59 | VK1-8 | 0 | 0 |
| ADI-24825 | Unknown | 0.338 VH1-8 | VK2-28 | 0 | 0 |
| ADI-24826 | Site III | 0.102 VH3-21 | VL2-14 | 0 | 1 |
| ADI-24827 | Site 0 | 0.000 VH3-66 | VK3-15 | 1 | 0 |
| ADI-24828 | Site III | 0.109 VH3-21 | VL1-40 | 9 | 2 |
| ADI-24829 | Site III | 0.000 VH3-21 | VL1-40 | 0 | 0 |
| ADI-24830 | Site V | 0.000 VH1-69 | VK2-28 | 0 | 0 |
| ADI-24831 | Site III | 0.164 VH3-21 | VL1-40 | 0 | 0 |
| ADI-24832 | Site III | 0.360 VH3-21 | VL1-40 | 6 | 1 |
| ADI-24833 | Site III | 0.000 VH3-21 | VL1-40 | 0 | 0 |
| ADI-24834 | Site I | 0.293 VH3-23 | VK1-5 | 1 | 1 |
| ADI-24835 | Site III | 0.000 VH3-21 | VL1-40 | 5 | 5 |
| ADI-24836 | Unknown | 0.106 VH3-9 | VK1-39 | 0 | 0 |
| ADI-24837 | Unknown | 0.000 VH4-59 | VL1-51 | 0 | 0 |
| ADI-24838 | Site III | 0.122 VH3-21 | VL1-40 | 0 | 0 |
| ADI-24839 | Site III | 0.000 VH3-21 | VL1-40 | 0 | 0 |
| ADI-24840 | Site III | 0.000 VH3-21 | VL1-40 | 0 | 0 |
| ADI-24841 | Unknown | 0.144 VH1-3 | VK3-15 | 0 | 0 |
| ADI-24842 | Site III | 0.000 VH3-21 | VL1-40 | 0 | 2 |
| ADI-24843 | Unknown | 0.039 VH4-304 | VK4-1 | 0 | 0 |
| ADI-24845 | Site III | 0.000 VH3-21 | VL2-14 | 0 | 0 |
| ADI-24846 | Unknown | 0.000 VH3-21 | VL1-47 | 0 | 0 |
| ADI-24847 | Unknown | 0.012 VH3-21 | VL1-40 | 1 | 0 |
| ADI-24848 | Site V | 0.644 VH3-21 | VL1-40 | 0 | 0 |
| ADI-24849 | Site 0 | 0.741 VH3-43 | VK1-33 | 2 | 0 |
| ADI-24850 | Site III | 0.574 VH3-21 | VL1-40 | 0 | 0 |
| ADI-24851 | Site I | 0.675 VH1-2 | VL2-8 | 0 | 0 |
| ADI-24852 | Site IV | 0.277 VH1-3 | VL3-1 | 1 | 2 |
| ADI-24854 | Unknown | 0.658 VH3-21 | VL1-40 | 0 | 0 |
| ADI-24855 | Site III | 0.600 VH3-21 | VL1-40 | 0 | 0 |
| ADI-24856 | Site I | 0.101 VH1-18 | VK3-20 | 0 | 0 |
| ADI-24857 | Site III | 0.000 VH3-21 | VL1-40 | 0 | 0 |
| ADI-24858 | Site III | 0.119 VH3-21 | VL1-40 | 0 | 0 |
| ADI-24859 | Site III | 0.000 VH3-21 | VL1-40 | 0 | 0 |
| ADI-24860 | Site III | 0.000 VH3-11 | VL1-40 | 4 | 2 |
| ADI-24861 | Site III | 0.000 VH3-21 | VL1-40 | 2 | 0 |
| ADI-24862 | Unknown | 0.000 VH4-31 | VL3-1 | 0 | 0 |
| ADI-24863 | Site III | 0.000 VH3-21 | VL1-40 | 1 | 0 |
| ADI-19467 | Site III | 0.010 VH3-21 | VL1-40 | 0 | 0 |

TABLE 2-continued

| | | | | | | |
|---|---|---|---|---|---|---|
| | | Summary of antibody characteristics | | | | |
| ADI-19468 | Site I | 0.000 | VH4-39 | VL6-57 | 0 | 0 |
| ADI-19469 | Site I | 0.143 | VH4-b | VK3-11 | 0 | 0 |
| ADI-19470 | Site II | 0.110 | VH3-30 | VL3-1 | 0 | 0 |
| ADI-19471 | Unknown | 0.040 | VH3-64 | VL6-57 | 0 | 0 |
| ADI-19473 | Site I | 0.063 | VH5-51 | VL6-57 | 0 | 0 |
| ADI-19474 | Site I | 0.032 | VH5-51 | VL6-57 | 0 | 0 |
| ADI-19475 | Site V | 0.000 | VH1-18 | VK2-30 | 10 | 2 |
| ADI-19476 | Unknown | 0.093 | VH2-5 | VL2-11 | 2 | 3 |
| ADI-19478 | Unknown | 0.033 | VH4-39 | VL1-36 | 5 | 2 |
| ADI-19479 | Unknown | 0.012 | VH1-69 | VK2-30 | 2 | 3 |
| ADI-19480 | Site IV | 0.012 | VH3-21 | VL6-57 | 6 | 3 |
| ADI-19481 | Unknown | 0.000 | VH3-43 | VK1-39 | 1 | 3 |
| ADI-19482 | Site II | 0.159 | VH4-34 | VK1-5 | 11 | 1 |
| ADI-19483 | Site IV | 0.050 | VH5-51 | VL6-57 | 4 | 2 |
| ADI-19484 | Unknown | 0.000 | VH4-30 | VK1-39 | 5 | 2 |
| ADI-19485 | Site I | 0.039 | VH4-31 | VK3-15 | 11 | 3 |
| ADI-19486 | Site I | 0.006 | VH4-59 | VL2-14 | 5 | 0 |
| ADI-19487 | Unknown | 0.104 | VH2-70 | VK1-39 | 3 | 0 |
| ADI-19488 | Unknown | 0.000 | VH1-24 | VK2-28 | 0 | 0 |
| ADI-19489 | Site IV | 0.000 | VH2-70 | VK1-17 | 2 | 0 |
| ADI-19490 | Unknown | 0.000 | VH3-15 | VK2-28 | 0 | 0 |
| ADI-19491 | Unknown | 0.000 | VH2-5 | VL1-40 | 0 | 0 |
| ADI-19492 | Site IV | 0.034 | VH5-51 | VL6-57 | 1 | 2 |
| ADI-19493 | Site I | 0.037 | VH4-34 | VL3-1 | 0 | 0 |
| ADI-19494 | Site 0 | 0.065 | VH1-69 | VL2-14 | 4 | 1 |
| ADI-19495 | Unknown | 0.047 | VH4-59 | VK1-12 | 0 | 0 |
| ADI-19496 | Unknown | 0.000 | VH3-30 | VK4-1 | 1 | 1 |
| ADI-19497 | Site I | 0.002 | VH1-46 | VL6-57 | 0 | 0 |
| ADI-19498 | Site I | 0.045 | VH3-66 | VL3-25 | 1 | 0 |
| ADI-19499 | Site I | 0.089 | VH4-39 | VL6-57 | 0 | 0 |
| ADI-19500 | Unknown | 0.000 | VH3-48 | VK1-8 | 0 | 0 |
| ADI-19501 | Site V | 0.000 | VH1-18 | VK2-30 | 6 | 2 |
| ADI-19502 | Unknown | 0.000 | VH3-30 | VK4-1 | 5 | 2 |
| ADI-19503 | Site I | 0.040 | VH1-46 | VL3-10 | 0 | 0 |
| ADI-19505 | Site IV | 0.039 | VH5-51 | VL3-9 | 5 | 1 |
| ADI-22756 | Unknown | 0.171 | VH3-30 | VK3-20 | 6 | 4 |
| ADI-22757 | Site V | 0.000 | VH1-18 | VK2-30 | 7 | 4 |
| ADI-22758 | Site III | 0.000 | VH3-21 | VL1-40 | 5 | 3 |
| ADI-22759 | Site III | 0.018 | VH3-21 | VL1-40 | 9 | 3 |
| ADI-22760 | Site II | 0.000 | VH3-9 | VL1-47 | 5 | 4 |
| ADI-22762 | Site I | 0.000 | VH6-1 | VL1-40 | 7 | 4 |
| ADI-22763 | Site I | 0.000 | VH3-48 | VK1-39 | 9 | 3 |
| ADI-22764 | Site I | 0.336 | VH4-4 | VK1-39 | 5 | 12 |
| ADI-22765 | Site V | 0.000 | VH3-21 | VL1-40 | 0 | 0 |
| ADI-22766 | Unknown | 0.000 | VH3-9 | VL2-8 | 0 | 1 |
| ADI-22767 | Site III | 0.033 | VH3-21 | VL1-40 | 0 | 0 |
| ADI-22768 | Site I | 0.000 | VH3-48 | VK1-39 | 0 | 0 |
| ADI-22769 | Unknown | 0.011 | VH3-72 | VL3-1 | 0 | 0 |
| ADI-22770 | Unknown | 0.004 | VH2-70 | VL3-1 | 0 | 0 |
| ADI-22771 | Site III | 0.010 | VH3-21 | VL1-40 | 0 | 0 |
| ADI-22772 | Unknown | 0.000 | VH3-30 | VL3-1 | 0 | 0 |
| ADI-22773 | Site V | 0.000 | VH1-18 | VK2-30 | 0 | 0 |
| ADI-22774 | Site III | 0.000 | VH3-21 | VL1-40 | 0 | 4 |
| ADI-22775 | Unknown | 0.000 | VH3-33 | VK1-12 | 4 | 2 |
| ADI-22776 | Unknown | 0.000 | VH3-11 | VL3-21 | 0 | 0 |
| ADI-22777 | Site II | 0.000 | VH1-02 | VL3-01 | 12 | 13 |
| ADI-22778 | Site I | 0.109 | VH4-59 | VK1-39 | 12 | 7 |
| ADI-22779 | Site I | 0.000 | VH4-34 | VK1-39 | 7 | 8 |
| ADI-22780 | Site III | 0.004 | VH4-31 | VL2-14 | 0 | 2 |
| ADI-22781 | Site I | 0.033 | VH3-48 | VL3-01 | 0 | 0 |
| ADI-14333 | Site III | 0.046 | VH3-21 | VL1-40 | 7 | 4 |
| ADI-14334 | Site III | 0.005 | VH3-21 | VL1-40 | 14 | 4 |
| ADI-14335 | Site IV | 0.000 | VH3-49 | VK1-39 | 4 | 6 |
| ADI-14336 | Site V | 0.005 | VH1-18 | VK2-30 | 4 | 5 |
| ADI-14337 | Site III | 0.000 | VH3-21 | VL1-40 | 0 | 0 |
| ADI-14338 | Site I | 0.000 | VH3-30 | VK1-39 | 13 | 3 |
| ADI-14339 | Site IV | 0.040 | VH3-30 | VL3-25 | 14 | 4 |
| ADI-14340 | Site 0 | 0.050 | VH3-21 | VL3-21 | 7 | 5 |
| ADI-14341 | Unknown | 0.111 | VH3-48 | VK1-5 | 7 | 1 |
| ADI-14342 | Site I | 0.000 | VH2-26 | VK1-39 | 3 | 6 |
| ADI-14343 | Site I | 0.003 | VH1-69 | VK2-28 | 8 | 5 |
| ADI-14344 | Unknown | 0.113 | VH3-23 | VL3-1 | 8 | 7 |
| ADI-14345 | Site IV | 0.059 | VH1-24 | VK1-39 | 9 | 1 |
| ADI-14346 | Site III | 0.102 | VH3-21 | VL1-40 | 8 | 1 |
| ADI-14347 | Site III | 0.040 | VH3-21 | VL1-40 | 6 | 1 |
| ADI-14348 | Site I | 0.105 | VH3-30 | VL2-11 | 10 | 5 |
| ADI-14349 | Unknown | 0.000 | VH1-69 | VK4-1 | 9 | 3 |
| ADI-14350 | Site II | 0.027 | VH4-61 | VL1-40 | 13 | 2 |

TABLE 2-continued

| | | | | | |
|---|---|---|---|---|---|
| | | Summary of antibody characteristics | | | |
| ADI-14351 | Site IV | 0.027 VH3-74 | VL3-21 | 9 | 3 |
| ADI-14352 | Unknown | 0.142 VH4-304 | VK3-20 | 5 | 3 |
| ADI-14353 | Site I | 0.051 VH1-69 | VL2-14 | 10 | 4 |
| ADI-14354 | Site I | 0.069 VH1-69 | VL2-14 | 8 | 6 |
| ADI-14355 | Site IV | 0.038 VH2-5 | VL2-14 | 4 | 7 |
| ADI-14356 | Site I | 0.034 VH4-34 | VL3-25 | 0 | 0 |
| ADI-14357 | Unknown | 0.000 VH3-30 | VK1-39 | 5 | 4 |
| ADI-14358 | Site I | 0.103 VH3-11 | VL2-14 | 7 | 12 |
| ADI-14359 | Site I | 0.000 VH2-70 | VK1-39 | 1 | 0 |
| ADI-14360 | Site IV | 0.000 VH1-3 | VK2-28 | 2 | 0 |
| ADI-14361 | Unknown | 0.068 VH3-23 | VL1-40 | 14 | 7 |
| ADI-14362 | Site I | 0.389 VH3-23 | VK1-39 | 2 | 1 |
| ADI-14363 | Site IV | 0.000 VH3-11 | VK3-20 | 6 | 4 |
| ADI-14364 | Site 0 | 0.104 VH5-51 | VL3-21 | 3 | 0 |
| ADI-14365 | Site IV | 0.000 VH1-24 | VK1-39 | 8 | 4 |
| ADI-14366 | Unknown | 0.000 VH1-18 | VK1-39 | 8 | 8 |
| ADI-14367 | Unknown | 0.000 VH3-23 | VK3-20 | 10 | 2 |
| ADI-14368 | Site II | 0.106 VH3-15 | VL3-21 | 4 | 6 |
| ADI-14369 | Unknown | 0.059 VH1-69 | VL1-44 | 6 | 6 |
| ADI-14370 | Unknown | 0.726 VH3-30 | VL2-8 | 6 | 0 |
| ADI-14371 | Unknown | 0.000 VH3-23 | VK1-39 | 10 | 8 |
| ADI-14372 | Unknown | 0.000 VH3-23 | VK1-6 | 11 | 3 |
| ADI-14373 | Site I | 0.000 VH4-34 | VK3-15 | 4 | 0 |
| ADI-14374 | Unknown | 0.103 VH3-43 | VL3-21 | 6 | 13 |
| ADI-14375 | Unknown | 0.019 VH3-23 | VL1-40 | 10 | 6 |
| ADI-14376 | Site I | 0.085 VH3-74 | VL3-10 | 7 | 3 |
| ADI-14377 | Unknown | 0.000 VH3-30 | VK1-17 | 5 | 0 |
| ADI-14378 | Unknown | 0.000 VH3-74 | VK1-39 | 3 | 3 |
| ADI-14379 | Unknown | 0.487 VH3-30 | VL3-1 | 5 | 11 |
| ADI-14380 | Unknown | 0.102 VH5-51 | VL1-51 | 5 | 2 |
| ADI-14381 | Site I | 0.009 VH3-48 | VK1-6 | 7 | 1 |
| ADI-14382 | Site I | 0.118 VH3-33 | VL2-14 | 8 | 5 |
| ADI-14383 | Site II | 0.100 VH2-5 | VL2-23 | 6 | 4 |
| ADI-14384 | Site I | 0.062 VH4-30 | VL3-21 | 7 | 7 |
| ADI-14385 | Site I | 0.028 VH5-51 | VL6-57 | 0 | 1 |
| ADI-14386 | Site I | 0.070 VH3-23 | VL3-1 | 6 | 7 |
| ADI-14388 | Unknown | 0.147 VH3-30 | VL7-43 | 2 | 4 |
| ADI-14389 | Site I | 0.181 VH3-15 | VK1-39 | 12 | 6 |
| ADI-14390 | Unknown | 0.129 VH4-b | VL2-23 | 1 | 3 |
| ADI-14391 | Unknown | 0.033 VH3-23 | VL3-10 | 11 | 4 |
| ADI-14392 | Unknown | 0.000 VH1-69 | VK3-11 | 2 | 0 |
| ADI-14393 | Site III | 0.199 VH3-21 | VL1-40 | 14 | 4 |
| ADI-14394 | Site III | 0.038 VH3-21 | VL1-40 | 0 | 0 |
| ADI-14395 | Site IV | 0.128 VH3-30 | VK1-5 | 0 | 0 |
| ADI-14396 | Unknown | 0.000 VH3-30 | VK1-33 | 0 | 0 |
| ADI-14397 | Site IV | 0.120 VH3-30 | VK1-5 | 0 | 0 |
| ADI-14399 | Unknown | 0.004 VH4-304 | VK3-11 | 7 | 4 |
| ADI-14400 | Unknown | 0.000 VH3-30 | VK1-6 | 8 | 1 |
| ADI-14401 | Site III | 0.005 VH3-21 | VL1-40 | 9 | 4 |
| ADI-14402 | Site V | 0.000 VH1-18 | VK2-30 | 3 | 2 |
| ADI-14403 | Site III | 0.010 VH3-11 | VL1-40 | 7 | 4 |
| ADI-14404 | Unknown | 0.037 VH3-48 | VK1-5 | 7 | 5 |
| ADI-14405 | Site IV | 0.031 VH1-18 | VL3-21 | 11 | 5 |
| ADI-14406 | Site I | 0.060 VH5-51 | VK2-28 | 10 | 1 |
| ADI-14407 | Site I | 0.000 VH3-33 | VK1-39 | 5 | 7 |
| ADI-14408 | Site I | 0.000 VH2-70 | VK1-39 | 5 | 5 |
| ADI-14409 | Unknown | 0.014 VH1-18 | VK4-1 | 6 | 4 |
| ADI-14410 | Unknown | 0.101 VH4-34 | VL1-47 | 8 | 6 |
| ADI-14411 | Unknown | 0.047 VH1-46 | VK1-39 | 7 | 5 |
| ADI-14412 | Site IV | 0.000 VH1-18 | VK3-20 | 9 | 5 |
| ADI-14413 | Unknown | 0.028 VH3-43 | VL1-44 | 9 | 6 |
| ADI-14414 | Unknown | 0.109 VH1-69 | VK3-11 | 15 | 7 |
| ADI-14415 | Unknown | 0.000 VH4-59 | VK1-9 | 7 | 5 |
| ADI-14416 | Site IV | 0.053 VH5-51 | VL6-57 | 23 | 5 |
| ADI-14417 | Unknown | 0.297 VH3-21 | VK3-15 | 9 | 3 |
| ADI-14418 | Site II | 0.000 VH1-69 | VK1-5 | 10 | 3 |
| ADI-14419 | Unknown | 0.325 VH3-30 | VK3-20 | 9 | 1 |
| ADI-14420 | Site IV | 0.000 VH3-43 | VK1-5 | 4 | 3 |
| ADI-14421 | Unknown | 0.055 VH5-51 | VK3-15 | 20 | 2 |
| ADI-14422 | Site I | 0.000 VH1-69 | VL1-40 | 1 | 0 |
| ADI-14423 | Unknown | 0.000 VH3-43 | VK1-17 | 7 | 0 |
| ADI-14424 | Site II | 0.051 VH5-51 | VL6-57 | 16 | 9 |
| ADI-14425 | Site I | 0.027 VH4-61 | VL2-14 | 5 | 2 |
| ADI-14426 | Site I | 0.072 VH3-30 | VL3-19 | 8 | 5 |
| ADI-14427 | Site I | 0.108 VH1-69 | VL2-11 | 9 | 1 |
| ADI-14428 | Unknown | 0.110 VH3-11 | VL3-21 | 4 | 2 |
| ADI-14654 | Unknown | 0.106 VH1-69 | VL3-19 | 10 | 5 |
| ADI-14655 | Site I | 0.000 VH3-15 | VK1-39 | 0 | 0 |

TABLE 2-continued

| | | | | | |
|---|---|---|---|---|---|
| | | | Summary of antibody characteristics | | |
| ADI-14656 | Site I | 0.050 | VH3-30 | VL3-19 | 8 | 5 |
| ADI-14657 | Site IV | 0.000 | VH1-18 | VK1-27 | 9 | 1 |
| ADI-14658 | Site I | 0.040 | VH3-33 | VL2-14 | 0 | 1 |
| ADI-14659 | Unknown | 0.000 | VH3-11 | VK3-20 | 9 | 10 |
| ADI-14571 | Unknown | 0.000 | VH1-69 | VK1-9 | 10 | 1 |
| ADI-14572 | Unknown | 0.148 | VH3-15 | VL1-44 | 4 | 3 |
| ADI-14573 | Unknown | 0.031 | VH1-18 | VL3-21 | 7 | 3 |
| ADI-14575 | Site I | 0.096 | VH1-69 | VL2-14 | 0 | 1 |
| ADI-14576 | Site V | 0.000 | VH1-18 | VK2-30 | 0 | 0 |
| ADI-14577 | Site V | 0.000 | VH1-18 | VK2-30 | 11 | 3 |
| ADI-14578 | Unknown | 0.120 | VH1-69 | VL1-51 | 6 | 6 |
| ADI-14579 | Site I | 0.117 | VH5-51 | VK1-27 | 2 | 0 |
| ADI-14580 | Unknown | 0.000 | VH1-69 | VK4-1 | 12 | 3 |
| ADI-14581 | Unknown | 0.000 | VH1-69 | VK3-15 | 13 | 3 |
| ADI-14582 | Site II | 0.104 | VH5-51 | VL6-57 | 15 | 8 |
| ADI-14583 | Site V | 0.000 | VH1-18 | VK2-30 | 10 | 4 |
| ADI-14584 | Unknown | 0.000 | VH1-18 | VK1-39 | 20 | 2 |
| ADI-14585 | Site V | 0.000 | VH1-18 | VK2-30 | 5 | 5 |
| ADI-14586 | Site III | 0.000 | VH3-11 | VL1-40 | 0 | 0 |
| ADI-14587 | Site III | 0.010 | VH3-21 | VL1-40 | 3 | 2 |
| ADI-14588 | Site IV | 0.000 | VH1-24 | VK1-39 | 9 | 2 |
| ADI-14589 | Site I | 0.000 | VH2-26 | VK1-39 | 6 | 8 |
| ADI-14590 | Site II | 0.000 | VH5-51 | VK1-13 | 3 | 2 |
| ADI-14591 | Unknown | 0.116 | VH5-a | VK1-39 | 7 | 4 |
| ADI-14592 | Site IV | 0.083 | VH5-51 | VL6-57 | 12 | 4 |
| ADI-14593 | Site IV | 0.017 | VH5-51 | VL6-57 | 7 | 4 |
| ADI-14594 | Unknown | 0.030 | VH1-18 | VL3-21 | 10 | 2 |
| ADI-14595 | Site I | 0.101 | VH3-48 | VK3-11 | 10 | 5 |
| ADI-14596 | Unknown | 0.052 | VH3-23 | VK1-39 | 2 | 0 |
| ADI-14597 | Site IV | 0.000 | VH3-43 | VK3-20 | 6 | 1 |
| ADI-14598 | Site I | 0.000 | VH1-69 | VK1-27 | 8 | 1 |
| ADI-14599 | Site IV | 0.092 | VH3-49 | VL6-57 | 7 | 2 |
| ADI-14600 | Site III | 0.069 | VH3-11 | VL1-40 | 3 | 1 |
| ADI-14601 | Unknown | 0.045 | VH3-23 | VK1-12 | 5 | 5 |
| ADI-14602 | Site IV | 0.114 | VH3-30 | VL3-1 | 6 | 5 |
| ADI-14603 | Unknown | 0.036 | VH5-51 | VK1-27 | 6 | 4 |
| ADI-14604 | Unknown | 0.110 | VH3-23 | VL1-44 | 11 | 7 |
| ADI-14605 | Unknown | 0.103 | VH2-70 | VL3-25 | 5 | 6 |
| ADI-14606 | Unknown | 0.000 | VH3-66 | VK3-15 | 4 | 5 |
| ADI-14607 | Site IV | 0.075 | VH3-30 | VL3-25 | 10 | 8 |
| ADI-20959 | Site V | 0.000 | VH1-18 | VK2-30 | 7 | 5 |
| ADI-20960 | Site II | 0.102 | VH4-34 | VK1-5 | 14 | 7 |
| ADI-20961 | Site III | 0.059 | VH3-21 | VL1-40 | 20 | 5 |
| ADI-20962 | Site V | 0.000 | VH1-18 | VK2-30 | 10 | 2 |
| ADI-20963 | Site I | 0.051 | VH3-21 | VL3-21 | 17 | 9 |
| ADI-20964 | Site V | 0.000 | VH1-18 | VK2-30 | 4 | 2 |
| ADI-20965 | site IV | 0.109 | VH1-18 | VL3-21 | 11 | 6 |
| ADI-20966 | Site III | 0.035 | VH3-21 | VL1-40 | 20 | 8 |
| ADI-20967 | Site I | 0.000 | VH3-30 | VK2-28 | 11 | 1 |
| ADI-20968 | site IV | 0.000 | VH4-34 | VK1-33 | 11 | 10 |
| ADI-20969 | Site III | 0.094 | VH3-21 | VL1-40 | 13 | 6 |
| ADI-20970 | Unknown | 0.000 | VH3-15 | VK1-33 | 3 | 5 |
| ADI-20971 | Site I | 0.000 | VH3-21 | VK3-15 | 20 | 7 |
| ADI-20972 | Site I | 0.103 | VH4-34 | VL2-14 | 13 | 5 |
| ADI-20973 | Site III | 0.096 | VH3-21 | VL1-40 | 13 | 6 |
| ADI-20974 | Site III | 0.107 | VH3-21 | VL1-40 | 18 | 6 |
| ADI-20975 | site IV | 0.028 | VH1-18 | VL3-21 | 20 | 8 |
| ADI-20976 | Site I | 0.000 | VH3-23 | VK1-39 | 33 | 10 |
| ADI-20977 | Unknown | 0.000 | VH3-23 | VK3-20 | 3 | 1 |
| ADI-20978 | Site V | 0.000 | VH1-18 | VK2-30 | 8 | 1 |
| ADI-20979 | Site 0 | 0.034 | VH4-59 | VL2-14 | 8 | 5 |
| ADI-20980 | Unknown | 0.000 | VH4-61 | VK3-11 | 9 | 7 |
| ADI-20981 | Unknown | 0.352 | VH4-304 | VK1-12 | 18 | 8 |
| ADI-20982 | Unknown | 0.000 | VH4-61 | VK1-5 | 15 | 7 |
| ADI-20983 | Site I | 0.000 | VH3-64 | VK1-33 | 13 | 5 |
| ADI-20984 | Site IV | 0.026 | VH1-24 | VK1-39 | 23 | 32 |
| ADI-20986 | Site 0 | 0.000 | VH3-7 | VK3-20 | 9 | 6 |
| ADI-20987 | Unknown | 0.000 | VH3-33 | VK3-20 | 7 | 2 |
| ADI-20988 | Site V | 0.000 | VH1-18 | VK2-30 | 12 | 3 |
| ADI-20989 | Site I | 0.000 | VH4-4 | VK1-39 | 9 | 9 |
| ADI-20990 | Site I | 0.000 | VH3-30 | VK2-28 | 16 | 4 |
| ADI-20991 | Site III | 0.022 | VH3-11 | VL1-40 | 8 | 2 |
| ADI-20992 | Site V | 0.000 | VH3-7 | VK1-39 | 9 | 6 |
| ADI-20993 | Site I | 0.135 | VH3-30 | VK2-28 | 13 | 7 |
| ADI-20994 | site IV | 0.020 | VH1-18 | VL3-21 | 16 | 3 |
| ADI-20995 | Unknown | 0.000 | VH5-51 | N/A | 9 | 0 |
| ADI-20996 | Site I | 0.015 | VH2-70 | VK1-39 | 3 | 8 |
| ADI-20997 | Site I | 0.000 | VH3-30 | VK3-20 | 14 | 9 |

TABLE 2-continued

| | | | Summary of antibody characteristics | | |
|---|---|---|---|---|---|
| ADI-20998 | Site 0 | 0.109 | VH3-30 | VL2-11 | 9 | 5 |
| ADI-20999 | Unknown | 0.088 | VH4-39 | VL1-51 | 15 | 5 |
| ADI-21000 | Site I | 0.000 | VH2-26 | VK1-39 | 12 | 4 |
| ADI-21001 | Site IV | 0.000 | VH4-39 | VK4-1 | 10 | 1 |
| ADI-21002 | Site I | 0.010 | VH4-4 | VK1-39 | 16 | 7 |
| ADI-21003 | Site IV | 0.000 | VH4-34 | VK2-28 | 4 | 2 |
| ADI-21004 | Site IV | 0.000 | VH3-33 | VK4-1 | 8 | 12 |
| ADI-21005 | Unknown | 0.000 | VH3-43 | VK3-20 | 16 | 6 |
| ADI-21006 | Site III | 0.000 | VH2-5 | VK2-30 | 6 | 8 |
| ADI-21007 | Site IV | 0.082 | VH1-46 | VL6-57 | 12 | 3 |
| ADI-21008 | Site I | 0.000 | VH4-34 | VK3-11 | 15 | 2 |
| ADI-21009 | Unknown | 0.040 | VH1-18 | VL2-23 | 20 | 9 |
| ADI-21010 | Site III | 0.000 | VH3-33 | VK1-5 | 15 | 6 |
| ADI-21011 | Site I | 0.109 | VH4-59 | VK1-39 | 23 | 9 |
| ADI-21012 | Site I | 0.018 | VH2-70 | VK1-39 | 7 | 7 |
| ADI-21013 | Site V | 0.000 | VH4-39 | VK3-20 | 13 | 6 |
| ADI-21014 | Site 0 | 0.112 | VH4-59 | VK1-33 | 24 | 10 |
| ADI-21015 | Site IV | 0.000 | VH1-24 | VK1-39 | 15 | 4 |
| ADI-21017 | Site V | 0.000 | VH1-18 | VK2-30 | 8 | 4 |
| ADI-21018 | Site III | 0.031 | VH3-21 | VL1-40 | 8 | 5 |
| ADI-21019 | Site IV | 0.000 | VH3-23 | VK2-28 | 15 | 3 |
| ADI-21021 | Site IV | 0.000 | VH4-34 | VK1-5 | 10 | 11 |
| ADI-21022 | Unknown | 0.003 | VH4-59 | VL3-21 | 8 | 3 |
| ADI-21023 | Site III | 0.060 | VH3-21 | VL1-40 | 16 | 8 |
| ADI-21025 | Site III | 0.033 | VH3-21 | VL1-40 | 11 | 4 |
| ADI-21026 | Site I | 0.225 | VH4-31 | VK4-1 | 9 | 7 |
| ADI-21027 | Site III | 0.008 | VH4-4 | VL1-40 | 15 | 5 |
| ADI-21028 | Unknown | 0.000 | VH3-11 | VK1-5 | 10 | 10 |
| ADI-21029 | Unknown | 0.000 | VH5-51 | VK1-39 | 14 | 3 |
| ADI-21030 | Site III | 0.060 | VH3-11 | VL1-40 | 12 | 8 |
| ADI-21031 | Unknown | 0.004 | VH4-61 | VK3-11 | 21 | 7 |
| ADI-21032 | Site III | 0.054 | VH3-21 | VL1-40 | 14 | 5 |
| ADI-21033 | Site 0 | 0.000 | VH5-51 | VK1-33 | 20 | 8 |
| ADI-21034 | Site I | 0.015 | VH5-a | VK3-20 | 11 | 5 |
| ADI-21035 | Site I | 0.033 | VH1-18 | VK1-5 | 14 | 8 |
| ADI-21036 | Site I | 0.101 | VH5-51 | VL2-23 | 16 | 16 |
| ADI-21037 | Site I | 0.122 | VH3-30 | VK2-28 | 13 | 4 |
| ADI-21038 | Site I | 0.000 | VH5-51 | VK3-20 | 15 | 1 |
| ADI-21039 | Site I | 0.102 | VH1-46 | VK2-28 | 11 | 0 |
| ADI-21040 | Unknown | 0.046 | VH4-4 | VL1-40 | 14 | 6 |
| ADI-21041 | Unknown | 0.000 | VH3-43 | VK1-39 | 3 | 3 |
| ADI-21042 | Site I | 0.000 | VH4-31 | VK1-5 | 18 | 7 |
| ADI-21043 | Site I | 0.059 | VH1-18 | VL3-21 | 8 | 4 |
| ADI-21044 | Unknown | 0.000 | VH5-51 | VK1-39 | 16 | 6 |
| ADI-21045 | Site III | 0.032 | VH3-21 | VL1-40 | 18 | 5 |
| ADI-21046 | Site IV | 0.089 | VH5-51 | VL1-40 | 16 | 7 |
| ADI-21047 | Site IV | 0.000 | VH4-34 | VK1-33 | 14 | 4 |
| ADI-21048 | site IV | 0.087 | VH1-18 | VL3-21 | 8 | 3 |
| ADI-21049 | Site III | 0.102 | VH3-21 | VL1-40 | 7 | 3 |
| ADI-21050 | Site V | 0.000 | VH1-18 | VK2-30 | 10 | 7 |
| ADI-21051 | Unknown | 0.000 | VH4-61 | VK3-11 | 14 | 6 |
| ADI-21052 | site IV | 0.085 | VH1-18 | VL3-21 | 2 | 3 |
| ADI-21053 | Site I | 0.027 | VH4-31 | VK1-39 | 37 | 1 |
| ADI-21054 | Site IV | 0.000 | VH3-30 | VK1-5 | 21 | 9 |
| ADI-21055 | Site I | 0.110 | VH3-33 | VL1-44 | 12 | 10 |
| ADI-21056 | Site III | 0.020 | VH3-21 | VL1-40 | 15 | 6 |
| ADI-21057 | Site 0 | 0.000 | VH5-51 | VK3-15 | 13 | 1 |
| ADI-21058 | Site III | 0.000 | VH4-304 | VK3-15 | 20 | 3 |
| ADI-21059 | Unknown | 0.000 | VH5-51 | VK1-39 | 14 | 8 |
| ADI-21060 | Site III | 0.105 | VH3-11 | VL1-40 | 26 | 6 |
| ADI-21061 | Site I | 0.084 | VH1-69 | VL2-14 | 22 | 8 |
| ADI-21062 | Site I | 0.000 | VH3-21 | VK1-39 | 20 | 9 |
| ADI-21063 | Site V | 0.000 | VH3-64 | VK1-39 | 7 | 3 |
| ADI-21064 | Site V | 0.000 | VH1-18 | VK2-30 | 16 | 3 |
| ADI-21065 | Unknown | 0.000 | VH3-23 | VK3-20 | 7 | 2 |
| ADI-21067 | Site IV | 0.000 | VH4-34 | N/A | 11 | 0 |
| ADI-21068 | Site III | 0.021 | VH4-4 | VL1-40 | 19 | 3 |
| ADI-21069 | site IV | 0.000 | VH1-18 | VL3-21 | 16 | 5 |
| ADI-21070 | Site II | 0.000 | VH3-23 | VK3-15 | 12 | 3 |
| ADI-21071 | Site I | 0.019 | VH3-33 | VK1-39 | 14 | 7 |
| ADI-21072 | Site III | 0.010 | VH3-21 | VL1-40 | 16 | 3 |
| ADI-21073 | Site I | 0.000 | VH3-48 | VK1-39 | 18 | 8 |
| ADI-21075 | Site III | 0.021 | VH3-21 | VL1-40 | 17 | 2 |
| ADI-21076 | Site III | 0.015 | VH3-21 | VL1-40 | 16 | 7 |
| ADI-21077 | Site III | 0.018 | VH3-11 | VL1-40 | 9 | 2 |
| ADI-21078 | Site III | 0.017 | VH3-11 | VL1-40 | 10 | 5 |
| ADI-21079 | Site III | 0.064 | VH3-11 | VL1-40 | 5 | 1 |
| ADI-21080 | Site III | 0.006 | VH3-11 | VL1-40 | 16 | 2 |

TABLE 2-continued

| | | | | Summary of antibody characteristics | | |
|---|---|---|---|---|---|---|
| ADI-21081 | Site III | 0.031 | VH3-11 | VL1-40 | 12 | 5 |
| ADI-21082 | Site III | 0.004 | VH3-21 | VL1-40 | 13 | 5 |
| ADI-21083 | Site 0 | 0.101 | VH4-4 | VL2-11 | 12 | 6 |
| ADI-21084 | site IV | 0.100 | VH1-18 | VL3-21 | 19 | 6 |
| ADI-21085 | Site III | 0.167 | VH3-21 | VL1-40 | 9 | 6 |
| ADI-21086 | Site III | 0.024 | VH3-11 | VL1-40 | 16 | 4 |
| ADI-21087 | Unknown | 0.000 | VH3-48 | VK1-5 | 7 | 1 |
| ADI-21089 | Site III | 0.065 | VH3-21 | VL1-40 | 11 | 3 |
| ADI-21090 | Site IV | 0.000 | VH3-11 | VK3-15 | 28 | 6 |
| ADI-21091 | Site I | 0.005 | VH5-a | VL1-51 | 13 | 6 |

Analysis of the relationship between binding affinity and neutralization potency demonstrated that the majority of highly potent neutralizing antibodies bound with high apparent affinity to preF ($K_D<1.0$ nM) and failed to bind to postF (FIG. 3D). In addition, although approximately 20% of the neutralizing antibodies isolated from infants≥6 mo. recognized both preF and postF, this type of neutralizing antibody was very rare in infants<3 mo. (FIGS. 3D and 4B), demonstrating that nearly all neutralizing antibodies in very young infants are preF-specific.

Figures 5A, 5B:
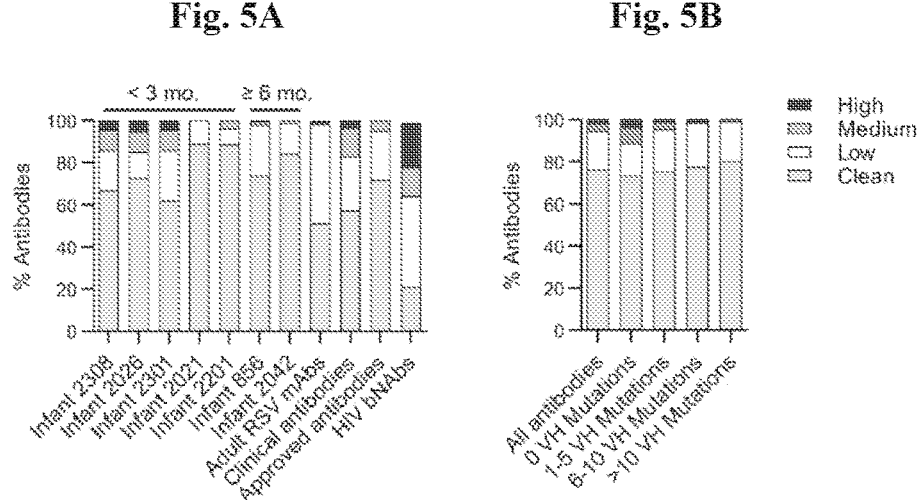
FIGS. 5A and 5B show that polyreactivity of infant antibodies decreases with increasing levels of somatic hypermutation. The percent of antibodies with high, medium, low, or undetectable polyreactivity is shown for each infant (FIG. 5A). Four panels of control antibodies, each with a variety of specificities, are shown for comparison: 364 RSV F-specific antibodies previously isolated from healthy adults, 138 antibodies currently in clinical trials, 39 antibodies that are approved for clinical use, and 14 broadly neutralizing HIV-1 antibodies. Infant antibodies are grouped according to the number of nucleotide mutations present in the $V_H$ gene (FIG. 5B).

Next, the polyreactivity of the infant antibodies was assessed using a previously described assay (Jain et al., 2017; Kelly et al., 2015; Xu et al., 2013). Although the fraction of medium-to-highly polyreactive antibodies was relatively low (≤15%) for all infants, there was a higher frequency of polyreactive antibodies in the infants<3 mo. compared to the infants≥6 mo. (FIG. 5A). This result could be related to differences in tolerance mechanisms in these two infant populations or to the higher frequency of anti-bodies containing little to no SHM in the younger infants. In support of the latter hypothesis, stratification of the antibodies based on their SHM levels showed that 12% of antibodies that lacked SHM displayed medium-to-high levels of polyreactivity, compared with only 2% of antibodies that contained>5 $V_H$ gene substitutions (FIG. 5B). This result is consistent with aprior study showing that the process of affinity maturation can result in decreased polyreactivity of human antibodies (Reed et al., 2016).

Figures 6A, 6B, 6C:
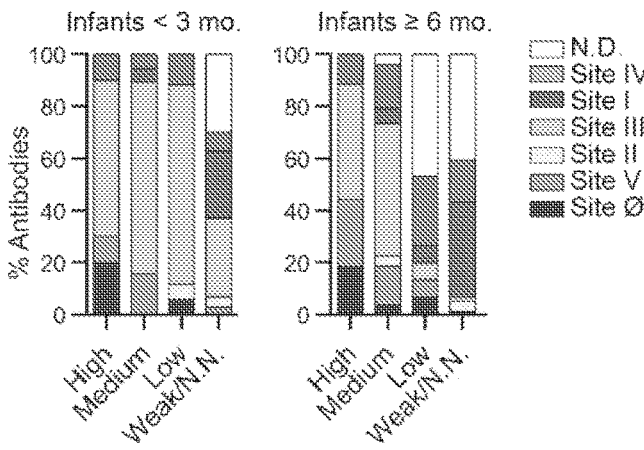
FIGS. 6A-6C show that infant responses are focused toward two antigenic sites with different neutralization sensitivities.
Figure 7A:
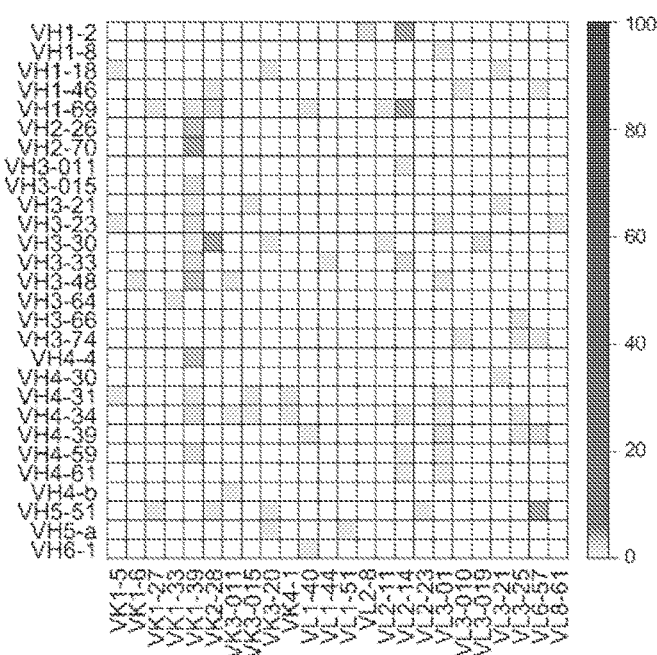
FIGS. 7A-7E show antibodies directed towards sites I and III utilize convergent sequence features and preferentially bind to different conformations of RSV F. Heat map of $V_H$ and VL germline gene usage for all site I-directed antibodies for which at least one $V_H/VL$ pairing was used in ≥0.5% of the antibodies directed against site I (FIG. 7A). A heat map of $V_H$ and VL germline gene usage for all site III-directed antibodies for which at least one $V_H/VL$ pairing was used in ≥0.5% of the antibodies directed against site III (FIG. 7B). WebLogos showing the CDR H3 sequence motifs for site I-directed (top) and site III-directed (bottom) antibodies (FIG. 7C). Apparent binding affinities for postF are plotted against apparent affinities for preF for antibodies directed against site I and site III (FIG. 7D, left panel). Antibodies that are preF-specific are boxed in. Apparent preF affinity for preF-specific antibodies is shown (FIG. 7D, right panel). Antibodies are grouped according to antigenic site and the percentage of antibodies in each group with high, medium, low, or weak neutralization potency is shown (FIG. 7E, left panel). Neutralization $IC_{50}$s is plotted for the antibodies in each group with detectable neutralization activity (FIG. 7E, right panel). Top, middle, and bottom dotted lines show $IC_{50}$s for motavizumab, MPE8 and D25, respectively.

Infant Antibody Responses are Focused Primarily on Two Antigenic Sites that have Different Neutralization Sensitivity To define the epitopes targeted by the infant antibodies, each antibody was tested for competition with other known RSV F-specific antibodies and assigned to an antigenic site based on the resulting competition profile (FIGS. 6A and 6B). In the three youngest infants, responses were dominated by antibodies directed against site III, whereas in the other infants, a larger proportion of the responses were directed against site I, and in some cases site IV (FIG. 6B). The proportion of antibodies recognizing preF-specific sites Ø and V at the apex of the preF molecule was low, particularly in the three youngest infants. Interestingly, analysis of the VH and VL germline gene usage for the site I-directed antibodies revealed that over 25% of the antibodies that recognized site I utilized the VK1-39 light chain gene (FIG. 7A). Although these site I-directed antibodies utilized a variety of $V_H$ genes, many possessed a convergent CDR H3 motif, generated from recombination of the DH3-

Figure 7B:
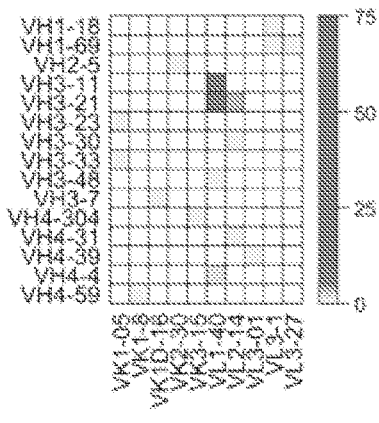
Figure 7C:
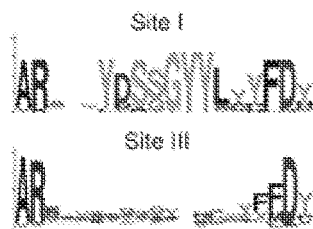

22 and JH-4 genes (FIG. 7C). In contrast, nearly 85% of antibodies that recognized site III utilized either the VH3-21/VL1-40 or the related VH3-11/VL1-40 germline gene pairing (FIG. 7B) and did not show evidence of a convergent CDR H3 sequence.

Figure 7D:
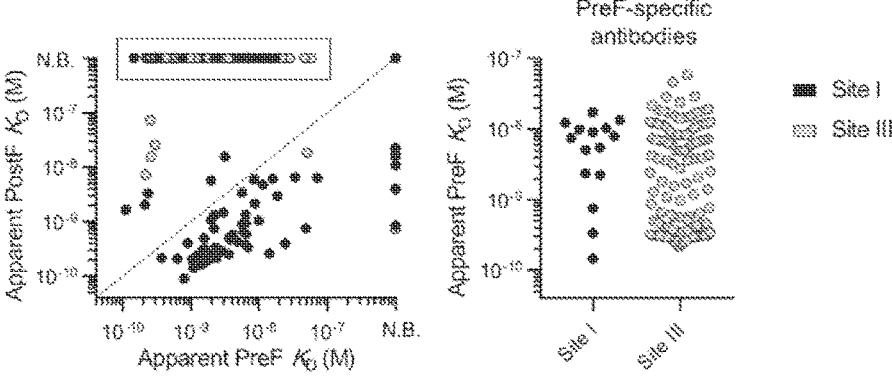
Figure 7E:
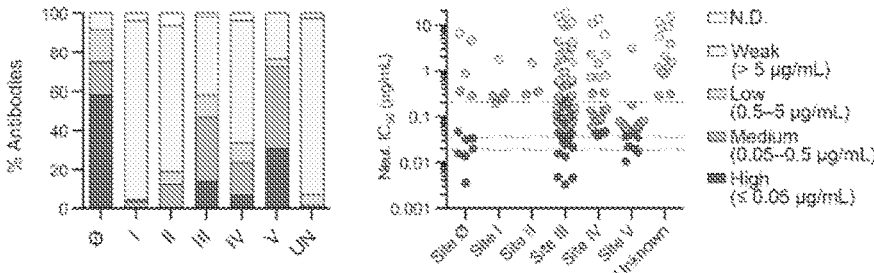

The majority of site III-directed antibodies were preF-specific and neutralizing, whereas antibodies that recognized site I preferentially bound to postF and tended to be weak or non-neutralizing (FIGS. 6C, 7D, and 7E). In infants<3 mo., 60% of antibodies that displayed highly potent neutralizing activity ($IC_{50}<0.05$ ug/ml) were directed against site III (FIG. 6C). Therefore, although antibodies against both sites I and III are readily elicited during natural RSV infection in infants, site III-directed antibodies can potently neutralize RSV whereas site I-directed antibodies are typically non-neutralizing.

Figures 8A, 8B, 8C, 8D:
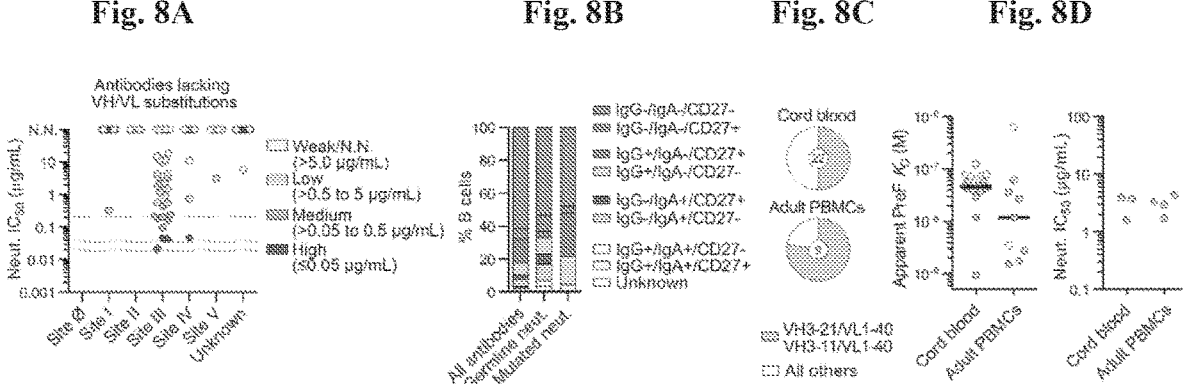
FIGS. 8A-8D show that germline antibodies targeting antigenic site III can potently neutralize RSV and are present in the naïve B cell repertoire.
Figure 10A:
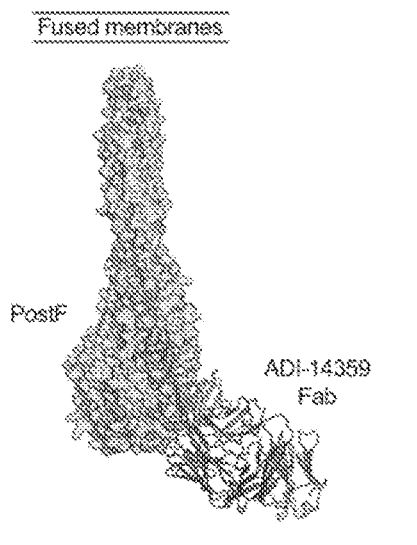
FIGS. 10A-10D show that the light chain mediates postF preference of ADI-14359. The crystal structure of ADI-14359 ($V_H2$-70/VK1-39) in complex with postF is shown at a 180° rotation with respect to FIG. 9 (FIG. 10A). Two protomers of postF are shown as molecular surfaces and the third protomer and ADI-14359 are shown as ribbons. The ADI-14359 heavy chain is gray and the light chain is white. The position of the fused viral and host-cell membranes is shown for orientation. The predicted interaction between preF and ADI-14359 was predicted by aligning the unbound preF structure to the ADI-14359-bound postF structure (FIG. 10B). The unfused viral membrane is shown for orientation. A magnified view of the ADI-14359-postF interface (FIG. 10C). One protomer is shown in ribbons. The ADI-14359 light chain CDR1 and FW3 form hydrogen bonds with two residues on β1 (Glu31 and Tyr33). A magnified view of the predicted ADI-14359-preF interface (FIG. 10D). In preF, β22 blocks access to β1 and would clash with the ADI-14359 light chain FW3 and CDR1. In addition, Glu31 is rotated away from ADI-14359 in preF, which would prevent hydrogen bonding with this residue.
Figure 10B:
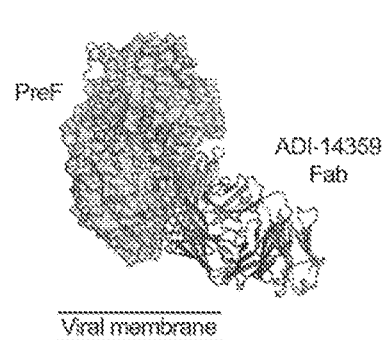
Figure 10C:
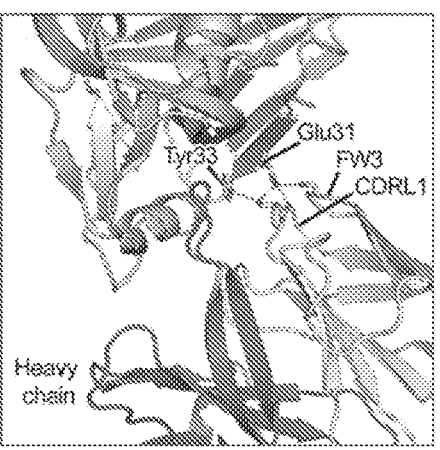
Figure 10D:
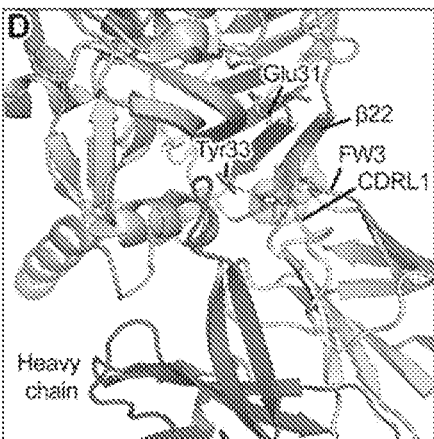

Site III-Directed Antibodies can Potently Neutralize RSV in the Absence of SHM and are Present in the Naïve B Cell Repertoire Next, the epitope specificities of the neutralizing antibodies that lacked SHM were analyzed (FIG. 8A). Of the 33 germline antibodies that displayed RSV-neutralizing activity, 27 targeted antigenic site III. Analysis of the index sort data revealed that approximately half of these antibodies originated from naïve B cells (IgG⁻IgA⁻ CD27⁻) and the other half originated from memory B cells that expressed IgG, IgA, or CD27 (FIG. 8B). The identification of neutralizing site III-directed antibodies from B cells that lacked both SHM and classical memory B cell markers led to an investigation of the occurrence of these antibody specificities in the naïve B cell repertoire. Therefore, 112 and 19 antibodies from RSV F-reactive cord blood B cells and adult naïve B cells, respectively, were cloned and expressed. Due to the low affinity of naïve B cell-derived antibodies, only 22/112 (20%) antibodies sorted from cord blood and 9/19 (47%) antibodies from adult naïve B cells bound with measurable affinity to RSV F as full-length IgGs. However, 11/22 (50%) and 7/9 (78%) of the RSV F binding antibodies from cord blood and adult naïve B cells, respectively, utilized VH3-21/VL1-40 or VH3-11/VL1-40 germline gene pairing (FIG. 8C). Of these 18 antibodies, the 13 with binding affinities that allowed for analysis in a competition assay were all shown to recognize antigenic site III (Table 3). Antibodies derived from naïve B cells isolated from cord blood or the PMBCs of healthy adults were tested for competition with three control IgGs and displayed profiles consistent with recognition of antigenic site III. Results are expressed as the fold reduction in antigen binding in the presence of saturating concentrations of competitor Fab relative to an antigen-only control. N.D.; not determined due to low binding affinity.

TABLE 3

| | | Competitor Fab | | |
|---|---|---|---|---|
| | | D25 (Antigenic site 0) | MPE8 (Antigenic site III) | Motavizumab (Antigenic site II) |
| Control IgGs | D25 | 153 | 1 | 1 |
| | MPE8 | 1 | 228 | 20 |
| | Motavizumab | 1 | 1 | 39 |
| IgGs derived from naïve B cells | ADI-32365 | 8 | 11 | 19 |
| | ADI-28517 | 11 | 23 | 55 |
| | ADI-32361 | 7 | 50 | 169 |
| | ADI-32367 | 7 | 13 | 35 |
| | ADI-31917 | 3 | 69 | 190 |
| | ADI-31918 | 2 | 11 | 30 |
| | ADI-31919 | 1 | 55 | 159 |
| | ADI-28537 | 3 | 52 | 156 |
| | ADI-31921 | 3 | 37 | 112 |
| | ADI-32360 | 2 | 128 | 416 |
| | ADI-32362 | 3 | 117 | 370 |
| | ADI-32363 | 2 | 176 | 537 |
| | ADI-32366 | 3 | 61 | 10 |
| | ADI-28522 | N.D. | N.D. | N.D. |
| | ADI-31920 | N.D. | N.D. | N.D. |
| | ADI-28523 | N.D. | N.D. | N.D. |
| | ADI-28526 | N.D. | N.D. | N.D. |
| | ADI-28527 | N.D. | N.D. | N.D. |

Naïve B cells that utilize the VH3-21/VL1-40 and VH3-11/VL1-40 gene pairs recognize site III The apparent binding affinities of these antibodies for preF were relatively high, ranging from 1.0-60 nM (FIG. 8C). In addition, approximately 40% of these site-III directed antibodies displayed neutralizing activity, with $IC_{50}$s ranging from 1.5-4.0 µg/mL (FIG. 8C). In contrast, none of the naïve B cell-derived antibodies that utilized other germline gene combinations showed detectible neutralizing activity (FIG. 8C). Collectively, these results indicate that site III-directed antibodies can neutralize RSV in the absence of SHM and that these types of antibodies are present in the naïve B cell repertoire.

a Site I-Directed Non-Neutralizing Antibody Recognizes postF Using a Convergent CDR H3 Motif and Germline-Encoded Regions of the VK1-39 Light Chain The structure of a site I-directed antibody, ADI-14359, in complex with postF was characterized to define the molecular determinants of the convergent antibody features (FIG. 9A) (Table 4).

TABLE 4

Crystallographic data collection and refinement statistics

| | Postfusion RSV F + ADI-14359 Fab | ADI-19425 Fab | Prefusion RSV F + ADI-19425 Fab + AM22 Fab |
|---|---|---|---|
| PDB ID | 6APB | 6APC | 6APD |
| Data collection | | | |
| Space group | $P2_12_12_1$ | $P2_12_12_1$ | $P4_12_12$ |
| Cell constants | | | |
| a, b, c (Å) | 88.5, 99.0, 323.3 | 61.2, 66.5, 126.0 | 229.5, 229.5, 304.1 |
| α, β, γ (°) | 90, 90, 90 | 90, 90, 90 | 90, 90, 90 |
| Wavelength (Å) | 1.1809 | 0.9792 | 0.9793 |
| Resolution (Å) | 51.1-3.0 (3.08-3.00) | 26.1-1.7 (1.73-1.70) | 50.9-4.1 (4.20-4.10) |
| Unique reflections | 57,978 (4,439) | 57,347 (2,940) | 64,175 (4,439) |
| $R_{merge}$ | 0.449 (1.662) | 0.069 (0.328) | 0.364 (1.545) |
| $R_{pim}$ | 0.177 (0.650) | 0.028 (0.153) | 0.108 (0.443) |
| I/σI | 5.2 (1.6) | 16.8 (4.2) | 6.3 (1.9) |
| $CC_{1/2}$ | 0.952 (0.564) | 0.998 (0.930) | 0.995 (0.609) |
| Completeness (%) | 100.0 (100.0) | 99.9 (99.4) | 99.9 (100.0) |
| Redundancy | 7.3 (7.4) | 6.8 (5.5) | 12.2 (13.0) |
| Wilson B-factors | 11.5 | 29.4 | 117.9 |
| Refinement | | | |
| Resolution (Å) | 51.1-3.0 (3.05-3.00) | 26.1-1.7 (1.73-1.70) | 50.9-4.1 (4.16-4.10) |
| Unique reflections | 57,820 (2,724) | 57,181 (2,645) | 64,084 (2,497) |
| $R_{work}/R_{free}$ (%) | 22.0/25.3 | 17.4/20.4 | 20.9/26.1 |
| No. atoms | | | |
| Protein | 13,264 | 3,233 | 30,005 |
| Ligand/ion | 42 | 10 | — |
| Water | — | 692 | — |

TABLE 4-continued

| | Crystallographic data collection and refinement statistics | | |
|---|---|---|---|
| | Postfusion RSV F + ADI-14359 Fab | ADI-19425 Fab | Prefusion RSV F + ADI-19425 Fab + AM22 Fab |
| B-factors | | | |
| Protein | 37.2 | 15.9 | 167.2 |
| Ligand/ion | 76.5 | 21.3 | — |
| Water | — | 30.2 | — |
| R.m.s. deviations | | | |
| Bond lengths (Å) | 0.004 | 0.003 | 0.003 |
| Bond angles (°) | 0.91 | 0.667 | 0.632 |
| Ramachandran | | | |
| Favored (%) | 95.9 | 97.5 | 95.1 |
| Allowed (%) | 3.8 | 2.1 | 4.7 |
| Outliers (%) | 0.4 | 0.5 | 0.2 |

Values in parentheses are for the highest-resolution shell.

The structure revealed that the CDR H3, generated from the convergent usage of DH3-22/JH-4, is inserted into a small groove near the top of the postF trimer (FIG. 9B) and makes a number of hydrogen bonds with postF residues in and around this groove (FIG. 9C). CDR H3 residues Tyr 100c and Tyr 100d (Kabat numbering), which are uncommon in D genes other than DH3-22, form hydrogen bonds with postF residues Glu31 and Glu378, respectively, which are located on the ridge surrounding the site I groove. The tip of the CDR H3 loop is composed of three small amino acids that allow the loop to fit into the groove and make hydrogen bonds with residues Lys42, Asp344, and Asn380 of postF. These small residues also allow the CDR H3 to stack against Trp314, which is positioned at the floor of the groove. In addition, ADI-14359 heavy chain residue Tyr 100g, which is unique to the JH4 gene, stacks against Tyr49 in the light chain, which may help properly orient the CDR H3.

Antibodies that utilized this convergent CDR H3 also showed a strong bias towards pairing with the VK1-39 light chain gene. Several germline-encoded residues within CDR L1 and the framework region 3 of VK1-39 form hydrogen bonds with Glu31 on postF (FIG. 9C). In addition, Tyr92 at the start of the CDR L3 is a unique feature of VK1-39, and forms a hydrogen bond with Ser35 on the $F_2$ subunit of postF. The light chain of ADI-14359 is predicted to clash substantially with β22 of preF, which rearranges during the transition to postF to allow formation of the six-helix bundle (FIG. 10). Therefore, preferential binding to postF by this type of antibody is mediated by the light chain.

Although site I-directed antibodies did not show convergent $V_H$ gene usage, the heavy chain utilized by ADI-14359 also makes critical interactions with postF (FIG. 9C). The only residue that is mutated from germline in ADI-14359, Arg50, forms a salt bridge with Asp52 in the CDR H2 and appears to assist in coordinating the electrpostatic interaction between Asp52, Asp56 and Asp58 of the CDR H2 with Lys390 on postF. Arg50 also forms a hydrogen bond with light chain residue Tyr96, a residue that is unique to the IGK-J2 gene utilized by ADI-14359. To investigate the contribution of these $V_H$ gene-mediated interactions to binding, the binding affinity of ADI-14359 Fab and the germline reverted variant (R50L) to postF was measured using surface plasmon resonance (SPR). This analysis revealed that the affinity of the germline reverted variant was reduced by more than 30-fold (FIG. 9D). Also, it was found that substitution of Lys390 on postF with alanine (K390A) almost entirely ablated ADI-14359 binding (FIG. 9D). The presence of three acidic residues in the CDR H2 therefore appears to be critical for the interaction of ADI-14359 with postF. However, the contribution of the CDR H2 to binding may vary among other members of this group, since many of the VH germlines utilized lack this acidic motif.

Figures 11A, 11B:
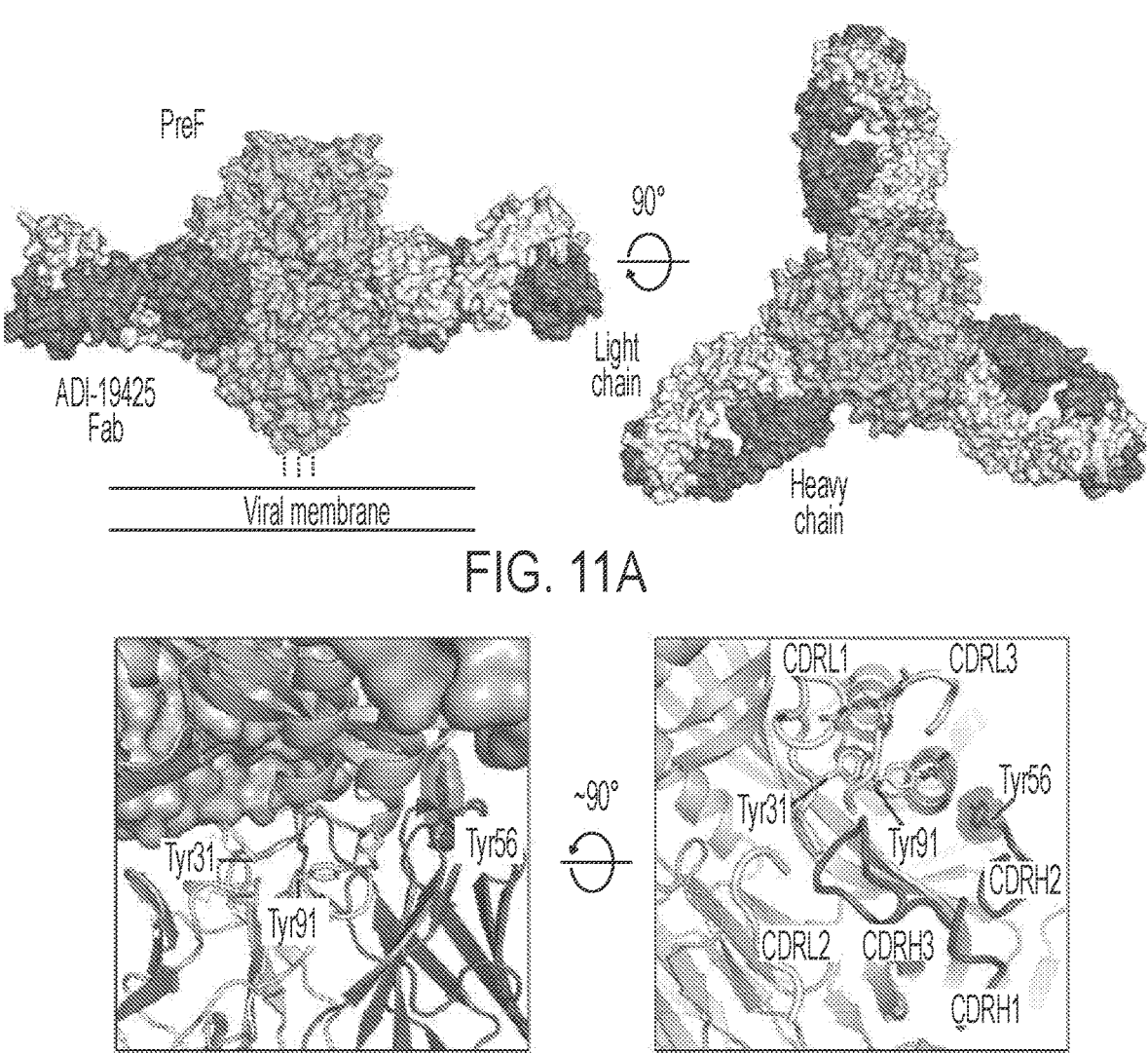
FIGS. 11A-11C show that neutralizing antibody ADI-19425 uses germline-encoded features for high-affinity binding to antigenic site III on preF.
Figure 11C:
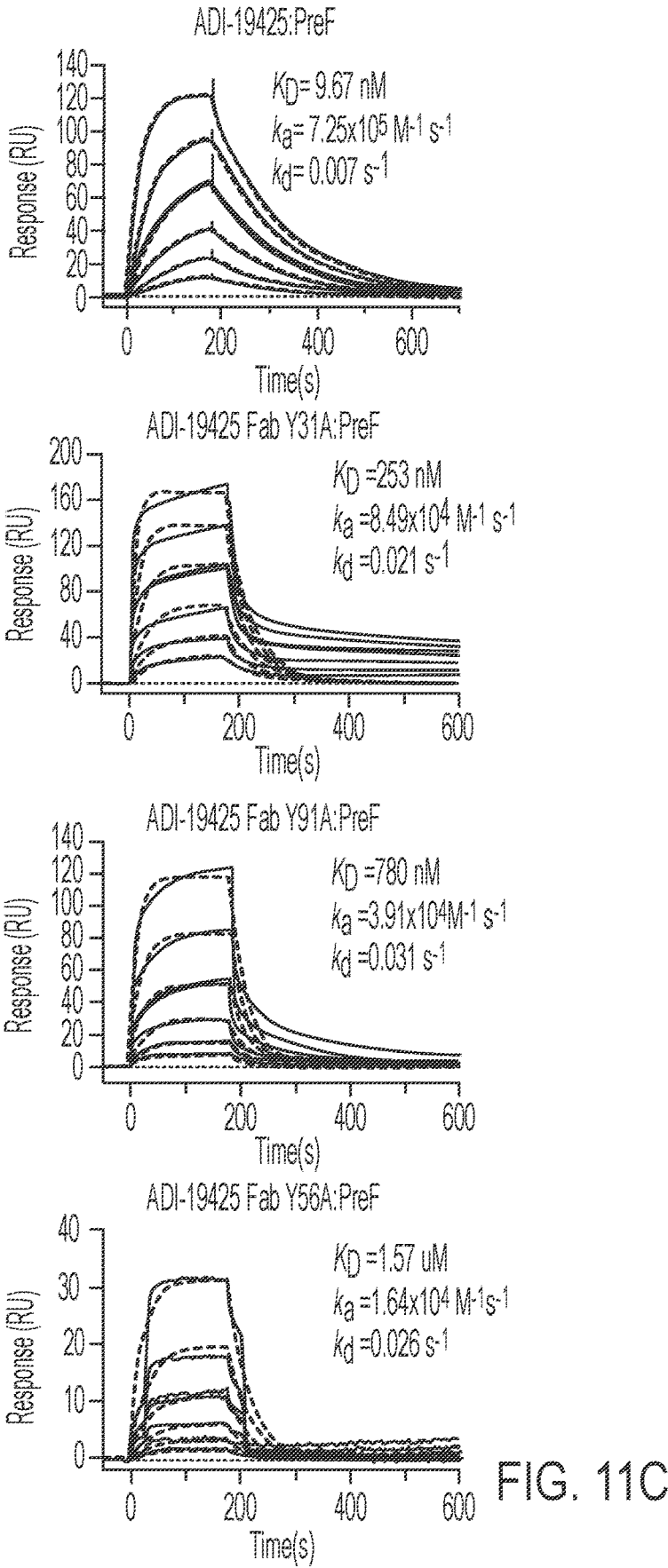

A Site III-Directed Neutralizing Antibody Utilizes Germline-Encoded Features of the VH3-21 and VL1-40 Genes for High-Affinity Recognition of preF To investigate the molecular basis of preferential germline gene pairing in antibodies targeting site III, the crystal structure of ADI-19425 bound to a preF-stabilized variant of RSV F (PR-DM) was determined (FIGS. 11A and 12A, Table 4) (Krarup et al., 2015). This antibody, which was isolated from a 2.8-month old infant, showed potent neutralizing activity despite lacking SHM (Table 2, FIG. 12B). The structure revealed that the majority of contacts between ADI-19425 and preF are formed by the light chain, particularly Tyr31 in CDR L1 and Tyr91 in CDR L3, both of which contact the loop connecting α6 to α7 (FIG. 11B). Tyr91 is the only residue in the CDR L3 that directly interacts with F, although contacts between Asp94 and Ser96 may play a role in positioning this loop and preventing a steric clash between ADI-19425 and antigenic site II (α6-α7) of RSV F. Consistent with the structural analysis, substitution of Tyr31 or Tyr91 with alanine resulted in greater than 20- or 80-fold reductions in affinity, respectively, as measured by SPR (FIG. 11C).

In addition to the contacts formed by the light chain, CDR H2 contains a stretch of five consecutive serine residues that form a network of hydrogen bonds with Asp310 on β6 of preF. Notably, the VH3-11 germline gene, which has 92% sequence identity with VH3-21, was utilized by site III-directed antibodies at a much lower frequency than VH3-21 (11% compared with 76%). Onc explanation for this could be the presence of a tyrosine residue directly following the polyserine motif in VH3-21, but not VH3-11. The structure shows that this residue (Tyr56) is buried in a small groove neighboring antigenic site II (FIG. 11B). Consistent with these observations, substitution of Tyr56 with alanine resulted in a more than 150-fold decrease in affinity (FIG. 11C). Interestingly, although the VH3-48 germline gene also contains the polyserine motif and is present in the naïve B cell repertoire at approximately the same frequency as VH3-11 (DeKosky et al., 2013), only a single site III-directed antibody (ADI-19440) that utilizes VH3-48/VL1-40 was isolated (see Table 2).

The structure also shows that Tyr56 of ADI-19425 is buried in a small groove neighboring antigenic site II on preF (FIG. 11B). Consistent with these observations, substitution of Tyr56 with alanine resulted in a more than 150-fold decrease in affinity (FIG. 11C).

In contrast to the clear VH- and VL-specific features highlighted above, there were fewer restrictions on the sequences of the CDR H3s of site III antibodies, and sequence analysis demonstrated that the CDR H3s varied in length, with some preference towards usage of glycine, serine and tyrosine residues at positions 96-100c (FIG. 7C). The structure reveals that although the ADI-19425 CDR H3 buries approximately 250 Å of preF, it does not form hydrogen bonds or salt bridges with either protomer (FIG. 11B). Notably, the cross-neutralizing antibody MPE8, which has recently been structurally characterized (Wen et al., 2017), utilizes the VH3-21 and VL1-40 germline gene pair to recognize site III with a binding mode nearly identical to that of ADI-19425, despite substantial differences in the sequences of the two CDR H3s (FIGS. 12C and 12D). This is consistent with our observation that multiple CDR H3 sequences can be utilized by this family of antibodies to recognize preF.

Discussion

Although RSV causes substantial mortality in infants, little is known about the specificities and functional characteristics of the infant antibody response to natural RSV infection. Here, it is shown that infant antibody responses to RSV F differ substantially from those of healthy adults, not only in affinity and neutralization potency, but also in the patterns of epitope recognition. The infant responses were focused on two major regions of the RSV F trimer-antigenic sites I and III-neither of which are dominant in adult responses (Gilman et al., 2016). These differences were the most extreme in infants under three months of age, with infants older than six months exhibiting responses that began to resemble healthy adults. This observation is consistent with previous studies showing that the infant immune system begins to mature at around six months of age, but does not attain stable, adult-like characteristics until later in life, at around six years of age (IJspeert et al., 2016; Ridings et al., 1998).

The majority of antibodies that recognized antigenic site III utilized the same $V_H$ and $V_L$ germline gene pairing, but were not restricted in D- and J-gene usage. Importantly, a subset of these antibodies showed potent neutralizing activity despite containing little to no SHM. Approximately half of these antibodies were derived from memory B cells and the other half were derived from B cells that lacked surface expression of CD27, IgG and IgA, suggesting that they originated from naïve B cells.

Recent work has shown that polyclonal IgM antibodies purified from RSV naive infant sera are capable of neutralizing RSV and it was suggested that these antibodies may represent natural anti-RSV antibodies that react with the N- and O-linked glycans present on the RSV surface glycoproteins (Jans et al., 2016). However, unlike natural IgM antibodies—which rely on avidity, typically recognize common surface antigens, and exhibit some degree of polyreactivity (Panda and Ding, 2015)—the site III-directed antibodies described here bind with high affinity in an IgG backbone, specifically recognize an epitope on RSV F that lacks N-linked glycans, and generally show limited polyreactivity, suggesting that they are distinct from previously described natural antibodies. In addition, the presence of this class of antibodies in the memory compartment of older infants and adults indicates that these B cells can be activated in response to antigen exposure and undergo affinity maturation. Similar germline-mediated recognition in the adaptive immune response has also been described for other viral pathogens, including influenza (Ekiert et al., 2009; Kashyap et al., 2008; Sui et al., 2009; Throsby et al., 2008), hepatitis C virus (Bailey et al., 2017) and human cytomegalovirus (Thomson et al., 2008), and for bacterial pathogens such as *Staphylococcus aureus* (Yeung et al., 2016). The presence of functional germline antibodies in the human antibody repertoire has been proposed to serve as a type of innate humoral response to life-threatening pathogens that are likely to be encountered early in life (Lerner, 2011). The isolation of this class of antibodies from all seven infants studied here, as well as from cord blood B cells, adult naïve B cells, and memory B cells from previously characterized adult donors (Gilman et al., 2016), suggests that the naïve B cell precursors encoding these antibody specificities are likely present in most individuals. The results suggest that expansion of these cells may be a feasible goal for infant vaccination strategies (in contrast to, e.g., certain types of HIV-neutralizing antibodies, whose inferred germline precursors display limited reactivity with native HIV Env antigens only develop in a subset of HIV-1 infected individuals, and require complex vaccination strategies to elicit (Doria-Rose et al., 2010; Gray et al., 2011; Jardine et al., 2016; Sather et al., 2009; Simek et al., 2009; Sok et al., 2016; Yacoob et al., 2016)).

Antibody responses directed specifically against preF are associated with potent neutralization of RSV in human sera (Magro et al., 2012; Ngwuta et al., 2015), and monoclonal antibodies that bind exclusively to preF have been shown to be substantially more potent than antibodies that recognize both preF and postF (Corti et al., 2013; Gilman et al., 2016; Gilman et al., 2015; Mclellan et al., 2013; Mousa et al., 2017). Interestingly, neutralizing antibodies that react with both preF and postF were identified in healthy adults and infants over 6 months old, but were almost entirely absent in the youngest infants analyzed here. Although postF antigens are capable of eliciting neutralizing antibodies that also bind to preF, their inability to elicit preF-specific antibodies would likely prove problematic for use in a young infant population. In addition, our results show that a large fraction of the infant antibody response (15-30%) is directed against antigenic site I, which is preferentially expressed on postF. Since antibodies targeting this site generally showed poor neutralizing activity, vaccination with a postF antigens could drive infant antibody responses toward ineffective recognition of RSV F. Recently, it was shown that formalin inactivated RSV (FI-RSV), the preparation that resulted in vaccine-enhanced disease when administered to infants in the 1960s, displays an abundance of postF on the surface of the virus (Killikelly et al., 2016). Although many factors contribute to the development of vaccine-enhanced disease (Acosta et al., 2015), the high abundance of postF on FI-RSV could result in the induction of high levels of site I-directed antibodies and a low fraction of neutralizing antibodies, which are properties previously associated with the formation of immune complexes that contribute to lung pathology in vaccine-enhanced illness (Murphy and Walsh, 1988; Polack et al., 2002).

An age-dependent increase in the response against antigenic sites Ø and V, which are both present near the apex of the preF trimer, was also observed. Although infant antibodies that targeted these epitopes tended to be potently neutralizing, they were present at low abundance in the responses analyzed here, particularly in infants under three months of age. These data suggest that although the presence of site Ø is likely important for generating neutralizing antibody responses later in life, eliciting a neutralizing response in young infants will likely depend on the presentation of antigenic site III. The observed differences in the dominant epitopes targeted by infant and adult responses provides a unique opportunity for prevention strategies that seek to combine passive and active immunization. For example, vaccines could be designed to preferentially elicit site III antibodies, which would not compete for binding with certain second-generation prophylactic antibodies that target antigenic site Ø, such as MEDI8897. In addition, antibodies elicited by a site-III-specific vaccine would not block access to the apex of the preF trimer on infectious virions, allowing the development of neutralizing antibodies directed against antigenic sites in this region to occur during natural RSV infection.

Materials & Methods

Human Subjects

Families of infants were approached at the time of hospitalization for documented RSV infection. At that point a Dartmouth Committee for the Protection of Human Subjects approved consent was signed to obtain $5^{-10}$ cc of blood approximately 1 month after discharge from the Children's Hospital at Dartmouth (CHaD). Families were contacted at the planned time for phlebotomy and arrangements made for blood to be drawn either at CHaD or at a medical facility closer to their home.

Plasma Neutralization Titers

Infant plasma samples were tested for RSV neutralization in microtiter assays using an RSV construct containing green fluorescent protein (GFP) and luciferase reporter genes (RSV-GFP1-Luc2, ViraTrec). Hep2 cells were added to 96-well plates at a density of $1.8 \times 10^4$ cells per well in 100 μL of MEM with 2% FBS/1× penicillin-streptomycin solution (2% MEM) and allowed to adhere overnight at 37° C. On the day of the assay, plasma samples were serially diluted two-fold (1:4 to 1:128,000) in 2% MEM containing RSV-GFP1-Luc2 and incubated for 1 hr at 37° C. Culture media was aspirated from the Hep2 cells followed by the addition of 100 μL/well of the plasma-RSV-GFP1-Luc2 mixture to triplicate wells. Cultures were maintained at 37° C. for 24 hrs and luciferase expression was quantified in cell lysates using the *Renilla*-Glo® assay system (Promega). Relative light units (RLU) were measured on a BioTek Synergy 2 microplate reader. Neutralization is expressed as the reciprocal of the highest plasma dilution to yield a 60% reduction in RLU as compared to control wells with no added plasma Production of RSV F Sorting Probes To generate sorting probes with high avidity, and uniformly oriented F proteins, preF (DS-Cav1) and postF (F ΔFP) trimers with a single biotinylated C-terminal AviTag were produced before coupling to streptavidin-PE or -APC (Gilman et al., 2016).

Single B-Cell Sorting from Infants Less than 3 Months of Age

Peripheral blood mononuclear cells from RSV-infected infants were stained using anti-human IgG (BV605), IgA (FITC), CD27 (BV421), CD8 (PerCP-Cy-5.5), CD14 (PerCP-Cy5.5), CD19 (PECy7), CD20 (PECy7) and a mixture of dual-labeled preF and postF tetramers (50 nM each). For naïve B cell sorting, cord blood or peripheral blood mononuclear cells were stained with anti-human IgG (BV605), IgM (FITC), CD27 (BV421), CD8 (PerCP-Cy5.5), CD14 (PerCP-Cy5.5), CD19 (PECy7), CD20 (PECy7) and a mixture of dual-labeled preF and postF tetramers (50 nM each). Tetramers were prepared fresh for each experiment. Single cells were sorted on a BD fluorescence-activated cell sorter Aria II into 96-well PCR plates (BioRad) containing 20 μL/well of lysis buffer [5 μL of 5λ first strand cDNA buffer (Invitrogen), 0.25 μL RNascOUT (Invitrogen), 1.25 μL dithiothreitol (Invitrogen), 0.625 μL NP-40 (New England Biolabs), and 12.6 μL dH2O]. Plates were immediately frozen on dry ice before storage at −80° C.

Amplification and Cloning of Antibody Variable Sequences

Single B cell PCR and cloning were performed as described previously (Gilman et al., 2016). Briefly, antibody variable genes were amplified by RT-PCR and PCR reactions using cocktails of IgG and IgA specific primers and then cloned into *S. cerevisiae* using the lithium acetate method for chemical transformation (Gietz and Schiestl, 2007). Transformation reactions contained 20 u L of unpurified heavy chain and light chain PCR product and 200 ng of digested heavy and light chain plasmids. After transformation, yeast cells were plated and individual yeast colonies were picked for sequencing and characterization.

Production of Full-Length Human Antibodies

Anti-RSV F IgGs were expressed in *S. cerevisiae* as described previously (Gilman et al., 2016). Briefly, *S. cerevisiae* cultures were grown in 24-well plates, and after six days of growth the yeast culture supernatants were harvested by centrifugation and purified over protein A.

High-Throughput Antibody Affinity Measurements

IgG binding affinities for preF and postF were determined by BLI measurements as described previously (Gilman et al., 2016).

Antibody Competition Experiments

Antibody competition assays were performed as previously described (Gilman et al., 2016). The degree of competition was analyzed by measuring the fold reduction in antigen binding in the presence of competitor Fab relative to an antigen-only control. Antibodies that showed a greater than five-fold reduction in binding in the presence of competitor Fab were considered competitors.

Polyreactivity Assay

Antibody polyreactivity was performed essentially as described previously (Jain et al., 2017). Yeast-expressed IgGs were incubated with biotinylated CHO cell membrane preparations and incubated on ice for 20 minutes. Cells were then washed and re-suspended in secondary antibody mix (Extravidin-R-PE, anti-human LC-FITC, and propidium iodide). The mixture was incubated on ice for 20 minutes and then washed twice with PBSF. Cells were then re-suspended in PBSF and run on a FACSCanto II (BD Biosciences). The mean fluorescence intensities of binding were normalized using control antibodies that display high, medium, or low polyreactivity to assess non-specific binding.

High-Throughput Fluorescence Plate Reader Neutralization Assay

A total of $2.4 \times 10^4$ HEp-2 cells/well in 30 μL culture medium were seeded in 384-well black optical-bottom plates (Nunc®384-well plates, Thermo Scientific). Antibodies were diluted four-fold starting at 100 μg/mL. An equal volume of recombinant mKate-RSV A2 or mKate-RSV B 18537 was then added and incubated at 37° C. for 1 hour. After incubation, 50 μl of the antibody-virus mixture was added to the HEp-2 cells and incubated at 37° C. for 22-24 hours. After incubation, the fluorescence intensity of each well was measured using a microplate reader at an excitation of 588 nm and an emission of 635 nm (SpectraMax Paradigm). Neutralization $IC_{50}$s were calculated using GraphPad Prism (GraphPad Software Inc.).

Production of ADI-14359, ADI-19425, and AM22 Fabs and Variants

Plasmids encoding the heavy and light chains of ADI-14359, ADI-19425 or AM22 were co-transfected at a 1:1 ratio into Expi293F cells. Point mutants were generated using MegaPrimer PCR and were expressed in FreeStyle 293-F cells. Fabs were purified using CaptureSelect IgG-CHI affinity matrix (Life Technologies) and were further purified by size-exclusion chromatography on a Superdex 200 column (GE Healthcare).

Production of Protein Complexes for Crystallization

A mammalian expression vector encoding RSV F ΔFP (postF) with a C-terminal HRV 3C cleavage site, 8× HisTag and StrepTagII was transfected into FreeStyle 293-F cells and 5 μM kifunensine was added approximately 4 hours after transfection. The secreted protein was purified using Strep-Tactin resin (IBA), then treated with 10% (wt/wt) EndoH to remove N-linked glycans, followed by 10 U/mg of HRV 3C to remove tags. The protein was then purified by size-exclusion chromatography using a Superdex 200 column (GE) in buffer containing 2 mM Tris pH 8, 200 mM NaCl and 0.02% $NaN_3$.

To produce the ADI-14359 Fab-postF complex, purified F ΔFP was combined with a 1.5-fold molar excess of ADI-14359 Fab and incubated at room temperature for approximately 30 minutes. Excess Fab was separated from the complex by size-exclusion chromatography using a Superose 6 column (GE Healthcare Biosciences) in buffer containing 2 mM Tris pH 8, 200 mM NaCl and 0.02% $NaN_3$. The complex eluted with a retention volume indicative of a complex with 1-2 Fabs bound per postF trimer, suggesting that ADI-14359 Fab may bind sub-stoichiometrically to postF.

To produce the ADI-19425-AM22-preF ternary complex, purified PR-DM was combined with a 1.5-fold molar excess of both ADI-19425 Fab and AM22 Fab. Binding took place at room temperature for roughly 30 minutes before the ternary complex and excess Fab were separated by size-exclusion chromatography using a Superdex 200 column (GE Healthcare) in 2 mM Tris pH 8, 200 mM NaCl and 0.02% $NaN_3$.

Crystallization and Data Collection

The ADI-14359 Fab-postF complex was crystallized by the hanging-drop vapor-diffusion method by mixing 1.33 μL of protein at a concentration of 4.45 mg/mL with 0.67 μL of reservoir solution composed of 13% polyethylene glycol (PEG) 8000 and 0.43 M ammonium citrate pH 8.5. Cryopreservation was performed by hanging the looped crystal over a 1 M sodium chloride solution for approximately 2 minutes prior to plunge freezing in liquid nitrogen. Data were collected to 3.0 Å resolution at SSRL (Stanford Synchrotron Radiation Lightsource, National Accelerator Laboratory).

The unbound ADI-19425 Fab was initially crystallized using the sitting-drop vapor-diffusion method using 50 nL protein at 8.78 mg/ml and 100 nL reservoir solution containing 2.0 M ammonium sulfate and 0.1 M HEPES pH 7.5. These crystals were used to generate a seek solution and the final crystals were obtained using 50 nL protein at 8.78 mg/ml, 50 nL seed solution and 100 nL reservoir solution containing 1.5 M ammonium sulfate, 0.1 M sodium chloride, and 0.1 M Bis-Tris pH 6.5. Crystals were soaked in a solution of reservoir containing a final concentration of 2.5 M ammonium sulfate before being frozen in liquid nitrogen. Data were collected to 1.7 A resolution at the SBC beamline 19-ID (Advanced Photon Source, Argonne National Laboratory).

The ADI-19425-AM22-preF ternary complex was crystallized by the sitting-drop vapor-diffusion method using 100 nL of protein solution at a concentration of 4.80 mg/mL and 100 nL of reservoir solution containing 0.1 M sodium citrate pH 5.5, 10% isopropanol and 10% PEG 4000. Crystals were soaked in a cryoprotectant solution containing reservoir solution plus 15% 2R,3R-butanediol before being frozen in liquid nitrogen. Data were collected to 4.3 Å at the SBC beamline 19-ID (Advanced Photon Source, Argonne National Laboratory).

Structure Determination, Model Building and Refinement

Diffraction data were indexed and integrated using iMOSFLM (Battye et al., 2011) and merged and scaled with AIMLESS (Evans and Murshudov, 2013). Molecular replacement solutions were obtained with PHASER (McCoy et al., 2007) and the structures were refined using PHENIX (Adams et al., 2002) and built manually using Coot (Emsley and Cowtan, 2004). Software used for processing and visualization of X-ray diffraction data was curated by SBGrid and accessed using the CCP4i interface (Collaborative Computational Project, 1994; Morin et al., 2013; Potterton et al., 2003). Data collection and refinement statistics for the three crystal structures are presented in Table 2.

The ADI-14359-postF complex formed crystals in space group $P2_12_12_1$ and a molecular replacement solution was found using the previously solved postF structure (PDB ID: 3RRT), the heavy chain from 2D1 Fab (PDB ID: 3QHZ), and the light-chain from 5-51/O12 Fab (PDB ID: 4KMT) as search models. The asymmetric unit contained one postF trimer with only one ADI-14359 Fab bound per trimer. The model was built manually in Coot and refined in PHENIX using non-crystallographic symmetry (NCS) and reference model restraints to an Rwork/Rfree of 22.0/25.3%.

The unbound ADI-19425 Fab also formed crystals in $P2_12_12_1$, and the heavy chain from MJ5 Fab (PDB ID: 3EYQ) and the light chain from LDLR competitive Fab (PDB ID: 3H42) were used as search models in molecular replacement. The structure was manually built in Coot and refined in PHENIX to an Rwork/Rfree of 17.4/20.4%. The ADI-19425-AM22-preF complex formed crystals in space group $P4_12_12$ and a molecular replacement solution was found using the refined structures of the unbound ADI-19425 Fab and the complex of preF bound to AM22 Fab as search ensembles. The asymmetric unit contained a single preF trimer bound by three molecules of AM22 Fab and three molecules of 19425 Fab. The model was built manually in Coot and refined in PHENIX using non-crystallographic symmetry (NCS) and reference model restraints to an Rwork/Rfree of 22.2/25.5%.

Fab Affinity Measurements for ADI-14359, ADI-19425, and Variants

The affinity of ADI-14359 Fab for postF was measured using surface plasmon resonance (SPR). Purified postF (RSV F ΔFP) with a C-terminal HRV 3C cleavage site, 8×HisTag and StrepTagII was captured on the sample flow cell of an NTA sensor chip to approximately 115 RU per cycle using a Biacore X100 (GE Healthcare). The NTA chip was regenerated between each cycle with 0.35 M EDTA followed by 0.5 mM $NiCl_2$. A buffer-only reference sample (HBS-P+pH 8) was injected over both flow cells, followed by a 2-fold serial dilution of ADI-14359 Fab from 800 nM to 6.25 nM, starting with the lowest concentration, and a duplication of the 100 nM sample. The data were double-reference subtracted, then fit to a 1:1 binding model using Scrubber. Binding of ADI-14359 Fab to the postF K390A variant was measured in a similar manner, with capture of approximately 100 RU per cycle and injection of a buffer-only reference, followed by a 2-fold serial dilution of Fab from 1.6 µM to 6.25 nM, with a duplication of the 100 nM concentration. The data were double-reference subtracted, but the total response was too low to allow an affinity to be calculated. For the germline variant of ADI-14359 (R50L), approximately 115 RU of postF was captured on the NTA chip before injection of a buffer-only reference, followed by a 2-fold serial dilution of ADI-14359 R50L Fab from 20 µM to 78 nM. The data were double reference subtracted and fit using a steady-state affinity model in Scrubber.

Similar SPR experiments were performed to measure the binding between ADI-19425 Fab and preF. Purified preF (DS-Cav1) with a C-terminal 8×HisTag and AviTag was captured on the sample flow cell of an NTA sensor chip to approximately 150 RU. A buffer-only reference sample (HBS-P+pH 8.0) was injected over both the sample and reference flow cells, followed by a 2-fold serial dilution of ADI-19425 Fab from 40 nM to 1.25 nM, with a duplication of the 10 nM concentration. For the ADI-19425 Fab variants (heavy chain Y56A, light chain Y31A, and light chain Y91A), roughly 150 RU of preF was captured on the NTA chip before the injection of a buffer-only reference, followed by a 2-fold serial dilution of ADI-19425 Fab variant from 1000 nM to 31.25 nM, with a duplication of the 250 nM concentration. The data were double reference subtracted and fit using a 1:1 binding model in Scrubber.

Data Resources

Antibody sequences will be deposited in GenBank. Atomic coordinates and structure factors for the 14359-postF complex structure, the unbound 19425 Fab, and the 19425-AM22-preF complex structure have been deposited with the Protein Data Bank under accession codes 6APB, 6APC, and 6APD.

REFERENCES

All references cited herein including, without limitation, patents, patent applications, and non-patent references and publications referenced throughout, are hereby expressly incorporated by reference in their entireties for all purposes.

Acosta, P. L., Caballero, M. T., and Polack, F. P. (2015). Brief History and Characterization of Enhanced Respiratory Syncytial Virus Disease. Clin Vaccine Immunol 23, 189-195.

Adams, P. D., Grosse-Kunstleve, R. W., Hung, L. W., Ioerger, T. R., McCoy, A. J., Moriarty, N. W., Read, R. J., Sacchettini, J. C., Sauter, N. K., and Terwilliger, T. C. (2002). PHENIX: building new software for automated crystallographic structure determination. Acta Crystallogr D Biol Crystallogr 58, 1948-1954.

Anderson, L. J., Dormitzer, P. R., Nokes, D. J., Rappuoli, R., Roca, A., and Graham, B. S. (2013). Strategic priorities for respiratory syncytial virus (RSV) vaccine development. Vaccine 31 Suppl 2, B209-215.

Anderson, L. J., Hierholzer, J. C., Stone, Y. O., Tsou, C., and Fernie, B. F. (1986). Identification of epitopes on respiratory syncytial virus proteins by competitive binding immunoassay. J Clin Microbiol 23, 475-480.

Bailey, J. R., Flyak, A. I., Cohen, V. J., Li, H., Wasilewski, L. N., Snider, A. E., Wang, S., Learn, G. H., Kose, N., Loerinc, L., et al. (2017). Broadly neutralizing antibodies with few somatic mutations and hepatitis C virus clearance. JCI Insight 2.

Battles, M. B., Langedijk, J. P., Furmanova-Hollenstein, P., Chaiwatpongsakorn, S., Costello, H. M., Kwanten, L., Vranckx, L., Vink, P., Jaensch, S., Jonckers, T. H., et al. (2016). Molecular mechanism of respiratory syncytial virus fusion inhibitors. Nat Chem Biol 12, 87-93.

Battye, T. G., Kontogiannis, L., Johnson, O., Powell, H. R., and Leslie, A. G. (2011). iMOSFLM: a new graphical interface for diffraction-image processing with MOSFLM. Acta Crystallogr D Biol Crystallogr 67, 271-281.

Beeler, J. A., and van Wyke Coelingh, K. (1989). Neutralization epitopes of the F glycoprotein of respiratory syncytial virus: effect of mutation upon fusion function. J Virol 63, 2941-2950.

Bornholdt, Z. A., Turner, H. L., Murin, C. D., Li, W., Sok, D., Souders, C. A., Piper, A. E., Goff, A., Shamblin, J. D., Wollen, S. E., et al. (2016). Isolation of potent neutralizing antibodies from a survivor of the 2014 Ebola virus outbreak. Science 351, 1078-1083.

Chin, J., Magoffin, R. L., Shearer, L. A., Schieble, J. H., and Lennette, E. H. (1969). Field evaluation of a respiratory syncytial virus vaccine and a trivalent parainfluenza virus vaccine in a pediatric population. Am J Epidemiol 89, 449-463.

Collaborative Computational Project, N. (1994). The CCP4 suite: programs for protein crystallography. Acta Crystallogr D Biol Crystallogr 50, 760-763.

Corti, D., Bianchi, S., Vanzetta, F., Minola, A., Perez, L., Agatic, G., Guarino, B., Silacci, C., Marcandalli, J., Marsland, B. J., et al. (2013). Cross-neutralization of four paramyxoviruses by a human monoclonal antibody. Nature 501, 439-443.

Crooks, G. E., Hon, G., Chandonia, J. M., and Brenner, S. E. (2004). WebLogo: a sequence logo generator. Genome Res 14, 1188-1190.

DeKosky, B. J., Ippolito, G. C., Deschner, R. P., Lavinder, J. J., Wine, Y., Rawlings, B. M., Varadarajan, N., Giesecke, C., Dorner, T., Andrews, S. F., et al. (2013). High-throughput sequencing of the paired human immunoglobulin heavy and light chain repertoire. Nat Biotechnol 31, 166-169.

Doria-Rose, N. A., Klein, R. M., Daniels, M. G., O'Dell, S., Nason, M., Lapedes, A., Bhattacharya, T., Migueles, S. A., Wyatt, R. T., Korber, B. T., et al. (2010). Breadth of human immunodeficiency virus-specific neutralizing activity in sera: clustering analysis and association with clinical variables. J Virol 84, 1631-1636.

Ekiert, D. C., Bhabha, G., Elsliger, M. A., Friesen, R. H., Jongeneelen, M., Throsby, M., Goudsmit, J., and Wilson, I. A. (2009). Antibody recognition of a highly conserved influenza virus epitope. Science 324, 246-251.

Emsley, P., and Cowtan, K. (2004). Coot: model-building tools for molecular graphics. Acta Crystallogr D Biol Crystallogr 60, 2126-2132.

Esposito, S., Scarselli, E., Lelii, M., Scala, A., Vitelli, A., Capone, S., Fornili, M., Biganzoli, E., Orenti, A., Nicosia, A., et al. (2016). Antibody response to respiratory syncytial virus infection in children<18 months old. Hum Vaccin Immunother 12, 1700-1706.

Evans, P. R., and Murshudov, G. N. (2013). How good are my data and what is the resolution? Acta Crystallogr D Biol Crystallogr 69, 1204-1214.

Fuentes, S., Coyle, E. M., Beeler, J., Golding, H., and Khurana, S. (2016). Antigenic Fingerprinting following Primary RSV Infection in Young Children Identifies Novel Antigenic Sites and Reveals Unlinked Evolution of Human Antibody Repertoires to Fusion and Attachment Glycoproteins. PLOS Pathog 12, e1005554.

Fulginiti, V. A., Eller, J. J., Sieber, O. F., Joyner, J. W., Minamitani, M., and Meiklejohn, G. (1969). Respiratory virus immunization. I. A field trial of two inactivated respiratory virus vaccines; an aqueous trivalent parainfluenza virus vaccine and an alum-precipitated respiratory syncytial virus vaccine. Am J Epidemiol 89, 435-448.

Gans, H., Yasukawa, L., Rinki, M., DeHovitz, R., Forghani, B., Beeler, J., Audet, S., Maldonado, Y., and Arvin, A. M. (2001). Immune responses to measles and mumps vaccination of infants at 6, 9, and 12 months. J Infect Dis 184, 817-826.

Garcia-Barreno, B., Palomo, C., Penas, C., Delgado, T., Perez-Brena, P., and Melero, J. A. (1989). Marked differences in the antigenic structure of human respiratory syncytial virus F and G glycoproteins. J Virol 63, 925-932.

Gietz, R. D., and Schiestl, R. H. (2007). High-efficiency yeast transformation using the LiAc/SS carrier DNA/PEG method. Nat Protoc 2, 31-34.

Gilman, M. S., Castellanos, C. A., Chen, M., Ngwuta, J. O., Goodwin, E., Moin, S. M., Mas, V., Melero, J. A., Wright, P. F., Graham, B. S., et al. (2016). Rapid profiling of RSV antibody repertoires from the memory B cells of naturally infected adult donors. Sci Immunol 1.

Gilman, M. S., Moin, S. M., Mas, V., Chen, M., Patel, N. K., Kramer, K., Zhu, Q., Kabeche, S. C., Kumar, A., Palomo, C., et al. (2015). Characterization of a Prefusion-Specific Antibody That Recognizes a Quaternary, Cleavage-Dependent Epitope on the RSV Fusion Glycoprotein. PLOS Pathog 11, e1005035.

Glezen, W. P., Taber, L. H., Frank, A. L., and Kasel, J. A. (1986). Risk of primary infection and reinfection with respiratory syncytial virus. Am J Dis Child 140, 543-546.

Graham, B. S. (2017). Vaccine development for respiratory syncytial virus. Curr Opin Virol 23, 107-112.

Gray, E. S., Madiga, M. C., Hermanus, T., Moore, P. L., Wibmer, C. K., Tumba, N. L., Werner, L., Mlisana, K., Sibeko, S., Williamson, C., et al. (2011). The neutralization breadth of HIV-1 develops incrementally over four years and is associated with CD4$^+$ T cell decline and high viral load during acute infection. J Virol 85, 4828-4840.

Griffin, M. P., Khan, A. A., Esser, M. T., Jensen, K., Takas, T., Kankam, M. K., Villafana, T., and Dubovsky, F. (2017). Safety, Tolerability, and Pharmacokinetics of MEDI8897, the Respiratory Syncytial Virus Prefusion F-Targeting Monoclonal Antibody with an Extended Half-Life, in Healthy Adults. Antimicrob Agents Chemother 61.

Group, T. I.-R. S. (1998). Palivizumab, a humanized respiratory syncytial virus monoclonal antibody, reduces hospitalization from respiratory syncytial virus infection in high-risk infants. Pediatrics 102, 531-537.

Hall, C. B., Walsh, E. E., Long, C. E., and Schnabel, K. C. (1991). Immunity to and frequency of reinfection with respiratory syncytial virus. J Infect Dis 163, 693-698.

Henderson, F. W., Collier, A. M., Clyde, W. A., Jr., and Denny, F. W. (1979). Respiratory-syncytial-virus infections, reinfections and immunity. A prospective, longitudinal study in young children. N Engl J Med 300, 530-534.

Homaira, N., Rawlinson, W., Snelling, T. L., and Jaffe, A. (2014). Effectiveness of Palivizumab in Preventing RSV Hospitalization in High Risk Children: A Real-World Perspective. Int J Pediatr 2014, 571609.

Huang, K., Incognito, L., Cheng, X., Ulbrandt, N. D., and Wu, H. (2010). Respiratory syncytial virus-neutralizing monoclonal antibodies motavizumab and palivizumab inhibit fusion. J Virol 84, 8132-8140.

IJspeert, H., van Schouwenburg, P. A., van Zessen, D., Pico-Knijnenburg, I., Driessen, G. J., Stubbs, A. P., and van der Burg, M. (2016). Evaluation of the Antigen-Experienced B-Cell Receptor Repertoire in Healthy Children and Adults. Front Immunol 7, 410.

Jain, T., Sun, T., Durand, S., Hall, A., Houston, N. R., Nett, J. H., Sharkey, B., Bobrowicz, B., Caffry, I., Yu, Y., et al. (2017). Biophysical properties of the clinical-stage antibody landscape. Proc Natl Acad Sci USA 114, 944-949.

Jans, J., Pettengill, M., Kim, D., van der Made, C., de Groot, R., Henriet, S., de Jonge, M. I., Ferwerda, G., and Levy, O. (2016). Human newborn B cells mount an interferon-alpha/beta receptor-dependent humoral response to respiratory syncytial virus. J Allergy Clin Immunol.

Jardine, J. G., Kulp, D. W., Havenar-Daughton, C., Sarkar, A., Briney, B., Sok, D., Sesterhenn, F., Ereno-Orbea, J., Kalyuzhniy, O., Deresa, I., et al. (2016). HIV-1 broadly neutralizing antibody precursor B cells revealed by germline-targeting immunogen. Science 351, 1458-1463.

Kamal-Bahl, S., Doshi, J., and Campbell, J. (2002). Economic analyses of respiratory syncytial virus immunoprophylaxis in high-risk infants: a systematic review. Arch Pediatr Adolesc Med 156, 1034-1041.

Kapikian, A. Z., Mitchell, R. H., Chanock, R. M., Shvedoff, R. A., and Stewart, C. E. (1969). An epidemiologic study of altered clinical reactivity to respiratory syncytial (RS) virus infection in children previously vaccinated with an inactivated RS virus vaccine. Am J Epidemiol 89, 405-421.

Kashyap, A. K., Steel, J., Oner, A. F., Dillon, M. A., Swale, R. E., Wall, K. M., Perry, K. J., Faynboym, A., Ilhan, M., Horowitz, M., et al. (2008). Combinatorial antibody libraries from survivors of the Turkish H5N1 avian influenza outbreak reveal virus neutralization strategies. Proc Natl Acad Sci USA 105, 5986-5991.

Kelly, R. L., Sun, T., Jain, T., Caffry, I., Yu, Y., Cao, Y., Lynaugh, H., Brown, M., Vasquez, M., Wittrup, K. D., et al. (2015). High throughput cross-interaction measures for human IgG1 antibodies correlate with clearance rates in mice. MAbs, 0.

Killikelly, A. M., Kanekiyo, M., and Graham, B. S. (2016). Pre-fusion F is absent on the surface of formalin-inactivated respiratory syncytial virus. Sci Rep 6, 34108.

Kim, H. W., Canchola, J. G., Brandt, C. D., Pyles, G., Chanock, R. M., Jensen, K., and Parrott, R. H. (1969). Respiratory syncytial virus disease in infants despite prior administration of antigenic inactivated vaccine. Am J Epidemiol 89, 422-434.

Krarup, A., Truan, D., Furmanova-Hollenstein, P., Bogaert, L., Bouchier, P., Bisschop, I. J., Widjojoatmodjo, M. N., Zahn, R., Schuitemaker, H., Mclellan, J. S., et al. (2015). A highly stable prefusion RSV F vaccine derived from structural analysis of the fusion mechanism. Nat Commun 6, 8143.

Kristjansson, S., Bjarnarson, S. P., Wennergren, G., Palsdottir, A. H., Arnadottir, T., Haraldsson, A., and Jonsdottir, I. (2005). Respiratory syncytial virus and other respiratory viruses during the first 3 months of life promote a local TH2-like response. J Allergy Clin Immunol 116, 805-811.

Lambert, D. M., Barney, S., Lambert, A. L., Guthrie, K., Medinas, R., Davis, D. E., Bucy, T., Erickson, J., Merutka, G., and Petteway, S. R., Jr. (1996). Peptides from conserved regions of paramyxovirus fusion (F) proteins are potent inhibitors of viral fusion. Proc Natl Acad Sci USA 93, 2186-2191.

Lambert, L., Sagfors, A. M., Openshaw, P. J., and Culley, F. J. (2014). Immunity to RSV in Early-Life. Front Immunol 5, 466.

Legg, J. P., Hussain, I. R., Warner, J. A., Johnston, S. L., and Warner, J. O. (2003). Type 1 and type 2 cytokine imbalance in acute respiratory syncytial virus bronchiolitis. Am J Respir Crit Care Med 168, 633-639.

Lerner, R. A. (2011). Rare antibodies from combinatorial libraries suggests an S.O.S. component of the human immunological repertoire. Mol Biosyst 7, 1004-1012.

Magro, M., Mas, V., Chappell, K., Vazquez, M., Cano, O., Luque, D., Terron, M. C., Melero, J. A., and Palomo, C. (2012). Neutralizing antibodies against the preactive form of respiratory syncytial virus fusion protein offer unique possibilities for clinical intervention. Proc Natl Acad Sci USA 109, 3089-3094.

McCoy, A. J., Grosse-Kunstleve, R. W., Adams, P. D., Winn, M. D., Storoni, L. C., and Read, R. J. (2007). Phaser crystallographic software. J Appl Crystallogr 40, 658-674.

Mclellan, J. S., Chen, M., Chang, J. S., Yang, Y., Kim, A., Graham, B. S., and Kwong, P. D. (2010a). Structure of a major antigenic site on the respiratory syncytial virus fusion glycoprotein in complex with neutralizing antibody 101F. J Virol 84, 12236-12244.

McLellan, J. S., Chen, M., Kim, A., Yang, Y., Graham, B. S., and Kwong, P. D. (2010b). Structural basis of respiratory syncytial virus neutralization by motavizumab. Nat Struct Mol Biol 17, 248-250.

Mclellan, J. S., Chen, M., Leung, S., Graepel, K. W., Du, X., Yang, Y., Zhou, T., Baxa, U., Yasuda, E., Beaumont, T., et al. (2013). Structure of RSV fusion glycoprotein trimer bound to a prefusion-specific neutralizing antibody. Science 340, 1113-1117.

McLellan, J. S., Yang, Y., Graham, B. S., and Kwong, P. D. (2011). Structure of respiratory syncytial virus fusion glycoprotein in the postfusion conformation reveals preservation of neutralizing epitopes. J Virol 85, 7788-7796.

Morin, A., Eisenbraun, B., Key, J., Sanschagrin, P. C., Timony, M. A., Ottaviano, M., and Sliz, P. (2013). Collaboration gets the most out of software. Elife 2, e01465.

Mousa, J. J., Kose, N., Matta, P., Gilchuk, P., and Crowe, J. E., Jr. (2017). A novel pre-fusion conformation-specific neutralizing epitope on the respiratory syncytial virus fusion protein. Nat Microbiol 2, 16271.

Murphy, B. R., Alling, D. W., Snyder, M. H., Walsh, E. E., Prince, G. A., Chanock, R. M., Hemming, V. G., Rodriguez, W. J., Kim, H. W., Graham, B. S., et al. (1986). Effect of age and preexisting antibody on serum antibody response of infants and children to the F and G glycoproteins during respiratory syncytial virus infection. J Clin Microbiol 24, 894-898.

Murphy, B. R., and Walsh, E. E. (1988). Formalin-inactivated respiratory syncytial virus vaccine induces antibodies to the fusion glycoprotein that are deficient in fusion-inhibiting activity. J Clin Microbiol 26, 1595-1597.

Ngwuta, J. O., Chen, M., Modjarrad, K., Joyce, M. G., Kanekiyo, M., Kumar, A., Yassine, H. M., Moin, S. M., Killikelly, A. M., Chuang, G. Y., et al. (2015). Prefusion F-specific antibodies determine the magnitude of RSV neutralizing activity in human sera. Sci Transl Med 7, 309ra162.

Panda, S., and Ding, J. L. (2015). Natural antibodies bridge innate and adaptive immunity. J Immunol 194, 13-20.

PATH (2017). RSV Vaccine and mAb Snapshot.

Polack, F. P., Teng, M. N., Collins, P. L., Prince, G. A., Exner, M., Regele, H., Lirman, D. D., Rabold, R., Hoffman, S. J., Karp, C. L., et al. (2002). A role for immune complexes in enhanced respiratory syncytial virus disease. J Exp Med 196, 859-865.

Potterton, E., Briggs, P., Turkenburg, M., and Dodson, E. (2003). A graphical user interface to the CCP4 program suite. Acta Crystallogr D Biol Crystallogr 59, 1131-1137.

Rechavi, E., Lev, A., Lee, Y. N., Simon, A. J., Yinon, Y., Lipitz, S., Amariglio, N., Weisz, B., Notarangelo, L. D., and Somech, R. (2015). Timely and spatially regulated maturation of B and T cell repertoire during human fetal development. Sci Transl Med 7, 276ra225.

Reed, J. H., Jackson, J., Christ, D., and Goodnow, C. C. (2016). Clonal redemption of autoantibodies by somatic hypermutation away from self-reactivity during human immunization. J Exp Med 213, 1255-1265.

Reichert, J. M. (2016). Antibodies to watch in 2016. MAbs 8, 197-204.

Ridings, J., Dinan, L., Williams, R., Roberton, D., and Zola, H. (1998). Somatic mutation of immunoglobulin V (H) 6 genes in human infants. Clin Exp Immunol 114, 33-39.

Rossey, I., Gilman, M. S., Kabeche, S. C., Sedeyn, K., Wrapp, D., Kanekiyo, M., Chen, M., Mas, V., Spitaels, J., Melero, J. A., et al. (2017). Potent single-domain antibodies that arrest respiratory syncytial virus fusion protein in its prefusion state. Nat Commun 8, 14158.

Sande, C. J., Cane, P. A., and Nokes, D. J. (2014). The association between age and the development of respiratory syncytial virus neutralising antibody responses following natural infection in infants. Vaccine 32, 4726-4729.

Saravia, J., You, D., Shrestha, B., Jaligama, S., Siefker, D., Lee, G. I., Harding, J. N., Jones, T. L., Rovnaghi, C., Bagga, B., et al. (2015). Respiratory Syncytial Virus Disease Is Mediated by Age-Variable IL-33. PLOS Pathog 11, e1005217.

Sastre, P., Melero, J. A., Garcia-Barreno, B., and Palomo, C. (2005). Comparison of affinity chromatography and adsorption to vaccinia virus recombinant infected cells for depletion of antibodies directed against respiratory syncytial virus glycoproteins present in a human immunoglobulin preparation. J Med Virol 76, 248-255.

Sather, D. N., Armann, J., Ching, L. K., Mavrantoni, A., Sellhorn, G., Caldwell, Z., Yu, X., Wood, B., Self, S., Kalams, S., et al. (2009). Factors associated with the development of cross-reactive neutralizing antibodies during human immunodeficiency virus type 1 infection. J Virol 83, 757-769.

Shi, T., McAllister, D. A., O'Brien, K. L., Simoes, E. A. F., Madhi, S. A., Gessner, B. D., Polack, F. P., Balsells, E., Acacio, S., Aguayo, C., et al. (2017). Global, regional, and national disease burden estimates of acute lower respiratory infections due to respiratory syncytial virus in young children in 2015: a systematic review and modelling study. Lancet.

Shinoff, J. J., O'Brien, K. L., Thumar, B., Shaw, J. B., Reid, R., Hua, W., Santosham, M., and Karron, R. A. (2008). Young infants can develop protective levels of neutralizing antibody after infection with respiratory syncytial virus. J Infect Dis 198, 1007-1015.

Siegrist, C. A., and Aspinall, R. (2009). B-cell responses to vaccination at the extremes of age. Nat Rev Immunol 9, 185-194.

Simek, M. D., Rida, W., Priddy, F. H., Pung, P., Carrow, E., Laufer, D. S., Lehrman, J. K., Boaz, M., Tarragona-Fiol, T., Miiro, G., et al. (2009). Human immunodeficiency virus type 1 elite neutralizers: individuals with broad and potent neutralizing activity identified by using a high-throughput neutralization assay together with an analytical selection algorithm. J Virol 83, 7337-7348.

Sok, D., Briney, B., Jardine, J. G., Kulp, D. W., Menis, S., Pauthner, M., Wood, A., Lee, E. C., Le, K. M., Jones, M., et al. (2016). Priming HIV-1 broadly neutralizing antibody precursors in human Ig loci transgenic mice. Science 353, 1557-1560.

Sui, J., Hwang, W. C., Perez, S., Wei, G., Aird, D., Chen, L. M., Santelli, E., Stec, B., Cadwell, G., Ali, M., et al. (2009). Structural and functional bases for broad-spectrum neutralization of avian and human influenza A viruses. Nat Struct Mol Biol 16, 265-273.

Swanson, K. A., Settembre, E. C., Shaw, C. A., Dey, A. K., Rappuoli, R., Mandl, C. W., Dormitzer, P. R., and Carfi, A. (2011). Structural basis for immunization with postfusion respiratory syncytial virus fusion F glycoprotein (RSV F) to elicit high neutralizing antibody titers. Proc Natl Acad Sci USA 108, 9619-9624.

Swers, J. S., Kellogg, B. A., and Wittrup, K. D. (2004). Shuffled antibody libraries created by in vivo homologous recombination and yeast surface display. Nucleic Acids Res 32, e36.

Thomson, C. A., Bryson, S., McLean, G. R., Creagh, A. L., Pai, E. F., and Schrader, J. W. (2008). Germline V-genes sculpt the binding site of a family of antibodies neutralizing human cytomegalovirus. EMBO J 27, 2592-2602.

Throsby, M., van den Brink, E., Jongeneelen, M., Poon, L. L., Alard, P., Cornelissen, L., Bakker, A., Cox, F., van Deventer, E., Guan, Y., et al. (2008). Heterosubtypic neutralizing monoclonal antibodies cross-protective against H5N1 and HINI recovered from human IgM+ memory B cells. PLOS One 3, e3942.

Tiller, T., Meffre, E., Yurasov, S., Tsuiji, M., Nussenzweig, M. C., and Wardemann, H. (2008). Efficient generation of monoclonal antibodies from single human B cells by single cell RT-PCR and expression vector cloning. J Immunol Methods 329, 112-124.

Trang, N. V., Braeckman, T., Lernout, T., Hau, V. T., Anh le, T. K., Luan le, T., Van Damme, P., and Anh, D. D. (2014). Prevalence of rotavirus antibodies in breast milk and inhibitory effects to rotavirus vaccines. Hum Vaccin Immunother 10, 3681-3687.

Troisi, C. L., Hollinger, F. B., Krause, D. S., and Pickering, L. K. (1997). Immunization of seronegative infants with hepatitis A vaccine (HAVRIX; SKB): a comparative study of two dosing schedules. Vaccine 15, 1613-1617.

Wang, J., He, Y., Jin, D., Liu, J., Zheng, J., Yuan, N., Bai, Y., Yan, T., Yang, Y., Liu, Y., et al. (2017). No response to hepatitis B vaccine in infants born to HBsAg (+) mothers is associated to the transplacental transfer of HBsAg. Infect Dis (Lond), 1-8.

Wen, X., Mousa, J. J., Bates, J. T., Lamb, R. A., Crowe, J. E., Jr., and Jardetzky, T. S. (2017). Structural basis for antibody cross-neutralization of respiratory syncytial virus and human metapneumovirus. Nat Microbiol 2, 16272.

Williams, J. V., Weitkamp, J. H., Blum, D. L., LaFleur, B. J., and Crowe, J. E., Jr. (2009). The human neonatal B cell response to respiratory syncytial virus uses a biased antibody variable gene repertoire that lacks somatic mutations. Mol Immunol 47, 407-414.

Wu, S. J., Schmidt, A., Beil, E. J., Day, N. D., Branigan, P. J., Liu, C., Gutshall, L. L., Palomo, C., Furze, J., Taylor, G., et al. (2007). Characterization of the epitope for anti-human respiratory syncytial virus F protein monoclonal antibody 101F using synthetic peptides and genetic approaches. J Gen Virol 88, 2719-2723.

Xu, Y., Roach, W., Sun, T., Jain, T., Prinz, B., Yu, T. Y., Torrey, J., Thomas, J., Bobrowicz, P., Vasquez, M., et al. (2013). Addressing polyspecificity of antibodies selected from an in vitro yeast presentation system: a FACS-based, high-throughput selection and analytical tool. Protein Eng Des Sel 26, 663-670.

Yacoob, C., Pancera, M., Vigdorovich, V., Oliver, B. G., Glenn, J. A., Feng, J., Sather, D. N., McGuire, A. T., and Stamatatos, L. (2016). Differences in Allelic Frequency and CDRH3 Region Limit the Engagement of HIV Env Immunogens by Putative VRC01 Neutralizing Antibody Precursors. Cell Rep 17, 1560-1570.

Yeung, Y. A., Foletti, D., Deng, X., Abdiche, Y., Strop, P., Glanville, J., Pitts, S., Lindquist, K., Sundar, P. D., Sirota, M., et al. (2016). Germline-encoded neutralization of a *Staphylococcus aureus* virulence factor by the human antibody repertoire. Nat Commun 7, 13376.

Zhang, X., Zhivaki, D., and Lo-Man, R. (2017). Unique aspects of the perinatal immune system. Nat Rev Immunol.

Zhu, Q., McLellan, J. S., Kallewaard, N. L., Ulbrandt, N. D., Palaszynski, S., Zhang, J., Moldt, B., Khan, A., Svabek, C., McAuliffe, J. M., et al. (2017). A highly potent extended half-life antibody as a potential RSV vaccine surrogate for all infants. Sci Transl Med 9

Example 2. Isolation and Characterization of Anti-RSV F-Specific Human Infant Antibodies from Adenoid and PBMCs Applicant has comprehensively profiled the human infant antibody response to RSV F by isolating and characterizing over 800 RSV F-specific monoclonal antibodies from paired nasopharyngeal adenoid (adenoid) and peripheral blood samples (PBMCs) of RSV-infected infants, and used these antibodies to characterize the infant antibody response as well as develop a framework for the rational design of age-specific RSV vaccines. RSV F-specific memory B cell responses were detected in the adenoids of all 6 children, and the adenoid-derived antibodies showed overall higher binding affinities and neutralization potencies compared to antibodies isolated from paired peripheral blood samples. Approximately 25% of the neutralizing antibodies isolated from adenoid tissue were derived from a unique population of IgM+ and/or IgD+ memory B cells that contained a high load of somatic mutations but lacked expression of classical memory B cell markers. The collective results provide insight into the mucosal B cell response to RSV and have implications for the development of vaccines that stimulate potent local responses.

Isolation of RSV F-Specific B Cells from Paired Adenoid and Peripheral Blood Samples To analyze and compare the mucosal and systemic B cell response to natural RSV infection, paired adenoid tissue and peripheral blood samples were obtained from 6 young children between the ages of 2 and 4 years old who were undergoing tonsillectomy (Supplementary Table 1). Adenoids were used as a representative source of respiratory mucosal lymphocytes because this lymphoid tissue has been previously shown to be an important induction site for B cells that migrate to the respiratory tract and associated glands (Czerkinsky et al 1994, McGhee 2000, Brandtzaeg P1. 2011). The adenoid's location at the site of entry into the upper respiratory tract also suggests a role in anti-RSV immunity. Although none of the children had a documented history of RSV infection, previous studies have shown that essentially all children have been infected by RSV at least once by the age of 2. Consistent with the notion of prior RSV exposure, serum samples obtained from all six children displayed neutralizing activity against RSV-A2 (Supplementary Table 1).

SUPPLEMENTARY TABLE 1

Neutralizing activity against RSV-A2

| | | | | 50% RSV neutralization titer | |
|---|---|---|---|---|---|
| Subject | Gender | Age (yrs) | Plasma | Adenoid filter | Adenoid supernatant |
| 2635 | M | 3.60 | 545 | 9 | 9 |
| 2637 | F | 3.13 | 639 | <4 | 13 |
| 2665 | M | 2.82 | 506 | <4 | <4 |
| 2666 | F | 3.05 | 1702 | 13 | 177 |
| 2849 | M | 2.79 | 5133 | 4 | 55 |
| 2850 | M | 2.97 | 720 | 6 | 5 |

Figures 13B, 13C:
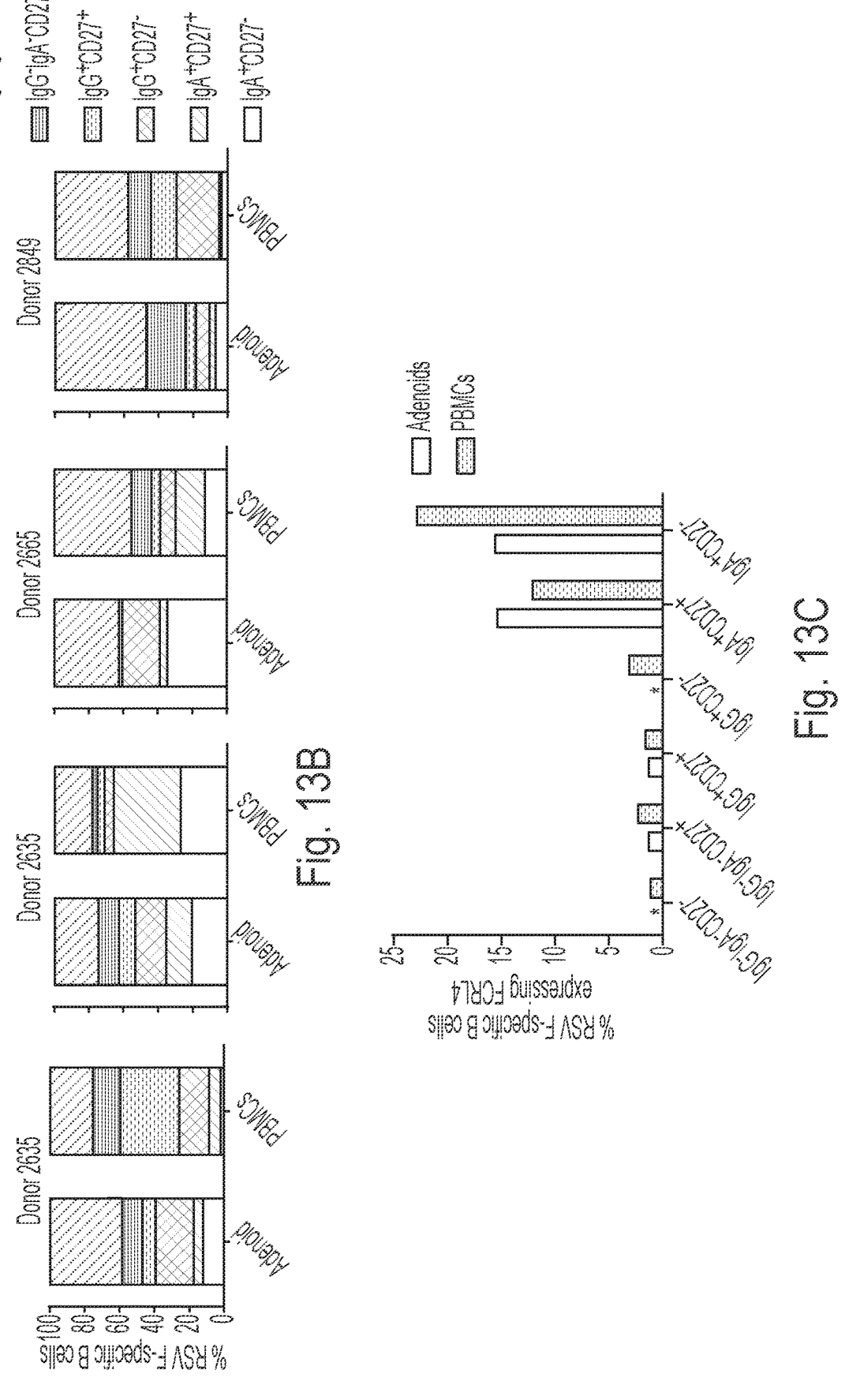
Figures 14A, 14B:
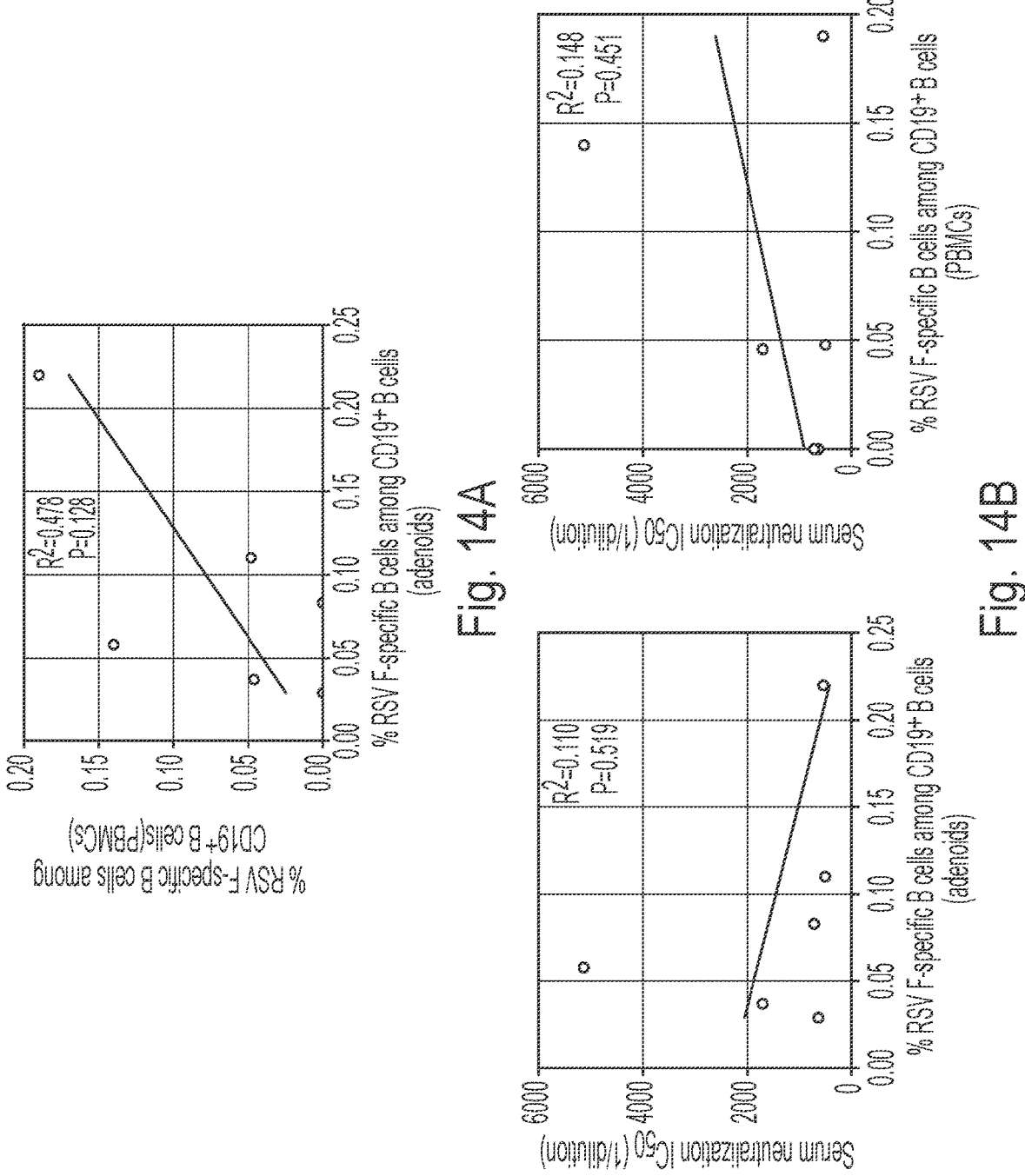
FIGS. 14A-B show the lack of a clear correlation between the frequency of RSV F-reactive B cells in either compartment and serum neutralization titer.

To assess the magnitude of the RSV F-specific B cell response in both anatomical compartments, the adenoid and PBMC samples were stained with a panel of B cell markers (CD19, CD20, IgG, IgA, CD27, and FCRL4) and fluorescently-labeled tetramers of RSV preF and postF and analyzed by flow cytometry (FIG. 13A). RSV F-reactive B cells were detected in the adenoid samples from all 6 donors but in only 4 of the 6 corresponding PBMC samples (FIG. 13B). The frequency of RSV F-specific B cells in the adenoid and PBMC samples ranged from 0.03-0.22% and 0-0.19%, respectively. There was no clear correlation between 1) the frequency of RSV F-reactive B cells in peripheral blood and adenoid tissue, and 2) the frequency of RSV F-reactive B cells in either compartment (FIG. 14A) and serum neutralization titer (FIG. 14B). The latter result is consistent with previous studies showing a lack of correlation between the frequencies of antigen-specific memory B cells and serum titers of antigen specific IgG.

Next, between 100-300 RSV F-reactive B cells from both the adenoid and PBMC samples from each of the four donors that had detectable RSV F-specific B cell responses in both compartments were single-cell sorted. Although all RSV F-reactive B cells were sorted, index sorting allowed for the determination of the B cell surface markers expressed on each sorted cell. This analysis showed that the RSV F-specific B cell subset distribution varied considerably between the two compartments and among the four donors (FIG. 13B). For example, in some donors, there was a higher proportion of RSV F-specific IgG+ memory B cells in peripheral blood compared to adenoid tissue (e.g. donor 2635 and donor 2849), whereas the converse was observed in other donors (e.g. donor 2665). Notably, in all four donors, there was little to no enrichment for RSV F-specific IgA$^+$ B cells in the adenoid samples relative to the corresponding PBMC samples, and in one donor (donor 2665) there was a substantially higher proportion of RSV F-specific IgA$^+$ B cells in peripheral blood compared to adenoid tissue (FIG. 13B). Furthermore, in all donors, a considerable proportion (21-52%) of RSV F-specific B cells in both compartments were not class-switched and lacked the expression of the classical memory B cell marker CD27. Since previous studies have shown that the inhibitory receptor FcRL4 is expressed on a proportion of tissue-resident memory B cells (Ehrhardt et al, J Exp Med 2005), it was analyzed whether this marker was preferentially expressed on certain subsets of adenoid-derived B cells. A proportion of B cell clones within most of the subsets in both compartments expressed FcRL4, with the exception of the IgG IgA CD27 and adenoid-resident IgG+CD27$^-$ subsets, and the large majority of FcRL4$^+$ B cells in both compartments were of the IgA isotype (FIG. 13C). Therefore, it was concluded that natural RSV infection induces memory B cell responses in the adenoids of young children, and the contribution of different memory B cell populations to the RSV-specific response varies among donors and between the mucosal and systemic compartments.

Figure 15A:
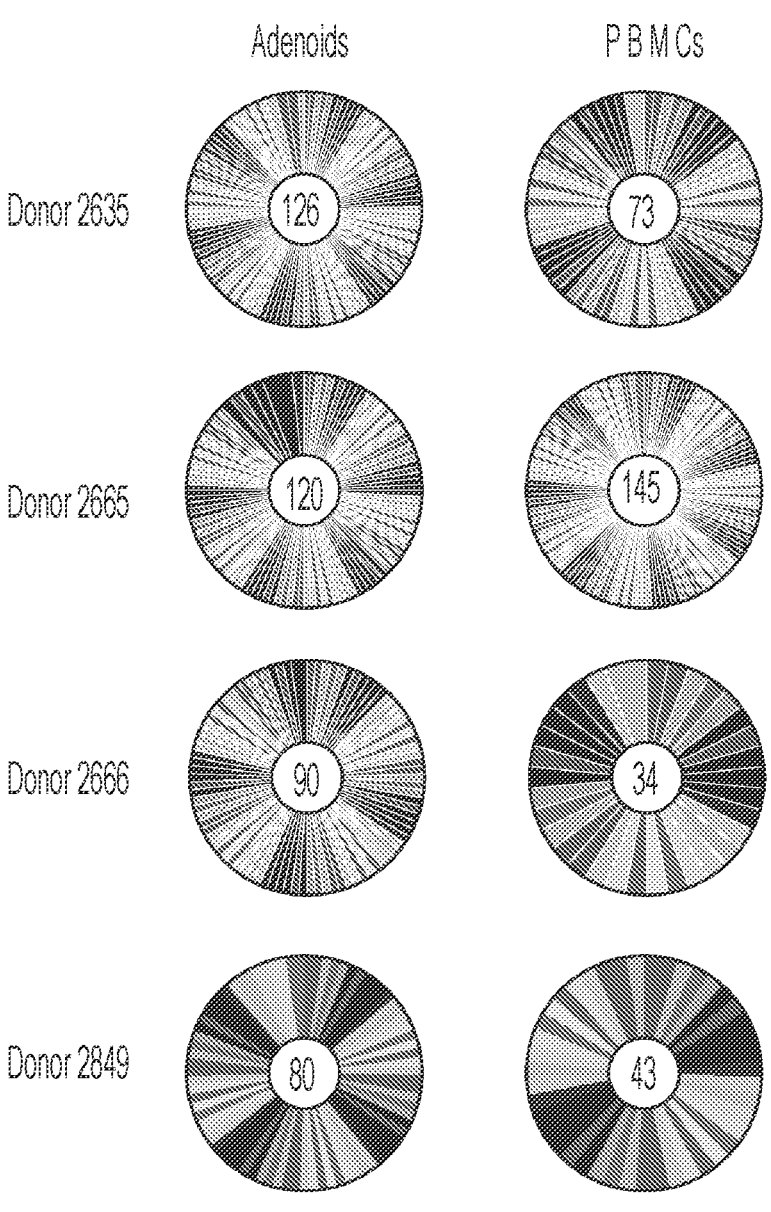
FIGS. 15A-C characterize the RSV-specific mucosal B cell response.

An Atypical Population of RSV-Specific Memory B Cells is Enriched in Adenoid Tissue To further characterize the RSV-specific mucosal B cell response, the antibody variable heavy (VH) and variable light (VL) chain sequences from the sorted B cells were amplified by single cell-PCR. Over 800 cognate VH-VL pairs were cloned into an IgG1 expression vector for sequencing and IgG production. Sequence analysis revealed that the RSV F-specific antibody repertoires were highly diverse in both compartments in all donors, each containing few to no expanded clonal lineages (FIG. 15A). Although deeper sequencing would be required to accurately determine the degree of overlap between the RSV F-specific clones in each compartment, one clonal lineage was identified in both the adenoid- and PBMC-derived antibody panels isolated from donor 2635 (supplementary table 2), suggesting that at least a proportion of RSV F-specific B cells recirculate between the mucosal and systemic compartments.

| Supplementary Table 2. Clonal lineage from donor 2635 | | |
| --- | --- | --- |
| VL CDR1 | VL FR2 | VL CDR2 |
| RSSQSLLHSNGFNYLD (SEQ ID NO: 1895) | WYLQKPGQSPQLLIY (SEQ ID NO: 1896) | LGSNRAS (SEQ ID NO: 1897) |
| RSSQSLLHSNGFNYLD (SEQ ID NO: 1895) | WYLQKPGQSPQLLIY (SEQ ID NO: 1896) | LGSNRAS (SEQ ID NO: 1897 |
| VL FR3 | VL CDR3 | VL FR4 |
| GVPDRFSGSGSGTDFTLKISRVEAEDVGVYYC (SEQ ID NO: 1898) | MQALQTLT (SEQ ID NO: 1899) | FGꟼGTKVEIK (SEQ ID NO: 1900) |
| GVPDRFSGSGSGTDFTLKISRVEAEDVGVYYC (SEQ ID NO: 1898) | MQALQTLT (SEQ ID NO: 1899) | FGGGTKVEIK (SEQ ID NO: 1901) |

Figure 15B:
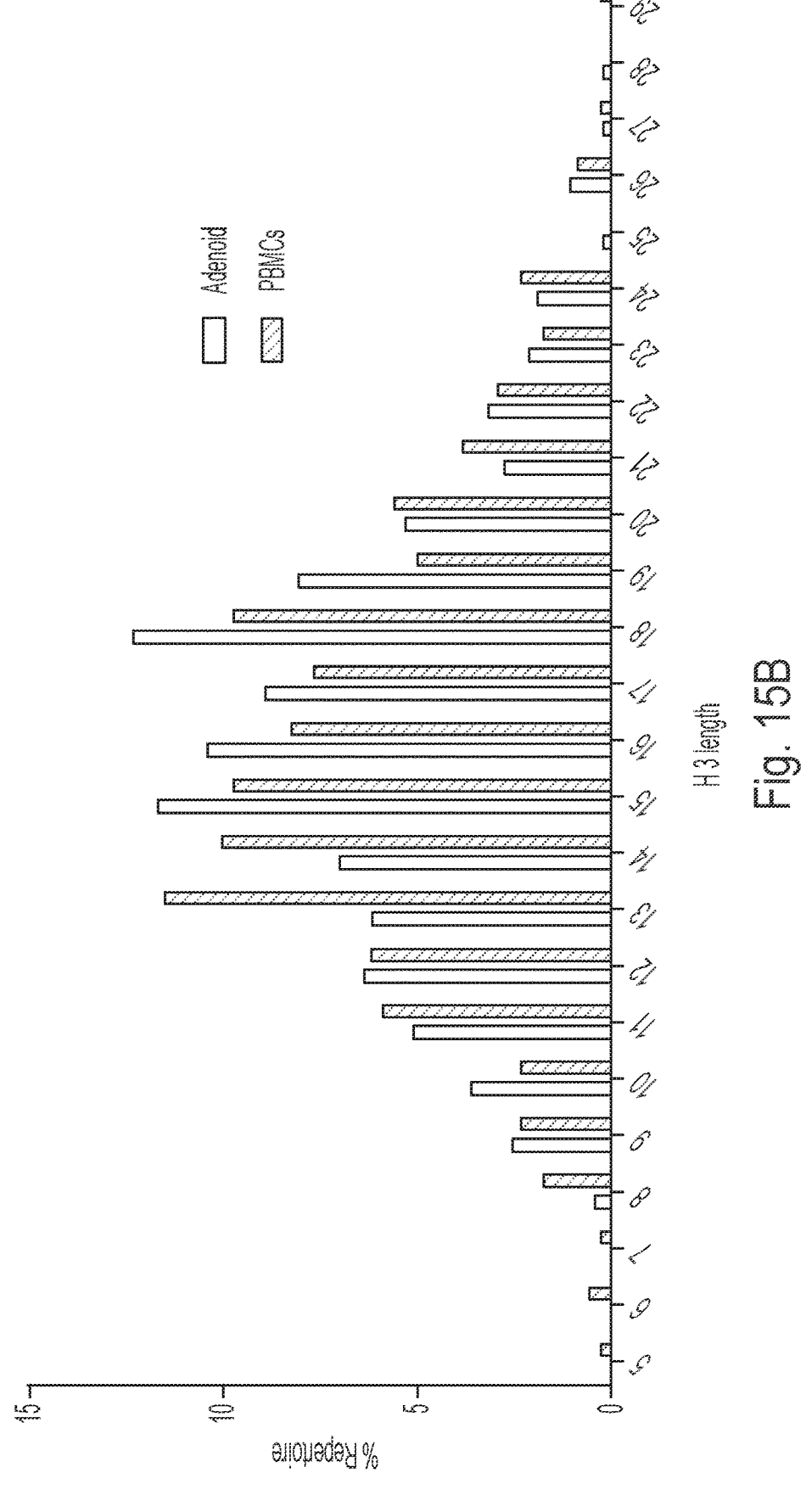
Figure 15C:
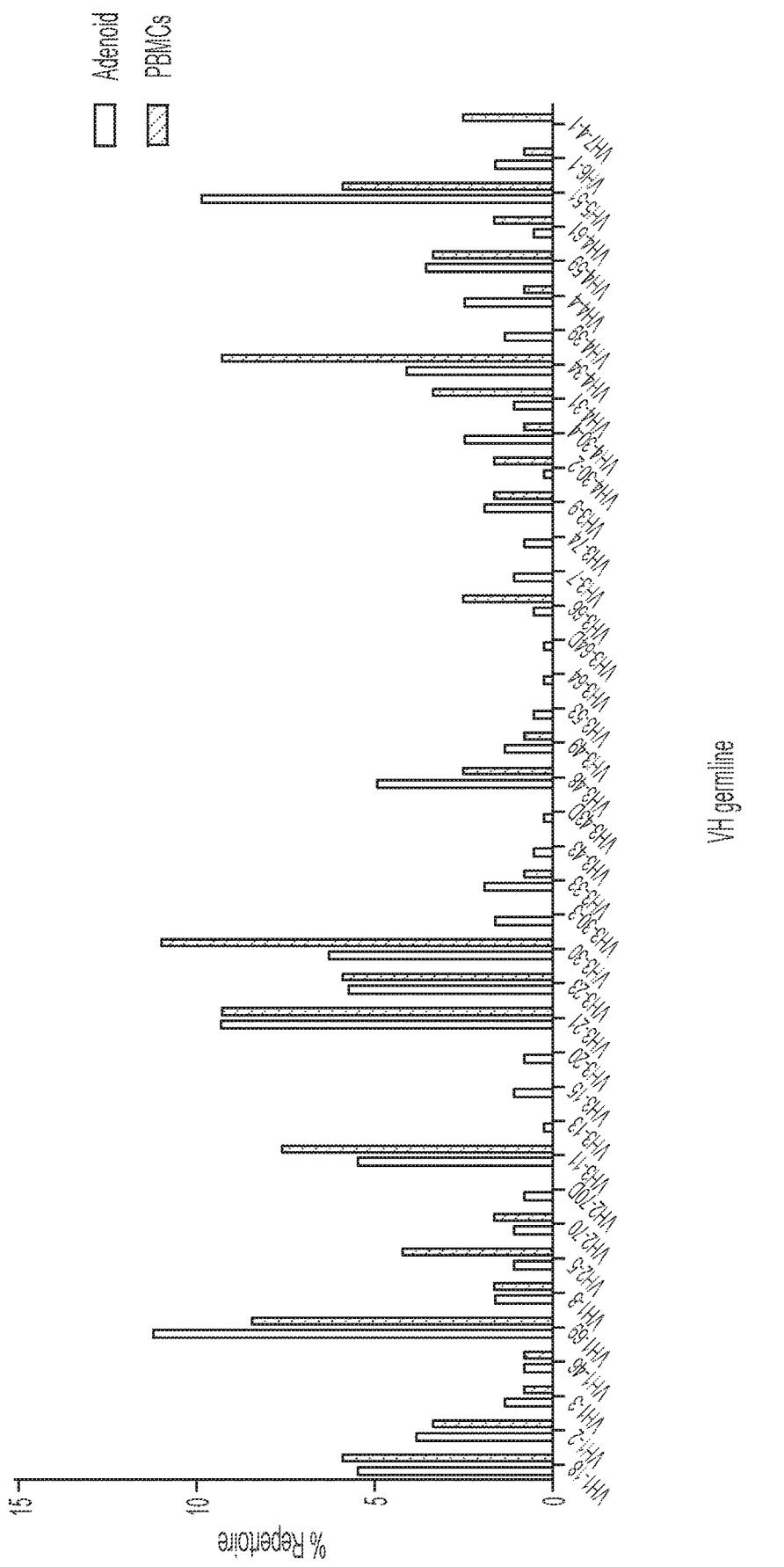

Next, the CDRH3 length distribution, $V_H$ germline gene usage, and load of somatic mutations in the antibodies isolated from the two compartments were analyzed (FIG. 15B). The median CDRH3 lengths of the antibodies isolated from PBMCs and adenoids were 15 and 16 amino acids, respectively, which is consistent with previously reported median CDRH3 lengths for anti-viral antibodies (Gilman et al., Sci Immunol. 2016; Bornholdt et al., Science 2016; Collis and Martin, J M B 2003). Although the $V_H$ germline gene usage was also comparable between the two compartments, there was an enrichment for $V_H$5-51 and $V_H$1-69 in the adenoid-derived antibodies and an enrichment for $V_H$4-34 and $V_H$3-30 in the PBMC-derived antibodies across all four donor repertoires (FIG. 15C). The level of somatic mutation in the antibodies varied among the 4 donors, with the median number of $V_H$ nucleotide substitutions ranging from 8-11 in the adenoid-derived antibodies and 7-9 in the PBMC-derived antibodies (FIG. 16A and FIG. 17A-D). For 3 out of 4 donors, the load of somatic mutations trended higher in the adenoid-derived antibodies relative to the PBMC-derived antibodies, but this difference only reached statistical significance in donor 2665.

Figure 16A:
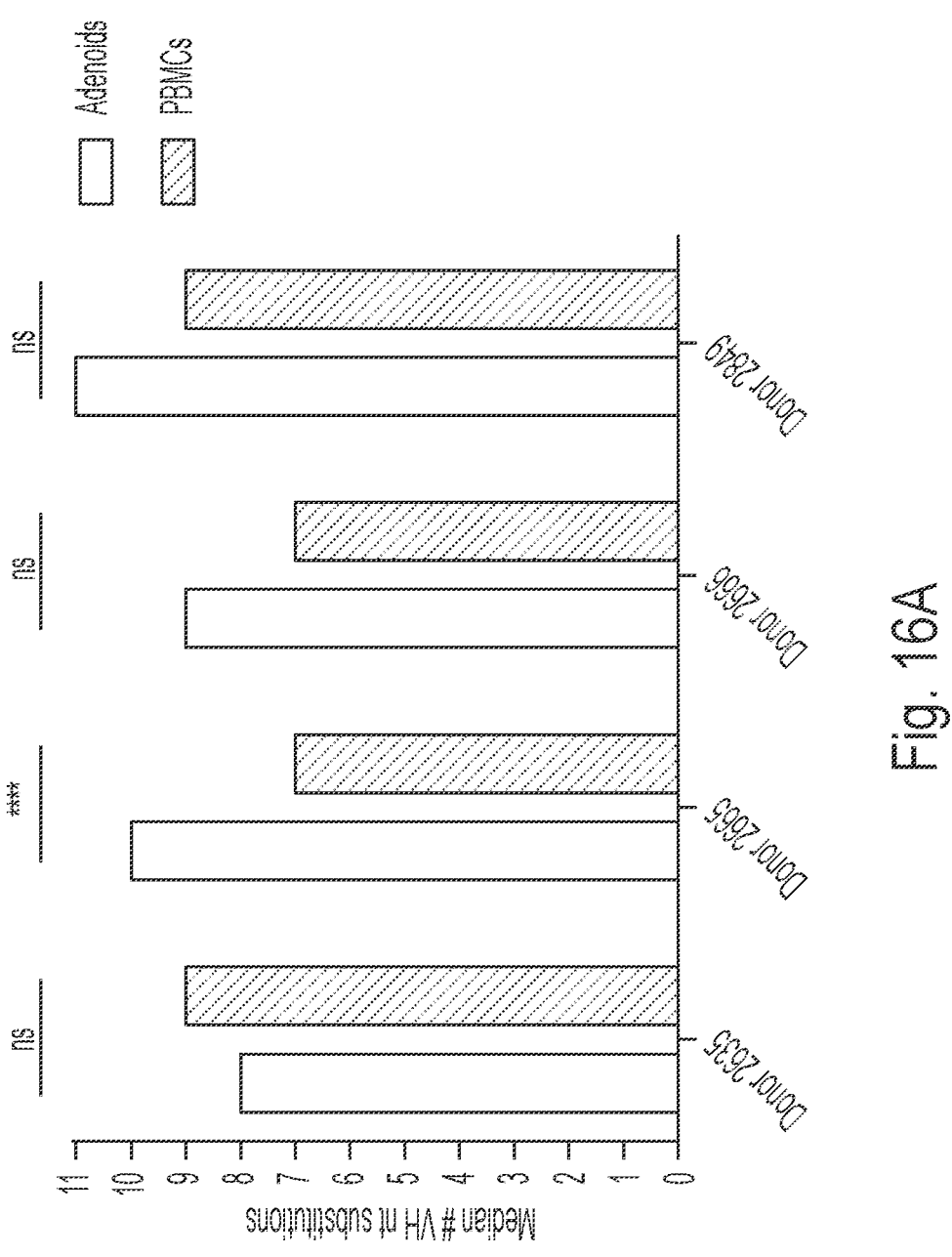
FIGS. 16A-E show the level of somatic mutation in the antibodies was varied among the 4 donors.
Figure 16B:
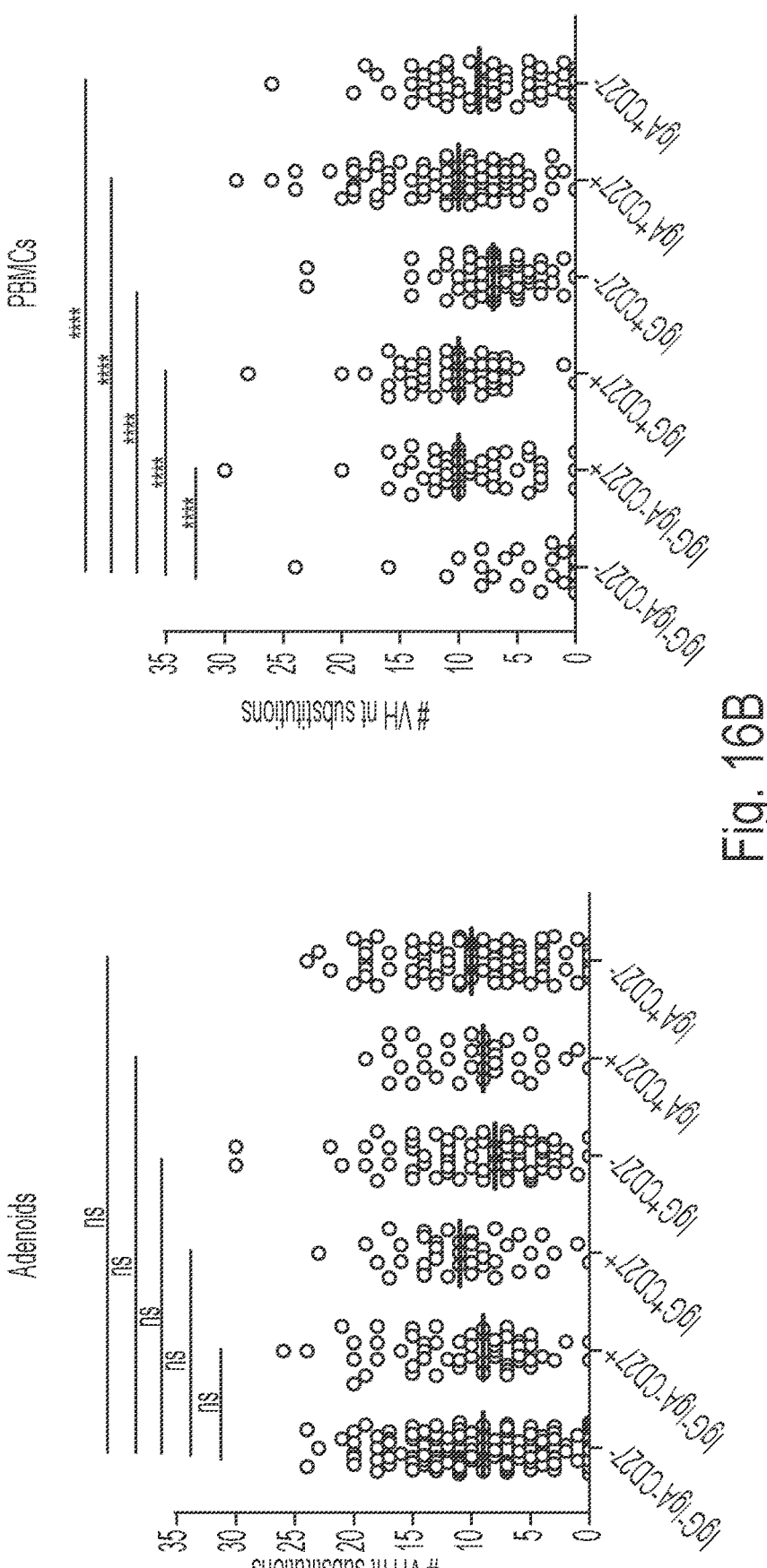
Figure 16D:
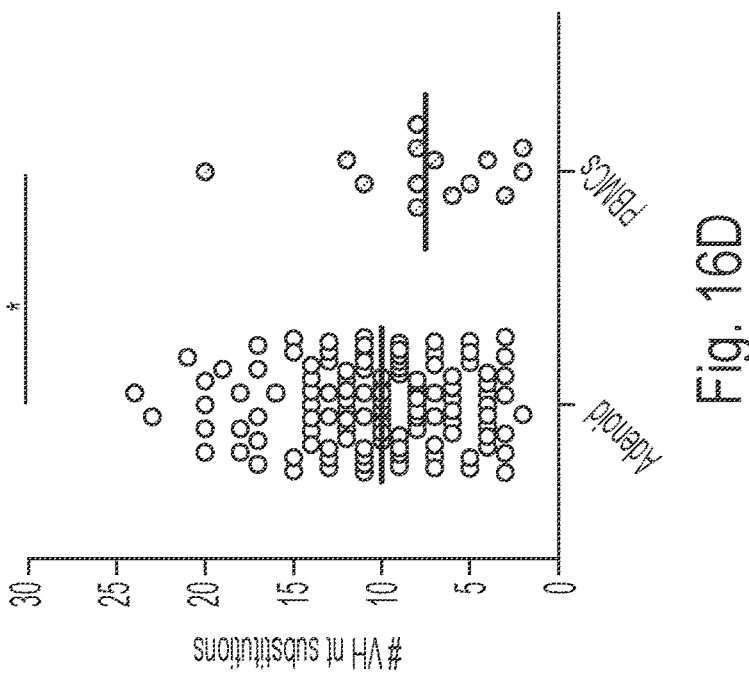
Figure 16C:
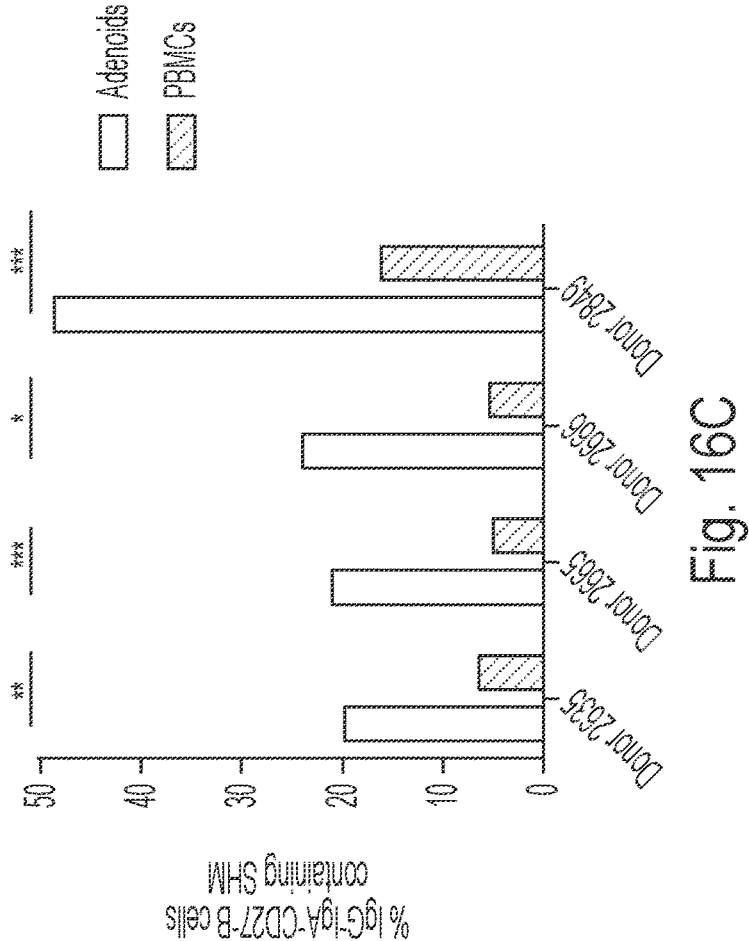
Figure 16E:
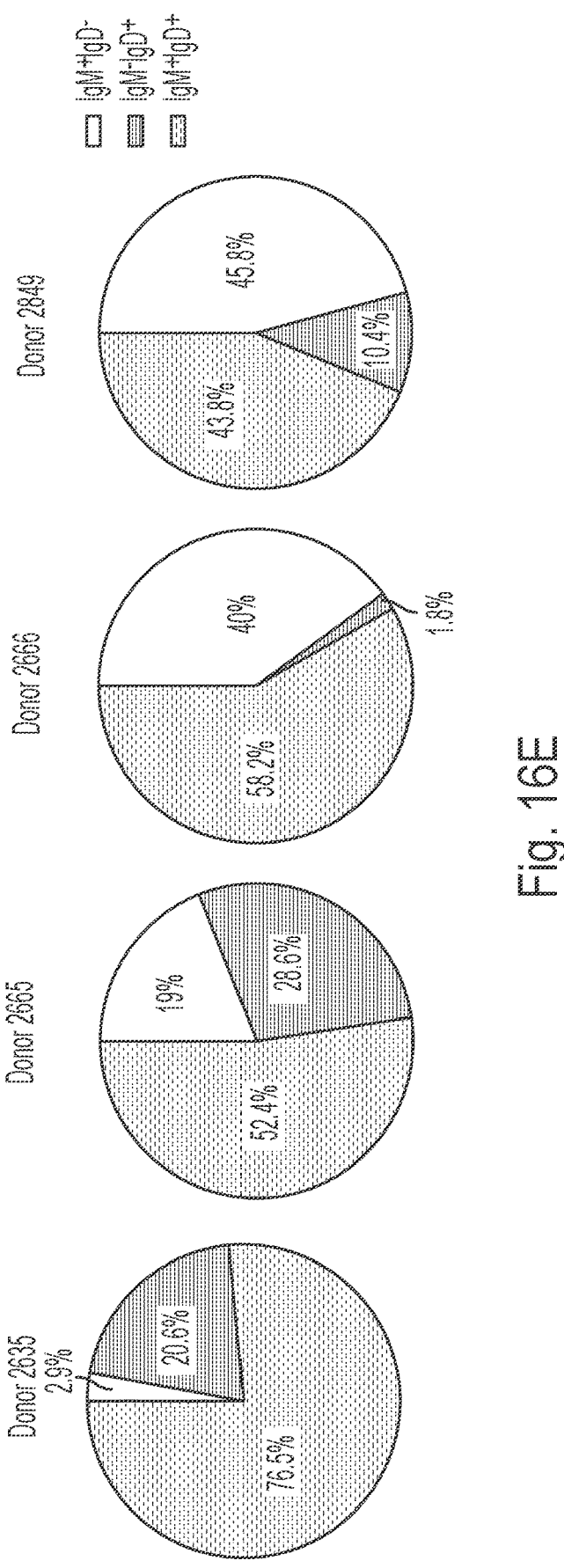
Figures 17A, 17B, 17C, 17D:
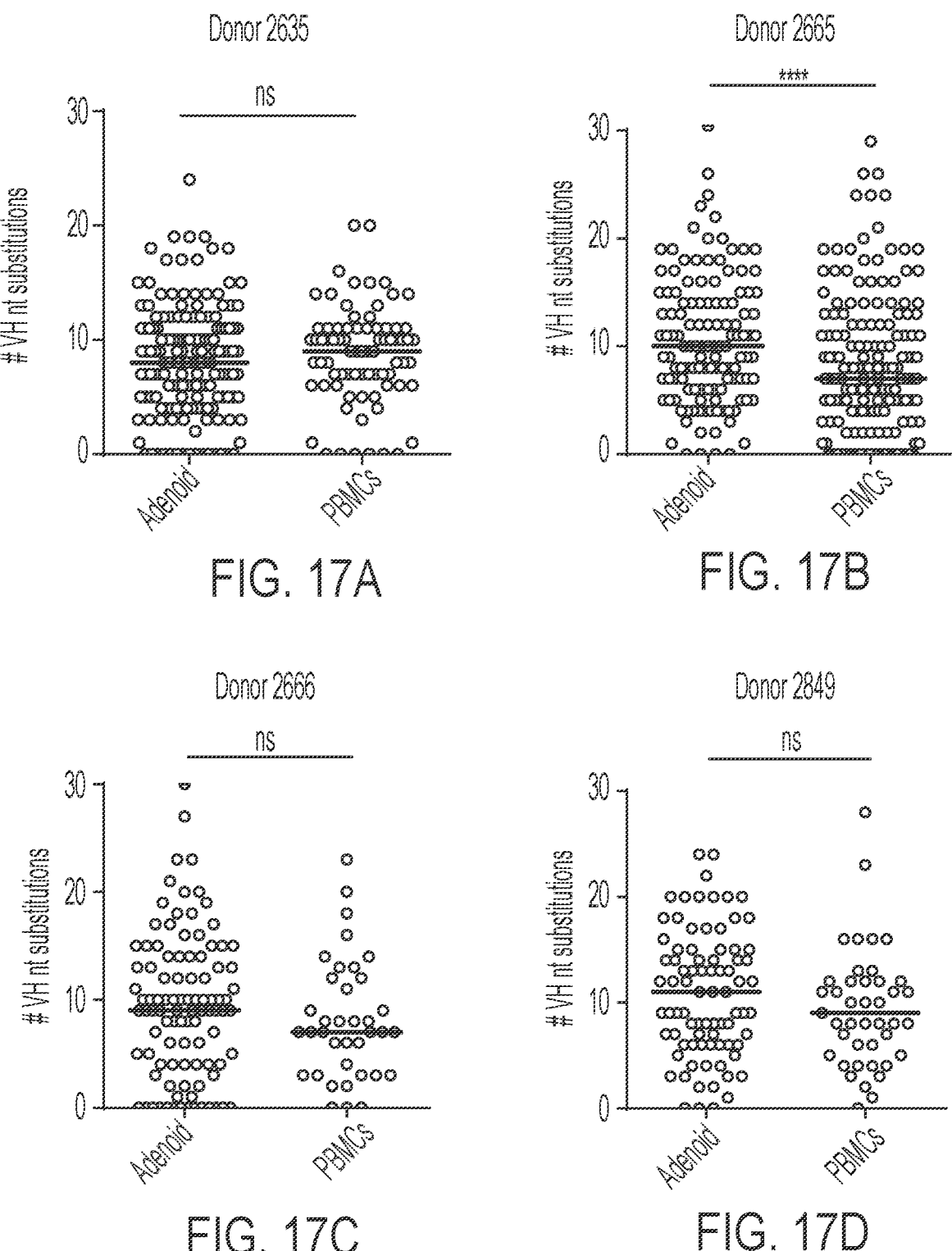
FIGS. 17A-D show the number of $V_H$ nucleotide substitutions in the adenoid-derived antibodies and PBMC-derived antibodies for each donor.
Figure 18A:
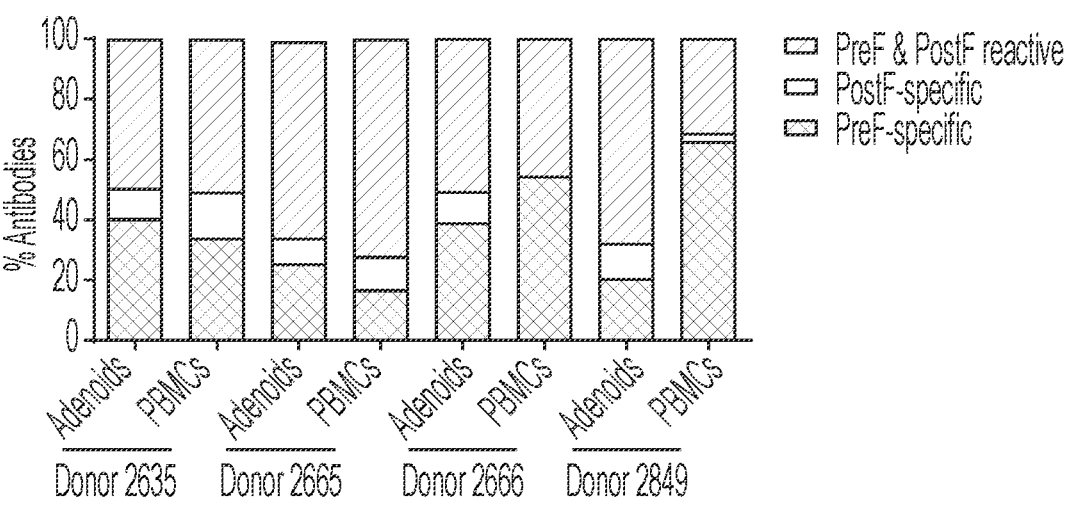
FIGS. 18A-B show the binding properties of the adenoid and PBMC-derived antibodies.

Analysis of the level of SHM within each individual B cell subset revealed that the antibodies derived from the IgG⁻IgA⁻ CD27⁻ adenoid B cells contained similar levels of SHM as classical IgG⁺ CD27⁺ and IgA⁺ CD27⁺ memory B cells, providing evidence that these B cells are germinal center-experienced (FIG. 16B). In contrast, the majority of antibodies derived from IgG IgA⁻ CD27 peripheral blood B cells lacked SHM, indicating a naïve B cell origin. In all 4 donors, the percentage of RSV F-specific IgG⁻IgA⁻ CD27⁻ B cells containing SHM was significantly higher in adenoids compared to PBMCs (FIG. 16C). Furthermore, even the small subset of somatically mutated antibodies derived from IgG⁻IgA⁻ CD27⁻ peripheral blood B cells contained lower levels of SHM compared to antibodies derived from IgG⁻IgA⁻ CD27⁻ adenoid B cells (FIG. 16D). To investigate the IgM and IgD expression profiles of the RSV F-specific IgG⁻IgA⁻ CD27⁻ adenoid B cells, the adenoid samples were restained with fluorescently labeled RSV F and a panel of secondary antibodies that included anti-human IgG, IgA, IgM, IgD, and CD27. This analysis revealed a high level of heterogeneity in IgM and IgD expression within this population of RSV F-specific B cells, with some of these B cells expressing only IgM or IgD and others co-expressing both markers (FIG. 16E). These B cells appear to belong to a unique population IgM and/or IgD memory B cells that contain somatic mutations but lack expression of previously described memory B cell markers.

a Higher Proportion of Adenoid-Derived Antibodies Display High Affinity Binding and Potent Neutralizing Activity Compared to PBMC-Derived Antibodies The apparent (IgG) binding affinities of the antibodies for RSV preF and postF were then measured using biolayer interferometry. The percentage of antibodies that bound exclusively to either preF or postF varied across the 4 donors but was similar between the two compartments within individual donors, with the exception of donor 2849, in which preF-specific antibodies were present at higher frequency in PBMCs compared to adenoid tissue (FIG. 18A). As observed in previous studies, a larger proportion of antibodies bound exclusively to preF (16-65%) than to postF (0-15%), demonstrating that the unique surfaces on preF are likely more immunogenic than those on postF. Although finer epitope mapping is required to better resolve the differences in epitope distribution between the two compartments, the results suggest that the relative immunogenicity of the different antigenic surfaces on RSV F is probably more dependent on the donor repertoire and/or immune history than on the anatomical site of B cell activation (FIG. 18A).

Figure 18B:
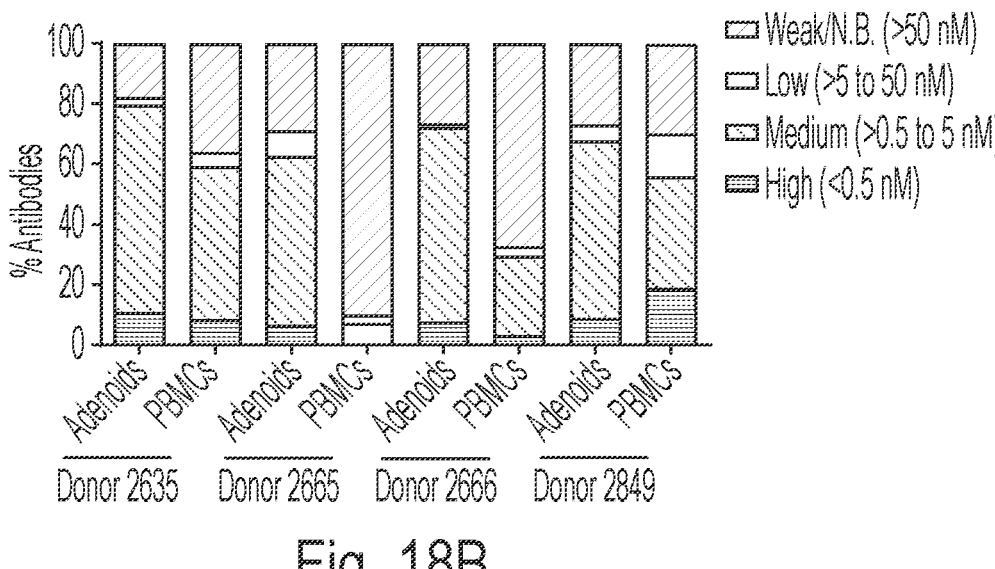

In 3 out of 4 donors, a higher proportion of RSV F-specific antibodies isolated from adenoids bound with medium to high affinity to preF (apparent $K_D$<5.0 nM) compared to antibodies derived from RSV F-reactive peripheral blood B cells (FIG. 18B). For example, 70% of the adenoid-derived antibodies cloned from donor 2666 displayed medium to high binding affinity to preF compared to only about 30% of the PBMC-derived antibodies. This result, combined with the observation that two additional donors had detectable RSV F-specific B cell responses in adenoid tissue but not in peripheral blood (FIG. 13B), suggests that the mucosal B cell response to RSV may be more robust than the corresponding systemic B cell response.

Figure 19A:
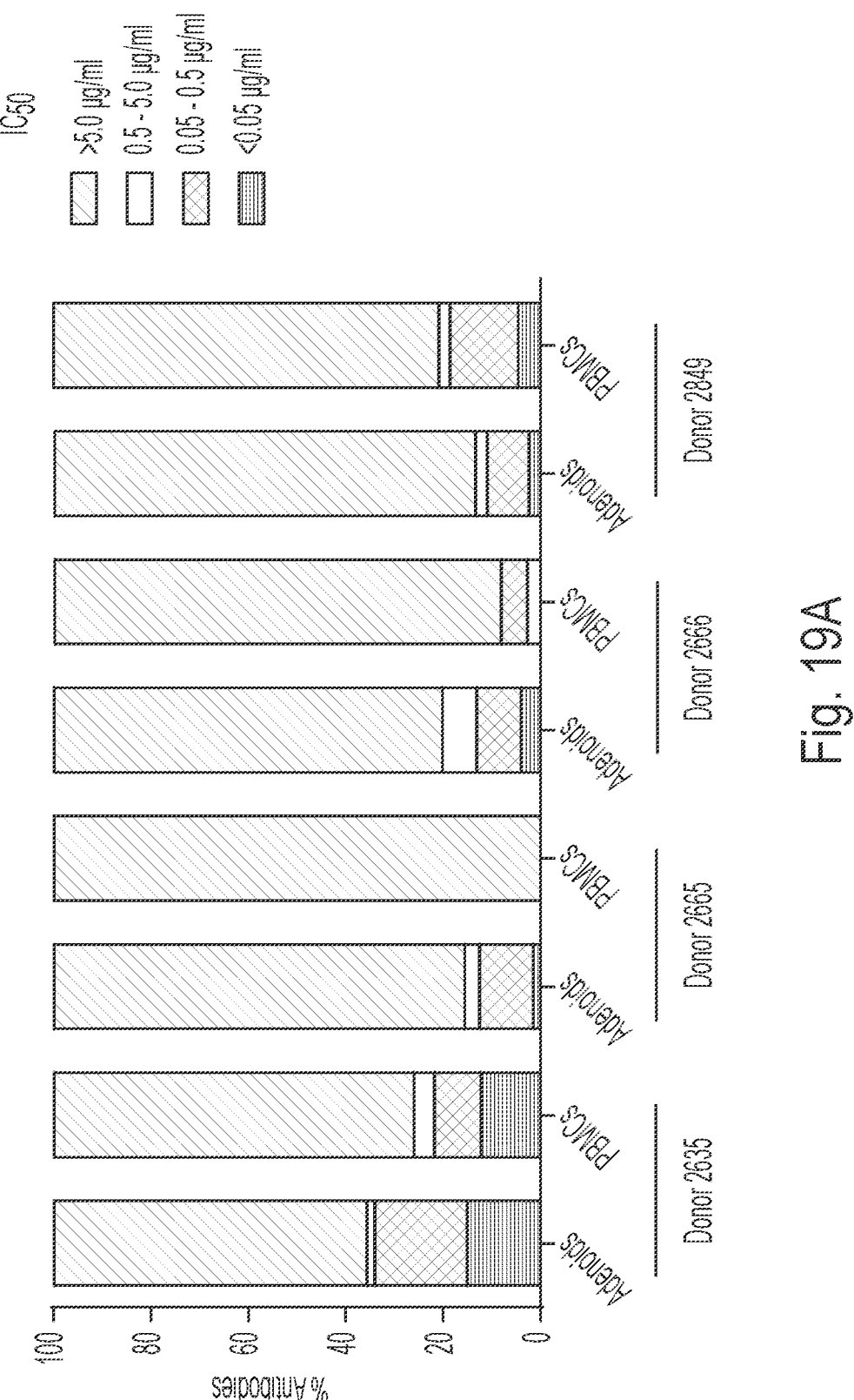

Next, the antibodies were tested for neutralizing activity against RSV-A2 using a previously described luciferase-based assay. 14% to 36% of the adenoid-derived antibodies and 0% to 26% of the PBMC-derived antibodies showed detectable neutralizing activity ($IC_{50}$<25 µg/mL) (FIG. 19A). In all donors, less than 20% of antibodies from both compartments showed highly potent neutralizing activity ($IC_{50}$<0.05 ug/mL), which is lower than that observed for three previously characterized healthy adult donors, in which 19-38% of isolated antibodies neutralized with high potency. The low fraction of highly potent neutralizing antibodies may be due to the young age of these donors, some of which have likely only experienced a single RSV infection. Consistent with this explanation, the antibody panel isolated from the oldest donor (donor 2635) contained the highest proportion of highly potent antibodies (FIG. 19A).

Figure 19B:
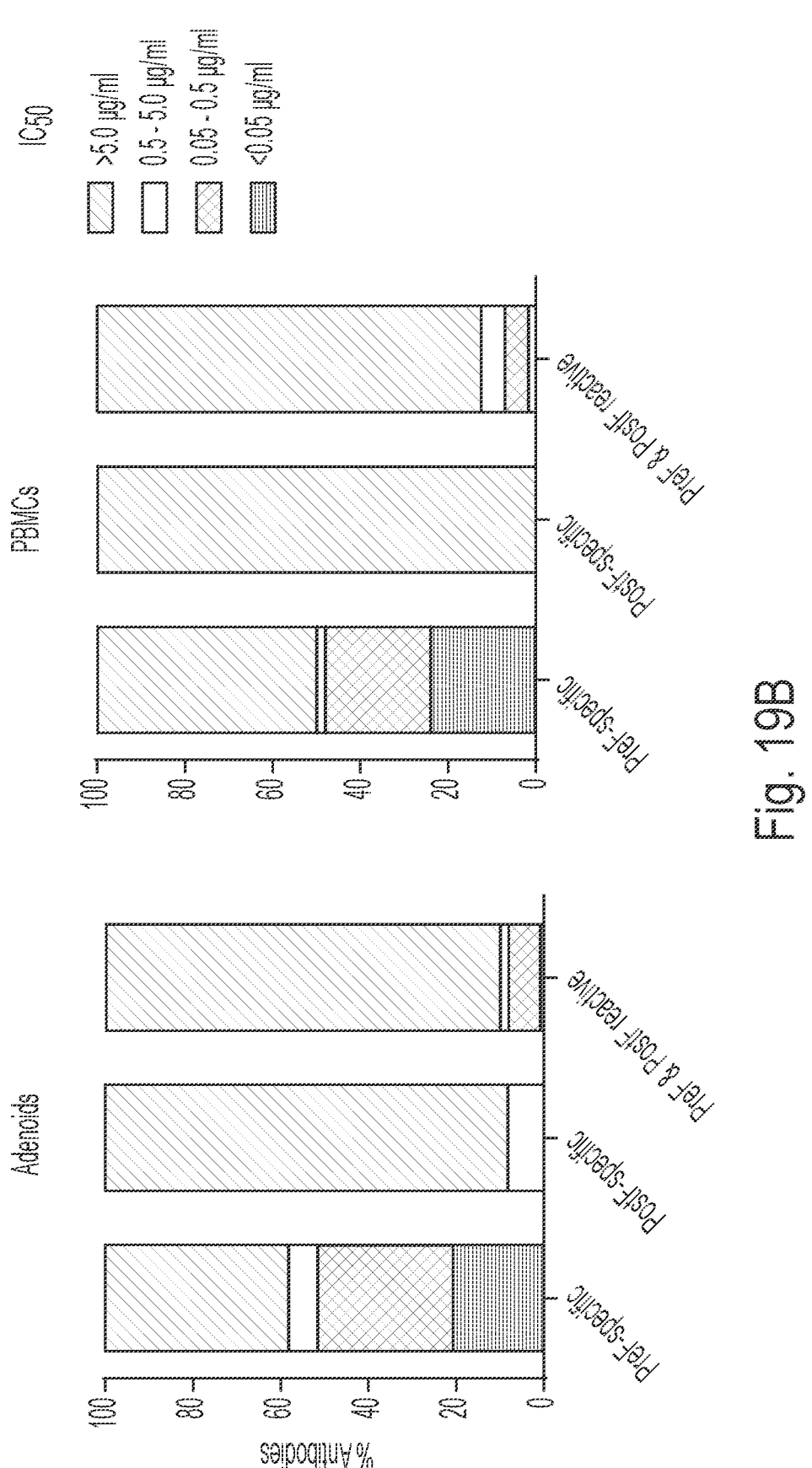

Consistent with the binding analysis, for 3 out of 4 donors, a larger proportion of adenoid-derived antibodies showed neutralizing activity compared to PBMC-derived antibodies (FIG. 19A). For example, for donor 2665, approximately 15% of adenoid-derived antibodies neutralized with an $IC_{50} \leq 25$ µg/mL whereas none of the PBMC-derived antibodies showed detectable activity at this concentration. Analysis of the relationship between preF- and postF binding activity and neutralization potency revealed that 50-60% of preF-specific antibodies isolated from both adenoids and PBMCs showed neutralizing activity compared to only 0-8% of postF-specific antibodies and 10-12% of conformation-independent antibodies (FIG. 19B). Importantly, greater than 90% of highly potent antibodies ($IC_{50}$<0.05 ug/mL) isolated from both compartments bound exclusively to preF. The antibody characteristics for antibodies derived from adenoid tissue and PBMCs are shown in Tables 6 and 7, respectively.

Finally, the relationship between memory B cell subset and neutralizing activity was analyzed. Approximately 90% of the PBMC-derived neutralizing antibodies originated from only three B cell subsets ($IgG^+$ $CD27^+$, $IgG^+$ $CD27^-$, and $IgG^-IgA^-$ $CD27^+$ B cells). In contrast, the adenoid-derived neutralizing antibodies were more evenly distributed across the six different memory B cell populations, with the largest proportion (25%) originating from the atypical $IgG^-IgA^-$ $CD27^-$ memory B cell subset (FIG. 19C). The antibodies isolated from this atypical memory B cell subset showed similar apparent binding affinities and neutralization potencies compared to the antibodies derived from other memory B cell subsets. These findings demonstrate that 1) adenoid tissue contains a larger proportion of high affinity neutralizing antibodies compared to peripheral blood, 2) a relatively large fraction of RSV F-specific adenoid-derived neutralizing antibodies originate from atypical memory B cells, and 3) the vast majority of neutralizing antibodies isolated from both compartments target epitopes exclusively expressed on preF.

TABLE 6

Summary of antibody characteristics for antibodies isolated from adenoid tissue

| Name | Donor | RSV preF KD | RSV postF KD | Neutralization IC50 (RSV subtype A) | Specificitiy | PSR score | VH Germline | VL Germline | VH Protein Muts | VL Protein Muts |
|---|---|---|---|---|---|---|---|---|---|---|
| ADI-36669 | 2635 | 1.09E−09 | N.B. | 0.02 | preF | 0.01 | VH1-46 | VK1-17 | 11 | 1 |
| ADI-36670 | 2635 | 7.49E−10 | N.B. | 0.01 | preF | 0.01 | VH1-69 | VK3-15 | 17 | 5 |
| ADI-36671 | 2635 | 7.28E−10 | N.B. | 0.01 | preF | 0.05 | VH3-11 | VL1-40 | 11 | 5 |
| ADI-36672 | 2635 | 7.03E−10 | N.B. | 0.02 | preF | 0.07 | VH3-11 | VL1-40 | 13 | 6 |
| ADI-36674 | 2635 | 7.45E−10 | N.B. | 0.01 | preF | 0.01 | VH3-21 | VL1-40 | 9 | 8 |
| ADI-36677 | 2635 | 5.40E−10 | N.B. | 0.02 | preF | 0.05 | VH3-48 | VK1-33 | 8 | 6 |
| ADI-36679 | 2635 | 8.78E−10 | N.B. | 0.01 | preF | 0.10 | VH5-51 | VK1-33 | 13 | 12 |
| ADI-36680 | 2635 | 7.19E−10 | N.B. | 0.01 | preF | 0.10 | VH5-51 | VK3-15 | 10 | 10 |
| ADI-36681 | 2635 | 1.20E−09 | N.B. | 0.01 | preF | 0.08 | VH5-51 | VK3-15 | 8 | 9 |
| ADI-41144 | 2635 | 9.40E−10 | 7.59E−10 | 0.37 | Both | 0.52 | VH1-2 | VK1-16 | 14 | 7 |
| ADI-41145 | 2635 | 3.18505E−09 | 8.14745E−10 | >25 | Both | 0.24 | VH4-59 | VK1-39 | 4 | 3 |
| ADI-41146 | 2635 | 4.44E−09 | 7.46E−10 | >25 | Both | 0.23 | VH5-51 | VK1-12 | 14 | 7 |
| ADI-41147 | 2635 | 4.6744E−10 | N.B. | 0.06 | preF | 0.21 | VH3-11 | VL1-40 | 10 | 7 |
| ADI-41149 | 2635 | 4.34E−09 | 8.57E−10 | >25 | Both | 0.16 | VH3-33 | VK3-15 | 6 | 6 |
| ADI-41153 | 2635 | 9.27936E−10 | 4.45077E−10 | >25 | Both | 0.14 | VH3-21 | VK1-39 | 17 | 12 |
| ADI-41154 | 2635 | 4.63E−09 | 1.35E−09 | >25 | Both | 0.14 | VH4-34 | VK1-39 | 9 | 7 |
| ADI-41155 | 2635 | 3.51668E−09 | 4.77633E−10 | >25 | Both | 0.13 | VH4-39 | VL1-47 | 10 | 5 |
| ADI-41156 | 2635 | N.B. | 1.69623E−09 | >25 | PostF | 0.133957365 | VH3-48 | VK1-39 | 4 | 9 |
| ADI-41157 | 2635 | 5.07E−10 | N.B. | 0.22 | preF | 0.13 | VH4-59 | VL1-47 | 6 | 13 |
| ADI-41158 | 2635 | 4.48646E−09 | N.B. | >25 | preF | 0.13 | VH3-48 | VK3-15 | 9 | 0 |
| ADI-41159 | 2635 | N.B. | 9.86775E−09 | >25 | PostF | 0.13 | VH5-51 | VK1-39 | 4 | 4 |
| ADI-41160 | 2635 | 2.41078E−09 | 3.36863E−10 | >25 | Both | 0.13 | VH1-69 | VL2-14 | 3 | 8 |
| ADI-41161 | 2635 | 2.53811E−09 | 3.63868E−10 | >25 | Both | 0.12 | VH3-48 | VL2-14 | 12 | 12 |
| ADI-41162 | 2635 | 4.06E−09 | 7.48E−10 | >25 | Both | 0.12 | VH1-69 | VK3-20 | 12 | 6 |
| ADI-41163 | 2635 | 4.65418E−09 | 6.03726E−10 | >25 | Both | 0.12 | VH3-33 | VK2-28 | 14 | 5 |
| ADI-41164 | 2635 | N.B. | 9.61753E−10 | >25 | PostF | 0.12 | VH3-48 | VK1-5 | 10 | 14 |
| ADI-41165 | 2635 | 2.40E−09 | N.B. | >25 | preF | 0.11 | VH5-51 | VK1-33 | 0 | 0 |
| ADI-41166 | 2635 | 3.15262E−09 | 4.40318E−10 | >25 | Both | 0.11 | VH1-2 | VL2-14 | 19 | 12 |
| ADI-41168 | 2635 | 1.33E−07 | N.B. | >25 | preF | 0.11 | VH3-30 | VL2-14 | 1 | 10 |
| ADI-41169 | 2635 | 4.94324E−09 | 1.18611E−09 | >25 | Both | 0.11 | VH5-51 | VK4-1 | 13 | 6 |
| ADI-41170 | 2635 | 5.67E−09 | 2.64E−09 | >25 | Both | 0.11 | VH3-23 | VK1-5 | 12 | 6 |
| ADI-41171 | 2635 | 9.80E−09 | 4.26E−09 | >25 | Both | 0.11 | VH4-31 | VK3-20 | 17 | 9 |
| ADI-41172 | 2635 | 3.05696E−09 | 7.48831E−10 | >25 | Both | 0.11 | VH3-64D | VK4-1 | 10 | 3 |
| ADI-41173 | 2635 | 3.15494E−10 | 2.93512E−10 | 0.08 | Both | 0.11 | VH1-69 | VK1-17 | 9 | 3 |
| ADI-41174 | 2635 | N.B. | 7.51319E−10 | >25 | PostF | 0.11 | VH1-18 | VL3-25 | 11 | 6 |
| ADI-41175 | 2635 | 4.25E−09 | 1.07E−09 | >25 | Both | 0.10 | VH3-33 | VK2-28 | 7 | 2 |
| ADI-41176 | 2635 | N.B. | 4.07E−09 | >25 | PostF | 0.10 | VH4-39 | VK1-27 | 13 | 6 |
| ADI-41177 | 2635 | 8.37277E−10 | N.B. | >25 | preF | 0.10 | VH1-2 | VL1-44 | 5 | 4 |
| ADI-41178 | 2635 | 1.71747E−09 | 6.01837E−10 | >25 | Both | 0.10 | VH1-2 | VK3-15 | 3 | 0 |
| ADI-41179 | 2635 | 9.48366E−10 | 3.4151E−10 | >25 | Both | 0.10 | VH1-69 | VL2-11 | 9 | 19 |
| ADI-41180 | 2635 | 4.70488E−10 | N.B. | 0.07 | preF | 0.10 | VH3-11 | VL1-40 | 8 | 9 |
| ADI-41181 | 2635 | 1.95174E−09 | 9.35655E−10 | >25 | Both | 0.10 | VH1-69 | VL2-14 | 7 | 8 |
| ADI-41182 | 2635 | 2.5543E−09 | 4.62114E−10 | >25 | Both | 0.10 | VH5-51 | VK3-15 | 6 | 6 |
| ADI-41183 | 2635 | 4.08E−09 | 1.00E−09 | >25 | Both | 0.10 | VH4-34 | VK1-39 | 15 | 13 |
| ADI-41184 | 2635 | 2.84503E−09 | 5.31986E−10 | >25 | Both | 0.10 | VH3-23 | VK1-39 | 7 | 5 |
| ADI-41185 | 2635 | 3.22683E−9 | 8.08927E−10 | >25 | Both | 0.10 | VH4-34 | VK3-20 | 5 | 6 |
| ADI-41186 | 2635 | 3.01027E−09 | 7.03469E−10 | >25 | Both | 0.10 | VH5-51 | VK3-15 | 4 | 5 |

TABLE 6-continued

Summary of antibody characteristics for antibodies isolated from adenoid tissue

| Name | Donor | RSV preF KD | RSV postF KD | Neutralization IC50 (RSV subtype A) | Specificitiy | PSR score | VH Germline | VL Germline | VH Protein Muts | VL Protein Muts |
|---|---|---|---|---|---|---|---|---|---|---|
| ADI-41188 | 2635 | 2.23985E−10 | N.B. | 0.15 | preF | 0.10 | VH4-34 | VL1-40 | 8 | 12 |
| ADI-41189 | 2635 | 2.86473E−09 | 6.07729E−10 | >25 | Both | 0.10 | VH3-21 | VL1-40 | 4 | 1 |
| ADI-41190 | 2635 | 2.29E−09 | 9.71E−10 | >25 | Both | 0.08 | VH1-3 | VK3-20 | 9 | 5 |
| ADI-41191 | 2635 | 5.01606E−10 | N.B. | 0.07 | preF | 0.08 | VH1-18 | VK2-30 | 8 | 6 |
| ADI-41192 | 2635 | 3.38603E−09 | 5.89066E−10 | >25 | Both | 0.07 | VH1-18 | VK1-39 | 12 | 3 |
| ADI-41193 | 2635 | 7.40214E−10 | N.B. | 0.07 | preF | 0.07 | VH3-11 | VL1-40 | 13 | 8 |
| ADI-41194 | 2635 | N.B. | 1.16E−09 | >25 | PostF | 0.07 | VH4-31 | VK3-20 | 10 | 7 |
| ADI-41196 | 2635 | 2.9157E−09 | 5.95141E−10 | >25 | Both | 0.07 | VH3-23 | VK1-39 | 12 | 3 |
| ADI-41197 | 2635 | 7.95E−10 | 5.31E−10 | 0.27 | Both | 0.07 | VH1-2 | VK1-39 | 12 | 5 |
| ADI-41198 | 2635 | 7.56E−10 | N.B. | 0.32 | preF | 0.06 | VH3-43 | VK1-33 | 18 | 12 |
| ADI-41199 | 2635 | 1.73E−09 | N.B. | 0.23 | preF | 0.06 | VH3-11 | VK3-15 | 7 | 24 |
| ADI-41200 | 2635 | 3.34299E−10 | 3.18362E−10 | >25 | Both | 0.05 | VH3-23 | VK2-28 | 14 | 9 |
| ADI-41201 | 2635 | 3.82297E−09 | 6.37241E−10 | >25 | Both | 0.05 | VH3-48 | VK3-11 | 15 | 9 |
| ADI-41202 | 2635 | 1.12088E−09 | 3.32852E−10 | >25 | Both | 0.05 | VH1-69 | VL2-11 | 9 | 19 |
| ADI-41203 | 2635 | 3.99236E−10 | N.B. | 0.01 | preF | 0.05 | VH5-51 | VK3-15 | 9 | 10 |
| ADI-41204 | 2635 | 5.44567E−10 | N.B. | 0.06 | preF | 0.04 | VH3-21 | VL1-40 | 3 | 3 |
| ADI-41205 | 2635 | 1.16405E−09 | 5.3591E−10 | >25 | Both | 0.04 | VH4-4 | VK4-1 | 3 | 6 |
| ADI-41206 | 2635 | 4.09075E−10 | N.B. | 0.07 | preF | 0.04 | VH3-21 | VL1-40 | 11 | 10 |
| ADI-41207 | 2635 | 2.53175E−10 | 4.37767E−10 | >25 | Both | 0.04 | VH2-70 | VL2-11 | 3 | 13 |
| ADI-41208 | 2635 | 4.83434E−10 | N.B. | 0.08 | preF | 0.04 | VH3-11 | VL1-40 | 11 | 7 |
| ADI-41209 | 2635 | 1.32E−09 | 1.59E−09 | 2.97 | Both | 0.03 | VH4-34 | VK2-28 | 11 | 3 |
| ADI-41210 | 2635 | 4.70023E−10 | N.B. | 0.10 | preF | 0.02 | VH1-18 | VK2-30 | 7 | 4 |
| ADI-41212 | 2635 | 3.17532E−10 | 4.00134E−10 | >25 | Both | 0.02 | VH1-2 | VL2-14 | 11 | 13 |
| ADI-41213 | 2635 | 3.4719E−09 | 5.76926E−10 | >25 | Both | 0.02 | VH3-53 | VL3-1 | 4 | 2 |
| ADI-41214 | 2635 | 5.6989E−09 | 1.01699E−09 | >25 | Both | 0.01 | VH3-7 | VK1-39 | 4 | 5 |
| ADI-41215 | 2635 | 4.37E−10 | 5.63E−10 | 0.32 | Both | 0.01 | VH3-20 | VL2-23 | 3 | 10 |
| ADI-41216 | 2635 | 9.03E−10 | N.B. | 0.19 | preF | 0.01 | VH3-11 | VL1-40 | 9 | 8 |
| ADI-41217 | 2635 | 4.88862E−10 | N.B. | 0.04 | preF | 0.01 | VH3-21 | VL1-40 | 7 | 5 |
| ADI-41218 | 2635 | N.B. | 7.28659E−10 | >25 | PostF | 0.01 | VH1-18 | VL1-40 | 10 | 7 |
| ADI-41219 | 2635 | N.B. | 1.28064E−09 | >25 | PostF | 0.01 | VH3-48 | VK1-39 | 7 | 4 |
| ADI-41221 | 2635 | 2.98426E−10 | 3.16654E−10 | 0.04 | Both | 0.01 | VH3-21 | VL2-11 | 8 | 18 |
| ADI-41222 | 2635 | 4.30995E−10 | N.B. | 0.02 | preF | 0.01 | VH3-30 | VL3-21 | 10 | 11 |
| ADI-41223 | 2635 | N.B. | 1.80931E−09 | >25 | PostF | 0.00 | VH3-30 | VL2-14 | 6 | 11 |
| ADI-41224 | 2635 | 5.24E−10 | 5.58E−10 | 0.13 | Both | 0.00 | VH3-49 | VL6-57 | 7 | 5 |
| ADI-41225 | 2635 | 4.15E−09 | 7.33E−10 | >25 | Both | 0.00 | VH3-11 | VK1-5 | 11 | 8 |
| ADI-41226 | 2635 | 8.20E−10 | N.B. | 0.15 | preF | 0.00 | VH3-11 | VL1-40 | 15 | 2 |
| ADI-41227 | 2635 | 4.62E−09 | N.B. | >25 | preF | 0.00 | VH1-69 | VL1-36 | 19 | 0 |
| ADI-41228 | 2635 | 4.86239E−09 | 6.1786E−10 | >25 | Both | 0.00 | VH4-59 | VL2-14 | 6 | 3 |
| ADI-41229 | 2635 | 1.14E−09 | 7.08E−10 | 0.07 | Both | 0.00 | VH3-30 | VK1-33 | 10 | 3 |
| ADI-41230 | 2635 | 1.83E−09 | 4.07E−10 | 24.10 | Both | 0.00 | VH5-51 | VL6-57 | 11 | 3 |
| ADI-41231 | 2635 | 3.05E−09 | 4.26E−10 | >25 | Both | 0.00 | VH5-51 | VL6-57 | 14 | 8 |
| ADI-41232 | 2635 | 7.05E−10 | N.B. | 0.03 | preF | 0.00 | VH1-18 | VK2-30 | 6 | 1 |
| ADI-41233 | 2635 | 1.06E−09 | N.B. | 0.15 | preF | 0.00 | VH3-11 | VL1-40 | 5 | 3 |
| ADI-41234 | 2635 | 1.46E−09 | N.B. | 0.10 | preF | 0.00 | VH3-30 | VK2-28 | 47 | 4 |
| ADI-41235 | 2635 | 4.72E−09 | 3.24E−09 | >25 | Both | 0.00 | VH4-34 | VL1-40 | 8 | 7 |
| ADI-41236 | 2635 | N.B. | 6.13E−08 | >25 | PostF | 0.00 | VH3-11 | VL1-40 | 7 | 14 |
| ADI-41237 | 2635 | 7.94E−10 | N.B. | 0.04 | preF | 0.00 | VH3-11 | VL1-40 | 5 | 3 |
| ADI-41238 | 2635 | 1.03E−09 | N.B. | 0.13 | preF | 0.00 | VH3-11 | VL1-40 | 5 | 6 |
| ADI-41239 | 2635 | 4.25E−09 | 1.47E−09 | >25 | Both | 0.00 | VH2-5 | VK2-28 | 6 | 1 |
| ADI-41240 | 2635 | 2.15E−09 | 1.20E−09 | >25 | Both | 0.00 | VH4-34 | VK1-5 | 13 | 10 |
| ADI-41241 | 2635 | 3.84E−09 | 9.27E−10 | 18.76 | Both | 0.00 | VH1-2 | VK1-39 | 4 | 6 |
| ADI-41242 | 2635 | 4.18E−09 | 9.07E−10 | >25 | Both | 0.00 | VH3-33 | VK2-28 | 12 | 2 |
| ADI-41243 | 2635 | 3.55E−09 | 4.18E−10 | >25 | Both | 0.00 | VH5-51 | VL6-57 | 9 | 4 |
| ADI-41244 | 2635 | N.B. | 8.43E−10 | >25 | PostF | 0.00 | VH3-53 | VK4-1 | 7 | 6 |
| ADI-41245 | 2635 | 7.75E−10 | N.B. | 0.71 | preF | 0.00 | VH3-11 | VL1-40 | 8 | 2 |
| ADI-41246 | 2635 | 3.07945E−09 | N.B. | >25 | preF | 0.00 | VH4-59 | VK3-20 | 4 | 6 |
| ADI-41247 | 2635 | 2.76078E−09 | 1.0202E−09 | >25 | Both | 0.00 | VH1-2 | VL6-57 | 10 | 1 |
| ADI-41248 | 2635 | 3.35413E−09 | 3.91839E−10 | >25 | Both | 0.00 | VH3-33 | VK1-39 | 7 | 5 |
| ADI-41249 | 2635 | 3.91497E−10 | N.B. | 0.01 | preF | 0.00 | VH5-51 | VK1-33 | 14 | 4 |
| ADI-41250 | 2635 | 7.30505E−10 | 5.04204E−10 | >25 | Both | 0.00 | VH4-34 | VL2-14 | 10 | 8 |
| ADI-41251 | 2635 | 5.92669E−10 | N.B. | 0.11 | preF | 0.00 | VH3-11 | VL1-40 | 5 | 2 |
| ADI-41252 | 2635 | 1.3715E−09 | 1.00354E−09 | >25 | Both | 0.00 | VH5-51 | VK1-33 | 11 | 2 |
| ADI-41253 | 2635 | 1.11084E−09 | N.B. | 0.03 | preF | 0.00 | VH4-39 | VK3-20 | 19 | 8 |
| ADI-41254 | 2635 | 7.75513E−10 | N.B. | >25 | preF | 0.00 | VH3-48 | VL1-44 | 8 | 8 |
| ADI-41255 | 2635 | 2.04133E−10 | 1.54027E−09 | >25 | Both | 0.00 | VH3-23 | VK3-15 | 6 | 3 |
| ADI-41256 | 2635 | 3.53762E−10 | N.B. | 0.02 | preF | 0.00 | VH1-69 | VK2-30 | 18 | 3 |
| ADI-41257 | 2635 | 3.81012E−09 | N.B. | >25 | preF | 0.00 | VH1-69 | VK1-39 | 10 | 6 |
| ADI-41258 | 2635 | 9.68014E−10 | N.B. | >25 | preF | 0.00 | VH3-23 | VL3-25 | 12 | 2 |
| ADI-41259 | 2635 | 3.35934E−10 | N.B. | 0.02 | preF | 0.00 | VH3-11 | VK2-30 | 9 | 8 |
| ADI-41261 | 2665 | 3.08217E−09 | 1.66794E−09 | >25 | Both | 0.33 | VH1-69 | VK3-20 | 7 | 0 |
| ADI-41263 | 2665 | 2.90427E−09 | 3.45081E−10 | >25 | Both | 0.25 | VH1-46 | VL6-57 | 13 | 5 |
| ADI-41264 | 2665 | N.B. | 4.83588E−10 | >25 | PostF | 0.15 | VH3-15 | VL3-10 | 9 | 13 |
| ADI-41265 | 2665 | 1.50426E−08 | 3.0791E−09 | >25 | Both | 0.15 | VH5-51 | VL1-51 | 15 | 6 |
| ADI-41266 | 2665 | 4.05839E−09 | N.B. | >25 | preF | 0.14 | VH6-1 | VL3-21 | 0 | 11 |

TABLE 6-continued

Summary of antibody characteristics for antibodies isolated from adenoid tissue

| Name | Donor | RSV preF KD | RSV postF KD | Neutralization IC50 (RSV subtype A) | Specificitiy | PSR score | VH Germline | VL Germline | VH Protein Muts | VL Protein Muts |
|---|---|---|---|---|---|---|---|---|---|---|
| ADI-41267 | 2665 | 1.0722E−08 | 1.09048E−08 | >25 | Both | 0.12 | VH4-4 | VL3-1 | 6 | 10 |
| ADI-41268 | 2665 | 5.80544E−10 | N.B. | 0.176867623 | preF | 0.11 | VH3-21 | VL2-14 | 12 | 7 |
| ADI-41270 | 2665 | 4.91907E−09 | 6.17282E−10 | >25 | Both | 0.11 | VH3-30-3 | VL2-23 | 5 | 5 |
| ADI-41271 | 2665 | N.B. | 3.11283E−09 | >25 | PostF | 0.11 | VH6-1 | VK4-1 | 2 | 3 |
| ADI-41273 | 2665 | 3.06182E−09 | 1.17234E−09 | >25 | Both | 0.11 | VH3-48 | VL2-11 | 17 | 12 |
| ADI-41274 | 2665 | 4.79702E−10 | N.B. | 0.109081031 | preF | 0.10 | VH3-21 | VL1-40 | 11 | 10 |
| ADI-41275 | 2665 | 5.74247E−10 | 1.32887E−09 | >25 | Both | 0.10 | VH3-21 | VK2-28 | 14 | 7 |
| ADI-41276 | 2665 | N.B. | 3.14914E−09 | >25 | PostF | 0.10 | VH3-49 | VK3-20 | 7 | 2 |
| ADI-41277 | 2665 | 3.59859E−09 | 7.80097E−10 | >25 | Both | 0.10 | VH4-4 | VK1-39 | 12 | 6 |
| ADI-41278 | 2665 | 1.28256E−09 | 4.82496E−10 | >25 | Both | 0.10 | VH2-70D | VK1-39 | 7 | 8 |
| ADI-41279 | 2665 | 5.04148E−08 | 4.78337E−08 | >25 | Both | 0.10 | VH5-51 | VL1-40 | 16 | 10 |
| ADI-41280 | 2665 | 3.62407E−09 | 4.82968E−10 | >25 | Both | 0.10 | VH4-59 | VK3-20 | 8 | 8 |
| ADI-41281 | 2665 | 6.69584E−09 | 1.57901E−09 | >25 | Both | 0.10 | VH1-3 | VK1-39 | 18 | 12 |
| ADI-41282 | 2665 | 3.24641E−09 | 1.25067E−09 | >25 | Both | 0.10 | VH3-30-3 | VK3-20 | 11 | 9 |
| ADI-41283 | 2665 | 2.74028E−08 | 7.95247E−09 | >25 | Both | 0.10 | VH2-5 | VK1-39 | 4 | 14 |
| ADI-41284 | 2665 | 3.05821E−09 | 5.47248E−10 | >25 | Both | 0.10 | VH3-15 | VL1-51 | 9 | 3 |
| ADI-41285 | 2665 | 5.11231E−10 | 4.12147E−10 | >25 | Both | 0.10 | VH1-69 | VL1-47 | 12 | 3 |
| ADI-41286 | 2665 | 7.59591E−09 | 5.48535E−09 | >25 | Both | 0.10 | VH1-18 | VK1-12 | 4 | 6 |
| ADI-41287 | 2665 | 3.22264E−09 | 5.97933E−10 | 5.845176257 | Both | 0.09 | VH3-9 | VL2-11 | 10 | 4 |
| ADI-41288 | 2665 | 8.99143E−09 | N.B. | >25 | preF | 0.08 | VH3-23 | VK3-20 | 14 | 12 |
| ADI-41289 | 2665 | N.B. | 8.81474E−10 | >25 | PostF | 0.08 | VH5-51 | VL2-23 | 8 | 10 |
| ADI-41291 | 2665 | 2.9847E−09 | 1.20178E−09 | >25 | Both | 0.07 | VH4-34 | VK1-39 | 16 | 9 |
| ADI-41292 | 2665 | 8.83038E−07 | 1.94972E−07 | >25 | Both | 0.06 | VH3-30 | VK1-5 | 10 | 12 |
| ADI-41293 | 2665 | 4.95631E−10 | 4.10968E−10 | 0.159400369 | Both | 0.05 | VH4-30-4 | VK3-20 | 6 | 6 |
| ADI-41294 | 2665 | 5.11755E−10 | N.B. | 0.080516504 | preF | 0.05 | VH3-48 | VL2-8 | 10 | 9 |
| ADI-41296 | 2665 | 3.35264E−09 | N.B. | >25 | preF | 0.04 | VH5-51 | VL3-25 | 20 | 19 |
| ADI-41297 | 2665 | 3.90841E−09 | 6.27923E−10 | >25 | Both | 0.04 | VH1-69 | VL2-14 | 5 | 6 |
| ADI-41299 | 2665 | 3.48237E−09 | 2.24822E−09 | >25 | Both | 0.04 | VH3-30 | VL2-23 | 14 | 12 |
| ADI-41302 | 2665 | 6.54219E−10 | N.B. | 0.006 | preF | 0.03 | VH3-30 | VL2-8 | 10 | 7 |
| ADI-41303 | 2665 | 2.95589E−09 | 9.43837E−10 | >25 | Both | 0.03 | VH3-23 | VK3-20 | 18 | 14 |
| ADI-41304 | 2665 | 3.37926E−10 | 3.30067E−10 | >25 | Both | 0.03 | VH4-30-4 | VL1-44 | 9 | 9 |
| ADI-41305 | 2665 | 3.63645E−09 | 4.31019E−10 | >25 | Both | 0.03 | VH4-31 | VK3-20 | 7 | 4 |
| ADI-41306 | 2665 | 4.61555E−10 | 4.54221E−10 | 0.173227379 | Both | 0.02 | VH4-30-4 | VK3-11 | 21 | 10 |
| ADI-41307 | 2665 | 2.98694E−09 | 8.29508E−10 | >25 | Both | 0.02 | VH3-21 | VK3-15 | 15 | 14 |
| ADI-41308 | 2665 | 4.00249E−09 | 5.18915E−10 | >25 | Both | 0.02 | VH6-1 | VL2-14 | 4 | 15 |
| ADI-41309 | 2665 | 4.33574E−09 | 1.36177E−09 | >25 | Both | 0.02 | VH4-30-4 | VK3-20 | 8 | 4 |
| ADI-41310 | 2665 | 3.3197E−09 | N.B. | >25 | preF | 0.02 | VH5-51 | VL3-25 | 18 | 22 |
| ADI-41311 | 2665 | 7.53938E−10 | 5.24E−10 | >25 | Both | 0.01 | VH2-70 | VK1-39 | 7 | 8 |
| ADI-41312 | 2665 | 3.37922E−09 | 8.56857E−10 | >25 | Both | 0.01 | VH4-4 | VL1-44 | 8 | 2 |
| ADI-41313 | 2665 | 4.54784E−10 | 3.41756E−10 | >25 | Both | 0.01 | VH1-18 | VL3-9 | 11 | 13 |
| ADI-41314 | 2665 | 2.40926E−09 | 4.14355E−10 | >25 | Both | 0.01 | VH1-69 | VL3-25 | 13 | 18 |
| ADI-41315 | 2665 | 2.93399E−09 | 1.0343E−09 | >25 | Both | 0.01 | VH4-59 | VK3-20 | 8 | 5 |
| ADI-41316 | 2665 | 3.73659E−09 | 1.04515E−09 | >25 | Both | 0.01 | VH3-30 | VK3-15 | 9 | 5 |
| ADI-41317 | 2665 | 4.81624E−08 | N.B. | 4.657687235 | preF | 0.01 | VH3-7 | VL1-40 | 12 | 11 |
| ADI-41318 | 2665 | 4.26427E−07 | 3.53944E−08 | >25 | Both | 0.01 | VH1-69 | VK1-13 | 16 | 9 |
| ADI-41319 | 2665 | 4.4099E−09 | 5.86603E−10 | >25 | Both | 0.01 | VH4-30-4 | VK3-20 | 4 | 4 |
| ADI-41320 | 2665 | 3.20131E−09 | N.B. | >25 | preF | 0.01 | VH5-51 | VL3-25 | 24 | 18 |
| ADI-41322 | 2665 | 2.98155E−09 | N.B. | >25 | preF | 0.00 | VH1-69 | VK1-12 | 9 | 3 |
| ADI-41323 | 2665 | 1.94986E−09 | 3.30643E−10 | >25 | Both | 0.00 | VH3-20 | VL6-57 | 10 | 5 |
| ADI-41324 | 2665 | 2.4749E−09 | 4.26392E−10 | >25 | Both | 0.00 | VH3-66 | VK3-20 | 4 | 6 |
| ADI-41340 | 2665 | 3.50828E−09 | N.B. | >25 | preF | 0.00 | VH1-69 | VL2-14 | 18 | 11 |
| ADI-41341 | 2665 | 2.83245E−10 | 1.96942E−09 | >25 | Both | 0.00 | VH1-69 | VL1-51 | 6 | 9 |
| ADI-41342 | 2665 | 3.99333E−09 | 5.90775E−10 | >25 | Both | 0.00 | VH1-69 | VK3-20 | 9 | 7 |
| ADI-41343 | 2665 | 7.21165E−10 | N.B. | 0.177309561 | preF | 0.00 | VH3-21 | VL1-40 | 5 | 3 |
| ADI-41344 | 2665 | 4.94249E−10 | N.B. | 0.063680457 | preF | 0.00 | VH3-21 | VL1-40 | 7 | 4 |
| ADI-41345 | 2665 | 2.28687E−09 | 3.48826E−10 | >25 | Both | 0.00 | VH5-51 | VL6-57 | 7 | 2 |
| ADI-41346 | 2665 | 1.88377E−09 | 2.67433E−10 | >25 | Both | 0.00 | VH5-51 | VL6-57 | 15 | 9 |
| ADI-41347 | 2665 | 2.60039E−09 | 5.2114E−10 | >25 | Both | 0.00 | VH4-4 | VK2-28 | 11 | 5 |
| ADI-41348 | 2665 | 4.75842E−10 | 4.3847E−10 | 0.076469111 | Both | 0.00 | VH4-31 | VK1-39 | 3 | 9 |
| ADI-41349 | 2665 | 6.24824E−09 | | >25 | Both | 0.00 | VH3-49 | VK1-33 | 12 | 8 |
| ADI-41350 | 2665 | N.B. | 6.01842E−10 | >25 | PostF | 0.00 | VH3-23 | VL2-14 | 4 | 9 |
| ADI-41351 | 2665 | 8.86433E−10 | N.B. | 0.148889821 | preF | 0.00 | VH3-64 | VK3-15 | 15 | 3 |
| ADI-41352 | 2665 | 3.35674E−09 | N.B. | >25 | preF | 0.00 | VH3-48 | VK4-1 | 4 | 0 |
| ADI-41353 | 2665 | 3.90918E−09 | N.B. | >25 | preF | 0.00 | VH5-51 | VL3-25 | 19 | 17 |
| ADI-41354 | 2665 | 7.71337E−10 | 4.28593E−10 | >25 | Both | 0.00 | VH3-23 | VK1-33 | 2 | 19 |
| ADI-41355 | 2665 | 3.84279E−09 | 1.17814E−09 | >25 | Both | 0.00 | VH3-11 | VL3-21 | 10 | 11 |
| ADI-41356 | 2665 | 7.24816E−10 | N.B. | 0.115429214 | preF | 0.00 | VH1-8 | VL3-1 | 4 | 7 |
| ADI-41357 | 2665 | 3.30683E−09 | N.B. | >25 | preF | 0.00 | VH3-48 | VK1-16 | 7 | 4 |
| ADI-41358 | 2665 | 8.64199E−10 | N.B. | 0.388841883 | preF | 0.00 | VH3-21 | VL1-40 | 5 | 4 |
| ADI-41359 | 2665 | 5.27247E−10 | N.B. | >25 | preF | 0.00 | VH3-21 | VL1-40 | 4 | 4 |
| ADI-41360 | 2665 | 2.45821E−09 | 3.58127E−10 | >25 | Both | 0.00 | VH3-48 | VL6-57 | 11 | 1 |
| ADI-41361 | 2665 | N.B. | 3.8252E−10 | 2.539820038 | PostF | 0.00 | VH3-30 | VK3-15 | 8 | 3 |
| ADI-41362 | 2665 | 3.37246E−09 | N.B. | 0.910656137 | preF | 0.00 | VH3-7 | VK1-33 | 14 | 11 |
| ADI-41363 | 2665 | 1.84993E−09 | N.B. | 0.143419355 | preF | 0.00 | VH1-69 | VK1-33 | 5 | 6 |

TABLE 6-continued

Summary of antibody characteristics for antibodies isolated from adenoid tissue

| Name | Donor | RSV preF KD | RSV postF KD | Neutralization IC50 (RSV subtype A) | Specificitiy | PSR score | VH Germline | VL Germline | VH Protein Muts | VL Protein Muts |
|---|---|---|---|---|---|---|---|---|---|---|
| ADI-41364 | 2665 | 1.31503E−09 | N.B. | 0.140467535 | preF | 0.00 | VH1-2 | VL2-23 | 17 | 6 |
| ADI-41365 | 2665 | 2.87064E−09 | 2.22411E−09 | >25 | Both | 0.00 | VH3-11 | VL1-40 | 7 | 8 |
| ADI-41366 | 2665 | 1.79472E−09 | 2.78051E−10 | >25 | Both | 0.00 | VH5-51 | VL6-57 | 10 | 8 |
| ADI-41367 | 2665 | 1.75638E−08 | 4.7231E−09 | >25 | Both | 0.00 | VH1-3 | VL2-14 | 19 | 13 |
| ADI-41368 | 2665 | 3.07672E−09 | 8.77542E−10 | >25 | Both | 0.00 | VH3-30 | VK1-5 | 14 | 9 |
| ADI-41369 | 2665 | 6.84843E−10 | 3.07855E−10 | >25 | Both | 0.00 | VH3-30 | VL6-57 | 6 | 4 |
| ADI-41370 | 2665 | 5.58964E−09 | 1.63921E−09 | >25 | Both | 0.00 | VH3-21 | VL3-25 | 6 | 6 |
| ADI-41371 | 2665 | 2.96473E−09 | 5.42686E−10 | >25 | Both | 0.00 | VH4-30-4 | VK3-20 | 14 | 11 |
| ADI-41372 | 2665 | 2.47619E−09 | 4.2465E−10 | >25 | Both | 0.00 | VH1-69 | VL3-25 | 8 | 19 |
| ADI-41373 | 2665 | 3.71092E−09 | 1.18174E−09 | >25 | Both | 0.00 | VH3-11 | VL1-40 | 15 | 7 |
| ADI-41374 | 2665 | 1.38715E−09 | 3.69047E−10 | >25 | Both | 0.00 | VH1-69 | VK1-33 | 17 | 9 |
| ADI-41375 | 2665 | 2.96439E−09 | 1.01798E−09 | >25 | Both | 0.00 | VH3-30 | VK1-13 | 8 | 8 |
| ADI-41376 | 2665 | 4.15159E−09 | 7.0539E−10 | >25 | Both | 0.00 | VH3-30 | VK3-15 | 8 | 4 |
| ADI-41377 | 2665 | 1.73768E−09 | N.B. | 0.239614261 | preF | 0.00 | VH6-1 | VL3-21 | 11 | 15 |
| ADI-41378 | 2665 | 2.98284E−09 | 7.38719E−10 | >25 | Both | 0.00 | VH4-4 | VK1-39 | 5 | 10 |
| ADI-41379 | 2665 | N.B. | 1.10788E−09 | >25 | PostF | 0.00 | VH5-51 | VK1-33 | 5 | 6 |
| ADI-41380 | 2665 | 2.56169E−10 | N.B. | 0.054916106 | preF | 0.00 | VH5-51 | VK1-33 | 0 | 4 |
| ADI-41381 | 2665 | 2.60472E−09 | 1.33733E−09 | >25 | Both | 0.00 | VH4-30-4 | VK3-20 | 13 | 5 |
| ADI-41382 | 2666 | 4.91343E−10 | N.B. | 0.02 | preF | 0.00 | VH3-9 | VK3-15 | 10 | 2 |
| ADI-41384 | 2666 | 3.45299E−09 | 5.63124E−10 | >25 | Both | 0.20 | VH1-69 | VK3-20 | 10 | 7 |
| ADI-41385 | 2666 | 4.52281E−09 | 6.00686E−10 | >25 | Both | 0.10 | VH3-33 | VL1-40 | 3 | 2 |
| ADI-41386 | 2666 | 4.03244E−10 | N.B. | >25 | preF | 0.10 | VH1-2 | VL1-44 | 11 | 7 |
| ADI-41389 | 2666 | 2.58276E−09 | 5.12803E−10 | >25 | Both | 0.10 | VH3-30-3 | VL3-25 | 7 | 1 |
| ADI-41390 | 2666 | 6.40545E−10 | N.B. | 0.62 | preF | 0.10 | VH3-21 | VL1-40 | 7 | 4 |
| ADI-41391 | 2666 | 8.82233E−10 | 4.78533E−10 | >25 | Both | 0.10 | VH4-59 | VL2-14 | 3 | 5 |
| ADI-41392 | 2666 | 3.29102E−10 | 3.58725E−10 | 0.18 | Both | 0.10 | VH3-30-3 | VL2-14 | 14 | 8 |
| ADI-41393 | 2666 | 1.66525E−09 | 2.46585E−10 | >25 | Both | 0.10 | VH5-51 | VL6-57 | 2 | 3 |
| ADI-41394 | 2666 | 3.06807E−09 | N.B. | >25 | preF | 0.10 | VH1-69 | VL4-60 | 11 | 9 |
| ADI-41396 | 2666 | 5.1704E−10 | N.B. | 1.37 | preF | 0.10 | VH3-21 | VL1-40 | 9 | 3 |
| ADI-41397 | 2666 | 5.81313E−10 | N.B. | 0.09 | preF | 0.10 | VH3-21 | VL1-40 | 10 | 2 |
| ADI-41398 | 2666 | 6.00144E−10 | N.B. | 0.17 | preF | 0.09 | VH1-18 | VK2-30 | 1 | 4 |
| ADI-41399 | 2666 | 3.14259E−09 | N.B. | >25 | preF | 0.09 | VH1-3 | VL2-14 | 3 | 5 |
| ADI-41400 | 2666 | N.B. | 5.47444E−10 | >25 | PostF | 0.09 | VH3-48 | VK1-5 | 8 | 4 |
| ADI-41401 | 2666 | 3.21615E−09 | N.B. | >25 | preF | 0.07 | VH3-9 | VK1-39 | 5 | 5 |
| ADI-41403 | 2666 | 3.04427E−09 | 8.41083E−10 | >25 | Both | 0.04 | VH3-21 | VK2-28 | 9 | 3 |
| ADI-41404 | 2666 | 4.73759E−08 | 1.3574E−08 | >25 | Both | 0.04 | VH1-69 | VK3-20 | 8 | 3 |
| ADI-41405 | 2666 | 2.72169E−09 | 4.58099E−10 | >25 | Both | 0.02 | VH3-48 | VK3-11 | 9 | 2 |
| ADI-41406 | 2666 | N.B. | 5.71343E−10 | >25 | PostF | 0.02 | VH3-23 | VK1-16 | 8 | 6 |
| ADI-41407 | 2666 | 2.08406E−09 | 3.71284E−10 | >25 | Both | 0.01 | VH3-23 | VK1-27 | 9 | 7 |
| ADI-41408 | 2666 | 2.13579E−10 | N.B. | >25 | preF | 0.00 | VH5-51 | VK1-33 | 9 | 7 |
| ADI-41409 | 2666 | 6.26652E−10 | N.B. | 0.29 | preF | 0.00 | VH1-18 | VK2-30 | 4 | 2 |
| ADI-41414 | 2666 | 2.70176E−09 | 1.1037E−09 | >25 | Both | 0.00 | VH3-66 | VK1-5 | 14 | 4 |
| ADI-41415 | 2666 | 1.08103E−09 | 6.43742E−10 | >25 | Both | 0.11 | VH2-70D | VK1-39 | 9 | 10 |
| ADI-41416 | 2666 | 4.43792E−10 | N.B. | 0.05 | preF | 0.10 | VH3-21 | VL1-40 | 8 | 5 |
| ADI-41417 | 2666 | 9.19338E−10 | N.B. | 0.71 | preF | 0.10 | VH3-21 | VL1-40 | 3 | 2 |
| ADI-41418 | 2666 | 1.58304E−09 | 3.41314E−10 | >25 | Both | 0.10 | VH3-15 | VL3-10 | 13 | 5 |
| ADI-41419 | 2666 | 3.0463E−10 | N.B. | 0.01 | preF | 0.10 | VH3-9 | VL2-14 | 4 | 6 |
| ADI-41420 | 2666 | N.B. | 1.09885E−07 | >25 | PostF | 0.10 | VH3-30-3 | VL2-18 | 0 | 0 |
| ADI-41421 | 2666 | 2.51681E−09 | N.B. | 4.78 | preF | 0.10 | VH1-18 | VL3-10 | 18 | 4 |
| ADI-41423 | 2666 | 5.86859E−08 | N.B. | >25 | preF | 0.10 | VH3-21 | VL2-14 | 0 | 1 |
| ADI-41424 | 2666 | 7.44001E−10 | N.B. | 0.28 | preF | 0.00 | VH1-18 | VK2-30 | 14 | 13 |
| ADI-41425 | 2666 | 1.13708E−09 | 4.96097E−10 | >25 | Both | 0.00 | VH2-70 | VK1-39 | 13 | 9 |
| ADI-41427 | 2666 | 2.69701E−09 | 9.17353E−10 | >25 | Both | 0.21 | VH4-59 | VL2-14 | 5 | 1 |
| ADI-41429 | 2666 | 3.61957E−09 | 1.00206E−09 | >25 | Both | 0.10 | VH1-69 | VL2-14 | 3 | 2 |
| ADI-41431 | 2666 | 7.44349E−10 | 3.44594E−10 | 2.38 | Both | 0.10 | VH1-18 | VL1-51 | 14 | 7 |
| ADI-41432 | 2666 | 2.04914E−09 | 2.86037E−10 | >25 | Both | 0.10 | VH1-69 | VL2-11 | 14 | 8 |
| ADI-41433 | 2666 | N.B. | 1.2267E−09 | >25 | PostF | 0.10 | VH3-30 | VL2-11 | 8 | 4 |
| ADI-41434 | 2666 | 6.13319E−10 | N.B. | >25 | preF | 0.10 | VH3-9 | VK3-15 | 5 | 3 |
| ADI-41435 | 2666 | N.B. | 3.47214E−09 | >25 | PostF | 0.10 | VH3-21 | VL1-44 | 6 | 4 |
| ADI-41436 | 2666 | 1.10343E−09 | 2.3675E−10 | >25 | Both | 0.10 | VH3-30-3 | VL6-57 | 11 | 5 |
| ADI-41437 | 2666 | 3.5009E−10 | N.B. | >25 | preF | 0.04 | VH1-18 | VK4-1 | 13 | 4 |
| ADI-41438 | 2666 | 3.1446E−09 | N.B. | >25 | preF | 0.00 | VH1-69 | VK3-15 | 22 | 11 |
| ADI-41439 | 2666 | 5.00975E−10 | N.B. | 0.34 | preF | 0.00 | VH1-18 | VK2-30 | 10 | 2 |
| ADI-41440 | 2666 | 3.18018E−09 | 1.23422E−09 | >25 | Both | 0.00 | VH3-21 | VK3-15 | 8 | 4 |
| ADI-41441 | 2666 | 3.11642E−10 | N.B. | >25 | preF | 0.00 | VH4-39 | VK1-9 | 12 | 5 |
| ADI-41442 | 2666 | 5.21389E−10 | N.B. | 0.04 | preF | 0.00 | VH3-9 | VK3D-15 | 3 | 3 |
| ADI-41443 | 2666 | 2.39989E−09 | 3.73358E−10 | >25 | Both | 0.00 | VH3-33 | VK2-28 | 7 | 7 |
| ADI-41444 | 2666 | 3.01394E−09 | 5.40812E−10 | >25 | Both | 0.00 | VH4-30-4 | VK1-5 | 17 | 10 |
| ADI-41445 | 2666 | 3.04263E−09 | 7.71859E−10 | >25 | Both | 0.19 | VH1-69 | VK3-20 | 17 | 6 |
| ADI-41446 | 2666 | 3.60473E−09 | 7.21955E−10 | >25 | Both | 0.12 | VH3-23 | VK3-11 | 10 | 6 |
| ADI-41447 | 2666 | 5.40998E−08 | N.B. | >25 | preF | 0.12 | VH3-23 | VK3-20 | 4 | 3 |
| ADI-41448 | 2666 | 2.74846E−09 | 4.28394E−10 | >25 | Both | 0.10 | VH1-69 | VL2-14 | 16 | 12 |
| ADI-41449 | 2666 | 5.07579E−10 | N.B. | 0.16 | preF | 0.10 | VH3-21 | VL1-40 | 10 | 5 |
| ADI-41450 | 2666 | 6.13101E−10 | N.B. | 0.21 | preF | 0.10 | VH3-21 | VL1-40 | 12 | 9 |

TABLE 6-continued

Summary of antibody characteristics for antibodies isolated from adenoid tissue

| Name | Donor | RSV preF KD | RSV postF KD | Neutralization IC50 (RSV subtype A) | Specificitiy | PSR score | VH Germline | VL Germline | VH Protein Muts | VL Protein Muts |
|---|---|---|---|---|---|---|---|---|---|---|
| ADI-41451 | 2666 | 1.82249E−09 | 1.66981E−09 | 0.84 | Both | 0.10 | VH3-48 | VL3-1 | 13 | 16 |
| ADI-41452 | 2666 | 3.33249E−09 | N.B. | >25 | preF | 0.10 | VH1-3 | VL2-14 | 19 | 6 |
| ADI-41453 | 2666 | 2.16827E−09 | 4.02833E−10 | >25 | Both | 0.10 | VH1-8 | VL3-9 | 8 | 4 |
| ADI-41454 | 2666 | 5.87531E−10 | N.B. | 0.88 | preF | 0.10 | VH1-18 | VK2-30 | 7 | 4 |
| ADI-41455 | 2666 | 1.52555E−09 | 6.37546E−10 | >25 | Both | 0.08 | VH4-30-4 | VK3-11 | 8 | 1 |
| ADI-41456 | 2666 | 1.48371E−09 | 2.66707E−10 | >25 | Both | 0.08 | VH3-74 | VL6-57 | 13 | 3 |
| ADI-41488 | 2849 | N.B. | 6.05E−10 | >25 | PostF | 0.10 | VH4-59 | VL2-11 | 12 | 6 |
| ADI-41489 | 2849 | 8.80E−08 | N.B. | >25 | preF | 0.10 | VH3-30 | VK3-15 | 13 | 6 |
| ADI-41491 | 2849 | 4.39E−10 | N.B. | >25 | preF | 0.08 | VH3-48 | VL3-21 | 7 | 4 |
| ADI-41492 | 2849 | 1.82E−07 | 5.48E−08 | >25 | Both | 0.07 | VH1-69 | VK1-39 | 11 | 6 |
| ADI-41493 | 2849 | 4.50E−10 | 3.72E−10 | >25 | Both | 0.06 | VH5-51 | VL2-8 | 5 | 2 |
| ADI-41494 | 2849 | 2.61E−09 | 4.40E−10 | >25 | Both | 0.06 | VH3-49 | VL2-14 | 16 | 7 |
| ADI-41495 | 2849 | 7.72E−08 | 5.73E−08 | >25 | Both | 0.05 | VH3-15 | VL6-57 | 12 | 4 |
| ADI-41496 | 2849 | 1.65E−09 | 1.37E−09 | >25 | Both | 0.04 | VH1-8 | VL2-23 | 3 | 6 |
| ADI-41497 | 2849 | 1.44E−09 | 2.68E−10 | >25 | Both | 0.04 | VH3-30 | VL3-21 | 12 | 7 |
| ADI-41498 | 2849 | 1.22E−09 | 2.20E−10 | >25 | Both | 0.04 | VH3-21 | VL3-21 | 13 | 4 |
| ADI-41499 | 2849 | 1.99E−09 | 2.97E−10 | >25 | Both | 0.04 | VH3-43 | VL2-11 | 13 | 9 |
| ADI-41501 | 2849 | 3.21E−09 | N.B. | >25 | preF | 0.03 | VH1-69 | VK4-1 | 13 | 4 |
| ADI-41502 | 2849 | 1.34E−09 | 3.08E−10 | >25 | Both | 0.01 | VH1-69 | VL2-11 | 12 | 5 |
| ADI-41503 | 2849 | 3.14E−09 | 4.93E−10 | >25 | Both | 0.01 | VH3-23 | VL2-14 | 9 | 3 |
| ADI-41504 | 2849 | 2.80E−09 | 5.08E−10 | >25 | Both | 0.01 | VH4-59 | VL1-40 | 8 | 3 |
| ADI-41505 | 2849 | 2.87E−09 | 5.23E−10 | >25 | Both | 0.00 | VH4-34 | VL1-40 | 11 | 4 |
| ADI-41507 | 2849 | N.B. | 1.40E−07 | >25 | PostF | 0.00 | VH2-5 | VL1-40 | 4 | 5 |
| ADI-41508 | 2849 | 4.15E−09 | 5.55E−10 | 0.10 | Both | 0.00 | VH1-18 | VL3-1 | 13 | 6 |
| ADI-41515 | 2849 | 3.33E−10 | N.B. | >25 | preF | 0.00 | VH3-23 | VL3-10 | 13 | 7 |
| ADI-41516 | 2849 | 4.14E−10 | N.B. | 0.08 | preF | 0.00 | VH4-4 | VL1-47 | 16 | 7 |
| ADI-41517 | 2849 | 5.01E−10 | N.B. | 0.02 | preF | 0.00 | VH3-23 | VL1-40 | 10 | 4 |
| ADI-41518 | 2849 | 7.76E−10 | N.B. | >25 | preF | 0.00 | VH3-21 | VL1-40 | 2 | 0 |
| ADI-41519 | 2849 | 9.75E−10 | N.B. | >25 | preF | 0.00 | VH4-39 | VK3-20 | 15 | 2 |
| ADI-41520 | 2849 | 9.98E−10 | N.B. | >25 | preF | 0.00 | VH3-20 | VK1-39 | 6 | 8 |
| ADI-41521 | 2849 | 1.68E−09 | N.B. | >25 | preF | 0.00 | VH3-9 | VK3-20 | 9 | 11 |
| ADI-41522 | 2849 | 2.20E−09 | N.B. | >25 | preF | 0.00 | VH1-69 | VL2-14 | 10 | 5 |
| ADI-41523 | 2849 | 2.91E−09 | N.B. | >25 | preF | 0.00 | VH5-51 | VK1-39 | 6 | 2 |
| ADI-41524 | 2849 | 3.18E−09 | N.B. | >25 | preF | 0.00 | VH3-49 | VK2-28 | 6 | 3 |
| ADI-41525 | 2849 | N.B. | 3.27E−10 | >25 | PostF | 0.00 | VH1-69 | VL2-14 | 19 | 4 |
| ADI-41526 | 2849 | 3.01E−10 | 3.36E−10 | >25 | Both | 0.00 | VH1-2 | VL1-44 | 8 | 6 |
| ADI-41527 | 2849 | 7.12E−10 | 3.37E−10 | >25 | Both | 0.00 | VH3-7 | VK1-12 | 4 | 6 |
| ADI-41528 | 2849 | 2.28E−09 | 3.48E−10 | >25 | Both | 0.00 | VH3-30 | VL3-1 | 5 | 8 |
| ADI-41529 | 2849 | 1.03E−09 | 3.51E−10 | >25 | Both | 0.00 | VH1-69 | VK3-20 | 19 | 7 |
| ADI-41530 | 2849 | 1.91E−09 | 3.55E−10 | >25 | Both | 0.00 | VH1-8 | VL3-9 | 10 | 8 |
| ADI-41531 | 2849 | 2.08E−09 | 3.77E−10 | >25 | Both | 0.00 | VH3-23 | VK1-33 | 12 | 11 |
| ADI-41532 | 2849 | 1.92E−09 | 3.92E−10 | >25 | Both | 0.00 | VH5-51 | VL1-44 | 5 | 3 |
| ADI-41533 | 2849 | 1.47E−09 | 4.23E−10 | >25 | Both | 0.00 | VH3-30 | VL3-1 | 10 | 9 |
| ADI-41534 | 2849 | 3.31E−09 | 4.72E−10 | >25 | Both | 0.00 | VH3-30 | VL3-1 | 8 | 3 |
| ADI-41535 | 2849 | 1.93E−09 | 4.76E−10 | >25 | Both | 0.00 | VH2-70D | VK1-39 | 5 | 6 |
| ADI-41536 | 2849 | 3.05E−09 | 4.76E−10 | >25 | Both | 0.00 | VH4-34 | VL1-40 | 10 | 3 |
| ADI-41537 | 2849 | 2.58E−09 | 4.88E−10 | >25 | Both | 0.00 | VH3-23 | VK2-28 | 7 | 2 |
| ADI-41538 | 2849 | 3.44E−09 | 5.87E−10 | >25 | Both | 0.00 | VH3-21 | VK4-1 | 12 | 4 |
| ADI-41538 | 2849 | 3.44E−09 | 5.87E−10 | >25 | Both | 0.00 | VH3-21 | VK4-1 | 12 | 4 |
| ADI-41539 | 2849 | 3.38E−09 | 6.15E−10 | 0.18 | Both | 0.00 | VH1-18 | VK3-15 | 6 | 3 |
| ADI-41540 | 2849 | 3.54E−09 | 6.86E−10 | >25 | Both | 0.00 | VH4-34 | VK3-20 | 17 | 9 |
| ADI-41541 | 2849 | 2.47E−09 | 7.76E−10 | >25 | Both | 0.00 | VH2-5 | VL3-21 | 1 | 2 |
| ADI-41542 | 2849 | N.B. | 7.96E−10 | 0.69 | PostF | 0.00 | VH5-51 | VK1-33 | 9 | 9 |
| ADI-41543 | 2849 | 2.90E−09 | 7.96E−10 | >25 | Both | 0.00 | VH1-2 | VK2-28 | 16 | 4 |
| ADI-41544 | 2849 | N.B. | 8.05E−10 | >25 | PostF | 0.00 | VH5-51 | VK1-33 | 6 | 3 |
| ADI-41545 | 2849 | 1.36E−09 | 8.25E−10 | >25 | Both | 0.00 | VH4-59 | VL3-21 | 7 | 2 |
| ADI-41546 | 2849 | N.B. | 1.08E−09 | >25 | PostF | 0.00 | VH5-51 | VK1-9 | 4 | 1 |
| ADI-41547 | 2849 | 3.19E−09 | 1.08E−09 | 0.05 | Both | 0.00 | VH1-69 | VK3-20 | 11 | 7 |
| ADI-41548 | 2849 | 2.56E−09 | 1.45E−09 | >25 | Both | 0.00 | VH4-4 | VK3-15 | 13 | 5 |
| ADI-41549 | 2849 | 4.08E−10 | 1.56E−09 | >25 | Both | 0.00 | VH3-30 | VL2-14 | 5 | 2 |
| ADI-41550 | 2849 | 2.29E−10 | 2.57E−08 | >25 | Both | 0.00 | VH1-18 | VL3-21 | 10 | 2 |
| ADI-41551 | 2849 | 1.30E−08 | 2.38E−08 | >25 | Both | 0.00 | VH3-74 | VL3-1 | 8 | 8 |
| ADI-43643 | 2666 | 7.66E−08 | N.B. | >25 | preF | 0.10 | VH3-21 | VL1-40 | 0 | 0 |
| ADI-43644 | 2665 | 2.93206E−08 | N.B. | >25 | preF | 0.00 | VH3-23 | VK3-11 | 0 | 0 |
| ADI-43645 | 2666 | 8.70E−09 | N.B. | >25 | preF | 0.25 | VH1-69 | VK1-5 | 0 | 0 |
| ADI-43646 | 2635 | 5.34462E−09 | N.B. | >25 | preF | 0 | VH3-43D | VL2-14 | 0 | 1 |
| ADI-43647 | 2635 | N.B. | 4.4563E−08 | >25 | PostF | 0 | VH3-23 | VK1-12 | 3 | 0 |
| ADI-43648 | 2666 | N.B. | 2.86E−08 | >25 | PostF | 0.10 | VH1-8 | VL3-9 | 0 | 1 |

TABLE 7

Summary of antibody characteristics for antibodies isolated from PBMCs

| Name | Donor | RSV preF binding KD | RSV postF binding KD | Neutralization IC50 (RSV subtype A) | Specificiity | PSR score | VH Germline | VL Germline | VH Protein Muts | VL Protein Muts |
|---|---|---|---|---|---|---|---|---|---|---|
| ADI-36673 | 2635 | 6.20328E−10 | N.B. | 0.019954073 | preF | 0.00 | VH3-11 | VL1-40 | 7 | 5 |
| ADI-36675 | 2635 | 8.07354E−10 | N.B. | 0.006 | preF | 0.00 | VH3-23 | VL1-51 | 10 | 11 |
| ADI-36676 | 2635 | 2.82227E−10 | N.B. | 0.006 | preF | 0.00 | VH3-30 | VL3-21 | 10 | 5 |
| ADI-36678 | 2635 | 7.16249E−10 | N.B. | 0.006 | preF | 0.14 | VH3-66 | VL3-1 | 14 | 15 |
| ADI-41552 | 2635 | 3.44465E−09 | 5.21877E−10 | >25 | Both | 0.39 | VH3-48 | VK3-11 | 10 | 4 |
| ADI-41553 | 2635 | N.B. | 8.03693E−10 | >25 | postF | 0.22 | VH1-18 | VK1-5 | 7 | 1 |
| ADI-41554 | 2635 | 1.34614E−09 | 1.07074E−09 | >25 | Both | 0.21 | VH3-23 | VK1-5 | 8 | 7 |
| ADI-41555 | 2635 | 5.68885E−09 | 1.12393E−09 | 25 | Both | 0.20 | VH4-31 | VK3-11 | 8 | 7 |
| ADI-41556 | 2635 | N.B. | 2.27656E−09 | >25 | postF | 0.19 | VH3-21 | VK3-15 | 5 | 3 |
| ADI-41557 | 2635 | 3.08525E−08 | 8.61139E−08 | >25 | Both | 0.17 | VH4-59 | VK3-15 | 11 | 8 |
| ADI-41558 | 2635 | 3.01911E−09 | 7.00004E−10 | >25 | Both | 0.17 | VH3-11 | VK3-20 | 14 | 5 |
| ADI-41561 | 2635 | 3.32537E−09 | 5.15754E−10 | >25 | Both | 0.14 | VH2-5 | VK1-12 | 10 | 8 |
| ADI-41562 | 2635 | N.B. | 6.75971E−10 | >25 | postF | 0.12 | VH1-18 | VK3-15 | 20 | 6 |
| ADI-41563 | 2635 | 6.02208E−10 | N.B. | 0.032327297 | preF | 0.12 | VH4-59 | VL1-40 | 11 | 11 |
| ADI-41564 | 2635 | 4.43977E−09 | 5.95709E−10 | >25 | Both | 0.12 | VH1-69 | VK3-20 | 20 | 0 |
| ADI-41567 | 2635 | 7.16511E−10 | N.B. | 0.050532702 | preF | 0.11 | VH4-34 | VK1-9 | 12 | 4 |
| ADI-41568 | 2635 | N.B. | 2.0658E−09 | >25 | postF | 0.09 | VH4-34 | VL3-25 | 7 | 4 |
| ADI-41569 | 2635 | 3.29786E−09 | 1.60525E−09 | >25 | Both | 0.08 | VH1-69 | VK3D-15 | 10 | 7 |
| ADI-41570 | 2635 | 2.97345E−09 | 1.1235E−09 | 25 | Both | 0.08 | VH1-69 | VL1-51 | 11 | 6 |
| ADI-41571 | 2635 | 6.27081E−10 | N.B. | 0.031530527 | preF | 0.07 | VH3-11 | VL1-40 | 14 | 10 |
| ADI-41574 | 2635 | N.B. | 1.23235E−07 | >25 | postF | 0.02 | VH2-5 | VK1-5 | 1 | 7 |
| ADI-41576 | 2635 | N.B. | 1.42548E−09 | >25 | postF | 0.01 | VH2-5 | VK3-11 | 9 | 10 |
| ADI-41578 | 2635 | 2.48656E−10 | N.B. | 0.039833521 | preF | 0.00 | VH3-30 | VL3-21 | 11 | 12 |
| ADI-41579 | 2635 | 4.71437E−10 | 3.59718E−10 | 0.208709151 | Both | 0.00 | VH1-69 | VL2-14 | 15 | 13 |
| ADI-41580 | 2635 | 2.98246E−09 | 1.17422E−09 | 1.107269577 | Both | 0.00 | VH4-34 | VK4-1 | 10 | 10 |
| ADI-41581 | 2635 | 2.7729E−09 | 3.60691E−10 | >25 | Both | 0.00 | VH7-4-1 | VK2-28 | 10 | 4 |
| ADI-41582 | 2635 | N.B. | 9.11488E−10 | >25 | postF | 0.00 | VH4-31 | VL3-21 | 6 | 8 |
| ADI-41583 | 2635 | 6.63714E−10 | 3.80536E−10 | >25 | Both | 0.00 | VH1-69 | VK1-33 | 10 | 1 |
| ADI-41584 | 2635 | 3.08613E−09 | N.B. | >25 | preF | 0.00 | VH1-2 | VL1-40 | 10 | 5 |
| ADI-41585 | 2635 | 6.13E−10 | N.B. | 0.064052351 | preF | 0.00 | VH3-11 | VL1-40 | 6 | 3 |
| ADI-41586 | 2635 | 5.37539E−10 | 7.79176E−10 | 0.401663761 | Both | 0.00 | VH4-34 | VK2-28 | 9 | 3 |
| ADI-41587 | 2635 | 1.4048E−09 | 2.08899E−09 | 0.663851609 | Both | 0.00 | VH4-34 | VK2-28 | 8 | 5 |
| ADI-41588 | 2635 | 3.32826E−09 | 5.04922E−10 | >25 | Both | 0.00 | VH2-5 | VL3-1 | 5 | 2 |
| ADI-41589 | 2635 | 4.20258E−09 | N.B. | >25 | preF | 0.00 | VH3-23 | VK4-1 | 8 | 8 |
| ADI-41590 | 2635 | 3.0202E−09 | N.B. | >25 | preF | 0.00 | VH3-11 | VK1-39 | 7 | 10 |
| ADI-41591 | 2635 | 4.25861E−09 | N.B. | >25 | preF | 0.00 | VH3-11 | VL1-40 | 0 | 2 |
| ADI-41592 | 2635 | 3.73679E−09 | 4.40201E−10 | >25 | Both | 0.00 | VH7-4-1 | VL3-1 | 5 | 13 |
| ADI-41593 | 2635 | 1.8323E−09 | 5.29992E−10 | >25 | Both | 0.00 | VH5-51 | VK1-8 | 4 | 2 |
| ADI-41594 | 2635 | 4.13628E−10 | N.B. | 0.040569222 | preF | 0.00 | VH3-21 | VL1-40 | 10 | 4 |
| ADI-41595 | 2635 | 7.70076E−10 | N.B. | 0.047476327 | preF | 0.00 | VH3-30 | VK1-33 | 9 | 11 |
| ADI-41596 | 2635 | 3.04558E−10 | 4.37255E−10 | 0.053741113 | Both | 0.00 | VH4-34 | VK4-1 | 6 | 2 |
| ADI-41597 | 2635 | 3.56836E−10 | N.B. | 0.172508371 | preF | 0.00 | VH4-61 | VL3-21 | 6 | 3 |
| ADI-41598 | 2635 | 4.94657E−10 | N.B. | 0.174094146 | preF | 0.00 | VH4-59 | VK1-39 | 11 | 11 |
| ADI-41599 | 2635 | 7.90767E−10 | 4.32706E−10 | 0.636806381 | Both | 0.00 | VH3-48 | VK1-39 | 16 | 13 |
| ADI-41600 | 2635 | 4.93359E−09 | 7.54853E−10 | >25 | Both | 0.00 | VH3-30 | VK1D-12 | 15 | 9 |
| ADI-41601 | 2635 | 5.02595E−10 | N.B. | >25 | preF | 0.00 | VH3-11 | VL1-40 | 11 | 10 |
| ADI-41602 | 2635 | 2.85465E−09 | 4.54781E−10 | >25 | Both | 0.00 | VH4-59 | VL2-14 | 7 | 10 |
| ADI-41603 | 2635 | 3.49281E−09 | 4.89905E−10 | >25 | Both | 0.00 | VH3-49 | VK3-15 | 10 | 6 |
| ADI-41604 | 2635 | 1.7801E−08 | 2.92494E−08 | >25 | Both | 0.00 | VH1-2 | VK1-33 | 1 | 0 |
| ADI-41605 | 2635 | 3.18275E−09 | 5.5033E−10 | >25 | Both | 0.00 | VH4-31 | VK4-1 | 8 | 9 |
| ADI-41606 | 2635 | 3.38754E−09 | 1.02586E−09 | >25 | Both | 0.00 | VH4-61 | VK1D-12 | 9 | 7 |
| ADI-41607 | 2635 | 4.24282E−09 | 7.09182E−10 | >25 | Both | 0.00 | VH4-31 | VL2-11 | 7 | 11 |
| ADI-41608 | 2635 | 1.93484E−09 | 2.85427E−10 | >25 | Both | 0.00 | VH5-51 | VL6-57 | 15 | 3 |
| ADI-41609 | 2635 | 2.90676E−08 | N.B. | >25 | preF | 0.00 | VH1-46 | VL1-40 | 14 | 10 |
| ADI-41610 | 2635 | N.B. | 9.78084E−10 | >25 | postF | 0.00 | VH3-30 | VK1-39 | 12 | 1 |
| ADI-41611 | 2635 | 3.08502E−09 | 6.11386E−10 | >25 | Both | 0.00 | VH3-21 | VK1-39 | 6 | 6 |
| ADI-41626 | 2665 | 2.60E−09 | 8.91E−10 | >25 | Both | 0.17 | VH4-4 | VK1-39 | 9 | 9 |
| ADI-41644 | 2665 | 3.03E−09 | 1.10E−09 | >25 | Both | 0.11 | VH4-34 | VK3D-15 | 13 | 14 |
| ADI-41660 | 2665 | 2.94E−09 | 9.55E−10 | >25 | Both | 0.10 | VH1-69 | VL1-51 | 5 | 1 |
| ADI-41662 | 2665 | 5.24E−09 | 1.21E−09 | >25 | Both | 0.10 | VH5-51 | VL3-10 | 14 | 6 |
| ADI-41664 | 2665 | 2.94E−09 | 8.25E−10 | >25 | Both | 0.10 | VH1-18 | VL3-21 | 11 | 5 |
| ADI-41677 | 2665 | 1.28E−09 | 3.39E−10 | >25 | Both | 0.08 | VH2-70 | VK1-39 | 5 | 12 |
| ADI-41678 | 2665 | 2.92E−09 | 1.17E−09 | >25 | Both | 0.08 | VH3-30 | VL2-8 | 5 | 0 |
| ADI-41690 | 2665 | N.B. | 8.78E−09 | >25 | postF | 0.03 | VH5-51 | VK1-33 | 8 | 5 |
| ADI-41701 | 2665 | 1.93E−09 | 2.89E−10 | >25 | Both | 0.01 | VH5-51 | VL6-57 | 6 | 9 |
| ADI-41703 | 2665 | 4.20E−09 | 8.43E−10 | >25 | Both | 0.00 | VH4-30-2 | VK3-20 | 6 | 5 |
| ADI-41720 | 2665 | 2.20E−08 | 1.17E−09 | >25 | Both | 0.00 | VH3-33 | VK1-5 | 5 | 2 |
| ADI-41737 | 2665 | 3.58E−09 | 1.58E−09 | >25 | Both | 0.00 | VH4-30-4 | VK3-20 | 9 | 8 |
| ADI-41743 | 2665 | 5.45E−09 | 1.27E−09 | >25 | Both | 0.00 | VH4-30-2 | VK3-15 | 14 | 4 |
| ADI-41756 | 2665 | 2.90E−08 | N.B. | >25 | preF | 0.00 | VH3-30 | VL2-14 | 8 | 20 |
| ADI-41768 | 2666 | 1.61459E−09 | 3.38298E−10 | >25 | Both | 0.10 | VH3-9 | VL6-57 | 6 | 6 |
| ADI-41772 | 2666 | 7.10105E−10 | N.B. | 0.04 | preF | 0.10 | VH3-11 | VL3-10 | 12 | 7 |
| ADI-41778 | 2666 | 2.75256E−09 | 5.04199E−10 | >25 | Both | 0.10 | VH3-9 | VL2-11 | 5 | 4 |
| ADI-41781 | 2666 | 3.46456E−09 | 6.53361E−10 | >25 | Both | 0.07 | VH1-18 | VK1-27 | 16 | 4 |

TABLE 7-continued

Summary of antibody characteristics for antibodies isolated from PBMCs

| Name | Donor | RSV preF binding KD | RSV postF binding KD | Neutralization IC50 (RSV subtype A) | Specificiity | PSR score | VH Germline | VL Germline | VH Protein Muts | VL Protein Muts |
|---|---|---|---|---|---|---|---|---|---|---|
| ADI-41783 | 2666 | 5.42456E−10 | N.B. | 0.25 | preF | 0.10 | VH1-18 | VK2-30 | 7 | 0 |
| ADI-41787 | 2666 | 1.56237E−09 | N.B. | 0.38 | preF | 0.10 | VH3-30 | VL3-10 | 7 | 6 |
| ADI-41788 | 2666 | 2.755E−10 | N.B. | 0.47 | preF | 0.10 | VH1-8 | VL3-21 | 8 | 1 |
| ADI-41790 | 2666 | 3.15261E−09 | N.B. | >25 | preF | 0.10 | VH1-69 | VK3-11 | 7 | 6 |
| ADI-41792 | 2666 | 2.98373E−08 | N.B. | >25 | preF | 0.10 | VH3-21 | VL1-40 | 2 | 1 |
| ADI-41794 | 2666 | 3.30922E−09 | 3.01006E−09 | >25 | Both | 0.10 | VH4-34 | VL1-51 | 0 | 3 |
| ADI-41799 | 2666 | 3.27629E−09 | 1.10141E−09 | >25 | Both | 0.14 | VH1-69 | VK1-5 | 17 | 5 |
| ADI-41800 | 2849 | 3.24E−09 | N.B. | >25 | preF | 0.40 | VH1-2 | VL2-14 | 10 | 5 |
| ADI-41803 | 2849 | 1.99E−09 | 7.11E−10 | >25 | Both | 0.17 | VH4-34 | VK1-17 | 16 | 6 |
| ADI-41804 | 2849 | 3.31E−10 | 4.36E−10 | >25 | Both | 0.15 | VH4-34 | VK1-27 | 11 | 5 |
| ADI-41805 | 2849 | N.B. | 2.00E−09 | >25 | postF | 0.14 | VH5-51 | VL2-14 | 4 | 7 |
| ADI-41807 | 2849 | 1.50E−09 | 1.19E−09 | >25 | Both | 0.14 | VH2-70 | VK1-39 | 6 | 10 |
| ADI-41808 | 2849 | 1.39E−08 | 2.25E−08 | >25 | Both | 0.14 | VH1-69 | VK1-5 | 21 | 7 |
| ADI-41809 | 2849 | 2.65E−09 | N.B. | >25 | preF | 0.12 | VH3-23 | VL1-47 | 9 | 5 |
| ADI-41810 | 2849 | 2.03E−09 | N.B. | >25 | preF | 0.11 | VH3-30 | VK3-15 | 7 | 8 |
| ADI-41811 | 2849 | 1.64E−09 | 7.44E−10 | >25 | Both | 0.11 | VH6-1 | VK3-11 | 10 | 7 |
| ADI-41812 | 2849 | 3.14E−10 | N.B. | 0.17 | preF | 0.11 | VH3-21 | VL1-40 | 6 | 1 |
| ADI-41814 | 2849 | 3.39E−09 | 9.15E−10 | >25 | Both | 0.10 | VH2-5 | VL1-40 | 3 | 13 |
| ADI-41815 | 2849 | 3.21E−09 | N.B. | >25 | preF | 0.10 | VH3-21 | VK2-28 | 9 | 0 |
| ADI-41816 | 2849 | 6.56E−10 | N.B. | 0.91 | preF | 0.10 | VH1-2 | VL3-1 | 8 | 2 |
| ADI-41817 | 2849 | 6.94E−09 | 1.58E−08 | >25 | Both | 0.09 | VH5-51 | VL2-14 | 7 | 9 |
| ADI-41818 | 2849 | 6.76E−10 | 3.47E−10 | >25 | Both | 0.03 | VH3-66 | VK3-20 | 8 | 2 |
| ADI-41820 | 2849 | 6.49E−08 | N.B. | >25 | preF | 0.01 | VH3-30 | VL7-46 | 11 | 4 |
| ADI-41827 | 2849 | 1.86E−10 | N.B. | >25 | preF | 0.00 | VH3-30 | VL3-1 | 10 | 7 |
| ADI-41828 | 2849 | 2.41E−10 | N.B. | 5.53 | preF | 0.00 | VH3-48 | VL3-21 | 9 | 0 |
| ADI-41829 | 2849 | 2.71E−10 | N.B. | 0.12 | preF | 0.00 | VH3-21 | VL1-40 | 5 | 2 |
| ADI-41830 | 2849 | 2.90E−10 | N.B. | 0.12 | preF | 0.00 | VH1-18 | VK2-28 | 13 | 0 |
| ADI-41831 | 2849 | 3.29E−10 | N.B. | 5.21 | preF | 0.00 | VH3-21 | VL1-40 | 8 | 3 |
| ADI-41832 | 2849 | 6.31E−10 | N.B. | 0.19 | preF | 0.00 | VH3-23 | VK3-20 | 8 | 4 |
| ADI-41833 | 2849 | 7.23E−10 | N.B. | 0.02 | preF | 0.00 | VH3-23 | VK1-27 | 7 | 6 |
| ADI-41834 | 2849 | 1.20E−09 | N.B. | 0.07 | preF | 0.00 | VH3-66 | VK1-33 | 9 | 5 |
| ADI-41835 | 2849 | 1.43E−10 | N.B. | 0.45 | preF | 0.00 | VH3-23 | VL3-1 | 3 | 4 |
| ADI-41836 | 2849 | 5.74E−09 | N.B. | >25 | preF | 0.00 | VH1-3 | VL1-40 | 9 | 8 |
| ADI-41837 | 2849 | 7.09E−09 | N.B. | >25 | preF | 0.00 | VH1-18 | VK2-30 | 4 | 3 |
| ADI-41838 | 2849 | 3.21E−08 | N.B. | >25 | preF | 0.00 | VH3-30 | VL2-14 | 8 | 3 |
| ADI-41839 | 2849 | 7.88E−09 | N.B. | >25 | preF | 0.00 | VH3-30 | VL3-21 | 14 | 2 |
| ADI-41840 | 2849 | 3.33E−09 | N.B. | >25 | preF | 0.00 | VH1-69 | VK3-15 | 17 | 3 |
| ADI-41841 | 2849 | 1.21E−10 | 2.65E−10 | 0.04 | Both | 0.00 | VH3-21 | VK1-33 | 6 | 8 |
| ADI-41842 | 2849 | 7.17E−10 | 4.42E−10 | >25 | Both | 0.00 | VH1-8 | VK1-39 | 14 | 6 |
| ADI-43638 | 2665 | N.B. | 9.93404E−09 | >25 | postF | 0.16 | VH4-34 | VK4-1 | 0 | 0 |
| ADI-43639 | 2635 | N.B. | 2.32551E−07 | >25 | postF | 0.00 | VH7-4-1 | VK1-39 | 0 | 0 |
| ADI-43640 | 2665 | 2.15586E−08 | N.B. | >25 | preF | 0.08 | VH3-21 | VL1-40 | 0 | 0 |
| ADI-43641 | 2665 | 3.74656E−08 | N.B. | >25 | preF | 0.09 | VH3-11 | VL1-40 | 0 | 0 |
| ADI-43642 | 2635 | 4.31745E−08 | N.B. | >25 | preF | 0.00 | VH3-21 | VL1-40 | 0 | 0 |

Adenoid- and PBMC-Derived Antibodies Show Similar Levels of Polyreactivity

Figure 20A:
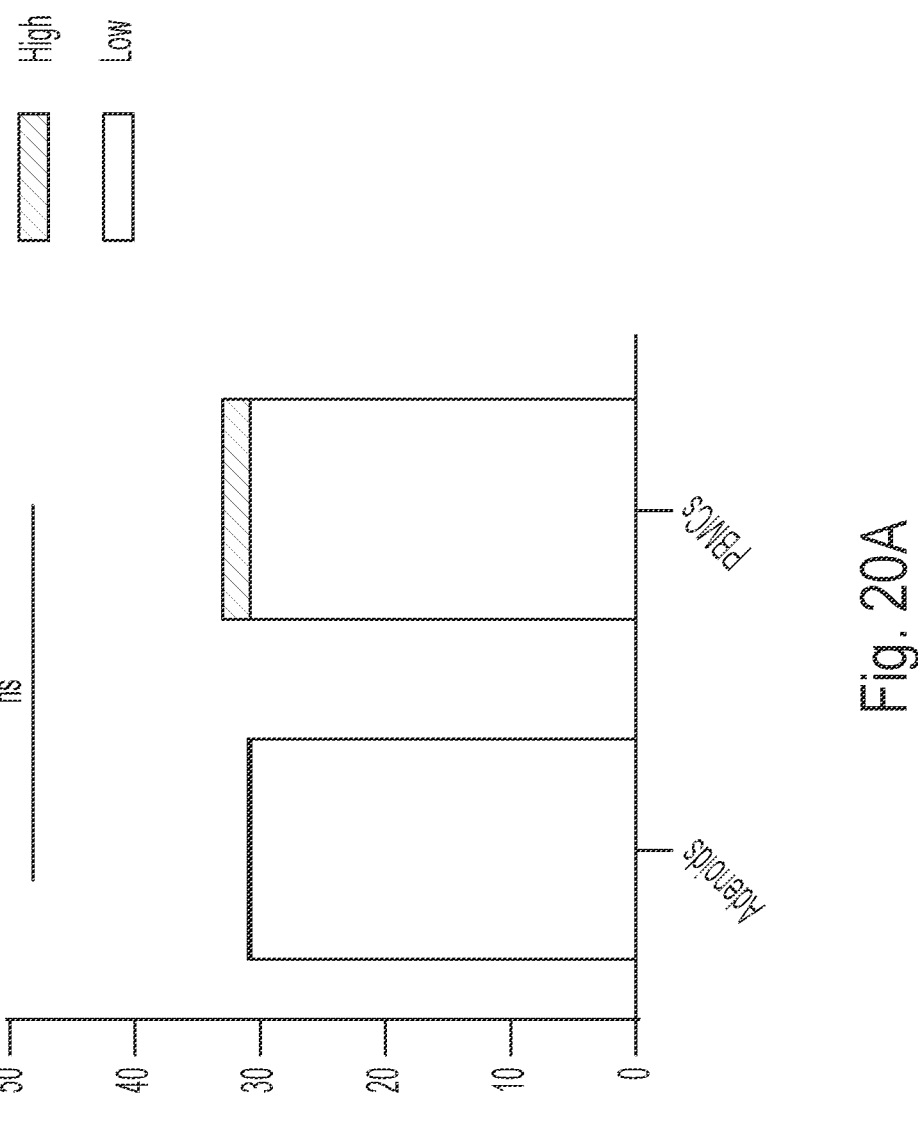
Figure 20C:
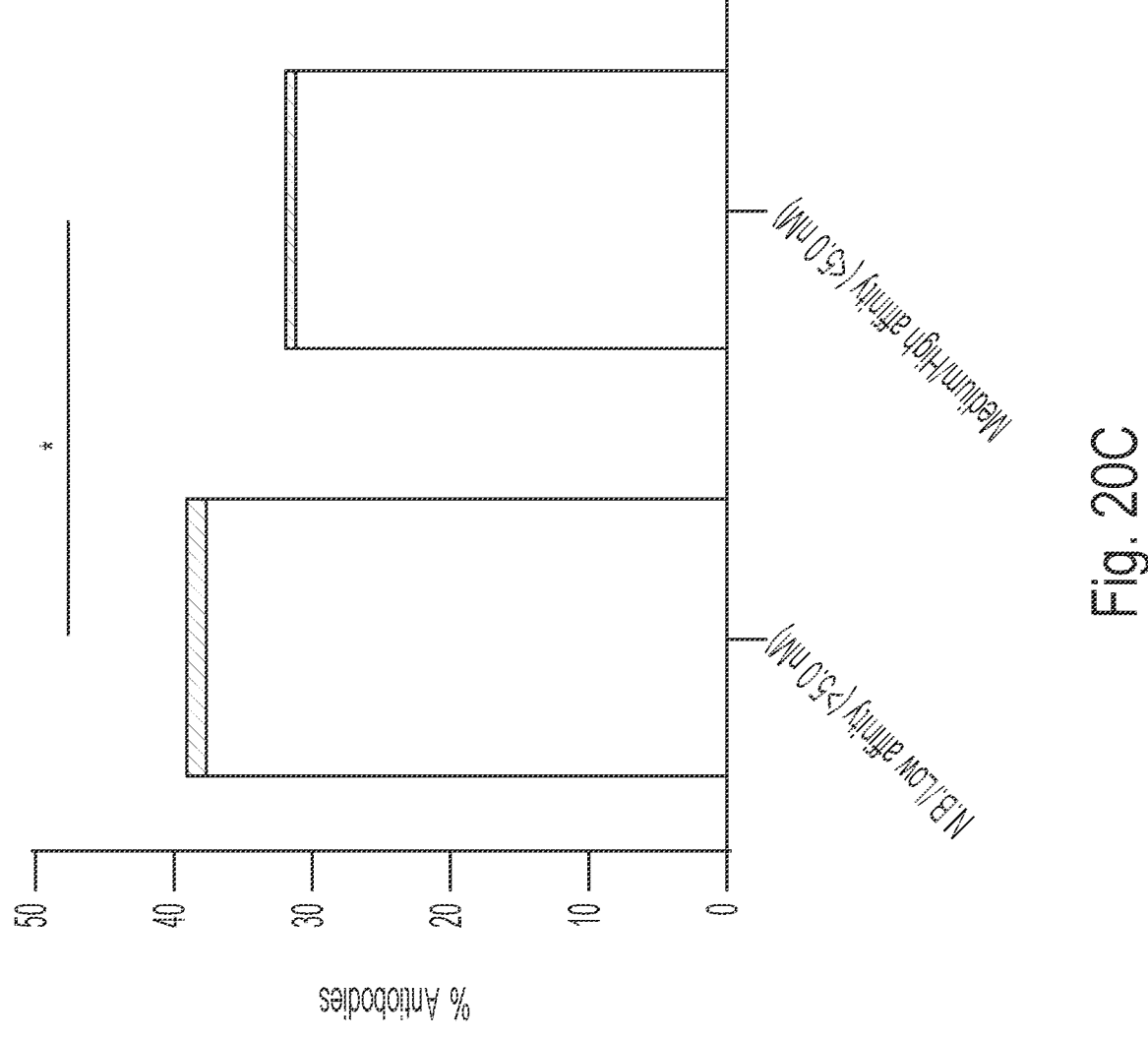

The specificity of each antibody was assessed using a previously described polyreactivity assay. In healthy adult donors, a relatively large proportion of memory B cell-derived antibodies have been shown to be polyreactive (Tiller, 2007). Consistent with these findings, approximately 35% of antibodies derived from both the adenoid and PBMC samples showed low levels of polyreactivity (FIG. 20A). The percentage of polyreactive clones was relatively similar across the different B cell subsets within each compartment, although the PBMC-derived IgG IgA CD27 B cell population showed a slighter higher proportion of polyreactive clones compared to many of the other B cell subsets (FIG. 20B). A slight enrichment for polyreactive clones was observed among the group of antibodies that bound with weak affinity to RSV F (FIG. 20C). In conclusion, the mucosal and systemic B cell compartments contain a similar proportion of polyreactive clones, with about a third of RSV F-specific B cells in both compartments showing some degree of polyreactivity.

DISCUSSION

A detailed understanding of mucosal and systemic immune responses to natural RSV infection can facilitate the design and evaluation of RSV vaccine candidates. Although previous studies have shown that mucosal antibody responses are important for protection against RSV in both humans and animal models, the specificities and functional activities of these antibodies have remained undefined. Furthermore, the anatomic location(s) and characteristics of RSV-specific memory B cells within mucosa-associated lymphoid tissues have not been thoroughly investigated. By collecting paired adenoid and blood samples from six young children undergoing elective tonsillectomy and using a high-throughput B cell cloning platform, the local and systemic B cell responses to natural RSV infection were analyzed and compared.

RSV F-specific B cell responses were observed in the adenoids of all 6 donors analyzed, whereas such responses were only detected in the peripheral blood samples of 4 of the 6 donors. In addition, in most donors studied, a higher proportion of adenoid-derived antibodies displayed high affinity binding and potent neutralizing activity compared to PBMC-derived antibodies. These results provide evidence that RSV-specific memory B cells are induced and maintained within adenoid tissue and suggest that this local response may be more robust and/or durable than the corresponding systemic response. Hence, adenoidectomy may result in a reduction of local immune competence against RSV, as previously demonstrated by diminished poliovirus-specific antibody levels in nasal secretions from children following tonsillectomy and adenoidectomy (Ogra P. L. (1971) Effect of tonsillectomy and adenoidectomy on nasopharyngeal antibody response to poliovirus. N. Engl. J. Med. 284:59-6).

The adenoids of all donors studied contained a high frequency of RSV F-specific memory B cells that displayed mutated v-regions but were not isotype-switched and lacked expression of the classical memory B cell marker CD27. Although RSV F-specific B cells that displayed this surface phenotype were also present in peripheral blood, the frequency was significantly lower than that observed in adenoid tissue and the majority of these B cells encoded antibodies that lacked somatic mutations. Unlike the tissue-based IgG$^+$ CD27$^-$ FCRL4$^+$ memory B cell population that has been previously described in human tonsils, the RSV F-specific IgG$^-$IgA$^-$ CD27$^-$ B cells observed in the adenoids of these donors did not express FCRL4 or IgG and were highly heterogeneous with respect to IgM and IgD expression. Previous studies have also described atypical memory B cells in peripheral blood that are isotyped-switched, lack CD27 expression, and display lower levels of SHM compared to their CD27$^+$ counterparts. In contrast to this population, the atypical adenoid-derived memory B cell subset described here shows similar levels of SHM compared to classical IgG$^+$ CD27$^+$ memory B cells, suggesting similar antigenic selection characteristics. A single clonal lineage present in both adenoid and peripheral blood of one donor was identified, and the PBMC-derived clone originated from an IgG$^+$ CD27$^-$ B cell whereas the adenoid-derived clone originated from an IgG$^-$IgA$^-$ CD27$^-$ B cell, suggesting a possible relationship between these two atypical B cell subsets. RSV F-specific IgA+ memory B cells were detected in both adenoid and peripheral blood for all donors.

Previous studies have shown that RSV antibodies that bind preF-specific surfaces are generally more potent than those that recognize epitopes expressed on both pre- and post-F or only on postF. Correspondingly, in the 4 young children analyzed here, over 90% of the neutralizing antibodies isolated from both adenoid and peripheral blood recognized epitopes exclusively expressed on preF. The high abundance of preF-specific neutralizing antibodies and near absence of postF-reactive neutralizing antibodies in adenoid tissue suggests that mucosal vaccines the preserve preF-specific antigenic surfaces may induce higher titers of protective antibodies than postF-based vaccines. Although the majority of mucosal vaccines are particle- or vector-based, it has been shown that preF can spontaneously trigger to adopt postF conformation on the viral surface, underscoring the importance of carefully evaluating the antigenic properties of such vaccine candidates. The extensive panel of antibodies described here could be used as reagents to measure the prefusion and postfusion F content of these vaccines.

Collectively, this demonstrates that 1) adenoids can serve as a major induction site for RSV-specific memory B cell responses and that a large proportion of this response is comprised of atypical IgM+ and/or IgD+ memory B cells; 2) the vast majority of adenoid-derived neutralizing antibodies target epitopes exclusively expressed on preF, which supports the development of preF-based mucosal vaccines that boost local responses.

Methods

Sample Collection

Heparinized blood and tonsillar tissue were collected from the patient after a planned therapeutic tonsillectomy for clinical indications (parental consent obtained during a pre-operative visit in accordance with approved IRB). Tonsillar tissue consisted of tonsils (palatine tonsils) and adenoids (pharyngeal tonsils), which together make up Waldeyer's ring.

After collection, tonsillar tissue was mechanically disrupted, e.g., grinding of tissue between the fritted glass at the end of microscope slides or by proteolytic digestion of the tissue typically with pronase, and mucosal lymphoid populations were isolated by standard methods, e.g., ficoll gradient. Several methods exist to recover secreted immunoglobulins from the mucosal surface of the tissue, e.g., Pope earwick or ex vivo culture systems. Peripheral blood was separated to recover plasma and then further fractionated to recover lymphoid cells.

Isolated lymphoid cells from paired tonsillar tissue and blood were used to identify and characterize monoclonal antibodies from single B cells.

Production of RSV F Sorting Probes

PreF (DS-Cav1) and postF (F ΔFP) trimers were produced with a single biotinylated C-terminal AviTag and then coupled to streptavidin-PE or -APC, as described previously (Gilman et al, Sci Immunol 2016). Expression vectors containing a C-terminal 6×His-tag-AviTag or a C-terminal Strep-tag II were co-transfected into FreeStyle 293-F cells at a 1:2 ratio for each variant. The protein was purified from the cell supernatant using Ni-nitrilotriacetic acid (NTA) resin to remove trimers lacking the 6×His-tag-AviTag, then purified over StrepTactin resin. The resin was washed to remove trimers containing only one StrepTagII, and the remaining proteins were then biotinylated using birA (Avidity). The biotinylated proteins were separated from excess biotin by size-exclusion chromatography using a Superdex 200 column (GE Healthcare) in PBS.

Single B Cell Sorting

PBMCs and adenoids from young children were stained using anti-human CD19 (APC-Cy7), CD20 (APC-Cy7), CD3 (PerCP-Cy5.5), CD8 (PerCP-Cy5.5), CD14 (PerCP-Cy5.5), CD16 (PerCP-Cy5.5), FcRL4 (PECy7), IgG (BV605), IgA (488), CD27 (BV421), and a mixture of dual-labeled preF and postF tetramers (25 nM each). To determine the percentage of RSV-F specific B cells expressing IgM or IgD, the adenoid samples were stained using human CD19 (APC-Cy7), CD20 (APC-Cy7), CD3 (PerCP-Cy5.5), CD8 (PerCP-Cy5.5), CD14 (PerCP-Cy5.5), CD16 (PerCP-Cy5.5), IgM (PECy7), IgD (BV510), IgG (BV605), IgA (488), CD27 (BV421), and a mixture of dual-labeled preF and postF tetramers (25 nM each). Tetramers were prepared fresh for each experiment, and total B cells binding to the RSV F tetramers were single cell sorted. Single cells were sorted using a BD FACS Aria II (BD Biosciences) into 96-well PCR plates (BioRAD) containing 20 uL/well of lysis buffer [5 uL of 5× first strand cDNA buffer (Invitrogen), 0.625 uL of NP-40 (New England Biolabs), 0.25 uL RNascOUT (Invitrogen), 1.25 uL dithiothreitol (Invitrogen), and 12.6 uL dH2O]. Plates were immediately stored at −80° C.

Amplification and Cloning of Antibody Variable Genes

Antibody variable genes (IgH, IgK, and IgL) were amplified by reverse transcription PCR and nested PCRs using cocktails of IgG-, IgA-, and IgM-specific primers, as described previously (Tiller et al, J Immunol 2008). The primers used in the second round of PCR contained 40 base pairs of 5' and 3' homology to the digested expression vectors, which allowed for cloning by homologous recombination into *S. cerevisiae*. The lithium acetate method for chemical transformation was used to clone the PCR products into *S. cerevisiae* (Gietz and Schiestl, Nat Protoc 2007). 10 uL of unpurified heavy chain and light chain PCR product and 200 ng of the digested expression vectors were used per transformation reaction. Following transformation, individual yeast colonies were picked for sequencing and characterization.

Expression and Purification of IgGs

IgGs were expressed in *S. cerevisiae* cultures grown in 24-well plates, as described previously (Bornholdt et al, Science 2016). After 6 days, the cultures were harvested by centrifugation and IgGs were purified by protein A-affinity chromatography. The bound antibodies were eluted with 200 mM acetic acid/50 mM NaCl (pH 3.5) into ⅛th volume 2 M Hepes (pH 8.0), and buffer-exchanged into PBS (pH 7.0).

Biolayer Interferometry Binding Analysis

IgG binding to preF (DS-Cav1) and postF (F ΔFP) was measured by biolayer interferometry (BLI) using a FortéBio Octet HTX instrument (Pall Life Sciences). For high-throughput $K_D$ determination, IgGs were immobilized on anti-human IgG quantitation biosensors (Pall Life Sciences) and exposed to 100 nM antigen in PBS with 0.1% BSA (PBSF) for an association step, followed by a dissociation step in PBSF. Data were analyzed using the FortéBio Data Analysis Software 7. Kd values were calculated for antibodies with BLI responses>0.1 nm, and the data were fit to a 1:1 binding model to calculate association and dissociation rate constants. The $K_D$ values were calculated using the ratio kd/ka.

Polyreactivity Assay

Polyspecificity reagent binding was assessed as previously described (Xu et al, Protein Eng Des Sel 2013). Briefly, soluble membrane protein (SMP) and soluble cytosolic protein (SCP) fractions were prepared from Chinese hamster ovary cells and biotinylated with NHS-LC-Biotin reagent (Pierce, ThermoFisher Cat #21336). 2 million IgG-presenting yeast were transferred to a 96-well assay plate, pelleted to remove supernatant, then the pellets were resuspended in 50 uL of 1:10 diluted stock of biotinylated SCPs and SMPs and incubated on ice for 20 minutes. Cells were washed twice with ice-cold PBSF, and the samples were incubated in 50 uL of secondary labeling mix (Extravadin-R-PE, goat F(ab')2-anti human kappa-FITC, and propidium iodide) on ice for 20 minutes. The samples were analyzed for polyspecificity reagent binding using a FACSCanto II (BD Biosciences) with HTS sample injector. Flow cytometry data were analyzed for mean fluorescence intensity in the R-PE channel and normalized to three control antibodies exhibiting low, medium, and high MFI values.

Plasma Neutralization Assay

Infant plasma samples were tested for RSV neutralization in microtiter assays using a recombinant RSV expressing Renilla luciferase (rA2-Rluc; a gift from Dr. Michael Teng, University of South Florida [Fuentes S, Crim R L, Beeler J, Teng M N, Golding H, Khurana S. Development of a simple, rapid, sensitive, high-throughput luciferase reporter based microneutralization test for measurement of virus neutralizing antibodies following Respiratory Syncytial Virus vaccination and infection. Vaccine. 2013 Aug. 20; 31 (37): 3987-94.]). Hep2 cells were added to 96-well plates at a density of 1.8×104 cells per well in 100<1 of MEM with 2% FBS/1× penicillin-streptomycin solution (2% MEM) and allowed to adhere overnight at 37° C. On the day of the assay, plasma samples were serially diluted 2-fold (1:200 to 1:128,000) in 2% MEM containing rA2-Rluc and incubated for 30 min at 37° C. Culture media was aspirated from the Hep2 cells followed by the addition of 100<<per well of the plasma+rA2-Rluc mixture to duplicate wells. Cultures were maintained at 37° C. for 24 hrs and luciferase expression was quantified in cell lysates using the Renilla Luciferase Assay System (E2820, Promega, Madison, WI). Relative light units (RLU) were measured on a BioTek Synergy 2 microplate reader. Neutralization is expressed as the reciprocal of the highest plasma dilution to yield a 50% reduction in RLU as compared to control wells with no added plasma.

Adenoid Neutralization Assay

Adenoid tissue collected on the day of surgery was placed in a sterile 10 cm culture dish. A 1.8 cm circular disc of soft absorbent filter paper (Leukosorb #BSP0669, Pall Corporation, Port Washington NY) was applied to the mucosal surface of the tissue. One ml of PBS with added protease inhibitors (Bestatin 0.1 ug/ml; Aprotinin 1 ug/ml; AEBSF 0.5 ug/ml; Loupeptin 5 ug/ml; Millipore Sigma, St. Louis MO) was added to directly to the tissue to moisten the disc. The tissue was allowed to stand for 30 min at room temperature. Excess PBS+PI was then pipeted from the tissue into a 15 ml conical tube. The filter paper disc was collected with sterile forceps and placed into a separate 15 ml tube. An additional 0.5 ml of PBS+PI was added and the tube was centrifuged at 1,900×g rpm for 10 min. Supernatant recovered directly from the tissue and from the filter disc was retained and tested for RSV neutralizing activity. Supernatants were serially diluted 2-fold (1:4 to 1:256) and tested using the rA2-Rluc microtiter assay. Data is expressed as the dilution corresponding to a 50% inhibitory concentration ($IC_{50}$) compared to control wells with rA2-Rluc alone.

Example 3. Cluster Analysis of Neutralizing Antibodies According to Biophysical Characteristics A set of RSV neutralizing antibodies were analysed for sequences of CDRH3 based on biophysical characteristics using a reduced alphabet scheme (Table 8).

The biophysical characteristics were classified as follows:

1. Group small amino acids with C-beta: AST

2. Backbone flexibility: G

3. Backbone rigidity: P

4. Positive charge: KR

5. Negative charge: ED

6. Medium sized polar NQH

7. Large Aromatic: FWY

8. Aliphatic: ILVMC

TABLE 8

Reduced alphabet consensus sequences of neutralizing antibodies

| ADI-Name | Parent | VH_GL | VL_GL | H3 | H3 | Cluster Number | Difference from Parent | Difference from Parent in Reduced alphabet |
|---|---|---|---|---|---|---|---|---|
| ADI-14583 | ADI-14583 | VH1-18 | VK2-30 | AREPPVIAAGDFQH (SEQ ID NO: 1902) | AREPPVIAAGDFQH (SEQ ID NO: 1902) | 1 | 0 | 0 |
| ADI-14336 | ADI-14583 | VH1-18 | VK2-30 | AREPPVIAAGDFQH (SEQ ID NO: 1902) | AREPPVIAAGDFQH (SEQ ID NO: 1902) | 1 | 0 | 0 |
| ADI-14402 | ADI-14583 | VH1-18 | VK2-30 | AREPPVIAAGDFSH (SEQ ID NO: 1903) | AREPPVIAAGDFSH (SEQ ID NO: 1903) | 1 | 1 | 1 |
| ADI-14576 | ADI-14583 | VH1-18 | VK2-30 | ARDPPVIAAGDFQH (SEQ ID NO: 1904) | ARDPPVIAAGDFQH (SEQ ID NO: 1904) | 1 | 1 | 0 |
| ADI-14577 | ADI-14583 | VH1-18 | VK2-30 | ARGPPVIAADDFQH (SEQ ID NO: 1905) | ARGPPVIAADDFQH (SEQ ID NO: 1905) | 1 | 2 | 2 |
| ADI-14585 | ADI-14583 | VH1-18 | VK2-30 | AREPPVIAAGDFPH (SEQ ID NO: 1906) | AREPPVIAAGDFPH (SEQ ID NO: 1906) | 1 | 1 | 1 |
| ADI-20975 | ADI-20975 | VH1-18 | VL3-21 | AREQFKWNDFYFDY (SEQ ID NO: 1907) | AREQFKWNDFYFDY (SEQ ID NO: 1907) | 2 | 0 | 0 |
| ADI-19422 | ADI-20975 | VH3-30 | VL3-21 | AKEGYNWNDYYFDY (SEQ ID NO: 1908) | AKEGYNWNDYYFDY (SEQ ID NO: 1908) | 2 | 5 | 2 |
| ADI-41788 | ADI-20975 | VH1-8 | VL3-21 | ARGFYKWNDWSFDY (SEQ ID NO: 1909) | ARGFYKWNDWSFDY (SEQ ID NO: 1909) | 2 | 5 | 3 |
| ADI-41191 | ADI-41191 | VH1-18 | VK2-30 | AREPPSLSAAATLDY (SEQ ID NO: 1910) | AREPPSLSAAATLDY (SEQ ID NO: 1910) | 3 | 0 | 0 |
| ADI-19501 | ADI-41191 | VH1-18 | VK2-30 | ARDPPSEGAAGLFDY (SEQ ID NO: 1911) | ARDPPSEGAAGLFDY (SEQ ID NO: 1911) | 3 | 6 | 5 |
| ADI-20962 | ADI-41191 | VH1-18 | VK2-30 | AREPPSDTAAGTGDY (SEQ ID NO: 1912) | AREPPSDTAAGTGDY (SEQ ID NO: 1912) | 3 | 4 | 3 |
| ADI-22757 | ADI-41191 | VH1-18 | VK2-30 | ARDPPAV-AASFMDV (SEQ ID NO: 1913) | ARDPPAV-AASFMDV (SEQ ID NO: 1913) | 3 | 8 | 3 |
| ADI-41424 | ADI-41191 | VH1-18 | VK2-30 | VRDTPAIAGAATLDF (SEQ ID NO: 1914) | VRDTPAIAGAATLDF (SEQ ID NO: 1914) | 3 | 8 | 3 |
| ADI-41454 | ADI-41191 | VH1-18 | VK2-30 | AREPPSTTAAATSDY (SEQ ID NO: 1915) | AREPPSTTAAATSDY (SEQ ID NO: 1915) | 3 | 3 | 2 |
| ADI-20964 | ADI-20964 | VH1-18 | VK2-30 | ARDVPVEAATSPEF (SEQ ID NO: 1916) | ARDVPVEAATSPEF (SEQ ID NO: 1916) | 4 | 0 | 0 |
| ADI-20988 | ADI-20964 | VH1-18 | VK2-30 | ARDVPVIAAHTFEY (SEQ ID NO: 1917) | ARDVPVIAAHTFEY (SEQ ID NO: 1917) | 4 | 5 | 3 |
| ADI-21050 | ADI-20964 | VH1-18 | VK2-30 | AREMGVDAAATFDY (SEQ ID NO: 1918) | AREMGVDAAATFDY (SEQ ID NO: 1918) | 4 | 9 | 2 |
| ADI-20974 | ADI-20974 | VH3-21 | VL1-40 | ARALMATAGGLAFDI (SEQ ID NO: 1919) | ARALMATAGGLAFDI (SEQ ID NO: 1919) | 5 | 0 | 0 |
| ADI-24839 | ADI-20974 | VH3-21 | VL1-40 | ARVLVATAYGNAFDI (SEQ ID NO: 1920) | ARVLVATAYGNAFDI (SEQ ID NO: 1920) | 5 | 4 | 3 |
| ADI-41203 | ADI-41203 | VH5-51 | VK3-15 | VSLYSDYDYGALDY (SEQ ID NO: 1921) | VSLYSDYDYGALDY (SEQ ID NO: 1921) | 6 | 0 | 0 |
| ADI-36680 | ADI-41203 | VH5-51 | VK3-15 | VSLFGDYDYGALDY (SEQ ID NO: 1922) | VSLFGDYDYGALDY (SEQ ID NO: 1922) | 6 | 2 | 1 |
| ADI-36681 | ADI-41203 | VH5-51 | VK3-15 | VTLYTDYDYGAPDH (SEQ ID NO: 1923) | VTLYTDYDYGAPDH (SEQ ID NO: 1923) | 6 | 4 | 2 |
| ADI-41344 | ADI-41344 | VH3-21 | VL1-40 | ARVSSPMIRGYYLDY (SEQ ID NO: 1924) | ARVSSPMIRGYYLDY (SEQ ID NO: 1924) | 7 | 0 | 0 |

TABLE 8-continued

| | | | | | | Clus-ter Num-ber | Differ-ence from Parent | Difference from Parent in Reduced alphabet |
|---|---|---|---|---|---|---|---|---|
| ADI-Name | Parent | VH_GL | VL_GL | H3 | H3 | | | |
| ADI-41343 | ADI-41344 | VH3-21 | VL1-40 | ARVDTPMVRGYYFDY (SEQ ID NO: 1925) | ARVDTPMVRGYYFDY (SEQ ID NO: 1925) | 7 | 4 | 2 |

Reduced alphabet consensus sequences of neutralizing antibodies

Example 4. Exemplary Antibodies

Antibodies were assessed for RSV neutralization activity and polyreactivity. A set of antibodies with exemplary characteristics are provided in Tables 9A-C.

TABLE 9A

Antibody binding and functional characteristics

| Antibody No. | ADI Name | Neutralization-RSV A2 IC50 (pM) | neut IC50 (ug/ml) subtype A (graham) | neut IC50 (ug/ml) subtype B (graham) | neut IC50 (ug/ml) subtype A (wright) | Antigenic site | RSV PreF subtype A KD | RSV PostF subtype A KD | Polyreactivity score |
|---|---|---|---|---|---|---|---|---|---|
| Ab 2 | ADI-14334 | 189.2 | 0.05 | 0.11 | | Site III | 3.2E-10 | N.B. | 0.00 |
| Ab 71 | ADI-14405 | 58.3 | 0.04 | 0.04 | | Site IV (but preF-preferring) | 1.4E-10 | 1.2E-08 | 0.03 |
| Ab 112 | ADI-14583 | 124.6 | 0.05 | 0.06 | | Site V | 4.7E-10 | N.B. | 0 |
| Ab 217 | ADI-20964 | 162.4 | 0.06 | 0.14 | | Site V | 3.6E-10 | N.B. | 0 |
| Ab 227 | ADI-20974 | 75.4 | 0.003 | 0.09 | | Site III | 2.9E-10 | N.B. | 0.11 |
| Ab 228 | ADI-20975 | 67 | 0.05 | 0.49 | | unknown | 9.2E-11 | 1.5E-10 | 0.03 |
| Ab 249 | ADI-20998 | 74 | 0.03 | >25 | | Site 0 | 2.6E-10 | N.B. | 0.11 |
| Ab 466 | ADI-36669 | 110.9 | | | 0.025 | | 1.1E-09 | N.B. | 0.01 |
| Ab 467 | ADI-36670 | 141 | | | 0.008 | | 7.5E-10 | N.B. | 0.01 |
| Ab 469 | ADI-36672 | 206.7 | | | 0.018 | Likely site III | 7.0E-10 | N.B. | 0.07 |
| Ab 470 | ADI-36674 | 189.8 | | | 0.014 | Likely site III | 7.5E-10 | N.B. | 0.01 |
| Ab 832 | ADI-36676 | 130.1 | | | 0.006 | | 2.8E-10 | N.B. | 0 |
| Ab 471 | ADI-36677 | 144.1 | | | 0.019 | | 5.4E-10 | N.B. | 0.05 |
| Ab 516 | ADI-41191 | 154.1 | | | 0.071 | Likely site V | 5.0E-10 | N.B. | 0.08 |
| Ab 527 | ADI-41203 | 23.9 | | | 0.006 | | 4.0E-10 | N.B. | 0.05 |
| Ab 532 | ADI-41208 | 310.5 | | | 0.077 | Likely site III | 4.8E-10 | N.B. | 0.04 |
| Ab 543 | ADI-41221 | 65.4 | | | 0.040 | | 3.0E-10 | 3.2E-10 | 0.01 |
| Ab 544 | ADI-41222 | 39.9 | | | 0.016 | | 4.3E-10 | N.B. | 0.01 |
| Ab 551 | ADI-41229 | 228.2 | | | 0.066 | | 1.1E-09 | 7.1E-10 | 0 |
| Ab 554 | ADI-41232 | 103.9 | | | 0.025 | Likely site V | 7.1E-10 | N.B. | 0.00 |
| Ab 571 | ADI-41249 | 51.7 | | | 0.006 | | 3.9E-10 | N.B. | 0 |
| Ab 578 | ADI-41256 | 85.8 | | | 0.019 | | 3.5E-10 | N.B. | 0.00 |
| Ab 581 | ADI-41259 | 122 | | | 0.015 | | 3.4E-10 | N.B. | 0.00 |
| Ab 592 | ADI-41274 | 26.6 | | | 0.109 | Likely site III | 4.8E-10 | N.B. | 0.10 |
| Ab 615 | ADI-41302 | 132.9 | | | 0.006 | | 6.5E-10 | N.B. | 0.03 |
| Ab 641 | ADI-41344 | 228.6 | | | 0.064 | Likely site III | 4.9E-10 | N.B. | 0 |
| Ab 843 | ADI-41563 | 139.3 | | | 0.032 | | 6.0E-10 | N.B. | 0.12 |
| Ab 868 | ADI-41594 | 208.3 | | | 0.041 | Likely site III | 4.1E-10 | Weak binder (low response) | 0 |
| Ab 870 | ADI-41596 | 179.7 | | | 0.054 | | 3.0E-10 | 4.4E-10 | 0 |

TABLE 9B

Antibody VH sequence information

| Antibody No. | VH Germline | VH FR1 | VH CDR1 | VH FR2 |
|---|---|---|---|---|
| Ab 2 | VH3-11 | EVQLVESGGGLVK PGGSLRLSCAASG (SEQ ID NO: 1926) | VTVSSYYMS (SEQ ID NO: 1927) | WVRQAPGKGL EFVS (SEQ ID NO: 1928) |
| Ab 71 | VH1-18 | QVQLVQSGSEVKK PGASVKVSCKASG (SEQ ID NO: 1933) | YTFTNYGIS (SEQ ID NO: 1934) | WVRQAPGQGL EWMG (SEQ ID NO: 1935) |

TABLE 9B-continued

| | | Antibody VH sequence information | | |
| --- | --- | --- | --- | --- |
| Ab 112 | VH1-18 | QVQLVQSGAEVKK PGASVKVSCKASG (SEQ ID NO: 1940) | YTFTNYGIS (SEQ ID NO: 1941) | WVRQAPGQGL EWLG (SEQ ID NO: 1942) |
| Ab 217 | VH1-18 | QVQLVQSGAEVKK PGASVKVSCKASG (SEQ ID NO: 1947) | YTFTHYGIS (SEQ ID NO: 1948) | WVRQAPGQGL EWMG (SEQ ID NO: 1949) |
| Ab 227 | VH3-21 | EVQLVESGGGLVK PGGSLRLSCAASG (SEQ ID NO: 1954) | FSFSSYQIN (SEQ ID NO: 1955) | WVRQAPGKGL EWVS (SEQ ID NO: 1956) |
| Ab 228 | VH1-18 | QVQLVESGHVKK PGASVKVSCKASD (SEQ ID NO: 1961) | DTRNXGIV (SEQ ID NO: 1962) | WVRQAPGQGL EWMG (SEQ ID NO: 1963) |
| Ab 249 | VH3-33 | QVQLVQSGGGVVQ PGRSLRLSCAASG (SEQ ID NO: 1968) | FTLSTYGMH (SEQ ID NO: 1969) | WVRQAPGKGL EWVA (SEQ ID NO: 1970) |
| Ab 466 | VH1-46 | EVQLVQSGAEVKK PGASVKVCKASG (SEQ ID NO: 1975) | YTFTNYYIH (SEQ ID NO: 1976) | WVRQAPGQGL EWMG (SEQ ID NO: 1977) |
| Ab 467 | VH1-69 | QVQLVQSGAEVKK PGSSVKVSCKASG (SEQ ID NO: 1982) | GTFSTYTIN (SEQ ID NO: 1983) | WVRQAPGQGL EWMG (SEQ ID NO: 1984) |
| Ab 469 | VH3-11 | EVQLVESGGGLVK PGGSLRLSCAASG (SEQ ID NO: 1989) | FAFNNYYMN (SEQ ID NO: 1990) | WVRQAPGKGL EWVS (SEQ ID NO: 1991) |
| Ab 470 | VH3-21 | EVQLLESGGGLVK PGGSLRLSCAASG (SEQ ID NO: 1996) | FKFRSYSMN (SEQ ID NO: 1997) | WVRQAPGKGL EWVS (SEQ ID NO: 1998) |
| Ab 832 | VH3-30 | EVQLLESGGGVVQ PGRSLRLSCAASG (SEQ ID NO: 2003) | FSFNNYDMH (SEQ ID NO: 2004) | WVRQAPGKGL EWVA (SEQ ID NO: 2005) |
| Ab 471 | VH3-48 | QVQLVQSGGGLVQ PGGSLRLSCAASG (SEQ ID NO: 2010) | FTFSSYEMN (SEQ ID NO: 2011) | WVRQAPGKGL EWLS (SEQ ID NO: 2012) |
| Ab 516 | VH1-18 | QVQLVQSGAEVKR PGASVKVSCKASG (SEQ ID NO: 2017) | YTFTHYGIS (SEQ ID NO: 2018) | WVRQAPGQGL EWMA (SEQ ID NO: 2019) |
| Ab 527 | VH5-51 | QVQLVQSGAEVKK PGESLKISCKASG (SEQ ID NO: 2024) | YRFTNYWIG (SEQ ID NO: 2025) | WVRQMPGKGL EWMG (SEQ ID NO: 2026) |
| Ab 532 | VH3-11 | QVQLVESGGLVK PGGSLRLSCAASG (SEQ ID NO: 2031) | FTLSHYMS (SEQ ID NO: 2032) | WIRQPPGKGL EWVS (SEQ ID NO: 2033) |
| Ab 543 | VH3-21 | EVQLLESGGGLVK PGGSLRLSCAASG (SEQ ID NO: 2038) | FTFSYYMN (SEQ ID NO: 2039) | WVRQAPGKGL EWVS (SEQ ID NO: 2040) |
| Ab 544 | VH3-30 | QVFLKESGGGVVQ PGRSQRLSCTASG | RNRNNYAMH (SEQ ID | WVRQAPGKGL EWVA |

TABLE 9B-continued

| | | | | |
|---|---|---|---|
| | | (SEQ ID NO: 2045) | NO: 2046) | (SEQ ID NO: 2047) |
| Ab 551 | VH3-30 | QVQLVQSGGGVVQ PGRSIKLSCAASG (SEQ ID NO: 2052) | FTRSYGMH (SEQ ID NO: 2053) | WVRQAPGKGL EWVA (SEQ ID NO: 2054) |
| Ab 554 | VH1-18 | QVQLVQSGAEVKK PGASVKVSCKASG (SEQ ID NO: 2059) | YTFTYGIS (SEQ ID NO: 2060) | WVRQAPGQGL EWMA (SEQ ID NO: 2061) |
| Ab 571 | VH5-51 | QVQLVQSGAEVKK PGESLKISCQVSR (SEQ ID NO: 2066) | DTSTYWIG (SEQ ID NO: 2067) | WVRQMPGKGL EWMG (SEQ ID NO: 2068) |
| Ab 578 | VH1-69 | QVQLVQSGAEVKS PGSSSTVSCKASG (SEQ ID NO: 2073) | GTRSYGIS (SEQ ID NO: 2074) | WVRQAPGQGL EWIG (SEQ ID NO: 2075) |
| Ab 581 | VH3-11 | QVQLVESGGRLVK PGGSLRLSCAASG (SEQ ID NO: 2080) | FTFSDYYMS (SEQ ID NO: 2081) | WIRQAPGKGL EWVS (SEQ ID NO: 2082) |
| Ab 592 | VH3-21 | EVQLVESGGGLVK PGGSLRLSCAASG (SEQ ID NO: 2087) | RSFSSYAMN (SEQ ID NO: 2088) | WVRQAPGKGL QWVS (SEQ ID NO: 2089) |
| Ab 615 | VH3-30 | QVQLVESGGGVVQ PGRSLRLSCAASG (SEQ ID NO: 2094) | FTFSSYAMQ (SEQ ID NO: 2095) | WVRQAPGKGL EWVA (SEQ ID NO: 2096) |
| Ab 641 | VH3-21 | EVQLVESGGGLVK PGGSLRLSCAASG (SEQ ID NO: 2101) | BFSSYYMN (SEQ ID NO: 2102) | WVRQAPGKGL EWVS (SEQ ID NO: 2103) |
| Ab 843 | VH4-59 | QVQLVESGPGLVK PSETLSLTCTVSD (SEQ ID NO: 2108) | DSISWNFWS (SEQ ID NO: 2109) | WIRQPPGKGL EWIG (SEQ ID NO: 2110) |
| Ab 868 | VH3-21 | EVQLVESGGGLVK PGGSLRLSCAASG (SEQ ID NO: 2115) | RSFSSYYMN (SEQ ID NO: 2116) | WVRQAPGKGL EWVS (SEQ ID NO: 2117) |
| Ab 870 | VH4-34 | QVQLQQWGAGLLK PSETLSLTCAVYG (SEQ ID NO: 2122) | DSFSGYYWS (SEQ ID NO: 2123) | WIRQPPGKGL EWIG (SEQ ID NO: 2124) |

| Antibody No. | VH CDR2 | VH FR3 | VH CDR3 | VH FR4 |
|---|---|---|---|---|
| Ab 2 | DISSSSYTNYA DSVKG (SEQ ID NO: 1929) | RFTISRDNAKNSLYL QMNNLRAEDTAVYYC (SEQ ID NO: 1930) | ARLGITVTGVGYFDL (SEQ ID NO: 1931) | WGRGTLVTVSS (SEQ ID NO: 1932) |
| Ab 71 | WISSSTGNTYA QNLQG (SEQ ID NO: 1936) | RLTMTTDTSTSTAYM ELRSLRSDDTAYYC (SEQ ID NO: 1937) | ARDNVGYASGNYFDY (SEQ ID NO: 1938) | WGQGTLVTVSS (SEQ ID NO: 1939) |
| Ab 112 | WISAYNGNMYA QKVQG (SEQ ID NO: 1943) | RVTMTTDTSTSTYM ELRSLRSDDTAVYYC (SEQ ID NO: 1944) | AREPPVIAAGDFQH (SEQ ID NO: 1945) | WGQGTLVTVSS (SEQ ID NO: 1946) |
| Ab 217 | WISAYNGNTNYA QKLQG | RVTMTTDTSTSTAYM BVRSLRKDDTAVYYC | ARDVPVEAATSPEF (SEQ ID | WGQGTLVTVSS (SEQ ID |

TABLE 9B-continued

| | | Antibody VH sequence information | | |
|---|---|---|---|
| | (SEQ ID NO: 1950) | (SEQ ID NO: 1951) | NO: 1952) | NO: 1953) |
| Ab 227 | SISGGSSYDYA DSIKG (SEQ ID NO: 1957) | RFTISRDNAKKSWL QMKSLRADDTAVYYC (SEQ ID NO: 1958) | ARALMATAGGLAFDI (SEQ ID NO: 1959) | WGQGTMVTVSS (SEQ ID NO: 1960) |
| Ab 228 | WIRPWNGNTKYA QKFQG (SEQ ID NO: 1964) | RVTMTTDASTNTAYM ELRSLRSGDTAVYYC (SEQ ID NO: 1965) | AREQFKWNDFYFDY (SEQ ID NO: 1966) | WGQGLVTVSS (SEQ ID NO: 1967) |
| Ab 249 | VIXYDSNKFYA DSWQG (SEQ ID NO: 1971) | RFTISRDSKNTIFL QMNSLRAEDTAVYYC (SEQ ID NO: 1972) | ARESRPRGYSYSD FDS (SEQ ID NO: 1973) | WGQGTLVTVSS (SEQ ID NO: 1974) |
| Ab 466 | MINPSGGTSYA QKFQG (SEQ ID NO: 1978) | RLTMKDTSTSTVYM EINXLRSEDTAVYYC (SEQ ID NO: 1979) | TRDFIYFYGSGDG FDY (SEQ ID NO: 1980) | WGQGTLVTVSS (SEQ ID NO: 1981) |
| Ab 467 | RITRLGVPLSA QKFQG (SEQ ID NO: 1985) | RKTIBADKSTTAYM ELSSLGSEDTAVYYC (SEQ ID NO: 1986) | ASLNYYDTTDYYL GYSDS (SEQ ID NO: 1987) | WGQGTLVTVSS (SEQ ID NO: 1988) |
| Ab 469 | SISSASTYDYA DSVKG (SEQ ID NO: 1992) | RFTISRDNAKNSLYL HLNSLRAEDTAVYYC (SEQ ID NO: 1993) | ARDYYGSGNYYNP KPLDV (SEQ ID NO: 1994) | WGQGTTVTVSS (SEQ ID NO: 1995) |
| Ab 470 | SISSSSSWDYA GSLKG (SEQ ID NO: 1999) | RFTISRDNAENSLYL QMNSLRAEDTAAYYC (SEQ ID NO: 2000) | ARAGSVPVAGTYNDY (SEQ ID NO: 2001) | WGQGTLVTVSS (SEQ ID NO: 2002) |
| Ab 832 | IISYDGSNK- YADSVKG (SEQ ID NO: 2006) | RFTISRDXSKNTLYL QMNSLRVEDTAVYYC (SEQ ID NO: 2007) | ARADSSGYYKGSE YFQH (SEQ ID NO: 2008) | WGQGTLVTVSS (SEQ ID NO: 2009) |
| Ab 471 | YISSSGXKYYA DSVKG (SEQ ID NO: 2013) | RFTVSRDNAKYSLYL QMWSLRAEDTAVYYC (SEQ ID NO: 2014) | ASLYDSRGYYWVFDY (SEQ ID NO: 2015) | WGQGTLVTVSS (SEQ ID NO: 2016) |
| Ab 516 | WISAYNGNTNYA QKLQG (SEQ ID NO: 2020) | RVTVTTDTSTSTAYM ELRSLRSDDTAVYYC (SEQ ID NO: 2021) | AREPPSLSAAATLDY (SEQ ID NO: 2022) | WGQGTLVTVSS (SEQ ID NO: 2023) |
| Ab 527 | VIYPGDSDTRYS PSFQG (SEQ ID NO: 2027) | QVTMSADKSXNTAYL QWSSLKASDTAXYYC (SEQ ID NO: 2028) | VSLYSDYDYGALDY (SEQ ID NO: 2029) | WGQGTLVTVSS (SEQ ID NO: 2030) |
| Ab 532 | SISGSTYTNYA DSVKG (SEQ ID NO: 2034) | RFTISRDNAENSLYL QMNSLRAEDTAVYYC (SEQ ID NO: 2035) | ARLAYSDYGPFYFDL (SEQ ID NO: 2036) | WGRGTLVTVSS (SEQ ID NO: 2037) |
| Ab 543 | SISISSHIYYA DSVKG (SEQ ID NO: 2041) | RFTISRDNAKNSLYL QTNSLRAEDTAAYYC (SEQ ID NO: 2042) | ARELGFASSSYSY YYGMDV (SEQ ID NO: 2043) | WGQGTTVTVSS (SEQ ID NO: 2044) |
| Ab 544 | VISYDGSNKNFA DSVKG (SEQ ID NO: 2048) | RFTISRDNSKNTLNL QMNNLRAEDTAVYYC (SEQ ID NO: 2049) | VRDIVRGSPLFDY (SEQ ID NO: 2050) | WGQGTLVTVSS (SEQ ID NO: 2051) |
| Ab 551 | VISYIXINKYYA DSVKG (SEQ ID NO: 2055) | RFTISRDYSKNTLSL QMNSLXTEDTAXYYC (SEQ ID NO: 2056) | AKPKTTGYYYLDA FDF (SEQ ID NO: 2057) | WGQGTMVTVSS (SEQ ID NO: 2058) |

TABLE 9B-continued

| Antibody VH sequence information | | | |
|---|---|---|---|
| Ab 554 | WISAYNGNTNYA QKLQG (SEQ ID NO: 2062) | RVTVTTDTSTSTAYM ELRSLRSDDTAVYYC (SEQ ID NO: 2063) | ARDSMGGTTLFDY (SEQ ID NO: 2064) | WGQGTLVTVSS (SEQ ID NO: 2065) |
| Ab 571 | IIFPGDSDTRYS PSFQG (SEQ ID NO: 2069) | QVTISADKSISTAYL QLSSLKASDTAMYYC (SEQ ID NO: 2070) | ATQALRGAFDI (SEQ ID NO: 2071) | WGQGTMVTVSS (SEQ ID NO: 2072) |
| Ab 578 | AISPFGTFNYA QKFQG (SEQ ID NO: 2076) | RVTMTADESTSTVYM DVSSLRSDTAVYYC (SEQ ID NO: 2077) | VRDVFYDILTGYY DADYYHHYMDV (SEQ ID NO: 2078) | WGKGTTVTVSS (SEQ ID NO: 2079) |
| Ab 581 | YISSSGDDFNYA DSVKG (SEQ ID NO: 2083) | RFTISRDNSKNSLYL QMNSLRAEDTAVYYC (SEQ ID NO: 2084) | ARDEVGWNNLDYY FGMDV (SEQ ID NO: 2085) | WGQGTTVTVSS (SEQ ID NO: 2086) |
| Ab 592 | SISAGSSYIDYA DSVKG (SEQ ID NO: 2090) | RFTISRDNAKNSLFL QMNSLRVEDTAVYYC (SEQ ID NO: 2091) | ARVGSYTHGYEFDY (SEQ ID NO: 2092) | WGQGTLVTVSS (SEQ ID NO: 2093) |
| Ab 615 | WINDGDDKYYA DSVKG (SEQ ID NO: 2097) | RFTISRDNSKNTLYL QMNSLRPEDTAVYYC (SEQ ID NO: 2098) | ARDLFEWWELLGY CYAMDV (SEQ ID NO: 2099) | WGQGTTVTVSS (SEQ ID NO: 2100) |
| Ab 641 | SISSSSYIDYA DSVKG (SEQ ID NO: 2104) | RFTISRDNAKNSLFL QMNSLRAEDTAVYYC (SEQ ID NO: 2105) | ARVSSPMIRGYYLDY (SEQ ID NO: 2106) | WGQGTLVTVSS (SEQ ID NO: 2107) |
| Ab 843 | YIYYSGSTNYNP SLKS (SEQ ID NO: 2111) | RVTMSVDLSKNQFSL KLSSVTAADTAVYYC (SEQ ID NO: 2112) | ARLTSGGVDY (SEQ ID NO: 2113) | WGQGTLVTVSS (SEQ ID NO: 2114) |
| Ab 868 | SISPSSSYINYA DSVKG (SEQ ID NO: 2118) | RFTISRDNAKDSLYL QMNSLRAEDTAVYYC (SEQ ID NO: 2119) | ARDGLLGITIFGV VQDY (SEQ ID NO: 2120) | WGQGTLVTVSS (SEQ ID NO: 2121) |
| Ab 870 | EINLSGSTNYNP SLKS (SEQ ID NO: 2125) | RVTILVDTSKNQFSL KLSSVTAADTAVYYC (SEQ ID NO: 2126) | ARGLHVSDDQDSS GYYFHPGSFDY (SEQ ID NO: 2127) | WGQGTLVTVSS (SEQ ID NO: 2128) |

TABLE 9C

| Antibody VL sequence information | | | | |
|---|---|---|---|---|
| Antibody No. | VL Germline | VL FR1 | VL CDR1 | VL FR2 |
| Ab 2 | VL1-40 | QPGLTQPPSVSG APGQRVTISC (SEQ ID NO: 2129) | TGSSSNIGAGY DVH (SEQ ID NO: 2130) | WYQQLPGTAP KLLIS (SEQ ID NO: 2131) |
| Ab 71 | VL3-21 | SYVLTQPPSVSV APGKTARITC (SEQ ID NO: 2136) | GGNNIGSKSVH (SEQ ID NO: 2137) | WYQQRPGQAP VLVIY (SEQ ID NO: 2138) |
| Ab 112 | VK2-30 | ETTLTQSPLSLP VTLGQPASISC (SEQ ID NO: 2143) | RSSQSLVHSNG NTYLS (SEQ ID NO: 2144) | WFQQRPGQSP RRLIY (SEQ ID NO: 2145) |
| Ab 217 | VK2-30 | DVVMTQTPLSLP VTLGQPASISC | RSSQSLVYSDG NTYLS | WFQQRPGQSP RRLIY |

TABLE 9C-continued

| | | Antibody VL sequence information | | |
|---|---|---|---|---|
| | | (SEQ ID NO: 2150) | (SEQ ID NO: 2151) | (SEQ ID NO: 2152) |
| Ab 227 | VL1-40 | QPVLTQPPSVSG APGQRVTISC (SEQ ID NO: 2157) | TGSSSNIGAGY DVH (SEQ ID NO: 2158) | WYQQVPGTAP KLLIL (SEQ ID NO: 2159) |
| Ab 228 | VL3-21 | SYELMQPPSVSV APGQTAXITC (SEQ ID NO: 2164) | GGNNIGSSTVH (SEQ ID NO: 2165) | WYQQKPGQAP VLVVB (SEQ ID NO: 2166) |
| Ab 249 | VL2-11 | QPGLTQPRSVSG SPGQSVTISC (SEQ ID NO: 2171) | TGTSSDVGYFN YVS (SEQ ID NO: 2172) | WYQQHPGKAP KLMIY (SEQ ID NO: 2173) |
| Ab 466 | VK1-17 | EIVMTQSPSAMS ASVGDRVTITC (SEQ ID NO: 2178) | RASQGISNYLA (SEQ ID NO: 2179) | WFQQKPGKVP KRLIY (SEQ ID NO: 2180) |
| Ab 467 | VK3-15 | DIVLTQPATLS VSPGERATLSC (SEQ ID NO: 2185) | RASHSVSSNLA (SEQ ID NO: 2186) | WYQQKPGQAP RLLIY (SEQ ID NO: 2187) |
| Ab 469 | VL1-40 | QPVLTQPPSVSG APGQRVTISC (SEQ ID NO: 2192) | TGSSSNIGAGY DVH (SEQ ID NO: 2193) | WYRQFPGTAP ELLIY (SEQ ID NO: 2194) |
| Ab 470 | VL1-40 | QSVLTQPPSVSG APGQRVTISC (SEQ ID NO: 2199) | TGSSSNIGAGY DVH (SEQ ID NO: 2200) | WYQRLPGTAP KLLIB (SEQ ID NO: 2201) |
| Ab 832 | VL3-21 | SYXLTQLPSVSV APGQTARITC (SEQ ID NO: 2206) | GGNNIGSKSVQ (SEQ ID NO: 2207) | WYQKKPGQAP VLVVY (SEQ ID NO: 2208) |
| Ab 471 | VK1-33 | DIVMTQSPSSLS ASVGDRVTITC (SEQ ID NO: 2213) | QASQDISSYLN (SEQ ID NO: 2214) | WYQKKPGKAP NLLIY (SEQ ID NO: 2215) |
| Ab 516 | VK2-30 | ELVMTQSPLSLP VTLGQPASISC (SEQ ID NO: 2220) | RSNQSLVYSDG NYLE (SEQ ID NO: 2221) | WFQQRPGQSP RRLIY (SEQ ID NO: 2222) |
| Ab 527 | VK3-15 | EIVMTQSPATLS VSPGERATLSC (SEQ ID NO: 2227) | RASEVGHNLA (SEQ ID NO: 2228) | WYQQKPGQAP RLLIY (SEQ ID NO: 2229) |
| Ab 532 | VL1-40 | QSVLTQPPSVSG APGQRVTISC (SEQ ID NO: 2234) | TGSSSNIGAGY DVH (SEQ ID NO: 2235) | WYQQLFGTAP KLLIF (SEQ ID NO: 2236) |
| Ab 543 | VL2-11 | QSALTQPRSVSG SPGQSVTISC (SEQ ID NO: 2241) | TGTSSDVGGYN SVS (SEQ ID NO: 2242) | WYQQHPGTAP KLIIF (SEQ ID NO: 2243) |
| Ab 544 | VL3-21 | QFVLTQPPSLSV APGQTAWITC (SEQ ID NO: 2248) | GGNNIGSKVH (SEQ ID NO: 2249) | WYQQKPGQAP WVVY (SEQ ID NO: 2250) |
| Ab 551 | VK1-33 | ETTLTQSPSSLS ASVGDRVTITC (SEQ ID NO: 2255) | QASQDISNYLN (SEQ ID NO: 2256) | WYQQKPGKAP KLLIY (SEQ ID NO: 2257) |

TABLE 9C-continued

| Antibody VL sequence information | | | |
|---|---|---|---|
| Ab 554 | VK2-30 | DIVMTQPLSLP VTLGQPASISC (SEQ ID NO: 2262) | RSSQSLVYSDG NTYLN (SEQ ID NO: 2263) | WFQQRPGQSP RRLIY (SEQ ID NO: 2264) |
| Ab 571 | VK1-33 | DIRLTQSPSSLS ASVGDRVTITC (SEQ ID NO: 2269) | QASQDISNYLN (SEQ ID NO: 2270) | WYQQKPGKAP KLLIY (SEQ ID NO: 2271) |
| Ab 578 | VK2-30 | DIVMTQSPLSLP VTLGQPASISC (SEQ ID NO: 2276) | RSSQSLVHSDG NTYLN (SEQ ID NO: 2277) | WFQQRPGQSP RRLIY (SEQ ID NO: 2278) |
| Ab 581 | VK2-30 | DIVMTQSPLSLP VTLGQPASISC (SEQ ID NO: 2283) | RSSQSLVHSDG NTYLS (SEQ ID NO: 2284) | WFHQRPGQSP RRLIY (SEQ ID NO: 2285) |
| Ab 592 | VL1-40 | QPVLTQPPSVSG APGQRVTISC (SEQ ID NO: 2290) | TGSNSNIGAGY DVH (SEQ ID NO: 2291) | WYQQLPGTAP KLLIY (SEQ ID NO: 2292) |
| Ab 615 | VL2-8 | QSVLTQPPSASG SPGQSVTISC (SEQ ID NO: 2297) | TGTSSDVGAYN YVS (SEQ ID NO: 2298) | WYQQHPGKAP KLIIY (SEQ ID NO: 2299) |
| Ab 641 | VL1-40 | QPVLTQPPSVSG APGQRVTISC (SEQ ID NO: 2304) | TGSSSNIGAGY DVH (SEQ ID NO: 2305) | WYQQLPGTAP KLVIH (SEQ ID NO: 2306) |
| Ab 843 | VL1-40 | QSVLTQPPSLSG APGQRVTISC (SEQ ID NO: 2311) | TGSSSNIGADY HVH (SEQ ID NO: 2312) | WYQQLPGTAP KLLIY (SEQ ID NO: 2313) |
| Ab 868 | VL1-40 | QSVVTQPPSVSG APGQRVTISC (SEQ ID NO: 2318) | TGSSSNIGAGY DVH (SEQ ID NO: 2319) | WYQQLPGTAP KLLIY (SEQ ID NO: 2320) |
| Ab 870 | VK4-1 | DIRMTQSPDSLA VSLGERATINC (SEQ ID NO: 2325) | KSSQSVLYSSN NKNYLA (SEQ ID NO: 2326) | WYQQKPGQPP KLLIN (SEQ ID NO: 2327) |

| Antibody No. | VL CDR2 | VL FR3 | VL CDR3 | VL FR4 |
|---|---|---|---|---|
| Ab 2 | DNNNRPS (SEQ ID NO: 2132) | GVPDRFSGSKSGTSASL AITGLQVEDEADYYC (SEQ ID NO: 2133) | QSYDSSLSNYV (SEQ ID NO: 2134) | FGGGTKLTVL (SEQ ID NO: 2135) |
| Ab 71 | YDSVRPS (SEQ ID NO: 2139) | GIPERFSGSNSGNTATL TISLVEAGDEADYYC (SEQ ID NO: 2140) | QVWDSSRDHEV (SEQ ID NO: 2141) | FGGGTKLTVL (SEQ ID NO: 2142) |
| Ab 112 | KVSNRDS (SEQ ID NO: 2146) | GVPDRFSGSGSGTDFTL KISRVEAEDVGVYYC (SEQ ID NO: 2147) | MQGTHWPPD (SEQ ID NO: 2148) | FGQGTRLEIK (SEQ ID NO: 2149) |
| Ab 217 | KVSNRDS (SEQ ID NO: 2153) | GVPNRFSGSGSGTDFTL KISRVEAEDVGVYYC (SEQ ID NO: 2154) | VQNTHWPAYT (SEQ ID NO: 2155) | FGQGTKVEIK (SEQ ID NO: 2156) |
| Ab 227 | RNNNRPS (SEQ ID NO: 2160) | GVPDRFSGSKSGTSASL AITGLQAEDEADYYC (SEQ ID NO: 2161) | QSYDRSLSVV (SEQ ID NO: 2162) | FGGGTKLTVL (SEQ ID NO: 2163) |

TABLE 9C-continued

| | | Antibody VL sequence information | | |
|---|---|---|---|---|
| Ab 228 | DDYDRPS (SEQ ID NO: 2167) | GIPERFSGSNSGNTATL TISSVEAGDEADYYC (SEQ ID NO: 2168) | QVRDSRTDDVV (SEQ ID NO: 2169) | FGGGTKLTVL (SEQ ID NO: 2170) |
| Ab 249 | DWQRPS (SEQ ID NO: 2174) | GVPDRFSGSKSGNTASL TISGLQAEDEADYYC (SEQ ID NO: 2175) | CAYAGYYS (SEQ ID NO: 2176) | FGGGTKLTVL (SEQ ID NO: 2177) |
| Ab 466 | AASSLQS (SEQ ID NO: 2181) | GVPSRFSGSGSGTEFTL TISSLQPEDFATYYC (SEQ ID NO: 2182) | LQHNSYPFT (SEQ ID NO: 2183) | FGGGTKVEIK (SEQ ID NO: 2184) |
| Ab 467 | GASTRAT (SEQ ID NO: 2188) | GIPARFSGRGSGTEFTL TISSLQPEDFAVYYC (SEQ ID NO: 2189) | QQYNNWPPEYT (SEQ ID NO: 2190) | FGQGTKVDIK (SEQ ID NO: 2191) |
| Ab 469 | GNYNRPS (SEQ ID NO: 2195) | GVPDRFSGSKSGTSASL AITGLQAEDEADYYC (SEQ ID NO: 2196) | QSYDSSLKGV (SEQ ID NO: 2197) | FGGGTKLTVL (SEQ ID NO: 2198) |
| Ab 470 | GNYNRPA (SEQ ID NO: 2202) | GVPDRFSGSKSGTSASL VITGLQAEDEADYYC (SEQ ID NO: 2203) | QSYDRSLSVL (SEQ ID NO: 2204) | FGGGTKVTVL (SEQ ID NO: 2205) |
| Ab 832 | DDSDRPS (SEQ ID NO: 2209) | DIPERFSGSNSGNTATL TISRVEAGDEADYYC (SEQ ID NO: 2210) | QVWDSSSDHYV (SEQ ID NO: 2211) | FGGGTKLTVL (SEQ ID NO: 2212) |
| Ab 471 | DASNLEP (SEQ ID NO: 2216) | GVPSRFSGSGSGTDFTF TISSLQPEDIATYYC (SEQ ID NO: 2217) | LQHDNLPPT (SEQ ID NO: 2218) | FGQGTKVDIK (SEQ ID NO: 2219) |
| Ab 516 | KVSNRDS (SEQ ID NO: 2223) | GVPDRFSGSGSGTDFTL KISRVEAEDVAVYYC (SEQ ID NO: 2224) | MQVTHWPHE (SEQ ID NO: 2225) | FGQGTKLEIK (SEQ ID NO: 2226) |
| Ab 527 | GASIRAT (SEQ ID NO: 2230) | GIIARFSGSGSGTEYTL TISSLQSEDFAVYYC (SEQ ID NO: 2231) | QQYHDWPSFT (SEQ ID NO: 2232) | FGPGTKVDIK (SEQ ID NO: 2233) |
| Ab 532 | DNWNRPS (SEQ ID NO: 2237) | GVPDRFSGSKSGTSASL AITGLQAEDEADYYC (SEQ ID NO: 2238) | QSYDSRLSAPYV (SEQ ID NO: 2239) | FGGGTKLTVL (SEQ ID NO: 2240) |
| Ab 543 | DVQRPS (SEQ ID NO: 2244) | GVPDRFSGSKSANTASL TISGLQEDEADYY- (SEQ ID NO: 2245) | CCSFAGNYV (SEQ ID NO: 2246) | FGTGTKVTVL (SEQ ID NO: 2247) |
| Ab 544 | DDYDRPS (SEQ ID NO: 2251) | GIPERFSGSNSGNTATL TISRVEYGDEADYYC (SEQ ID NO: 2252) | QVWDRSSDNYV (SEQ ID NO: 2253) | FGTGTKVBVL (SEQ ID NO: 2254) |
| Ab 551 | DASNLET (SEQ ID NO: 2258) | GVPSRFSGSGSGTDFTF TISSLQSEDIATYYC (SEQ ID NO: 2259) | QQHDNVPPT (SEQ ID NO: 2260) | FGQGTKVDIK (SEQ ID NO: 2261) |
| Ab 554 | KVSNRDS (SEQ ID NO: 2265) | GVPDRFGSGSGTDFTL KISRVEAEDVGVYYC (SEQ ID NO: 2266) | MQGTHWPPMYT (SEQ ID NO: 2267) | FGQGTKLEIK (SEQ ID NO: 2268) |
| Ab 571 | DASYLET (SEQ ID | GVPSRFSGSGSGTDFTF TISSLQPEDFATYYC | QQYDDLLFT (SEQ ID | FGPGTKLEIK (SEQ ID |

TABLE 9C-continued

| | | Antibody VL sequence information | | |
|---|---|---|---|---|
| | NO: 2272) | (SEQ ID NO: 2273) | NO: 2274) | NO: 2275) |
| Ab 578 | KVSNRGS (SEQ ID NO: 2279) | GVPDRFSGSGSGTDFTL KISRVEAEDVGVYC (SEQ ID NO: 2280) | MQGTHWPRT (SEQ ID NO: 2281) | FGQGTKVIK (SEQ ID NO: 2282) |
| Ab 581 | KVSNRDS (SEQ ID NO: 2286) | GVPNRFSGGGSGTDFTL KISRVEAEDVGFFYC (SEQ ID NO: 2287) | MQGTHWQKT (SEQ ID NO: 2288) | FGQGTKVEIK (SEQ ID NO: 2289) |
| Ab 592 | ASTIRPS (SEQ ID NO: 2293) | GVPDRFSGSKSGTSASL AITGLQAEDEADYYC (SEQ ID NO: 2294) | QSYDRNLSVV (SEQ ID NO: 2295) | FGGGTKVTVL (SEQ ID NO: 2296) |
| Ab 615 | EVYKRPS (SEQ ID NO: 2300) | GVPDRFFGSKSGNTASL TVSGLQAEDEADYYC (SEQ ID NO: 2301) | SSYAGSNTLGV (SEQ ID NO: 2302) | FGGGTKVTVL (SEQ ID NO: 2303) |
| Ab 641 | GNSNRPS (SEQ ID NO: 2307) | GVPDRFSGSKSGTSASL AITGLQGEDEADYYC (SEQ ID NO: 2308) | QSYDSSLSGSV (SEQ ID NO: 2309) | FGGGTKLTVL (SEQ ID NO: 2310) |
| Ab 843 | QNTNRPS (SEQ ID NO: 2314) | GVPDRFSASKSGTSVSL AITGLQAEDEADYYC (SEQ ID NO: 2315) | QSYDSSLSAWV (SEQ ID NO: 2316) | FGGGTKLTVL (SEQ ID NO: 2317) |
| Ab 868 | GNTNRPS (SEQ ID NO: 2321) | GVPDRFSASKSGTSASL AITGLQAEDEADYYC (SEQ ID NO: 2322) | QSYDSSLSVV (SEQ ID NO: 2323) | FGGGTKLTVL (SEQ ID NO: 2324) |
| Ab 870 | WASTRES (SEQ ID NO: 2328) | GVPDRFSGSGSGTDFTL AISSLQAEDVAVYYC (SEQ ID NO: 2329) | QQYYSTPLT (SEQ ID NO: 2330) | FGGGTKVEIK (SEQ ID NO: 2331) |

An informal sequence listing is provided below in Table 5.

TABLE 5

| | | Informal Sequence Listing | | |
|---|---|---|---|---|
| Anti-body No. | SEQ ID NO: | Sequence | Clone # (ADI) | Descriptors |
| Ab 1 | 1 | EVQLVETGGGLVKPGGSLRLSCADSGFPFSSYSMHWVRQAPGKGLEWVASISSSSS FINYADSVKGRFTISRDNAKNSLYLQMNSLRAEDTAVYFCAREAACGGDCYGYYFD YWGQGTLVTVSS | ADI-14333 | Heavy chain variable region ("HC") amino acid sequence |
| Ab 1 | 2 | QSVVTQPPSASGAPGQRVTISCTGSSSNIGAGYDVHWYQQLPGTAPKVLISGNSNR PSGVPARFSGSKSGTSASLAITGLQAEDEADYYCQSYDSSLSGSVFGGGTQLTVL | ADI-14333 | Light chain variable region ("LC") amino acid sequence |
| Ab 2 | 3 | EVQLVESGGGLVKPGGSLRLSCAASGVTVSSYYMTWVRQAPGKGLEFISDISSSSTY TNYADSVKGRFTISRDNAKSSLYLQMNNLRAEDTAVYYCARLGITVTGVGYFDLWG RGTLVTVSS | ADI-14334 | Heavy chain variable region ("HC") amino acid sequence |
| Ab 2 | 4 | QPGLTQPPSVSGAPGQRVTISCTGSSSNIGAGYDVHWYQQLPGTAPKLLIHDNNN RPSGVPDRFSGSKSGTSASLAITGLQVEDEADYYCQSYDSSLSNYVFGTGTKLTVL | ADI-14334 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 3 | 5 | EVQLVESGGGLVQPGRSLRLSCTASGFTFGDYAMSWVRQAPGKGLEWVGFIRSN AFGGTSEYAASVKGRFTISRDDSKSIAYLQMNSLKTEDTAVYYCTRDGIHDYGDSYY YYGMDVWGQGTTVTVSS | ADI-14335 | Heavy chain variable region ("HC") amino acid sequence |
| Ab 3 | 6 | DIQLTQSPSSLSASVGDRVTITCRASQTVTTYLNWYQQKPGKAPKLLIYGASSLQSG VPSRFSGSGSGTDFTLTINSLQPEDFATYYCQQTYSTVTFGPGTKVEIK | ADI-14335 | Light chain variable region ("LC") amino acid sequence |
| Ab 4 | 7 | EVQLLESGGEVKKPGASVKVSCKASGYTFTNYGISWVRQAPGQGLEWMGWISAY NGNTNYAQKLQGRVTMTTDTSTSTAYMEVRRLRSDDTAVYYCAREPPVIAAGDFQ HWGQGTLVTVSS | ADI-14336 | Heavy chain variable region ("HC") amino acid sequence |
| Ab 4 | 8 | DIVMTQTPLSLPVTLGQPASISCRSSQSLVHSDTNIYLSWFQQRPGQSPRRLIYKVS NRDSGVPDRFSGSGSGTDFTLRISRVEAEDVGVYYCMQGTHWPPDFGQGTRLEIK | ADI-14336 | Light chain variable region ("LC") amino acid sequence |
| Ab 5 | 9 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCAREYYDSSGYTNWFDP WGQGTLVTVSS | ADI-14337 | Heavy chain variable region ("HC") amino acid sequence |
| Ab 5 | 10 | QPVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLAWVFGGGTQLTVL | ADI-14337 | Light chain variable region ("LC") amino acid sequence |
| Ab 6 | 11 | EVQLVESGGGVVQPGRPLRLSCAASGFTFSTYDLYWVRQAPGKGLDWVAIISPDG NKKYYADSVKGRFTISRDNSKNTLFLHMNSLRAEDTAVYYCARDYGNYFGSGSYYR YFDLWGRGTLVTVSS | ADI-14338 | Heavy chain variable region ("HC") amino acid sequence |
| Ab 6 | 12 | DIQLTQSPSSLSASVGDRVTITCRASQSISSHLNWYQQKPGKAPKLLIYASSSLQSG VPSRFSGSGSGTDFTLTISGLQPEDFATYYCQQSYSTPFTFGPGTKVEIK | ADI-14338 | Light chain variable region ("LC") amino acid sequence |
| Ab 7 | 13 | QVQLVESGGGVLQPGRSLRLPCEASGFTFNKYAMHWVRQAPGKGLEWVAAVSY DGGNKFYAESVKGRFTISRDNSKNTLYLQMNSLKPEDTAVYYCARDRWELLHGLDY WGLGTLVTVSS | ADI-14339 | Heavy chain variable region ("HC") amino acid sequence |
| Ab 7 | 14 | SYELTQPPSVSVSPGQTARITCSGEALAKQYAYWYQQKPGQAPVLVIYKDNERPSGI SERFSGSSSGTTVTLTISGVQAEDEADYYCQSADSSGTYVFGTGTKVTVL | ADI-14339 | Light chain variable region ("LC") amino acid sequence |
| Ab 8 | 15 | EVQLVESGGGLVKPGGSLRLSCAASGFTLSSYTMNWVRQAPGRGLEWVSSIYSTSS YIYYADSVKGRFTISRDNAKNSLYLQMNSLRAEDTAVYYCARDSQAVTGTDLYFDS WGQGTLVTVSS | ADI-14340 | Heavy chain variable region ("HC") amino acid sequence |
| Ab 8 | 16 | QPGLTQPPSVSVAPGKTARITCGGNNIGRKNVHWYQQKPGQAPILVIYYDSDRPS GIPERFSGSNSGNTATLTISRVEDGDEADYYCQVWDSSNDHVIFGGGTQLTVL | ADI-14340 | Light chain variable region ("LC") amino acid sequence |
| Ab 9 | 17 | QVQLVQSGGGLVQPGGSLRLSCAGSGFTFSDYEMNWVRQAPGKGLEWLSYISSS GSIIYYADSVKGRFTISRDNAKNSLYLQMNSLRAEDTGLYYCARANHRHYYGMDV WGQGTTVTVSS | ADI-14341 | Heavy chain variable region ("HC") amino acid sequence |
| Ab 9 | 18 | DIRLTQSPSTLSASVGDRVTITCRASQSIGSWLAWYQQKPGKAPKLLIYKASSLESG VPSRFSGSGSGTEFTLTISSLQPDDFATYYCQQYNSYSYTFGRGTRLEIK | ADI-14341 | Light chain variable region ("LC") amino acid sequence |
| Ab 10 | 19 | QVTLKESGPVLVKPTETLTLTCTVSGFSLSNAKMGVSWIRQPPGKALEWLAYISSND EKSYSTSLKSRLTISKDTSKSQVVLTMTNMDPVDTATYYCARILLYDSSGYYLWYFD | ADI-14342 | Heavy chain variable region |

TABLE 5-continued

Informal Sequence Listing

| Anti-body No. | SEQ ID NO: | Sequence | Clone # (ADI) | Descriptors |
|---|---|---|---|---|
| | | LWGRGTLVTVSS | | ("HC") amino acid sequence |
| Ab 10 | 20 | DIQVTQSPSSLSASVGDRVTITCRASQRITSYLNWYQHKPGKAPKLLIFAASSLHSG VPSTFSGSGSGTDFTLTISSLQPEDFATYYCQQSYSTPWTFGQGTKVEIK | ADI-14342 | Light chain variable region ("LC") amino acid sequence |
| Ab 11 | 21 | QVQLVQSGAEVKKPGSSVKVSCKASGGTFSSYGVNWVRQAPGQGLEWMGRIIP MFGTSNYAQKFQGRVTITADGSTSTAYMELSSLRSEDTAVYYCARVGSPTTGAIMG VWGQGTTVTVSS | ADI-14343 | Heavy chain variable region ("HC") amino acid sequence |
| Ab 11 | 22 | DIVLTQTPLSLPVTPGEPASISCRSSQSLLQSNGFNYLDWYLQKPGQSPKLLIYMGS NRASGVPDRFSGSGSGTDFTLIISRVEAEDVGVYYCMQAIESPLTFGGGTKVDIK | ADI-14343 | Light chain variable region ("LC") amino acid sequence |
| Ab 12 | 23 | QVQLVQSGGGLVQPGGSLRLSCAASGFTFRTYALSWVRQAPGKGLEWVSSILGSG GSTYYADSVKGRFTISRDNSKNTLYLQLNSLRAEDTAVYFCAKLAVAGLLHHYYGLD VWGQGTTVTVSS | ADI-14344 | Heavy chain variable region ("HC") amino acid sequence |
| Ab 12 | 24 | SYELTQPPSVSVSPGQTASITCSGDKLENKYACWYQQKPGQSPVLLIYQDTKRPSGI PERFSGSNSGTTATLTISGTQALDEADYYCQAWDSSTASVLFGGGTQLTVL | ADI-14344 | Light chain variable region ("LC") amino acid sequence |
| Ab 13 | 25 | QITLKESGAEVKKPGASVKVSCKVSGYTLSDFSMHWVRQAPGKGLEWMGSFDPE DGETVDAQKFQGRVTMTEDRSTATAYMELRSLRSEDTAVYYCGTPASAGQVDYW GQGTLVTVSS | ADI-14345 | Heavy chain variable region ("HC") amino acid sequence |
| Ab 13 | 26 | DIVLTQSPSSLSASVGDRVTITCRASQSISSYLHWYQQKPGKAPKLLIYAASSLQSG VPSRFSGSGSGTDFTLTISSLQPEDFATYYCQQSYITPYTFGQGTKLEIK | ADI-14345 | Light chain variable region ("LC") amino acid sequence |
| Ab 14 | 27 | EVQLLESGGGLVKPGGSLRLSCAASGFRFSSYSMNWVRQAPGKWLEWVSSISASSS YTDYADSVKGRFTISRDNAKNSLYLQMNSLRAEDTAVYYCAREDYLSSGSLLHWFD PWGQGTLVTVSS | ADI-14346 | Heavy chain variable region ("HC") amino acid sequence |
| Ab 14 | 28 | QPVLTQPPSVSGAPGQRVTISCTGSSSNIGAGYDVHWYQQLPGTAPKLLIYGNNNR PSGVPDRFSGSKSGTSASLAITGLQAEDEADYYCQSYDSRLSVLFGGGTKVTVL | ADI-14346 | Light chain variable region ("LC") amino acid sequence |
| Ab 15 | 29 | EVQLVESGGGLVKPGGSLRLSCAASGFTFRDYYMNWIRQAPGKGLEWVSDISASSS YTNYADSVKGRFTISRDNAKTSLYLQMNSLRAEDTAVYYCAREVVTAMGGYYFDY WGQGTLVTVSS | ADI-14347 | Heavy chain variable region ("HC") amino acid sequence |
| Ab 15 | 30 | QSVVTQPPSVSGAPGQRVTISCTGSSSNIGAGYDVHWYQQLPGTAPKLLIYGNNN RPSGVPDRFSGSKSGTSASLAITGLQAEDEADYYCQSYDSSLSGSGVFGTGTKVTV L | ADI-14347 | Light chain variable region ("LC") amino acid sequence |
| Ab 16 | 31 | QVQLVESGGGVAQPGGSLRLSCVASGFTFSNYGMHWVRQAPGKGLEWVAFIRSD GSKKYYGDSGKGRFTISRDNSKNTLYLQMNSLRAEDTALYYCARERAGATFAFDIW GQGTTVTVSS | ADI-14348 | Heavy chain variable region ("HC") amino acid sequence |
| Ab 16 | 32 | QSALTQPRSVSGSPGQSVTISCTGTSSDVGGYNFVSWYQHHPGKAPKLMIYDVTN RPSGVPDRFSGSKSGNTASLTISGLQADDEADYYCCSYAGGFTFYVFGTGTKVTVL | ADI-14348 | Light chain variable region ("LC") amino acid sequence |
| Ab 17 | 33 | EVQLVESGAEVKKPGSSVKVSCKASGGTLSSYAFSWVRQAPGQGLEWMGGVIPIS ATSDYAQKFQGRVTITADESTSTVYMELRSLRSEDTAVYYCARDTRYSSGWFYDYW GQGTLVTVSS | ADI-14349 | Heavy chain variable region ("HC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 17 | 34 | DIRLTQSPDSLAVSLGERATINCKSSQSVLYSSNNKNYLAWYQQKPGQPPNLLIYWA STRDSGVPDRFSGSGSGTDFTLTISRLQAEDVAVYYCQQYYSTPYTFGQGTKLEIK | ADI-14349 | Light chain variable region ("LC") amino acid sequence |
| Ab 18 | 35 | EVQLVESGPGLVKPSETLSLTCTVSGDSVSNNNYYWNWIRQSPGKGLEWIGYIYYS GSTDYNPSLKSRVTISVDTSKNQFSLNLRSVTAADTAIYFCASAPWGMFTILGVVPS YYYGMDVWGQGTTVTVSS | ADI-14350 | Heavy chain variable region ("HC") amino acid sequence |
| Ab 18 | 36 | QSVLTQPPSVSGAPGQRVTISCTGSSSNIGAGYDVHWYQQLPGTAPKLLIYGSSNR PSGVPDRFSGSRSGTSASLAITGLQAEDEADYYCQSYDGSLGVYVFATGTKVTVL | ADI-14350 | Light chain variable region ("LC") amino acid sequence |
| Ab 19 | 37 | EVQLLESGGGLVQPGGSLRLSCSASGFTFSTYWMHWVRQAPGKGLVWVSRINGD GNDRNYADSVKGRFTISRDNAKNTVYLQMNSLRAEDTAVYYCARGGATGDFYFG MDVWGQGTTVTVSS | ADI-14351 | Heavy chain variable region ("HC") amino acid sequence |
| Ab 19 | 38 | SYELTQPPSVSVAPGKTAKITCGGNNIGTKSVHWYQQKPGQAPVLVIYYDTDRPSGI PERFSGSNSGNTATLTISRVEAGDEADYYCQVWDSSNSDHVGVFGGGTQLTVL | ADI-14351 | Light chain variable region ("LC") amino acid sequence |
| Ab 20 | 39 | EVQLLETGPGLVKPSQTLSLICAVSGGSISSGGYSWSWIRQPPGKGLEWVGYISYSG STYYNPSLKSRVTISVDTSKNQFSLKLNSVTAADTAVYFCARVDGIYSSGMRFDYWG QGTLVTVSS | ADI-14352 | Heavy chain variable region ("HC") amino acid sequence |
| Ab 20 | 40 | DIQLTQSPGTLSLSPGERATLSCRASQSVSSYYLAWYQQKPGQAPRLLIYGTSSRAT GIPDRFSGSGSGTDFTLTISRLEPEDFAVYYCQQYGRSPLFGQGTRLEIK | ADI-14352 | Light chain variable region ("LC") amino acid sequence |
| Ab 21 | 41 | QVQLVQSGAEVKKPGSSVKVSCKASGGTFSSYTISWVRQAPGQGLEWMGRIKPIIG IANNAQRFKGRVTITAEKSTGTAYMELSSLTSEDTAVYYCARGGYDYYGMDVWGQ GTTVTVSS | ADI-14353 | Heavy chain variable region ("HC") amino acid sequence |
| Ab 21 | 42 | QSALTQPASVSGSPGQSITISCTGTSSDVGGYNYVSWHQQHPGKAPKLLIYDVSNR PSGVSNRFSGSKSGNTASLSISGLQAEDEADYYCSSFTSTSTPYVFGTGTQLTVL | ADI-14353 | Light chain variable region ("LC") amino acid sequence |
| Ab 22 | 43 | QVQLVQSGAEVKKPGSSAKVSCKASGGTFSSYTISWVRQAPGQGLEWMGRIIPFL GIANYAQKFQGRVTFTADKSTSTVYMDLSRLRSEDTALYYCAREPMYYGGDSYAFD VWGQGTTVTVSS | ADI-14354 | Heavy chain variable region ("HC") amino acid sequence |
| Ab 22 | 44 | QSVLTQPASMSGSPGHSITISCTGTSSDVGAYNYVSWYQQHPGKAPKLMIYDVSN RPSGVSSRFSGSKSGNTASLTISGLQPEDEADYYCSSFTTSSTRVFGTGTKLTVL | ADI-14354 | Light chain variable region ("LC") amino acid sequence |
| Ab 23 | 45 | EVQLVESGPTLVKPTQTLTLTCTFSGFSLSTSGVGVGWIRQPPGKALEWLAVIYWD DDKTYSPSLKSRLTITKDTSKNQVVLTMTNMNPVDTATYYCARCPAPVYSYGVDV WGQGTTVTVSS | ADI-14355 | Heavy chain variable region ("HC") amino acid sequence |
| Ab 23 | 46 | QSALTQPASVSGSPGQSITISCTATSSDFGGYDYVSWYQQHPGEAPKLMISDVTNR PSGVSNRFSGSKSGNTASLTISGLQAEDEADYYCSSYTSYTTPYVFGTGTKLTVL | ADI-14355 | Light chain variable region ("LC") amino acid sequence |
| Ab 24 | 47 | QVQLQESGAGLLKPSETLSLTCAVYGGSFSGYYWSWIRQPPGKGLEWIGEINHSGS TNYNPSLKSRVTISVDTSKNQFSLKLSSVTAADTAVYYCARDQRIVVGAATEPYYY YYGMDVWGQGTTVTVSS | ADI-14356 | Heavy chain variable region ("HC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 24 | 48 | QPVLTQPPSVSVSPGQTARITCSGDALPKQYAYWYQQKPGQAPVLVIYKDSERPSG IPERFSGSSSGTTVTLTISGVQAEDEADYYCQSADSSGTYRVFGGGTKLTVL | ADI-14356 | Light chain variable region ("LC") amino acid sequence |
| Ab 25 | 49 | EVQLVESGGGVVQPGRSLRLSCAASGFTFSNYAMHWVRQAPGKGLEWVSIISYDG SNKYYADSVKGRFTISRDNSKNTLYLQINSLRTEDTAVYYCARARKRIPIVVVTAP YYYGMDVWGQGTTVTVSS | ADI-14357 | Heavy chain variable region ("HC") amino acid sequence |
| Ab 25 | 50 | DIRVTQSPSSLSASVGDRVTITCRASQSISSYLHWYQQQPGKAPNLLIYAASNLQSG VPSRFSGSGSGTDFTLTISSLQPEDFATYYCQQSYTTPHTFGQGTKVEIK | ADI-14357 | Light chain variable region ("LC") amino acid sequence |
| Ab 26 | 51 | QVQLVQSGGGLVKPGGSLRLSCVASGFTFSDYYMTWIRQAPGKGLEWVSYISGSS AYTIYADSVKGRFTISRDNAKNSLYLQMNGLRAEDTAVYYCARVSWVRSLDSWGQ GTLVTVSS | ADI-14358 | Heavy chain variable region ("HC") amino acid sequence |
| Ab 26 | 52 | QSALTQPASVSGSPGQSITISCTGSTSDVGLYNYVSWYQLHPGKAPKLIIYDVRHR PSGVSDRFSASKSGNTASLTISGLQAEDEADYYCCSYTSSSTYVFGSGTQLTVL | ADI-14358 | Light chain variable region ("LC") amino acid sequence |
| Ab 27 | 53 | QVQLVQSGPALVKPTQTLTLTCTFSGFSLSTSGMCVSWIRQPPGKALEWLARIDW DDDKYYSTSLKTRLTISKDTSKNQVVLTMTNMDPVDTATYYCARATNYDSSGYYSLY FDYWGQGTLVTVSS | ADI-14359 | Heavy chain variable region ("HC") amino acid sequence |
| Ab 27 | 54 | DIQMTQSPSSLSASVGDRVTITCRASQSISSYLNWYQQKPGKAPKLLIYAASSLQSG VPSRFSGSGSGTDFTLTISSLQPEDFATYYCQQSYSTPYTFGQGTKVEIK | ADI-14359 | Light chain variable region ("LC") amino acid sequence |
| Ab 28 | 55 | QVQLVQSGAEVKKPGASVKVSCKASGYTFTTYSMHWVRQAPGQRLEWMGWIN AGNGNTKYSQKFQGRVTITRDTSASTAYMELSSLRSEDTAVYYCARDGVGGAYYYG EMDVWGQGTTVTVSS | ADI-14360 | Heavy chain variable region ("HC") amino acid sequence |
| Ab 28 | 56 | EIVLTQSPLSLPVTPGEPASISCRSSQSLLHSNGYNYLDWYLQKPGQSPQLLIYLG SNRASGVPDRFSGSGSGTDFTLKISRVEAEDVGVYYCMQALQTPRFTFGPGTKVEIK | ADI-14360 | Light chain variable region ("LC") amino acid sequence |
| Ab 29 | 57 | EVQLLESGGGFVQPGGSLRLSCAASGFTFSSYAVNWVRQAPGKGLEWVSLISGSGR TDYTDSVKGRFTISRDNAKNTLFLQMNSLRVEDTAVYYCAKSWGSSGYGYLDYWG QGTLVTVSS | ADI-14361 | Heavy chain variable region ("HC") amino acid sequence |
| Ab 29 | 58 | QSGLTQPPSVSGAPGQRVTISCTGSSSNIGPGTDVHWYQHFPGTAPKLLIFGNSNR PSGVPDRFSGSKSGTSASLAITGLQAEDEAYYYCQSYDRTLSASVFGGGTKLTVL | ADI-14361 | Light chain variable region ("LC") amino acid sequence |
| Ab 30 | 59 | EVQLLESGGGLVQPGGSLRLSCAASGFTFSSYAMSWVRQAPGKGLEWVSGISGSG GSTYYADSVKGRFTISRDNSKNTLYLEMNSLRAEDTAVYYCAKRYYYGSGTYTFDI WGQGTMVTVSS | ADI-14362 | Heavy chain variable region ("HC") amino acid sequence |
| Ab 30 | 60 | DIRLTQSPSSLSASVGDRVTITCRASQSIISYLNWYQQKPGKAPKLLIYAASSLQS GVPSRFSGSGSGTDFTLTISSLQPEDFATYYCQQSYSTPYTFGQGTKVEIK | ADI-14362 | Light chain variable region ("LC") amino acid sequence |
| Ab 31 | 61 | QVQLVESGGGLVKPGGSLRLSCAASGFTFSDYYMSWIRQAPGKGLEWVSYISGGG TYTKYADSVKGRFTISRDNAKNSVYLQMNSLRAEDTAVYYCARDVALVGWELRYG MDVWGQGTTVTVSS | ADI-14363 | Heavy chain variable region ("HC") amino acid sequence |
| Ab 31 | 62 | ETTLTQSPGTLSLSPGERATLSCRARENVNSSYLAWYQQKPGQAPRLLIYGASSRAT GIPDRFSGSGSGTDFTLTISRLEPEDFAVYYCQQYAISPWTFGQGTKVEIK | ADI-14363 | Light chain variable region |

TABLE 5-continued

Informal Sequence Listing

| Anti-body No. | SEQ ID NO: | Sequence | Clone # (ADI) | Descriptors |
|---|---|---|---|---|
| | | | | ("LC") amino acid sequence |
| Ab 32 | 63 | QVQLVQSGAEVKKPGESLKISCKGSGYSFTSHWIGWVRQMPGKGLEWMGITDPG DSDTRYSPSFQGQVTISADKSISTAYLQWSSLKASDTAMYYCAREPRRWMTTETNG PYYFDNWGQGTLVTVSS | ADI-14364 | Heavy chain variable region ("HC") amino acid sequence |
| Ab 32 | 64 | SYVLTQPPSVSVAPGKTARITCGGNNIGSKSVHWYQQKPGQAPVLVIYYDSDRPSGI PERFSGSNSGNTATLTISRVEAGDEADYYCQVWDSSSDNRVFGGGTKVTVL | ADI-14364 | Light chain variable region ("LC") amino acid sequence |
| Ab 33 | 65 | QVQLVQSGAEVKKPGASVKVSCKVSGYTLTKLSMHWVRQAPGKGLEWMGFFDP EDGDTLYAQKFQGRVTMTEDTSSDTPYMELRSLRSEDTAVYYCASPAAAGQFDYW GQGTLVTVSS | ADI-14365 | Heavy chain variable region ("HC") amino acid sequence |
| Ab 33 | 66 | DIVMTQSPSSLSASVGDRVTITCRASQFISSYLHWYQQKTGKAPKLLIYAASSLQSG VPSRFSGSGSGTDFTLTISSLQPEDFATYYCQQSYNTPRTFGQGTKLEIK | ADI-14365 | Light chain variable region ("LC") amino acid sequence |
| Ab 34 | 67 | QVQLVQSGTEVKKPGASVKVSCKASGYTFNMYGVSWVRQAPGQGLEWMGWIS AYNGNTNYAQKFQGRVTMTIDTSTTTAYMELRSLRSDDTAMYYCARDFQAEEPLS NWFDPWGQGTLVTVSS | ADI-14366 | Heavy chain variable region ("HC") amino acid sequence |
| Ab 34 | 68 | DIVMTQTPSSLSASVGDRVIITCRASQSISRYINWYQKKPGKAPKFLIYAVSSLGSG VPSRFSGSGSGTDFTLTISSLQPEDFATYYCQQSYSTPFTFGPGTKVDIK | ADI-14366 | Light chain variable region ("LC") amino acid sequence |
| Ab 35 | 69 | EVQLLESGGGLVQPGGSLRLSCAASGFTFGSYDMNWVRQAPGKGLEWVSGISGS GDATYYADSVKGRFTISRDNSKNMLYLQMNSLSAEDMAVYYCARDRAFTMKYNS NWYKIYWGQGTMVTVSS | ADI-14367 | Heavy chain variable region ("HC") amino acid sequence |
| Ab 35 | 70 | EIVLTQSPGTLSLSPGERATLSCRASQSVTSSYLAWYQQKPGQAPRLLIYGAFSRAT GIPDRFSGSGSGTDFTLTISRLEPEDFAVYYCHHYGTSRWTFGQGTKVDIK | ADI-14367 | Light chain variable region ("LC") amino acid sequence |
| Ab 36 | 71 | EVQLVESGGGLVKPGGSLRLSCAASGFTFINAWMSWVRQAPGKGLEWVGRIKSK ADGGTTDDAAPVKGRFTISRDDSKNTLYLQMNSLKIEDTAVYYCATDVLPLYNWNL GWNFDLWGRGTLVTVSS | ADI-14368 | Heavy chain variable region ("HC") amino acid sequence |
| Ab 36 | 72 | SYVLTQPPSVSVAPGKTARITCGGNNIADKSVHWYQQKPGQAPVLVMYYDTDRPS GIPERFSGFNSGNTATLTISRVEAGDEADYYCQVWDSSSDHVVFGGGTKVTVL | ADI-14368 | Light chain variable region ("LC") amino acid sequence |
| Ab 37 | 73 | QVQLVQSGAEVKKPGSSVKVSCKASGGTFSSNAISWVRQAPGQGLEWMGGIIPIF ATANYAQNFQDRVTITADESTGTAYMELSSLRYEDTAVYYCAKSAIHSGYHGPARS GFYQNGMDVWGQGTTVTVSS | ADI-14369 | Heavy chain variable region ("HC") amino acid sequence |
| Ab 37 | 74 | SYELTQPPSASGTPGQRVTISCSGSSSNIGINPVNWYQHFPGTAPKLLIYRNNQRPS GVPDRFSGSKSGTSASLAISGLQSEDEAVYYCAAWDDRLNGPVFGGGTQLTVL | ADI-14369 | Light chain variable region ("LC") amino acid sequence |
| Ab 38 | 75 | EVQLVESGGGVVQPGKSLRLSCAASGFSFSTFAMHWVRQAPGKGLEWVAVISYD GSNKFYADSVKGRFTISRDSSKNTLYLQMNSLRAEDTAVYYCARGGYSSGWYVTHF DYWGQGTLVTVSS | ADI-14370 | Heavy chain variable region ("HC") amino acid sequence |
| Ab 38 | 76 | QSVLTQPPSASGSPGQSVTISCTGTSSDVGGYNYVSWYQQHPGKAPKLMIYEVSKR PSGVPDRFSGSKSGNTASLTVSGLQAEDEADYYCSSYAGSNNLYVFGTGTKLTVL | ADI-14370 | Light chain variable region ("LC") amino acid sequence |

TABLE 5-continued

| Antibody No. | SEQ ID NO: | Sequence | Clone # (ADI) | Descriptors |
|---|---|---|---|---|
| Ab 39 | 77 | EVQLVESGGGLVQPGGSLRLSCAASGFTFSNYAMTWVRQAPGKGLEWLSSISGSG GSTYYADSVKGRFTISRDNSRNTLYVQMNSLRVEDTAFYYCAKAFYEYGAGSPGDY WGQGTLVTVSS | ADI-14371 | Heavy chain variable region ("HC") amino acid sequence |
| Ab 39 | 78 | DIQLTQSPSSLSASVGDRVTITCRASQSIGTNLNWYQQKPGKAPKFLIYAASSLQRG VPSRFSGSGSGSEFTLTISSLQPEDFATYYCQQSYSTLPITFGQGTKLEIK | ADI-14371 | Light chain variable region ("LC") amino acid sequence |
| Ab 40 | 79 | QVQLLESGGGLVQPGGSLRLSCAASGFTFSNYAMGWVRQAPGQGLEWVSRISAT GGSTHYADSVRGRFTISRDNSKNTLYLQMNSLKAEDTAVYYCAKDRGYSRNLTPDY WGQGTLVTVSS | ADI-14372 | Heavy chain variable region ("HC") amino acid sequence |
| Ab 40 | 80 | ETTLTQSPSSLSASVGDRVTITCRASQGITNDLGWYQKPGKAPKLLIYVASSLQSG VPSRFSGSGSGTDFTLTISSLQPEDFATYYCLQDYNYPITFGQGTKVDIK | ADI-14372 | Light chain variable region ("LC") amino acid sequence |
| Ab 41 | 81 | QVQLQQWGAGLLKPSETLSLTCAVYGGSFSGSYWSWIRQPPGKGLEWIGEINHSG STSYNPSLKSRVTISVDTSKKQFSLKLSSMTAADTAVYYCAGGFYYDSSGSYAPHPT FDYWGQGTLVTVSS | ADI-14373 | Heavy chain variable region ("HC") amino acid sequence |
| Ab 41 | 82 | DIVMTQTPATLSVSPGERATLSCRASQSVSSNLAWYQQKPGQAPRLLIYGASTRAT GIPARFSGSGSGTEFTLTISSLQSEDFAVYYCQQYNNWPRTFGQGTKVEIK | ADI-14373 | Light chain variable region ("LC") amino acid sequence |
| Ab 42 | 83 | QVQLVQSGGVVVQPGGSLRLSCAASGFNFDDFTMHWVRQAPGKGLEWVSLITW DGGITYYADSVKGRFTISRDNGKNSLYLRMNSLRTEDTALYYCAKDGDRYSGYAFLD YWGQGTLVTVSS | ADI-14374 | Heavy chain variable region ("HC") amino acid sequence |
| Ab 42 | 84 | SYELTQPPSVSVAPGKTARLTCGGNNIGSESVHWYQQRPGQAPVLVSYYNGDRPS GIAERISASKSGNTATLTIYRVEAGDEADYYCQVWHSSSDHFVFGTGTQLTVL | ADI-14374 | Light chain variable region ("LC") amino acid sequence |
| Ab 43 | 85 | EVQLVESGGGLVQPGGSLRLSCAVSGFTFSNYAVSWVRQAPGKGLEWVSGISGSG GTTYYVDSVKGRFTVSRDNSKNTLFLQLNSLKAEDTAVYYCAKDWGYSGGRPYFDY WGQGTLVTVSS | ADI-14375 | Heavy chain variable region ("HC") amino acid sequence |
| Ab 43 | 86 | QSVLTQPPSVSGAPGQRVTISCTASSSNIGPIYDVHWYQQLPGTGPKLLIYGNNNRP SGVPDRFSGSKSGTSASLAITGLQAEDEADYYCQSYDTSLSVVFGGGTKLTVL | ADI-14375 | Light chain variable region ("LC") amino acid sequence |
| Ab 44 | 87 | EVQLVESGGGLVQPGGSLRLSCAASGFTFSSYWMHWVRQAPGKGPVWVSRINSD GSTTNYADYMKGRFTISRDNAKNTVYLQMNSLRAEDTAVYYCARDSDSYDDAFDI WGQGTTVTVSS | ADI-14376 | Heavy chain variable region ("HC") amino acid sequence |
| Ab 44 | 88 | SYELTQPPSVSVSPGQTARISCSGEALPKKYSYWYQQKSGQAPVLVIYEDSKRPSG IPERFSGSSSGTMATLTISGAQVEDEADYYCYSTDSSGNHRVFGGGTKVTVL | ADI-14376 | Light chain variable region ("LC") amino acid sequence |
| Ab 45 | 89 | EVQLVESGGGVVQPGGSLRLSCAVSGITFSSYGMHWVRQAPGKGLEWVAFIRYD GSNKYYGDSLRGRFTISRDNSKNTLYLQMNSLRAEDTAVYYCAKDAVGIGGYYGLD VWGQGTTVTVSS | ADI-14377 | Heavy chain variable region ("HC") amino acid sequence |
| Ab 45 | 90 | DIQMTQSPSSLSASVGDRVTITCRASQGIRNDLGWYQQKPGKAPKRLIYAASSLQS GVPSRFSGSGSGTEFTLTISSLQPEDFATYYCLQHNGYPWTFGQGTKVEIK | ADI-14377 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 46 | 91 | QVQLVESGGGLVQPGGSLRLSCAASGFTFSSYWMHWVRQAPGKGLVWVSRINS DGSSPTYADSVKGRFTISRDNAKNTVFLQMNSLRAEDTAVYYCARESWELIRGDAF DIWGQGTTVTVSS | ADI-14378 | Heavy chain variable region ("HC") amino acid sequence |
| Ab 46 | 92 | DIQMTQSPSSLSASVGDRVTITCRASQSISSSLNWYQQKPGKAPNLLIYAASTLQSG VPSRFSGSGSGTDFTLTISSLQPEDFATYYCQQSYRTPRTFGQGTKVEIK | ADI-14378 | Light chain variable region ("LC") amino acid sequence |
| Ab 47 | 93 | EVQLLESGGGVVQPGRSLRLSCAASGFTFSSYAMHWVRQAPGKGLEWVAVIGND GTNKYHADSVKGRFTISRDNSKNTLYLQMNSLRAEDTAVYYCARRRVGIMYSGSY WGGMDVWGQGTTVTVSS | ADI-14379 | Heavy chain variable region ("HC") amino acid sequence |
| Ab 47 | 94 | SYELTQPPSVSVSPGQTASITCSGDKLGGKYVSWYQQKPGQSPVLVMYQDTRRPS GIPERLSGSNSGSTATLTISATQAMDEADYYCQAWDITTVHVVFGGGTKLTVL | ADI-14379 | Light chain variable region ("LC") amino acid sequence |
| Ab 48 | 95 | QVQLVQSGAEVKKPGESLKISCKGSGYTFTSYWIGWVRQLPGKGLEWMGVIFPGD SDTRYSPSFQGQVTISADKSISTAYLQWSSLKAADTAMYYCARTRLGRGFYRFDSW GQGTLVTVSS | ADI-14380 | Heavy chain variable region ("HC") amino acid sequence |
| Ab 48 | 96 | QSVLTQPPSVSAAPGQKVTISCSGSSSNIGNNYVSWYQQLPGTAPRLLIYENNERPS GIPDRFSGSKSGTSATLGITGLQTGDEADYYCATWDSGLSAGYVFGTGTKLTVL | ADI-14380 | Light chain variable region ("LC") amino acid sequence |
| Ab 49 | 97 | EVQLVESGGGLVQPGGSLRLSCAASGFTFSSYSMNWVRQAPGKGLEWVSYIGSSS SSVYYGDSAKGRFTISRDNAKNSLYLQMNSLRDEDTALYYCARVGWLQYCRGGSCY ASFGMDVWGQGTTVTVSS | ADI-14381 | Heavy chain variable region ("HC") amino acid sequence |
| Ab 49 | 98 | DIQMTQSPSSLSASVGDRVTITCRASQGIRNDLGWYQQKPGIAPKLLIYAASSLQSG VPSRFSGSGSGTDFTLTISSLQPEDFATYYCLQDYDSPYTFGQGTKLEIK | ADI-14381 | Light chain variable region ("LC") amino acid sequence |
| Ab 50 | 99 | EVQLLESGGGVVQPGRSLRLSCAASGFTFSAYGFHWVRQAPGKGLEWVAVIWFD GNNKYYADSMKGRFIISRDNSKNTLYLQMNSLRAEDTAVYYCARDPKETGEFDYW GQGTLVTVSS | ADI-14382 | Heavy chain variable region ("HC") amino acid sequence |
| Ab 50 | 100 | QSALTQPASVSGSPGQSITISCTGTISDVGRYNYVSWYQQHPGKAPKLMIYDVTNR PSGVSNRFSGSKSGNTASLTISGLQAEDEAVYYCCSYTISSTYVFGTGTKLTVL | ADI-14382 | Light chain variable region ("LC") amino acid sequence |
| Ab 51 | 101 | QITLKESGPTLVKPTQTLTLTCTFSGFSLSTSGVGVGWIRQPPGKALEWLALIYWDE DKRYSPSLKTRLTITKDTSRNQVKLTMTNMDPVDTATYYCAHQYYDILTGYPSPGAF DIWGQGTTVTVSS | ADI-14383 | Heavy chain variable region ("HC") amino acid sequence |
| Ab 51 | 102 | QPVLTQPASVSGSPGQSITISCTGTSSDVVSYNLVSWFQQHPGKAPKLMIYEVTRRP SGVSNRFSGSKSGNTASLTISGLQAEDEADYYCCAYTGTPVVFGGGTKLTVL | ADI-14383 | Light chain variable region ("LC") amino acid sequence |
| Ab 52 | 103 | QVQLQESGSGLVKPSQTLSLTCTVSGGSISSVGYSWSWIRQPPGKGLEWIGYIYHSG SPYYSPSLNSRVTISVDRSKNQFSLKLSSVTAADTAVYFCARVFFGGGGAFDIWGQG TTVTVSS | ADI-14384 | Heavy chain variable region ("HC") amino acid sequence |
| Ab 52 | 104 | QPGLTQPPSVSVAPGQTARITCGGNNIGSKSVQWYQQKPGQAPVLVMYYDSDRP SGIPDRFSGSSSGNTATLTITRVEAGDEADYSCQVWDSVNVHPVIFGGGTKLTVL | ADI-14384 | Light chain variable region ("LC") amino acid sequence |
| Ab 53 | 105 | QVQLVQSGAEVKKPGESLKISCKGSGYSFTSYWIGWVRQMPGKGLEWMGIIYPGD SDTRYSPSFQGQVTISADKSISTAYLQWSSLKASDTAMYYCASSSYSNYFDYWGQG | ADI-14385 | Heavy chain variable region |

TABLE 5-continued

Informal Sequence Listing

| Anti-body No. | SEQ ID NO: | Sequence | Clone # (ADI) | Descriptors |
|---|---|---|---|---|
| | | TLVTVSS | | ("HC") amino acid sequence |
| Ab 53 | 106 | NFMLTQPHSVSESPGKTVTISCTRSSGSIASNYVQWYQQRPGSAPTTVIYEDNQRP SGVPDRFSGSIDSSSNSASLTISGLKTEDEADYYCQSYDSSNPWVFGGGTKLTVL | ADI-14385 | Light chain variable region ("LC") amino acid sequence |
| Ab 54 | 107 | EVQLVESGGGLVQPGGSLRLSCAASRFTFSSYAMSWVRQAPGKGLEWVSGIGASG GTTYYADSVKGRFTISRDNSKNTVYLQMNSLRAEDTAVYYCARCEYYYGSGSAGYYF DYWGQGTLVTVSS | ADI-14386 | Heavy chain variable region ("HC") amino acid sequence |
| Ab 54 | 108 | SYELTQPPSVSVSPGQTASITCSGDKLGSKFAFWYQQKPGQSPVLVIFQDVKRPSGI PERFSGSNSGNTATLTISGTQAMDEADYYCQAWDSGTAVFGGGTKVTVL | ADI-14386 | Light chain variable region ("LC") amino acid sequence |
| Ab 55 | 109 | EVQLVESGGGVVQPGRSLRLSCAASGFTFSSYPMHWVRQAPGKGLEWVAVISYD GSNKYYADSVKGRFTISRDNSKNTLYLQMNSLRAEDTAVYSCARAQSAAIFDHWG QGTLVTVSS | ADI-14388 | Heavy chain variable region ("HC") amino acid sequence |
| Ab 55 | 110 | QAVVTQEPSLTVSPGGTVTLTCASSTGAVTSGYYPNWFQQKPGQAPRALIYTTSKR HSWTPARFSGSLLGGKAALTLSGVQPEDEADYYCLLYYGGANWVFGGGTKLTVL | ADI-14388 | Light chain variable region ("LC") amino acid sequence |
| Ab 56 | 111 | EVQLVESGGGLVKPGGSLRLSCAASGFTFINAWMAWVRQAPGKGPEWVGRIKSR ADGGTTDYAAPVKGRFTISRDDSKNRLFLQMDSLKTDDTAVYFCTTGVRALRFYNG MDVWGQGTTVTVSS | ADI-14389 | Heavy chain variable region ("HC") amino acid sequence |
| Ab 56 | 112 | ETTLTQSPSSLSASIGDRVTITCRAGQSISSFLNWYQQKPGKAPKLLIYAASTLQSG VPSRFSGSKSGTDFTLTISSLQPEDFATYYCQQSYHTFTFGPGTKVEIK | ADI-14389 | Light chain variable region ("LC") amino acid sequence |
| Ab 57 | 113 | QVQLVESGPGLVKPSETLSLTCAVSGYSISSGYYWGWIRQPPGKGLEWIGNIYHSGS TYYNPSLKSRVTISVDTSKNQFSLKLSSVTAADTAVYYCARATLRFTLVREVVVTAC DAFDIWGQGTTVTVSS | ADI-14390 | Heavy chain variable region ("HC") amino acid sequence |
| Ab 57 | 114 | QSALTQPASVSGSPGQSITISCTGTSSDVGSYNLVSWYQQHPGKVPKLVIYEVNKRP SGVSNRFSGSKSGNTASLTISGLQAEDEADYYCCSYAGSSTFVVFGGGTKLTVL | ADI-14390 | Light chain variable region ("LC") amino acid sequence |
| Ab 58 | 115 | QVQLVESGGGLVQPGGSLRLSCAAAGFSFSNYAMSWVRQAPGKGLEWVAVISGN AGSTYYAESVKGRFTISRDNSKNTLHLQMNSLRGEDTAVYYCAKPPGIAVAGEYYW YFDLWGRGTLVTVSS | ADI-14391 | Heavy chain variable region ("HC") amino acid sequence |
| Ab 58 | 116 | QVQLMQPPSVSVSPGQTARITCSGDALPRENAYWYQQKSGQAPVLVIYEDSKRPS GIPERFSGSSSGTMATLTITGAQVEDEADYYCYSTDTSAYHWVFGGGTKLTVL | ADI-14391 | Light chain variable region ("LC") amino acid sequence |
| Ab 59 | 117 | EVQLLESGAEVKKPGSSVKVSCKASGGTFSSYGISWVRQAPGQGLEWMGGIIPIFG TSNYAQKFQGRVTITADESTSTAYMELSSLRSEDTAVYYCALDSSGRARYYAMDVW GQGTTVTVSS | ADI-14392 | Heavy chain variable region ("HC") amino acid sequence |
| Ab 59 | 118 | DIQVTQSPATLSLSPGERATLSCRASQSVSSYLAWYQQKPGQAPRLLIYDASNRATG IPARFSGSGSGTDFTLTISSLEPEDFAVYYCQQRNNWPPTFGPGTKVEIK | ADI-14392 | Light chain variable region ("LC") amino acid sequence |
| Ab 60 | 119 | QVQLVESGGGLVKPGGSLRLSCAASGFSFTGFYMNWVRQAPGKGLEWVSSISSSS TYKNYADSLQGRFTISRDNARSSLYLQMNSLRAEDTAVYYCARTRTEYTYGYYHDF WGQGTLVTVSS | ADI-14393 | Heavy chain variable region ("HC") amino acid sequence |

TABLE 5-continued

Informal Sequence Listing

| Antibody No. | SEQ ID NO: | Sequence | Clone # (ADI) | Descriptors |
|---|---|---|---|---|
| Ab 60 | 120 | QPVLTQPPSVSGAPGQRVTISCTGSSSNIGAGYDVHWYQQVPGTAPKLLIYNNNN RPSGVPDRFSGSKSGTSASLAITGLQAEDEADYYCQSYDSRLSGVFGGGTKLTVL | ADI-14393 | Light chain variable region ("LC") amino acid sequence |
| Ab 61 | 121 | EVQLLESGGGLVKPGGSLRLSCAASGFTFSSYSMNWVRQAPGKGLEWVSSISSSS YIYYADSVKGRFTISRDNAKNSLYLQMNSLRAEDTAVYYCARGSEYYFDYWGQGTL VTVSS | ADI-14394 | Heavy chain variable region ("HC") amino acid sequence |
| Ab 61 | 122 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSVVFGGGTKVTVL | ADI-14394 | Light chain variable region ("LC") amino acid sequence |
| Ab 62 | 123 | EVQLVESGGGVVQPGRSLRLSCAASGFTFSSYAMHWVRQAPGKGLEWVAVISYD GSNKYYADSVKGRFTISRDNSKNTLYLQMNSLRAEDTAVYYCARDDTYYYDSSGYS APFDYWGQGTLVTVSS | ADI-14395 | Heavy chain variable region ("HC") amino acid sequence |
| Ab 62 | 124 | DIQVTQSPSTLSASVGDRVTITCRASQSISSWLAWYQQKPGKAPKLLIYKASSLESG VPSRFSGSGSGTEFTLTISSLQPDDFATYYCQQYNSYPWTFGQGTKVEIK | ADI-14395 | Light chain variable region ("LC") amino acid sequence |
| Ab 63 | 125 | EVQLVESGGGVVQPGRSLRLSCAASGFTFSSYAMHWVRQAPGKGLEWVAVISYD GSNKYYADSVKGRFTISRDNSKNTLYLQMNSLRAEDTAVYYCARELRYFDWEYGG MDVWGQGTTVTVSS | ADI-14396 | Heavy chain variable region ("HC") amino acid sequence |
| Ab 63 | 126 | EIVLTQSPSSLSASVGDRVTITCQASQDISNYLNWYQQKPGKAPKLLIYDASNLETG VPSRFSGSGSGTDFTFTISSLQPEDIATYYCQQYDNLPMYTFGQGTKLEIK | ADI-14396 | Light chain variable region ("LC") amino acid sequence |
| Ab 64 | 127 | EVQLVESGGGVVQPGRSLRLSCAASGFTFSSYAMHWVRQAPGKGLEWVAVISYD GSNKYYADSVKGRFTISRDNSKNTLYLQMNSLRAEDTAVYYCARDDTYYYDSNGYS APFDYWGQGTLVTVSS | ADI-14397 | Heavy chain variable region ("HC") amino acid sequence |
| Ab 64 | 128 | DIQVTQSPSTLSASVGDRVTITCRASQSISSWLAWYQQKPGKAPKLLIYKASSLESG VPSRFSGSGSGTEFTLTISSLQPDDFATYYCQQYNSYPWTFGQGTKVDIK | ADI-14397 | Light chain variable region ("LC") amino acid sequence |
| Ab 65 | 129 | EVQLLESGPGLVKPSQTLSLTCAVSGGSINSGRYSWSWIRQPPGKGLEWIGYIYYSG TTYYNPSLESRVTISRDTSKNQFSLNLSSVTAADTAVYYCARTNSADSYASGSHYIR PQYFDFWGQGTLVTVSS | ADI-14399 | Heavy chain variable region ("HC") amino acid sequence |
| Ab 65 | 130 | DIQLTQSPATLSLSPGERATLSCRASQSVSSYLAWYQQKPGQAPRLLIYGASNRATG IPARFSGSGSGTDFTLTISRLEPEDFAVYYCQQRSNWLTFGGGTKVEIK | ADI-14399 | Light chain variable region ("LC") amino acid sequence |
| Ab 66 | 131 | QVQLVQSGGGVVQPGRSLRLSSAASGFTFSSYAMHWVRQAPGKGLEWVAVISHD GSKYYADSVKGRFTISRDNSKSTLNLQMNSLRPEDTAVYYCARGGDVRLYDDSNGY HYDTYYFDYWGQGTLVTVSS | ADI-14400 | Heavy chain variable region ("HC") amino acid sequence |
| Ab 66 | 132 | EIVLTQSPSSLSASVGDRVTITCRASQGIRNDLGWYQQKPGKAPKLLIYAASTLQSG VPSRFSGSGSGTDFTLTISSLQPEDFATYYCLQDYNYPLTFGGGTKVEIK | ADI-14400 | Light chain variable region ("LC") amino acid sequence |
| Ab 67 | 133 | QVQLVQSGGGLVKPGGSLRLSCAASGFTFSSYSMHWVRQAPGKGLEWVSSISASS SYLNYADSVKGRFTISRDNAKKSLYLQLNTLRADDTAVYYCAREDHDSGTYYLNWF DPWGQGTLVTVSS | ADI-14401 | Heavy chain variable region ("HC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 67 | 134 | QSVVTQPPSVSGAPGQRVTISCTGSSSNIGAGYDVHWYQQFPGTGPKLLIYGNSHR PSGVPDRFSGSKSGPSASLAITGLQAEDEADYYCQSYDSSLSGYVFGTGTKVTVL | ADI-14401 | Light chain variable region ("LC") amino acid sequence |
| Ab 68 | 135 | QVQLVQSGAEVKKPGASVKVSCKTSGYTFTNYGISWVRQAPGQGLEWMGWISAY NGNRNYAQKLQGRVTMTTDTSTSTAYMELRSLRSDDTAVYYCAREPPVIAAGDFS HWGQGTLVTVSS | ADI-14402 | Heavy chain variable region ("HC") amino acid sequence |
| Ab 68 | 136 | EIVLTQSPLSLPVTLGQPASISCRSSQSLVHSDANTYLSWFQQRPGQSPRRLIYKVS NRDSGVPDRFSGSGSGTDFTLKISRVEAEDVGVYYCMQGTHWPPDFGQGTRLEIK | ADI-14402 | Light chain variable region ("LC") amino acid sequence |
| Ab 69 | 137 | QVQLVESGGGLGKPGGSLRLSCAASGFTFSGYYMSWIRQAPGKGLEWVSDISSGSS FTNYADSVKGRFTISRDNAKNSLYLQMNSLKAEDTAVYYCARVPPDSYGSGSYSGD SWGQGTLVTVSS | ADI-14403 | Heavy chain variable region ("HC") amino acid sequence |
| Ab 69 | 138 | QSVVTQPPSVSGAPGQRVTISCTGSSSNIGAGYGVHWYQQLPGTAPKLLIYGNTNR PSGVPDRISGSKSGTSASLVITGLQAEDEADYYCQSYDSSLSGWVFGGGTKLTVL | ADI-14403 | Light chain variable region ("LC") amino acid sequence |
| Ab 70 | 139 | EVQLVESGGGLVQPGGSLRLSCAASGFTFSNFEMNWVRQAPGKGLEWVSYISSSG RIIYYADSVKGRFTISRDNARNSLYVQMNSLRVEDTAVYYCARAKAAAGHDLWGQ GTLVTVSS | ADI-14404 | Heavy chain variable region ("HC") amino acid sequence |
| Ab 70 | 140 | EIVLTQSPSTLSASVGDRVTITCRASQSISPWLAWYQQKPGKAPKLLIYRASSLESG VPSRFSGSGSGTEFTLTISSLQPDDFATYYCQHYNSYLYTFGQGTKVEIK | ADI-14404 | Light chain variable region ("LC") amino acid sequence |
| Ab 71 | 141 | QVQLVQSGTEVKKPGASVKVSCKASGYTFTNYDISWVRQAPGQGLEWMGWISGS TGNTIYAQNLQGRLTMTTDTSTSTAYMELRSLRSDDTAIYYCARDNVGYASGNYFD YWGQGTLVTVSS | ADI-14405 | Heavy chain variable region ("HC") amino acid sequence |
| Ab 71 | 142 | SYVLTQPPSVSVAPGKTARIPCGGNNIGSKSVHWYQQRPGQAPVLVIYYDSVRPSG IPERFSGSNSGNTATLTISTVEAGDEADFYCQVWDSSRDHEVFGGGTKLTVL | ADI-14405 | Light chain variable region ("LC") amino acid sequence |
| Ab 72 | 143 | QVQLVQSGAEVKKPGESLKISCKGSGYKFTNYWIAWVRQMPGKGLEWLGVIYPGA SDITYSPSFQGQVTISADKSISTAYLQWSSLKASDTAIYYCARQGSITAMSYWGQGT MVTVSS | ADI-14406 | Heavy chain variable region ("HC") amino acid sequence |
| Ab 72 | 144 | DIVMTQSPLSLPVTPGEPASISCRSSQSLLHSNGFNYLDWYLQKPGQSPQLLIYLGS NRASGVPDRFSGSGSGTDFTLKISRVEAEDVGVYYCMQALQTPFTFGPGTKVEIK | ADI-14406 | Light chain variable region ("LC") amino acid sequence |
| Ab 73 | 145 | QVQLVQSGGGVVQPGRSLRLSCAASGFTFSSYGMHWVRQAPGKGLEWVAVIWF DGNNKEYADSVKGRFAISRDNSKNTLYLQMNSLRAEDTAVYYCARDLIPVTIFGVV NPYSYYGMDVWGQGTTVTVSS | ADI-14407 | Heavy chain variable region ("HC") amino acid sequence |
| Ab 73 | 146 | EIVMTQSPSSLSASVGDRVTITCRASQSISTYLNWYQQKPGTAPKLLIYAASSLESG VPSRLSGSGSGTEFILTISSLQREDFATYYCQQSYSTPPTFGQGTKVEIK | ADI-14407 | Light chain variable region ("LC") amino acid sequence |
| Ab 74 | 147 | QVQLVQSGPALVKTTQTLTLTCTFSGFSLTTSGMCVSWIRQPPGKALEWLARIDW DDDKYYSTSLKTRLTISKDTSKNQVVLTLTNVDPVDTATYYCARMQKYDSSGYYLHY FDSWGQGTLVTVSS | ADI-14408 | Heavy chain variable region ("HC") amino acid sequence |
| Ab 74 | 148 | DIRLTQSPSSLSASVGDRVTIACRASQSISSYLNWYQQKPGKSPKVLIYAASILQTG VPSRFSGSGSGTDFTLTISSLQPEDFATYYCQQSYSINQYTFGQGTKVEIK | ADI-14408 | Light chain variable region |

TABLE 5-continued

| | | | | |
|---|---|---|---|---|
| | | Informal Sequence Listing | | |

| Anti-<br>body<br>No. | SEQ<br>ID<br>NO: | Sequence | Clone<br>#<br>(ADI) | Descriptors |
|---|---|---|---|---|
| | | | | ("LC") amino acid<br>sequence |
| Ab 75 | 149 | QVQLVQSGGEVKKPGASVKVSCKASGYTFTYYGISWVRQAPGQGLEWMGWISAY<br>NGNTNYEQKFQGRVTMTTDTSTGTAYMELRSLTSDDTAVYYCARDRIVVVTAANY<br>YGLDVWGQGTTVTVSS | ADI-<br>14409 | Heavy chain<br>variable region<br>("HC") amino acid<br>sequence |
| Ab 75 | 150 | DIQLTQSPDSLAVSLGERATINCKSSQSVLYRPNNKNFLAWYQQKPGQPPKLLIYW<br>ASTRQSGVPDRFSGSGSGTDFTLTISSLQAEDVAVYYCQQYHTTPLTFGGGTKVDIK | ADI-<br>14409 | Light chain<br>variable region<br>("LC") amino acid<br>sequence |
| Ab 76 | 151 | QVQLQQWGAGLLKPSETLSLTCAIYSGSFSGYYWSWIRQPPGKGLEWIGQINYSGS<br>AYYTPSLKSRVTISVDTSKNQFSLKLSSVTAADTAVYYCARVRITMVQGAIVPCAI<br>DVWGQGTTVTVSS | ADI-<br>14410 | Heavy chain<br>variable region<br>("HC") amino acid<br>sequence |
| Ab 76 | 152 | SYELTQPPSASGTPGQRVTISCSGSSSNIESNFVYWYQQLPGTAPKLLIHRNDQRPS<br>GVPDRFSGSKSGTSASLAISGLRSEDEADYSCAAWDDSLSGVVFGGGTKVTVL | ADI-<br>14410 | Light chain<br>variable region<br>("LC") amino acid<br>sequence |
| Ab 77 | 153 | QVQLVQSGAEVKKPGASVKLSCKASGYTFTRFYIHWVRQAPGQGLEWMGIIINPSG<br>GGTSYAQNFQDRVTMTRDTSTSTVYMELSSLRSEDTAVYYCARNGYSTRSLQNNW<br>FDPWGQGTLVTVSS | ADI-<br>14411 | Heavy chain<br>variable region<br>("HC") amino acid<br>sequence |
| Ab 77 | 154 | ETTLTQSPSSLSASVGDRVTITCRASQSIDNYLNWYQQKPGKAPKLLIYEASSLQSG<br>VPSRFSGSGSGTDFTLTISSLQPEDFATYYCQQTYSSLPYTFGQGTKVEIK | ADI-<br>14411 | Light chain<br>variable region<br>("LC") amino acid<br>sequence |
| Ab 78 | 155 | QVQLVQSGAEVKKPGASVKVSCKASGYTFTRYGISWVRQAPGQGLEWMGWISDY<br>NGNTKNAEKFQGRVTMTTDTYTNIAYMELRSLRSDDTAVYYCARDWWITVGGIIA<br>PFDYWGQGTLVTVSS | ADI-<br>14412 | Heavy chain<br>variable region<br>("HC") amino acid<br>sequence |
| Ab 78 | 156 | ETTLTQSPGTLSLSPGERATLSCRASQSVSSDYLAWFQQKPGQAPRLLIYGASSRAT<br>DIPDRFSGSGSGTDFTLTISRLESEDFAVYYCLHYAGARTFGQGTKVEIK | ADI-<br>14412 | Light chain<br>variable region<br>("LC") amino acid<br>sequence |
| Ab 79 | 157 | EVQLVESGGVVVQPGGSLRLSCAASGFNFDDYSMHWVRQAPGKGLEWVSVISW<br>DGGITYYADSVKGRFTMSRDNGKKSLYLQMNSLRTEDTAVYYCGKDGDIYSSSSAG<br>IDYWGQGTLVTVSS | ADI-<br>14413 | Heavy chain<br>variable region<br>("HC") amino acid<br>sequence |
| Ab 79 | 158 | SYVLTQPPSASGTPGQRVIISCSGSSSNIGSHTVKWYQQLPGTAPKLLIDRNNQRPS<br>GVPDRFSGPKSGTSASLAISGLQSEDEADYYCASWDDSLNGPVFGGGTQLTVL | ADI-<br>14413 | Light chain<br>variable region<br>("LC") amino acid<br>sequence |
| Ab 80 | 159 | QVQLVQSGAEVKKPGSSMKVSCKASGGSFSSYGISWLRQAPGQAPEWMGGIIPIF<br>GTINYAQKFQGRITISADESTSTVYMELSSLRIEDTAVYYCARDGRTSPRYYGWDVW<br>GQGTTVTVSS | ADI-<br>14414 | Heavy chain<br>variable region<br>("HC") amino acid<br>sequence |
| Ab 80 | 160 | DIRLTQSPATLSLSPGDRATLSCRASQSLYTYLSWYQQKPGQAPRLLIYDASNRATG<br>IPARFSGSGSGTDFTLTISSLEPEDFAVYYCHYRSNWPPCTFGGGTKVDIK | ADI-<br>14414 | Light chain<br>variable region<br>("LC") amino acid<br>sequence |
| Ab 81 | 161 | EVQLVESGPGLVKPSETLSLTCTVSGGSISNYYWTWIRQPPGEGLEWIGYIYYTGST<br>NYNPSLKNRVTISVDTPKNQFSLKLNSVTAADTAVYYCARGWGYSYGYESYYNGLD<br>VWGQGTTVTVSS | ADI-<br>14415 | Heavy chain<br>variable region<br>("HC") amino acid<br>sequence |
| Ab 81 | 162 | DIQLTQSPSFLSASVGDRVTITCRASQGISSYLAWYQLKPGKAPKLLIYAAATLETG<br>VPSRFSGSGSGTEFTLTISGLQPEDFATYYCQQLNSFPFTFGPGTKVEIK | ADI-<br>14415 | Light chain<br>variable region<br>("LC") amino acid<br>sequence |

TABLE 5-continued

| Anti-body No. | SEQ ID NO: | Sequence | Clone # (ADI) | Descriptors |
|---|---|---|---|---|
| Ab 82 | 163 | QVQLVQSGAEVKKPGESLKISCKGSGDTFSRNWIGWVRQMPGKGLEWMGIIWP GDSDTRYRQFFQGQQGQVIISVDKSISTAYLQWSSLKASDTATYYCATSPYGLGSYY EHWGQGTLVTVSS | ADI-14416 | Heavy chain variable region ("HC") amino acid sequence |
| Ab 82 | 164 | NFMLTQPHSLSDSPGKTVVISCTRSSGSIASNYVQWYQQRPGSAPTTVIYEDNQRP SGVPDRFSGSIDSSSNSASLTISGLKTEDEADYYCQSYDSSNPYVFGTGTKVTVL | ADI-14416 | Light chain variable region ("LC") amino acid sequence |
| Ab 83 | 165 | EVQLVESGGGLVKPGGSLRLSCAASGFSFSSYSMHWVRQAPGKGLEWVSSISGSST YIYHADSVKGRFTISRDNAERSLHLQMNSLRAEDTAVYYCARDPYSSGWLDSWGQ GTLVTVSS | ADI-14417 | Heavy chain variable region ("HC") amino acid sequence |
| Ab 83 | 166 | ETTLTQSPATLSVSPGERATLSCRASQSVSGNLAWYQQKPGQAPRLLIYGTSTRATG IPARFSGSGSGTEFTLSISSLQSEDFAVYYCQQYNKWPRYTFGQGTKLEIK | ADI-14417 | Light chain variable region ("LC") amino acid sequence |
| Ab 84 | 167 | QVQLVQSGAEVKKPGSSVKVSCKASGGTFTNYNINWVRQAPGQGLQWMGRISP TFAIANYAQKFQGRVTITADKSTSTAYMELSSLRSEDTAVYYCARAPHSGYDLALDY WGQGTLVTVSS | ADI-14418 | Heavy chain variable region ("HC") amino acid sequence |
| Ab 84 | 168 | DIQMTQSPSTLSASVGDRVTITCRASQSISSWLAWYQQKPGKAPKLLIYEASSLQSG VPSRFSGSGSGTEFTLTITSLQPDDFATYYCQQYNVYPWTFGQGTKVDIK | ADI-14418 | Light chain variable region ("LC") amino acid sequence |
| Ab 85 | 169 | EVQLVESGGGVVQPGGSLRLSCAASGFSFSDYGMHWVRQAPGKGLEWVSFIRYD ASYKFYADSVKGRFTISRDNAKNTLYLQINSLRAEDTAVYYCAKEIYGSGSYYYYYY AIDVWGQGTTVTVSS | ADI-14419 | Heavy chain variable region ("HC") amino acid sequence |
| Ab 85 | 170 | EIVLTQSPGTLSLSPGERATLSCRASQSVSSSHLAWYQQKPGQAPRLLIYGASSRAT GIPDRFSGSGSGTDFTLTISRLEPEDFAVYYCQQYFRSAWAFGQGTKVDIK | ADI-14419 | Light chain variable region ("LC") amino acid sequence |
| Ab 86 | 171 | EVQLVESGGVVVQPGGSLRLSCAASGFNFDDYAMHWVRQAPGKGLEWVSLISW DGGNTYYSDSVKGRFTISRDNGKNSLYLQMNSLRAEDTALYYCAKDIDRYSGYDYV FHYWGQGTLVTVSS | ADI-14420 | Heavy chain variable region ("HC") amino acid sequence |
| Ab 86 | 172 | DIRLTQSPSTLSAYVGDRVTITCRASQSISSWLAWYQQKPGKAPKLLIYKASSLESG VPSRFTGSGSGTEFTLTISGLQPDDFATYYCQQYNSYSTFGGGTKVDIK | ADI-14420 | Light chain variable region ("LC") amino acid sequence |
| Ab 87 | 173 | QVQLVQSGAEVKKPGESLKISCKGSGYNSSINWIGYWIGWVRQMPGKGLEWMGI INPGDSDTRYSPSFQGQVTISVDKSISTAYLQWGSLKASDTAMYYCARRAYRSGWH FDLWGRGTLVTVSS | ADI-14421 | Heavy chain variable region ("HC") amino acid sequence |
| Ab 87 | 174 | EIVMTQSPATLSVSPGERATLTCRASQSVSSNLAWYQQKPGQAPRLLIYGASTRAT GIPARFSGSGSGTQFTLTISSLQSEDFAVYYCQHYNNWPPYTFGQGTKVEIK | ADI-14421 | Light chain variable region ("LC") amino acid sequence |
| Ab 88 | 175 | QVQLVQSGAEVKKPGSSVKVSCKASGGTFSSYTINWVRQAPGQGLEWMGRIIPIL GIANYAQKFQGRVTITADKSTSTAYMELSSLRSEDTAVYYCARRHQDTYGMDVWG QGTTVTVSS | ADI-14422 | Heavy chain variable region ("HC") amino acid sequence |
| Ab 88 | 176 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGSVFGGGTKVTVL | ADI-14422 | Light chain variable region ("LC") amino acid sequence |

TABLE 5-continued

| Anti-body No. | SEQ ID NO: | Sequence | Clone # (ADI) | Descriptors |
|---|---|---|---|---|
| Ab 89 | 177 | EVQLVESGGGVVIQPGGSLRLSCAASGFNFDDYSMHWVRQAPGKGLEWVSLISWD GGITYYADSVKGRFTISRDNGKKSLYLQMNSLRTEDTALYYCAKDIDIYSDYAGYF DYWGQGTLVTVSS | ADI-14423 | Heavy chain variable region ("HC") amino acid sequence |
| Ab 89 | 178 | DIRMTQSPSSLSASVGDRVTITCRASQGIRNDLGWYQQKPGKAPKRLIYAASSLQSG VPSRFSGSGSGTEFTLTISSLQPEDFATYYCLQHNSYPFTFGQGTRLEIK | ADI-14423 | Light chain variable region ("LC") amino acid sequence |
| Ab 90 | 179 | QVQLVQSGAEVKKPGESLKISCKGPDSSFSVYWIAWVRQMPGKGLEWMGVIYVG DSDTRYSPSFRGQVTISADKSMNTAYLQWSSLKASDTAMYFCARHIPPGPFDLWG QGTMVTVSS | ADI-14424 | Heavy chain variable region ("HC") amino acid sequence |
| Ab 90 | 180 | NFMLTQPHSVSASPGKTITISCTRSSGSIASNSVQWYQQRPGSAPTNVIYEDDQRPL GVPNRFSGSIDSSSNSASLTISGLKTEDEADYYCHSYHNSDQVFGGGTKLTVL | ADI-14424 | Light chain variable region ("LC") amino acid sequence |
| Ab 91 | 181 | QVQLQESGPGLVKPSETLSLTCTVSGGSVRSGSYYWSWIRQPPGKALEWIGYIYYSG STNYNPALESRVTISVDTSKNQFSLMLSSVTAADTAVYYCARSAEGLARLYYFDHWG QGTLVTVSS | ADI-14425 | Heavy chain variable region ("HC") amino acid sequence |
| Ab 91 | 182 | QSVLIQPASVSGSPGQSITISCTGTSSDVGGYNYVSWYQQHPGKAPKLMIHDVSNR PSGVSNRFSGSKSGNTASLTISGLQAEDEADYYCSTYRSSNTLVVFGGGTKLTVL | ADI-14425 | Light chain variable region ("LC") amino acid sequence |
| Ab 92 | 183 | EVQLVESGGGVVQPGRSLRLSCAASGFTFSSFPMHWVRQAPGKGLEWVAVASYD GRNNYYAGSVKGRFTISRDNSKNTLYLQINSLRAEDTAVYYCAREVVIAAHFDYWG QGTLVTVSS | ADI-14426 | Heavy chain variable region ("HC") amino acid sequence |
| Ab 92 | 184 | SSELTQEPAVSVALGQTVRITCQGDSLRSFYANWYQQKPGQAPILVIYGKNDRPSGI PDRFSGSNSGNTASLTITGAQAEDEADYYCNSRDSSGNHRVFGGGTKVTVL | ADI-14426 | Light chain variable region ("LC") amino acid sequence |
| Ab 93 | 185 | QVQLVQSGAEVKKPGSSVKVSCKASGGTFNSYTINWVRQAPGQGLEWMGRIITIP GATNYAQKFQGRVTFTADKSTSTAYMELSSLRSEDTAVYFCAKRGTGYYGMDVW GQGTTVTVSS | ADI-14427 | Heavy chain variable region ("HC") amino acid sequence |
| Ab 93 | 186 | QSVLIQPRSVSGSPGQSVTISCTGTSSDVGGYNYVSWYQQHPGKAPKLMIYDVSER PSGVPDRFSGSKSGNTASLTISGLQAEDEADYYCCSFVGIYILVFGGGTKLTVL | ADI-14427 | Light chain variable region ("LC") amino acid sequence |
| Ab 94 | 187 | EVQLLESGGGLVKPGGSLRLSCAASGFTFSDHYMSWIRQAPGKGLEWVSYISSTSSF TNYADSLKGRFTISRDNAKNSLYLQMNSLRAEDTAVYYCARPYIVALGTRAFDIWG QGTTVTVSS | ADI-14428 | Heavy chain variable region ("HC") amino acid sequence |
| Ab 94 | 188 | SYVLTQPPSVSVAPGKTARITCGGNNIGSKTVHWYQQKPGQAPVLVSYYDSDRPSG IPERFSGSNSGNTATLTISRVEAGDEADYYCQVWDGSSEHYVFGTGTKVTVL | ADI-14428 | Light chain variable region ("LC") amino acid sequence |
| Ab 95 | 189 | QVQLVQSGTEVKKPGSSVKVSCKASGGTFSSYTISWVRQAPGQGLEWMGGITPM VGTPNYAQKFQGRVAITADKSTNTAYMELTSLISGDTAVYYCARLVYGSGSHFDYW GQGTLVTVSS | ADI-14564 | Heavy chain variable region ("HC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 95 | 190 | SSELSQDPAVSVALGQTVRITCQGDSLRSFYASWYQQQPGQAPVLVLYGQDNRPS GIPDRFSGSSSGNTASLTITGAQAEDEADYYCNSRNSSGHHWVFGGGTKVTVL | ADI-14564 | Light chain variable region ("LC") amino acid sequence |
| Ab 96 | 191 | EVQLLESGGGLVKPGGSLRLSCAASGFTFSNAWMSWVRQAPGKGLEWVGRIKSKT DGGTTDYAAPVKGRFTISRDDSKNTLYLQMNSLKTEDTAVYYCTTDRFCSSTSCEYY YYYYGMDVWGQGTTVTVSS | ADI-14565 | Heavy chain variable region ("HC") amino acid sequence |
| Ab 96 | 192 | ETTLTQSPSSLSASVGDRVTITCRASQSISSYLNWYQQKPGKAPKLLIYAASSLQSG VPSRFSGSGSGTDFTLTISSLQPEDFATYYCQQSYSTPYTFGQGTKVEIK | ADI-14565 | Light chain variable region ("LC") amino acid sequence |
| Ab 97 | 193 | QVQLLESGGGVVQPGRSLRLSCAASGFTFSSFPMHWVRQAPGKGLEWVAVASYD GRNNYYAGSVKGRFTISRDNSKNTLYLQINSLRAEDTAVYYCAREVVIAAHFDYWG QGTLVTVSS | ADI-14566 | Heavy chain variable region ("HC") amino acid sequence |
| Ab 97 | 194 | SSELTQEPAVSVALGQTVRITCQGDSLRSFYANWYQQKPGQAPILVIYGKNDRPSGI PDRFSGSNSGNTASLTITGAQAEDEADYYCNSRDSSGNHRVFGGGTKVTVL | ADI-14566 | Light chain variable region ("LC") amino acid sequence |
| Ab 98 | 195 | QVQLVQSGAEVKKPGASVRVSCKASGYTFNSYSISWVRQAPGQGLEWMGWISVH NGNTNYTQKFQGRVTMTTDTSTSTTYMELRSLRSDDTAVYYCIFGELLYDVWGQG TTVTVSS | ADI-14567 | Heavy chain variable region ("HC") amino acid sequence |
| Ab 98 | 196 | DIQLTQSPSSLSASVGDRVTITCRASQGISNYLAWYQQKPGKVPNLLIYAASTLQSG VPSRFSGSGSGTDFTLTISSLQPEDVATYYCQKYNSAPLTFGPGTKVEIK | ADI-14567 | Light chain variable region ("LC") amino acid sequence |
| Ab 99 | 197 | EVQLVESGGGVVQPGRSLRLSCAASGFTFSSYGMHWVRQAPGKGLEWVAVIWYD GSNKYYADSVKGRFTISRDNSKNTLYLQMNSLRAEDTAVYYCARDIAAAGTMRAFD IWGQGTTVTVSS | ADI-14568 | Heavy chain variable region ("HC") amino acid sequence |
| Ab 99 | 198 | QSVLIQPASVSGSPGQSITISCTGTSSDVGGYNYVSWYQQHPGKAPKLMIYDVSNR PSGVSNRFSGSKSGNTASLTISGLQAEDEADYYCSSYTSSSTLVVFGGGTKLTVL | ADI-14568 | Light chain variable region ("LC") amino acid sequence |
| Ab 100 | 199 | QVQLVESGGGFVKPGGSLRLSCAASGFTFSDYYMSWIRQAPGKGLEWLSYISSTSLF TYYADSVKGRFTISRDNAKNSLYLQMNSLRADDTAVYYCARAYGKGTMVGYWGQ GTMVTVSS | ADI-14569 | Heavy chain variable region ("HC") amino acid sequence |
| Ab 100 | 200 | EIVMTQSPGTLSLAPGERATLSCRASQSVSIDYLAWYQHKPGQAPRLLIYTASNRAT GIPDRFSGSGSGTDFTLTISRLEPEDVAMYYCQQYGNSPYTFGQGTKVEIK | ADI-14569 | Light chain variable region ("LC") amino acid sequence |
| Ab 101 | 201 | QVQLVQSGAEVKKPGSSVKVSCKASGGTFSTYTITWVRQAPGQGLEWMGRIVPIF GVVNNAQKFLGRLTITADKSTSTAYMELSSLRSEDTAVYYCARIPCSGNCQDYYYG MDVWGQGTTVTVSS | ADI-14571 | Heavy chain variable region ("HC") amino acid sequence |
| Ab 101 | 202 | DIQLTQSPSFLSASVGDRVTITCRASQGISSYLVWYQQKPGKAPKLLIYAASTLQSG VPSRFSGSGSGTEFTLTISSLQPEDFATYYCQQLNNYPPTFGPGTKVDIK | ADI-14571 | Light chain variable region ("LC") amino acid sequence |
| Ab 102 | 203 | QVQLVQSGGGLVKPGGSLRLSCAASGFTFSNAWISWVRQAPGKGLEWVGRIKSAT DGGTTDYAAPVKGRFTISRDDSKNTLYLQMDSLKTEDTAVYYCTTSYPYFDWLPFSV DYWGQGTLVTVSS | ADI-14572 | Heavy chain variable region ("HC") amino acid sequence |
| Ab 102 | 204 | SYELMQPPSASGTPGQRVTISCSGSNSNIGSNTVSWYQQLPGTAPKLLIYNNNQRP SGVPDRFSGSKSGTSASLAISGLQSEDEADYYCATWDDSLNGWVFGGGTKLTVL | ADI-14572 | Light chain variable region |

TABLE 5-continued

Informal Sequence Listing

| Antibody No. | SEQ ID NO: | Sequence | Clone # (ADI) | Descriptors |
|---|---|---|---|---|
| | | | | ("LC") amino acid sequence |
| Ab 103 | 205 | QVQLVQSGAEVKKPGASVKVSCKASGYTFTTYGISWVRQAPGQGLEWMGWISTY KTYTNYAQKFQGRVTMTTDTSTSTAYMELRSLRSDDTAVYYCAKVAGGSGSYGDY WGQGTLVTVSS | ADI-14573 | Heavy chain variable region ("HC") amino acid sequence |
| Ab 103 | 206 | QPVLTQPPSVSVAPGKTARITCGGNNIGSKSVHWYLQKPGQAPVLVIYYDSDRPSGI PERFSGSNSGNTATLTISRVEAGDEADFFCQVWDSSSDHWVFGGGTKVTVL | ADI-14573 | Light chain variable region ("LC") amino acid sequence |
| Ab 104 | 207 | QVQLVQSGAEVKKPGSSVKVSCKASGGTFSSYTISWVRQAPGQGLEWMGRIIPILG IANYAQKFQGRVTITADKSTSTAYMELSSLRSEDTAVYYCARPSSSSFAFDYWGQGT LVTVSS | ADI-14575 | Heavy chain variable region ("HC") amino acid sequence |
| Ab 104 | 208 | QSVLTQPASVSGSPGQSITISCTGTSSDVGGYNYVSWYQQHPGKAPKLMIYDVSNR PSGVSNRFSGSKSGNTASLTISGLQAEDEADYYCSSYTSSSTPVVFGGGTKVTVL | ADI-14575 | Light chain variable region ("LC") amino acid sequence |
| Ab 105 | 209 | QVQLVQSGAEVKKPGASVKVSCKASGYTFTSYGISWVRQAPGQGLEWMGWISAY NGNTNYAQKLQGRVTMTTDTSTSTAYMELRSLRSDDTAVYYCARDPPVIAAGDFQ HWGQGTLVTVSS | ADI-14576 | Heavy chain variable region ("HC") amino acid sequence |
| Ab 105 | 210 | DIVLTQSPLSLPVTLGQPASISCRSSQSLVHSDGNTYLNWFQQRPGQSPRRLIYKVS NRDSGVPDRFSGSGSGTDFTLKISRVEAEDVGVYYCMQGTHWPPDFGQGTRLEIK | ADI-14576 | Light chain variable region ("LC") amino acid sequence |
| Ab 106 | 211 | QVQLVQSGAEVKKPGASVKVSCKASGYTFTNYGITWVRQAPGQGLEWMGWISA YNGVRNYAQKLQGRVTMTIDTSRTTAYMELKNLRSDDTAMYYCARGPPVIAADDF QHWGQGTMVTVSS | ADI-14577 | Heavy chain variable region ("HC") amino acid sequence |
| Ab 106 | 212 | DIQMTQSPLSLPVTLGQPASISCRSSQSLVHSNGDTYLNWFQQRPGRSPRRLIYKVS NRDSGVPDRFSGSGSGTDFTLKISRVEAEDVGVYYCMQGTHWPPDFGQGTRLEIK | ADI-14577 | Light chain variable region ("LC") amino acid sequence |
| Ab 107 | 213 | QVQLVQSGAEVKKPGSSVKVSCKASGGTFNNYAINWVRQAPGQGLEWMGGIIP MFGTANYAQKFQGRVTMTADESTSTAYMELSSLRSEDTAVYYCASSQIFVGGNYY KLEFDNWGQGTLVTVSS | ADI-14578 | Heavy chain variable region ("HC") amino acid sequence |
| Ab 107 | 214 | QSVLTQPPSVSAAPGQKVTISCSGSNSNIGYNDVSWYQQLPGTAPQLLIYDNNKRT SGIPDRFSGSKFGTSATLGITGLQTGDEADYYCGTWDSSLSTVIFGGGTKLTVL | ADI-14578 | Light chain variable region ("LC") amino acid sequence |
| Ab 108 | 215 | QVQLVQSGAEVKKPGESLKISCKVSGYSFTSYWIGWVRQMPGKGLEWMGIIYPGD SDTRYSPSFQGQVTISADKSITTAYLQWSSLKASDTAMYYCARPAHSSSWYGAFDL WGQGTTVTVSS | ADI-14579 | Heavy chain variable region ("HC") amino acid sequence |
| Ab 108 | 216 | DIQMTQSPSSLSASVGDRVTITCRASQGISNYLAWYQQKPGKVPKLLIYAASTLQSG VPSRFSGSGSGTDFTLTISSLQPEDVATYYCQKYNSAPLTFGGGTKVEIK | ADI-14579 | Light chain variable region ("LC") amino acid sequence |
| Ab 109 | 217 | QVQLVQSGAEVKKPGSSVKVSCKASGGTFSSYTINWVRQAPGQGLEWMGRIIPVL GMASYVQNFQGRVSITADESTSTAYMELSSLTSEDTALYYCAKGAVAAANDVFDV WGQGTTVTVSS | ADI-14580 | Heavy chain variable region ("HC") amino acid sequence |
| Ab 109 | 218 | DIQMTQSPDSLAVSLGERATINCKSSQSVFYSSNNKHYLAWYQQKPGQPPKLLFY WASTRESGVPDRFSGSGSGTDFTLTISSLQAEDVAVYYCQQYYRIPYTFGQGTKVEI K | ADI-14580 | Light chain variable region ("LC") amino acid sequence |

TABLE 5-continued

Informal Sequence Listing

| Anti- body No. | SEQ ID NO: | Sequence | Clone # (ADI) | Descriptors |
|---|---|---|---|---|
| Ab 110 | 219 | QVQLVQSGAEVKKPGSSVKVSCKASGGTFSSHAFSWVRQAPGQGLEWMGGIIPSL NTANYAQKFQGRVSITADESTGTAYMELSSLRSDDTAVYFCAREVFGYGYYFDYWG QGTLVTVSS | ADI- 14581 | Heavy chain variable region ("HC") amino acid sequence |
| Ab 110 | 220 | ETTLTQSPATLSVSPGERATLSCRASQNVNSNLAWYQQKPGQAPRLLIYGASTRAT GIPARFSGSGSGTDFTLTISSLQSEDFAVYYCQQYNMWPPFTFGQGTKLEIK | ADI- 14581 | Light chain variable region ("LC") amino acid sequence |
| Ab 111 | 221 | QVQLVQSGAEVKKPGESLKISCKGPDSSFSVYWIAWVRQMPGKGLEWMGVIYVG DSDTRYSPSFRGQVTISADKSINTAYLQWSSLKASDTAMYFCARHIPPGPFDLWGQ GTTVTVSS | ADI- 14582 | Heavy chain variable region ("HC") amino acid sequence |
| Ab 111 | 222 | NFMLTQPHSVSASPGKTITISCTRSSGSIASNSVQWYQQRPGSAPTNVIYEDNQRP LGVPNRFSGSIDSSSNSASLTISGLKTEDEADYYCQSYHSSDQVFGGGTKVTVL | ADI- 14582 | Light chain variable region ("LC") amino acid sequence |
| Ab 112 | 223 | QVQLVQSGAEVKEPGASVKVSCKASGYTFTNYGISWVRQAPGQGLEWLGWISAY NGNIHYAQKVQGRVTMTTDTSTSTGFMELRSLRSDDTAVYYCAREPPVIAAGDFQ HWGQGTLVTVSS | ADI- 14583 | Heavy chain variable region ("HC") amino acid sequence |
| Ab 112 | 224 | ETTLTQSPLSLPVTLGQPASISCRSSQSLVHSNGNTYLSWFQQRPGQSPRRLIYRV SNRDSGVPDRFSGSGSGTDFTLKISRVEAEDVGLYYCMQGTHWPPDFGQGTRLEIK | ADI- 14583 | Light chain variable region ("LC") amino acid sequence |
| Ab 113 | 225 | QVQLVQSGAEVKKPGASVKVSCKASGFTFTNYGTSYGITWVRQAPGQGLEWMG WINTSNGNPNYAQKLQGRVTMTADTSTSTAYMELRSLISDDTAVYYCARGHRMV RGVVPTGYYGLDVWGQGTTVTVSS | ADI- 14584 | Heavy chain variable region ("HC") amino acid sequence |
| Ab 113 | 226 | DIQLTQSPSSLSASVGDRVTITCRASQSISSYLNWYQQKPGKAPKLLIFAASNLQS GVPSRFSGSGSGTDFTLTISSLQPEDFATYYCQQSYITPWTFGQGTKVEIK | ADI- 14584 | Light chain variable region ("LC") amino acid sequence |
| Ab 114 | 227 | QVQLVQSGAEVKKPGASVKVSCKASGYTFANYGIGWVRQAPGQGLEWMGWISA YNGKTNYAQKFQGRVTMTTDTSTSTAYMELRSLRSDDTAVYYCAREPPVIAAGDFP HWGQGTLVTVSS | ADI- 14585 | Heavy chain variable region ("HC") amino acid sequence |
| Ab 114 | 228 | ETTLTQSPLSLPVTLGQPASISCRSSQSLEHSDLNTYLSWFQQRPGQSPRRLIYKV SNRDSGVPDRFSGSGSGTDFTLRISRVEAEDVGVYYCMQGTHWPPDFGQGTRLEIK | ADI- 14585 | Light chain variable region ("LC") amino acid sequence |
| Ab 115 | 229 | QVQLVQSGGGLVKPGGSLRLSCAASGFTFSDYYMSWIRQAPGKGLEWVSYISSSSS YTNYADSVKGRFTISRDNAKNSLYLQMNSLRAEDTAVYYCAKRTEYCSSTGCAYYF DYWGQGTLVTVSS | ADI- 14586 | Heavy chain variable region ("HC") amino acid sequence |
| Ab 115 | 230 | QSVVTQPPSVSGAPGQRVTISCTGSSSNIGAGYDVHWYQQLPGTAPKLLIYGNSR PSGVPDRFSGSKSGTSASLAITGLQAEDEADYYCQSYDSSLSGSVFGGGTKVTVL | ADI- 14586 | Light chain variable region ("LC") amino acid sequence |
| Ab 116 | 231 | EVQLLESGGGLVKPGGSLRLSCAASGFTLTSYSMNWVRQAPGKGLEWVSSISSSS YIHYADSVKGRFTISRDNAKNSLYLQMNSLRAEDTAVYYCAGSSLYPPFFDYWGQG TLVTVSS | ADI- 14587 | Heavy chain variable region ("HC") amino acid sequence |
| Ab 116 | 232 | QSVVTQPPSVSGAPGQRVTISCTGSSSNLGAGYDVHWYQQLPGTAPKLLIYGNNN RPSGVPDRFSGSKSGTSASLAITGLQAEDEADYYCQSYDSSLSSVVFGGGTKLTVL | ADI- 14587 | Light chain variable region ("LC") amino acid sequence |
| Ab 117 | 233 | QVQLVQSGAEVKKPGASVKVSCKVSGDTLTELSIHWVRQAPGKGHEWMGYFDHE DGEIMYAQKFQGRVTMTGDTSTDTAYMELSSLRSEDTAVYYCATVAAAGQFDYW | ADI- 14588 | Heavy chain variable region |

TABLE 5-continued

Informal Sequence Listing

| Anti-body No. | SEQ ID NO: | Sequence | Clone # (ADI) | Descriptors |
|---|---|---|---|---|
| | | GQGTLVTVSS | | ("HC") amino acid sequence |
| Ab 117 | 234 | DIQLTQSPSSLSASVGDRVTITCRARQSISTYLNWYQQKPGKAPKLLIYAASSLQS GVPSRFSGSGSGTDFTLTISSLQPEDFATYYCQQSYSSPYTFGQGTKVDIK | ADI-14588 | Light chain variable region ("LC") amino acid sequence |
| Ab 118 | 235 | QITLKESGPVLVKPSETLTLTCTVSGFSLSNAKMGVSWIRQPPGKALEWLAHIFSN DEKSYNTSLKNRLTISKDTSKSQVVLTMTNMDTVDTATYYCARINYYDSSGYYLAN FDYWGQGTLVTVSS | ADI-14589 | Heavy chain variable region ("HC") amino acid sequence |
| Ab 118 | 236 | NIRLTQSPSSLSASVGDRVTITCRASQRIASYLNWYQQKPGHAPKLLIHAASSLQS GVPSRFSGSGSGTDFTLTINSLLPEDFATYYCQQSYSSPPHSSPPLTFGGGTKVEI K | ADI-14589 | Light chain variable region ("LC") amino acid sequence |
| Ab 119 | 237 | EVQLVESGAEVKKPGESLKISCKGSGYSFATYWIGWVRQMPGKGLEWMGIIYPGD SDTRYSPSFQGQVTISADKSISTAYLQWSSLKASDTAIYYCARAKLPVAGLYYFDY WGQGTLVTVSS | ADI-14590 | Heavy chain variable region ("HC") amino acid sequence |
| Ab 119 | 238 | DIQLTQSPSSLSASVGDRVTITCRASQGISSTLAWYQQKPGKAPKLLIYDASSLES GVPSRFSGSGSGTDFTLTISSLHPEDFATYYCQQFNTYPTFGGGTKVEIK | ADI-14590 | Light chain variable region ("LC") amino acid sequence |
| Ab 120 | 239 | QVQLVQSGAEVKKPGESLRISCTGSGYTFTNYWISWVRQMPGKGLEWMGRIDPT DSYTNYSPSFQGHVTISADKSISTAYLQSSSLKASDTATYYCARHRRLVPAAMSRG YYGMDVWGQGTTVTVSS | ADI-14591 | Heavy chain variable region ("HC") amino acid sequence |
| Ab 120 | 240 | EIVMTQSPSSLSASVGDRATITCRASQSISSYLNWYQQKPGKAPKLLIYAASNLQS GAPSRFSGSGSGTDFTLTISSLQPEDFATYFCQQTYSTPYTFGQGTKVEIK | ADI-14591 | Light chain variable region ("LC") amino acid sequence |
| Ab 121 | 241 | QVQLVQSGAEVKKPGESLKISCKGSGYTFTNYWIGWVRQMPGKGLEWMGIIYPD DSDTRYSPSFQGQVTISVDKSINTAYLQWSSLRASDTAIYYCACSNWPHYFDSWGQ GTLVTVSS | ADI-14592 | Heavy chain variable region ("HC") amino acid sequence |
| Ab 121 | 242 | NFMLTQPHSVSESPGKTVTISCTRSSGNIAGNYVQWYQQRPGSAPTTVIYEDNQRP SGVPDRFSGSIDSSSNSASLTISGLKTEDEAVYYCQSYHPGNWVFGGGTKLTVL | ADI-14592 | Light chain variable region ("LC") amino acid sequence |
| Ab 122 | 243 | QVQLVQSGAEVKKPGESLKISCKGSGYSFSSYWVAWVRQMPGKGLEWMGIIYPA DSDTRYSPSFQGQVTISADKSDSTAYLQWGSLKASDTAMYYCARSLYGSGDYFDY WGQGTLVTVSS | ADI-14593 | Heavy chain variable region ("HC") amino acid sequence |
| Ab 122 | 244 | NFMLTQPHSVSESPGRTVIISCTRSSGSIATNYVQWYQQRPGSAPTTVIYEDNQRP SGVPDRFSGSIDSSSNSASLTISGLKTEDEADYYCQSYGSGDVVFGGGTKVTVL | ADI-14593 | Light chain variable region ("LC") amino acid sequence |
| Ab 123 | 245 | QVQLVQSGAEVKKPGASVKLSCKASGYTFTTYTINWVRQAPGQGLEWMGWISGY NGNTDYAQKLQGRFTMTTDTSTNTAYMELRSLTSDDTAVYYCAKGGGGSESYFDY WGQGTLVTVSS | ADI-14594 | Heavy chain variable region ("HC") amino acid sequence |
| Ab 123 | 246 | SYELTQPPSVSVAPGKTARISCGGNNIGSKSVHWYQQKPGQAPVLVIYYDRDRPSG IPERFSGSNSGNTATLTISRVEAGDEADYYCQLWDRSSDHPYVFGTGTKVTVL | ADI-14594 | Light chain variable region ("LC") amino acid sequence |
| Ab 124 | 247 | EVQLLESGGGLVQPGGSLRLSCAASGFTFSIYSMNWVRQAPGKGLEWISYISRSGS TIFYADSVKGRFTISRDDAKNSLFLQMTSLRDADTAVYYCARVDCSNNKCYDYWGQ GTLVTVSS | ADI-14595 | Heavy chain variable region ("HC") amino acid sequence |

TABLE 5-continued

| Antibody No. | SEQ ID NO: | Sequence | Clone # (ADI) | Descriptors |
|---|---|---|---|---|
| Ab 124 | 248 | DIQLTQSPATLSLSPGERATLSCRASQSISSFLAWYQQKPGQAPRLLIYDASKRAT GTPARFSGGGSGRDFTLTISSLEPEDFAVYYCQQRSSWPLYTFGQGTKVEIK | ADI-14595 | Light chain variable region ("LC") amino acid sequence |
| Ab 125 | 249 | EVQLVESGGGVVVQPGGSLRLSCAVSGFNFDDYSMHWVRQLPGKGLEWVSLISWD GGITYYADSVKGRFTISRDNSKNSLYLQMNSLRTEDTALYYCAKDGNRYSDNDYYF DYWGQGTLVTVSS | ADI-14597 | Heavy chain variable region ("HC") amino acid sequence |
| Ab 125 | 250 | DIRLTQSPGTLSLSPGERATLSCRASQGVSSSYLAWYQQKPGQAPRLLIYGASSRAT GIPDRFSGSGSGTDFTLTISRLEPEDFAVYYCQQYGSSPLFGPGTKVEIK | ADI-14597 | Light chain variable region ("LC") amino acid sequence |
| Ab 126 | 251 | QVQLVQSGAEVKKPGSSVKVSCKASGGTFSSYAIYWVRQAPGQGLECMGGIIPIFG SANYAQKFQGRVTITADESTSTAYMELSSLRSEDTAVYYCATDSLKTTYYYGSSGYF RDHVWGQGTTVTVSS | ADI-14598 | Heavy chain variable region ("HC") amino acid sequence |
| Ab 126 | 252 | ETTLTQSPSSLSASVGDRVTITCRASQGISNYLAWYQQKPGKVPKLLIFAASTLQSG VPSRFSGSGSGTDFTLTISSLQPEDVATYYCQNFNSVLSFTFGPGTKVDIK | ADI-14598 | Light chain variable region ("LC") amino acid sequence |
| Ab 127 | 253 | EVQLVESGGGLVQPGRSLRLSCKTSGFTFGDYAMSWVRQAPGQGLDWVGFIRTK AYGGTTEYAASVKGRFTLSRDDSKSIAYLQMNSLKTEDTAVYYCKSGGQFDYWGR GTLVTVSS | ADI-14599 | Heavy chain variable region ("HC") amino acid sequence |
| Ab 127 | 254 | NFMLTQPHSVSGSPGKTVTISCTGSSGSIASNYVQWYQQRPGSAPTTVICEDNQRP SGVPDRFSGSIDSSSNSASLTISGLKTEDEADYYCQSYDRSNQEVFGGGTKLTVL | ADI-14599 | Light chain variable region ("LC") amino acid sequence |
| Ab 128 | 255 | QVQLVQSGGGLVKPGGSLRLSCAASGFSFSDYYMNWIRQAPGKGLEWVSYISSSSS YTNYADSVKGRFTISRDNAKKSLYLQMNSLRAEDTAVYYCASQTYSDYARGGAFDI WGQGTTVTVSS | ADI-14600 | Heavy chain variable region ("HC") amino acid sequence |
| Ab 128 | 256 | QSVLTQPPSVSGAPGQRVTISCTGSSSNIGAGYDVHWYQQLPGTAPKLLIYGNNNR PSGVPDRFSGSKSGTSASLAITGLQAEDEADYYCQSYDSSLSGSVFGTGTKVTVL | ADI-14600 | Light chain variable region ("LC") amino acid sequence |
| Ab 129 | 257 | EVQLLESGGGLVQPGGSLRLSCAASGFTFSSYAMNWVRQAPGKGLEWVSTISGSG SSTYYADSVEGRFTISRDNSKNTLYLQMNSLRAEDTAIYYCAKEPRDMYIQQWLDS WGQGTLVTVSS | ADI-14601 | Heavy chain variable region ("HC") amino acid sequence |
| Ab 129 | 258 | GIRLTQSPSSVSASVGDRVIITCRASQGIRSWLAWYQQKPGKAPKLLIYAASRLQSG VPSRFSGSGSETDFTLTISSLQPEDFASYYCQQANSFPLTFGGGTKVEIK | ADI-14601 | Light chain variable region ("LC") amino acid sequence |
| Ab 130 | 259 | EVQLVESGGGVVQPGGSLRLSCAASGFSFSSCGMHWVRQVSGKGLEWVAFIRYD GSNKFYADSVKGRFTISRDNSKNTLYLQMNSLRVEDTAVYYCAKGGLEDVSTGYSP HYYYGMDVWGQGTTVTVSS | ADI-14602 | Heavy chain variable region ("HC") amino acid sequence |
| Ab 130 | 260 | QPVLTQPPSVSVSPGQTASITCSGDKLAYKYTCWYQQKPGQSPVLVIFQDSKRPSGI PERFSGSNSGNTATLTISGTQALDEADYYCQAWDSSTVVFGGGTKLTVL | ADI-14602 | Light chain variable region ("LC") amino acid sequence |
| Ab 131 | 261 | QVQLVQSGAEVKKPGESLKISCKGSGYTFTNYWIGWVRQMPGKGLEWMGIIYPG DSDTRYSPSFQGQVTISADKSITTAYLQWRVLKASDTAMYYCATMRGSSSHFHHW GQGTLVTVSS | ADI-14603 | Heavy chain variable region ("HC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 131 | 262 | DIQVTQSPSSLSASVGDRVTITCRAGQGIGNYLAWYQQKPGKVPKVLIYAASTLQSG VPSRFSGSGSGTEFTLTISSLQPEDVATYYCQKYNNAPYAFGQGTRLEIK | ADI-14603 | Light chain variable region ("LC") amino acid sequence |
| Ab 132 | 263 | EVQLLESGGGLVQPGGSLRLSCSASGFTFNNYVMHWVRQAPGKGLEDASAISSNG VSTNYADSVKGRFTISRDNSKNTLYLQMRSLRAEDTALYYCVRDLIPHDSSAYYGYH GMDVWGQGTTVTVSS | ADI-14604 | Heavy chain variable region ("HC") amino acid sequence |
| Ab 132 | 264 | QPVLTQPPSASGTPGQSVTISCSGSSSNIGTNVVNWYQQLPGTAPKLLIYSNDLRPS GVPDRFSGSKSGTSASLAISGLQSEDEANYYCAAWDDSLNGVLFGGGTKLTVL | ADI-14604 | Light chain variable region ("LC") amino acid sequence |
| Ab 133 | 265 | EVQLLESGPALVKPTQTLTLTCTFSGFSLTTSGMCVSWIRQPPGKALEWLARIDWD DDQYFSTSLRTRLSISKDTSKNQVVLTMTNMDPVDTATYYCARSALNIAARGFDIW GQGTTVTVSS | ADI-14605 | Heavy chain variable region ("HC") amino acid sequence |
| Ab 133 | 266 | QPGLTQPPSVSVSPGQTARITCSGDVLPKHFSYWYQQKPGQAPVLVIHRDSERPSG IPERFSGSSSGTTVTLTISGVQAEDEADYYCQFSDITNTVFGGGTKLTVL | ADI-14605 | Light chain variable region ("LC") amino acid sequence |
| Ab 134 | 267 | QVQLVQSGGGLVQPGGSLRLSCAASGFTVSSNYMGWVRQAPGKGLEWVSVIYTG GSTYYADSVKGRFTISRDNFKNTLYLQMNSLRAEDTALYYCARDLYSSGWFGYWG QGTLVTVSS | ADI-14606 | Heavy chain variable region ("HC") amino acid sequence |
| Ab 134 | 268 | DIRLTQSPATLSVSPGERATLSCRASQSVSINLGWFQQKPGQSPRLLIYGTSTRATG IPARFSGSGSGTEFTLTISSLQSEDFAVYYCHQYNNWPYTFGQGTKVEIK | ADI-14606 | Light chain variable region ("LC") amino acid sequence |
| Ab 135 | 269 | EVQLLESGGGVVQSGRSLRLSCAASGFTFNNYAMHWVRQAPGKGLEWVAVISFD GGNKFYGDSVQGRFTISRDNSKNTLYLQTNSLRPEDTAVYYCARDRWEIQIGLDIW GQGTTVTVSS | ADI-14607 | Heavy chain variable region ("HC") amino acid sequence |
| Ab 135 | 270 | SYVLTQPPSVSVSPGQTARITCSGDALARQNAYWYQQKPGQAPVLVMYRDTGRPS GIPERFSGSSSGTTVTLTISEVQAEDEADYYCQSADSSGAYVFGTGTKVTVL | ADI-14607 | Light chain variable region ("LC") amino acid sequence |
| Ab 136 | 271 | EVQLLESGGGLVKPGGSLRLSCAASGFTFSSYSMNWVRQAPGKGLEWVSSISSSS YIYYADSVKGRFTISRDNAKNSLYLQMNSLRAEDTAVYYCARVGWGYSYGYWFDP WGQGTLVTVSS | ADI-19420 | Heavy chain variable region ("HC") amino acid sequence |
| Ab 136 | 272 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGVVFGGGTKLTVL | ADI-19420 | Light chain variable region ("LC") amino acid sequence |
| Ab 137 | 273 | EVQLLESGGGVVQPGRSLRLSCAASGFTFSSYGMHWVRQAPGKGLEWVAVISYD GSNKYYADSVKGRFTISRDNSKNTLYLQMNSLRAEDTAVYYCAKDIHHVLRFLDPD YWGQGTLVTVSS | ADI-19421 | Heavy chain variable region ("HC") amino acid sequence |
| Ab 137 | 274 | QSVLIQPASVSGFPGQSITISCTGTSSDVGGYNYVSWYQQHPGKAPKLMIYEVSNR PSGVSNRFSGSKSGNTASLTISGLQAEDEADYYCSSYTSSSTLVFGGGTKLTVL | ADI-19421 | Light chain variable region ("LC") amino acid sequence |
| Ab 138 | 275 | EVQLVESGGGVVQPGRSLRLSCAASGFTFSSYGMHWVRQAPGKGLEWVAVISYD GSNKYYADSVKGRFTISRDNSKNTLYLQMNSLRAEDTAVYYCAKEGYNWNDYYFD YWGQGTLVTVSS | ADI-19422 | Heavy chain variable region ("HC") amino acid sequence |
| Ab 138 | 276 | QPVLTQPPSVSVAPGKTARITCGGNNIGSKSVHWYQQKPGQAPVLVVYDDSDRPS GIPERFSGSNSGNTATLTISRVEAGDEADYYCQVWDSSSDHWVFGGGTKLTVL | ADI-19422 | Light chain variable region |

TABLE 5-continued

Informal Sequence Listing

| Antibody No. | SEQ ID NO: | Sequence | Clone # (ADI) | Descriptors |
|---|---|---|---|---|
| | | | | ("LC") amino acid sequence |
| Ab 139 | 277 | EVQLLESGGGLVQPGGSLRLSCAASGFTVSSNYMSWVRQAPGKGLEWVSDIYSGG RTDYADSVKGRFTISRDNSKNTLDLQMNSLRAEDTAVYYCARETLGMDHWYFDL WGRGTLVTVSS | ADI-19424 | Heavy chain variable region ("HC") amino acid sequence |
| Ab 139 | 278 | QPGLTQPPSVSVAPGKTARITCGGNNIGSKSVHWYQQKPGQAPVLVVYDDSDRPS GIPERFSGSNSGNTATLTISRVEAGDEADYYCQVWDSTSDHPVFGGGTKLTVL | ADI-19424 | Light chain variable region ("LC") amino acid sequence |
| Ab 140 | 279 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARLGYCSGGSCHFDYW GQGTLVTVSS | ADI-19425 | Heavy chain variable region ("HC") amino acid sequence |
| Ab 140 | 280 | QPVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGFYVFGTGTKLTVL | ADI-19425 | Light chain variable region ("LC") amino acid sequence |
| Ab 141 | 281 | QVQLQESGPGLVKPSETLSLTCTVSGGSISSYYWSWIRQPPGKGLEWIGYIYYSGS TNYNPSLKSRVTISVDTSKNQFSLKLSSVTAADTAVYYCARGNEELGTGSNWFDPW GQGTLVTVSS | ADI-19426 | Heavy chain variable region ("HC") amino acid sequence |
| Ab 141 | 282 | SYVLTQPPSVSVSPGQTASITCSGDKLGDKYACWYQQKPGQSPVLVIYQDSKRPSG IPERFSGSNSGNTATLTISGTQAMDEADYYCQAWDSSTVVFGGGTKLTVL | ADI-19426 | Light chain variable region ("LC") amino acid sequence |
| Ab 142 | 283 | EVQLVESGGGLVKPGGSLRLSCAASGFTFSSYSMNWVRQAPGKGLEWVSSISSSSS FISYADSVKGRFTISRDSAKNSLYLQMNSLRAEDTAVYYCARDHPNWNGLAYFDY WGQGTLVTVSS | ADI-19427 | Heavy chain variable region ("HC") amino acid sequence |
| Ab 142 | 284 | QSVLTQPPSISGAPGQRVTISCTGSSSNIGAGYDVQWHQQLPGTAPKLLIYGNSNR PSGVPDRFSGSKSGTSASLAITGLQAEDEADYYCQSYDSSLSGWVFGGGTKLTVL | ADI-19427 | Light chain variable region ("LC") amino acid sequence |
| Ab 143 | 285 | EVQLLESGGGLVKPGGSLRLSCAASGFTFSSYSMNWVRQAPGKGLEWVSSISSSSS YIYYADSVKGRFTISRDNAKNSLYLQMNSLRAEDTAVYYCARDSCSGGSCYSPRFD PWGQGTLVTVSS | ADI-19428 | Heavy chain variable region ("HC") amino acid sequence |
| Ab 143 | 286 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSTVVFGGGTKLTVL | ADI-19428 | Light chain variable region ("LC") amino acid sequence |
| Ab 144 | 287 | EVQLQESGPGLVKPSETLSLTCTVSGGSISSSYYWGWIRQPPGKGLEWIGSIYYS GSTYYNPSLKSRVTISVDTSKNQFSLKLSSVTAADTAVYYCARTPLYSYGRVVGFY YYGMDVWGQGTTVTVSS | ADI-19429 | Heavy chain variable region ("HC") amino acid sequence |
| Ab 144 | 288 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGWVFGGGTKLTVL | ADI-19429 | Light chain variable region ("LC") amino acid sequence |
| Ab 145 | 289 | QVQLVQSGAEVKKPGSSVKVSCKASGGTFSSYTISWVRQAPGQGLEWMGRIIPILG IANYAQKFQGRVTITADKSTSTAYMELSSLRSEDTAVYYCARDGGPYYYDSSGYYR LDYWGQGTLVTVSS | ADI-19430 | Heavy chain variable region ("HC") amino acid sequence |
| Ab 145 | 290 | DIRMTQSPLSLPVTLGQPASISCRSSQSLVYSDGNTYLNWFQQRPGQSPRRLIYKV SNRDSGVPDRFSGSGSGTDFTLKISRVEAEDVGVYYCMQGTHWTYTFGQGTKLEIK | ADI-19430 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 146 | 291 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARELYDYVWGSYRDYW GQGTLVTVSS | ADI-19431 | Heavy chain variable region ("HC") amino acid sequence |
| Ab 146 | 292 | QPGLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGSVFGGGTKVTVL | ADI-19431 | Light chain variable region ("LC") amino acid sequence |
| Ab 147 | 293 | QVQLVQSGAEVKKPGASVKVSCKVSGYTLTELSMHWVRQAPGKGLEWMGGFDP EDGETIYAQKFQGRVTMTEDTSTDTAYMELSSLRSEDTAVYYCATEREEGGYSGYD DAFDIWGQGTMVTVSS | ADI-19432 | Heavy chain variable region ("HC") amino acid sequence |
| Ab 147 | 294 | DIRMTQSPSTLSASVGDRVTITCRASQSISSWLAWYQQKPGKAPKLLIYKASSLES GVPSRFSGSGSGTEFTLTISSLQPDDFATYYCQQYNSYSYTFGQGTKLEIK | ADI-19432 | Light chain variable region ("LC") amino acid sequence |
| Ab 148 | 295 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARAPPSVGGWYFDLW GRGTLVTVSS | ADI-19433 | Heavy chain variable region ("HC") amino acid sequence |
| Ab 148 | 296 | QPVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLVFGGGTKLTVL | ADI-19433 | Light chain variable region ("LC") amino acid sequence |
| Ab 149 | 297 | QVQLQESGPGLVKPSQTLSLTCTVSGGSISSGSYYWSWIRQPAGKGLEWIGRIYTS GSTNYNPSLKSRVTISVDTSKNQFSLKLSSVTAADTAVYYCAREGRGGAFDIWGQG TLVTVSS | ADI-19435 | Heavy chain variable region ("HC") amino acid sequence |
| Ab 149 | 298 | SYELTQPPSVSVSPGQTARITCSADALPKQYAYWYQQKPGQAPVLVIYKDSERPSGI PERFSGSSSGTTVTLTISGVQAEDEADYYCQSADSSGTYVVFGGGTQLTVL | ADI-19435 | Light chain variable region ("LC") amino acid sequence |
| Ab 150 | 299 | QVQLVQSGPGLVKPSETLSLTCTVSGGSISSSSYYWGWIRQPPGKGLEWIGSIYYSG STYYNPSLKSRVTISVDTSKNQFSLKLSSVTAADTAVYYCARSLMNYSNYVLGFDPW GQGTLVTVSS | ADI-19436 | Heavy chain variable region ("HC") amino acid sequence |
| Ab 150 | 300 | QPVLTQPPSVSVSPGQTASITCSGDKLGDKYACWYQQKPGQSPVLVIYQDSKRPSG IPERFSGSNSGNTATLTISGTQAMDEADYYCQAWDSSTVVFGGGTKLTVL | ADI-19436 | Light chain variable region ("LC") amino acid sequence |
| Ab 151 | 301 | EVQLVQSGAEVKKPGASVKVSCKASGYTFTSYGISWVRQAPGQGLEWMGWISAY NGNTNYAQKLQGRVTMTTDTSTSTAYMELRSLRSDDTAVYYCARDGIAAAGTLFD YWGQGTLVTVSS | ADI-19437 | Heavy chain variable region ("HC") amino acid sequence |
| Ab 151 | 302 | DIQLTQSPSSVSASVGDRVTITCRASQGISSWLAWYQQKPGKAPKLLIYAASSLQS GVPSRFSGSGSGTDFTLTISSLQPEDFATYYCQQANSFPLTFGGGTKVEIK | ADI-19437 | Light chain variable region ("LC") amino acid sequence |
| Ab 152 | 303 | EVQLVESGGGLVQPGGSLRLSCAASGFTFSSYAMSWVRQAPGKGLEWVSAISGSG GSTYYADSVKGRFTISRDNSKNTLYLQMNSLRAEDTAVYYCAKYSNYGSFDYWGQ GTLVTVSS | ADI-19439 | Heavy chain variable region ("HC") amino acid sequence |
| Ab 152 | 304 | DIQMTQSPSTLSASVGDRVTITCRASQSISSWLAWYQQKPGKAPKLLIYKASSLESG VPSRFSGSGSGTEFTLTISSLQPDDFATYYCQQYNSYSTFGQGTKVEIK | ADI-19439 | Light chain variable region ("LC") amino acid sequence |
| Ab 153 | 305 | EVQLVESGGGLVQPGGSLRLSCAASGFTFSSYSMNWVRQAPGKGLEWVSYISSSSS TIYYADSVKGRFTISRDNAKNSLYLQMNSLRAEDTAVYYCAREGYSGSYGYYFDYW | ADI-19440 | Heavy chain variable region |

TABLE 5-continued

Informal Sequence Listing

| Anti-body No. | SEQ ID NO: | Sequence | Clone # (ADI) | Descriptors |
|---|---|---|---|---|
| | | GQGTLVTVSS | | ("HC") amino acid sequence |
| Ab 153 | 306 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGSVFGTGTKLTVL | ADI-19440 | Light chain variable region ("LC") amino acid sequence |
| Ab 154 | 307 | QVQLVQSGAEVKKPGSSVKVSCKASGGTFSSYAISWVRQAPGQGLEWMGRIIPILG IANYAQKFQGRVTITADKSTSTAYMELSSLRSEDTAVYYCARGPLTGYSSSWFDPW GQGTLVTVSS | ADI-19441 | Heavy chain variable region ("HC") amino acid sequence |
| Ab 154 | 308 | EIVMTQSPSSLSASVGDRVTITCRASQSISSYLNWYQQKPGKAPKLLIYAASSLQS GVPSRFSGSGSGTDFTLTISSLQPEDFATYYCQQSYSTLPYTFGQGTKVEIK | ADI-19441 | Light chain variable region ("LC") amino acid sequence |
| Ab 155 | 309 | QVQLVQSGAEVKKPGASVKVSCKASGYTFTSYGISWVRQAPGQGLEWMGWISAY NGNTNYAQKLQGRVTMTTDTSTSTAYMELRSLRSDDTAVYYCARDEALVGATFDY WGQGTLVTVSS | ADI-19444 | Heavy chain variable region ("HC") amino acid sequence |
| Ab 155 | 310 | DIVMTQSPDSLAVSLGERATINCKSSQSVLYSSNNKNYLAWYQQKPGQPPKLLIYW ASTRESGVPDRFSGSGSGTDFTLTISSLQAEDVAVYYCQQYYSTPRTFGQGTKVEIK | ADI-19444 | Light chain variable region ("LC") amino acid sequence |
| Ab 156 | 311 | EVQLVESGPGLVKPSGTLSLTCAVSGGSISSSNWWSWVRQPPGKGLEWIGEIYHSG STNYNPSLKSRVTISVDKSKNQFSLKLSSVTAADTAVYYCARDVETDGYNYGYYFDY WGQGTLVTVSS | ADI-19445 | Heavy chain variable region ("HC") amino acid sequence |
| Ab 156 | 312 | SYELIQPPSVSVAPGKTARITCGGNNIGSKSVHWYQQKPGQAPVLVVYDDSDRPSG IPGRFSGSNSGNTATLTISRVEAGDEADYYCQVWDSSSDHKVFGGGTKLTVL | ADI-19445 | Light chain variable region ("LC") amino acid sequence |
| Ab 157 | 313 | QVQLQESGPGLVKPSETLSLTCTVSGGSISSSSYYWGWIRQPPGKGLEWIGSIYYSG STYYNPSLKSRVTISVDTSKNQFSLKLSSVTAADTAVYYCARDRVVTTYFDYWGQGT LVTVSS | ADI-19447 | Heavy chain variable region ("HC") amino acid sequence |
| Ab 157 | 314 | SYELTQPPSVSVSPGQTARITCSGDALPKKYAYWYQQKSGQAPVLVIYEDSKRPSGI PERFSGSSSGTMATLTISGAQVEDEADYYCYSTDSSGNHRVFGGGTKLTVL | ADI-19447 | Light chain variable region ("LC") amino acid sequence |
| Ab 158 | 315 | EVQLLESGGGLVKPGGSLRLSCAASGFTFSSYSMNWVRQAPGKGLEWVSSISSSS YIYYADSVKGRFTISRDNAKNSLYLQMNSLRAEDTAVYYCARELLDPGIAAAGFDYW GQGTLVTVSS | ADI-19448 | Heavy chain variable region ("HC") amino acid sequence |
| Ab 158 | 316 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSVNYVFGTGTKVTVL | ADI-19448 | Light chain variable region ("LC") amino acid sequence |
| Ab 159 | 317 | EVQLVESGGGLVKPGGSLRLSCAASGFTFSSYSMNWVRQAPGKGLEWVSSISSSS YIYYADSVKGRFTISRDNAKNSLYLQMNSLRAEDTAVYYCARDSGSYLSYAFDIWGQ GTMVTVSS | ADI-19449 | Heavy chain variable region ("HC") amino acid sequence |
| Ab 159 | 318 | SYELTQPPSVSGAPGQRVTISCTGSSSNIGAGYDVHWYQQLPGTAPKLLIYGNSRP SGVPDRFSGSKSGTSASLAITGLQAEDEADYYCQSYDSSLSGYVFGTGTKVTVL | ADI-19449 | Light chain variable region ("LC") amino acid sequence |
| Ab 160 | 319 | EVQLLESGGGLVQPGGSLRLSCAASGFTFSSYWMHWVRQAPGKGLVWVSRINSD GSSTSYADSVKGRFTISRDNAKNTLYLQMNSLRAEDTAVYYCARAPISILRFLGGY FDYWGQGTLVTVSS | ADI-19450 | Heavy chain variable region ("HC") amino acid sequence |
| Ab 160 | 320 | EIVMTQSPSTLSASVGDRVTITCRASQSISSWLAWYQQKPGKAPKLLIYKASSLES GVPSRFSGSGSGTEFTLTISSLQPDDFATYYCQQYNSYSSFGQGTKLEIK | ADI-19450 | Light chain variable region |

TABLE 5-continued

Informal Sequence Listing

| Anti-body No. | SEQ ID NO: | Sequence | Clone # (ADI) | Descriptors |
|---|---|---|---|---|
| | | | | ("LC") amino acid sequence |
| Ab 161 | 321 | EVQLLESGGGLVKPGGSLRLSCAASGFTFSSYSMNWVRQAPGKGLEWVSSISSSSS YIYYADSVKGRFTISRDNAKNSLYLQMNSLRAEDTAVYYCARGYCSGGSCYSHYFQ HWGQGTLVTVSS | ADI-19454 | Heavy chain variable region ("HC") amino acid sequence |
| Ab 161 | 322 | QSVLTQPASVSGSPGQSITISCTGTSSDVGGYNYVSWYQQHPGKAPKLMIYDVSNR PSGVSNRFSGSKSGNTASLTISGLQAEDEADYYCSSYTSSSTVVFGGGTKVTVL | ADI-19454 | Light chain variable region ("LC") amino acid sequence |
| Ab 162 | 323 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARSQSGSYYSSDYWGQ GTLVTVSS | ADI-19455 | Heavy chain variable region ("HC") amino acid sequence |
| Ab 162 | 324 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGWVFGGGTKVTVL | ADI-19455 | Light chain variable region ("LC") amino acid sequence |
| Ab 163 | 325 | EVQLLESGGGLVKPGGSLRLSCAASGFTFSSYSMNWVRQAPGKGLEWVSSISSSSS YIYYADSVKGRFTISRDNAKNSLYLQMNSLRAEDTAVYYCARQGYCSGGSCYHIDY WGQGTLVTVSS | ADI-19457 | Heavy chain variable region ("HC") amino acid sequence |
| Ab 163 | 326 | QSVVTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGWVFGGGTKLTVL | ADI-19457 | Light chain variable region ("LC") amino acid sequence |
| Ab 164 | 327 | EVQLVESGGGRVKPGGSLRLSCAASGFTFRSYSMNWVRQAPGKGLEWVSSISSSSS YINYADSVKGRFTISRDNAKNSLYLQMNSLRAEDTAVYYCARDGSGMTIFGVVIDY WGQGTLVTVSS | ADI-19458 | Heavy chain variable region ("HC") amino acid sequence |
| Ab 164 | 328 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDRSLTVVFGGGTKLTVL | ADI-19458 | Light chain variable region ("LC") amino acid sequence |
| Ab 165 | 329 | QVQLVESGGGLVQPGGSLRLSCAASGFTVSSNYMSWVRQAPGKGLEWVSVIYSG GSTYYADSVKGRFTISRDNSKNTLYLQMNSLRAEDTAVYYCAREALGMDHWYFDL WGRGTLVTVSS | ADI-19459 | Heavy chain variable region ("HC") amino acid sequence |
| Ab 165 | 330 | SYELMQPPSVSVAPGKTARITCGGNNIGSKSVHWYQQKPGQAPVLVVYDDSDRPS GIPERFSGSNSGNTATLTISRVEAGDEADYYCQVWDSSSDHPVFGGGTKVTVL | ADI-19459 | Light chain variable region ("LC") amino acid sequence |
| Ab 166 | 331 | QVQLQQWGAGLLKPSETLSLTCAVYGGSFSGYYWSWIRQPPGKGLEWIGEINHSG STNYNPSLKSRVTISVDTSKNQFSLKLSSVTAADTAVYYCARGGITAYYYYGMDV WGQGTTVTVSS | ADI-19460 | Heavy chain variable region ("HC") amino acid sequence |
| Ab 166 | 332 | DIQMTQSPSSLSASVGDRVTITCRASQSISSYLNWYQQKPGKAPKLLIYAASSLQSG VPSRFSGSGSGTDFTLTISSLQPEDFATYYCQQSYSTPYTFGQGTKVEIK | ADI-19460 | Light chain variable region ("LC") amino acid sequence |
| Ab 167 | 333 | EVQLVESGGGLVKPGGSLRLSCAASGFTFSDYYMSWIRQAPGKGLEWVSYISSSGS TIYYADSVKGRFTISRDNAKNSLYLQMNSLRAEDTAVYYCASSLTVTSRSDAFDIWG QGTMVTVSS | ADI-19461 | Heavy chain variable region ("HC") amino acid sequence |
| Ab 167 | 334 | QPGLTQLPSVSVAPGKTARITCGGNNIGSKSVHWYQQKPGQAPVLVVYDDSDRPS GIPERFSGSNSGNTATLTISRVEAGDEADYYCQVWDSSSDHVVFGGGTKLTVL | ADI-19461 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 168 | 335 | QITLKESGPTLVKPTQTLTLTCTFSGFSLSTSGVGVGWIRQPPGKALEWLALIYWDD DKRYSPSLKSRLTITKDTSKNQVVLTMTNMDPVDTATYYCAHAANWGYYFDYWG QGTLVTVSS | ADI- 19462 | Heavy chain variable region ("HC") amino acid sequence |
| Ab 168 | 336 | DIVMTQSPSTLSASVGDRVTITCRASQSISSWLAWYQQKPGKAPKLLIYKASSLESG VPSRFSGSGSGTEFTLTISSLQPDDFATYYCQQYNSYWTFGQGTKVEIK | ADI- 19462 | Light chain variable region ("LC") amino acid sequence |
| Ab 169 | 337 | QVQLQESGPGLVKPSQTLSLTCTVSGGSISSGDYYWSWIRQPPGKGLEWIGYIYYSG STYYNPSLKSRVTISVDTSKNQFSLKLSSVTAADTAVYYCARDRLGIFDYWGQGTLV TVSS | ADI- 19463 | Heavy chain variable region ("HC") amino acid sequence |
| Ab 169 | 338 | EIVLTQSPDSLAVSLGERATINCKSSQSVLYSSNNKNYLAWYQQKPGQPPKLLIYWA STRESGVPDRFSGSGSGTDFTLTISSLQAEDVAVYYCQQYYSTPWTFGQGTKVEIK | ADI- 19463 | Light chain variable region ("LC") amino acid sequence |
| Ab 170 | 339 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCAREGSSSWYYFDYWGQ GTLVTVSS | ADI- 19465 | Heavy chain variable region ("HC") amino acid sequence |
| Ab 170 | 340 | QSVVTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGPWVFGGGTKLTVL | ADI- 19465 | Light chain variable region ("LC") amino acid sequence |
| Ab 171 | 341 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCASLSSSSELGYYFDYWG QGTLVTVSS | ADI- 19467 | Heavy chain variable region ("HC") amino acid sequence |
| Ab 171 | 342 | QPVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGYVFGTGTKLTVL | ADI- 19467 | Light chain variable region ("LC") amino acid sequence |
| Ab 172 | 343 | EVQLVESGPGLVKPSETLSLTCTVSGGSISSSSYYWGWIRQPPGKGLEWIGSIYYS GSTYYNPSLKSRVTISVDTSKNQFSLKLSSVTAADTAVYYCARRDGYNYGWFDPWG QGTLVTVSS | ADI- 19468 | Heavy chain variable region ("HC") amino acid sequence |
| Ab 172 | 344 | NFMLTQPHSVSESPGKTVTISCTGSSGSIASNYVQWYQQRPGSAPTTVIYEDNQRP SGVPDRFSGSIDSSSNSASLTISGLKTEDEADYYCQSYDSSNVVFGGGTKVTVL | ADI- 19468 | Light chain variable region ("LC") amino acid sequence |
| Ab 173 | 345 | QVQLQESGPGLVKPSETLSLTCAVSGYSISSGYYWGWIRQPPGKGLEWIGSIYHSG STYYNPSLKSRVTISVDTSKNQFSLKLSSVTAADTAVYYCARWTVMYYFDYWGQGT LVTVSS | ADI- 19469 | Heavy chain variable region ("HC") amino acid sequence |
| Ab 173 | 346 | EIVMTQSPATLSLSPGERATLSCRASQSVSSYLAWYQQKPGQAPRLLIYDASNRAT GIPARFSGSGSGTDFTLTISSLEPEDFAVYYCQQRSNWPTFGGGTKLEIK | ADI- 19469 | Light chain variable region ("LC") amino acid sequence |
| Ab 174 | 347 | EVQLLESGGGVVQPGRSLRLSCAASGFTFSSYGMHWVRQAPGKGLEWVAVISYD GSNKYYADSVKGRFTISRDNSKNTLYLQMNSLRAEDTAVYYCAKGRGDFWSGYGM DVWGQGTTVTVSS | ADI- 19470 | Heavy chain variable region ("HC") amino acid sequence |
| Ab 174 | 348 | SYELTQPPSVSVSPGQTASITCSGDKLGDKYACWYQQKPGQSPVLVIYQDSKRPSG IPERFSGSNSGNTATLTISGTQAMDEADYYCQAWDSSTAVFGGGTKVTVL | ADI- 19470 | Light chain variable region ("LC") amino acid sequence |
| Ab 175 | 349 | EVQLVESGGGLVQPGGSLRLSCSASGFTFSSYAMHWVRQAPGKGLEYVSAISSNG GSTYYADSVKGRFTISRDNSKNTLYLQMSSLRAEDTAVYYCVKADQGSSGWFPDY | ADI- 19471 | Heavy chain variable region |

TABLE 5-continued

Informal Sequence Listing

| Anti-body No. | SEQ ID NO: | Sequence | Clone # (ADI) | Descriptors |
|---|---|---|---|---|
| | | WGQGTLVTVSS | | ("HC") amino acid sequence |
| Ab 175 | 350 | NFMLTQPHSVSESPGKTVTISCTRSSGSIASNYVQWYQQRPGSSPTTVIYEDNQRP SGVPDRFSGSIDSSSNSASLTISGLKTEDEADYYCQSYDSSNWVFGGGTKLTVL | ADI-19471 | Light chain variable region ("LC") amino acid sequence |
| Ab 176 | 351 | EVQLVESGAEVKKPGESLKISCKGSGYSFTSYWIGWVRQMPGKGLEWMGIIYPGD SDTRYSPSFQGQVTISADKSISTAYLQWSSLKASDTAMYYCARLIAAAGIDYWGQG TLVTVSS | ADI-19473 | Heavy chain variable region ("HC") amino acid sequence |
| Ab 176 | 352 | NFMLTQPHSVSESPGKTVTISCTRSSGSIASNYVQWYQQRPGSSPTTVIYEDNQRP SGVPDRFSGSIDSSSNSASLTISGLKTEDEADYYCQSYDSSNIWVFGGGTKVTVL | ADI-19473 | Light chain variable region ("LC") amino acid sequence |
| Ab 177 | 353 | QVQLVQSGAEVKKPGESLKISCKGSGYSFTSYWIGWVRQMPGKGLEWMGIIYPGD SDTRYSPSFQGQVTISADKSISTAYLQWSSLKASDTAMYYCARPYSGSYYAFDIWG QGTTVTVSS | ADI-19474 | Heavy chain variable region ("HC") amino acid sequence |
| Ab 177 | 354 | NFMLTQPHSVSESPGKTVTISCTRSSGSIASNYVQWYQQRPGSSPTTVIYEDNQRP SGVPDRFSGSIDSSSNSASLTISGLKTEDEADYYCQSYDSSNQVFGGGTKLTVL | ADI-19474 | Light chain variable region ("LC") amino acid sequence |
| Ab 178 | 355 | EVQLLESGAEVKKPGASVKVTCKASGYTFTHFGINWVRQAPGQGLEWLGWISAYN GNTNYVQKIQGRVTMTTDTSTNTAYMELRSLRSDDTAVYYCARGPPVEAAGTFDY WGQGTLVTVSS | ADI-19475 | Heavy chain variable region ("HC") amino acid sequence |
| Ab 178 | 356 | DIVLTQSPLSLPVTLGQPASISCRSSQSLVYSDGNTYLTWFQQRPGQSPRRLIYKV SNRDSGVPDRFSGSGSGTDFTLQISRVEAEDVGVYYCMQGTHWPFTFGPGTKVEIK | ADI-19475 | Light chain variable region ("LC") amino acid sequence |
| Ab 179 | 357 | QVQLVESGPTLVKPTQTLTLTCTFSGFSLSTSRVGVGWIRQPPGKALEWLALIYWD DDKRYSPSLKSRLTITKDTSKNQVVLTMTNMDPVDTARYYCAHRSTYDILGGYYYF DYWGQGTLVTVSS | ADI-19476 | Heavy chain variable region ("HC") amino acid sequence |
| Ab 179 | 358 | QPVLTQPRSVSGSPGQSVTISCTGTSSDVGGYNYVSWFQQHPGKAPKLMIYDVSK RPSGVPNRFSGSKSGNTASLTISGLQAEDEADYFCCSYAGTYEVFGGGTKLTVL | ADI-19476 | Light chain variable region ("LC") amino acid sequence |
| Ab 180 | 359 | QVQLVESGPGVVKPSETLSLTCTVSGGPVSSRSYYWGWIRQPPGKGLEWIGSIYYS GSTYYNTSLKSRVTISVDTSKNQFSLKLSSVTAADTAVYYCAKLQYSTSGFDYWGQ GTLVTVSS | ADI-19478 | Heavy chain variable region ("HC") amino acid sequence |
| Ab 180 | 360 | QPVLTQPPSVSEAPRQRVTISCSGSSSNIGNNAVSWYQQLPGKAPKLLIYYDDLVP SGVSDRFSGSKSGTSASLAISGLQSEDEADYYCAAWDDSLNGVVFGGGTKLTVL | ADI-19478 | Light chain variable region ("LC") amino acid sequence |
| Ab 181 | 361 | QVQLVQSGAEVKKPGSSVKVSCKASGGTFSSNAINWVRQAPGQGLEWMGGIIPIF GTANYAQKFQGRVTITTDESTSTAYMELSSLRSEDTAVYYCATTFYYGSGADYWGQ GTLVTVSS | ADI-19479 | Heavy chain variable region ("HC") amino acid sequence |
| Ab 181 | 362 | DIQMTQSPLSLPVTLGQPASISCRSSQSLVYSDGNMYLSWFQQRPGQSPRRLIYKVS NRDSGVPDRFSGSGSGTDFTLKISRVEAEDVGVYYCMQGTHWWTFGQGTKVEIK | ADI-19479 | Light chain variable region ("LC") amino acid sequence |
| Ab 182 | 363 | EVQLVESGGGLVKPGGSLRLSCAASGFTFSAYSMNWVRQAPGKGLEWVSSISSTT NYISYADSVKGRFTISRDNAKNSLYLQMNSLRAEDTAVYYCARDPKYYGLGTYYKDD YWGQGTLVTVSS | ADI-19480 | Heavy chain variable region ("HC") amino acid sequence |

TABLE 5-continued

Informal Sequence Listing

| Anti-<br>body<br>No. | SEQ<br>ID<br>NO: | Sequence | Clone<br>#<br>(ADI) | Descriptors |
|---|---|---|---|---|
| Ab 182 | 364 | NFMLTQPHSVSESPGKTVTISCTRSGGSIASNYVQWYQQRPGSSPTTVIYEDNQRP<br>SGVPDRFSGSIDSSFNSASLTVSGLKTEDEADYYCQSFDNNNRWVFGGGTKLTVL | ADI-<br>19480 | Light chain<br>variable region<br>("LC") amino acid<br>sequence |
| Ab 183 | 365 | EVQLVESGGVVVQPGGSLRLSCAASGFTFDDYTMHWVRQAPGKGLEWVSLISWD<br>GGITYYADSVKGRFTISRDNSKNSLYLQMNSLRTEDTALYYCVKGGYYDGSGYYYFD<br>YWGQGTLVTVSS | ADI-<br>19481 | Heavy chain<br>variable region<br>("HC") amino acid<br>sequence |
| Ab 183 | 366 | DIQMTQSPSSLSASVGDRVTVTCRASQSISSYLNWYQHKPGNAPKLLIYAASSLQSG<br>VPSRFSGSGSGTDFTLTISSLQPEDFATYYCQQSYSTPYTFGQGTKVEIK | ADI-<br>19481 | Light chain<br>variable region<br>("LC") amino acid<br>sequence |
| Ab 184 | 367 | QVQLQQWGAGLLKPSETLSLTCGAFHGSFSGYYWSWIRQPPGKGLEWIGEVTHSR<br>STNYNPSLKSRITISVDTSRNQFSLKLNSVTAADTAVYYCARGSGEWYFDIWGRGTL<br>VTVSS | ADI-<br>19482 | Heavy chain<br>variable region<br>("HC") amino acid<br>sequence |
| Ab 184 | 368 | DIQLTQSPSTLSASVGDRVTITCRASQSISSWLAWYQQKPGRAPKLLIYKASSLESG<br>VPSRFSGSGSGTEFTLTISSLQPDDFATYYCQQYNSYSPEIFGQGTKVEIK | ADI-<br>19482 | Light chain<br>variable region<br>("LC") amino acid<br>sequence |
| Ab 185 | 369 | QVQLVQSGAEVKKPGESLKISCKGSGYSFTTYWIGWVRQMPGKGLEWMGIIFPGD<br>SDTRYSPSFQGQVTISADKSISTAYLQWSSLKASDTAMYFCARSAFPFGFDIWGQG<br>TMVTVSS | ADI-<br>19483 | Heavy chain<br>variable region<br>("HC") amino acid<br>sequence |
| Ab 185 | 370 | SYVLTQPHSVSESPGKTVTISCTRSSGSIASNYVQWYQQRPGSSPTTVIYEDHQRPS<br>GVPDRFSGSIDSSSNSASLTISGLQTEDEADYYCQSYGSGNPWVFGGGTKVTVL | ADI-<br>19483 | Light chain<br>variable region<br>("LC") amino acid<br>sequence |
| Ab 186 | 371 | QVQLQESGSGGLVKPSQTLSLTCVVSGGSISSGGNSWSWIRQPPGKGLEWIGYIYDS<br>GNTYYNPSLKSRVTISVDRSKNQFSLKVSSVTAADTAVYYCARGAETGTTGWYDPW<br>GQGTLVTVSS | ADI-<br>19484 | Heavy chain<br>variable region<br>("HC") amino acid<br>sequence |
| Ab 186 | 372 | DIRLTQSPSSLSASVGDRVTITCRASQTISSYLNWYQQKPGKAPRLLIYAASSLQSG<br>VPSRFSGSGSGTDFTLTISSLQPEDFATYYCQQSYGTPRTFGQGTKVEIK | ADI-<br>19484 | Light chain<br>variable region<br>("LC") amino acid<br>sequence |
| Ab 187 | 373 | QVQLQESGPGLVKPSQTLSLSCTVSGGSISSTNYYWTWIRQHPGKGLEWIGFIYNR<br>GSTYYNPSLTSRVTISVDTSKNQFSLKLTSVTAADTAVYYCARAPYYYDRNGYYTAF<br>DIWGQGTTVTVSS | ADI-<br>19485 | Heavy chain<br>variable region<br>("HC") amino acid<br>sequence |
| Ab 187 | 374 | EIVLTQSPATLSVSPGERATLSCRASQSVSSNLAWYQQKPGQAPRLLIYDASTRATD<br>IPARFSGGGSGTEFTLTISSLQSEDFAVYYCQQYNNWPRTFGLGTKVDIK | ADI-<br>19485 | Light chain<br>variable region<br>("LC") amino acid<br>sequence |
| Ab 188 | 375 | QVQLQESGPGLVKPSETLSLTCSVSGGSLTSYYWSWIRQPPGKGLEWIGYIYYSGST<br>NYNPSLKSRLTISVDTSKNQFSLKLSSVTAADTAVYYCARVGGRGVINVFDYWGQG<br>TLVTVSS | ADI-<br>19486 | Heavy chain<br>variable region<br>("HC") amino acid<br>sequence |
| Ab 188 | 376 | QPVLTQPASVSGSPGQSITISCTGTSSDVGGYNYVSWYQQHPGKAPKLMIYEVSNR<br>PSGVSNRFSGSKSGNTASLTISGLQAEDEADYYCDSYRSNSASVVFGGGTKLTVL | ADI-<br>19486 | Light chain<br>variable region<br>("LC") amino acid<br>sequence |
| Ab 189 | 377 | QVTLKESGPALVKPTQTLTLTCTFSGLSISTSGMCVSWIRQPPGKALEWLARIDWD<br>DDKYYSTSLKTRLTISKDTSKNQVVLTMTNMDPVDTATYYCARINYYDSSGYYVYY<br>FDYWGQGTLVTVSS | ADI-<br>19487 | Heavy chain<br>variable region<br>("HC") amino acid<br>sequence |
| Ab 189 | 378 | DIQMTQSPSSLSASVGDRVTITCRASQSISSYLNWYQQKPGKAPKLLIYAASSLQS<br>GVPSRFSGSGSGTDFTLTISSLQPEDFATYYCQQSYSTPPFTFGPGTKVDIK | ADI-<br>19487 | Light chain<br>variable region |

TABLE 5-continued

Informal Sequence Listing

| Anti-body No. | SEQ ID NO: | Sequence | Clone # (ADI) | Descriptors |
|---|---|---|---|---|
| | | | | ("LC") amino acid sequence |
| Ab 190 | 379 | QVQLVQSGAEVKKPGASVKVSCKVSGYTLTELSMHWVRQAPGKGLEWMGGFDP EDGETIYAQKFQGRVTMTEDTSTDTAYMELSSLRSEDTAVYYCATARFLEWLSGTN WFDPWGQGTLVTVSS | ADI- 19488 | Heavy chain variable region ("HC") amino acid sequence |
| Ab 190 | 380 | DIQLTQSPLSLPVTPGEPASISCRSSQSLLHSNGYNYLDWYLQKPGQSPQLLIYLG SNRASGVPDRFSGSGSGTDFTLKISRVEAEDVGVYYCMQALQTPPTFGGGTKVEIK | ADI- 19488 | Light chain variable region ("LC") amino acid sequence |
| Ab 191 | 381 | QITLKESGPALVKPTQTLTLTCTFSGFSLSTSGMCVSWIRQPPGKALEWLARIDWD DDKYYSTSLKTRLTISKDTSKNQVVLTMTNMDPVDTATYYCARMCWGNYVPIDAFDI WGQGTMVTVSS | ADI- 19489 | Heavy chain variable region ("HC") amino acid sequence |
| Ab 191 | 382 | DIQLTQSPSSLSASVGDRVTITCRASQGIRNDLGWYQQKPGKAPKRLIYAASSLQSG VPSRFSGSGSGTEFTLTISSLQPEDFATYYCLQHNSYPPTFGQGTKVDIK | ADI- 19489 | Light chain variable region ("LC") amino acid sequence |
| Ab 192 | 383 | EVQLVESGGGLVKPGGSLRLSCAASGFTFSNAWMSWVRQAPGKGLEWVGRIKSK TDGGTTDYAAPVKGRFTISRDDSKNTLYLQMNSLKTEDTAVYYCTTDSSSGGMDV WGQGTTVTVSS | ADI- 19490 | Heavy chain variable region ("HC") amino acid sequence |
| Ab 192 | 384 | DIVLTQSPLSLPVTPGEPASISCRSSQSLLHSNGYNYLDWYLQKPGQSPQLLIYLG SNRASGVPDRFSGSGSGTDFTLKISRVEAEDVGVYYCMQALQTPLTFGGGTKVDIK | ADI- 19490 | Light chain variable region ("LC") amino acid sequence |
| Ab 193 | 385 | QVQLVQSGPTLVKPTQTLTLTCTFSGFSLSTSGVGVGWIRQPPGKALEWLALIYWD DDKRYSPSLKSRLTITKDTSKNQVVLTMTNMDPVDTATYYCAHRRATTVTTGYFDY WGQGTLVTVSS | ADI- 19491 | Heavy chain variable region ("HC") amino acid sequence |
| Ab 193 | 386 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGHYVFGTGTKVTVL | ADI- 19491 | Light chain variable region ("LC") amino acid sequence |
| Ab 194 | 387 | QVQLVQSGAEVKKPGESLKISCKGSGYRFTSYWIGWVRQMPGKGLEWMGIIYPG DSDTRYSPSFQGQVTISADKSISTAYLQWSSLKASDTAMYYCARSGSHYAFDLWGQ GTMVTVSS | ADI- 19492 | Heavy chain variable region ("HC") amino acid sequence |
| Ab 194 | 388 | NFMLTQPHSVSESPGKTVTISCTRSSGNIASNYVQWYQQRPGSSPTTVLYEDNQRP SGVPDRFSGSIDSSSNSASLTISGLKTEDEADYYCQSYDSSNPWVFGGGTKLTVL | ADI- 19492 | Light chain variable region ("LC") amino acid sequence |
| Ab 195 | 389 | QVQLQQWGAGLLKPSETLSLTCAVYGGSFSGYYWSWIRQPPGKGLEWIGEINHSG STNYNPSLKSRVTISVDTSKNQFSLKLSSVTAADTAVYYCARLIENTRVGEYYFDY WGQGTLVTVSS | ADI- 19493 | Heavy chain variable region ("HC") amino acid sequence |
| Ab 195 | 390 | SYELTQPPSVSVSPGQTASITCSGDKLGDKYACWYQQKPGQSPVLVIYQDSKRPSGI PERFSGSNSGNTATLTISGTQAMDEADYYCQAWDSSTVVFGGGTQLTVL | ADI- 19493 | Light chain variable region ("LC") amino acid sequence |
| Ab 196 | 391 | QVQLVQSGAEVKKPGSSVKVSCKASGGTFSSYVISWVRQAPGQGLEWMGGIIPIF GTTYYAQKFQDRVTITTDESTSTAYMELSSLRSEDTAVYYCARDLRYRYNAYDGADA FDIWGQGTTVTVSS | ADI- 19494 | Heavy chain variable region ("HC") amino acid sequence |
| Ab 196 | 392 | QSALTQPASVSGSPGQSITISCTGTSSDVGGYNYVSWYQQHPGKAPKLMIFEVSNR PSGVSNRFSGSKSGNTASLTISGLQAEDEADYYCTSYTKSNSVVFGGGTKLTVL | ADI- 19494 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 197 | 393 | QVQLQESGPGLVKPSETLSLTCTVSGGSISSYYWSWIRQPPGKGLEWIGYIYTSGST NYNPSLKSRVTISVDTSKNQFSLKLSSVTAADTAVYYCARVGSYYDLQHWGQGTLV TVSS | ADI-19495 | Heavy chain variable region ("HC") amino acid sequence |
| Ab 197 | 394 | DIQLTQSPSSVSASVGDRVTITCRASQGISSWLAWYQQKPGKAPKLLIYAASSLQSG VPSRFSGSGSGTDFTLTISSLQPEDFATYYCQQANSFPLTFGGGTKVEIK | ADI-19495 | Light chain variable region ("LC") amino acid sequence |
| Ab 198 | 395 | EVQLVESGGGVVQPGGSLRLSCAASGFTFSSYGMHWVRQAPGKGLEWVAFIRYD GSNKYYADSVKGRFTISRDNSKSTLYLQMNSLRAEDTAVYYCAKDATFGYSSSWYN FDYWGQGTLVTVSS | ADI-19496 | Heavy chain variable region ("HC") amino acid sequence |
| Ab 198 | 396 | DIQMTQSPDSLAVSLGERATINCKSSQSVLFSSNNKNYLAWYQQKPGQPPKLLIYW ASTRESGVPDRFSGSGSGTDFTLTISSLQAEDVAVYYCQQYYSTPTFGQGTKVEIK | ADI-19496 | Light chain variable region ("LC") amino acid sequence |
| Ab 199 | 397 | QVQLVQSGAEVKKPGASVKVSCKASGYTFTSYYMHWVRQAPGQGLEWMGIINPS GGSTSYAQKFQGRVTMTRDTSTSTVYMELSSLRSEDTAVYYCSRGYSYGYDYWGQ GTLVTVSS | ADI-19497 | Heavy chain variable region ("HC") amino acid sequence |
| Ab 199 | 398 | NFMLTQPHSVSESPGKTVTISCTRSSGSIASNYVQWYQQRPGSSPTTVIYEDNQRPS GVPDRFSGSIDSSSNSASLTISGLKTEDEADYYCQSYDSSNWVFGGGTKLTVL | ADI-19497 | Light chain variable region ("LC") amino acid sequence |
| Ab 200 | 399 | EVQLVESGGGLVQPGGSLRLSCAASGFTVSSNYMSWVRQAPGKGLEWVSVIYSGG SAYYADSVKGRFTISRDNSKNTLYLQMNSLRAEDTAVYYCAREARISPPQGAFDIW GQGTMVTVSS | ADI-19498 | Heavy chain variable region ("HC") amino acid sequence |
| Ab 200 | 400 | SYVLTQPPSVSVSPGQTARITCSGDALPKQYAYWYQQKPGQAPVLVIYKDSERPSGI PERFSGSSSGTTVTLTISGVQAEDEADYYCQSADSSGTLYVFGTGTKVTVL | ADI-19498 | Light chain variable region ("LC") amino acid sequence |
| Ab 201 | 401 | EVQLLESGPGLVKPSETLSLTCTVSGGSISSSSYYWGWIRQPPGKGLEWIGSIYYSG STYYNPSLKSRVTISVDTSKNQFSLKLSSVTAADTAVYYCAVLLYSSSSFDYWGQGT LVTVSS | ADI-19499 | Heavy chain variable region ("HC") amino acid sequence |
| Ab 201 | 402 | NFMLTQPHSVSESPGKTVTISCTRSSGSIASNYVQWYQQRPGSSPTTVIYEDNQRPS GVPDRFSGSIDSSSNSASLTISGLKTEDEADYYCQSYDSSNQAVFGGGTQLTVL | ADI-19499 | Light chain variable region ("LC") amino acid sequence |
| Ab 202 | 403 | EVQLVESGGGLVQPGGSLRLSCAASGFTFSSYSMNWVRQAPGKGLEWVSYISSSSS TIYYADSVKGRFTISRDNAKNSLYLQMNSLRAEDTAVYYCARGNTVTTFLDYWGQG TLVTVSS | ADI-19500 | Heavy chain variable region ("HC") amino acid sequence |
| Ab 202 | 404 | DIRLTQSPSSFSASTGDRVTITCRASQGISSYLAWYQQKPGKAPKLLIYAASTLQS GVPSRFSGSGSGTDFTLTISCLQSEDFATYYCQQYYSYPPLTFGGGTKVDIK | ADI-19500 | Light chain variable region ("LC") amino acid sequence |
| Ab 203 | 405 | QVQLVQSGAEVKKPGASVKVSCKASGYAFTNYGVSWVRQAPGQGLEWMGWISV YNGNTNYAQKLQGRVTMTTDTSTSTAYMELRSLRSDDTALYYCARDPPSEGAAGL FDYWGQGTLVTISS | ADI-19501 | Heavy chain variable region ("HC") amino acid sequence |
| Ab 203 | 406 | DIVMTQSPLSLPVTLGQPASFSCRSSQSLVYSDGNTYLSWFQQRPGQSPRRLIYKV SNRDSGVPDRFSGSGSGTDFTLKISRVEAEDVGVYYCMQGTHWPCTFGQGTKVEIK | ADI-19501 | Light chain variable region ("LC") amino acid sequence |

TABLE 5-continued

| Anti-body No. | SEQ ID NO: | Sequence | Clone # (ADI) | Descriptors |
|---|---|---|---|---|
| Ab 204 | 407 | EVQLVESGGGVVQPGGSLRLSCAASGFTFSSDGMHWVRQAPGKGLEWVAFIQYD GTNKYYVDSVKGRFTISRDNSKNTLYLQMNSLRAEDTAVYYCAKDQGFRYSSSWYA FDIWGQGTMVTVSS | ADI-19502 | Heavy chain variable region ("HC") amino acid sequence |
| Ab 204 | 408 | EIVMTQSPDSLAVSLGERATINCKSSQSVLFNSNNKNYLAWYQQKPGQPPKLLIYW ASTRESGVPDRFSGSGSGTDFTLTISSLQAEDVAVYYCQQYYSTPTFGQGTRLEIK | ADI-19502 | Light chain variable region ("LC") amino acid sequence |
| Ab 205 | 409 | QVQLVQSGAEVKKPGASVKVSCKASGYTFTSYYMHWVRQAPGQGLEWMGIINPS GGSTSYAQKFQGRVTMTRDTSTSTVYMELSSLRSEDTAVYYCARDSLVNCSGGSCP GGPDYWGQGTLVTVSS | ADI-19503 | Heavy chain variable region ("HC") amino acid sequence |
| Ab 205 | 410 | SYVLTQPPSVSVSPGQTARITCSGDALPKKYAYWYQQKSGQAPVLVIYEDSKRPSGI PERFSGSSSGTMATLTISGAQVEDEADYYCYSTDSSGNHRVFGGGTKLTVL | ADI-19503 | Light chain variable region ("LC") amino acid sequence |
| Ab 206 | 411 | QVQLVQSGAEVKKPGESLKISCKGSGYSFTNYWIGWVRQMPGKGLEWMGITYPG DSDTRYSPSFQGQVTISADKSISTAHLQWDSLKASDTAMYYCARLRCTGSICYDAFD IWGQGTTVTVSS | ADI-19505 | Heavy chain variable region ("HC") amino acid sequence |
| Ab 206 | 412 | SYVLTQPLSVSVALGQTARITCGGNNIGSKNVHWYQQKPGQAPVLVIYRDNNRPS GIPERFSGSNSGNTATLTISRAQAGDEADYYCQVWDSSTGGDVFGAGTKVTVL | ADI-19505 | Light chain variable region ("LC") amino acid sequence |
| Ab 207 | 413 | QVQLVQSGAEVKKPGASVKVSCKASGYTFTSYGISWVRQAPGQGLEWMGWISAY NGNTNYAQKLQGRVTMTTDTSTSTAYMELRSLRSDDTAVYYCARVRSVGRFGELL YYYYGMDVWGQGTTVTVSS | ADI-19506 | Heavy chain variable region ("HC") amino acid sequence |
| Ab 207 | 414 | DIRLTQSPLSLPVTPGEPASISCRSSQSLLHSNGYNYLDWYLQKPGQSPQLLIYLG SNRASGVPDRFSGSGSGTDFTLKISRVEAEDVGVYYCMQALQTPWTFGQGTKLEIK | ADI-19506 | Light chain variable region ("LC") amino acid sequence |
| Ab 208 | 415 | EVQLVESGGGLVKPGGSLRLSCAASGFTFSSYSMNWVRQAPGKGLEWVSSISSSS YIYYADSVKGRFTISRDNAKNSLYLQMNSLRAEDTAVYYCAREVLTGDYLGWFDPW GQGTLVTVSS | ADI-19507 | Heavy chain variable region ("HC") amino acid sequence |
| Ab 208 | 416 | QSVVTQPPSVSGAPGQRVTISCTGSSSNIGAGYDVHWYQQLPGTAPKLLIYGNSR PSGVPDRFSGSKSGTSASLAITGLQAEDEADYYCQSYDSSHWVFGGGTKLTVL | ADI-19507 | Light chain variable region ("LC") amino acid sequence |
| Ab 209 | 417 | EVQLVESGGGLVKPGGSLRLSCAASGFTFSSYSMNWVRQAPGKGLEWVSSISSSS YIYYADSVKGRFTISRDNAKNSLYLQMNSLRAEDTAVYYCASSRRSLTGDRGGWFD PWGQGTLVTVSS | ADI-19509 | Heavy chain variable region ("HC") amino acid sequence |
| Ab 209 | 418 | QSVLTQPPSVSGAPGQRVTISCTGSSSNIGAGYDVHWYQQLPGTAPKLLIYGNSR PSGVPDRFSGSKSGTSASLAITGLQAEDEADYYCQSYDSSLSGWVFGGGTKLTVL | ADI-19509 | Light chain variable region ("LC") amino acid sequence |
| Ab 210 | 419 | EVQLVESGGGLVKPGGSLRLSCAASGFSLSSYYMNWVRQAPGKGLEWVSSISSSST YINYADSVKGRFTISRDNAKNSLYLQMNSLRAEDTAVYYCARGGSITIFGVVFDSWG QGTLVTVSS | ADI-19510 | Heavy chain variable region ("HC") amino acid sequence |
| Ab 210 | 420 | SYELTQPPSVSGAPGQRVTISCTGTSSNIGAGYDVHWYQQLPGTAPKLLIYVNSNRP SGVPDRFSGSKSGTSASLAITGLQAEDEADYYCQSYDSSLSGGVFGTGTKVTVL | ADI-19510 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 211 | 421 | QITLKESGPTLVKPTQTLTLTCTFSGFSLSTSGVGVGWIRQPPGKALEWLALIYWDD DKRYSPSLKSRLTITKDTSKNQVVLTMTNMDPVDTATYYCAHSVYYDFWSGYYVPN YFDYWGQGTLVTVSS | ADI-19511 | Heavy chain variable region ("HC") amino acid sequence |
| Ab 211 | 422 | DIQMTQSPSSLSASVGDRVTITCRASQGIRNDLGWYQQKPGKAPKRLIYAASSLQS GVPSRFSGSGSGTEFTLTISSLQPEDFATYYCLQHNSYPLTFGGGTKVEIK | ADI-19511 | Light chain variable region ("LC") amino acid sequence |
| Ab 212 | 423 | EVQLLESGAEVKKPGASVKVSCKTSGYTFSNYGVSWVRQAPGQGLEWLGWISAYN GNTNYAQKLQGRVTMTTDSSTSTAYMEVRSLRSDDTAVYYCARDVAPVAASLFDY WGQGTLVTVSS | ADI-20959 | Heavy chain variable region ("HC") amino acid sequence |
| Ab 212 | 424 | DIRLTQSPLSLPVTLGQPASISCRSSQSLEFTDGNTYLSWFQQRPGQSPRRLIYKVS NRDSGVPDRFSGSGSGTDFTLKINRVEAEDVGVYYCMQGIHWPPTFGPGTKVEIK | ADI-20959 | Light chain variable region ("LC") amino acid sequence |
| Ab 213 | 425 | QVQLQQWGAGVLKPSETLSLTCAVNGRSLSGHYWSWIRQTPGKGLEWIGEINNS GGTHYSPSLKSRVIISGDTAKNQLSLKLSSVTAADTAVYYCAKGSAEWYFDLWGRGT LVTVSS | ADI-20960 | Heavy chain variable region ("HC") amino acid sequence |
| Ab 213 | 426 | DIRVTQSPSTLSASVGDRVTITCRASQSVSTWLAWYQQKPGKPPSLLIFKASTLESG VPSRFSGSGSGTEFTLTISSLQPDDFATYYCQQYNTYSPWTFGPGTKVEIK | ADI-20960 | Light chain variable region ("LC") amino acid sequence |
| Ab 214 | 427 | QVQLVESGGGLVKPGGSLRLSCAASGFKFSSYYMHWVRQAPGKGLEWVSSVSGG STYTSYADSVKGRFTISRDNAKHSLFLQLNSLRAEDTAVYHCVRGDYHPSGTSLNWF DPWGQGTLVTVSS | ADI-20961 | Heavy chain variable region ("HC") amino acid sequence |
| Ab 214 | 428 | QPGLTQPPSVSGAPGQRVTISCTGSSSNIGAGYDVHWYKQLPGTVPKLLIYANNNR PSGVPDRFSGSESGTSASLAITGLQAEDEADYYCQSYDSSLNAYVFGTGTKVTVL | ADI-20961 | Light chain variable region ("LC") amino acid sequence |
| Ab 215 | 429 | QVQLVQSGAEVKKPGASVKVSCKASGYTFSHYGLSWVRQAPGQGLEWMGWISA YNHNTNYAQKFQGRVTITTDTSTSTAYLEMRSLRSDDTAVYYCAREPPSDTAAGTG DYWGQGTLVTVSS | ADI-20962 | Heavy chain variable region ("HC") amino acid sequence |
| Ab 215 | 430 | DIVMTQSPLSLSVTLGQPASISCRSSQSLVYSDGNTYLTWFQQRPGQSPRRLIYKVS NRDSGVPDRFSGSGSGTDFTLKISRVEAEDVGVYYCMQGTQWPRTFGQGTKVDIK | ADI-20962 | Light chain variable region ("LC") amino acid sequence |
| Ab 216 | 431 | EVQLVESGGGLAKPGGSLRLSCAASGFTFSHYNMNWVRQAPGKGLEWVSSISSTG FHIYYADSVKGRFVISRDNAENSLHLQMNSLRADDTGLYYCVRAEYYYGSGSAGHY FDSWGQGTLVTVSS | ADI-20963 | Heavy chain variable region ("HC") amino acid sequence |
| Ab 216 | 432 | SYVLTQPPSVSVAPGHTAKITCGGSIIGTKSVHWYQQKPGQAPVLVVYDDSDRPSGI PERLSGSRSGNTATLTITRVEAGDEADYYCQVWDSSSEHAGVFGGGTKLTVL | ADI-20963 | Light chain variable region ("LC") amino acid sequence |
| Ab 217 | 433 | QVQLVQSGAEVKKPGASVKVSCKASGYTFTHYGISWVRQAPGQGLEWMGWISAY NGNTNYAQKLQGRVTMTTDTSTSTAYMEVRSLRYDDTAVYYCARDVPVEAATSPE FWGQGTLVTVSS | ADI-20964 | Heavy chain variable region ("HC") amino acid sequence |
| Ab 217 | 434 | DIVMTQTPLSLPVTLGQPASISCRSSQSLVYSDGNTYLSWFQQRPGQSPRRLIYKVS NRDSGVPNRFSGSGSGTDFTLKISRVEAEDVGVYYCVQNTHWPAYTFGQGTKVEIK | ADI-20964 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 218 | 435 | QVQLVQSGAEVKKPGASVKVSCKASGYNFTNYGISWVRQAPGQGLEWMGWIST SNGNTHYAQKSQGRITLTTDTSTNTAYMEVRSLRSDDTAVYYCAREGPESTYDWY HFDSWGQGTLVTVSS | ADI-20965 | Heavy chain variable region ("HC") amino acid sequence |
| Ab 218 | 436 | QSVVTQPPSVSVAPGQTAKITCGGNNIGSKTVHWYQLKAGQAPVLVVYDDSDRPS GIPERFSGSNSGNTATLTIRRVEAGDEADYFCQVWESASDHWVFGGGTKLTVL | ADI-20965 | Light chain variable region ("LC") amino acid sequence |
| Ab 219 | 437 | EVQLLESGGGLGKPGGSLRLSCAASGFKLSSYYMHWVRQAPGKGPEWVSSISASSS YINYADSVRGRFTVSRDNAKNSLFLQMNSLRVDDTAIYYCARGAPLTNFGMVLDS WGQGTLVTVSS | ADI-20966 | Heavy chain variable region ("HC") amino acid sequence |
| Ab 219 | 438 | QSVLTQPPSVSGAPGQRVTISCTGSGSNIGAGYDVHWYQQVPGRVPKLLIYANNN RPSGVPDRFSGSKSGTSASLAITGLQADDEADYYCQSYDRSLNVVFGGGTKLTVL | ADI-20966 | Light chain variable region ("LC") amino acid sequence |
| Ab 220 | 439 | EVQLLESGGGVVQPGRSVRLSCAASGFSFSSYALHWVRQAPGKGLEWVGVIWYEE SNKYYADPVKGRFTISRDNSKNTLYLQMNSLRDEDTAVYYCARKGVATAGLDYWG QGTLVTVSS | ADI-20967 | Heavy chain variable region ("HC") amino acid sequence |
| Ab 220 | 440 | EIVLTQSPLSLPVTPGEPASISCRSSQSLLNSNGYNYLDWYLQKPGQSPQLLIYLG SNRASGVPDRFSGSGSGTDFTLKISRVEAEDVGVYYCMQALQTPQTFGPGTKVDIK | ADI-20967 | Light chain variable region ("LC") amino acid sequence |
| Ab 221 | 441 | QVQLQQWGAGLLKPSETLSLTCAMYGGSFSDDYWSWIRQPPGKGLEWIGEVNH GGSTNYNTSLKSRVTISADTSKKQFSLKLRSVTAADTAVYFCARGWRYCNATTCY SKAFDIWGQGTMVTVSS | ADI-20968 | Heavy chain variable region ("HC") amino acid sequence |
| Ab 221 | 442 | DIQMTQSPSSLSASVGDRVTITCQASQDIDIYLIWYQQKPGRAPKLLIYDASNLKT GVPSRFSGSGSGTEFTFTINNLQPEDFATYYCQQFHDLPLTFGGGTKLEIK | ADI-20968 | Light chain variable region ("LC") amino acid sequence |
| Ab 222 | 443 | EVQLVESGGGLVKPGGSLRLSCAASGFKFSSYTMNWVRQAPGKGLEWVSSVSASS SYIFYADSVQGRFIISRDNAQNSLYLQMNSLRADDTAVYYCARDQYGPGHYYNPA WFDPWGQGTLVTVSS | ADI-20969 | Heavy chain variable region ("HC") amino acid sequence |
| Ab 222 | 444 | QPVLTQPPSVSGAPGQRVTISCTGTSSNIGAGYDVHWYKQLPGTAPKVLIYGNTNR PSGIPDRFSGSKSGTSASLAITGLKAEDEADYYCQSYDRSGSKVFGTGTKLTVL | ADI-20969 | Light chain variable region ("LC") amino acid sequence |
| Ab 223 | 445 | EVQLLESGGGLVKPGGSLRLSCAVSGFSFSNAWMSWVRQAPGKGLEWVGRIRSKT DGGTTDYAAPVKGRFTISRDDSKNTLYLQMNSLKTEDTAVYYCTTAPRYSTSWYPG YYYYYYMDVWGKGTTVTVSS | ADI-20970 | Heavy chain variable region ("HC") amino acid sequence |
| Ab 223 | 446 | DIQMTQSPSSLSASVGDRVTITCQASQDINFYLNWYQQKPGKAPKLLIYDASNLETG VPSRFSGSVSGTDFTFTISSLQPEDFATYYCQQYDDLPAFGGGTKVEIK | ADI-20970 | Light chain variable region ("LC") amino acid sequence |
| Ab 224 | 447 | EVQLVESGGGLVKPGESLRLSCAASGFTFSDYSMTWIRQAPGKGLLEWIAYINSQS NYMDYADSVKGRFTISRDNAKNSLYLQMNGLRADDTAVYFCARDRRTFVAATLG WFDPWGQGTLVTVSS | ADI-20971 | Heavy chain variable region ("HC") amino acid sequence |
| Ab 224 | 448 | ETTLTQSPATLSVSPGERATLSCRASQSVSNNVAWYQQKPGQAPRVLIYAASTRAT GIPARFSGSESGTEFTLTISSLQSEDFAVYYCQQYNNWPRTFGQGTKLEIK | ADI-20971 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 225 | 449 | QVQLQQWGAGLLRPSETLSLTCAVSGGSFSGHYWSWIRQPPGKGLEWIGGINHS GNTNYSPSLRSRVTMSVDTSRNQFSLMLRSVTAADTAVYFCARNVPNLYGDYPRW FDPWGQGTLVTVSS | ADI-20972 | Heavy chain variable region ("HC") amino acid sequence |
| Ab 225 | 450 | QSVLTQPASVSGSPGQSITISCTGTSSDVGGFNYVSWYQHHPGKAPKLMIYDVNN RPSGASNRFSGSKSGNTASLTISGLQAEDEADYYCSSYRSSDTLYVFGTGTKVTVL | ADI-20972 | Light chain variable region ("LC") amino acid sequence |
| Ab 226 | 451 | EVQLLESGGGLVKPAGSLRLSCAASGFSFSSYYMNWIRQAPGKGLEWVSDISGGSS YTNYADSVKGRFTVSRDNAKNSVYLQMNSLRGEDTAVYYCARGASTAATYTPTFD YWGQGILVTVSS | ADI-20973 | Heavy chain variable region ("HC") amino acid sequence |
| Ab 226 | 452 | QPVLTQPPSVSGAPGQRVTISCTGSSSNIGAGYDVHWYQQLPGTAPKLLMFGNNN RPSGVPDRFSGSKSGTSASLAITGLRPEDEADYYCQSYDRRLTVVFGGGTKLTVL | ADI-20973 | Light chain variable region ("LC") amino acid sequence |
| Ab 227 | 453 | EVQLVESGGGLVKPGGSLRLSCAASGFSFSSYQINWVRQAPGKGLEWVSSISGGSS YTDYADSIKGRFTISRDNAKKSAFLQMKSLRADDTAVYYCARALMATAGGLAFDIW GQGTMVTVSS | ADI-20974 | Heavy chain variable region ("HC") amino acid sequence |
| Ab 227 | 454 | QPVLTQPPSVSGAPGQRVTISCTGSGSNIGAGYDVHWYQQVPGTAPKLLILRNTNR PSGVPDRFSGSKSGTSASLAITGLQAEDEADYYCQSYDRSLSVVFGGGTKLTVL | ADI-20974 | Light chain variable region ("LC") amino acid sequence |
| Ab 228 | 455 | QVQLVESGTHVKKPGASVKVSCEASDDTFNNKGIVWVRQAPGQGLEWMGWIRP NNGNTKYAQKFQGRVTMTTDASTNTAYMELRSLRSGDTAVYYCAREQFKWNDFY FDYWGQGILVTVSS | ADI-20975 | Heavy chain variable region ("HC") amino acid sequence |
| Ab 228 | 456 | SYELMQPPSVSVAPGQTATITCGGSNIGSETVHWYQQKPGQAPVLVVHDDTDRPS GIPERFSGSNSGNTATLTISGVEAGDEADFYCQVRDSRTDDVVFGGGTKLTVL | ADI-20975 | Light chain variable region ("LC") amino acid sequence |
| Ab 229 | 457 | QVQLVESGGDLVQKGGSLRLSCAASGFTFDNYAMTWIRQAPGQGLEWVSTVSGF VLGTGYTTYYADSVKGRFTISRDSSKNTVYLQLNSLRAEDTAVYYCAKCAATRNEC LWDYLQQWGQGTTVTVSS | ADI-20976 | Heavy chain variable region ("HC") amino acid sequence |
| Ab 229 | 458 | EIVMTQSPSSLSASVGDRVTITCRASQSVSIYLNWYQQKGGKAPKLLIYGASALQR GVPSRFSGSGSGTDFTLTITSLQPEDFATYFCHQSYSAPQTFGQGTKVDIK | ADI-20976 | Light chain variable region ("LC") amino acid sequence |
| Ab 230 | 459 | EVQLVESGGGLVQPGGSLRLSCAASGFTFTNYAMSWVRQAPGKGLEWVSGISGS GGSTYYADSVKGRFTISRDNSKNTLYLQMNSLRAEDTAVYYCAKDQGYAVVVADA TRNLPPRRYGMDVWGQGTTVTVSS | ADI-20977 | Heavy chain variable region ("HC") amino acid sequence |
| Ab 230 | 460 | EIVLTQSPGTLSLSPGERATLSCRASHSVSSSYLAWYQQKPGQAPRLLIYGASSRA TGIPDRFSGSGSGTDFTLTISRLEPEDFAVYYCQQYGSSPPLTFGGGTKVDIK | ADI-20977 | Light chain variable region ("LC") amino acid sequence |
| Ab 231 | 461 | EVQLVESGAEVKKPGASVKVSCKASGYTFGNYGISWVRQAPGQGLEWMGWISAY NGNSNYAQKFQGRVTMTTDTSASTAYMEVRSLRSDDTAVYYCARDVPVTAARLLD YWGQGTLVTVSS | ADI-20978 | Heavy chain variable region ("HC") amino acid sequence |
| Ab 231 | 462 | DIVLTQTPLSLPVTLGQPASISCRSSQSLVYSDGNTYLSWFQQRPGQSPRRLIYKV SNRDSGVPDRFSGSGSGTDFTLKISRVEAEDVGVYYCMQATDWLGYTFGQGTKLEI K | ADI-20978 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 232 | 463 | EVQLQESGPGLVKPSETLSLTCTVSGGSLRSYYWSWIRQPPGKGLEWIGNIYYGGS TNYNSSLKGRVTISIDTSKNQFSLRLSSVTAADTAVYYCARDGLFPMGEWDYWGQG ILVTVSS | ADI-20979 | Heavy chain variable region ("HC") amino acid sequence |
| Ab 232 | 464 | QSALTQPASVSGSPGQSITISCTGTSNDVGDYNYVSWYQQHPGEAPKLMIYEVTNR PSGVSDRFSGSKSGNTASLTISGLQAEDEADYYCSSYTSSTSVVFGGGTQLTVL | ADI-20979 | Light chain variable region ("LC") amino acid sequence |
| Ab 233 | 465 | QVQLQESGPGLVKPSQTLSLTCSVSGGSVSSGDYYWTWIRQPAGKGLEWIGRIYNS GGTDYSPSLKSRVTISVDTSKNQFSLKLSSVTAADTAVYYCARGRGYYESPWGQGTL VTVSS | ADI-20980 | Heavy chain variable region ("HC") amino acid sequence |
| Ab 233 | 466 | EIVLTQSPATLSLSPGERATLSCRASQSVGIYIGWYQQKPGQAPRLLMYDASNRATG IPDRFSGSGSGTDFSLTISSLEPEDFAVYYCQLRSKWLTFGPGTKVEIK | ADI-20980 | Light chain variable region ("LC") amino acid sequence |
| Ab 234 | 467 | QVQLQESGPRLVKPSETLSLTCTVSGDSISSRNYFWAWIRQPPGKGLEWIGTIYYSG NTYSNPSLKSRVTISVDTSKKQFSLNLSSVTAADTAVYYCARGAYGGDAFDIWGQG TVVTVSS | ADI-20981 | Heavy chain variable region ("HC") amino acid sequence |
| Ab 234 | 468 | DIRVTQSPSSVSASVGDRVTITCRASQGIGTWLAWYQQKPGKAPHLLIYAASRLQS GVPSRFSGSGSGTDFTLSISSLHPEDFATYYCQQAYAFPRTFGQGTKVEIK | ADI-20981 | Light chain variable region ("LC") amino acid sequence |
| Ab 235 | 469 | EVQLVESGPGLVKPSQTLSLTCSVSGVSISRGSYYWSWIRQPAGGGLEWIGRIYTSG VTRYNPSLESRVTISLDSSQNQFFLRLSSVTAADTAVYYCATRESASYSSGPDAFDI WGQGTTVTVSS | ADI-20982 | Heavy chain variable region ("HC") amino acid sequence |
| Ab 235 | 470 | DIQMTQSPSTLSASVGDRVIITCRASQSVNSWLAWYQQKPGKAPKLLIYQASSLESG VPSRFSGSGSGTEFTLTINSLQPDDFATYYCQQYKTFSRPFGQGTKVEIK | ADI-20982 | Light chain variable region ("LC") amino acid sequence |
| Ab 236 | 471 | EVQLVESGGALVQPGGSLRLSCSASGFTFSSYAMHWVRQAPGKGLEYVSAINNFG DKTYYTDSVEGRFTISRDNSKKTLYLQMSSLRPEDTAVYYCVKDRGYCSSPSCYAVP YYYFYGMDVWGQGTTVTVSS | ADI-20983 | Heavy chain variable region ("HC") amino acid sequence |
| Ab 236 | 472 | EIVMTQSPSSLSASVGDRVTITCQASQGISNYLHWYQQKPGKAPKLLIYDASNLEAG VPSRFSGSGAGTDFTFTISSLQPEDVATYYCQHYNNLPFTFGPGTKVDIK | ADI-20983 | Light chain variable region ("LC") amino acid sequence |
| Ab 237 | 473 | EVQLLETGAEVKKPGASVKVSCHVSGYGLTDLSMHWVRQAPGKRLQWMGSFDP QYGETIDTQNFQGRVTMTVDTSTATLYMQLSGLRSEDTAMYYCATPQSTGALDN WGQGTLVTVSS | ADI-20984 | Heavy chain variable region ("HC") amino acid sequence |
| Ab 237 | 474 | DIRVTQSPSSLSASVGDRVTITCRASQSISSYLSWYQQKPGKAPRLVIFAASNLQSG VPSRFSGTGSSRFSDSGSWTDFTLTISSLQPEDFAIYYCQQTYITPFTFGQGTKVDI K | ADI-20984 | Light chain variable region ("LC") amino acid sequence |
| Ab 238 | 475 | EVQLVESGGGLVQPGGSLRLSCVASGFTFSNYWMNWVRQAPGKGLEWVANIKE DGSEIKYVDSVKGRFTISRDNAKNSLYLQMNSLRAEDTAVYYCARTEDSSSWFVAI DYYNYMDVWGKGTTVTVSS | ADI-20986 | Heavy chain variable region ("HC") amino acid sequence |
| Ab 238 | 476 | DIQVTQSPGTLSLSPGERATLSCRASQTVSSSYLAWYQQKPGQAPRLLFYGASSRA TDIPDRFSASGSGTDFTLTIHRLEPEDFAVYYCQLYGRSPPYTFGQGTKVEIK | ADI-20986 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 239 | 477 | QVQLVQSGGGVVHPGRSLRLSCAASGFSFSDYGMHWVRQAPGKGLEWVAVIWY DGINKYYADSVKGRFAISRDNSKNTLYLQMNSLRAGDTAVYYCARGGIAAAQRYFD YWGQGTLVTVSS | ADI-20987 | Heavy chain variable region ("HC") amino acid sequence |
| Ab 239 | 478 | ETTLTQSPGTLSLSPGERATLSCRASQTVSSSNLAWYQQKPGQAPRLLIYGASSRA TGIPDRFSGSGSGTDFTLTISRLEPEDFAVYYCQQSGTSFGQGTKVDIK | ADI-20987 | Light chain variable region ("LC") amino acid sequence |
| Ab 240 | 479 | EVQLVESGGEVKKPGASVKVSCKTSGYPFSNYGISWMRLAPGQGLEWMGWISSY NGNTYYTKKFQGRVSMTTDTSTSTAYMELRSLRSDDTAVYYCARDVPVIAAHTFEY WGQGTLVTVSS | ADI-20988 | Heavy chain variable region ("HC") amino acid sequence |
| Ab 240 | 480 | ETTLTQSPLSLPVTLGQPASISCRSSESLVYSDGNTYLSWFQQRPGQSPRRIIYKV SNRDSGVPDRFSGSGSGTDFTLKISRVEAEDVGVYYCMQATHWPRDTFGQGTKVDI K | ADI-20988 | Light chain variable region ("LC") amino acid sequence |
| Ab 241 | 481 | EVQLLESGPGLVKPSGTLSLTCAVSGGSIINSNWWSWVRQSPGKGLEWIGDIYHSG STTYNPSLKSRVTISVDRSKNQYSLRLTSVTAADTAVYYCAKIGPDNRSGPDYYYF MDVWGKGTTVTVSS | ADI-20989 | Heavy chain variable region ("HC") amino acid sequence |
| Ab 241 | 482 | EIVLTQSPSSLPASVGDRVTISCRASQSISNYVYWYQQKPGKAPKLLIYAASSLQS GVPSRFSGSGSGTDFTLSISSLQFEDFATYFCQQSYSTPPTFGQGTKLEIK | ADI-20989 | Light chain variable region ("LC") amino acid sequence |
| Ab 242 | 483 | EVQLVESGGGVVQPGRSLRLSCSASGFPFHSYAMHWVRQAPGKGLEWVAGIWYE GSSESYADSVKGRLTISRDNSRNTLYLQMNSLRVEDTAVYYCARRGSFSGFDSWGQ GSLVTVSS | ADI-20990 | Heavy chain variable region ("HC") amino acid sequence |
| Ab 242 | 484 | DIVMTQSPLSLPVTPGEPASISCRSSQSLLHSNGYNYLDWYLQKPGQSPQLLISLG SNRASGVPDRFSGSVAGTDFTLKISRVEAEDVGVYYCMQSSQTPYTFGQGTKVDIK | ADI-20990 | Light chain variable region ("LC") amino acid sequence |
| Ab 243 | 485 | EVQLVESGGNLVKPGGSLRLSCAASGFTFSGYYMSWIRQAPGKGLEWISDISGGSS YTNYADSVKGRFTISRDNAKNSLYLQMNSLRAEDTAMYYCARVEYDTTGPFHFDY WGQGTLVTVSS | ADI-20991 | Heavy chain variable region ("HC") amino acid sequence |
| Ab 243 | 486 | QPVLTQPPSVSGAPGQRVTISCTGSSSNIGAGYDVHWYQQLPGTAPKLLIYGNNNR PSGVPDRLSGSKSGTSASLAITGLQAEDEADYYCQSYDSSLSGYVFGTGTKVTVL | ADI-20991 | Light chain variable region ("LC") amino acid sequence |
| Ab 244 | 487 | EVQLVESGGGLVQPGGSLRLSCVVSGFTFKSYWMTWVRQAPGKGLEWVANIKED GSEKYYVDSVKGRFTISRDNARNSLFLQMNSLRADDTAVYYCARNLEVSNEFYVVT DNYYLMDVWGQGTTVTVSS | ADI-20992 | Heavy chain variable region ("HC") amino acid sequence |
| Ab 244 | 488 | DIQLTQSPSSLSASVGDRVTITCRASQSISFFLNWYRQKPGKAPKLLIYAASTLQS GVPSRFSGSGSGTDFTLTISSLQPEDFASYYCQQSYSTPHTFGQGTKVEIK | ADI-20992 | Light chain variable region ("LC") amino acid sequence |
| Ab 245 | 489 | EVQLVESGGGVVQPGRSLRLTCAASGFPFSSYAMHWVRQAPGKGLEWVAVTWY DGPNRDYADSVKGRFTVSRDNSKNTLYLQMTSLRADDTAVYYCARRGSWGSFDY WGQGTLVTVSS | ADI-20993 | Heavy chain variable region ("HC") amino acid sequence |
| Ab 245 | 490 | DIVMTQSPLSLSATPGEPASISCRPSQSLLHSNGYNYLEWYLQKPGQSPQLLIYL GSNRASGVPDRFSGGGSGTDFTLRISRVEADDVGVYYCMQASQTPYTFGQGTKVEI K | ADI-20993 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 246 | 491 | QVQLVQSGAEVKKPGASVKVSCKASGYTFSSNVIGWVRQAPGQGLEWMGWIST NNGNTKYGQKFQGRVTMTTDPSTSTAYMELRSLRSDDTAFYYCARESLGMGGFYF DYWGQGTLVTVSS | ADI-20994 | Heavy chain variable region ("HC") amino acid sequence |
| Ab 246 | 492 | QPVLTQPPSVSVAPGQTARITCGGDNIGSKSVHWYQQKPGQAPVLVVYDDSDRPS GIPERFSGSNSGNTASLTISRVEAGDEADYCCQVWDSGSDLWVFGGGTKLTVL | ADI-20994 | Light chain variable region ("LC") amino acid sequence |
| Ab 247 | 493 | QVQLVESGPALVKPTQTLTLTCTFSGFSLTTRGMCVSWIRQPPGKALEWLARIDWD DDKYYSTSLKTRLTISKDTSKNQVVLTMTNMDPVDTATYYCARASTLTTAGYYLHY KDVWGNGTTVTVSS | ADI-20996 | Heavy chain variable region ("HC") amino acid sequence |
| Ab 247 | 494 | DIRMTQSPSSLSASVGDRVTITCRASQSIGTYLNWFQQKPGKAPNLLIYAASILHS GVPSRFSGSGSGTDFTLTIRTLQPEDFATYYCQQSYPTVTFGQGTKVEIK | ADI-20996 | Light chain variable region ("LC") amino acid sequence |
| Ab 248 | 495 | EVQLVESGGGVVQPGRSLRLSCAASGFPFNSYGMHWVRQAPGKGLEWLAVIYFD ESTAYYADSVKGRFTISRDNSKSTLYLQMNSLRAADTAIYYCTTTVMIPYGGVFWG QGTLVTVSS | ADI-20997 | Heavy chain variable region ("HC") amino acid sequence |
| Ab 248 | 496 | EIVMTQSPGTLSLSPGDRATLSCRASQSVGSTHFAWYQQKPGQAPRLLIYAASIRAT GIPDRFSGGGSGTDFTLTISRLAPEDFAVYYCQQYGSTPITFGQGTRLEIK | ADI-20997 | Light chain variable region ("LC") amino acid sequence |
| Ab 249 | 497 | QVQLVQSGGGVVQPGRSLRLSCAASGFTLSTYGMHWVRQAPGKGLEWVAVIYYD ESNKFYADSVQGRFTISRDDSKNTLFLQMNSLRAEDTAVYYCARESRPRGYSYSDFD SWGQGTLVTVSS | ADI-20998 | Heavy chain variable region ("HC") amino acid sequence |
| Ab 249 | 498 | QPGLTQPRSVSGSPGQSVTISCTGTSSDVGTFNYVSWYQQHPGKAPKLMIYDVNQ RPSGVPDRFSGSKSGNTASLTISGLQAEDEADYYCCAYAGYYSFGGGTKLTVL | ADI-20998 | Light chain variable region ("LC") amino acid sequence |
| Ab 250 | 499 | QVQLQESGPVLVKPSETLSLTCTVSGGSITSSAYYWGWIRQPPGKGLEWIGSVSYSG TTSYTPSLKSRVTISGDASKEQFSLNLRSVTAADTAVYYCARQTKAFGRRDYGMDV WGQGTTVTVSS | ADI-20999 | Heavy chain variable region ("HC") amino acid sequence |
| Ab 250 | 500 | QPVLTQPPSVSAAPGQKVTISCSGSNSNIGSNFVSWYQQLPGTAPKLLIYENNKRPS GIPDRFSGSKSGPSATLGITGLQTEDEADYYCGTWDTGLSAHWVFGGGTKLTVL | ADI-20999 | Light chain variable region ("LC") amino acid sequence |
| Ab 251 | 501 | EVQLVESGPVLVKPRGTLTLTCTVSGFSLSDARMGVSWIRQPPGKALEWLAHIFWD DEKSYSTSLKNRLTISKDTSRGQVVLRMTNMDPVDTGTYFCARVNTYHSGGYYLYY FDVWGQGTLVTVSS | ADI-21000 | Heavy chain variable region ("HC") amino acid sequence |
| Ab 251 | 502 | EIVLTQSPSSLSASVGDRVTITCRASQIIASYLNWYQQKPGQAPKLLIYAASSLQS GVPSRFSGSGSGTDFTLTISSLQPEDFATYYCQQSYSTRMYTFGQGTKVEIK | ADI-21000 | Light chain variable region ("LC") amino acid sequence |
| Ab 252 | 503 | EVQLVESGPGLVKPSETLSLTCTVSGGSISDIDYYWGWIRQPPGKGLEWIGSIYYS GSTYYNPSLESRVTISVDTSKNQFSLKLRSVSAADTALYHCARHGPPWVVTAIRGH AFDVWGQGTTVTVSS | ADI-21001 | Heavy chain variable region ("HC") amino acid sequence |
| Ab 252 | 504 | DIRVTQSPDSLAVSLGERATINCKSSQSILYSSNNKNYLAWYQQKPGQPPKLLIYWA STRESGVPDRFSGSGSGTDFTLTISSLQAEDVAVYYCQEYYSYPPMYTFGQGTKVDI K | ADI-21001 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 253 | 505 | QVQLVESGPGLVKPSGTLSLTCAVSGDSINSGNWWNWVRQAPGKGLEWIGEIYH RGTSNYNPSLKSRVTISVDQSKNQFSLKVTSLTAADTAIYYCARARGYSSGPSYY YLDVWGKGTLVTVSS | ADI-21002 | Heavy chain variable region ("HC") amino acid sequence |
| Ab 253 | 506 | EIVMTQSPSSLSASVGDRVTISCRASQSISTYLNWYQQKPGKAPKVIIYGASNLQS GVPSRFSGSGSGTDFTLTISSLQPEDFATYYCQKSFNPCVFGQGTKVDIK | ADI-21002 | Light chain variable region ("LC") amino acid sequence |
| Ab 254 | 507 | QVQLQQWGAGLLKPSETLSLSCAVSGGSFSGYYWTWIRQPPGKGLEWIGEINHSG STNYNPSLKSRVTISVDTSKNQFSLKLSSVTAADTAVYYCARARYFDYLAHWSFDL WGRGTLVTVSS | ADI-21003 | Heavy chain variable region ("HC") amino acid sequence |
| Ab 254 | 508 | GIQMTQSPLSLPVTPGEPASISCRSSQSLLHSNGYKYLDWYLQKPGQSPQLLIYLG SDRASGVPDRFSGSGSGTDFTLKISRVEAEDVGVYYCMQALQTPWTFGQGTKLEIK | ADI-21003 | Light chain variable region ("LC") amino acid sequence |
| Ab 255 | 509 | QVQLQESGGGVVQPGRSLTLSCAASGFTFSSYGMHWVRQAPGKGLDWVAEIWY DGSNKYYVDSVKGRFTISRDNSKNTLYLQMKSLRAEDTAIYYCARDGGYESPFFDK WGQGTLVTVSS | ADI-21004 | Heavy chain variable region ("HC") amino acid sequence |
| Ab 255 | 510 | EIVMTQSPDSLGVSLGERATINCKSSQSLYTSNHENSLAWYQQKPGQPPRLLIYWA STRELGVPDRFSGSGSGTDFTLTISSLQAEDVAVYYCQQYHTTPLTFGPGTKVEIK | ADI-21004 | Light chain variable region ("LC") amino acid sequence |
| Ab 256 | 511 | EVQLVESGGAVVQPGGSLRLSCVASGLAFDEYTMHWVRQSSAKGLEWISLISWNG GITYYADSVKGRFTISRDNSKNSLYLQMNSLRTEDTATYFCARLGYGSGSDYGDDY WGQGTLVTVSS | ADI-21005 | Heavy chain variable region ("HC") amino acid sequence |
| Ab 256 | 512 | ETTLTQSPGTLSLSPGERATLSCRASQSVSNNYLAWYQQKPGQAPRLLIHGASTRVT GIPARFSGSGSGTDFTLTISRLEPEDFAVYYCHQYHSSPRTFGQGTKVDIK | ADI-21005 | Light chain variable region ("LC") amino acid sequence |
| Ab 257 | 513 | QVTLKESGPTLVKPTQTLTLTCTFSGFSLSISGVGVGWIRQPPGKALEWLAVMYWD DDKRYSPSLKTRLTITKDTSKNQVVLTMTNMAPVDTAIYYCAHLWFGEAAFDPWG QGTLVTVSS | ADI-21006 | Heavy chain variable region ("HC") amino acid sequence |
| Ab 257 | 514 | EIVLTQSPLSLPVTLRQTASISCRSGQSLLYSDGNTYLNWFQQRPGQSPRRLISIVS KRDSGVPDRFSGSGSGTDFTLKISRVEAEDVGVYYCMQGTHWPYTFGQGTKVEIK | ADI-21006 | Light chain variable region ("LC") amino acid sequence |
| Ab 258 | 515 | QVQLVQSGADVKKPGASVKVSCKSSGYTFSNHSMHWVRQAPGQGLEWMGRIHP SSGTTTYAQKFQGRVTMTRDTSTSTVYMEVSSLRSEDTAVYYCARSPFFDFDFWG QGTMVTVSS | ADI-21007 | Heavy chain variable region ("HC") amino acid sequence |
| Ab 258 | 516 | SYVLTQPHSVSESPGKTVTISCTRSSGSIASNYVQWYQQRPGSAPTSVIYEDNQRPS GVPDRFSGSIDSTSNSASLTISGLKTEDEADYYCQSYYSSGWVFGGGTKLTVL | ADI-21007 | Light chain variable region ("LC") amino acid sequence |
| Ab 259 | 517 | QVQLQESGAGLLKPSETLSLTCTVYGGTFSGYHWNWIRQPPGKGLEWIGEINHRE NTDYNASLESRVTISVDTSKRQFSLKMNSVTVADTAVYYCARGIQVLTNLGTEVRVH QFLDLWGRGTLVTVSS | ADI-21008 | Heavy chain variable region ("HC") amino acid sequence |
| Ab 259 | 518 | DIVLTQTPATLSLSPGERATLSCRASQSVSTYLAWYQQKPGQAPRLLIYDASNRAA GIPARFSGSGSGTDFTLTISSLEPEDFAVYYCQQRTNWLPLTFGGGTKVDIK | ADI-21008 | Light chain variable region ("LC") amino acid sequence |
| Ab 260 | 519 | QVQLVQSGAEMKTPGASVKVSCKASGYSFSNYGFTWVRQAPGQGLEWMGWIS GYSAKTNYAQDLQGRVTMTIDTSTSTSYMELRSLRSDDTAVYYCARDPLGYFGSGT | ADI-21009 | Heavy chain variable region |

TABLE 5-continued

Informal Sequence Listing

| Antibody No. | SEQ ID NO: | Sequence | Clone # (ADI) | Descriptors |
|---|---|---|---|---|
| | | YRGGAFDFWGQGTTVTVSS | | ("HC") amino acid sequence |
| Ab 260 | 520 | QSALTQPASVSGSPGQSITLSCTGTNNDVGSYHLVSWYQQYPGKAPKLVIYEVTKR PSGVSNRFSGSKSGNTASLTISGLQPEDEADYYCCSYAGDRRIFGGGTKVTVL | ADI-21009 | Light chain variable region ("LC") amino acid sequence |
| Ab 261 | 521 | EVQLVESGGGVVQPGRSLRLSCAASGFSFSTYGMHWVRQAPGKGLEWVGVIWY DETTKYYADSVKGRFSISRDNSKNMVYVQMNSLRADDTALYYCAREVWGGVFDI WGQGTTVTVSS | ADI-21010 | Heavy chain variable region ("HC") amino acid sequence |
| Ab 261 | 522 | DIQMTQSPATLSASVGDRVTITCRASQNIVTWLAWYQQKPGKAPNLLIYKASSLES GVPSRFSGSGSGTEFTLTISSLQPDDFATYYCQHYNSYSGAFGQGTKVDIK | ADI-21010 | Light chain variable region ("LC") amino acid sequence |
| Ab 262 | 523 | QVQLQESGPGLVKPSETLSLSCTASGDSISDYYWSWIRQPPGKGLEWIGFVSDTWG TNYSPSLTSRVAISLDTSRSQVSLRLRSVTAADTAVYYCVRTHLYDRGGYYLYYFD YWGQGTLVTVSS | ADI-21011 | Heavy chain variable region ("HC") amino acid sequence |
| Ab 262 | 524 | DIRMTQSPPSLSASVGDRVTITCRASQRIASYLNWYQQKPDTAPKLLIYAASNLQT GVPSRFSGSGSGTDFTLTISSLQPEDFATYYCQQSYSTPYTFGQGTKLEIK | ADI-21011 | Light chain variable region ("LC") amino acid sequence |
| Ab 263 | 525 | QVQLVQSGPAVVKPTQTLTLTCSFSGFSLSTSRMSVSWIRQPPGKALEWLARIDWD GDKYYSTSLKSRLTISKDTSKNQVVLTMTNMDPVDTATYYCARGSYYVSSGYYLNY FDYWGQGTLVTVSS | ADI-21012 | Heavy chain variable region ("HC") amino acid sequence |
| Ab 263 | 526 | DIRMTQSPSSLSASVGDRVTITCRTSQTIASYLNWYQQKPGKAPNLLIYAASILQT GVPSRFSGSGSGTDFTLTISSLQPEDFATYYCQQSYGTPQTFGQGTKVEIK | ADI-21012 | Light chain variable region ("LC") amino acid sequence |
| Ab 264 | 527 | QVQLQESGPGVVKPSETLSLTCTVSGGSISNTHSYWGWIRQSPGKGLEWIGSIYYT GSTYYNPSFRSRVTLSVDTSKNQFSLKLSSVTAADTAVYYCAAPDYFVLTDYKSTF DYWGRGALVTVSS | ADI-21013 | Heavy chain variable region ("HC") amino acid sequence |
| Ab 264 | 528 | DIVMTQSPGTLSLSPGGRATLSCRASQSVGSSSLAWYQQKPGQAPRLLIYGASSRA AGIPDRFSGSGSGTDFTLTINRLEPEDFAMYYCQQYGSSPLTFGGGTKVEIK | ADI-21013 | Light chain variable region ("LC") amino acid sequence |
| Ab 265 | 529 | QVQLQESGPGLVKPSETLSLICTVSGGSISNYYWSWIRQPPGKGLEWIGYVWFGTT KYNPSLKNRVTISVDTGKNQVSLKVNSVTAADTAIYYCARDSSIWYRGAFEIWGQG TTVTVSS | ADI-21014 | Heavy chain variable region ("HC") amino acid sequence |
| Ab 265 | 530 | DIRLTQSPSSLSASVGDRVTITCQASQDISNHLNWYQQRPGKAPELLIYDASTLET GGPSRFSGSGSGTDFTLTISSLQPEDFADYYCQQYDNLPVTFGGGTKVDIK | ADI-21014 | Light chain variable region ("LC") amino acid sequence |
| Ab 266 | 531 | QVQLVQSGAEVKKPGASVRVSCKVPGNTLSDLSMHWVRHTPGEGLEWMGSFDP EYGETIPAQRFQGRVTMTEDTSTDTAYMELTSLRFEDTAVYYCAAPHASGALQHW GQGTLVTVSS | ADI-21015 | Heavy chain variable region ("HC") amino acid sequence |
| Ab 266 | 532 | DIVMTQSPSSLSASVGDRVTITCRASQIISAYLNWYQQKAGKAPKLLIYAASSLQS GVPSRFSGSGSGTDFTLTISSLQPEDFATYYCQQTYITPFTFGQGTKLEIK | ADI-21015 | Light chain variable region ("LC") amino acid sequence |
| Ab 267 | 533 | QVQLVESGTEVKKPGASVKVSCKASGYTFTNYGITWVRQAPGQGLEWMGCISGY NGNTNYAQNLQGRVTMTTDTSTNTAYMELRSLISDDTAVYYCARDTGLTAAALLD YWGQGTLVTVSS | ADI-21017 | Heavy chain variable region ("HC") amino acid sequence |

TABLE 5-continued

Informal Sequence Listing

| Antibody No. | SEQ ID NO: | Sequence | Clone # (ADI) | Descriptors |
|---|---|---|---|---|
| Ab 267 | 534 | DIVLTQSPLSLPVTLGQPASISCRSSQSLVYSDGNTYLSWFQQRPGQSPRRLIYKV SNRDSGVPDRFGGSGSGTYFTLKISRVEAEDVGIYYCMQAIHWPLTFGGGTKVEIK | ADI-21017 | Light chain variable region ("LC") amino acid sequence |
| Ab 268 | 535 | EVQLLESGGGLVKPGGSLRLSCAGSGFTLSSYGMNWVRQAPGQGLEWISSISSSS YINYADSVKGRFTISRDNAQNSLYLQLNSLRAEDTAVYYCARGGLGYDYGLGSYTY ADYWGQGTLVTVSS | ADI-21018 | Heavy chain variable region ("HC") amino acid sequence |
| Ab 268 | 536 | QSVVTQPPSVSGAPGQRVTISCTGSSSNTGAGYDIHWYQQLPGTGPKLLIYGNKNR PSGVPDRFSGSKSGTSASLAITGLQAEDEADYYCQSYDSSLSGWVFGGGTKVTVL | ADI-21018 | Light chain variable region ("LC") amino acid sequence |
| Ab 269 | 537 | EVQLLESGGGLVRPGGSLRLSCAVSGFTFSGNALTWIRRAPGKGLEWVSTIGDSGG GSYYADSVKGRFTISRDNSKSTLYLQMNSLTAEDTAVYYCARDPYGDYRDYYGIDV WGQGTTVTVSS | ADI-21019 | Heavy chain variable region ("HC") amino acid sequence |
| Ab 269 | 538 | EIVMTQSPLSLPVTPGEPASISCRSSQSLRHSNGYNYVDWYLQKPGQSPQLLIYLGS NRASGVPDRFRGSGSGTDFTLKISRVEAEDVGVYYCMQALQTPLTFGQGTKVEIK | ADI-21019 | Light chain variable region ("LC") amino acid sequence |
| Ab 270 | 539 | QVQLQQWGAGLLKPSETLSLTCAVHGGSFSGFYWSWIRQSPGKGLEWIAEINDSG NTNHNPSLKSRVTISIDTSKNQFSLNVSSVTAADTAVYYCAKNGGGHHYVGTLRFRS RAFDIWGQGTMVTVSS | ADI-21021 | Heavy chain variable region ("HC") amino acid sequence |
| Ab 270 | 540 | EIVMTQSPSTLSASVGDRVTITCRASQSIGNRLAWYQQKPGKAPKLLISLASGLET GVPSRFSGSGSGTEFTLTITSLQPDDFATYYCQQYSSYGTFGQGTKLEIK | ADI-21021 | Light chain variable region ("LC") amino acid sequence |
| Ab 271 | 541 | EVQLVETGPGLVKPSETLSLTCSVSGGSISSYYWSWLRQPPGKGLEWIGYIYNSGRT NYNPSLRSRVTISVDTSQNQFSLRLGSVTAADTAVYYCARGGAGDDLLRGSYRYLNF WGQGTLVTVSS | ADI-21022 | Heavy chain variable region ("HC") amino acid sequence |
| Ab 271 | 542 | QSVLTQPPSVSVAPGQTARITCGGNNIGSKSVHWYQQKPGQAPVLVVYDDTERPS GIPERISGSNSGNTATLTISRVEAGDEADYYCQVWDSSSDHPDLLFGGGTKLTVL | ADI-21022 | Light chain variable region ("LC") amino acid sequence |
| Ab 272 | 543 | EVQLVESGGGLVKPGGSLRLSCAASGFRFSSYGMHWVRQAPGRGLEWVSSITAGS SYMDYADSVKGRFSISRDNAKTSLYLQMNSLRAEDTAIYYCARENYDTGRGLNWF DPWGQGTLVTVSS | ADI-21023 | Heavy chain variable region ("HC") amino acid sequence |
| Ab 272 | 544 | QSVVTQPPSVSGAPGQRVTISCTGSSSNIGAGYDVHWYRQLPGTAPEVLIYGNNN RPSGVPDRFSGSKTGTSASLAITGLLAEDGADYYCQSYDRSQLWVFGGGTQLTVP | ADI-21023 | Light chain variable region ("LC") amino acid sequence |
| Ab 273 | 545 | EVQLVESGGGLVRPGGSLRLSCEASGLKLSGYSMNWVRQAPGKGLEWVSSISASSS YIHYADSLKGRFTISRDNAKNSLYLQMNSLRAEDTAVYYCVASWLTPGWFDPWGQ GTLVTVSS | ADI-21025 | Heavy chain variable region ("HC") amino acid sequence |
| Ab 273 | 546 | QPVLTQPPSVSGAPGQTVTISCTGSSSNIGAGYDVHWYQQLPGTAPKLLIYGNTNR PSGVPDRFSGSKSGTSASLAVTGLQAEDEGDYYCQSYDSSLSGSAFGGGTKLTVL | ADI-21025 | Light chain variable region ("LC") amino acid sequence |
| Ab 274 | 547 | QVQLVQSGPGLVKPSQTLSLTCTVSGVSISSGGFYWSWIRQHPGKGLEWIGHIYYS RSTYYNPSLKSRVTMSLNMSKNQFSLRLSSVTAADTAVYYCARERREWLHGELDY WGQGTTVTVSS | ADI-21026 | Heavy chain variable region ("HC") amino acid sequence |

TABLE 5-continued

Informal Sequence Listing

| Antibody No. | SEQ ID NO: | Sequence | Clone # (ADI) | Descriptors |
|---|---|---|---|---|
| Ab 274 | 548 | DIQMTQSPDSLAVSLGEGATINCKSSQSVLDSSKNKNYLAWYQQRPGQPPKLLISW<br>ASTRESGVPDRFSGSGSGTDFTLTISSLQAEDVAVYSCQQYFSPPATFGQGTKLEI<br>K | ADI-21026 | Light chain variable region ("LC") amino acid sequence |
| Ab 275 | 549 | QVQLQESGPGLVKPSGTLSLTCVVSGGSIRSHNYWTWVRQPPGKGLEWIGEIYHS<br>GNTNYNPSLKSRVTLSIDKSKNVFSLRLNSVTAADTAVYYCVGGGPFAPYYFENWG<br>QGTLVTVSS | ADI-21027 | Heavy chain variable region ("HC") amino acid sequence |
| Ab 275 | 550 | QSVLTQPPSVSGAPGQRVTISCTGSSSNIGAGYAVHWYHQLPGTAPKLLIYDNNR<br>PSGVPDRFSGSKSGSSASLAITGLQAEDEADYYCQSYDRSLSGYVFGTGTKLTVL | ADI-21027 | Light chain variable region ("LC") amino acid sequence |
| Ab 276 | 551 | EVQLVESGGALVKPGGSLRLSCVASGFTFSDYYMHWVRQAPGKGLEWVSYISSTSS<br>FTNYADSVKGRFIISRDNAKNSLYLQLNSLRAEDTAVYYCARDESSGWQTRRHFGM<br>DVWGQGTLVTVSS | ADI-21028 | Heavy chain variable region ("HC") amino acid sequence |
| Ab 276 | 552 | EIVMTQSPSTLSASVGDRVTITCRASQSLNTWLAWYQHKPGKAPKLLISTASSLQS<br>GVPSRFSASGSGTEFTLTISSLQPDDFATYYCQQFRGTFGPGTKVEIK | ADI-21028 | Light chain variable region ("LC") amino acid sequence |
| Ab 277 | 553 | QVQLVQSGAEVRKPGESLKISCKASGYSFTNYWIGWVRQMPGKGLEWMGIVYPA<br>DSHPVYSPSFQGQVTFSTDKSINTAYLQWSSLKASDTAMYFCARRDGGTDYLSDAF<br>DIWGQGTMVTVSS | ADI-21029 | Heavy chain variable region ("HC") amino acid sequence |
| Ab 277 | 554 | DIVMTQSPSSLSASVGDRVTITCRTSQSIRRYLNWYQQKPGKAPKLLIYAASSLQS<br>GVPSRFSGSGSGTDFTLTISSLQPEDFATYYCQQSYSTPNTFGQGTKVEIK | ADI-21029 | Light chain variable region ("LC") amino acid sequence |
| Ab 278 | 555 | EVQLVESGGGLVKPGGSLRLSCAASGFKFSTYYMSWIRQAPGKGLEWVSNISGGSS<br>YSNHADSVKGRFTISRDNAKNSLYLEMNSLRAEDTAVYYCAREDLMGVSGLAYFEY<br>WGQGILVTVSS | ADI-21030 | Heavy chain variable region ("HC") amino acid sequence |
| Ab 278 | 556 | QPVLTQPPSVSGAPGQRVTISCTGRSSNIGAGYDVNWYKQLPGAVPKVLIYGNTNR<br>PSGVPDRFSGSKSGNSASLAITGLQAEDEADYYCQSYDRNLGYVFGTGTKLTVL | ADI-21030 | Light chain variable region ("LC") amino acid sequence |
| Ab 279 | 557 | EVQLVESGPGLVKPSQTLSLTCTVSGGSISNSNYFWSWIRQPAGKGLEWIGRVHSS<br>GTTSYNPSLKSRITISVDASESQFSLNLTSVTAADTAIYYCARDSSDWGLGWYFDLW<br>GRGTLVTVSS | ADI-21031 | Heavy chain variable region ("HC") amino acid sequence |
| Ab 279 | 558 | ETTLTQSPATLSLSPGERATLSCRASQSVTFYLAWYQHKPGQAPRLLIFDASKRATG<br>IPARFSGSGSGTDFTLTISSLEPEDFALYYCQQRSDWPQTFGQGTKVDIK | ADI-21031 | Light chain variable region ("LC") amino acid sequence |
| Ab 280 | 559 | EVQLVESGGGLVKPGGSLRLSCAVSGFKFSSYTMNWVRQAPGKGLEWVSSVSASS<br>SYIFYADSVQGRFIISRDNAQNSLYLQMNSLRADDTAVYYCTRDQYGPGHYYNPA<br>WFDPWGQGTLVTVSS | ADI-21032 | Heavy chain variable region ("HC") amino acid sequence |
| Ab 280 | 560 | QPVLTQPPSASGAPGQRVTISCTGSSSNIGAGYDVHWYQQLPGTAPKVLIYGNTNR<br>PSGIPDRFSGSKSGTSASLAIIGLQAEDEADYYCQSYDRNGSKVFGTGTKLTVL | ADI-21032 | Light chain variable region ("LC") amino acid sequence |
| Ab 281 | 561 | QVQLVQSGAEVRKPGDSLKISCKFSENIFTTYYWTGWVRQMPGRGLEWMGIIFPG<br>DSDTRYSPSFQGHVTISVDKSIATAFLQWSSLKASDSAMYYCARAKYEGSFDMWG<br>QGTMVTVSS | ADI-21033 | Heavy chain variable region ("HC") amino acid sequence |

TABLE 5-continued

Informal Sequence Listing

| Antibody No. | SEQ ID NO: | Sequence | Clone # (ADI) | Descriptors |
|---|---|---|---|---|
| Ab 281 | 562 | DIQVTQSPSSLSASVGDRVSITCQASQDIRNRLNWYQQKPGKAPKLLIYDASILET GVPSRFSGSGSGTDFTFSISSLQPEDFATYYCQQYDSFSLFTFGPGTKVEIK | ADI-21033 | Light chain variable region ("LC") amino acid sequence |
| Ab 282 | 563 | QVQLQQSGAEVKKPGESLTISCKGSGYSFGNYWISWVRQMPGKGLEWMGRIDPS DSYVNYSPSFQGNVTMSVDKSSSTAYLQWSSLKASDTAMYYCARLAGYSTLWGQ GTLVTVSS | ADI-21034 | Heavy chain variable region ("HC") amino acid sequence |
| Ab 282 | 564 | EIVLTQSPGTLSLSPGERATLSCRASQSFGSIYLAWYQQKPGQAPRLLIYGTSSRA TGIPDRFSGSGSGTDFTLTIRRLEPEDFAVYYCLYYGSSPGATFGPGTKVDIK | ADI-21034 | Light chain variable region ("LC") amino acid sequence |
| Ab 283 | 565 | EVQLVESGHEVKKPGASVKVSCKASGYTFPSYGISWVRQAPGQGLEWMGWIVPY NGNTKYAQRFQGRITMTTDSPTSTASMELRGLRSDDTAVYYCARVFGDGYSYGYE YWGQGTLVTVSS | ADI-21035 | Heavy chain variable region ("HC") amino acid sequence |
| Ab 283 | 566 | DIVLTQSPSTLSASVGDRVTITCRASQSISIWLAWYQQKPGKAPKLLIYKTSELV SGVPSRFSGSGSGTEFTLTISGLQPDDFATYYCQQGNSYSHTFGQGTKVEIK | ADI-21035 | Light chain variable region ("LC") amino acid sequence |
| Ab 284 | 567 | QVQLVQSGAEVKEPGKSLKISCKGSGNHFGNYWIAWVRQMPGKGLEWMGIIYPG DSDTRYSPSFQDQVTISVDKSINTVYLQWSSLKAADTATYYCAGSKLGNSWYTIY DSWGQGTLVTVSS | ADI-21036 | Heavy chain variable region ("HC") amino acid sequence |
| Ab 284 | 568 | NFMLTQPASVSGSPGQSITISCAGPSALIGVYNLVSWYQQVPGKAPKLIIYEGSK RPSGVSHRFSGSKSGYTASLTISGLQTEDEADYYCCSYAGSGTSVVFGGGTKVTVL | ADI-21036 | Light chain variable region ("LC") amino acid sequence |
| Ab 285 | 569 | QVQLVQSGGGVVQPGRSLRLSCAASGFPFSSYAMHWVRQAPGKGLEWVAVIWY PGGEKYSADSVTGRFTISRDNSKNTLYLQMSSLRVEDTAVYYCARRSVGAFDYWGQ GTLVTVSS | ADI-21037 | Heavy chain variable region ("HC") amino acid sequence |
| Ab 285 | 570 | DIQMTQSPLSLPVTPGEPASISCRSSQSLLNSNGYNYLDWYLQKPGQSPQVLIYLG SHRASGVPDRFSGSGSGTDFTLRISRVEAEDVGVYYCMQAVQTPYTFGQGTKVEIK | ADI-21037 | Light chain variable region ("LC") amino acid sequence |
| Ab 286 | 571 | QVQLVQSGAEVKKPGESLKISCQGFGFSFTSYWIGWVRQTPGKGLEWMGTIYPGD SETRKSPSIQGQVTFSADRSISTAYLQWSGLTASDTAVYYCARLKGGWGTTMAGIR DYFYYGLDVWGQGTTVTVSS | ADI-21038 | Heavy chain variable region ("HC") amino acid sequence |
| Ab 286 | 572 | EIVLTQSPGTLSLSPGERATLSCRASQSVSSSYLAWYQQKPGQAPRLLIYGASSRA TGIPDRFTGSGSGTDFTLTISRLEPEDFAVYYCQQYATSLGGFTFGPGTKVDIK | ADI-21038 | Light chain variable region ("LC") amino acid sequence |
| Ab 287 | 573 | EVQLVQSGAEVKKPGASVKVSCKASGYTFISYYIHWVRQAPGQGLEWMGVINPSG GITDYAPKFQGRVSMTRDTSTRTVYLELSSLRSDDTAVYYCARDLCITTSCPRYYD YAWRSYRSEGYFDSWGQGTLVTVSS | ADI-21039 | Heavy chain variable region ("HC") amino acid sequence |
| Ab 287 | 574 | EIVMTQSPLSLPVTPGEPASISCRSSQSLLHSNGYNYLDWYLQKPGQSPQLLIYLG SNRASGVPDRFSGSGSGTDFTLKISRVEAEDVGVYYCMQAQQAPFTFGGGTKVEIK | ADI-21039 | Light chain variable region ("LC") amino acid sequence |
| Ab 288 | 575 | EVQLLESGPGLVKPSGTPSLTCAVSGVSITNSNNWWTWVRQPPGKGLEWIGEIYSS GSTNYSPSLKSRVTISLDKSKNQFSLKLSSVTAADTAVYYCARVLGYYGSGGGHLHS WGPGTLVTVSS | ADI-21040 | Heavy chain variable region ("HC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 288 | 576 | SYELTQPPSASGTPGQRVTISCSGSSSNIGAGYDVHWYQQLPGTAPKLLISVNSNRP SGVPDRFSGSKSGTSASLAITGLQAEDEANYYCQSYDNSLSGYVVFGGGTKLTVL | ADI-21040 | Light chain variable region ("LC") amino acid sequence |
| Ab 289 | 577 | EVQLVESGGGVVVQPGGSLRLSCAASGFTFDDYTMHWVRQAPGKGLEWVSLISWV GDTTYYADSVKGRFTISRDNSKNSLYLQMNSLRTEDTALYYCAKGGYYDGSGYYYFD YWGQGTLVTVSS | ADI-21041 | Heavy chain variable region ("HC") amino acid sequence |
| Ab 289 | 578 | DIRLTQSPSSLSASVGDRVTITCRASQSISNYLNWYQQKPGKAPKLLMYAASSLQSG VPSRFSGSGSGTDFTLTISSLQPEDFATYSCQQSYSTPYTFGQGTKVEIK | ADI-21041 | Light chain variable region ("LC") amino acid sequence |
| Ab 290 | 579 | EVQLVESGPRLVKPSQTLSLTCNVSGVPVNTGGYYWSWIRRHPIKGLEWIGYIYYSG STHYNPSLRGRATMSVDTSKNQFSLRLSSVTAADTAVYYCAKDTITVLRGVAKKGVF DPWGQGILVTVSS | ADI-21042 | Heavy chain variable region ("HC") amino acid sequence |
| Ab 290 | 580 | DIQMTQSPSTLSASVGDRVIITCRASQSISSWLAWYQYKPGKAPNLLIYKATTLDSG VPSRFSGSGSGTEFTLTISSLQPDDFATYYCQQYDSYPTFGQGTKVEIK | ADI-21042 | Light chain variable region ("LC") amino acid sequence |
| Ab 291 | 581 | QVQLVQSGAEVKKPGASVKVSCKASGYTFTSYGITWVRQAPGQGLEWMGWISTY NGKTNYAQKFKGRVTMTTDTSTSTAYVELTSLRSDDTAVYYCAREFPTRIVDSFYM DVWGKGTTVTVSS | ADI-21043 | Heavy chain variable region ("HC") amino acid sequence |
| Ab 291 | 582 | SYELTQPPSVSVAPGQTARITCGGSNIGSETVHWYQQKPGQAPVLVVYGDSDRPS GIPERFSGSNSGNTATLTISRVEAGDEADYYCQVWDSRSDDFHVFGSGTKLTVL | ADI-21043 | Light chain variable region ("LC") amino acid sequence |
| Ab 292 | 583 | QVQLVQSGAELKKPGESLKISCKTSGYTFANYWIGWVRQMPGKGLEWMGIIYPGD SDTRYSPSFQGQVTFSADKSINSAYLQWHSLKASDSAIYYCARRFSPDYSDGAAPPT LSDAFDVWGQGTTVTVSS | ADI-21044 | Heavy chain variable region ("HC") amino acid sequence |
| Ab 292 | 584 | DIVMTQSPSSLSASVGDRVTITCRASQNINIYLNWYQQKPGKAPKLLIYAASTLQSG VPSRFSGSGSATDFTLTISSLQPEDFATYYCQQSYRTPNDFGRGTKVDIK | ADI-21044 | Light chain variable region ("LC") amino acid sequence |
| Ab 293 | 585 | EVQLVESGGGLVKPGGSLRLSCLASGFKFRSYSMNWVRQAPGTGLVWVASISASSS FIFYADSLKGRFTISRDNDKNSLYLQMNSLTVEDTAVYYCVRDMSGISSGGKTFDYW GQGTLVTVSS | ADI-21045 | Heavy chain variable region ("HC") amino acid sequence |
| Ab 293 | 586 | QSVLTQPPSVSGAPGQRVTISCTGSSSNLGAGYDVQWYQQLPGTAPKLLIYGNNN RPSGVPDRFSGSKSGTSASLAITGLRAEDEADYYCQSYDTSPVFGGGTKLTVL | ADI-21045 | Light chain variable region ("LC") amino acid sequence |
| Ab 294 | 587 | EVQLVESGAEAKKPGESLRISCTVSGYSFSKYWVGWVRQTPGKGLEWMGIIDPTDS DTRYSPSFQGQVTISVDNSINTAYLQWSSLKASDTAIYYCARRGQAKCVGNCPRDF MDVWGKGTTVTVSS | ADI-21046 | Heavy chain variable region ("HC") amino acid sequence |
| Ab 294 | 588 | SYVLTQPPSVSGAPGQRVTISCAGSSSNIGAGYEVHWYQQLPGTAPKLLIYANRNR PSGVPDRFSGSRSGTSASLAISGLQAEDEADYYCQSYDNNLSGSWVFGGGTKLTVL | ADI-21046 | Light chain variable region ("LC") amino acid sequence |
| Ab 295 | 589 | QVQLQQWGAGLLKPSETLSLTCAVYGGSFSGKYWSWIRQPPGKGLEWIGEFNHD GTTYYNPSLKSRVTISADTPKNQFSLTLHSVTAADTAVYYCARLTILSDWGQGTLV TVSS | ADI-21047 | Heavy chain variable region ("HC") amino acid sequence |

TABLE 5-continued

Informal Sequence Listing

| Antibody No. | SEQ ID NO: | Sequence | Clone # (ADI) | Descriptors |
|---|---|---|---|---|
| Ab 295 | 590 | DIRMTQSPSSLSASVGDRVTITCQASQDISNYLHWYQQKPGKAPKLLIYDASNLETG VPSRFSGSGSGTDFTFTIHSLQPEDLATYYCQQYYDLPRTFGQGTKLEIK | ADI-21047 | Light chain variable region ("LC") amino acid sequence |
| Ab 296 | 591 | EVQLVESGAEVKKPGASVKVSCKASGYTFSSHAISWVRQAPGHGLEWMGWISVF NGNTNYAQKFQGRVTMTTDTSTSTAYMELRSLRSDDAAVYYCAREVIGVGEFYFD YWGQGTLVTVSS | ADI-21048 | Heavy chain variable region ("HC") amino acid sequence |
| Ab 296 | 592 | QSVLTQPPSVSVAPGQTARITCGGNNIGSKSVHWYQQKAGQAPVLVVYDDSDRPS GIPERFLGSNSGNTATLTISRVEAGDEADYYCQVWDSSGDFHVFGTGTKVTVL | ADI-21048 | Light chain variable region ("LC") amino acid sequence |
| Ab 297 | 593 | EVQLVESGGGLVKPGGSLRLSCSASGFAFSSYSMNWVRQAPGKGLEWVSSISASSS YIFYADSVKGRFTISRDNAKNSLYLQMNSLRAEDTAFYYCARALSPGYGDYRDYWG QGTLVTVSS | ADI-21049 | Heavy chain variable region ("HC") amino acid sequence |
| Ab 297 | 594 | QSVVTQPPSVSGAPGQRVTISCTGSSSNIGAGYDVHWYQQLPGAAPKLLIYGNNN RPSGVPDRFSGSKSGTSASLAITGLQAEDEADFYCQSYDHNLSVVFGGGTKLTVL | ADI-21049 | Light chain variable region ("LC") amino acid sequence |
| Ab 298 | 595 | QVQLVQSGAEVKKPGASVKVSCTASGYTFANNGISWVRQAPGQGLEWMGWISA YNGNTKYAQTVQGRVTLTTDTSTSTAYMELRSLTSDDTAVYYCAREMGVDAAATF DYWGQGTLVTVSS | ADI-21050 | Heavy chain variable region ("HC") amino acid sequence |
| Ab 298 | 596 | EIVMTQSPLFLSVTLGQPASISCRSSQSLVYSDTNTYLTWFQQRPGQSPRRLIYKV SNRDSGVPDRFSGSGSGTYFTLKISRVEAEDIGVYYCMQAIHWPRTFGQGTKLEIK | ADI-21050 | Light chain variable region ("LC") amino acid sequence |
| Ab 299 | 597 | QVQLVESGPGLVRPSQTLSLTCNVSGDFISRGTYYWSWIRQSAGKGLEWIGRIYTS GITDYSPSLKSRVTISVDTSKNQFFLKLASVTAADTAVYYCARGRGYYDSPWGQGT LVTVSS | ADI-21051 | Heavy chain variable region ("HC") amino acid sequence |
| Ab 299 | 598 | ETTLTQSPATLSLSPGERATLSCRASESVSTFLGWYQQKPGQAPRLLIYDASNRAS GVPARFSGSGSGTDFTLTISSLEPEDFAVYYCQLRNKWLTFGPGTKVDIK | ADI-21051 | Light chain variable region ("LC") amino acid sequence |
| Ab 300 | 599 | QVQLVQSGAEVKKPGASVKVSCKASGYTFTSYGISWVRQAPGQGLEWMGWISAY NGNTNYAQNLQGRVTMTTDTSTSTAYMELRSLRSDDTAMYYCARDAFSRVGYWY FDLWGRGTLVTVSS | ADI-21052 | Heavy chain variable region ("HC") amino acid sequence |
| Ab 300 | 600 | SYELTQPPSVSVAPGQAARITCGGNNIGSKTVHWYQQKPSQAPVLVVYDDSDRPS GIPERFSGSNSGNTATLTISRVEAGDEADYYCQVWDSSGDHPVFGGGTKLTVL | ADI-21052 | Light chain variable region ("LC") amino acid sequence |
| Ab 301 | 601 | QVQLQESGPGLVKPSQTLSLTCTVSGVSISNSSGGYYWSWIRQHPGKGLEWIGYIY YSGSTYYNPSSGSTYYNPSLKSRVTVSVDTSKNQFSLKLTSVTAADTAVYYCARDI RGPHKHSLYNWFHPWGQGTLVTVSS | ADI-21053 | Heavy chain variable region ("HC") amino acid sequence |
| Ab 301 | 602 | DIQMTQSPSSLSASVGDRVTITCRASQSISSYLNWYQQKPGKAPKLLIYAASSLQT GVPSRFSGSGSGTDFTLTISSLQPEDFATYYCQQSYSTLRTFGQGTKVDIK | ADI-21053 | Light chain variable region ("LC") amino acid sequence |
| Ab 302 | 603 | QVQLVESGGGVVQPGRSLRLSCAASGFSFSNYGMHWVRQAPGKGLEWVVGISFD GSYIFHGGSVTGRFNISRDNSKNTLYLQVNSVRAEDTAVYYCARDPQYYDDWSGYS GLLHYYLYMDVWGKGTTVTVSS | ADI-21054 | Heavy chain variable region ("HC") amino acid sequence |

TABLE 5-continued

Informal Sequence Listing

| Antibody No. | SEQ ID NO: | Sequence | Clone # (ADI) | Descriptors |
|---|---|---|---|---|
| Ab 302 | 604 | DIQLTQSPSTLSASVGDRVTITCRASQSIGTSLAWYQQIPGKAPKLLIYRASSLES GVPSRFSGGGSGTQFTLTISSLQPDDFATYYCQQYNNYSPTFGQGTKLEIK | ADI-21054 | Light chain variable region ("LC") amino acid sequence |
| Ab 303 | 605 | EVQLVESGGGVVQPGRSLRLSCVGSGFTFSRYGMQWVRQAPGKGLEWAAVIWN DGSNEHYADSVKGRFTISRDNSKNTMYLQMNSLRAEDTALYYCAREGEYSSSWSH WSYLDLWGRGTLVTVSS | ADI-21055 | Heavy chain variable region ("HC") amino acid sequence |
| Ab 303 | 606 | QPGLTQPPSASGTPGQRVTISCSGSTSNIGGNTVNWYQQLPGTAPTVLIYQNRQRP SGVPDRFSGSKSGTSASLAISGLQSDDEADYYCAAWDDSLNGWVFGGGTKLTVL | ADI-21055 | Light chain variable region ("LC") amino acid sequence |
| Ab 304 | 607 | EVQLLESGGGLVKPGGSLKLSCAASGFTLRSYYMHWVRQAPGRGLEWVSSISASSS YINYVDAVKGRFTVSRDNAKNSLFLQMNSLRAEDTAVYYCAREGGAMTNFGVVIDI WGQGTMVTVSS | ADI-21056 | Heavy chain variable region ("HC") amino acid sequence |
| Ab 304 | 608 | SYVLTQPPSVSGAPGQRVTISCTGSSSNIGAGYDVHWYQQLPGTAPKLLIYTNTNRP SGVPDRFSGSKSGTSASLAITGLQSDDEADYYCQSYDSSLSGPVVFGGGTKLTVL | ADI-21056 | Light chain variable region ("LC") amino acid sequence |
| Ab 305 | 609 | QVQLVQSGAEVKKPGESLKISCKASGYSLSNNWIAWVRQMPGKGLEWMGIVYLG DSDARYSPSPQGQVTFSADKSISTAYLQWSSLQASDTAMYFCARHHGDLVVTSDSR YFYGLDVWGQGTTVTVSS | ADI-21057 | Heavy chain variable region ("HC") amino acid sequence |
| Ab 305 | 610 | DIVMTQSPATLSVSPGERATLSCRASQSISSNLAWYQQKPGQAPRLLIYGASTRATG IPARFSGSGSGTEFTLTISSLQSEDFAVYYCQQYNNWPPSDTFGQGTRLEIK | ADI-21057 | Light chain variable region ("LC") amino acid sequence |
| Ab 306 | 611 | QVQLQESGPGLVKPSETLSLTCTVSGGSISGTTYYWAWIRQPPGKGLEWIGTIFYSG STYYNPSLQSRVTTSVDASKNQMSLRLSSVTAADTAMYYCARHTSIYDNLTGFYSHL TGVLDMWGQGTMVTVSS | ADI-21058 | Heavy chain variable region ("HC") amino acid sequence |
| Ab 306 | 612 | DIQLTQSPATLSVSPGERATLSCRASQSVSTNLAWYQQKRGQAPRLLIYGASTRAIG IPARFSGSGSGTEFTLTISSLQSEDFAVYYCQQYNNWPPAYTFGQGTKVDIK | ADI-21058 | Light chain variable region ("LC") amino acid sequence |
| Ab 307 | 613 | QVQLVQSGAEVKRPGDSLKISCKGSGYSFTTSWIGWVRQVPGKGLEWMGIIYPGD SNTVYGPSLQGQVTISADKSTNTAYLQWSSLKASDTAMYYCARRDGGTDYLSDAF DIWGQGTFVTVSS | ADI-21059 | Heavy chain variable region ("HC") amino acid sequence |
| Ab 307 | 614 | DIQMTQSPSSLSASVGDRVTITCRTSQNIVIYLNWYQQKPGKAPKLLIFAASSLPS GVPSRFSGSGSGTDFTLTISSLQPEDVATYYCQQSYNTPGTFGQGTKVDIK | ADI-21059 | Light chain variable region ("LC") amino acid sequence |
| Ab 308 | 615 | EVQLVESGGGLVKPGGSLRLSCEASGFRLSDYYMTWIRQAPGKGLECISYISGGSTF KSYSDSVKGRFTISRDNTNLYLQMNSLRVEDTAVYYCARAPYLIYYMDVWGKGTTV TVSS | ADI-21060 | Heavy chain variable region ("HC") amino acid sequence |
| Ab 308 | 616 | QPVLTQPPSVSGAPGQRVSISCTGSNSNIGAGYDVHWYQQLPGTPPKLLIYDNNN RPSGVPDRFSGSKSGTSASLAITGLQAEDEADYYCQSYDNRLSGSQVLFGGGTKVTV L | ADI-21060 | Light chain variable region ("LC") amino acid sequence |
| Ab 309 | 617 | QVQLVQSGAEVKKPGSSVKVSCKASGGTFSNYPISWVRQAPGHGLEWMGRVVPT VGLANYAQNLQGRVTITADTSTNTVYMELRSLRSEDTGLYYCARRAVVDTYAFDIW GQGTLVTVSS | ADI-21061 | Heavy chain variable region ("HC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 309 | 618 | QSALIQPASVSGFPGQSITISCTGASSDVGGYNFVSWYQQHPGKAPKLIIYEVTKR PSGVSNRFSGSESGNTASLTISGLQAEDEADYYCSSFRYTSSIVYVFGSGTKVTVL | ADI-21061 | Light chain variable region ("LC") amino acid sequence |
| Ab 310 | 619 | EVQLLESGGGLVKPGGSLRLSCAASGFTFSDYDMIWVRQAPGKGLEWVSSISRGSD YIYYADSLKGRFTISRDNARNSVTLQMNSLRAGDTALYFCARAELLDSGGYYLYYFD HWGQGTLVTVSS | ADI-21062 | Heavy chain variable region ("HC") amino acid sequence |
| Ab 310 | 620 | DIRMTQSPSSLSASVGDRVTITCRASQIIASYVNWYQKKPGKAPKVLIYAASRLQNG VPSRFSGSGSGTEFTLTISSLQPEDFATYYCQQSYSTSFTFGQGTKVDIK | ADI-21062 | Light chain variable region ("LC") amino acid sequence |
| Ab 311 | 621 | EVQLVESGGGLVQPGGSLRLSCSASGFTFRTYVMQWVRQAPGKGLEYVSAISSDG GSTDYADSVKGRFTVSRDNSKNTLYLQMSSLRAEDTAVYYCVKRGEGGNDYLYYY MDVWGKGTTVTVSS | ADI-21063 | Heavy chain variable region ("HC") amino acid sequence |
| Ab 311 | 622 | DIQVTQSPSSLSASVGDRVTITCRASQSITNYLNWYQQKPGKAPKVLIYAASSLQSG VPSRFSGSGSGTDFTLTISSLQPEDFATYYCQQSYLRPPTFGGGTKVEIK | ADI-21063 | Light chain variable region ("LC") amino acid sequence |
| Ab 312 | 623 | EVQLVESGGEVKKPGASVKVSCKASGYIFSNHGVSWVRQAPGQGLEWMGWISAY NGNAIYAQNLQGRVTLTTDTSTSTAYMELTSLTSDDTAIYYCARESGATAAAVMDY WGQGTLVTVSS | ADI-21064 | Heavy chain variable region ("HC") amino acid sequence |
| Ab 312 | 624 | DIVLTQTPLSLPVILGQPASISCRSSQSLVYSDGNTYLTWFQQRPGQSPRRLIYKVS NRDSGVPDRFSGSGSDTDFTLKISRVEAEDVGVYYCMQGIDWPRTFGQGTKVDIK | ADI-21064 | Light chain variable region ("LC") amino acid sequence |
| Ab 313 | 625 | EVQLLESGGGLVQPGGSLRLSCAASGFTFSSYAMNWVRQAPGKGLEWVSGISGSG ESTYYADSVKGRFTISRDSSKNTVYLQMNSLRADDTAVYYCAKDQGYGVVVPAATR ALPPRRYGMDVWGQGTTVTVSS | ADI-21065 | Heavy chain variable region ("HC") amino acid sequence |
| Ab 313 | 626 | EIVLTQSPGTLSLSPGERATLSCRASQSVSSTYLAWYQQKPGQAPRLLIYGASSRAT GIPDRFSGSGSGTDFTLTITRLEPEDFAVYYCQQYGSSPPLTFGGGTKVDIK | ADI-21065 | Light chain variable region ("LC") amino acid sequence |
| Ab 314 | 627 | QVQLQESGPGLVKPSGTLSLTCVVSGGSIKSHNYWTWVRQPPGKGLEWVGEIYQS GRTNYNPSLNSRVTLSMDKSKNQLSLRLTSVTAADTAVYFCVGGGPFAPYYFQTW GQGTLVTVSS | ADI-21068 | Heavy chain variable region ("HC") amino acid sequence |
| Ab 314 | 628 | QSVLTQPPSVSGAPGQRVTISCTGSSSNIGAGYDVHWYQQLPGTAPKLLIYNNNNR PSGVPDRFSGSKSGTSASLAITGLQAEDEADYYCQSYDTSLSGYVFGTGTKVTVL | ADI-21068 | Light chain variable region ("LC") amino acid sequence |
| Ab 315 | 629 | EVQLVESGAEVRKPGASVKVSCKASGYTFSSNAISWVRQAPGQGLEWMGYISVFN GNTKYAQNLQGRVTMTTDTATSTVYMELRSLRYDDTAIYYCARESLGMGGFYFDH WGQGTLVTVSS | ADI-21069 | Heavy chain variable region ("HC") amino acid sequence |
| Ab 315 | 630 | SYELTQPPSVSVAPGQTARITCGANNIGSDSVHWYQQKPGQAPVLVVFDDRDRPS GIPERFSGSNSGNTATLTISRVEAGDEADYYCQVWMTSDRSVFGGGTKLTVL | ADI-21069 | Light chain variable region ("LC") amino acid sequence |
| Ab 316 | 631 | EVQLVESGGGLVQPGGSLRLSCAASGFTFSRYAMGWVRQAPGKGLEWVSTISDSG GSTFYADSVEGRFTIARDSSKNTLSLHMNSLRAEDTAIYYCAREAYSSSWYSGGWF | ADI-21070 | Heavy chain variable region |

TABLE 5-continued

| Anti-body No. | SEQ ID NO: | Sequence | Clone # (ADI) | Descriptors |
|---|---|---|---|---|
| | | DRWGQGTLVTVSS | | ("HC") amino acid sequence |
| Ab 316 | 632 | ETTLTQSPATLSVSPGERATLSCRASQSVSSNLAWYQQKPGQAPRLLIYGASTRAT GIPARFSGSGSGAEFTLTINSLQSEDFAIYYCQQYNNWPQYTFGQGTKVDIK | ADI-21070 | Light chain variable region ("LC") amino acid sequence |
| Ab 317 | 633 | EVQLVESGGGVVQPGKSLRLSCAVSGFTFSDHDMHWVRQAPGKGLEWVAAIWS DRTTKYYGDFVKGRFTISRDNSKNTLYLQMNSLRAEDTAVYYCARGQIYKSGGYYL VHLDHWGQGTLVTVSS | ADI-21071 | Heavy chain variable region ("HC") amino acid sequence |
| Ab 317 | 634 | DIQVTQSPSSLSASVGDRVTITCRASQSIASYLNWYQQKPGKAPNLLIYAASNLQS EVPSRFSGSGSGTDFTLTISGLQPEDFATYYCQQSYNIRLLTFGGGTKVEIK | ADI-21071 | Light chain variable region ("LC") amino acid sequence |
| Ab 318 | 635 | QVQLVQSGGGLVKPGGSLRLSCEASGFNFRSYHMSWVRQAPGKGLEWVSSITAG SSYINYADSVKGRFTISRDNAKNSVFLQMNSLSAEDTAVYYCAREGLNMGVGGTW FDPWGQGTLVTVSS | ADI-21072 | Heavy chain variable region ("HC") amino acid sequence |
| Ab 318 | 636 | QAVVTQEPSVSGAPGQRVTISCTGSSSNIGAGYDVHWYQQLPGTAPKLLIYGNNN RPSGVPDRFSGSKSATSASLAITGLQADDEADYYCQSYDRSLSGSWVFGTGTKVTV L | ADI-21072 | Light chain variable region ("LC") amino acid sequence |
| Ab 319 | 637 | EVQLVESGGGLVRPGRSLRLSCAASGFTFSMFSMNWVRQAPGKGLEWLAYIGGS GSTIDYANSVSGRFTISRDNAKNSLYLQMNSLRDEDTAVYYCARIGLQTYNSHSSS SSPARAFDVWGQGTTVTVSS | ADI-21073 | Heavy chain variable region ("HC") amino acid sequence |
| Ab 319 | 638 | DIVLTQSPSSLSASVGDRVTITCRASQSIGRFLNWYQQKPGKAPKLLIYAASSLES GVPSRFSGSGSGTQFSLTISSLQPEDFTTYYCQQSYSTPTTFGGGTKVDIK | ADI-21073 | Light chain variable region ("LC") amino acid sequence |
| Ab 320 | 639 | EVQLVESGGGLVKPGGSLRLSCAASGFSFSNYYMSWVRQAPGKGLEWISYISGGST YANLADSVKGRFTISRDNTKNSMYLQMTSLRPDDTAVYYCARIHGTHGPFYFDYW GQGTLVTVSS | ADI-21075 | Heavy chain variable region ("HC") amino acid sequence |
| Ab 320 | 640 | QSVLTQPPSVSGAPGQRVTISCTGSSSNIGAGYDVHWYQQLPGTAPKLLIHANSNR PSGVPDRFSGSKSGTSASLAITGLQAEDEADYYCQSYDNSLNAYYVFGTGTKLTVL | ADI-21075 | Light chain variable region ("LC") amino acid sequence |
| Ab 321 | 641 | EVQLVESGGGLVRPGGSLRLSCAASGFTFSSYAMDWVRQAPGKGLEWVSSISASSS FISYTDSVKGRFTISRDNAKNSLFLQMDNVTAEDTAVYYCARDYYESGRYFYGNPFD IWGQGTMVTVSS | ADI-21076 | Heavy chain variable region ("HC") amino acid sequence |
| Ab 321 | 642 | QPVLTQPPSVSGAPGQRVTISCTGSGSNIGAGFDVHWYQQLPGTAPKLLIYANSDR PSGVPDRFSASKSGTSASLAITGLQAEDEAHYYCQSYDNSLGGLCVFGTGTKLTVL | ADI-21076 | Light chain variable region ("LC") amino acid sequence |
| Ab 322 | 643 | QVQLVESGGGLVKPGGSLRLSCVVSGFTFRDYYMSWIRQAPGKGLEWISYISPSSTY TNYADSVRGRFTISRDNAENSLYLQMNSLRAEDTAVYYCARVNIAATGAGGVFLDY WGQGTTVTVSS | ADI-21077 | Heavy chain variable region ("HC") amino acid sequence |
| Ab 322 | 644 | QPVLTQPPSVSGAPGQRVTISCAGSSSNIGAGYDVHWYQQLPGTAPKLLIYGNINR PSGVPDRFSGSKSGTSASLAITGLQAEDEADYYCQSYDSSLSGSYVFGTGTKVTVL | ADI-21077 | Light chain variable region ("LC") amino acid sequence |
| Ab 323 | 645 | EVQLVESGGGLVKPGGSLRLSCAASGFRLSDYYMSWIRQAPGKGLEWISDISGGST YTNYADSVKGRLTISRDNAQNSLYLQMNSLRAEDTAVYYCARWGSGGPDAFHFW GQGTTVTVSS | ADI-21078 | Heavy chain variable region ("HC") amino acid sequence |

TABLE 5-continued

| Anti-body No. | SEQ ID NO: | Sequence | Clone # (ADI) | Descriptors |
|---|---|---|---|---|
| Ab 323 | 646 | QSVLTQPPSVSGVPGQRVTISCTGSRSNIGAGYDVHWYRQLPGTAPKLLIYGNSNR PSGVPDRFSGSKSGTSASLAITGLQADDEADYYCQSYDSSLSGSVIFGGGTKVTVL | ADI-21078 | Light chain variable region ("LC") amino acid sequence |
| Ab 324 | 647 | EVQLLESGGGLVKPGGSLRLSCAASGFTFSDYYMSWIRQAPGKGLEWVSNISGGST YTNYADSVKGRFTISRDNAKNSLYLQMNSLRAEDTAVYYCAREAYGSGNYYNPNW LDPWGQGTLVTVSS | ADI-21079 | Heavy chain variable region ("HC") amino acid sequence |
| Ab 324 | 648 | QSVLTQPPSVSGAPGQRVTISCTGSSSNIGAGYDVHWYQQLPGTAPKLLIYGNRNR PSGVPDRFSGSKSGTSASLAITGLQAEDEADYYCQSYDSSLSGSVFGGGTKLTVL | ADI-21079 | Light chain variable region ("LC") amino acid sequence |
| Ab 325 | 649 | EVQLLESGGGLVKPGGSLRLSCEVSGFRLSDYYMSWIRQAPGKGLEWVSHISGGST YTNYADSVKGRFTISRDNGKKSMYLQMNSLRAEDTALYYCAKWGSGGPEAFDIW GRGTMVTVSS | ADI-21080 | Heavy chain variable region ("HC") amino acid sequence |
| Ab 325 | 650 | QSALIQPPSVSGAPGQRVTISCTGSSSNIGAGYDVHWYQQIPGTAPKLLIYGNNNR PSGVPDRFSGSKSGTSASLAITGLQAEDEADYYCQSYDNSLSGSVVFGGGTKLTVL | ADI-21080 | Light chain variable region ("LC") amino acid sequence |
| Ab 326 | 651 | EVQLLESGGGLVKPGGSLRLSCAASRFAFSNYYMTWIRQAPGKGLEWISNISGGST FTNYADSVKGRFTISRDNAKNSVHLQMNSLRAEDTAVYYCVREASVAAGTPEGFDI WGQGTMVTVSS | ADI-21081 | Heavy chain variable region ("HC") amino acid sequence |
| Ab 326 | 652 | QSVLTQPPSVSGAPGQRVIISCTGSSSNIGAGYDVNWYQQLPGTAPKLLMYGNRN RASGVPDRFSGSKSGTSASLAITGLQAEDEADYYCHSYDSSLGGSVFGGGTKLTVL | ADI-21081 | Light chain variable region ("LC") amino acid sequence |
| Ab 327 | 653 | EVQLVESGGGLVKPGGSLKLSCVASGLKFSSYSMNWVRQAPGKGLEWVSSVSAGS SYTNYADSVKGRFTISRDNAKNSLYLQMNSLRVDDTAVYYCATERCSGGSCYLHGF DPWGQGTTVTVSS | ADI-21082 | Heavy chain variable region ("HC") amino acid sequence |
| Ab 327 | 654 | QSVLTQPPSVSGAPGQRVTISCTGSSSNIGAGYDVHWYQQLPGTAPKLLIFDNIIR PSGVPDRFSGSKSGTSASLAITGLQADDEADYYCQSYDKSGDYVFGTGTKVTVL | ADI-21082 | Light chain variable region ("LC") amino acid sequence |
| Ab 328 | 655 | QVQLQESGPGLVKPSGTLSLTCAVSGDSITTSNWWSWVRQPPGKGLEWIGEIYHS GVTRYNPSLKSRLSISLDKSRNQFSLKLSSVTAADTAVYYCARDEALFGHWFDPWG QGTLVTVSS | ADI-21083 | Heavy chain variable region ("HC") amino acid sequence |
| Ab 328 | 656 | QSVLTQPRSVSGSPGQSVTISCTGSSSDIGSYNYVSWYQQHPGKAPKLMLYDVSKR PSGVPDRFSGSKSVKTASLTISGLQAEDEADYYCCTYAGNSVVFGGGTKLTVL | ADI-21083 | Light chain variable region ("LC") amino acid sequence |
| Ab 329 | 657 | EVQLVESGAEVKKPGASVTVSCKASGYTFTSNTISWLRQAPGQGLEWLGWVSASN GNTKYAQKFQGRVTMTTDTSATTAYMEVRTLRHDDTAIYYCARDILDMGGFHFD NWGQGTLVTVSS | ADI-21084 | Heavy chain variable region ("HC") amino acid sequence |
| Ab 329 | 658 | SYVLTQPPSVSVAPGQTARITCGGNNIGNKHVHWYKQKPGQAPVLVVYDDSDRPS GIPERFSGSNSGNTATLTVSRVEAGDEADFYCQVWDNTNDHPVFGGGTKVTVL | ADI-21084 | Light chain variable region ("LC") amino acid sequence |
| Ab 330 | 659 | EVQLVETGGGLVKPGGSLRLSCEASGFNFRSYSMNWVRQAPGKGLEWVSSISASSS YINYADSVKGRFTISRDNSKNSLYLQMNSLRAEDTGVYYCARVLVHYYYGMDVWG QGTTVTVSS | ADI-21085 | Heavy chain variable region ("HC") amino acid sequence |
| Ab 330 | 660 | QSVLTQPPSVSAAPGQRVTISCTGTSSNIGAGYDVHWYQQLPGRAPKLLILGNNNR PSGVPDRFSGSKSGTSASLAITGLQAEDEADYYCQTYDKTLMEIFGGGTKLTVL | ADI-21085 | Light chain variable region |

TABLE 5-continued

Informal Sequence Listing

| Anti-body No. | SEQ ID NO: | Sequence | Clone # (ADI) | Descriptors |
|---|---|---|---|---|
| | | | | ("LC") amino acid sequence |
| Ab 331 | 661 | EVQLVETGGGLVKPGGSLRLSCAASPFAFSNYYMSWIRQAPGKGLEWISNISGGST FTNYADSVKGRFTISRDNARNSLYLLMNNLRTEDTAVYYCAREASVAAGTPEGFDV WGQGTTVTVSS | ADI-21086 | Heavy chain variable region ("HC") amino acid sequence |
| Ab 331 | 662 | QSVVTQPPSVSGAPGQRVTISCTGSSSNIGAGYDVNWYQQFPGTAPKLLIYGNRNR PSGVPARFSGSKSGASASLAITGLQAEDEADYYCHSYDSGLSGSVFGGGTKLTVL | ADI-21086 | Light chain variable region ("LC") amino acid sequence |
| Ab 332 | 663 | EVQLVESGGGLVQPGGSLRLSCAASGFTFSGYEMNWVRQAPGKGLEWLSYISSSG GIIYYADSVKGRFTISRDNARNSLFLQMNSLRAEDTAVYSCARARLLDGFDIWGQG TMVTVSS | ADI-21087 | Heavy chain variable region ("HC") amino acid sequence |
| Ab 332 | 664 | DIQVTQSPSTLSASVGDRVTITCRASQSIGSWLAWYQQKPGKAPKLLIYKASSLESG VPSRFSGSGSGTEFTLTISSLQPDDFATYYCQQYNSYSYTFGQGTKVEIK | ADI-21087 | Light chain variable region ("LC") amino acid sequence |
| Ab 333 | 665 | EVQLLESGGGLVKPGGSLRLSCVASGFRFTSYSMNWVRQAPGKGLEWVSSISASSS YVDYADSLKGRFTISRDNAQNSLFLQMNSLRAEDTAVYYCARDYYDSGNYHSPFP MDVWGQGTTVTVSS | ADI-21089 | Heavy chain variable region ("HC") amino acid sequence |
| Ab 333 | 666 | QSVLTQPPSVSGAPGQRVTISCTGSRSNIGAGYDVHWYQQLPGTAPKLLIYGNNKR PSGVPDRFSGSKSGTSASLAITGLQAEDEADYYCQSYDSGPIFGGGTKVTVL | ADI-21089 | Light chain variable region ("LC") amino acid sequence |
| Ab 334 | 667 | EVQLLESGGGLVKPGGSLRLSCAASGFTSGFTFSDFYMSWIRLTPGKGLEWISYIS THSTSTNYADSVRGRFIISRDDARNSLFLQMNSLRAEDTAVYYCAGYYYGSGSYFF DHWGQGTLVTVSS | ADI-21090 | Heavy chain variable region ("HC") amino acid sequence |
| Ab 334 | 668 | ETTLTQSPATLSVSPGERATLSCRASQSVSSNVAWYQQKPGQAPRLLIYSASSRDT GIPVRFSGSGSGTEFTLSISSLQSEDFAVYYCQQYSDWPTFGQGTKVEIK | ADI-21090 | Light chain variable region ("LC") amino acid sequence |
| Ab 335 | 669 | QVQLVQSGAEVKKPGESLRISCQYSAYGFSTYWISWVRQLPGKGLEWMGRIDPSD SHTTYSPSFQGHVTLSADKSISTVYLQWSSLKASDTAMYYCARHQEYSGSDLDSW GQGTLVTVSS | ADI-21091 | Heavy chain variable region ("HC") amino acid sequence |
| Ab 335 | 670 | QPVLTQPPSVSAAPGQRVTISCSGTRSNIGYNFVSWYQQLPGTAPKLLIYDNNKR PSGIPDRFSGSKSGTSATLAITGLQTGDEADYYCGTWDSSLSALFGGGTKVTVL | ADI-21091 | Light chain variable region ("LC") amino acid sequence |
| Ab 336 | 671 | EVQLLESGGGVVQPGRSLRLSCVASGFTFSTYGVHWVRQAPGKGLEWVAVISYDG ANKDYADSVKGRFTISRDNSKNTLYLQMNSLRAEDTAVYYCAKMITRVLPGGFDR WGQGTLVTVSS | ADI-22756 | Heavy chain variable region ("HC") amino acid sequence |
| Ab 336 | 672 | EIVMTQSPGTLSLSPGERATLSCRASQSVSSAYLAWYQQKPGQAPRLLIYDASRRA TGIPDRFSGSGSGTDFTLTISRLEPEDFAVYYCQQYGSSRFTFGQGTKVEIK | ADI-22756 | Light chain variable region ("LC") amino acid sequence |
| Ab 337 | 673 | EVQLLESGAEVKKPGASVKVSCKASGYTFSNYGISWVRQAPGQGLEWMGWISVY NGNTEYAQKFQGRLTMTTDTSTSTAYMELRSLRSDDTAVYYCARDPPAVAASFMD VWGQGTTVTVSS | ADI-22757 | Heavy chain variable region ("HC") amino acid sequence |
| Ab 337 | 674 | EIVLTQSPLSLPVTLGQPASISCRSSQSLVHSEGNTYLSWFQQRPGQSPRRLIYKV SNRDSGVPDRFSGSGSGTDFTLKISRVEAEDVGLYFCMQGTHWPPTFGGGTKVEIK | ADI-22757 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 338 | 675 | QVQLVESGGGLVKPGGSLRLSCAASGFSISSYSMNWVRQAPGKGLEWVSSISGSSS YIYYGDSVKGRFTISRDNARNSLYLQMNSLRAEDTAVYYCARGDIAAAGTITYYFAH WGQGTLVTVSS | ADI-22758 | Heavy chain variable region ("HC") amino acid sequence |
| Ab 338 | 676 | QSVLTQPPSVSGAPGQRVTISCTGSSSNIGAGYDVHWYQQLTGTAPKLLIFGNNNR PSGVPDRFSGSKSGTSASLAITGLQAEDEADYYCQSYDSSLSGAVFGGGTQLTVL | ADI-22758 | Light chain variable region ("LC") amino acid sequence |
| Ab 339 | 677 | EVQLLESGGGLVKPGGSLRLSCAASGFSFSSYTMNWVRQAPGKGLEWVSSITGSS YIDYAGSLKGRFTISRDNAKNSLYLQMNSLRVEDTAVYYCARDFPNIAVGGKTLDY WGQGTLVTVSS | ADI-22759 | Heavy chain variable region ("HC") amino acid sequence |
| Ab 339 | 678 | QPVLTQPPSVSGAPGQRVTISCTGSSSNIGAGYDVHWFQQLPGTAPKLLIYVNNNR PSGVPDRFSGSKSGTSASLAITGLQAEDEADYYCQSYDRLSAVVFGGGTKVTVL | ADI-22759 | Light chain variable region ("LC") amino acid sequence |
| Ab 340 | 679 | EVQLVESGGGLVQPGRSLRLSCVASGFTFDDYAMHWVRQAPGKGLEWVSGINW NSGGIGYADSVKGRFTISRDNTKNSLYLQMNSLRAEDTALYYCAKDGSALMGYGVE VWGQGTTVTVSS | ADI-22760 | Heavy chain variable region ("HC") amino acid sequence |
| Ab 340 | 680 | SYELTQPPSASGTPGQRVTISCSGSNSNIGNNYVYWYQQLPGTAPKLLIYRNNQWP SGVPDRFSASKSGTSASLAISGLRSEDEADYYCASWDDSLSALVFGGGTKLTVL | ADI-22760 | Light chain variable region ("LC") amino acid sequence |
| Ab 341 | 681 | EVQLVESGPGLVKPSQTLSLTCAISGDSVSSNSVAWNWIRQSPSRGLEWLGRTYYQ SKWYNDYAVSVKSRISVNPDTSKNQFSLQLNSLTPEDTAVYYCVRGCSWGFGWYF DLWGRGTLVTVSS | ADI-22762 | Heavy chain variable region ("HC") amino acid sequence |
| Ab 341 | 682 | QSVLTQPPSVSGAPGQRVTISCTGSSSNIGAIYDVHWYQQFPGTAPKLLIYGNTNR PSGVPDRFSGSKSGTSASLAITGLQAEDEADYYCQSYDSSLSGYVFGTGTKVTVL | ADI-22762 | Light chain variable region ("LC") amino acid sequence |
| Ab 342 | 683 | EVQLVESGGGLIQPGGSLRLSCAASGFTFSTYEMNWVRQAPGKGLEWVSSISTSGS TKDYAGSVKGRFTVSRDNAKNSLYLQMNSLRAEDTAIYYCARVYYYDSSGYYLALF DYWGQGTLVTVSS | ADI-22763 | Heavy chain variable region ("HC") amino acid sequence |
| Ab 342 | 684 | EIVLTQSPSSLSASVGDRVTITCRASQSIASYLNWYQQKPGKAPKLLIYAASSLRS GVPSRFSGSGSGTDFTLTISSLQPEDFATYYCQQSYSTPSLTFGGGTKLEIK | ADI-22763 | Light chain variable region ("LC") amino acid sequence |
| Ab 343 | 685 | QVQLVESGPGLVRPSGTLSLTCAVSGGSISGKNWWSWVRQPPGKGLEWIGEIDHS GSTNYNPSLKSRVTISVDKSKNQFSLKLSSVTAADTAVYYCARTGLYDSSGYYLYY FNYWGQGTLVTVSS | ADI-22764 | Heavy chain variable region ("HC") amino acid sequence |
| Ab 343 | 686 | EIVMTQSPSSLSASVGDRVTISCRASQTIASYVNWYQQRPGKAPNLLIFAASNLQTG VPSRFRGSGSGTVFTLTISSLQPEDFATYYCQQSYSTPRTFGQGTKVDIK | ADI-22764 | Light chain variable region ("LC") amino acid sequence |
| Ab 344 | 687 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARDRGDGYNYDYWGQ GTLVTVSS | ADI-22765 | Heavy chain variable region ("HC") amino acid sequence |
| Ab 344 | 688 | QPVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSVVFGGGTKVTVL | ADI-22765 | Light chain variable region ("LC") amino acid sequence |
| Ab 345 | 689 | EVQLVESGGGLVQPGRSLRLSCAASGFTFDDYAMHWVRQAPGKGLEWVSGISW NSGSIGYADSVKGRFTISRDNAKNSLYLQMNSLRAEDTALYYCAKDGRFSLSHTYY | ADI-22766 | Heavy chain variable region |

TABLE 5-continued

Informal Sequence Listing

| Antibody No. | SEQ ID NO: | Sequence | Clone # (ADI) | Descriptors |
|---|---|---|---|---|
| | | FDYWGQGTLVTVSS | | ("HC") amino acid sequence |
| Ab 345 | 690 | QPVLTQPPSASGSPGQSVTISCTGTSSDVGGYNYVSWYQQHPGKAPKLMIYEVSKR PSGVPNRFSGSKSGNTASLTVSGLQAEDEADYYCSSYAGSNNLYVFGTGTKVTVL | ADI-22766 | Light chain variable region ("LC") amino acid sequence |
| Ab 346 | 691 | QVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCAREANWGVAFDIWGQ GTMVTVSS | ADI-22767 | Heavy chain variable region ("HC") amino acid sequence |
| Ab 346 | 692 | QSVVTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSYVFGTGTKVTVL | ADI-22767 | Light chain variable region ("LC") amino acid sequence |
| Ab 347 | 693 | EVQLVESGGGLVQPGGSLRLSCAASGFTFSSYEMNWVRQAPGKGLEWVSYISSSG STIYYADSVKGRFTISRDNAKNSLYLQMNSLRAEDTAVYYCAKSYIYDSSGYYLYY FDYWGQGTLVTVSS | ADI-22768 | Heavy chain variable region ("HC") amino acid sequence |
| Ab 347 | 694 | EIVMTQSPSSLSASVGDRVTITCRASQSISSYLNWYQQKPGKAPKLLIYAASSLQS GVPSRFSGSGSGTDFTLTISSLQPEDFATYYCQQSYSTPGTFGQGTKVDIK | ADI-22768 | Light chain variable region ("LC") amino acid sequence |
| Ab 348 | 695 | QVQLVQSGGGLVQPGGSLRLSCAASGFTFSDHYMDWVRQAPGKGLEWVGRTRN KANSYTTEYAASVKGRFTISRDDSKNSLYLQMNSLKTEDTAVYYCARVGYYYYYGM DVWGQGTTVTVSS | ADI-22769 | Heavy chain variable region ("HC") amino acid sequence |
| Ab 348 | 696 | SYVLTQPPSVSVSPGQTASITCSGDKLGDKYACWYQQKPGQSPVLVIYQDSKRPSGI PERFSGSNSGNTATLTISGTQAMDEADYYCQAWDSSTPLFGGGTKVTVL | ADI-22769 | Light chain variable region ("LC") amino acid sequence |
| Ab 349 | 697 | QVTLKESGPALVKPTQTLTLTCTFSGFSLSTSGMCVSWIRQPPGKALEWLALIDWD DDKYYSTSLKTRLTISKDTSKNQVVLTMTNMDPVDTATYYCARSPGRAVAGTDYW GQGTLVTVSS | ADI-22770 | Heavy chain variable region ("HC") amino acid sequence |
| Ab 349 | 698 | SYELTQPPSVSVSPGQTASITCSGDKLGDKYACWYQQKPGQSPVLVIYQDSKRPSGI PERFSGSNSGNTATLTISGTQAMDEADYYCQAWDSSTAVVFGGGTKLTVL | ADI-22770 | Light chain variable region ("LC") amino acid sequence |
| Ab 350 | 699 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARDYSSGWYYFDYWG QGTLVTVSS | ADI-22771 | Heavy chain variable region ("HC") amino acid sequence |
| Ab 350 | 700 | QPVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGSVFGGGTKLTVL | ADI-22771 | Light chain variable region ("LC") amino acid sequence |
| Ab 351 | 701 | EVQLVESGGGVVQPGRSLRLSCAASGFTFSSYAMHWVRQAPGKGLEWVAVISYD GSNKYYADSVKGRFTISRDNSKNTLYLQMNSLRAEDTAVYYCARAVEQQLFIWYYG MDVWGQGTTVTVSS | ADI-22772 | Heavy chain variable region ("HC") amino acid sequence |
| Ab 351 | 702 | SYELIQPPSVSVSPGQTASITCSGDKLGDKYACWYQQKPGQSPVLVIYQDSKRPSG IPERFSGSNSGNTATLTISGTQAMDEADYYCQAWDSSTDVVFGGGTQLTVL | ADI-22772 | Light chain variable region ("LC") amino acid sequence |
| Ab 352 | 703 | QVQLVQSGAEVKKPGASVKVSCKASGYTFTSYGISWVRQAPGQGLEWMGWISAY NGNTNYAQKLQGRVTMTTDTSTSTAYMELRSLRSDDTAVYYCARESALSRDGYNY GDVDYWGQGTLVTVSS | ADI-22773 | Heavy chain variable region ("HC") amino acid sequence |
| Ab 352 | 704 | ETTLTQSPLSLPVTLGQPASISCRSSQSLVYSDGNTYLNWFQQRPGQSPRRLIYKV SNRDSGVPDRFSGSGSGTDFTLKISRVEAEDVGVYYCMQGTHWPPTFGQGTKLEIK | ADI-22773 | Light chain variable region |

TABLE 5-continued

Informal Sequence Listing

| Anti-body No. | SEQ ID NO: | Sequence | Clone # (ADI) | Descriptors |
|---|---|---|---|---|
| | | | | ("LC") amino acid sequence |
| Ab 353 | 705 | EVQLLESGGGLVKPGGSLRLSCAASGFTFSSYSMNWVRQAPGKGLEWVSSISSSSS YIYYADSVKGRFTISRDNAKNSLYLQMNSLRAEDTAVYYCAREGASGYNYRYYFDY WGQGTLVTVSS | ADI-22774 | Heavy chain variable region ("HC") amino acid sequence |
| Ab 353 | 706 | QSVLTQPPSVSGAPGQRVTISCTGSSSNIGAGYDVHWYQQFPGAAPKLLIYGNNN RPSGVPDRFSGSKSGTSASLAITGLQADDEADYYCQSYDSSLSGYVVFGGGTKLTV L | ADI-22774 | Light chain variable region ("LC") amino acid sequence |
| Ab 354 | 707 | EVQLLESGGGVVQPGRSLRLSCAASGFTFSDYGMHWVRQAPGKGLEWVAVIWYD GSYKYYADSVKGRFTISRDNSKNTLFLQMNSLRAEDTAVYYCARESLQTHDAFDIW GQGTMVTVSS | ADI-22775 | Heavy chain variable region ("HC") amino acid sequence |
| Ab 354 | 708 | DIQMTQSPSSLSASVGDRVTITCRASQGISNSLAWYQQKPGKAPKLLLYAASRLESG VPSRFSGSGSGTDYTLTINSLQPEDFATYFCQQYYSTLTWTFGQGTKVDIK | ADI-22775 | Light chain variable region ("LC") amino acid sequence |
| Ab 355 | 709 | EVQLLESGGGLVKPGGSLRLSCAASGFTFSDYYMSWIRQAPGKGLEWVSYISSSGST IYYADSVKGRFTISRDNAKNSLYLQMNSLRAEDTAVYYCAREIGGSYTGGAFDIWG QGTMVTVSS | ADI-22776 | Heavy chain variable region ("HC") amino acid sequence |
| Ab 355 | 710 | SYELTQPPSVSVAPGQTARITCGGNNIGSKSVHWYQQKPGQAPVLVVYDDSDRPS GIPERFSGSNSGNTATLTISRVEAGDEADYYCQVWDSSSDHVVFGGGTKVTVL | ADI-22776 | Light chain variable region ("LC") amino acid sequence |
| Ab 356 | 711 | QVQLVQSGAEVKRPGASVKVSCKASEYTFNFHDINWVRQAPGQGLEWMGWMN PKSGNTGYAQKFQGRVTMTRDTSKNTAYLELSSLRSEDTAVYYCARGYGTSWSSDS WWGQGTLVTVSS | ADI-22777 | Heavy chain variable region ("HC") amino acid sequence |
| Ab 356 | 712 | SYELTQLPSVSVSPGQTARITCSGDALSKQFVYWYQQKPGLAPMLVIYKDTNRPSW IPERFSGSGSGTTATLTISEVQAEDEADYYCQSVDNSGTYGWVFGGGTKVTVL | ADI-22777 | Light chain variable region ("LC") amino acid sequence |
| Ab 357 | 713 | EVQLVESGPGLVKPSETLSLTCTVSGGSINSYSWTWIRQPPGKGLEWLGSFDYSGSN TYNPSLKSRVTIAVDTSKNQFSLKLTSATAADTAVYYCARAPVYDSSGYYLYYFDNW GQGTLVTVSS | ADI-22778 | Heavy chain variable region ("HC") amino acid sequence |
| Ab 357 | 714 | DIQMTQSPSSLSASVGDRVTITCRASQSIASYLNWYQQKPGKAPKLLIFAASNLHSG VPSRFSGSGSGTTFTLTISSLQPEDFATYYCQQSYSIRFFTFGPGTKLEIK | ADI-22778 | Light chain variable region ("LC") amino acid sequence |
| Ab 358 | 715 | QVQLQQWGAGLLKPSETLSLTCAVYGGSFSDYSWTWIRQPPGKGLEWIGEISHTGI TNYNPSLKSRVNISVDTSKNQFSLKLSSVTAADTAVYYCARADAYDSSGYYVYYFDY WGQGTLVTVSS | ADI-22779 | Heavy chain variable region ("HC") amino acid sequence |
| Ab 358 | 716 | DIQVTQSPPSLSASVGDRVTITCRASQTIASYLNWYHQKPGKAPELLIYAASSLQSG VPSRFSGSGSGTAFTLTISSLQPEDFATYYCQQSYSAPPSFGQGTKVEIK | ADI-22779 | Light chain variable region ("LC") amino acid sequence |
| Ab 359 | 717 | EVQLVESGPTLVKPTQTLTLTCTFSGFSLSTSGVGVGWIRQPPGKALEWLALIYWDD DKRYSPSLKSRLTITKDTSKNQVVLTMTNMDPVDTATYYCAHRGRQYSYGYYYFDY WGQGTLVTVSS | ADI-22780 | Heavy chain variable region ("HC") amino acid sequence |
| Ab 359 | 718 | QSVLIQPASVSGSPGQSITISCTGTSSDVGGYNFVSWYQQHPGKAPKLMIYDVSNR PSGVSNRFSGSKSGNTASLTISGLQAEDEADYYCSSYTSSTLDVFGTGTKVTVL | ADI-22780 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 360 | 719 | EVQLVESGGGLVQPGGSLRLSCAASGFTFSSYEMNWVRQAPGKGLEWVSYISSSG STIYYADSVKGRFTISRDNAKNSLYLQMNSLRAEDTAVYYCARGGAVAGTRTGGFDI WGQGTTVTVSS | ADI-22781 | Heavy chain variable region ("HC") amino acid sequence |
| Ab 360 | 720 | SYELTQPPSVSVSPGQTARITCSGDALPKQYAYWYQQKPGQAPVLVIYKDSERPSGI PERFSGSSSGTTVTLTISGVQAEDEADYYCQSADSSGTYQVFGGGTKLTVL | ADI-22781 | Light chain variable region ("LC") amino acid sequence |
| Ab 361 | 721 | EVQLVESGGGLVKPGGSLRLSCAASGFIFSDYYMSWIRQAPGKGLEWVSNISGGSS FTNYADSVKGRFTISRDNAKNSLYLQMNSLRAEDTAVYYCARDLGYCSSNSCLDAF DIWGQGTTVTVSS | ADI-24792 | Heavy chain variable region ("HC") amino acid sequence |
| Ab 361 | 722 | QSVLTQPPSVSGAPGQRVTISCTGSSSNIGAGYDVHWYQQLPGTAPKLLIYGNTNR PSGVPDRFSGSRSGTSASLAITGLQAEDEADYYCQSYDSSLSGSLFGGGTKVTVL | ADI-24792 | Light chain variable region ("LC") amino acid sequence |
| Ab 362 | 723 | QVQLVQSGAEVKKPGESLKISCKGSGYSFTSYWIGWVRQMPGKGLEWMGIIYPGD SDTRYSPSFQGQVTISADKSISTAYLQWSSLKASDTAMFYCVMGSYSYYFDYWGQG TLVTVSS | ADI-24793 | Heavy chain variable region ("HC") amino acid sequence |
| Ab 362 | 724 | NFMLTQPHSVSESPGKTVTISCTRSSGSIASNYVQWYQQRPGSAPTTVIYEDNLRPS GVPDRFSGSIDSSSNSASLTISGLKTEDEADYYCQSYDSSNQVFGGGTKLTVL | ADI-24793 | Light chain variable region ("LC") amino acid sequence |
| Ab 363 | 725 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARVGYSSSSGAFDYWG QGTLVTVSS | ADI-24795 | Heavy chain variable region ("HC") amino acid sequence |
| Ab 363 | 726 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGSVFGGGTKVTVL | ADI-24795 | Light chain variable region ("LC") amino acid sequence |
| Ab 364 | 727 | QVQLVQSGGGVVQPGRSLRLSCAASGFTFSSYGMHWVRQAPGKGLEWVAVIWY DGSNKYYADSVKGRFTISRDNSKNTLYLQMNSLRAEDTAVYYCARTAYGSGSYPIYY YYYMDVWGKGTTVTVSS | ADI-24796 | Heavy chain variable region ("HC") amino acid sequence |
| Ab 364 | 728 | SYELTQPPSVSVSPGQTASITCSGDKLGDKYACWYQQKPGQSPVLVIYQDSKRPSGI PERFSGSNSGNTATLTISGTQAMDEADYYCQAWDSSTVVFGGGTKLTVL | ADI-24796 | Light chain variable region ("LC") amino acid sequence |
| Ab 365 | 729 | EVQLLESGPGLVKPSETLSLTCTVSGGSISSYYWSWIRQPPGKGLEWIGYIYYSGST NYNPSLKSRVTISVDTSKNQFSLKLSSVTAADTAVYYCARILGHCSGGSCYRIIDYW GQGTLVTVSS | ADI-24798 | Heavy chain variable region ("HC") amino acid sequence |
| Ab 365 | 730 | QPVLTQPPSVSVSPGQTASITCSGDKLGDKYACWYQQKPGQSPVLVIYQDSKRPSG IPERFSGSNSGNTATLTISGTQAMDEADYYCQAWDSSTGVFGGGTKLTVL | ADI-24798 | Light chain variable region ("LC") amino acid sequence |
| Ab 366 | 731 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCAREGRDGYNYYFDYWG QGTLVTVSS | ADI-24799 | Heavy chain variable region ("HC") amino acid sequence |
| Ab 366 | 732 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGSVFGGGTKLTVL | ADI-24799 | Light chain variable region ("LC") amino acid sequence |
| Ab 367 | 733 | EVQLLESGGGLVKPGGSLRLSCAASGFTFSSYSMNWVRQAPGKGLEWVSSISSSSS YIYYADSVKGRFTISRDNAKNSLYLQMNSLRAEDTAVYYCARVRGGYSYGYGMDV | ADI-24800 | Heavy chain variable region |

TABLE 5-continued

Informal Sequence Listing

| Anti-body No. | SEQ ID NO: | Sequence | Clone # (ADI) | Descriptors |
|---|---|---|---|---|
| | | WGQGTTVTVSS | | ("HC") amino acid sequence |
| Ab 367 | 734 | QSVVTQPPSVSGAPGQRVTISCTGSSSNIGAGFDVHWYQQLPGTAPKLLIYGNSNR PSGVPDQFSGSKSGTSASLAITGLQAEDEADYYCQSYDSSLSGVVFGGGTKLTVL | ADI-24800 | Light chain variable region ("LC") amino acid sequence |
| Ab 368 | 735 | QVQLVQSGAEVKKPGASVKVSCKASGYTFTSYGISWVRQAPGQGLEWMGWISAY NGNTNYAQKLQGRVTMTTDTSTSTAYMELRSLRSDDTAVYYCARVTARTFGGIRK GYYYGMDVWGQGTTVTVSS | ADI-24801 | Heavy chain variable region ("HC") amino acid sequence |
| Ab 368 | 736 | SYELTQPPSVSVSPGQTASITCSGDKLGDKYACWYQQKPGQSPVLVIYQDSKRPSGI PERFSGSNSGNTATLTISGTQVMDEADYYCQAWDSSTVVFGGGTKLTVL | ADI-24801 | Light chain variable region ("LC") amino acid sequence |
| Ab 369 | 737 | EVQLLESGGGLVLPGGSLRLSCAASGFTFSSYAMSWVRQAPGKGLEWVSAISGSGI YTYYADSVKGRFTISRDNSKNTLYLQMSSLRAEDTAVYYCAKGSLGMAYSAFDIWG LGTTVTVSS | ADI-24803 | Heavy chain variable region ("HC") amino acid sequence |
| Ab 369 | 738 | DIQLTQSPGTLSLSSGERATLSCRASQSVSSNYLAWYQQKPGQPPRLLIYGASSRAT GIPDRFSGSGSGTDFTLTISRLEPEDFAVYYCQQYGSSPLTFGGGTKVDIK | ADI-24803 | Light chain variable region ("LC") amino acid sequence |
| Ab 370 | 739 | QVQLVQSGGGLVKPGGSLRLSCAASGFTFSSYSMNWVRQAPGKGLEWVSSISSSS SYIYYADSVKGRFTISRDNAKNSLYLQMNSLRAEDTAVYYCAREGYSSSSGYYYYMD VWGKGTTVTVSS | ADI-24805 | Heavy chain variable region ("HC") amino acid sequence |
| Ab 370 | 740 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGSVFGTGTKVTVL | ADI-24805 | Light chain variable region ("LC") amino acid sequence |
| Ab 371 | 741 | EVQLVESGPGLVKPSETLSLTCTVSGGSISSSSYYWGWIRQPPGKGLEWIGSIYYS GSTYYNPSLKSRVTISVDTSKNQFSLKLSSVTAADTAVYYCARHVNPYYDSSGTPY YYYGMDVWGQGTTVTVSS | ADI-24807 | Heavy chain variable region ("HC") amino acid sequence |
| Ab 371 | 742 | SYELTQPPSVSVSPGQTASITCSGDKLGDKYACWYQQKPGQSPVLVIYQDSKRPSGI PERFSGSNSGNTATLTISGTQAMDEADYYCQAWDSGTVVFGGGTKLTVL | ADI-24807 | Light chain variable region ("LC") amino acid sequence |
| Ab 372 | 743 | QVQLVQSGAEVKKPGASVKVSCKASGYTFTGYYMHWVRQAPGQGLEWMGWIN PNSGGTNYAQKFQGWVTMTRDTSISTAYMELSRLRSDDTAVYYCARGDPAANDY WGQGTLVTVSS | ADI-24808 | Heavy chain variable region ("HC") amino acid sequence |
| Ab 372 | 744 | QPVLTQPPSASGSPGQSVTISCTGTSSDVGGYNYVSWYQQHPGKAPKLMIYEVSKR PSGVPDRFSGSKSGNTASLTVSGLQAEDEADYYCSSYAGSNNVVFGGGTKLTVL | ADI-24808 | Light chain variable region ("LC") amino acid sequence |
| Ab 373 | 745 | QVQLVQSGAEVKKPGASVKVSCKASGYTFTSYDINWVRQATGQGLEWMGWMN PNSGNTGYAQKFQGRVTMTRNTSISTAYMELSSLRSEDTAVYYCARGLPGQWLEY YFDYWGQGTLVTVSS | ADI-24811 | Heavy chain variable region ("HC") amino acid sequence |
| Ab 373 | 746 | SYVLTQPPSVSVAPGKTARITCGGNNIGSKSVHWYQQKPGQAPVLVIYYDSDRPSGI PERFSGSNSGNTATLTISRVEAGDEADYYCQVWDSSSDHPVFGGGTKVTVL | ADI-24811 | Light chain variable region ("LC") amino acid sequence |
| Ab 374 | 747 | EVQLVESGGGLVQPGGSLRLSCAASGFSFSTYAMSWVRQAPGKGLEWVSAISGGG GSTYYADSVKGRFTISRDNSKNTLYLQVNSLRAEDTAVYYCARGGYCSSDSCYPFDF WGQGTLVTVSS | ADI-24812 | Heavy chain variable region ("HC") amino acid sequence |

TABLE 5-continued

Informal Sequence Listing

| Anti-<br>body<br>No. | SEQ<br>ID<br>NO: | Sequence | Clone<br>#<br>(ADI) | Descriptors |
|---|---|---|---|---|
| Ab 374 | 748 | QPVLTQPPSVSVSPGQTAMITCSGDALPKQYAYWYQQKPGQAPVLVIYKDSERPS<br>GIPERFSGSSSGTTVTLTISGVQAEDEADYYCQSADNSGSYAVFGGGTQLTVL | ADI-<br>24812 | Light chain<br>variable region<br>("LC") amino acid<br>sequence |
| Ab 375 | 749 | EVQLLESGGGLVQPGRSLRLSCAASGFTFDDYAMHWVRQAPGKGLEWVSGISWN<br>SGSIGYADSVKGRFTISRDNAKNSLYLQMNSLRAEDTALYYCAKDGDSSSWRDSNF<br>DYWGQGTLVTVSS | ADI-<br>24813 | Heavy chain<br>variable region<br>("HC") amino acid<br>sequence |
| Ab 375 | 750 | QSVLTQPPSVSGAPGQRVTISCTGSSSNIGAGYDVHWYQQLPGTAPKLLIYGNSNR<br>PSGVPDRFSGSKSGTSASLAITGLQAEDEADYYCQSYDSSLSGVVFGGGTKLTVL | ADI-<br>24813 | Light chain<br>variable region<br>("LC") amino acid<br>sequence |
| Ab 376 | 751 | EVQLLESGGGVVQPGRSLRLSCAASGFTFNSYTMHWVRQAPGKGLEWVAVISYD<br>GSNKYYADSVKGRFTISRDNSKNTLYLQMNSLRAEDTAVYYCARGRPYDFWSGYYT<br>DYYYYMDVWGKGTTVTVSS | ADI-<br>24814 | Heavy chain<br>variable region<br>("HC") amino acid<br>sequence |
| Ab 376 | 752 | EIVLTQSPGTLSLSPGERATLSCRASQSVYSNYLAWYQQKPGQAPRLLIYGASSRAT<br>GIPDRFSGSGSGTDFTLTISRLEPEDFAVYYCQQCGSSWTFGQGTKVEIK | ADI-<br>24814 | Light chain<br>variable region<br>("LC") amino acid<br>sequence |
| Ab 377 | 753 | EVQLVESGGGLVKPGGSLRLSCAASGFTFSSYSMNWVRQAPGKGLEWVSSISSSSS<br>YIYYADSVKGRFTISRDNAKNSLYLQMNSLRAEDTAVYYCAREGYSSSSGYYYMDV<br>WGKGTTVTVSS | ADI-<br>24815 | Heavy chain<br>variable region<br>("HC") amino acid<br>sequence |
| Ab 377 | 754 | QSVLTQPPSVSGAPGQRVTISCTGSSSNIGAGYDVHWYQQLPGTAPKLLIYGNSNR<br>PSGVPDRFSGSKSGTSASLAITGLQAEDEADYYCQSYDSSLSGVFGTGTKVTVL | ADI-<br>24815 | Light chain<br>variable region<br>("LC") amino acid<br>sequence |
| Ab 378 | 755 | QVQLVQSGAEVKKPGASVKVSCKASGYTFTSYDINWVRQATGQGLEWMGWMN<br>PNSGNTGYAQKFQGRVTMTRNTSISTAYMELSSLRSEDTAVYYCARGIPGYYYYGM<br>DVWGQGTTVTVSS | ADI-<br>24816 | Heavy chain<br>variable region<br>("HC") amino acid<br>sequence |
| Ab 378 | 756 | SYELTQPPSVSVSPGQTASITCSGDKLGDKYACWYQQKPGQSPVLVIYQDSKRPSGI<br>PERFSGSNSGNTATLTISGTQAMDEADYYCQAWDSSTYVFGTGTKVTVL | ADI-<br>24816 | Light chain<br>variable region<br>("LC") amino acid<br>sequence |
| Ab 379 | 757 | EVQLVESGGGLVKPGGSLRLSCAASGFTFSSYSMNWVRQAPGKGLEWVSSISSSSS<br>YIYYADSVKGRFTISRDNAKNSLYLQMNSLRAEDTAVYYCARDSMALLYSNYWFDP<br>WGQGTLVTVSS | ADI-<br>24817 | Heavy chain<br>variable region<br>("HC") amino acid<br>sequence |
| Ab 379 | 758 | QSVVTQPPSVSGAPGQRVTISCTGSSSNIGAGYDVHWYQQLPGTAPKLLIYGNSNR<br>PSGVPDRFSGSKSGTSASLAITGLQAEDEADYYCQSYDSSLSGVFGGGTKLTVL | ADI-<br>24817 | Light chain<br>variable region<br>("LC") amino acid<br>sequence |
| Ab 380 | 759 | QVQLVQSGAEVKKPGASVKVSCKASGYTFTGYYMHWVRQAPGQGLEWMGWIN<br>PNSGGTNYAQKFQGRVTMTRDTSISTAYMELSRLRSDDTAVYYCARGGTGVEFDY<br>WGQGTLVTVSS | ADI-<br>24818 | Heavy chain<br>variable region<br>("HC") amino acid<br>sequence |
| Ab 380 | 760 | QPVLTQPASVSGSPGQSITISCTGTSSDVGGYNYVSWYQQHPGKAPKLMIYDVSNR<br>PSGVSNRFSGSKSGNTASLTISGLQAEDEADYYCSSYTSSSTLVFGGGTQLTVL | ADI-<br>24818 | Light chain<br>variable region<br>("LC") amino acid<br>sequence |
| Ab 381 | 761 | EVQLLESGGGLVKPGGSLRLSCAASGFTFSSYSMNWVRQAPGKGLEWVSSISSSSS<br>YIYYADSVKGRFTISRDNAKNSLYLQMNSLRAEDTAVYYCARESGSGWYYFDYWG<br>QGTLVTVSS | ADI-<br>24819 | Heavy chain<br>variable region<br>("HC") amino acid<br>sequence |

TABLE 5-continued

Informal Sequence Listing

| Antibody No. | SEQ ID NO: | Sequence | Clone # (ADI) | Descriptors |
|---|---|---|---|---|
| Ab 381 | 762 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDGSLSGVFGGGTKVTVL | ADI-24819 | Light chain variable region ("LC") amino acid sequence |
| Ab 382 | 763 | QVQLVQSGAEVKKPGSSVKVSCKASGGTFSSYTISWVRQAPGQGLEWMGRIIPILG IANYAQKFQGRVTITADKSTSTAYMELSSLRSEDTAVYYCARDPPYLRAFDIWGQG TTVTVSS | ADI-24820 | Heavy chain variable region ("HC") amino acid sequence |
| Ab 382 | 764 | ETTLTQSPSSLSASVGDRVTITCRASQSISSYLNWYQQKPGKAPKLLIYAASSLQS GVPSRFSGSGSGTDFTLTISSLQPEDFATYYCQQSYSTPLLTFGGGTKVEIK | ADI-24820 | Light chain variable region ("LC") amino acid sequence |
| Ab 383 | 765 | EVQLVESGGGLVQPGRSLRLSCAASGFTFDDYAMHWVRQAPGKGLEWVSGISW NSGSIGYADSVKGRFTISRDNAKNSLYLQMNSLRAEDTALYYCAKDKDNWNYDAF DIWGQGTMVTVSS | ADI-24821 | Heavy chain variable region ("HC") amino acid sequence |
| Ab 383 | 766 | SYELTQPPSASGTPGQRVTISCSGSSSNIGSNTVNWYQQLPGTAPKLLIYSNNQRPS GVPDRFSGSKSGTSASLAISGLQSEDEADYYCAAWDDSLNGPVFGGGTKLTVL | ADI-24821 | Light chain variable region ("LC") amino acid sequence |
| Ab 384 | 767 | QVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARDSGLGSRGDAFDIW GQGTMVTVSS | ADI-24822 | Heavy chain variable region ("HC") amino acid sequence |
| Ab 384 | 768 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGYVFGTGTKVTVL | ADI-24822 | Light chain variable region ("LC") amino acid sequence |
| Ab 385 | 769 | EVQLLESGGGLVKPGGSLRLSCAASGFTFSSYSMNWVRQAPGKGLEWVSSISSSSS YIYYADSVKGRFTISRDNAKNSLYLQMNSLRAEDTAVYYCAREGDYYGSGRPFDYW GQGTLVTVSS | ADI-24823 | Heavy chain variable region ("HC") amino acid sequence |
| Ab 385 | 770 | QSVVTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSVVFGGGTKLTVL | ADI-24823 | Light chain variable region ("LC") amino acid sequence |
| Ab 386 | 771 | QVQLQESGPGLVKPSETLSLTCTVSGGSISSYYWSWIRQPPGKGLEWIGYIYYSGST NYNPSLKSRVTISVDTSKNQFSLKLSSVTAADTAVYYCAISLYGDYRTDAFDIWGQG TTVTVSS | ADI-24824 | Heavy chain variable region ("HC") amino acid sequence |
| Ab 386 | 772 | EIVLTQSPSSFSASTGDRVTITCRASQGISSYLAWYQQKPGKAPKLLIYAASTLQS GVPSRFSGSGSGTDFTLTISCLQSEDFATYYCQQYYSYPLFGGGTKVEIK | ADI-24824 | Light chain variable region ("LC") amino acid sequence |
| Ab 387 | 773 | QVQLVQSGAEVKKPGASVKVSCKASGYTFTSYDINWVRQATGQGLEWMGWMN PNSGNTGYAQKFQGRVTMTRNTSISTAYMELSSLRSEDTAVYYCSSVGGYYYYGM DVWGQGTTVTVSS | ADI-24825 | Heavy chain variable region ("HC") amino acid sequence |
| Ab 387 | 774 | EIVMTQSPLSLPVTPGEPASISCRSSQSLLHSNGYNYLDWYLQKPGQSPQLLIYLG SNRASGVPDRFSGSGSGTDFTLKISRVEAEDVGVYYCMQALQTLYTFGQGTKVEIK | ADI-24825 | Light chain variable region ("LC") amino acid sequence |
| Ab 388 | 775 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARDRGYGSGALDYWG QGTLVTVSS | ADI-24826 | Heavy chain variable region ("HC") amino acid sequence |
| Ab 388 | 776 | QPVLTQPASVSGSPGQSITISCTGTSSDVGGYNYVSWYQQHPGKAPKLMIYDVSNR PSGVSNRFSGSKSGNTASLTISGLQAEDEADYYCSSYTSSSTVVFGGGTKLTVL | ADI-24826 | Light chain variable region |

TABLE 5-continued

Informal Sequence Listing

| Antibody No. | SEQ ID NO: | Sequence | Clone # (ADI) | Descriptors |
|---|---|---|---|---|
| | | | | ("LC") amino acid sequence |
| Ab 389 | 777 | EVQLVESGGGLVQPGGSLRLSCAASGFTVSSNYMSWVRQAPGKGLEWVSVIYSDG STYYADSVKGRFTISRHNSKNTLYLQMNSLRAEDTAVYYCARCSTYGDYIDWYFDL WGRGTLVTVSS | ADI-24827 | Heavy chain variable region ("HC") amino acid sequence |
| Ab 389 | 778 | ETTLTQSPATLSVSPGERATLSCRASQSVSSNLAWYQQKPGQAPRLLIYGASTRATG IPARFSGSGSGTEFTLTISSLQSEDFAVYYCQQYNNWPLSFGGGTKLEIK | ADI-24827 | Light chain variable region ("LC") amino acid sequence |
| Ab 390 | 779 | EVQLVESGGGLVKPGGSLRLACAASGFSFRSYRMNWVRQAPGKGLEWVSSISSSSS YIDYADSVKGRFTISRDNAKNTVYLQVNSLRAEDTAVYYCARDGRTIFGVVIDYWG QGTLVTVSS | ADI-24828 | Heavy chain variable region ("HC") amino acid sequence |
| Ab 390 | 780 | QSVLTQPPSVSGAPGQRVTISCTGSSSNIGAGYDVHWYQQLPGTAPKLLIYGNNNR PSGVPDRFSGSKSGTSASLVITGLQAEDEADYYCQSYDSSLSVVFGGGTKLTVL | ADI-24828 | Light chain variable region ("LC") amino acid sequence |
| Ab 391 | 781 | EVQLLESGGGLVKPGGSLRLSCAASGFTFSSYSMNWVRQAPGKGLEWVSSISSSSS YIYYADSVKGRFTISRDNAKNSLYLQMNSLRAEDTAVYYCARGPHYYGSGSHDAFDI WGQGTMVTVSS | ADI-24829 | Heavy chain variable region ("HC") amino acid sequence |
| Ab 391 | 782 | QPVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGVFGGGTKLTVL | ADI-24829 | Light chain variable region ("LC") amino acid sequence |
| Ab 392 | 783 | QVQLVQSGAEVKKPGSSVKVSCKASGGTFSSYAISWVRQAPGQGLEWMGGIIPIF GTANYAQKFQGRVTITADESTSTAYMELSSLRSEDTAVYYCARGGSMVRGLGFDP WGQGTLVTVSS | ADI-24830 | Heavy chain variable region ("HC") amino acid sequence |
| Ab 392 | 784 | DIQLTQSPLSLPVTPGEPASISCRSSQSLLHSNGYNYLDWYLQKPGQSPQLLIYLG SNRASGVPDRFSGSGSGTDFTLKISRVEAEDVGVYYCMQALQTPLTFGGGTKLEIK | ADI-24830 | Light chain variable region ("LC") amino acid sequence |
| Ab 393 | 785 | QVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARVPSDFWSGYYNDYW GQGTLVTVSS | ADI-24831 | Heavy chain variable region ("HC") amino acid sequence |
| Ab 393 | 786 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGSWVFGGGTKLTVL | ADI-24831 | Light chain variable region ("LC") amino acid sequence |
| Ab 394 | 787 | EVQLVESGGGLVKPGGSLRLSCAASGFTFSSYSMNWVRQAPGKGLEWVSSISASSS YIFYSDLVKGRFTISRDNAKNSLYLQMNSLRAEDTAVYYCARAGYYYGSGSYYVDYW GQGTLVTVSS | ADI-24832 | Heavy chain variable region ("HC") amino acid sequence |
| Ab 394 | 788 | QSVLTQPPSVSGAPGQRVAISCTGSSSNIGAGYDVHWYQQLPGTAPKLLIYGNSNR PSGVPDRFSGSKSGTSASLAITGLQAEDEADYYCQSYGSSLSGWVFGGGTKLTVL | ADI-24832 | Light chain variable region ("LC") amino acid sequence |
| Ab 395 | 789 | QVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARALTYYYDSSGHGADY WGQGTLVTVSS | ADI-24833 | Heavy chain variable region ("HC") amino acid sequence |
| Ab 395 | 790 | QSVVTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSVVFGGGTKLTVL | ADI-24833 | Light chain variable region ("LC") amino acid sequence |

TABLE 5-continued

| Anti-body No. | SEQ ID NO: | Sequence | Clone # (ADI) | Descriptors |
|---|---|---|---|---|
| Ab 396 | 791 | QVQLVQSGGGLVQPGGSLRLSCAASGFTFSSYAMSWVRQAPGKGLEWVSTISGS GGSTYYADSVKGRFTISRDNSKNTLYLQMNSLRAEDTAVYYCATWKRWGSGYYYS YMDVWGKGTTVTVSS | ADI-24834 | Heavy chain variable region ("HC") amino acid sequence |
| Ab 396 | 792 | DIQLTQSPSTLSASVGDRVTITCRASQSISSWLAWYQQKPGKAPKLLIYDAFSLES GVPSRFSGSGSGTEFTLTISSLQPDDFATYYCQQYNSYSVTFGGGTKVEIK | ADI-24834 | Light chain variable region ("LC") amino acid sequence |
| Ab 397 | 793 | EVQLVESGGGLVKPGGSLRLSCAASGFPFSTSSMNWVRQAPGKGLEWVSSISSSSS YIDYADSVKGRFTISRDNAKNSLYLQMNSLRAGDTAVYYCARVPRSDWYYFDYWG QGTLVTVSS | ADI-24835 | Heavy chain variable region ("HC") amino acid sequence |
| Ab 397 | 794 | QSVVTQPPSVSGAPGQRVTISCTGSSSNIGAGYDVHWYQQLPGTAPKFLIYDNKYR PSGVPDRFSGSKSGTSASLAITGLQAEDEADYYCQSYDSSLSGYVFGTGTKLTVL | ADI-24835 | Light chain variable region ("LC") amino acid sequence |
| Ab 398 | 795 | EVQLLESGGGLVQPGRSLRLSCAASGFTFDDYAMHWVRQAPGKGLEWVSGISWN SGSIGYADSVKGRFTISRDNAKNSLYLQMNSLRAEDTALYYCAKDLRGGTYYYYGM DVWGQGTTVTVSS | ADI-24836 | Heavy chain variable region ("HC") amino acid sequence |
| Ab 398 | 796 | DIRVTQSPSSLSASVGDRVTITCRASQSISSYLNWYQQKPGKAPKLLIYAASSLQS GVPSRFSGSGSGTDFTLTISSLQPEDFATYYCQQSYSTPPTFGGGTKVEIK | ADI-24836 | Light chain variable region ("LC") amino acid sequence |
| Ab 399 | 797 | QVQLQESGPGLVKPSETLSLTCTVSGGSISSYYWSWIRQPPGKGLEWIGYIYYSGST NYNPSLKSRVTISVDTSKNQFSLKLSSVTAADTAVYYCARAIYYYDSSGYYYVGDAF DIWGQGTTVTVSS | ADI-24837 | Heavy chain variable region ("HC") amino acid sequence |
| Ab 399 | 798 | QSVLTQPPSVSAAPGQKVTISCSGSSSNIGNNYVSWYQQLPGTAPKLLIYENNKRPS GIPDRFSGSKSGTSATLGITGLQTGDEADYYCGTWDSSLSAGVFGGGTKLTVL | ADI-24837 | Light chain variable region ("LC") amino acid sequence |
| Ab 400 | 799 | EVQLLESGGGLVKPGGSLRLSCAASGFTFSSYSMNWVRQAPGKGLEWVSSISSSSS YIYYADSVKGRFTISRDNAKNSLYLQMNSLRAEDTAVYYCARQGVGTVTTWNYYYY YMDVWGKGTTVTVSS | ADI-24838 | Heavy chain variable region ("HC") amino acid sequence |
| Ab 400 | 800 | QSVVTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSWVFGGGTKLTVL | ADI-24838 | Light chain variable region ("LC") amino acid sequence |
| Ab 401 | 801 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARVLVATAYGNAFDIW GQGTMVTVSS | ADI-24839 | Heavy chain variable region ("HC") amino acid sequence |
| Ab 401 | 802 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLTVVFGGGTKLTVL | ADI-24839 | Light chain variable region ("LC") amino acid sequence |
| Ab 402 | 803 | EVQLLESGGGLVKPGGSLRLSCAASGFTFSSYSMNWVRQAPGKGLEWVSSISSSSS YIYYADSVKGRFTISRDNAKNSLYLQMNSLRAEDTAVYYCARDQVYSYGYYFDYWG QGTLVTVSS | ADI-24840 | Heavy chain variable region ("HC") amino acid sequence |
| Ab 402 | 804 | QSVLAQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGSHVVFGGGTKLTVL | ADI-24840 | Light chain variable region ("LC") amino acid sequence |
| Ab 403 | 805 | QVQLVQSGAEVKKPGASVKVSCKASGYTFTSYAMHWVRQAPGQRLEWMGWIN AGNGNTKYSQKFQGRVTITRDTSASTAYMELSSLRSEDTAVYYCARDGFPTNYDFW | ADI-24841 | Heavy chain variable region |

TABLE 5-continued

Informal Sequence Listing

| Anti-body No. | SEQ ID NO: | Sequence | Clone # (ADI) | Descriptors |
|---|---|---|---|---|
| | | SGYSDDAFDIWGQGTMVTVSS | | ("HC") amino acid sequence |
| Ab 403 | 806 | DIVMTQSPATLSVSPGERATLSCRASQSVSSNLAWYQQKPGQAPRLLIYGASTRAT GIPARFSGSGSGTEFTLTISSLQSEDFAVYYCQQYNNWPPLTFGQGTKVDIK | ADI-24841 | Light chain variable region ("LC") amino acid sequence |
| Ab 404 | 807 | QVQLVQSGGGLVKPGGSLRLSCAASGFTFSSYSMNWVRQAPGKGLEWVSSISSSS SYIYYADSVKGRFTISRDNAKNSLYLQMNSLRAEDTAVYYCARVPPHDYGGYYFDY WGQGTLVTVSS | ADI-24842 | Heavy chain variable region ("HC") amino acid sequence |
| Ab 404 | 808 | QSVVTQPPSVSGAPGQRVTISCTGSSSNIGAGYDVHWYQQLPGTAPKLLIYRNSNR PSGVPDRFSGSKSGTSASLAIIGLQAEDEADYYCQSYDSSLSVVFGGGTKLTVL | ADI-24842 | Light chain variable region ("LC") amino acid sequence |
| Ab 405 | 809 | EVQLVESGPGLVKPSQTLSLTCTVSGGSISSGDYYWSWIRQPPGKGLEWIGYIYYSG STYYNPSLKSRVTISVDTSKNQFSLKLSSVTAADTAVYYCARESIVGAVDYWGQGTL VTVSS | ADI-24843 | Heavy chain variable region ("HC") amino acid sequence |
| Ab 405 | 810 | DIQMTQSPDSLAVSLGERATINCKSSQSVLYSSNNKNYLAWYQQKPGQPPKLLIYW ASTRESGVPDRFSGSGSGTDFTLTISSLQAEDVAVYYCQQYYSTPHTFGQGTKLEIK | ADI-24843 | Light chain variable region ("LC") amino acid sequence |
| Ab 406 | 811 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARDYCSGGSCYLAAFDI WGQGTTVTVSS | ADI-24845 | Heavy chain variable region ("HC") amino acid sequence |
| Ab 406 | 812 | QPVLTQPASVSGSPGQSITISCTGTSSDVGGYNYVSWYQQHPGKAPKLMIYEVSNR PSGVSNRFSGSKSGNTASLTISGLQAEDEADYYCSSYTSSSTPVVFGGGTKLTVL | ADI-24845 | Light chain variable region ("LC") amino acid sequence |
| Ab 407 | 813 | EVQLLESGGGLVKPGGSLRLSCAASGFTFSSYSMNWVRQAPGKGLEWVSSISSSSS YIYYADSVKGRFTISRDNAKNSLYLQMNSLRAEDTAVYYCARDDGILWLDYWGQG TLVTVSS | ADI-24846 | Heavy chain variable region ("HC") amino acid sequence |
| Ab 407 | 814 | QPGLTQPPSASGTPGQRVTISCSGSSSNIGSNYVYWYQQLPGTAPKLLIYRNNQRPS GVPDRFSGSKSGTSASLAISGLRSEDEADYYCAAWDDSLSGQVFGGGTKLTVL | ADI-24846 | Light chain variable region ("LC") amino acid sequence |
| Ab 408 | 815 | EVQLVESGGGLVKPGGSLRLSCAASGFTFSSYSMNWVRQAPGKGLEWVSSISSSSN YIYYADSVKGRFTISRDNAKNSLYLQMNSLRAEDTAVYYCARDRIAAYTFDYWGQG TLVTVSS | ADI-24847 | Heavy chain variable region ("HC") amino acid sequence |
| Ab 408 | 816 | QSVVTQPPSVSGAPGQRVTISCTGSSSNIGAGYDVHWYQQLPGTAPKLLIYGNSNR PSGVPDRFSGSKSGTSASLAITGLQAEDEADYYCQSYDSSLPYVFGTGTKVTVL | ADI-24847 | Light chain variable region ("LC") amino acid sequence |
| Ab 409 | 817 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARDTVVAGIYFDYWGQ GTLVTVSS | ADI-24848 | Heavy chain variable region ("HC") amino acid sequence |
| Ab 409 | 818 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGVVFGGGTKLTVL | ADI-24848 | Light chain variable region ("LC") amino acid sequence |
| Ab 410 | 819 | QVQLVQSGGVVVQPGGSLRLSCAASGFTFDDYTMHWVRQAPGKGLEWVSLIGW DGGSTYYADSVKGRFTISRDNSKYSLYLQMNSLRTEDTALYYCAKDLGSSSGYFLG RDYYGMDVWGQGTTVTVSS | ADI-24849 | Heavy chain variable region ("HC") amino acid sequence |

TABLE 5-continued

Informal Sequence Listing

| Antibody No. | SEQ ID NO: | Sequence | Clone # (ADI) | Descriptors |
|---|---|---|---|---|
| Ab 410 | 820 | DIQLTQSPSSLSASVGDRVTITCQASQDISNYLNWYQQKPGKAPKLLIYDASNLET GVPSRFSGSGSGTDFTFTISSLQPEDIATYYCQQYNNLPTFGGGTKLEIK | ADI-24849 | Light chain variable region ("LC") amino acid sequence |
| Ab 411 | 821 | QVQLVQSGGGLVKPGGSLRLSCAASGFTFSSYSMNWVRQAPGKGLEWVSSISSSS SYIYYADSVKGRFTISRDNAKNSLYLQMNSLRAEDTAVYYCAREDYGDYYYYYMDV WGKGTTVTVSS | ADI-24850 | Heavy chain variable region ("HC") amino acid sequence |
| Ab 411 | 822 | QPVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGYVFGTGTKVTVL | ADI-24850 | Light chain variable region ("LC") amino acid sequence |
| Ab 412 | 823 | QVQLVQSGAEVKKPGASVKVSCKASGYTFTGYYMHWVRQAPGQGLEWMGWIN PNSGGTNYAQKFQGRVTMTRDTSISTAYMELSRLRSDDTAVYYCARAYELELDYW GQGTLVTVSS | ADI-24851 | Heavy chain variable region ("HC") amino acid sequence |
| Ab 412 | 824 | QSVLIQPPSASGSPGQSVTISCTGTSSDVGGYNYVSWYQQHPGKAPKLMIYEVSKR PSGVPDRFSGSKSGNTASLTVSGLQAEDEADYYCSSYAGSNNVVFGGGTKLTVL | ADI-24851 | Light chain variable region ("LC") amino acid sequence |
| Ab 413 | 825 | QVQLVESGAEVKKPGASVKVSCKASGYTFTSYAIHWVRQAPGQRLEWMGWINAG NGNTKYSQKFQGRVTITRDTSASTAYMELSSLRSEDTAVYYCASEESGYFDYWGQG TLVTVSS | ADI-24852 | Heavy chain variable region ("HC") amino acid sequence |
| Ab 413 | 826 | SYELMQPPSVPVSPGQTASITCSGDKLGDKYACWYQQKPGQSPVLVIYQDRKRPS GIPERFSGSNSGNTATLTISGTQAMDEADYYCQAWDSSTVVFGGGTKVTVL | ADI-24852 | Light chain variable region ("LC") amino acid sequence |
| Ab 414 | 827 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARDRRFGELFYFDYWG QGTLVTVSS | ADI-24854 | Heavy chain variable region ("HC") amino acid sequence |
| Ab 414 | 828 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGNWVFGGGTKLTVL | ADI-24854 | Light chain variable region ("LC") amino acid sequence |
| Ab 415 | 829 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARRYCTNGVCYDAFDI WGQGTMVTVSS | ADI-24855 | Heavy chain variable region ("HC") amino acid sequence |
| Ab 415 | 830 | QSVVTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSYVFGTGTKVTVL | ADI-24855 | Light chain variable region ("LC") amino acid sequence |
| Ab 416 | 831 | QVQLVQSGAEVKKPGASVKVSCKASGYTFTSYGISWVRQAPGQGLEWMGWISAY NGNTNYAQKLQGRVTMTTDTSTSTAYMELRSLRSDDTAVYYCARAGIVVVPKYYY MDVWGKGTTVTVSS | ADI-24856 | Heavy chain variable region ("HC") amino acid sequence |
| Ab 416 | 832 | DIVMTQSPGTLSLSPGERATLSCRASQSVSSSYLAWYQQKPGQAPRLLIYGASSRAT GIPDRFSGSGSGTDFTLTISRLEPEDFAVYYCQQYGSSPMYTFGQGTKVEIK | ADI-24856 | Light chain variable region ("LC") amino acid sequence |
| Ab 417 | 833 | EVQLLESGGGLVKPGGSLRLSCAASGFTFSSYSMNWVRQAPGKGLEWVSSISSSSS YIYYADSVKGRFTISRDNAKNSLYLQMNSLRAEDTAVYYCAREGYYYGSGSYLDYW GQGTLVTVSS | ADI-24857 | Heavy chain variable region ("HC") amino acid sequence |
| Ab 417 | 834 | QSVVTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSVVFGGGTKLTVL | ADI-24857 | Light chain variable region |

TABLE 5-continued

Informal Sequence Listing

| Anti- body No. | SEQ ID NO: | Sequence | Clone # (ADI) | Descriptors |
|---|---|---|---|---|
| | | | | ("LC") amino acid sequence |
| Ab 418 | 835 | EVQLLESGGGLVKPGGSLRLSCAASGFTFSSYSMNWVRQAPGKGLEWVSSISSSSS YIYYADSVKGRFTISRDNAKNSLYLQMNSLRAEDTAVYYCARGGYSYGYSFDYWGQ GTLVTVSS | ADI-24858 | Heavy chain variable region ("HC") amino acid sequence |
| Ab 418 | 836 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSVVFGGGTKLTVL | ADI-24858 | Light chain variable region ("LC") amino acid sequence |
| Ab 419 | 837 | EVQLLESGGGLVKPGGSLRLSCAASGFTFSSYSMNWVRQAPGKGLEWVSSISSSSS YIYYADSVKGRFTISRDNAKNSLYLQMNSLRAEDTAVYYCARDGSPINWVSPFPFDY WGQGTLVTVSS | ADI-24859 | Heavy chain variable region ("HC") amino acid sequence |
| Ab 419 | 838 | QPVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGSVFGGGTQLTVL | ADI-24859 | Light chain variable region ("LC") amino acid sequence |
| Ab 420 | 839 | EVQLLESGGGLVKPGGSLRLSCAASGLTFSDYYMSWIRQAPGKGLEWVSYISGGSS YSNYADSVKGRFTISRDNAKNSLYLQMNSLRAEDTAVYYCARGYCSGSSCYEAFDI WGQGTTVTVSS | ADI-24860 | Heavy chain variable region ("HC") amino acid sequence |
| Ab 420 | 840 | SYVLTQPPSVSGAPGQRVTISCTGSSSNIGAGFDVHWYQQLPGTAPKLLIYGNSDRP SGVPDRFSGSKSGTSASLAITGLQAEDEADYYCQSYDSSLSGYVFGTGTKVTVL | ADI-24860 | Light chain variable region ("LC") amino acid sequence |
| Ab 421 | 841 | QVQLVQSGGGLVKPGGSLRLSCAASGFTFSSYSMNWVRQAPGKGLEWVSSISGGS SYIYYADSVKGRFTISRDNAKNSLYLQMNSLRAEDTAVYYCAREAYYYDSSGLKWFD PWGQGTLVTVSS | ADI-24861 | Heavy chain variable region ("HC") amino acid sequence |
| Ab 421 | 842 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLGWVFGGGTKLTVL | ADI-24861 | Light chain variable region ("LC") amino acid sequence |
| Ab 422 | 843 | EVQLLESGPGLVKPSQTLSLTCTVSGGSISSGGYYWSWIRQHPGKGLEWIGYIYYSG STYYNPSLKSRVTISVDTSKNQFSLKLSSVTAADTAVYYCARLEIGDGSGSYLHWYF DLWGRGTLVTVSS | ADI-24862 | Heavy chain variable region ("HC") amino acid sequence |
| Ab 422 | 844 | SYELTQPPSVSVSPGQTASITCSGDKLGDKYACWYQQKPGQSPVLVIYQDSKRPSGI PERFSGSNSGNTATLTISGTQAMDEADYYCQAWDSSTAVFGGGTKLTVL | ADI-24862 | Light chain variable region ("LC") amino acid sequence |
| Ab 423 | 845 | EVQLVESGGGLVKPGGSLRLSCAASGFTFSSYSMNWVRQAPGKGLEWVSSISSSRS YIYYADSVKGRFTISRDNAKNSLYLQMNSLRAEDTAVYYCARVGSGGSGTYGDYWG QGTLVTVSS | ADI-24863 | Heavy chain variable region ("HC") amino acid sequence |
| Ab 423 | 846 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGWVFGGGTKLTVL | ADI-24863 | Light chain variable region ("LC") amino acid sequence |
| Ab 424 | 847 | EVQLVESGGGLVKPGGSLRLSCAASGFTFSSYSMNWVRQAPGKGLEWVSSISSSSS YIYYADSVKGRFTISRHNAKNSLYLQMNSLRAEDTAVYYCARGSSSSWFCFDYWGQ GTLVTVSS | ADI-25462 | Heavy chain variable region ("HC") amino acid sequence |
| Ab 424 | 848 | SYVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSYVFGTGTKLTVL | ADI-25462 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 425 | 849 | GVQLVESGPGLVKPSETLSLTCTVSGGSISSYYWSWIRQPPGKGLEWIGYIYYSGST NYNPSLKSRVTISVDTSKNQFSLKLSSVTAADTAVYYCARGYYYDSSGYYPNDAFDI WGQGTMVTVSS | ADI-25467 | Heavy chain variable region ("HC") amino acid sequence |
| Ab 425 | 850 | DIQVTQSPSSLSASVGDRVTITCRASQSISSYLNWYQQKPGKAPKLLIYAASSLQSG VPSRFSGSGSGTDFTLTISSLQPEDFATYYCQQSYSTPYTFGQGTKVEIK | ADI-25467 | Light chain variable region ("LC") amino acid sequence |
| Ab 426 | 851 | QVQLVQSGAEVKKPGESLKISCKGSGYSFTSYWIGWVRQMPGKGLEWMGIIYPGD SDTRYSPSFQGQVTISADKSISTAYLQWSSLKASDTAMYYCARHVGQVYCSSTSCYT SREYYFDYWGQGTLVTVSS | ADI-25468 | Heavy chain variable region ("HC") amino acid sequence |
| Ab 426 | 852 | SYVLTQPPSVSVSPGQTASITCSGDKLGDKYACWYQQKPGQSPVLVIYQDSKRPSGI PERFSGSNSGNTATLTISGTQAMDEADYYCQAWDSSTAVVFGGGTKLTVL | ADI-25468 | Light chain variable region ("LC") amino acid sequence |
| Ab 427 | 853 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARDDSSSWYYFDYWGQ GTLVTVSS | ADI-25472 | Heavy chain variable region ("HC") amino acid sequence |
| Ab 427 | 854 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGYVFGTGTKVTVL | ADI-25472 | Light chain variable region ("LC") amino acid sequence |
| Ab 428 | 855 | EVQLLESGGGLVKPGGSLRLSCAASGFTFSSYSMNWVRQAPGKGLEWVSSISSSSS YIYYADSVKGRFTISRDNAKNSLYLQMNSLRAEDTAVYYCARLDYSNYYYYMDVWG KGTTVTVSS | ADI-25478 | Heavy chain variable region ("HC") amino acid sequence |
| Ab 428 | 856 | QPVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGYVFGTGTKLTVL | ADI-25478 | Light chain variable region ("LC") amino acid sequence |
| Ab 429 | 857 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARGGYSYGAYYYYYMD VWGKGTTVTVSS | ADI-25479 | Heavy chain variable region ("HC") amino acid sequence |
| Ab 429 | 858 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGYWVFGGGTKLTVL | ADI-25479 | Light chain variable region ("LC") amino acid sequence |
| Ab 430 | 859 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARGGYSYGAYYYYYMD VWGKGTTVTVSS | ADI-25480 | Heavy chain variable region ("HC") amino acid sequence |
| Ab 430 | 860 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGYWVFGGGTKVTVL | ADI-25480 | Light chain variable region ("LC") amino acid sequence |
| Ab 431 | 861 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARSIAVAGTGYGMDVW GQGTTVTVSS | ADI-25484 | Heavy chain variable region ("HC") amino acid sequence |
| Ab 431 | 862 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSVVFGGGTKLTVL | ADI-25484 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 432 | 863 | EVQLLESGPGLVKPSQTLSLTCTVSGGSISSGGYYWSWIRQHPGKGLEWIGYIYYSG STYYNPSLKSRVTISVDTSKNQFSLKLSSVTAADTAVYYCAREVVPAAIRAGYYFDY WGQGTLVTVSS | ADI-25491 | Heavy chain variable region ("HC") amino acid sequence |
| Ab 432 | 864 | SYELMQPPSVSVSPGQTASITCSGDKLGDKYACWYQQKPGQSPVLVIYQDSKRPSG IPERFSGSNSGNTATLTISGTQAMDEADYYCQAWDSSTGGVFGTGTQLTVL | ADI-25491 | Light chain variable region ("LC") amino acid sequence |
| Ab 433 | 865 | QVQLVQSGGGLVKPGGSLRLSCAASGFTFSSYSMNWVRQAPGKGLEWVSSISSSS SYIYYADSVKGRFTISRDNAKNSLYLQMNSLRAEDTAVYYCARGYCTNGVCYLDAFD IWGQGTTVTVSS | ADI-25495 | Heavy chain variable region ("HC") amino acid sequence |
| Ab 433 | 866 | QSVLIQPASVSGSPGQSITISCTGTSSDVGGYNYVSWYQQHPGKAPKLMIYDVSNR PSGVSNRFSGSKSGNTASLTISGLQAEDEADYYCSSYTSSSTPVVFGGGTKVTVL | ADI-25495 | Light chain variable region ("LC") amino acid sequence |
| Ab 434 | 867 | QVQLVQSGGGLVKPGGSLRLSCAASGFTFSSYSMNWVRQAPGKGLEWVSSISSSS SYIYYADSVKGRFTISRDNAKNSLYLQMNSLRAEDTAVYYCARVASEVWFFDLWGR GTLVTVSS | ADI-25496 | Heavy chain variable region ("HC") amino acid sequence |
| Ab 434 | 868 | QPVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGYVFGTGTKLTVL | ADI-25496 | Light chain variable region ("LC") amino acid sequence |
| Ab 435 | 869 | EVQLLESGGGLVQPGGSLRLSCAASGFTFSSYWMSWVRQAPGKGLEWVANIKQD GSEKYYVDSVKGRFTISRDNAKNSLYLQMNSLRAEDTAVYYCARDGLLQYDFWSGY YDYWGQGTLVTVSS | ADI-25497 | Heavy chain variable region ("HC") amino acid sequence |
| Ab 435 | 870 | EIVLTQSPSSLSASVGDRVTITCRASQGISSWLAWYQQKPEKAPKSLIYAASSLQS GVPSRFSGSGSGTDFTLTISSLQPEDFATYYCQQYNSYPFTFGPGTKVDIK | ADI-25497 | Light chain variable region ("LC") amino acid sequence |
| Ab 436 | 871 | QVQLVQSGAEVKKPGSSVKVSCKASGGTFSSYAISWVRQAPGQGLEWMGGIIPIF GTANYAQKFQGRVTITADESTSTAYMELSSLRSEDTAVYYCARDHWSNPLYYYGM DVWGQGTTVTVSS | ADI-25502 | Heavy chain variable region ("HC") amino acid sequence |
| Ab 436 | 872 | SYELTQPPSVSVSPGQTARITCSGDVLAKKYARWFQQKPGQAPVLVIYKDSERPSGI PERFSGSSSGTTVTLTISGAQVEDEADYYCYSAADNNLGVFGGGTQLTVL | ADI-25502 | Light chain variable region ("LC") amino acid sequence |
| Ab 437 | 873 | EVQLLESGAEVKKPGSSVKVSCKASGGTFSSYAISWVRQAPGQGLEWMGGIIPIFG TANYAQKFQGRVTITADESTSTAYMELSSLRSEDTAVYYCARSRYSGSYYYYYGMDV WGQGTTVTVSS | ADI-25503 | Heavy chain variable region ("HC") amino acid sequence |
| Ab 437 | 874 | QPVLTQPPSVSVSPGQTASITCSGDKLGDKYACWYQQKPGQSPVLVIYQDSKRPSG IPERFSGSNSGNTATLTISGTQAMDEADYYCQAWDSSTYVFGTGTKLTVL | ADI-25503 | Light chain variable region ("LC") amino acid sequence |
| Ab 438 | 875 | EVQLVESGGGLVKPGGSLRLSCAASGFTFSSYSMNWVRQAPGKGLEWVSSISSSS YIYYADSVKGRFTISRDNAKNSLYLQMNSLRAEDTAVYYCARVVGYSGSYLDYWGQ GTLVTVSS | ADI-25505 | Heavy chain variable region ("HC") amino acid sequence |
| Ab 438 | 876 | QSVVTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGVVFGGGTKLTVL | ADI-25505 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 439 | 877 | EVQLVQSGAEVKKPGSSVKVSCKASGGTFSSYAISWVRQAPGQGLEWMGGIIPIFG TANYAQKFQGRVTITADESTSTAYMELSSLRSEDTAVYYCARSRYSGSYYYYYGMDV WGQGTTVTVSS | ADI-25514 | Heavy chain variable region ("HC") amino acid sequence |
| Ab 439 | 878 | SYELTQPPSVSVSPGQTASITCSGDKLGDKYACWYQQKPGQSPVLVIYQDSKRPSGI PERFSGSNSGNTATLTISGTQAMDEADYYCQAWDSSTYVFGTGTKLTVL | ADI-25514 | Light chain variable region ("LC") amino acid sequence |
| Ab 440 | 879 | QVQLVQSGAEVKKPGASVKVSCKASGYTFTGYYMHWVRQAPGQGLEWMGWIN PNSGGTNYAQKFQGRVTMRDTSISTAYMELSRLRSDDTAVYYCARDWAWDAFD IWGQGTMVTVSS | ADI-25517 | Heavy chain variable region ("HC") amino acid sequence |
| Ab 440 | 880 | QPGLTQPASVSGSPGQSITISCTGTSSDVGGYNYVSWYQQHPGKAPKLMIYDVSN RPSGVSNRFSGSKSGNTASLTISGLQAEDEADYYCSSYTSSSTLVFGGGTKLTVL | ADI-25517 | Light chain variable region ("LC") amino acid sequence |
| Ab 441 | 881 | EVQLVESGAEVKKPGASVKVSCKASGYTFTGYYMHWVRQAPGQGLEWMGWINP NSGGTNYAQKFQGRVTMRDTSISTAYMELSRLRSDDTAVYYCARDWAWDAFDI WGQGTMVTVSS | ADI-25518 | Heavy chain variable region ("HC") amino acid sequence |
| Ab 441 | 882 | QSVLIQPASVSGSPGQSITISCTGTSSDVGGYNYVSWYQQHPGKAPKLMIYDVSNR PSGVSNRFSGSKSGNTASLTISGLQAEDEADYYCSSYTSSSTLVFGGGTQLTVL | ADI-25518 | Light chain variable region ("LC") amino acid sequence |
| Ab 442 | 883 | EVQLLESGGGLVKPGGSLRLSCAASGFTFSSYSMNWVRQAPGKGLEWVSSISSSS YIYYADSVKGRFTISRDNAKNSLYLQMNSLRAEDTAVYYCAREWSPIVVVTNAFDI WGQGTMVTVSS | ADI-25524 | Heavy chain variable region ("HC") amino acid sequence |
| Ab 442 | 884 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGWVFGGGTKVTVL | ADI-25524 | Light chain variable region ("LC") amino acid sequence |
| Ab 443 | 885 | QVQLVQSGGGLVKPGGSLRLSCAASGFTFSSYSMNWVRQAPGKGLEWVSSISSSS SYIYYADSVKGRFTISRDNAKNSLYLQMNSLRAEDTAVYYCARGSSSSWYYFDYWG QGTLVTVSS | ADI-25532 | Heavy chain variable region ("HC") amino acid sequence |
| Ab 443 | 886 | QSVVTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSYVFGTGTKVTVL | ADI-25532 | Light chain variable region ("LC") amino acid sequence |
| Ab 444 | 887 | QVQLVQSGAEVKKPGASVKVSCKASGYTFTGYYMHWVRQAPGQGLEWMGWIN PNSGGTNYAQKFQGWVTMRDTSISTAYMELSRLRSDDTAVYYCARDANWGAFD IWGQGTMVTVSS | ADI-25533 | Heavy chain variable region ("HC") amino acid sequence |
| Ab 444 | 888 | QSVLIQPASVSGSPGQSITISCTGTSSDVGGYNYVSWYQQHPGKAPKLMIYDVSNR PSGVSNRFSGSKSGNTASLTISGLQAEDEADYYCSSYTSSSTWVFGGGTKLTVL | ADI-25533 | Light chain variable region ("LC") amino acid sequence |
| Ab 445 | 889 | EVQLVESGGGLVQPGGSLRLSCAASGFTFSSYAMSWVRQAPGKGLEWVSAISGSG GSTYYADSVKGRFTISRDNSKNTLYLQMNSLRAEDTAVYYCAKDYYYDSSGYPPYGI GVWGQGTTVTVSS | ADI-25542 | Heavy chain variable region ("HC") amino acid sequence |
| Ab 445 | 890 | QTVVTQEPSFSVSPGGTVTLTCGLSSGSVSTSYYPSWYQQTPGQAPRTLIYSTNTRS SGVPDRFSGSILGNKAALTITGAQADDESDYYCVLYMGSGIWVFGGGTKVTVL | ADI-25542 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 446 | 891 | EVQLLESGGGLIQPGGSLRLSCAASGFTVSSNYMSWVRQAPGKGLEWVSVIYSGGS TYYADSVKGRFTISRDNSKNTLYLQMNSLRAEDTAVYYCARGGIADAFDIWGQGT MVTVSS | ADI-25547 | Heavy chain variable region ("HC") amino acid sequence |
| Ab 446 | 892 | ETTLTQSPSSVSASVGDRVTITCRASQGISSWLAWYQQKPGKAPKLLIYAASSLQSG VPSRFSGSGSGTDFTLTISSLQPEDFATYYCQQANSFPRTFGQGTKLEIK | ADI-25547 | Light chain variable region ("LC") amino acid sequence |
| Ab 447 | 893 | EVQLVESGGGLIQPGGSLRLSCAASGFTVSSNYMSWVRQAPGKGLEWVSVIYSGG STYYADSVKGRFTISRDNSKNTLYLQMNSLRAEDTAVYYCARGPQFGVSYSSGWYS FDYWGQGTLVTVSS | ADI-25548 | Heavy chain variable region ("HC") amino acid sequence |
| Ab 447 | 894 | QSVLIQPRSVSGSPGQSVTISCTGTSSDVGGYNYVSWYQQHPGKAPKLMIYDVSKR PSGVPDRFSGSKSGNTASLTISGLQAEDEADYYCCSYAGSYTFVVFGGGTKLTVL | ADI-25548 | Light chain variable region ("LC") amino acid sequence |
| Ab 448 | 895 | QVQLVQSGGGLVKPGGSLRLSCAASGFTFSSYSMNWVRQAPGKGLEWVSSISSSS SYIYYADSVKGRFTISRDNAKNSLYLQMNSLRAEDTAVYYCARVSSGWYGGGAYYF DYWGQGTLVTVSS | ADI-25549 | Heavy chain variable region ("HC") amino acid sequence |
| Ab 448 | 896 | QSVVTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSALYVFGTGTKVTVL | ADI-25549 | Light chain variable region ("LC") amino acid sequence |
| Ab 449 | 897 | QVQLVQSGGGLVKPGGSLRLSCAASGFTFSSYSMNWVRQAPGKGLEWVSSISSSS SYIYYADSVKGRFTISRDNAKNSLYLQMNSLRAEDTAVYYCARQRGGIAVAGTYFD LWGRGTLVTVSS | ADI-25555 | Heavy chain variable region ("HC") amino acid sequence |
| Ab 449 | 898 | QPVLTQPPSVSGAPGQRVTISCTGSSSNIGAGYDVHWYQQLPGTAPKLLIYGNSNR PSGVPDRFSGSKSGTSASLAITGLQAEDEADYYCQSYDSTVVFGGGTKLTVL | ADI-25555 | Light chain variable region ("LC") amino acid sequence |
| Ab 450 | 899 | QVQLVQSGGGLVKPGGSLRLSCAASGFTFSSYSMNWVRQAPGKGLEWVSSISSSS SYIYYADSVKGRFTISRDNAKNSLYLQMNSLRAEDTAVYYCARQRGGIAVAGTYFD LWGRGTLVTVSS | ADI-25556 | Heavy chain variable region ("HC") amino acid sequence |
| Ab 450 | 900 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSTVVFGGGTKVTVL | ADI-25556 | Light chain variable region ("LC") amino acid sequence |
| Ab 451 | 901 | EVQLLESGGGLVKPGGSLRLSCAASGFTFSSYSMNWVRQAPGKGLEWVSSISSSSS YIYYADSVKGRFTISRDNAKNSLYLQMNSLRAEDTAVYYCARGYGSGSYLDYFDYW GQGTLVTVSS | ADI-25557 | Heavy chain variable region ("HC") amino acid sequence |
| Ab 451 | 902 | QPGLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGFYVFGTGTKLTVL | ADI-25557 | Light chain variable region ("LC") amino acid sequence |
| Ab 452 | 903 | EVQLLESGGGLVKPGGSLRLSCAASGFTFSSYSMNWVRQAPGKGLEWVSSISSSSS YIYYADSVKGRFTISRDNAKNSLYLQMNSLRAEDTAVYYCARDAAAKYYFDYWGQG TLVTVSS | ADI-25559 | Heavy chain variable region ("HC") amino acid sequence |
| Ab 452 | 904 | QPVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGKVFGTGTKLTVL | ADI-25559 | Light chain variable region ("LC") amino acid sequence |

TABLE 5-continued

| Antibody No. | SEQ ID NO: | Sequence | Clone # (ADI) | Descriptors |
|---|---|---|---|---|
| Ab 453 | 905 | QVQLVESGGGLVKPGGSLRLSCAASGFTFSDYYMSWIRQAPGKGLEWVSYISSSSS YTNYADSVKGRFTISRDNAKNSLYLQMNSLRAEDTAVYYCARVGYSSSWYNYFDY WGQGTLVTVSS | ADI-25562 | Heavy chain variable region ("HC") amino acid sequence |
| Ab 453 | 906 | SYVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGPVFGGGTKLTVL | ADI-25562 | Light chain variable region ("LC") amino acid sequence |
| Ab 454 | 907 | EVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARIRFDYGSGSYAFDI WGQGTMVTVSS | ADI-25565 | Heavy chain variable region ("HC") amino acid sequence |
| Ab 454 | 908 | QPVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGSVFGGGTKLTVL | ADI-25565 | Light chain variable region ("LC") amino acid sequence |
| Ab 455 | 909 | QVQLQQWGAGLLKPSETLSLTCAVYGGSFSGYYWSWIRQPPGKGLEWIGEINHSG STNYNPSLKSRVTISVDTSKNQFSLKLSSVTAADTAVYYCARGLPRFGVVTPNWFD PWGQGTLVTVSS | ADI-25567 | Heavy chain variable region ("HC") amino acid sequence |
| Ab 455 | 910 | EIVLTQSPDSLAVSLGERATINCKSSQSVLYSSNNKNYLAWYQQKPGQPPKLLIYW ASTRESGVPDRFSGSGSGTDFTLTISSLQAEDVAVYYCQQYYSTPYTFGQGTKLEI K | ADI-25567 | Light chain variable region ("LC") amino acid sequence |
| Ab 456 | 911 | EVQLLESGGGLVQPGGSLRLSCAASGFTFSSYWMHWVRQAPGKGLVWVSRINSD GGSTSYADSVKGRFTISRDNAKNTLYLQMNSLRAEDTAVYYCAREGDSSGWPGGA FDIWGQGTMVTVSS | ADI-25569 | Heavy chain variable region ("HC") amino acid sequence |
| Ab 456 | 912 | SYVLTQPPSVSVSPGQAARITCSGDALPKQYAYWYQQKPGQAPVLVIYKDSERPSG IPERFSGSSSGTTVTLTISGVQAEDEADYYCQSADSSGTFYVFGTGTKLTVL | ADI-25569 | Light chain variable region ("LC") amino acid sequence |
| Ab 457 | 913 | QVQLVQSGAEVKKPGASVKVSCKASGYTFTGYYMHWVRQAPGQGLEWMGWIN PNSGGTNYAQKFQGRVTMTRDTSISTAYMELSRLRSDDTAVYYCARDPYSSSSYYY YGMDVWGQGTTVTVSS | ADI-25572 | Heavy chain variable region ("HC") amino acid sequence |
| Ab 457 | 914 | DIVLTQSPLSLPVTPGEPASISCRSSQSLLHSNGYNYLDWYLQKPGQSPQLLIYLG SNRASGVPDRFSGSGSGTDFTLKISRVEAEDVGVYYCMQALQTLYTFGQGTKVDIK | ADI-25572 | Light chain variable region ("LC") amino acid sequence |
| Ab 458 | 915 | EVQLVESGAEVKKPGASVKVSCKASGYTFTSYYMHWVRQAPGQGLEWMGIINPS GGSTSYAQKFQGRVTMTRDTSTSTVYMELSSLRSEDTAVYYCARGPYDSSGYCDY WGQGTLVTVSS | ADI-25573 | Heavy chain variable region ("HC") amino acid sequence |
| Ab 458 | 916 | SYELMQPPSVSVAPGKTARITCGGNNIGSKSVHWYQQKPGQAPVLVVYDDSDRPS GTPERFSGSNSGNTATLTISRVEAGDEADYYCQVWDSSSDQVFGGGTKVTVL | ADI-25573 | Light chain variable region ("LC") amino acid sequence |
| Ab 459 | 917 | EVQLVESGAEVKKPGASVKVSCKASGYTFTSYYMHWVRQAPGQGLEWMGIINPS GGSTSYAQKFQGRVTMTRDTSTSTVYMELSSLRSEDTAVYYCARGPYDSSGYCDY WGQGTLVTVSS | ADI-25575 | Heavy chain variable region ("HC") amino acid sequence |
| Ab 459 | 918 | SYELTQPPSVSVAPGKTARITCGGNNIGSKSVHWYQQKPGQAPVLVVYDDSDRPS GIPERFSGSNSGNTATLTISRVEAGDEADYYCQVWDSSSDQVFGGGTKLTVL | ADI-25575 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 460 | 919 | EVQLVESGGGLVQPGGSLRLSCAASGFTFSSYWMHWVRQAPGKGLVWVSRINSD<br>GSSTSYADSVKGRFTISRDNAKNTLYLQMNSLRAEDTAVYYCARGLYNWNHDYW<br>GQGTLVTVSS | ADI-25576 | Heavy chain variable region ("HC") amino acid sequence |
| Ab 460 | 920 | NFMLTQPHSVSESPGKTVTISCTRSSGSIASNYVQWYQQRPGSSPTTVIYEDNQRP<br>SGVPDRFSGSIDSSSNSASLTISGLKTEDEADYYCQSYDSSNVVFGGGTKVTVL | ADI-25576 | Light chain variable region ("LC") amino acid sequence |
| Ab 461 | 921 | QVTLKESGGGLVKPGGSLRLSCAASGFTFSSYSMNWVRQAPGKGLEWVSSISSSSS<br>YIYYADSVKGRFTISRDNAKNSLYLQMNSLRAEDTAVYYCARYSSSLGAFDIWGQG<br>TMVTVSS | ADI-25577 | Heavy chain variable region ("HC") amino acid sequence |
| Ab 461 | 922 | QSALTQPPSVSGAPGQRVTISCTGSSSNIGAGYDVHWYQQLPGTAPKLLIYGNSR<br>PSGVPDRFSGSKSGTSASLAITGLQAEDEADYYCQSYDSSLSDVFGTGTKLTVL | ADI-25577 | Light chain variable region ("LC") amino acid sequence |
| Ab 462 | 923 | QVQLVESGGGVVQPGRSLRLSCAASGFTFSSYGMHWVRQAPGKGLEWVAVIWY<br>DGSNKYYADSVKGRFTISRDNSKNTLYLQMNSLRAEDTAVYYCARDSTYSEAFDIW<br>GQGTMVTVSS | ADI-25587 | Heavy chain variable region ("HC") amino acid sequence |
| Ab 462 | 924 | QSVLIQPASVSGSPGQSITISCTGTSSDVGGYNYVSWYQQHPGKAPKLMIYDVSNR<br>PSGVSNRFSGSKSGNTASLTISGLQAEDEADYYCSSYTSSSTWVFGGGTKVTVL | ADI-25587 | Light chain variable region ("LC") amino acid sequence |
| Ab 463 | 925 | EVQLVESGGGLVKPGGSLRLSCAASGFTFSSYSMNWVRQAPGKGLEWVSSISSSSS<br>YIYYADSVKGRFTISRDNAKNSLYLQMNSLRAEDTAVYYCARYSSSLGAFDIWGQGT<br>TVTVSS | ADI-25588 | Heavy chain variable region ("HC") amino acid sequence |
| Ab 463 | 926 | QSVLTQPPSVSGAPGQRVTISCTGSSSNIGAGYDVHWYQQLPGTAPKLLIYGNSR<br>PSGVPDRFSGSKSGTSASLAITGLQAEDEADYYCQSYDSSLSDVFGTGTKLTVL | ADI-25588 | Light chain variable region ("LC") amino acid sequence |
| Ab 464 | 927 | EVQLVESGGGLVKPGGSLRLSCAASGFTFSSYSMNWVRQAPGKGLEWVSSISSSSS<br>YIYYADSVKGRFTISRDNAKNSLYLQMNSLRAEDTAVYYCARYQSSSWYYFDYWGQ<br>GTLVTVSS | ADI-25595 | Heavy chain variable region ("HC") amino acid sequence |
| Ab 464 | 928 | SYVLTQPPSVSGAPGQRVTISCTGSSSNIGAGYDVHWYQQLPGTAPKLLIYGNSR<br>PSGVPDRFSGSKSGTSASLAITGLQAEDEADYYCQSYDSSLSGVVFGGGTKLTVL | ADI-25595 | Light chain variable region ("LC") amino acid sequence |
| Ab 465 | 929 | QVQLQESGPGLVKPSETLSLTCTVSPPSISSSSYYWGWIRQPPGKGLEWIGSIYYS<br>GSTYYNPSLKSRVTISVDTSKNQFSLKLSSVTAADTAVYYCARPDSSGAFDIWGQG<br>TMVTVSS | ADI-25598 | Heavy chain variable region ("HC") amino acid sequence |
| Ab 465 | 930 | SYELTQPPSVSVSPGQTARITCSADALPKQYAYWYQQKPGQAPVLVIYKDSERPSGI<br>PERFSGSSSGTTVTLTISGVQAEDEADYYCQSADSSGTYVVFGGGTKLTVL | ADI-25598 | Light chain variable region ("LC") amino acid sequence |
| Ab 466 | 931 | EVQLVQSGAEVKKPGASVRVYCKASGYTFTTYYIHWVRQAPGQGLEWMGMINPS<br>GGTTSYAQKFQGRLTMTGDTSTSTVYMELNYLRSEDTAVYYCTRDFIYFYGSGDGF<br>DYWGQGTLVTVSS | ADI-36669 | Heavy chain variable region ("HC") amino acid sequence |
| Ab 466 | 932 | EIVMTQSPSAMSASVGDRVTITCRASQGISNYLAWFQQKPGKVPKRLIYAASSLQS<br>GVPSRFSGSGSGTEFTLTITSLQPEDFATYYCLQHNSYPFTFGPGTKVEIK | ADI-36669 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 467 | 933 | QVQLVQSGAEVKKPGSSVKVSCKASGGTFSTYTINWVRQAPGQGLEWMGRITPSL GVPLSAQKFQGRITISADKSTTTAYMELSSLGSEDTAVYYCASLNYYDTTDYYLGY SDSWGQGTLVTVSS | ADI-36670 | Heavy chain variable region ("HC") amino acid sequence |
| Ab 467 | 934 | DIVLTQTPATLSVSPGERATLSCRASHSVSNNLAWYQQKPGQAPRLLIYSASTRAT GIPARFSGRGSGTEFTLTISSLQPEDFAVYYCQQYNNWPPEYTFGQGTKVDIK | ADI-36670 | Light chain variable region ("LC") amino acid sequence |
| Ab 468 | 935 | EVQLLESGGGLVKPGGSLRLSCAASGFTFSGYYMTWIRQAPEKGLEWVSYISGGST YTNYADSVRGRFTISRDNARNSLYLQMNSLRAEDTAVYYCARDGGYGIGPLYWGQG SLVTVSS | ADI-36671 | Heavy chain variable region ("HC") amino acid sequence |
| Ab 468 | 936 | QPVLTQPPSVSGAPGQRVTISCTGSSSNIGAPFDVHWYQQLPGTAPKPLIYGNSNR PSGVPDRFSGSKSGTSASLAITGLQAEDEADYYCQSYDSSLGGYVFGTGTKLTVL | ADI-36671 | Light chain variable region ("LC") amino acid sequence |
| Ab 469 | 937 | EVQLVESGGGLVKPGGSLRLSCAASGFAFNNYYMNWVRQAPGKGLEWVSSISSAS TYTDYADSVKGRFTISRDNAKNSLYLHLNSLRAEDTAVYYCARDYYGSGNYYNPKP LDVWGQGTTVTVSS | ADI-36672 | Heavy chain variable region ("HC") amino acid sequence |
| Ab 469 | 938 | QPVLTQPPSVSGAPGQRVTISCTGSSSNIGAGYDVHWYRQFPGTAPELLIYGNTNR PSGVPDRFSGSKSGTSASLAITGLQAEDEADYYCQSYDSSLKGVFGGGTKLTVL | ADI-36672 | Light chain variable region ("LC") amino acid sequence |
| Ab 470 | 939 | EVQLLESGGGLVKPGGSLRLSCAASGFKFRSYSMNWVRQAPGKGLEWVSSISSSSS YVDYAGSLKGRFTISRDNAENSLYLQMNSLRAEDTAMYYCARAGSVPVAGTYNDY WGQGTLVTVSS | ADI-36674 | Heavy chain variable region ("HC") amino acid sequence |
| Ab 470 | 940 | QSVLTQPPSVSGAPGQRVTISCTGSSSNIGAGYDVHWYQHLPGTAPKLLIHGNNNR PAGVPDRFSGSKSGTSASLVITGLQADDEADYYCQSYDRSLSVLFGGGTKVTVL | ADI-36674 | Light chain variable region ("LC") amino acid sequence |
| Ab 471 | 941 | QVQLVQSGGGLVQPGGSLRLSCAASGFTFSSYEMNWVRQAPGKGLEWISYISSSG DTKYYADSVKGRFTVSRDNAKYSLYLQMDSLRAEDTAVYYCASLYDSRGYYWVFDY WGQGTLVTVSS | ADI-36677 | Heavy chain variable region ("HC") amino acid sequence |
| Ab 471 | 942 | DIVMTQSPSSLSASVGDRVTITCQASQDISTYLNWYQHKPGKAPNLLIYDASNLEPG VPSRFSGSGSGTDFTFTISSLQPEDIATYYCLQHDNLPPTFGQGTKVDIK | ADI-36677 | Light chain variable region ("LC") amino acid sequence |
| Ab 472 | 943 | QVQLVQSGAEVKKPGESLKISCKGSGYSFRSYWIAWVRQMPGKGLEWMGTIFPG DSDVTYSPSFQGQVTISVDKSTSTAYLQWGSLKASDTAIYYCARRYDYIDFWGQGTL VTVSS | ADI-36679 | Heavy chain variable region ("HC") amino acid sequence |
| Ab 472 | 944 | DIQMTQSPSSLSASVGDRVTITCQASQDIINHLNWYQQKPGKAPKLLIYDASNLHP GVPSRFSGSGSGTYFTFTISSLQPDDFATYYCQQYDFLAHITFGPGTKVDIK | ADI-36679 | Light chain variable region ("LC") amino acid sequence |
| Ab 473 | 945 | QVTLKESGAELRKPGESLKISCKASGYRFTNYWIGWVRQMPGKGLEWMGVIYPGD SDTKYSPSFQGQVTMSADKSINTAYLQWSSLKASDTAIYYCVSLFGDYDYGALDYW GQGTLVTVSS | ADI-36680 | Heavy chain variable region ("HC") amino acid sequence |
| Ab 473 | 946 | ETTLTQSPATLSMSPGERATLSCRASQSVGRNLAWYQQKPGQAPRLLIYGASIRAT GILARFSGSGSGTEYTLTISSLQPEDFAVYYCQQYHDWPSFTFGPGTKVDIK | ADI-36680 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 474 | 947 | EVQLVESGAEVKKPGESLKISCKASGYSFTRYWIGWVRQMPGKGLEWMGIIFPGD SDTRYCPSFEGQVTISADRSINTAYLQWSSLKASDSAMYYCVTLYTDYDYGAPDHW GQGTLVTVSS | ADI-36681 | Heavy chain variable region ("HC") amino acid sequence |
| Ab 474 | 948 | DIVLTQSPATLSVSPGERATLSCRASQSLSGDLAWYQQKPGQAPRLLIYATSTRAT GIPARFSGSGSGAEFTLTISSLQSEDFAVYYCQQYYDWPLLTFGPGTKVEIK | ADI-36681 | Light chain variable region ("LC") amino acid sequence |
| Ab 475 | 949 | EVQLVQSGAEVKKPGGSVKVSCKASGYTFSEYYMHWVRQAPGQGPEWVGRINPK SGRTNYAQNFQGRVTMTRDRSISTVYMDLSRLRSDDTAVYYCARWEVMDYGSGI YYNQDHFDYWGQGTLVTVSS | ADI-41144 | Heavy chain variable region ("HC") amino acid sequence |
| Ab 475 | 950 | DIRVTQSPSSLSASVGDRVTITCRASQDITNYLAWFQQKPGKAPKSLMYAASTLQSG VPSRFSGSGSGTDFTLTISSLQPEDFATYYCQQYKTYPITFGQGTRLEIK | ADI-41144 | Light chain variable region ("LC") amino acid sequence |
| Ab 476 | 951 | QVQLVQSGPGLVKPSETLSLTCTVSAGSISNFYWSWIRQPPGKGLEWIGYIYYSGST SYNPSLKSRVTISVDTSKNQFSLKLSSVTAADTAVYYCARSRSGWSLYDYWGQGTLV TVSS | ADI-41145 | Heavy chain variable region ("HC") amino acid sequence |
| Ab 476 | 952 | DIQVTQSPSSLSASVGDRVTITCRASQSISSFLNWYQQKPGKAPKLLIYVASSLQSGV PSRFSGSGSGTDFTLTISSLQPEDFATYYCQQSYNTPLTFGGGTKVDIK | ADI-41145 | Light chain variable region ("LC") amino acid sequence |
| Ab 477 | 953 | QVQLVQSGAEVKKPGESLKISCKGSGHSFATFWIGWVRQVPGNGLELMGIINLGD SDTKYSPSFQGQVTISADESIGTAYLQWSSLKASDTAMYYCARVSLPHYYYYMDVW GKGTTVTVSS | ADI-41146 | Heavy chain variable region ("HC") amino acid sequence |
| Ab 477 | 954 | DIVMTQSPSSVSASVGDRVTITCRASQGISTWLAWYRQPGKAPELLIYAASRLQSG VPSRFSGSGSGTDFTLTISSLQPEDFATYYCQQANSFLGAFGPGTKLEIK | ADI-41146 | Light chain variable region ("LC") amino acid sequence |
| Ab 478 | 955 | EVQLVESGGGLVKPGGSLRLSCAASGFTLSGYYMSWVRQAPGKGLEWISYISGGST YTNYADSVNGRFTISRDNAKNSLYLQMDSLRAEDTAVYYCARLEYGDYGPYYLGLW GRGTLVTVSS | ADI-41147 | Heavy chain variable region ("HC") amino acid sequence |
| Ab 478 | 956 | QSVLTQPPSVSGAPGQRVTISCTGTSSNIGAGYDVHWYQKLPGTAPKLLIYANNNR PSGVPDRFSGSKSGTSASLAITGLQAEDEADYYCQSYDTSLSAHYVFGTGTKLTVL | ADI-41147 | Light chain variable region ("LC") amino acid sequence |
| Ab 479 | 957 | QVQLVQSGGGVVQPGRSLRLSCAASGFTFSDYGMHWVRQAPGKGLEWVAVIWF DGSNKNYADSVKGRFTISRDNSMNTLYLQMNNLRAEDTAVYYCARAPYSFWSGYY LDYWGQGSLVTVSS | ADI-41149 | Heavy chain variable region ("HC") amino acid sequence |
| Ab 479 | 958 | DIVMTQSPATLSVSPGERATLSCRASQSISSNLAWYQQKSGQAPRLLIYGASTRATG IPARFSGSGSGTEFTLTISSLQSEDFAVYSCQQYSKWPQTFGQGTKVEIK | ADI-41149 | Light chain variable region ("LC") amino acid sequence |
| Ab 480 | 959 | EVQLVESGGGLVKPGGSLRLSCAASQFTFSTYDMSWVRQAPGKGLEWVASISSGS TYIYYADSVKGRFTISRDNAKHSLFLQMKSLRAEDTALYYCARQVLYDRGGYYLYYF DHWGQGTLVTVSS | ADI-41153 | Heavy chain variable region ("HC") amino acid sequence |
| Ab 480 | 960 | DIQVTQSPSSLSASVGDRVTITCRASQTIASYLNWYQQKPGKAPNLLIYAASNLQSG VPSRFSGSGSGTEFTLTINTLQPEDFATYYCQQSYNFPYTFGQGTKVEIK | ADI-41153 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 481 | 961 | QVQLQQWGAGLSKPSETLSVTCAVYGGSLSGHYWSWFRQPPGKGLEWIGEIDHS GSTTYNPSLKSRVTISVDTSKNQFSLKLTSVTAADTAMYYCARATRYNYGYTFDYWG QGTLVTVSS | ADI-41154 | Heavy chain variable region ("HC") amino acid sequence |
| Ab 481 | 962 | DIPLTQSPSSLSASVGDRVTITCRASQIISSYLNWYQQKPGKAPKLLIYAASTLQSG VPSRFSGSRSGTDFTLTISSLQPEDFASYYCQQSYIIPFTFGPGTKVEIK | ADI-41154 | Light chain variable region ("LC") amino acid sequence |
| Ab 482 | 963 | QVQLQESGPGLVKPSETLSLTCTVSGGSIGNNFYYWGWIRQPPGKGLEWIGSIYYS GTTYDNPSLKSRVTISVEPSKNQFSLKLSSVTAADTAVYHCARRYCDSTRCYEAFDI WGQGTTVTVSS | ADI-41155 | Heavy chain variable region ("HC") amino acid sequence |
| Ab 482 | 964 | SYELTQPPSASGTPGQRVTISCSGSSSNIGSNYVSWYQQLPGTAPKLLIYKNDQRPS GVPDRFSGSKSGTSASLAISGLRSEDEAEYYCAAWDDSLSGFYVFGTGTKVTVL | ADI-41155 | Light chain variable region ("LC") amino acid sequence |
| Ab 483 | 965 | QVQLVQSGGGLVQPGGSLRLSCVASGFIFSSYEMNWVRQAPGKGLEWVSYISSSG STIYYADSVKGRFTISRDNAKNSLYLQMNSLGAEDTAVYYCARAILYFDYWGQGTLV TVSS | ADI-41156 | Heavy chain variable region ("HC") amino acid sequence |
| Ab 483 | 966 | GIRLTQSPSSLSASVGDRVTITCRASQSITNYINWYQQKPGKAPKLLIYAISRLQSG VPSRFSGSGSGTDFTLTISSLQPEDFATYYCQQSYSTMYTFGQGTKVEIK | ADI-41156 | Light chain variable region ("LC") amino acid sequence |
| Ab 484 | 967 | EVQLVESGPGLVKPSETLSLTCTVSGGSISTYYWSWIRQPPGKGLEWIGYIYYTGST NYNPSLKSRVTISLDTSKNQFSLKLSSVSAADTAFYYCARSPPVPGTRSWFDPWGQG TLVTVSS | ADI-41157 | Heavy chain variable region ("HC") amino acid sequence |
| Ab 484 | 968 | SPGLTQPQSAFGTPGQRVTISCFGSSSNIGRNHIYWYQQVPGTAPKLLIYRNNQRPS GVPDRFFGSKFGTSASLAISGVRSEDEADYFCAAWDDSLSGPVFGGGTKLTVL | ADI-41157 | Light chain variable region ("LC") amino acid sequence |
| Ab 485 | 969 | EVQLVESGGGLVQPGGSLRLSCAASGFTFSSYNIAWVRQAPGKGLEWISYISSSSSV IYYADSVRGRFTISRDNAKNSLYLQMNSLRDEDTAMYYCARAGNDYNFWSGRSSEY FDYWGQGTLVTVSS | ADI-41158 | Heavy chain variable region ("HC") amino acid sequence |
| Ab 485 | 970 | DIVMTQSPATLSVSPGERATLSCRASQSVSSNLAWYQQKPGQAPRLLIYGASTRAT GIPARFSGSGSGTEFTLTISSLQSEDFAVYYCQQYDNWPLYTFGQGTKLEIK | ADI-41158 | Light chain variable region ("LC") amino acid sequence |
| Ab 486 | 971 | EVQLVESGAEVKKPGESLKISCKGSGYSFTTYWIGWVRQMPGKGLEWMGIMYPG DSQTRYSPSFQGQVTISADKSISTAYLQWSSLKASDTAMYYCARGGYCSGGSCYRG LDYWGQGTLVTVSS | ADI-41159 | Heavy chain variable region ("HC") amino acid sequence |
| Ab 486 | 972 | EIVMTQSPSSLSASVGDRVTITCRASQSISSFLNWYQQKPGKAPNLLIYAASSLLSG VPSRFSGSGSGTDFTLTISSLQPEDFATYYCQQSHSTPQTFGQGTKLEIK | ADI-41159 | Light chain variable region ("LC") amino acid sequence |
| Ab 487 | 973 | QVQLVQSGAEVKKPGSSVKVSCKASGGTFSSYPIIWVRQAPGQGLEWMGRIIPILGI ASYAQKFQGRVTITADKSTSTAYMELSSLRSEDTAVYYCARNSDFYYGMDVWGQG TTVTVSS | ADI-41160 | Heavy chain variable region ("HC") amino acid sequence |
| Ab 487 | 974 | QSALIQPASVSGSPGQSITISCTGTSSDVGGYNYVSWYQHHPGKAPKLMIYDVSNR PSGISNRFSGSKSGNTASLTISGLQAEDEADYYCSSYTSSSLYVFGTGTKVTVL | ADI-41160 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 488 | 975 | EVQLVESGGGLVQPGGSLRLSCAASGFTFSTFEFNWVRQAPGKGLEWLSYISSDDT TRYYADSVKGRFTISRDNAKNSLYLQMNSLRAEDTAYYYCVRGGPYDYVWGTYRYF DFWGQGTLVTVSS | ADI-41161 | Heavy chain variable region ("HC") amino acid sequence |
| Ab 488 | 976 | QSVLTQPASVSGSPGQSITISCTGTSSDIGGYNYVSWYQQHPGKAPKLMIYDVTNR PLGVSNRFSGSKSGNTASLIISGLQAEDEAEYYCCSYTSSNSLVFGGGTKLTVL | ADI-41161 | Light chain variable region ("LC") amino acid sequence |
| Ab 489 | 977 | EVQLVQSGAEVKKPGSSVKVSCKASGVTGGTFSSYAISWVRQAPGQGLEWMGGI MPMFGTTNYAQKFQGRVTITADKSTSTAYMELSSLRSEDTAVYYCARDYRDFSPHL DYYYMDVWGKGTTVTVSS | ADI-41162 | Heavy chain variable region ("HC") amino acid sequence |
| Ab 489 | 978 | DIRLTQSPGTLSLSPGERATLSCRASQSVSTSYLAWYQQKPGQAPRLLIYGASNRAT GIPDRFSGSGSGTDFTLTISRLEPEDFAVYYCQQYGRTSWTFGQGTKVDIK | ADI-41162 | Light chain variable region ("LC") amino acid sequence |
| Ab 490 | 979 | QVQLVQSGGGVVQPGRSLRLSCAASGFPFHSYAMHWVRQAPGKGLEWVAVIWY EGSEKHYADSVQGRFTISRDNSKNMLYLQMNNLRVADTAVYYCARRGAWGFDIW GQGTTVTVSS | ADI-41163 | Heavy chain variable region ("HC") amino acid sequence |
| Ab 490 | 980 | DIVMTQTPLSLPVTPGEPASISCRSSQSVLHSTGYNSLDWYLQKPGQSPQLLIFLGS NRASGVPDRFSGSGSGTDFTLKISRVEAEDVGVYYCMQGLQTPYTFGQGTKVEIK | ADI-41163 | Light chain variable region ("LC") amino acid sequence |
| Ab 491 | 981 | QVQLVQSGGDLVQPGGSLRLSCAASGFTFSDYEVNWVRQAPGKGLEWLSYISSSG RIIHYADSVRGRFTISRDNAKNSLYLQMNSLRAEDTAVYYCARAAGQWLVTYYYG MDVWGQGTTVTVSS | ADI-41164 | Heavy chain variable region ("HC") amino acid sequence |
| Ab 491 | 982 | QSVMTQSPSTLSASVGDTVTITCRASQSIINRLAWYQQKPGKPPKLLIYKSSSSES GVPSKFSGSGSGTEFTLTINSLQPDDFATYYCQHYNSYLYTFGQGTKVEIK | ADI-41164 | Light chain variable region ("LC") amino acid sequence |
| Ab 492 | 983 | EVQLVETGAEVKKPGESLKISCKGSGYSFTSYWIGWVRQMPGKGLEWMGIIYPGD SDTRYSPSFQGQVTISADKSISTAYLQWSSLKASDTAMYYCARRYDYIDIWGQGTM VTVSS | ADI-41165 | Heavy chain variable region ("HC") amino acid sequence |
| Ab 492 | 984 | DIRVTQSPSSLSASVGDRVTITCQASQDISNYLNWYQQKPGKAPKLLIYDASNLETG VPSRFSGSGSGTDFTFTISSLQPEDIATYYCQQYDNLAHITFGPGTKVEIK | ADI-41165 | Light chain variable region ("LC") amino acid sequence |
| Ab 493 | 985 | EVQLVQSGAEVKKPGASVKVSCKTSGYTFTGDYLHWVRQAPGQGLEWMGRLNP KSGGTVYAQRFQGRVTMTGDTSVTTAYMQLTRLRSDDTAIYYCARGIPVSGPVSID YWGQGTLVTVSS | ADI-41166 | Heavy chain variable region ("HC") amino acid sequence |
| Ab 493 | 986 | QSVLTQPASLSGSPGQSITISCTGTSSDVGGYGYVSWYQQHPGKAPKLMIYDVANR PSGVSHRFSGSKSGNTASLTISGLQADDEADYYCSSYTRSNTVVFGGGTKLTVL | ADI-41166 | Light chain variable region ("LC") amino acid sequence |
| Ab 494 | 987 | EVQLVETGGGVVQPGRSLRLSCAASGFTFSSYGMHWVRQAPGKGLEWVAVISYD GSNKYYADSVKGRFTISRDNSKNTLYLQMNSLRTEDTAVYYCAKGGGYYYYMDV WGKGTTVTVSS | ADI-41168 | Heavy chain variable region ("HC") amino acid sequence |
| Ab 494 | 988 | QPVLTQPASVSGSPGQSITISCTGTSSDVGGYNYVSWYQQHPGKAPKLMIYGVNN RPSGVSNRFSGSKSGNTASLTISGLQGEDEADYYCNSYRSGITVVFGGGTKLTVL | ADI-41168 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 495 | 989 | EVQLVESGAEVKKPGESLKISCEAFGYSFTSYWIGWVRQVPGRGLEWIGVIYPGDSD IRYTPSFRGQVTISADRSISTAYLQWNNLKASDTAMYYCARPGRDINYYHSRDYGAL DIWGQGTTVTVSS | ADI-41169 | Heavy chain variable region ("HC") amino acid sequence |
| Ab 495 | 990 | DIQLTQSPDSLAVSLGERVTINCKSSQSFLYSSNNKNYLAWYQQKPGQPPKLLIYWA SVRESGVPDRFSGSGSGTDFTLTISSLQAEDVAVYYCQEYYSPPMFTFGQGTKVEIK | ADI-41169 | Light chain variable region ("LC") amino acid sequence |
| Ab 496 | 991 | EVQLLESGGGLIQPGGSLRLSCAASGFTFNNYVMSWVRQAPGKGLEWVAAISSSG VSTYYAASVKGRFTISRDNSKNMLYVQLNSLRAEDTAVYYCAKETGSYYYFDSWGQ GTLVTVSS | ADI-41170 | Heavy chain variable region ("HC") amino acid sequence |
| Ab 496 | 992 | ETTLTQSPSTLSGSVGDRVTITCRASESISSWLAWYQQKPGKAPKLLIYKASNLESG VPSRFSGSGSGTEFTLTISSLQPDDFATYYCQQYNSYLITFGQGTRLEIK | ADI-41170 | Light chain variable region ("LC") amino acid sequence |
| Ab 497 | 993 | EVQLVESGPGLVKPSQTLSLTCTVSGGSISSGGDYWSWVRQRPGKGLEWIGYIYNS GSGYYNPSLKNRVSMSMHTSRNQFSLRLSSVTAADTAFYYCARDPFYRSGGIHYFD YWGQGALVTVSS | ADI-41171 | Heavy chain variable region ("HC") amino acid sequence |
| Ab 497 | 994 | DIVLTQTPGTLSLSPGEGATLSCRASPSVGSTSLAWYQQKPGQAPRLLIYGASSRAT GIPDRFSGSGSGTDFTLTISRLEPEDFAVYYCQQDGGLPITFGLGTRLEIK | ADI-41171 | Light chain variable region ("LC") amino acid sequence |
| Ab 498 | 995 | EVQLLESGGGLVQPGGSLRLSCSASGFTFSVYAMHWVRLAPGKGLEYVSTISGNGG STYYGDSVKGRFTTSRDNSKNTVYLQMSSLRAEDTAVYYCVKAPARDHYEILTLLGY FDYWGQGTLVTVSS | ADI-41172 | Heavy chain variable region ("HC") amino acid sequence |
| Ab 498 | 996 | DIVMTQSPDSLAVSLGERATINCKSSQSVLYSSSNKNYLAWYQQKPGQPPKLLIYW ASTRESGVPDRFSGSGSGTDFTLTISSLQAEDVAVYYCQQYYTIPPWTFGQGTKVEI K | ADI-41172 | Light chain variable region ("LC") amino acid sequence |
| Ab 499 | 997 | QVQLVQSGAEMKKPGSSAKVSCKASGGTLSSYAINWVRQAPGQGLEWMGGIIPIF GTTKYAPKFQDRVTITVDESTSTAYMELSSLRSEDTAVYYCSRESSTWDVAHYFDYW GQGTLVTVSS | ADI-41173 | Heavy chain variable region ("HC") amino acid sequence |
| Ab 499 | 998 | DIVMTQTPSAISASVGDRVTITCRASQGISNYLAWVQQKPGKVPKRLIYGASSLQSG VPSRFSGSGSGTEFTLTISSLQPEDFATYYCLQHNSYPYTFGQGTKVEIK | ADI-41173 | Light chain variable region ("LC") amino acid sequence |
| Ab 500 | 999 | EVQLVESGAEVEKPGASVKVSCKASGYTFINYDIIWVRQAPGQGLEWMGWISGYK GNTNYAQKLQGRITMSTDTSTRTAYMELRSLTSDDTAVYYCARVGGTARSTTPYYY GMDVWGQGTTVTVSS | ADI-41174 | Heavy chain variable region ("HC") amino acid sequence |
| Ab 500 | 1000 | SYVLTQPPSVSVSPGQTARITCSGDAVPKQFSYWYQQKPGQAPVLVIYKDIERPSG IPERFSGSSSGTTVTLTISGVQAEDEADYYCQSAHTSGTYHVFGTGTKLTVL | ADI-41174 | Light chain variable region ("LC") amino acid sequence |
| Ab 501 | 1001 | EVQLLESGGGVVQPGRSLRLSCATSGFTFSSYGMHWVRQAPGKGLEWVAVIYYEG SNKYYGDSVKGRFTISRDNSKSTLYLQMNRLRAEDTAVYYCARRPAGGFDYWGPG TLVTVSS | ADI-41175 | Heavy chain variable region ("HC") amino acid sequence |
| Ab 501 | 1002 | EIVMTQSPLSLPVTPGEPASISCRSSQNLLNSNGYNYLDWYLQKPGQSPQLLIYLGS NRASGVPDRFSGSGSGTDFTLKISRVEAEDVGVYYCMQALQTPYTFGQGTKLEIK | ADI-41175 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 502 | 1003 | EVQLVESGPGLVKPSETLSLTCTVSGGSIGNDYYYWGWIRQPPGKGLEWIGNISYSG STYYNPSLKSRVTISVGTSKNQFSLKLTSVSAADTAVYHCVGRTFWRDCSSTSCYEY YFDYWGQGTLVTVSS | ADI-41176 | Heavy chain variable region ("HC") amino acid sequence |
| Ab 502 | 1004 | ETTLTQSPTSLSASVGDRVTITCRASQGISNYLAWYQQKPGKVPKVLIYAASTLQS GVSSRFSGSGSGTGFTLTISNLQPEDVATYYCQNYNSAPWTFGQGTKVEIK | ADI-41176 | Light chain variable region ("LC") amino acid sequence |
| Ab 503 | 1005 | QVQLVQSGAEVKKPGASVKVSCKASGYMFTGYYMHWVRQAPGQGLEWMGRIN PNSGGTNYAQKFQGRVTMTRDTSISTGYMELSRLRSDDTAVYFCARDFFPLVIPT LIVGRGLYDMDVWGQGTMVTVSS | ADI-41177 | Heavy chain variable region ("HC") amino acid sequence |
| Ab 503 | 1006 | QPGLTQPPSASGTPGQRVTISCSGRSSNIGSNTVNWYQQLQGTAPKLLIYKNNQRP SGVPDRFSGSKSGTSASLAISGLQSEDEADYYCAAWDDSLNGVVFGGGTKVTVL | ADI-41177 | Light chain variable region ("LC") amino acid sequence |
| Ab 504 | 1007 | QVQLVESGAEVKKPGASVKVSCKASGYTFTDYYMHWVRQAPGQGLEWMGRINP NSGGTNYAQKFQGRVTMTRDTSISTAYMELSSLRSDDTAVYYCARDLTAGGYGST WYSCGDYWGQGTLVTVSS | ADI-41178 | Heavy chain variable region ("HC") amino acid sequence |
| Ab 504 | 1008 | EIVLTQSPATLSVSPGERATLSCRASQSVSSNLAWYQQKPGQAPRLLIYGASTRAT GIPARFSGSGSGTEFTLTISSLQSEDFAVYYCQQYNNWPRWTFGQGTKVEIK | ADI-41178 | Light chain variable region ("LC") amino acid sequence |
| Ab 505 | 1009 | QVQLVQSGAEVKKPGSSVKISCKASGGTFSSHPISWVRQAPGQGLEWMGRIVPIF GIANYAQKFQGRVTMIADKSTNTAYMELSNLRSEDTAVYYCANPVYDSSGFQWG QGTLVTVSS | ADI-41179 | Heavy chain variable region ("HC") amino acid sequence |
| Ab 505 | 1010 | QPVLTQPRSVSGSPGQSVTISCTGTSGDGGFYNYVSWYQQHPGKTPKLMIYDVDQ RPSGVPDRFSGSKSGNTASLTISGLQAEDEADYYCCSYPGNPLYVFGTGTKVTVL | ADI-41179 | Light chain variable region ("LC") amino acid sequence |
| Ab 506 | 1011 | EVQLVQSGGGLVKPGGSLRLSCAASGFTFIDYYMSWIRQAPGKGLEWVSSISGGST YTTYADSVKGRFTISRDNGKNSLYLQMDSLRAEDTAVYYCARLGGYSYYMDVWGK GTTVTVSS | ADI-41180 | Heavy chain variable region ("HC") amino acid sequence |
| Ab 506 | 1012 | QPVLTQPPSVSGAPGQRVTISCTGSSSNIGAGYDVHWYQHLPGAAPKLLIYDNTNR PSGIPDRFSGSKSGTSASLAITGLQAEDEADYYCQSYDSSLDWVFGGGTKVTVL | ADI-41180 | Light chain variable region ("LC") amino acid sequence |
| Ab 507 | 1013 | QVQLVQSGAEVKKPGSSVKVSCKASGGSFSSYTLNWVRQAPGQGLEWMGRFVPI VGIANYAQKFQGRVTITADKSTSTVYMELSSLRSEDTAVYYCATAPTAYCSGDCYS LFDPWGQGTLVTVSS | ADI-41181 | Heavy chain variable region ("HC") amino acid sequence |
| Ab 507 | 1014 | QSVLIQPASVSGSPGQSITISCTGISSDVGSYNLVSWYQQHPGKAPKLIIYEVNKR PSGVSNRFSGSKSGNTASLTISGLQAEDEADYYCCSYAVSRTSLYVFGTGTKVTVL | ADI-41181 | Light chain variable region ("LC") amino acid sequence |
| Ab 508 | 1015 | QVQLVQSGAEVKKPGESLKISCQGSGYSFTSYWIGWVRQMPGKDLEWMGIIYPSD SDTRYSPSFQGQVTISVDKSINTAYLQWTSLKASDTAMYYCARCDGAVYWYFDLW GRGTLVTVSS | ADI-41182 | Heavy chain variable region ("HC") amino acid sequence |
| Ab 508 | 1016 | EIVLTQSPATLSVSPGERVTLSCRASRSVSSHLAWYQQKPGQAPRLLMYGASTRAT GIPARFSGSGSGTEFTLTISSLQSEDFGVYYCQQYNNWPPALTFGGGTKLEIK | ADI-41182 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 509 | 1017 | QVQLQESGAGLVKPSETLSLTCGVYGESFSGHSWSWIRQPPGRGLEWIGEINQSGT TKYNPSLRSRVTISVDRSKNEFSLKVSSVTAADTAVYFCARYFRSFYTIGPDYYYM DVWGKGTTVTVSS | ADI-41183 | Heavy chain variable region ("HC") amino acid sequence |
| Ab 509 | 1018 | EIVLTQSPSSLSASVGDRVTITCRASQNINNYLNWYQQKPGKAPRLLIYAASSLQS GVPSRFTGSGSGTDFTLTIRSLQSEDFATYYCQHSYSSSLLTFGGGTKVDIK | ADI-41183 | Light chain variable region ("LC") amino acid sequence |
| Ab 510 | 1019 | EVQLLETGGGLVQPGGSLRLSCAASGFTFSSYDMNWVRQAPGKGLEWVSTISGSG GPTYYAGSVKGRFTISRDNSKNTLYLQMNSLRADDTAVYYCAKAQLYDTSGYYLYY FDYWGQGTLVTVSS | ADI-41184 | Heavy chain variable region ("HC") amino acid sequence |
| Ab 510 | 1020 | DIRMTQSPSSLSASVGDRVTITCRASQRITSYLNWYQQKPGKAPKLLIYAASSLQS GVPSRFSGSGSGTDFTLTISSLQPEDFATYFCQQSYSTSFTFGPGTKVDIK | ADI-41184 | Light chain variable region ("LC") amino acid sequence |
| Ab 511 | 1021 | QVQLQQWGAGLLKPSETLSLTCAVYGGSFSSYYYSWIRQPPGKGLEWIGEINQSGS TNYNPSLKSRVTISVDTSKNEFSLKLSSVTAADTAVYYCARIVREFNTRWYDYYYM DVWGKGTTVTVSS | ADI-41185 | Heavy chain variable region ("HC") amino acid sequence |
| Ab 511 | 1022 | DIRVTQSPATLSLSPGERATLSCRTSQSISSSYLAWYQQKFGQAPRLLIYGASSRA TGIPDRFSGSGSGTDFTLTISRLEPEDFAVYYCQQYGISPPMYTFGQGTKVEIK | ADI-41185 | Light chain variable region ("LC") amino acid sequence |
| Ab 512 | 1023 | EVQLLESGAEVKKPGESLKISCKGSGYSFSSYWIAWVRQMPGKGLEWMGIIYPSDS DTKYSPSFQGQVTISADKSISTAYLQWSSLKASDTAMYYCARQAGIQRPLDYWGQ GTLVTVSS | ADI-41186 | Heavy chain variable region ("HC") amino acid sequence |
| Ab 512 | 1024 | EIVMTQSPATLSVSPGERATLSCRASQSVRSNLAWYQQKPGQAPRLLIYDASTRAT GISARFSGSGSGTEFTLTISSLQSEDFAVYYCQQFHNWPPYTFGQGTKVEIK | ADI-41186 | Light chain variable region ("LC") amino acid sequence |
| Ab 513 | 1025 | QVQLQQWGAGLLKSSETLSLTCAVYGGSFSGYYWSWIRQSPGKGLEWIGEINHSG SANYNPSLKNRVTISRDTSKNQFSLWLSSVTAADTAVYYCARTSRSPEPDNYYYM DVWGRGTTVTVSS | ADI-41188 | Heavy chain variable region ("HC") amino acid sequence |
| Ab 513 | 1026 | QSVLTQPPSVSGAPGQRVSISCTGSSSDIGAGYDVHWYQQFPGTAPKLLMYANNN RPSGVPDRFSGSRSGTSASLAITGLQAEDEADYYCQSYDSNLDVVVFGGGTKLTVL | ADI-41188 | Light chain variable region ("LC") amino acid sequence |
| Ab 514 | 1027 | QVQLVESGGGLVKPGGSLRLSCAASGFTFSSYSMNWVRQAPGKGLEWVSSMSSS SGYIDYADSVKGRFTISRDNAKNSLYLQMNSLRVEDTAVYYCARRNAVVVPSLMVV ADYYYGMDVWGQGTTVTVSS | ADI-41189 | Heavy chain variable region ("HC") amino acid sequence |
| Ab 514 | 1028 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDTSLSGPGYVFGTGTKLTV L | ADI-41189 | Light chain variable region ("LC") amino acid sequence |
| Ab 515 | 1029 | QVQLVQSGAEVKKPGASVKVSCKAFGYTFRSYDMQWVRQAPGQRLEWMGWIN AVNGDTKYSQKFQGRVTITRDTSATTVYMELSSLRSEDTAVYYCARWGRFWNSRS LDYYAMDVWGQGTTVTVSS | ADI-41190 | Heavy chain variable region ("HC") amino acid sequence |
| Ab 515 | 1030 | DIVMTQSPGTLSLSPGERATLSCRASQSISSSYLVWYQHKPGQAPRLLIYGASTRA TDIPDRFSGSGSGTDFTLTISRLEPEDFAVYYCQQYGSSPLTFGQGTRLEIK | ADI-41190 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 516 | 1031 | QVQLVQSGAEVKRPGASVKVSCKASGYIFSHYGISWVRQAPGQGLEWMAWISAY NGNTNYAQKLQGRVTVTTDTSTSTAYMELRSLRSDDTAVYYCAREPPSLSAAATLD YWGQGTLVTVSS | ADI-41191 | Heavy chain variable region ("HC") amino acid sequence |
| Ab 516 | 1032 | EIVMTQSPLSLPVTLGQPASISCRSNQSLVYSDGNIYLSWFQQRPGQSPRRLIYK VSNRDSGVPDRFSGSGSGTDFTLKISRVEAEDVAVYYCMQVTHWPHEFGQGTKLEI K | ADI-41191 | Light chain variable region ("LC") amino acid sequence |
| Ab 517 | 1033 | QVQLVQSGAEVKKPGASVKVSCRTSGYTFTDYEINWVRQAPGQGLEWMGGISAY NGKTDYAQNLQDRVTMTTDTSTSTAYMELRSLRSDDTAVYYCARIFYYDRSGYYLA LFDSWGHGTLVTVSS | ADI-41192 | Heavy chain variable region ("HC") amino acid sequence |
| Ab 517 | 1034 | DIQMTQSPSSLSASVGDRVTITCRASQRIASYLNWYQQKPGKAPKLLIYAASSLQS GVPSRFSGSGSGTDFTLTISSLQPEDFATYYCQQSYSTPTLTFGGGTKMDIK | ADI-41192 | Light chain variable region ("LC") amino acid sequence |
| Ab 518 | 1035 | EVQLVESGGGLVKPGMSLRLSCAASGFRFSDHYMNWIRQAPGKGLEWVSYISSSS TYTDYTDSVKGRFTISRDNSKNSVYLQMNSLRAEDTAIYYCARVAPIRHNGDYIDY WGQGTTVTVSS | ADI-41193 | Heavy chain variable region ("HC") amino acid sequence |
| Ab 518 | 1036 | NFMLTQPPSASGTPGQRVTISCTGSSSNIGAGYDVHZYQQIPGTAPKLLIYGNNNR PSGVPDRFSGSKSGTSASLAITGLQTEDEADYYCQSYDRGLSGRVFGTGTKVTVL | ADI-41193 | Light chain variable region ("LC") amino acid sequence |
| Ab 519 | 1037 | QVQLQESGPGLVKPSQMLSLTCTVSGDSISSGDYYWSWIRHHPGKGLEWIGYISYS GSTYNNPSLKSRVTVSVDTSKNQFFLKLTSVTAADTAVYYCARATKPYHSYFYMDV WGKGTTVTVSS | ADI-41194 | Heavy chain variable region ("HC") amino acid sequence |
| Ab 519 | 1038 | EIVLTQSPGTLSLSPGERATLSCRASQSGSRSYLAWYQQRPGQAPRLLIYGASNRA TGIPDRFSGSGSGTDFTLTISRLEPEDFAVYYCQQYGNAPTFGGGTKVDIK | ADI-41194 | Light chain variable region ("LC") amino acid sequence |
| Ab 520 | 1039 | EVQLVESGGGLVQPGGSLRLSCIVSGFPFNTYAMSWVRQAPGKGLEWVSVVSASG GNTDYADSVKGRFTISRDNSKKTLYLQMNSLRAEDTAVYYCARTESNTLAPSWSGR YVTDWYFDLWGRGTLVTVSS | ADI-41196 | Heavy chain variable region ("HC") amino acid sequence |
| Ab 520 | 1040 | EIVMTQSPSSLSASVGDRVTITCRASQSISSFLNWYQQKPGKAPKLLISAASSLQS GVPSRFSGSGSGTDFTLTISSLQPEDFATYYCQQSYSIPTFGQGTRLEIK | ADI-41196 | Light chain variable region ("LC") amino acid sequence |
| Ab 521 | 1041 | QVQLVQSGAEVKKPGASVKVSCKASGYTFSGYYMHWVRQAPGQGLEWVGRINP KSGDTVYAQKFQGRVTMTRDTSISTAYMELSRLISDDTAKYYCARQEDHYYGSNF YNSFDFWGQGTLVTVSS | ADI-41197 | Heavy chain variable region ("HC") amino acid sequence |
| Ab 521 | 1042 | ETTLTQSPSSLSASVGDRVTITCRASQSISSNLNWYQQKPGKAPKLLIYGASTLQS GVPSRFSGSGSGTDFTLTISSLQPEDLATYYCQQSYSNPGKTFGQGTKVDIK | ADI-41197 | Light chain variable region ("LC") amino acid sequence |
| Ab 522 | 1043 | EVQLVQSGGVVIQPGGSLRLSCAASGFSFDEYLMHWVRQLPGKGLEWVALISWH GDITYYADSVKGRFTISRDNSRYSLYLQMNSLRSDDTALYYCVKDGWIEGAFNHTF GIGYYFENWGQGTLVTVSS | ADI-41198 | Heavy chain variable region ("HC") amino acid sequence |
| Ab 522 | 1044 | DIVLTQTPSSLSASVGDRVTITCQASQDINNCLNWYQQKPGKAPEVLIFDASNLET GVPLRFSGSGSGTHFTLTISSLQPEDIATYYCQQHENVPLTFGGGTKVEIK | ADI-41198 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 523 | 1045 | QVQLVESGGGLVKPGGSLRLSCGASGFTFPDYYMSWIRQAPGKGLEWLSYISSSSS FTDYADSVKGRFTISRDNAKKSLYLQMNSLRAEDTAVYYCARVRADYVGNSRIHFD YWGQGTLVTVSS | ADI-41199 | Heavy chain variable region ("HC") amino acid sequence |
| Ab 523 | 1046 | DIVMTQSPVTLSVSPGERATLSCRASQSLNGYLAWYQQKPGQAPRLLIYGASTRAT EPGWDTSGRGSGTEFTLTISSLQSEDFAVYYCQQYNDWPFTFGQGTRLEIK | ADI-41199 | Light chain variable region ("LC") amino acid sequence |
| Ab 524 | 1047 | EVQLLESGGGLVKPGGSLRLSCAASGLTFSDHDMSWVRQAPGKGLEWVSGIGGSG SNTYYAGSVKGRFTISRDNSKNTLYLQMDSLRVEDTAVYYCAKDPYGDYRDYYGM DVWGQGTTVTVSS | ADI-41200 | Heavy chain variable region ("HC") amino acid sequence |
| Ab 524 | 1048 | DIVLTQTPFSLPVTPGEPASISCRSSQSLLKSNGYNYLDWFLQKPGQSPQLLIYLG SNRASGVPDRFSGSGSGTDFTLKISRVEAEDVGVYYCMQTLQALYTFGQGTKVEIK | ADI-41200 | Light chain variable region ("LC") amino acid sequence |
| Ab 525 | 1049 | EVQLLESGGGLVQPGGSLRLSCAASGFAFDIYSMNWVRQAPGKGLEWLSYISSRGE TIYYADSVKGRFTISRDNARNSLYLQMNGLRDEDTATYYCYYYGSGISSHGGAFDY WGQGTLVTVSS | ADI-41201 | Heavy chain variable region ("HC") amino acid sequence |
| Ab 525 | 1050 | DIVMTQTPATLSLSPGERATLTSRASQSVSSFLAWYQQKPGQAPRLLIYDVSNRAT GVPARFSGSGSGTDFTLTISSLEPEDIAVYYCQQRNTWPAITFGQGTKVEIK | ADI-41201 | Light chain variable region ("LC") amino acid sequence |
| Ab 526 | 1051 | QVQLVESGAEVKKPGSSVKISCKASGGTFSSHPISWVRQAPGQGLEWMGRIVPIFG IANYAQKFQGRVTMIADKSTNTAYMELSNLRSEDTAVYYCASPVYDSSGFQWGQG TLVTVSS | ADI-41202 | Heavy chain variable region ("HC") amino acid sequence |
| Ab 526 | 1052 | QSALIQPRSVSGSPGQSVTISCTGTSGDGGFYNYVSWYQQHPGKTPKLMIYDVDQ RPSGVPDRFSGSKSGNTASLTISGLQAEDEADYYCCSYPGNPLYVFGTGTKLTVL | ADI-41202 | Light chain variable region ("LC") amino acid sequence |
| Ab 527 | 1053 | QVQLVQSGAEVRKPGESLKISCKASGYRFTNYWIGWVRQMPGKGLEWMGVIYPG DSDTRYSPSFQGQVTMSADKSTNTAYLQWSSLKASDTAIYYCVSLYSDYDYGALDY WGQGTLVTVSS | ADI-41203 | Heavy chain variable region ("HC") amino acid sequence |
| Ab 527 | 1054 | EIVMTQSPATLSVSPGERATLSCRASENVGRNLAWYQQKPGQAPRLLIYGASIRAT GILARFSGSGSGTEYTLTISSLQSEDFAVYYCQQYHDWPSFTFGPGTKVDIK | ADI-41203 | Light chain variable region ("LC") amino acid sequence |
| Ab 528 | 1055 | EVQLLESGGGLVKPGGSLRLSCAASGFTFSSYSMNWVRQAPGKGLEWVSSISAGSS YIYYADSVKGRFTISRDNAKNSLYLQMNSLRAEDTAVYYCARVPSYETTPYFDYWG QGTLVTVSS | ADI-41204 | Heavy chain variable region ("HC") amino acid sequence |
| Ab 528 | 1056 | QSVLTQPPSVSGAPGQRVTISCTGSSSNIGSGYDLHWYQQLPGTAPKLLIYVNSNRP SGVPDRFSGSKSGTSASLAITGLQAEDEADYYCQSYDSSLSGYVFGTGTKVTVL | ADI-41204 | Light chain variable region ("LC") amino acid sequence |
| Ab 529 | 1057 | QVQLQESGPGLVKPSGTLSLTCAVSGGSISSTNWWSWVRQPPGKGLEWIGEIYHS GSTNYNPSLKSRVTISVDKSNNQFSLNLSSVTAADTAVYYCARGVITYRGSWFLQYF DYWGQGTLVTVSS | ADI-41205 | Heavy chain variable region ("HC") amino acid sequence |
| Ab 529 | 1058 | DIRVTQSPDSLAVSLGERATINCKSSQSLFYSSNNQNYLAWYQQKPGQPPKLLIYW ASTRQSGVPHRFSGSGSGTDFTLTISSLQAEDVAVYYCQQYYSSPLTFGGGTKVEIK | ADI-41205 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 530 | 1059 | EVQLLESGGGLVKPGGSLRLSCAGSGFSFSSYSMNWVRQAPEKGLEWVSSISASSSF INYADSVKGRFIISRDNAKNSLFLQMDSLRAEDTAVYYCARDGVHPGGYIFGGYIDS WGQGTLVTVSS | ADI-41206 | Heavy chain variable region ("HC") amino acid sequence |
| Ab 530 | 1060 | QSVLTQPPSVSGAPGQRVTISCTGSSSNIGAGYDVHWFRQLPGTAPKLLIYGNNNR PSGVPDRFSGSKSGSSASLIITGLQAQDEATYYCQSYDSSLSGYVFGTGTKLTVL | ADI-41206 | Light chain variable region ("LC") amino acid sequence |
| Ab 531 | 1061 | QVQLVQSGPALVKPTQTLTLTCTFSGFSLSTKGMCVSWIRQPPGKALEWLALIDWD DDKFYSTSLKTRLTISKDTSKNQVVLTMTNMDPVDTATYYCARTLYFYGSGSLSDYC FDYWGQGTPVTVSS | ADI-41207 | Heavy chain variable region ("HC") amino acid sequence |
| Ab 531 | 1062 | QPVLTQPRSVSGSPGQSVTISCTGTSRDVGNYNFVSWYQQHPGKAPKLIIYDVTKR PSGVPDRFSGSKSGNTASLTISGLQAEDEADYYCCSYAGTYTWVFGGGTKVTVL | ADI-41207 | Light chain variable region ("LC") amino acid sequence |
| Ab 532 | 1063 | QVQLVESGGDLVKPGGSLRLSCAASGFTLSGHYMSWIRQPPGKGLEWVSSISGGST YTNYADSVKGRFTISRDNAENSLYLQMNSLRAEDTAVYYCARLAYSDYGPFYFDLW GRGTLVTVSS | ADI-41208 | Heavy chain variable region ("HC") amino acid sequence |
| Ab 532 | 1064 | QSVLTQPPSVSGAPGQRVTISCTGSSSNIGAGYDVHWYQQLTGTAPKLLIFDNNNR PSGVPDRFSGSKSGTSASLAITGLQAEDEADYYCQSYDSRLSAPYVFGTGTKLTVL | ADI-41208 | Light chain variable region ("LC") amino acid sequence |
| Ab 533 | 1065 | QVQLQESGAGLLKPSETLSLTCAVSGASFSGYSWSWIRQPPGKGLEWIGDIDHSGS TNYNSSLNSRVTISVDTSKNQFSLNLTSVTAADTAIYYCARVGGRSAYWGQGTLVT VSS | ADI-41209 | Heavy chain variable region ("HC") amino acid sequence |
| Ab 533 | 1066 | DIVMTQSPLSLPVTPGEPASISCRSSQSLLHSNGFNYLDWYLQKPGQSPQLLIYLG SNRASGVPDRFSGSGSGTDFTLKISRVEAEDVGVYYCMQALQTLTFGGGTKVEIK | ADI-41209 | Light chain variable region ("LC") amino acid sequence |
| Ab 534 | 1067 | QVQLVQSGAEVKKPGASVKVSCKASGYTFNNYGISWVRQAPGQGLEWMGWISA YNGDIKYAQKFQGRVTVTTDTSTSTAYMELRSLRSDDTAVYYCARDTPVGGGTQTF DYWGQGTLVTVSS | ADI-41210 | Heavy chain variable region ("HC") amino acid sequence |
| Ab 534 | 1068 | ETTLTQSPLSLPVTLGQPASISCRSSQSLVHSNGNTYLNWFQQRPGQSPRRLIYTV SNRDSGVPDRFSGSGSGTDFTLKISRVEAEDVGVYYCMQATHRPGTFGQGTKVEIK | ADI-41210 | Light chain variable region ("LC") amino acid sequence |
| Ab 535 | 1069 | EVQLLESGAEVKKPGASVKVSCKASGYTFTDYYIHWVRQAPGQGLEWMGRINPKN GDAIYAQNFQGRVTMTRDTSISTAYMEVSRLTSDDTAVYYCARDQMWLVLDYWG QGTLVTVSS | ADI-41212 | Heavy chain variable region ("HC") amino acid sequence |
| Ab 535 | 1070 | QSALTQPASVSGSPGQSITISCTGTSSDVGGYDYVSWYQQHPGKAPKLMIHDVTN RPSGISHRFSGSKSGNTASLTISGLQAGDEADYYCSSYTRSNTKVFGTGTKVTVL | ADI-41212 | Light chain variable region ("LC") amino acid sequence |
| Ab 536 | 1071 | EVQLVESGGGLIQPGGSLRLSCAASGFTVSSNYMSWVRQAAGKGLEWVSLIYSGD STYYADSVKGRFTISRDNSQNTLYLQMNSLRAEDTAVYYCARDASPNVGYYGMDV WGQGTTVTVSS | ADI-41213 | Heavy chain variable region ("HC") amino acid sequence |
| Ab 536 | 1072 | DIVLTQPPSVSVSPGQTASITCSGGKLGDTYACWYQQKPGQSPVLVIYQDSKRPS GIPERFSGSNSGNTATLTISGTQAMDEADYYCQAWDSSTARYVFGTGTKVTVL | ADI-41213 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 537 | 1073 | EVQLVESGGGLVQPGGSLRLSCAASGFTFSSYWMSWVRQAPGKGLEWVATIKQD GSEKYSVDSVKGRFTISRDNPKKSLYLQMNSLRAEDTAVYYCARDYRVEYYHSSD KLKRYYYYGMDVWGQGTTVTVSS | ADI-41214 | Heavy chain variable region ("HC") amino acid sequence |
| Ab 537 | 1074 | DIRVTQSPSSLSASVGDRVTITCRASQSISTYLNWYQQKPGKAPKFLIYAASSLES GVPSRFSGSGSGTDFSLTISSLQPEDFATYYCQQSYSIPITFGQGTRLEIK | ADI-41214 | Light chain variable region ("LC") amino acid sequence |
| Ab 538 | 1075 | QVQLVESGGGVVRPGGSLRLSCAASGFTFDDYGMSWVRQAPGKGLEWVSGINW SGGSTDYADSVKGRFTISRDNAKNSLYLQMNSLRAEDTALYYCAKEGQEWELLPW YFDLWGRGTLVTVSS | ADI-41215 | Heavy chain variable region ("HC") amino acid sequence |
| Ab 538 | 1076 | QPVLTQPASVSGSPGQSITIPCTGTSSDVGIYNLVSWYQQHPGKAPKLMIYDVSKRP SGVSNRFSGSKSGNTASLTISGLQAEDEADYYCCSYAGGSTYVFGTGTKLTVL | ADI-41215 | Light chain variable region ("LC") amino acid sequence |
| Ab 539 | 1077 | EVQLVESGGGLVKPGESLRLSCAASGFRFSDHYMSWIRQAPGKGLEWISYISSSSSY IHYADSVTGRFTISRDNAKNSMYLQMNSLRAEDTAVYYCAREIGRSYYMDVWGKG TTVTVSS | ADI-41216 | Heavy chain variable region ("HC") amino acid sequence |
| Ab 539 | 1078 | QSALIQPPSVSGAPGQRVTISCTGSSSNIGAGYDVHWYQQLPGTAPKLLIYGNNNR PSGVPDRFSASKSGISASLAITGVQTEDEADYYCQSYDRSLSEFYVFGSGTKVTVL | ADI-41216 | Light chain variable region ("LC") amino acid sequence |
| Ab 540 | 1079 | EVQLVQSGGGLVKPGGSLRLSCVASGFTFSSYSMNWVRQAPGKGLEWVSSISASSS YIDYADSVKGRFTISRDNDKKSLYLQMSSLRAEDTAVYYCAREDYDSLTGYYSPKRF DPWGQGTLVTVSS | ADI-41217 | Heavy chain variable region ("HC") amino acid sequence |
| Ab 540 | 1080 | QSVLTQPPSLSGAPGQRVTISCTGSSSNIGAGYDVHWYQQLPGTAPKLLIYGNNNR PSGVPDRFSGSKSGTSASLAITGLQAEDEADYYCQSYDRSLSVVFGGGTKVTVL | ADI-41217 | Light chain variable region ("LC") amino acid sequence |
| Ab 541 | 1081 | QVQLVQSGAEVKKPGASVKVSCKASGYTFISDGISWVRQAPGQGLEWMGWINPH NENTNYAQKFQGRVTMTTDTSTSTAYLELRGLRSDDTAVYYCARDPYHWSYLDYW GQGTLVTVSS | ADI-41218 | Heavy chain variable region ("HC") amino acid sequence |
| Ab 541 | 1082 | QSVVTQPPSVSGAPGQRVTITCTGSSSNIGANSDVHWYQQIPGTAPKLLIFGNSNR PSGVPDRFSGSKSGTSASLAITGLQAEDEADYYCQSYDRSLSGSRVFGGGTRLTVL | ADI-41218 | Light chain variable region ("LC") amino acid sequence |
| Ab 542 | 1083 | EVQLVESGGGLVQPAGSLRLSCAASGFTFSNYVMNWVRQAPGKGLEWVSYISSSG RTIHYADSVKGRFTISRDNAKNSLYLEMNSLRAEDTAVYYCARDPNYGGNSNRFDS WGQGTLVTVSS | ADI-41219 | Heavy chain variable region ("HC") amino acid sequence |
| Ab 542 | 1084 | DIVMTQTPSSLSASVGDRVTITCRASQTISNYLNWYQQKPGKAPKLLIFAASSLQS GVPSRFSGSGSGTDFTLTISSLQPEDFATYYCQQSYSAPRVTFGPGTKVDIK | ADI-41219 | Light chain variable region ("LC") amino acid sequence |
| Ab 543 | 1085 | EVQLLESGGGLVKPGGSLRLSCAASGFTFSDYTMNWVRQAPGKGLEWVSSISITSS HIYYADSVKGRFTISRDNAKNSLYLQINSLRAEDTAAYYCARELGFASSSYSYYYG MDVWGQGTTVTVSS | ADI-41221 | Heavy chain variable region ("HC") amino acid sequence |
| Ab 543 | 1086 | QSALTQPRSVSGSPGQSVTISCTGTSSDVGDYNSVSWYQQHPGTAPKLIIFDVTQR PSGVPDRFSGSKSANTASLTISGLQPEDEADYYCCSFAGNYVFGTGTKVTVL | ADI-41221 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 544 | 1087 | QVTLKESGGGVVQPGRSQRLSCTASGFNFHNYAMHWVRQAPGKGLEWVAVISY DGSNKNFADSVKGRFTISRDNSKNTLNLQMNNLRAEDTAVYYCVRDIVRGSPLFDY WGQGTLVTVSS | ADI-41222 | Heavy chain variable region ("HC") amino acid sequence |
| Ab 544 | 1088 | QPVLTQPPSLSVAPGQTAWITCGGNNIGSKIVHWYQQKPGQAPVVVVYDDDDRP SGIPERFSGSNSGNTATLTIRRVEVGDEADYYCQVWDRSSDNYVFGTGTKVSVL | ADI-41222 | Light chain variable region ("LC") amino acid sequence |
| Ab 545 | 1089 | QVQLVESGGGVVQPGRSLRISCAASGFTFSNYGMHWVRQAPGKGLEWVAVLSYD GSNEYYADSVKGRFTISRDNSKNTLYLQMNSLRAEDTAVYYCAKNLNDYNISWYKC FDLWGRGTLVTVSS | ADI-41223 | Heavy chain variable region ("HC") amino acid sequence |
| Ab 545 | 1090 | QPVLTQPASVSGSPGQSITISCTGTSSDVGGYNYVSWYQHHPGKAPKLIIYDVNNR PSGVSNRFSGSKSGNTASLTISGLQAEDEADYICSSYTTITTFVVFGGGTKLTVL | ADI-41223 | Light chain variable region ("LC") amino acid sequence |
| Ab 546 | 1091 | EVQLVETGGGLVQPGRSLRLSCTASGFTFGDYAMNWVRQAPGKGLEWIGIIRTKT YGGTTEYAASVKGRFTISRDDSKGIAYLQMNSLKTEDTGVYYCTMPVLNMDVWG QGTTVTVSS | ADI-41224 | Heavy chain variable region ("HC") amino acid sequence |
| Ab 546 | 1092 | QPVLTQPHSVSESPGKTVTISCTRNIGNIASNYVQWYQQRPGSSPTTVIYEDNQRP SGVPDRFSGSIDISSNSASLTISGLKTEDEADYYCQSYDSNNPWVFGGGTQLTVL | ADI-41224 | Light chain variable region ("LC") amino acid sequence |
| Ab 547 | 1093 | EVQLVESGGGLVKPGGSLRLSCAASGFSLSDYYMTWLRQAPGKGLEWVSSIGTTST YTNYAESVKDRFTISRDNAKNSLYLQMNSLRAEDTAVYYCARDWGFGVERGYFDL WGRGTLVTVSS | ADI-41225 | Heavy chain variable region ("HC") amino acid sequence |
| Ab 547 | 1094 | DIVLTQTPSTLSASVGDRVTITCRASQSISFWLAWYQQKPGKAPKLLIYKASTLESGV PSRFSGRGSGTDFTLTISSLQPDDFATYYCQQYNTYTWTFGQGTKVEIK | ADI-41225 | Light chain variable region ("LC") amino acid sequence |
| Ab 548 | 1095 | EVQLVESGGGLVKPGGSLRLSCAASRFTFAGYYMSWIRQAPGKGLEWVSDISPSST YTNYADSVKGRFTISRDNAGTSVSLQMDSLRADDTAVYYCARITPYGGSHYFDSWG QGTLVTVSS | ADI-41226 | Heavy chain variable region ("HC") amino acid sequence |
| Ab 548 | 1096 | QPVLTQPPSVSGAPGQRVTISCTGSSSNIGAGYDLHWYQQLPGTAPKLLIYGNSR PSGVPDRFSGSKSGTSASLAITGLQAEDEADYYCQSYDNSLSGFYVFGTGTKVTVL | ADI-41226 | Light chain variable region ("LC") amino acid sequence |
| Ab 549 | 1097 | RSSWCSVGAEVKKRGSSVKVSCKASGGTFGGYAVSWVRQAPGQGLEWMGGIIP MFYTTKYAQKLQGRVTITADESTNTAYMDLSSLTSDDTAIYFCAREWHLGRTAVTG TGAFLDAFDIWGQGTMVTVSS | ADI-41227 | Heavy chain variable region ("HC") amino acid sequence |
| Ab 549 | 1098 | SYELTQPPSVSEAPRQRVTISCSGSSSNIGNNAVNWYQQLPGKAPKLLIYYDDLLPS GVSDRFSGSKSGTSASLAISGLQSEDEADYCSAWDDSLNGWVFGGGTKLTVL | ADI-41227 | Light chain variable region ("LC") amino acid sequence |
| Ab 550 | 1099 | EVQLLESGPGLVKPSETLSLTCTVSGGSISSYQWNWIRQPPGKGLEWLGYVYYSGST NYNPSLKSRVTLSVDTSKNQFSLKLSSVTAADTAVYYCARDRRDGSFVFDYWGQGT LVTVSS | ADI-41228 | Heavy chain variable region ("HC") amino acid sequence |
| Ab 550 | 1100 | QSVLIQPASVSGSPGQSITISCTGTSSDVGGYNYVSWYQQHPGKAPKLMIYDVSNR PSGISNRFSGSKSGNTASLTISGLQAEDEADYYCSSYTSSTTLVFGTGTKVTVL | ADI-41228 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 551 | 1101 | QVQLVQSGGGVVQPGRSLKLSCAASGFTFKSYGMHWVRQAPGKGLEWVAVISYD EINKYYADSVKGRFTISRDYSKNTLSLQMNSLTTEDTAMYYCAKPKTTGYYYLDA FDFWGQGTMVTVSS | ADI-41229 | Heavy chain variable region ("HC") amino acid sequence |
| Ab 551 | 1102 | ETTLTQSPSSLSASVGDRVTITCQASQDISNYLNWYQQKPGKAPKLLIYDASNLE TGVPSRFSGSGSGTDFTFTISSLQSEDIATYYCQQHDNVPPTFGQGTKVDIK | ADI-41229 | Light chain variable region ("LC") amino acid sequence |
| Ab 552 | 1103 | QVQLVQSGAEVKKPGESLKISCKASGYSFTSHYWIGWVRQMPGKGLEWMGFIFP GDSDTRYSPSLQGQVTISADKSTNTAYLQWNSLKASDTAMYYCARLEYLVSGFEY WGQGTLVTVSS | ADI-41230 | Heavy chain variable region ("HC") amino acid sequence |
| Ab 552 | 1104 | QPGLTQPHSVSESPGKTVTISCTRSSGSIASNYVHWYQQRPGSFPTTVIYEDNQR GPSVPDRFSGSIDSSSNSASLTISGLRTEDEADYYCQSYDSSNPVVFGGGTKVTVL | ADI-41230 | Light chain variable region ("LC") amino acid sequence |
| Ab 553 | 1105 | QVQLVQSGAEVKKPGESLKISCKGSGYSFTNNWVGWVRQMPGKGLEWMGIIFPG DSDTRYSPSFRGQVTISVDTSINTAFLQWNSLGASDTAMYYCAMTDYNYSFKSWG QGTLVTVSS | ADI-41231 | Heavy chain variable region ("HC") amino acid sequence |
| Ab 553 | 1106 | NFMLTQPHSVSESPGKTITISCTRSSGNIGNNYVQWYQQRPGSSFTTVIYEDYQR PSGVPDRFSGSIDSSSNSATLTISGLKTEDEADYYCQSYDSSNPYVFGTGTKVTVL | ADI-41231 | Light chain variable region ("LC") amino acid sequence |
| Ab 554 | 1107 | QVQLVQSGAEVKKPGASVKVSCKASGYTFTHYGISWVRQAPGQGLEWMAWISAY NGNTNYAQKLQDRVTVTTDTSTSTAYMELRSLRSDDTALYYCARDSMGGTTLFDY WGQGTLVTVSS | ADI-41232 | Heavy chain variable region ("HC") amino acid sequence |
| Ab 554 | 1108 | DIVLTQTPLSLPVTLGQPASISCRSSQSLVYSDGNTYLNWFQQRPGQSPRRLIYKV SNRDSGVPDRFTGSGSGTDFTLKISRVEAEDVGVYYCMQGTHWPPMYTFGQGTKLE IK | ADI-41232 | Light chain variable region ("LC") amino acid sequence |
| Ab 555 | 1109 | EVQLLESGGGLVKPGGSLRLSCAASGFIFRDYYMIWIRQAPGKGLEWVSYISSSST YTNNADSVKGRFTISRDNAKNSLYLQMNSLRAEDTAVYYCARLFASRSDGAFDIWG QGTTVTVSS | ADI-41233 | Heavy chain variable region ("HC") amino acid sequence |
| Ab 555 | 1110 | QSVLTQPPSVSGAPGQRVTISCTGSSSNIGAGYDVHWYQQLPETAPKLLIYDNNR PSGVPDRFSGSKSGTSASLAITGLQAEDEADYYCQSYDSSLSGYVFGTGTTVTVL | ADI-41233 | Light chain variable region ("LC") amino acid sequence |
| Ab 556 | 1111 | QVQLVQSGGGVVQPGRSLRLSCAASGFTVSSYAIHWVRQSAGKGLEWVAVEGRF TISRDNSKNTLYLQMNSLRAEDTAVYYCARLSEALVEPAAHTQYKYHYGLDVWGQ GTTVTVSS | ADI-41234 | Heavy chain variable region ("HC") amino acid sequence |
| Ab 556 | 1112 | EIVLTQSPLSLPVTPGEPASISCKSSQSLLDSNGYNYLDWYLQKPGQSPQLLIYLV SNRASGVPDRFSGSGSGTDFTLKISRVEAEDVGIYYCMQALQTPWTFGQGTKVEIK | ADI-41234 | Light chain variable region ("LC") amino acid sequence |
| Ab 557 | 1113 | QVQLQQWGAGLLKPSETLSLTCGVYGESFSGHYWSWIRQPPGKGLEWMGEIHHS GTTNYNPSLKSRVTISVDTSKNQFSLKLNSVTAADTAVYYCARNPAEDILTGYSPP FHYYYMDVWGKGTTVTVSS | ADI-41235 | Heavy chain variable region ("HC") amino acid sequence |
| Ab 557 | 1114 | QSVLTQPPSVSGAPGQRVTISCTGSSSNIGAGYDVHWYQQIPGTAPKLLIHSNNNR PSGVPDRFSGSKSGTSASLAITGLQAEDEADYYCQSYDSSLSVVFGGGTKLTVL | ADI-41235 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 558 | 1115 | QVQLVQSGGGLVKPGGSLRLSCTASGFTFSDYYMDWIRQAPGKGLEWVSSISSSST YTKYADSVKGRFTISRDNAKNSLFLQMNSLRAEDTAVYYCVRNLGPYCSSTSCFVFD YWGQGTLVTVSS | ADI-41236 | Heavy chain variable region ("HC") amino acid sequence |
| Ab 558 | 1116 | QSVLTQPPSVSGAPGQRVSISCTGSSSNIGAGYEVHWYKQVPGTAPRLLMYDNTN RPSGVPDRVSGSKSGTSASLAITGLQAEDEADYYCQSYDNSLNKSVFGGGTKVTVL | ADI-41236 | Light chain variable region ("LC") amino acid sequence |
| Ab 559 | 1117 | EVQLVESGGGLVKPGGSLRLSCAASGFTFSDYYMNWIRQAPGKGLEWVSDISPSSS YTNYADSVKGRFTISRDNAKNSLYLQMNSLRAEDTAMYYCARRGSCTGGVCSFDY WGQGTLVTVSS | ADI-41237 | Heavy chain variable region ("HC") amino acid sequence |
| Ab 559 | 1118 | QPGLTQPPSVSGAPGQRVTISCTGSSSNIGAGYDVNWYQQLPGTAPKLLIYDNSNR PSGVPDRFSGSKSGTSASLAITGLQAEDEADFYCQSYDSSLSGFVFGTGTKVTVL | ADI-41237 | Light chain variable region ("LC") amino acid sequence |
| Ab 560 | 1119 | EVQLLESGGGLVKPGGSLRLSCAASGFTFRDYYMSWIRQAPGKGLEWVSYISSSSSY TEYADSVKGRFTISRDNAKKSLYLQMNSLRTEDTAVYYCARVITQAGTGTTYYMDV WGKGTTVTVSS | ADI-41238 | Heavy chain variable region ("HC") amino acid sequence |
| Ab 560 | 1120 | QSVLTQPPSVSGAPGQRVTISCTGSSSNIGTGYDVHWYQQLPGTAPKLLIYANNNR PSGVPDRFSGSKSGTSASLAITGLQAEDEADYYCQSYDSSLSLVFGGGTKLTVL | ADI-41238 | Light chain variable region ("LC") amino acid sequence |
| Ab 561 | 1121 | QITLKESGPTLVKPTQTLTLTCTFSGFSLTTTGVGVGWIRQPPGKALEWLALIYWDD DKRYSPSLKNRITITKDTSKKQVVLTMTNMDPADTATYYCAHISTVVTYDSSGSYYV LINWFDPWGQGTLVTVSS | ADI-41239 | Heavy chain variable region ("HC") amino acid sequence |
| Ab 561 | 1122 | EIVMTQSPLSLPVTPGEPASISCRSSHSLLHSNGYNYLDWYLQKPGQSPQLLIYLGS NRASGVPDRFSGSGSGTDFTLKISRVEAEDVGVYYCMQALQTPLTFGQGTKVDIK | ADI-41239 | Light chain variable region ("LC") amino acid sequence |
| Ab 562 | 1123 | QVQLQQWGAGLLKPSETLSLICDVYGGSFSDYYWSWIRQSPGKGLEWIGEINHSG STSFHPSLKSRISISIDTSNNQFSLNLSSMTAADTAVYYCARGTLRGYFDYWGQGT LVTVSS | ADI-41240 | Heavy chain variable region ("HC") amino acid sequence |
| Ab 562 | 1124 | EIVLTQSPSTLSAFVGDRVTITCRASQSISRWLAWYQQKPGKAPNLLISEASSLESG VPSRFSGSGSGTEFTLTISSLQPDDLGTYYCQQYNGYLWTFGQGTKVEIK | ADI-41240 | Light chain variable region ("LC") amino acid sequence |
| Ab 563 | 1125 | QVQLVQSGAEVKKPGASVQVSCKASGYTFTGDYMHWVRQAPGQGLEWMGRIN PNSGGTNYAQKFQGRVTMTRDTSISTAYMELSRLRSDDTAVYYCARAAAEYSSSSP TSYYYMDVWGKGTTVTVSS | ADI-41241 | Heavy chain variable region ("HC") amino acid sequence |
| Ab 563 | 1126 | EIQMTQSPSSLSASVGDRVTITCRASQNIYSFLNWYQQKPGKAPKLLIYAASSLQSG VPSRFSGSGSATDFTLTISSLQPEDFATYYCQQSYSPPQITFGQGTKVDIK | ADI-41241 | Light chain variable region ("LC") amino acid sequence |
| Ab 564 | 1127 | EVQLVESGGGVVQPGRSLRLSCAASGFPFSSYAMHWVRQAPGKGLEWVAVIWFE GNEKYFADSVEGRFTISRDNSKNTLYLQMNSLRAEDTARYYCARFYFGAFDIWGQG TLVTVSS | ADI-41242 | Heavy chain variable region ("HC") amino acid sequence |
| Ab 564 | 1128 | DIVMTQSPLSLPVTPGEPASISCRSSQSLLHSNGYNSLDWYLQKPGQSPQLLIYLA SNRASGVPDRFSGSGSGTDFTLKISRVEAEDVGVYYCMQALQTPYTFGQGTKVEIK | ADI-41242 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 565 | 1129 | QVQLVQSRAEVKKPGESLKISCKGSLHSFSNNWIGWVRQMPGKGLEWMGIIFPD DSDTRYSPSFQGQVTISADKSISTAYLQWSSLKASDTAIYYCGTVVTLIQGVADW GQGTLVTVSS | ADI-41243 | Heavy chain variable region ("HC") amino acid sequence |
| Ab 565 | 1130 | QPVLTQPHSVSESPGKTVTISCTRSSGSIDSSYVQWYQQRPGSSPTTVIYEDNLRP SGVPDRFSGSIDSSSNSASLTISGLKTEDEAEYYCQSYDSSNPVVFGGGTKLTVL | ADI-41243 | Light chain variable region ("LC") amino acid sequence |
| Ab 566 | 1131 | QVTLKESGGGLIQPGGSLRLSCAVSGFTVSSKYMSWVRQAPGKGLEWVSVIYGGG STYYTDSVKGRFTISRDNSNNTLYLQMNSLRAEDTAIYYCAREARSYNYDYVGNDA FDIWGQGTTVTVSS | ADI-41244 | Heavy chain variable region ("HC") amino acid sequence |
| Ab 566 | 1132 | DIVLTQTPDSLAVSLGERATINCKSSQSVLNNFNNKNYLAWYQQKPGQPPKLLIYW ASTRESGVPDRFSGSGSGTDFTLTITSLQAEDVAIYYCQQYYRTPPYTFGQGTKVD IK | ADI-41244 | Light chain variable region ("LC") amino acid sequence |
| Ab 567 | 1133 | QVQLVESGGGLVKPGGSLRLSCAASGFSFSAYYMSWIRQAPGKGLEWISNISGGSS YANYADSVEGRFTISRDNAKNSLYLQMNSLRAEDTAVYYCAREFQTYYYMDVWGK GTTVTVSS | ADI-41245 | Heavy chain variable region ("HC") amino acid sequence |
| Ab 567 | 1134 | QPVLTQPPSVSGAPGQRVTISCTGSSSNIGAGYEVHWYQQLPGTAPKLLIYGNNNR PSGVPDRFSGSKSGTSASLAITGLQAEDEADYYCQSYDSSLSGSVFGGGTKLTVL | ADI-41245 | Light chain variable region ("LC") amino acid sequence |
| Ab 568 | 1135 | EVQLLESGPGLVKPSETLSLTCIVSGGSISSYNWNWIRQPPGKGLEWIGYIYNSGS TNYNPSLKSRVTISVDTSKNQFSLKLSSVTAADTAVYYCARYFDYGSGGFDYWGQG TLVTVSS | ADI-41246 | Heavy chain variable region ("HC") amino acid sequence |
| Ab 568 | 1136 | ETTLTQSPGTLSLSPGERATLSCRASQSVTSTYLAWYQQKPGQAPRLLIYGASSRAT GIPDRFSGSGSGTDFTLTISRLEPEDFAVYYCQQFDSSLTFGGGTKVEIK | ADI-41246 | Light chain variable region ("LC") amino acid sequence |
| Ab 569 | 1137 | QVQLVQSGAEVKKPGASLQVSCKASGYTFTDSYFHWVRQAPGQGLEWMGRISPH SGGTNYAQKFQGRVTMTRDTSISTAYLELSRLRSDDTAVYYCATEGPRGPFRFDPW GQGTLVTVSS | ADI-41247 | Heavy chain variable region ("HC") amino acid sequence |
| Ab 569 | 1138 | NFMLTQPHSVSESPGKTVTISCTRSSGSIASNYVQWYQQRPGSSPTTVIYEDNQRPS GVPDRFSGSIDSSSNSASLTISGLMTEDEADYYCQSYDSSNWVFGGGTKLTVL | ADI-41247 | Light chain variable region ("LC") amino acid sequence |
| Ab 570 | 1139 | QVQLVQSGGGVVQPGRSLRLSCAASGFTFSSYSMHWVRQAPGKGLEWMAVCW YDGSNIYYADSVKGRFTISRDNSKNTVYLQMNSLRAEDTAVYYCARDDRYCSGGTC LSAFDIWGQGTMVTVSS | ADI-41248 | Heavy chain variable region ("HC") amino acid sequence |
| Ab 570 | 1140 | ETTLTQSPSSLSASVGDRVTITCRASQSISSYLNWYQQKPGRAPKLLIYTTSSLQS GVSSRFSGSGSGTDFTLTINSLQPEDFATYYCQQSYSTPNTFGQGTKVEIK | ADI-41248 | Light chain variable region ("LC") amino acid sequence |
| Ab 571 | 1141 | QVQLVQSGAEVKKPGESLKISCQVSRDTSTTYWIGWVRQMPGKGLEWMGIIFPG DSDTRYSPSFQGQVTISADKSIMTAYLQLTSLKASDTAMYYCATQALRGAFDIWGQ GTMVTVSS | ADI-41249 | Heavy chain variable region ("HC") amino acid sequence |
| Ab 571 | 1142 | DIRLTQSPSSLSASVGDRVTITCQASQDISNYLNWYQQKPGKAPKLLIYDASYLET GVPSRFSGSGSGTDFTFTISSLQPEDFATYYCQQYDDLLFTFGPGTKLEIK | ADI-41249 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 572 | 1143 | QVQLQQWGAGLLKPSETLSLTCAVSGESLTGYFWSWIRQPPGKGLEWIGEVSHSG STNYNPSLKSRVTMSVDTSKTQFSLKLNSVTAADTAVYYCARGYDYWSGTARYFDY WGQGILVTVSS | ADI-41250 | Heavy chain variable region ("HC") amino acid sequence |
| Ab 572 | 1144 | QPVLTQPASVSGSPGQSITISCTGTSSDVGGYNYVSWYQQHPGKAPKLMIYDVSNR PSGVSSRFSGSKSGNTASLTISGLQAEDEGDYYCSSYRSSTTSRVFGGGTKVTVL | ADI-41250 | Light chain variable region ("LC") amino acid sequence |
| Ab 573 | 1145 | EVQLVESGGGLVKPGGSLRLSCAASGFTFSDYYMTWIRQAPGKGLEWVSNISGGSS YTNYADSVKGRFTISRDNAKNSVYLQMNSLRAEDTAVYYCARVGCSGGVCNFFLDY WGQGTLVTVSS | ADI-41251 | Heavy chain variable region ("HC") amino acid sequence |
| Ab 573 | 1146 | QSVLTQPPSVSGAPGQRVTISCTGSSSNIGAGYDVHWYQQLPGTAPKLLIYDNTNR PSGVPDRFSGSKSGTSASLAITGLQAEDEADYYCQSYDSSLSGYVFGTGTKVTVL | ADI-41251 | Light chain variable region ("LC") amino acid sequence |
| Ab 574 | 1147 | EVQLVQSGAEVKKPGESLKISCMGSGYNFPNYWIGWVRQMSGKGLEWMGIIYPD DSDTTYSPSFQGQVIFSADKSISTAYLQWSSLKASDTAMYFCVRLDKTTQIDFWGQ GTLVTVSS | ADI-41252 | Heavy chain variable region ("HC") amino acid sequence |
| Ab 574 | 1148 | EIVLTQSPSSLSASVGDRVTITCQASQDISNYLNWYQQKPGKAPKLLIYDVSNLET GVPSRFSGSGSGTDFTFTISSLQPEDIATYYCQQHDNLPLTFGQGTRLEIK | ADI-41252 | Light chain variable region ("LC") amino acid sequence |
| Ab 575 | 1149 | EVQLVQSGPGLVKPSETLSLTCTVSGDSISSSDYSYYWGWIRQPPGKGLEWIASLS YSGKTYSQSSLKSRVIISVDTSKKQFSLKLSSVTAADTAVYYCAVTRCYVCTSEGD SFDMWGQGTMVTVSS | ADI-41253 | Heavy chain variable region ("HC") amino acid sequence |
| Ab 575 | 1150 | DIVLTQTPGTLSLSPGERATLSCRASQSISGNYLAWYQHKPGQAPRLLIYGASTRA TGIPDRFSGSGSGTDFPLTISRLEPEDFAVYYCQQYATSPYTFGQGTKVDIK | ADI-41253 | Light chain variable region ("LC") amino acid sequence |
| Ab 576 | 1151 | EVQLVESGGGLVQSGGSLRLSCAASGFTFSSYEMNWVRQAPGKGLEWVSYTTNN GRTIYYADSVKGRFTISRDNAKNSLFLQMNGLRAEDTAVYYCARGIQFSRVDYAMD VWGQGTTVTVSS | ADI-41254 | Heavy chain variable region ("HC") amino acid sequence |
| Ab 576 | 1152 | SYELTQPPSVSGTPGQRITISCSGSSSNIASNTVNWYQHLPGTAPKLLIYSDNQRPSG VPDRFSGSKSGTSASLAISGLQSEDEADYYCAIWDDSLNASYVFGTGTKLTVL | ADI-41254 | Light chain variable region ("LC") amino acid sequence |
| Ab 577 | 1153 | EVQLVESGGGLVQPGGSLRISCAASGLTFSSYAMSWVRQAPGQGLEWVSSVSGSG VSTYYADSVKGRFTISRDNSKNTLYLQMNSLRAEDTAVYYCAKEDYYHFYMDVWG NGTTVTVSS | ADI-41255 | Heavy chain variable region ("HC") amino acid sequence |
| Ab 577 | 1154 | ETTLTQSPATLSVSPGERATLSCRASQSVSSNLAWYQQKPGQAPRLLIYGASTRAA GIPARFSGSGSGTEFTLTISSLQSEDFAVYYCQQHDNWPSYTFGQGTKVEIK | ADI-41255 | Light chain variable region ("LC") amino acid sequence |
| Ab 578 | 1155 | QVQLVQSGAEVKSPGSSATVSCKASGGTFGSYGISWVRQAPGQGLEWIGAIMPM FGTTNYAQKFQGRVTMTADESTSTVYMDVSSLRPDDTAVYYCVRDVFYDILTGYYD ADYYHHYMDVWGKGTTVTVSS | ADI-41256 | Heavy chain variable region ("HC") amino acid sequence |
| Ab 578 | 1156 | DIVMTQSPLSLPVTLGQPASISCRSGQSLVHSDGNTYLNWFQQRPGQSPRRLIYKV SNRGSGVPDRFSGSGSGTDFTLKISRVEAEDVGVYFCMQGTHWPRTFGQGTKVDI K | ADI-41256 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 579 | 1157 | QVQLVESGAEVKKPGSSVKVSCKASEGTFSSYGISWVRQAPGQGPEWMGEINPM FGTAKYAQKFQGRVTITVDESTSTADMELSSLTSEDTAVYYCAREFLGQCSETNCP TPSRHLDYWGQGTLVTVSS | ADI-41257 | Heavy chain variable region ("HC") amino acid sequence |
| Ab 579 | 1158 | EIVMTQSPSSLSASVGDRVTITCRASRTISSYLNWYQQKPGKAPKLLIYATSNLQS GVPSRFSGSGSGADFTLTISSLQPEDFATYYCQQTYSTPGFGPGTKVDIK | ADI-41257 | Light chain variable region ("LC") amino acid sequence |
| Ab 580 | 1159 | QVQLVQSGGGLVQRGGSLRLSCAASGFSFRSYAMSWVRQAPGKGLEWVSSISDS GDNTFYADSVKGRFSISRDNSRDTLYLQMNSLRAEDTAVYYCARGGYCSGGNCFPF DYWGQGTLVTVSS | ADI-41258 | Heavy chain variable region ("HC") amino acid sequence |
| Ab 580 | 1160 | SYELMQLPSVSVSPGQTARITCSGDALPKQYGYWYQQKPGQAPVLVIYKDSERPSG IPERFSGSSSGTTVTLTISGVQAEDEADYYCQSADSGGTYVMFGGGTKLTVL | ADI-41258 | Light chain variable region ("LC") amino acid sequence |
| Ab 581 | 1161 | QVQLVESGGRLVKPGGSLRLSCAASGFTFSDFYMSWIRQAPGKGLEWVSYISSSGD DPNYADSVKGRFTISRDNSKNSLYLQMNSLRAEDTAVYYCARDEVGWNNLDYYFG MDVWGQGTTVTVSS | ADI-41259 | Heavy chain variable region ("HC") amino acid sequence |
| Ab 581 | 1162 | DIVMTQSPLSLPVTLGQPASISCRSSQSLVHSDGNTYLSWFHQRPGQSPRRLIYKV SNRDSGVPNRFSGGGSGTDFTLKISRVEAEDVGFFYCMQGTHWQKTFGQGTKVEIK | ADI-41259 | Light chain variable region ("LC") amino acid sequence |
| Ab 582 | 1163 | QVQLVQSGAEVKKPGSSVKVSCKASGGTFSSYGISWVRQAPGQGLEWMGGIIPM FGAANYAQKFQGRVTITAETSTSTAFMELSSLRSDDTAVYYCARIRWVPNWGGTA TSFYNGMDVWGQGTTVTVSS | ADI-41261 | Heavy chain variable region ("HC") amino acid sequence |
| Ab 582 | 1164 | EIVMTQSPGTLSLSPGERATLSCRASQSVSSSYLAWYQQKPGQAPRLLIYGASSRA TGIPDRFSGSGSGTDFTLTISRLEPEDFAVYYCQHYGSSLFTFGPGTKVDIK | ADI-41261 | Light chain variable region ("LC") amino acid sequence |
| Ab 583 | 1165 | QVQLVQSGAEVKKPGASVKVYCKASGYTFTSHYIHWVRQAPGQGLEWMGRMNP SGGSPMYAQKFQERVTMTRDTSTSTAYMELRSLRSEDTAVYYCAMAKFYSFDYW GQGTLVTVSS | ADI-41263 | Heavy chain variable region ("HC") amino acid sequence |
| Ab 583 | 1166 | QSVLTQPHSVSESPGKTVTISCTRSSGSIASYFVHWYQQRPGSAPTIVIYEDNQRP SGVPDRFSGSIDSSSNSASLTISGLKTEDEADYYCQSYDSSNWVFGGGTKLTVL | ADI-41263 | Light chain variable region ("LC") amino acid sequence |
| Ab 584 | 1167 | EVQLVESGGGLVKPGGSLRLSCAASGFTFSNTWMSWVRQAPGKGLEWVGHIKSK TDGGTTDYAAPVKGRFTISRDDSKSILNLHLNSLKTEDSAVYYCAALPPISGWYYT PGFWGQGTLVTVSS | ADI-41264 | Heavy chain variable region ("HC") amino acid sequence |
| Ab 584 | 1168 | SYELTQPPSMSVSPGQTARITCFGDAVPKKYVYWYQQKSGQAPVMVIYDDRRPS GIPERFSGSSSGARATLTISGAQVEDEADYYCYSTDGSGNPSFGGGTKLTVL | ADI-41264 | Light chain variable region ("LC") amino acid sequence |
| Ab 585 | 1169 | EVQLVQSGAEVKKPGESLTISCKDSGYSFTSYWIGWVRQVPGKGLEWMGIVYPGD SRYSPSFQGHVTMSADKSINTAYLQWSTLKASDTAMYYCAKVVTYGSAIRWFESW GQGTLVTVSS | ADI-41265 | Heavy chain variable region ("HC") amino acid sequence |
| Ab 585 | 1170 | QSVLTQPPSVSAAPGQKVSISCSGSSSNIGNNFVSWYQQVPGTAPKLLIIDNNKR PSGIPDRFSGSKSGTSATLGITGLQTGDEADYYCGTWDSRLSAEVFGGGTKLTVL | ADI-41265 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 586 | 1171 | QVQLQQSGPGLVKPSQTLSLTCAISGDSVSSNSAAWNWIRQSPSRGLEWLGRTYY RSKWYNDYAVSVKSRITINPDTSKNQFSLQLNSVTPEDTAVYYCARDLPQVDYFD GASFYFFDFWGQGTLVTVSS | ADI-41266 | Heavy chain variable region ("HC") amino acid sequence |
| Ab 586 | 1172 | QPVLTQPPSVSVAPGQTASITCGGNIIGNKGVHWYQQKPGRAPVLVVYDDSDRPS GIPERFSGSNSGNTATLTISRVEAADEADYYCQVWDTGSHPVVFGGGTKVTVL | ADI-41266 | Light chain variable region ("LC") amino acid sequence |
| Ab 587 | 1173 | QVQLVQSGPGLVKPSGTLSLTCAVSGGSISTTHWWSWVRQPPGKGLEWIGEIYHS GSTNYNPSLKSRVTISVDKSRSQFSLKLTSVTAADTAVYYCARGDPLCSGGICYS GYFDYWGQGTLVTVSS | ADI-41267 | Heavy chain variable region ("HC") amino acid sequence |
| Ab 587 | 1174 | SYVLTQPPSVSVSPGQTATITCSGDKLGDQYACWYQQKSGQSPVLVIYRDNKRPSG IPERFSGSNSGNTATLTISETQAMDEADYYCQAWGSSSVVFGGGTKVTVL | ADI-41267 | Light chain variable region ("LC") amino acid sequence |
| Ab 588 | 1175 | EVQLVESGGGLVKPGGSLRLSCVASGFGFTSYSMNWVRQAPGKGLEWVSSISASST YIHYADSVKGRFTISRDNARNSLYLQMISLRADDTAVYYCSRDGPTYGSGVHVWGQ GTMVTVSS | ADI-41268 | Heavy chain variable region ("HC") amino acid sequence |
| Ab 588 | 1176 | QSALIQPVSVSGSPGQSITISCTGTRSDVGGYNYVSWYQQHPGKAPKLMIYEVRNR PSGVSDRFSGSKSGNTASLTISGLQAEDEGDYYCSSYTSSDTLFYVFGSGTKLTVL | ADI-41268 | Light chain variable region ("LC") amino acid sequence |
| Ab 589 | 1177 | EVQLVESGGGVVQPGQSLRLSCAASGFTFSSFAMHWVRQAPGKGLEWVAVISYD GSNKYYADSVKGRFTISRDNSKNTLSLQVNSLRAEDTAVYYCARVSAEGSMGRFSD FNYWGLGTLVTVSS | ADI-41270 | Heavy chain variable region ("HC") amino acid sequence |
| Ab 589 | 1178 | QSALTQPASVSGSPGQSITISCTGTSSDVGSYNLVSWYQQHPGKAPKLMIYEVRKR PSGVSNRFSGSKSGNTASLTISGLQAEDEADYYCCSYAGSDTYVFGTGTKLTVL | ADI-41270 | Light chain variable region ("LC") amino acid sequence |
| Ab 590 | 1179 | QVQLQESGPGLVKPSQTLSLTCAISGDSVSSNNAAWNWIRQSPSRGLEWLGRTYY RSKWYNDYAVSVKSRITINPDTSKNQLSLQLNSVTPEDTAVYYCARAGVRQWLVRG MDAFDIWGQGTMVTVSS | ADI-41271 | Heavy chain variable region ("HC") amino acid sequence |
| Ab 590 | 1180 | DIRLTQSPDSLAVSLGERATVNCKSSQSVLYSSNNKNYLAWYQQKPGQPPKLLIYW ASTRESGVPDRFSGSGSGTDFTLTISSLQAEDVAVYYCQQYYNTPHTFGQGTKVEI K | ADI-41271 | Light chain variable region ("LC") amino acid sequence |
| Ab 591 | 1181 | EVQLLESGGDLVRPGGSLRLSCTASGFSFSSSEMNWVRQAPGKGLEWVASINSGG DDIYYADSVKGRFTISRDNAKNSLSLQMDSLRAEDTALYYCARSRSGYSSGWSRFF GNWGQGTLVTVSS | ADI-41273 | Heavy chain variable region ("HC") amino acid sequence |
| Ab 591 | 1182 | QSALTQPRSVSGSPGQSVTISCTGTISDIGAYNYVSWYQQHPGKAPKVMIYDVSKR PSGVPDRFSGSKSGFTASLTISGLQAEDEADYYCCSYAGRWVFGGGTKLTVL | ADI-41273 | Light chain variable region ("LC") amino acid sequence |
| Ab 592 | 1183 | EVQLVESGGGLVKPGGSLRLSCAASGFSFSSYAMNWVRQAPGKGLQWVSSISAGS SYIDYADSVKGRFTISRDNAENSLFLQMNSLRVEDTAVYYCARVGSYTHGYEFDYW GQGTLVTVSS | ADI-41274 | Heavy chain variable region ("HC") amino acid sequence |
| Ab 592 | 1184 | QPVLTQPPSVSGAPGQRVTISCTGSNSNIGAGYDVHWYQQLPGTAPKLLIYASTIR PSGVPDRFSGSKSGTSASLAITGLQAEDEADYYCQSYDRNLSVVFGGGTKVTVL | ADI-41274 | Light chain variable region ("LC") amino acid sequence |

TABLE 5-continued

| Antibody No. | SEQ ID NO: | Sequence | Clone # (ADI) | Descriptors |
|---|---|---|---|---|
| Ab 593 | 1185 | EVQLVESGGGLVKPGGSLRLSCAASGFMFSTYSMNWVRQAPGKGLEWVSFITGSS SDKYYAHSVKGRFTISRDNAKRTLYLQLNSLRAEDTAVYYCARFRGLYCDGDCSS RGNTYYNYYGMDVWGQGTTVTVSS | ADI-41275 | Heavy chain variable region ("HC") amino acid sequence |
| Ab 593 | 1186 | EIVMTQSPLSLSVIPGEPASISCRSSKSLLHSNGYTYLDWYLQKPGQSPQLLIHLG SNRASGVPDRFSGSGSGTDFTLKISRVEAEDVGVFYCMQALQAPPTFGPGTKVEIK | ADI-41275 | Light chain variable region ("LC") amino acid sequence |
| Ab 594 | 1187 | EVQLVESGGGLVQPGRSLRLSCRASGFTFRNYAMSWVRQAPGKGLEWVGFIRGK GYGGTTEYAASVKGRFTISSDDSRSIAYLQMNSLKTEDTAVYYCTRVREDGVIAVA EYYFDYWGQGTLVTVSS | ADI-41276 | Heavy chain variable region ("HC") amino acid sequence |
| Ab 594 | 1188 | GIQMTQSPGTLSLSPGERATLSCRASQSVSSSYLAWYQQKPGQAPRLLIHGASSRA TGIPDRFSGSGSGTDFTLTISRLEPEDFAVYHCQQYGSSPWTFGQGTKVEIK | ADI-41276 | Light chain variable region ("LC") amino acid sequence |
| Ab 595 | 1189 | QVQLQESGPGLVKPSGTLSLTCAVSGGSITGRNWWSWVRQPPGKELERIGEIYHG GSTEYNPSLKGRVTISVDKSKNQFSLRLNSVTAADTAVYYCARVAHYDSNGYYIGY FDLWGRGTLVTVSS | ADI-41277 | Heavy chain variable region ("HC") amino acid sequence |
| Ab 595 | 1190 | EIVLTQSPPSLSASVGDRVTITCRASQSISIYLNWYQQKPGKAPKLLIFAASSLQS GVPLRFSGSGSGTDFTLTISSLQPEDFATYYCHQSYSAPWTFGQGTKVDIK | ADI-41277 | Light chain variable region ("LC") amino acid sequence |
| Ab 596 | 1191 | EVQLVESGPALVKPTQTLTLTCTFSGFSLSTKRMGVSWIRQPPGKALEWLARIDWD DDKFYSTSLKTRLTISKDTSKNQVVLTLANMDPVDTATYFCARTTVYASGGYYLYY LDYWGQGTLVTVSS | ADI-41278 | Heavy chain variable region ("HC") amino acid sequence |
| Ab 596 | 1192 | DIVMTQTPSSLSASVGDRVTLTCRASQRIASYVNWYHQKPGKAPNLLIYAASNLQS GVPSRFSGSGSGTDFTLTISSLQPEDFATYYCQQSYSTPLTFGQGTKLEIK | ADI-41278 | Light chain variable region ("LC") amino acid sequence |
| Ab 597 | 1193 | QVQLVQSGAEVKKAGETLKISCRGPAHTFTSFWIGWVRQTPGKGLEWMGNIYPG DTDTTYSPSFRGQVTISADKSISTAYLQWNSLKASDTAIYYCATRVRHGYSSSGSF ESWGQGTMVTVSS | ADI-41279 | Heavy chain variable region ("HC") amino acid sequence |
| Ab 597 | 1194 | QSVVTQPPSVSGAPGQRITISCTGSNSNTGAGYDVHWYQQLPGAAPKLLIFANNN RPSGVPDRFSGSKSGTSASLAITGLQAEDEADYYCQSYDNSLSAYVFGTGTKLTVL | ADI-41279 | Light chain variable region ("LC") amino acid sequence |
| Ab 598 | 1195 | QVQLVESGPGLVKPSETLALTCTVSGGSLSTYYWSWIRQPPGKGLEWIGYIYYSGT TYYNPSLKSRVTISEDRSKNQFSLKLTSVTAADTAVYYCARHGPKTEFWSAQYYLE LWGRGTLVTVSS | ADI-41280 | Heavy chain variable region ("HC") amino acid sequence |
| Ab 598 | 1196 | EIVLTQSPGTLSLSPGERATLSCRASQSVSSDYLAWYQQKPGQAPSLLIYGVSTRAT GIPDRISGSGSGTDFTLTISRLEPEDFAVYYCHQYGTSPWTFGQGTKVEIK | ADI-41280 | Light chain variable region ("LC") amino acid sequence |
| Ab 599 | 1197 | QVQLVQSGAEVKKPGASVKVSCKASGYSFTNHGIHWVRQAPGQRLEWMGWINV ANGFTAYSQNLQGRVTFTRDTSASTAYLELTSLRSEDTAVYHCARDESYCSAGYCYL YFDYWGQGTTVTVSS | ADI-41281 | Heavy chain variable region ("HC") amino acid sequence |
| Ab 599 | 1198 | DIQVTQSPSSLSASVGDRVTITCRASQNIITYVNWYQQKPGKAPELLIFGASSVQSG VPSRFSGSGSGTDFTLTISSLRPDDFATYYCQQSYSNPRTFGGGTKVEIK | ADI-41281 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 600 | 1199 | QVQLVQSGGGVVQPGRSLRLSCAASGFMFTIYSMHWVRQAPGKGLEWVAVISN DGVNKYYSDSVKGRFTISRDNSKNTLYLQMNNLRAEDTAVYYCASDIVVLVTATDY WGQGTLVTVSS | ADI-41282 | Heavy chain variable region ("HC") amino acid sequence |
| Ab 600 | 1200 | ETTLTQSPVTLSLSPGERATLSCRTSQSFSSPLLAWYQQKPGQAPRLLIYGASNRAT GIPDRFSGSGSGTDFTLTISRLEPVDFAVYYCQQYGSSPYTFGQGTKLEIK | ADI-41282 | Light chain variable region ("LC") amino acid sequence |
| Ab 601 | 1201 | QVTLKESGPTLVKPTQTLTLTCTFSGFSLSTFGVAVGWIRQPPGKALEWLALIYWDD DKRYSPSLKSRLTITKDISKNQVVLTMTNMDPVDTATYYCAHRLRSLTARGVFDIWG QGTTVTVSS | ADI-41283 | Heavy chain variable region ("HC") amino acid sequence |
| Ab 601 | 1202 | DIRLTQSPSSLSASVGDRVTITCRASQSINNFLNWYQQRPGKAPTLLIYSASSLQSG VPSRFSGSGSGTDFTLTISSLQPEDFATYFCQQTDSFPWTFGQGTKVEIK | ADI-41283 | Light chain variable region ("LC") amino acid sequence |
| Ab 602 | 1203 | QVQLVQSGGGLVKPGGSLRLSCAASGFTFSNAWMSWVRQAPGKGLEWVGRIKSE VDGGTADYAANVKGRLTISRDDSKNMMYLQMNSLKTEDTAVYYCTTDPGVGWIF GEVKLFRTDPEYWGQGTLVTVSS | ADI-41284 | Heavy chain variable region ("HC") amino acid sequence |
| Ab 602 | 1204 | QSVLTQPPSVSAAPGQKVTISCSGSSSNIGNHYVSWYQQLPGTSPKLLIYDNNKRPS GIPDRFSGSKSGTSATLGITGLQPGDEADYYCGTWDSSLSAVRVFGGGTKVTVL | ADI-41284 | Light chain variable region ("LC") amino acid sequence |
| Ab 603 | 1205 | QVQLVQSGAEVKKPGSSVKVSCKASGGTFSYYAISWVRQAPGQGLEWMGGIIPIL GTVKNAQKFQGRVTITADKITSIAYMELSSLRHEDTAVYYCARDYYDSSGYYYNGYG MDVWGQGTTVTVSS | ADI-41285 | Heavy chain variable region ("HC") amino acid sequence |
| Ab 603 | 1206 | QSVLIQPPSASGTPGQRVTISCSGSSSNIGSNYVYWYQQLPGTAPKLLIYRNDQRPS GVPDRFSGSKSGTSASLAISGLRSGDEADYYCAAWDDSLGGPIWVFGGGTKLTVL | ADI-41285 | Light chain variable region ("LC") amino acid sequence |
| Ab 604 | 1207 | QVQLVQSGAEVKKPGASVKVSCKASGYTFISYGISWVRQAPGQGPEWMGWISTH NGNTNYAQKLQGRVTMTTDTSTSTAYMELRSLRSDDTAVYYCARDERSIAVEVYLG STFDIWGQGTMVTVSS | ADI-41286 | Heavy chain variable region ("HC") amino acid sequence |
| Ab 604 | 1208 | DIQVTQSPSSVSASVGDRVTITCRASQGISSWLAWYQQKPGKAPKLLIYAASTLQSG VPSRFSGSGSGTDFTLTISRLQPEDFATYYCQQANIFGVTFGPGTKVDIK | ADI-41286 | Light chain variable region ("LC") amino acid sequence |
| Ab 605 | 1209 | EVQLVESGGGLVQPGRSLRLSCAASGFTFDDYAMHWVRQAPGKGLEWVSSISWH SADIGYAASVEGRFTISRDNAKNSLFLQMNSLRPEDTALYYCAKEIVSTSWYSGYFQ DWGQGTLVTVSS | ADI-41287 | Heavy chain variable region ("HC") amino acid sequence |
| Ab 605 | 1210 | QPVLTQPRSVSGSPGQSVTISCTGTSSDVGDYNYVSWYQQHPGKAPKLMIYDVSK RPSGVPDRFSGSKSGNTASLTISGLQGEDEADYYCCSYAGRHTFVFGTATKVTVL | ADI-41287 | Light chain variable region ("LC") amino acid sequence |
| Ab 606 | 1211 | EVQLVESGGGLVQPGGSLRLSCAASGFTFSSYAMSWVRQAAGKGLEWVSAISGSG DDTFYADSVKDRFIISRDSSKRKVYLQMNSLRVEDTAVYYCAKTDIMVTFGGVVVD AYYFDHWGQGTLVTVSS | ADI-41288 | Heavy chain variable region ("HC") amino acid sequence |
| Ab 606 | 1212 | ETTLTQSPGTLSLSPGERATLSCRASQFVFRSYLAWYQQRPGQPPRLLIYGASSRA TGIPDRFSGRGSGTEFTLTISRLEPEDFAMYYCQHYDSSPPGTFGGGTKVEIK | ADI-41288 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 607 | 1213 | EVQLVQSGAEVKKPGESLKISCKGSGYSFSSFWIGWVRQMPGKGLEWMGIIYPGD SDTRYSPSFQGQVTISADQSIRTAYLQWNSLKASDTGLYYCAKGGLGDVEMATIAV WGQGTLVTVSS | ADI-41289 | Heavy chain variable region ("HC") amino acid sequence |
| Ab 607 | 1214 | QSVLIQPASVSGSPGQSITIPCTGTSSDVGSYNLVSWYQHHPGKAPKLIISEGSKR PLGVSNRFSGSKSGNTASLTISGLQAEDEADYYCSSYVRSRTFNYVFGTGTKLTVL | ADI-41289 | Light chain variable region ("LC") amino acid sequence |
| Ab 608 | 1215 | QVQLQQWGAGLLKPSETLSLTCVVYGESFSDSGYYWTWIRQPPEKGLEWIGEINH GGSTSYNPSLKSRVTISVDTSENQFSLKVTSVTGADTAVYYCARLRLGCSGGSCYS RFDYWGQGTLVTVSS | ADI-41291 | Heavy chain variable region ("HC") amino acid sequence |
| Ab 608 | 1216 | DIQLTQSPSSLSASVGDRVTITCRASQSINSYLNWYQQKPGKAPVLLIHAASSLQG GVPSRFSGSGSGTDFTLTISSLQPEDFATYYCQQSYNTRWTFGHGTKVDIK | ADI-41291 | Light chain variable region ("LC") amino acid sequence |
| Ab 609 | 1217 | EVQLLESGGGVVQPGRSLRLSCAASGFSFSSYGIHWVRQAPGKGLECVALMSYDGS EKYYADSVKGRFTISRDNSKNTLYLHMNSLRREDTAVYYCAKGSHLRWSHLDYYFH LWGRGTLVTVSS | ADI-41292 | Heavy chain variable region ("HC") amino acid sequence |
| Ab 609 | 1218 | DIVMTQSPSTLSASVGDRVTITCRASQSLSTWLAWYQQKPGKAPKLLISDASNLES GVPSRFSGRGSGTEFTLTISGLQPDDFATYYCQQERTFGQGTKVDIK | ADI-41292 | Light chain variable region ("LC") amino acid sequence |
| Ab 610 | 1219 | QVQLQQSGPGLAKPSQTLSLTCTVSGGPISGVDYYWSWIRQPPGKGLEWIGYIYYS GSTYYNPSLKSRVTISVDTSKKQFSLKMSSVTAADTAVYYCARDVGATPYYYYGMD VWGQGTTVTVSS | ADI-41293 | Heavy chain variable region ("HC") amino acid sequence |
| Ab 610 | 1220 | DIVLTQSPDTLSLSPGERATLSCRASQSVRSNYLAWYQHKPGQAPRLLIYGASSRVA GIPDRFSGSGSGTDFTLTISRLEPEDFAVYYCQQYGSSPPSVTFGGGTKVEIK | ADI-41293 | Light chain variable region ("LC") amino acid sequence |
| Ab 611 | 1221 | EVQLLESGGGLVQPGGSLRLSCAASGFTFSAYEMNWVRQAPGKGLEWVSYISSSG SNKHYADSVKGRFTISRDNAKNSLHLHMNSLRAEDTALYYCTRPHQEEWELLPNDA FDLWGQGTMVTVSS | ADI-41294 | Heavy chain variable region ("HC") amino acid sequence |
| Ab 611 | 1222 | QSALTQPPSASGSPGQSVTISCTGTSTDVGAYTYVSWYQQHPGKAPKLIIYEVYKRP SGVPNRFFGSKSGNTASLTVSGLQAEDEADYYCSSYGGSNNFGLFGGGTKLIVL | ADI-41294 | Light chain variable region ("LC") amino acid sequence |
| Ab 612 | 1223 | EVQLVESGVEVKKPGESLKISCRGSGYTFYNYWIAWVRQKPGKGLEYMGTIYLDDS ETIYSPSFQGEVTISADKSINTAYLQWNSLKASDTANYYCARQMDFYFDVWGRGTL VTVSS | ADI-41296 | Heavy chain variable region ("HC") amino acid sequence |
| Ab 612 | 1224 | SYELMQPPSVSVSPGQTARITCSGDPLPRESAYWYQQKPGQAPVVIIFNDIERPLGI PERFSGSRSGTTVTLTISGAQAEDEADYYCQSADSRKTFVFGTGTKLTVL | ADI-41296 | Light chain variable region ("LC") amino acid sequence |
| Ab 613 | 1225 | QVQLVQSGAEVKKPGSSVKVSCKASGGTFSTDAISWVRQAPGQGLEWMGGIIPLF GTANYAQKFQGRVTITADESTSTAYMELNSLRSVDTAVYYCGRTGAFDGEVVVRP HLDLWGQGTLVTVSS | ADI-41297 | Heavy chain variable region ("HC") amino acid sequence |
| Ab 613 | 1226 | QPVLTQPASVSGSPGQSITISCTGTSSDVGGYDYVSWYQHHPGKAPKLMIYEVSNR PSGVSNRFSGSKSGNTASLTISGLQADDEAAYYCSSYTRSNTLLFGGGTKLTVL | ADI-41297 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 614 | 1227 | EVQLVESGGGLVHPGRSLRLSCGASGFTFRSFAMHWVRQAPGKGLEWVAVISYD GSDEYYADSVKGRFTISRDNSRNTLFLQMNRLRPEDTAIYYCARAYCSTSNCPVLD YWGQGTLVTVSS | ADI-41299 | Heavy chain variable region ("HC") amino acid sequence |
| Ab 614 | 1228 | QSVLIQPASVSGSPGQSITISCTGTSSDVGGYSLVSWYQQHPGKAPKLIIFEGNKR PAGVSDRFSGSKYGDTASLTISGLQAEDEADYYCCSYAGGHSVFGGGTKVTVL | ADI-41299 | Light chain variable region ("LC") amino acid sequence |
| Ab 615 | 1229 | QVQLVESGGGVVQPGRSLRLSCAASGFTFSSYAMQWVRQAPGKGLEWVAVMTN DGDDKYYADSVRGRFTISRDNSKNTLYLQMNNLRPEDTAVYYCARDLFEWWELLG YCYAMDVWGQGTTVTVSS | ADI-41302 | Heavy chain variable region ("HC") amino acid sequence |
| Ab 615 | 1230 | QSVLTQPPSASGSPGQSVTISCTGTSSDVGAYNYVSWYQQHPGKAPKLIIYEVYKR PSGVPDRFFGSKSGNTASLTVSGLQAEDEADYYCSSYAGSNTLGVFGGGTKVTVL | ADI-41302 | Light chain variable region ("LC") amino acid sequence |
| Ab 616 | 1231 | QVQLVQSGGGLVRPGGSLRVSCAASGFIFNNYALTWVRQAPGKGLEWVSAISGSG SSTYYADSVKGRFTISRENSNNRLYLQLSGLRAEDTAVYFCARVRGLVWFEGRIDP YPNVFDYWGQGTLVTVSS | ADI-41303 | Heavy chain variable region ("HC") amino acid sequence |
| Ab 616 | 1232 | DIVLTQSPGTLSLSPGERATLSCRASQSVSNDYLAWYQQKPGQAPRLLIYDASSRA IGIPDRFSGSGSGTDFTLIISRLEPEDFAVYYCHHPGKFGQGTKVEIK | ADI-41303 | Light chain variable region ("LC") amino acid sequence |
| Ab 617 | 1233 | EVQLVESGPGLVKPSQTLSLTCTVSGGSIRSHDYYWSWIRQPPGKGLEWIGYSYYS GSTYYNPSLKSRVIISLDTSKNQFSLNLTSVTAADTAMYYCARDRPHTSSWIPGWF DPWGQGTLVTVSS | ADI-41304 | Heavy chain variable region ("HC") amino acid sequence |
| Ab 617 | 1234 | SYELTQPPSASGTPGQRVTISCSGSSSNIGSNTVSWYQQFPGKAPKLLIYSNNERP SGGPDRFSGSKSGTSASLAIGGLQSEDEANYYCAAWDDSLYAVVFGGGTKLTVL | ADI-41304 | Light chain variable region ("LC") amino acid sequence |
| Ab 618 | 1235 | QVTLKESGPGLVKPSQTLSLTCTVSGGSISGGGYYWSWIRQLPGKGLQWIGCIYDS GTTYYNPSLKSLVTISIDTSKNQFSLKLSSVTAADTAVYYCARGGSLDDFWSATWY FALWGRGTLVTVSS | ADI-41305 | Heavy chain variable region ("HC") amino acid sequence |
| Ab 618 | 1236 | EIVLTQSPGTLSLSPGERATLSCRASQSVSSNYLAWYQQKPGQAPRLLIYGASSRA TGIPDRFSGSGSGTDFTLTISRLEPEDFAFYYCQQYGRSPYTFGPGTKLEIK | ADI-41305 | Light chain variable region ("LC") amino acid sequence |
| Ab 619 | 1237 | QVQLVESGPRLVKPSQTLSLTCTVSGGSIYRGDYDWNWIRQPPGKGLEWIGYISYT GNTHYNSSLKSRLSISADTSGTHFSLKLSSVTAADTAIYYCARDVGYGGNAAHYYY YAMDVWGQGTTVTVSS | ADI-41306 | Heavy chain variable region ("HC") amino acid sequence |
| Ab 619 | 1238 | ETTLTQSPATLSLSPGERATLSCRASQSVGSSLAWYQQKVGQAPRLLIYDASSRVT GIPARFSGSGSGTDFTLTISSLEPGDFAVYYCQQRSNSLTFGGGTKVEIK | ADI-41306 | Light chain variable region ("LC") amino acid sequence |
| Ab 620 | 1239 | QVQLVESGGGLVKPGGSLRLSCAASGFPLSPYALNWVRQAPGKGLEWVSSITSSSA YIYYADSVKGRFTVSRDNPTNSLYLQMNSLRAEDTAVYYCARTIPQHYYDNNGDYY NYGMDVWGQGTTVTVSS | ADI-41307 | Heavy chain variable region ("HC") amino acid sequence |
| Ab 620 | 1240 | DIVLTQSPATLSVSPGQRITLSCRASQTVRSNLAWYQQKPGQPPRLLIYGASTRATG VPARFTGSGSGTEFTLTITSLQSDDFAVYYCHQYNDRPLTFGPGTKVEIK | ADI-41307 | Light chain variable region ("LC") amino acid sequence |

TABLE 5-continued

| Anti- body No. | SEQ ID NO: | Sequence | Clone # (ADI) | Descriptors |
|---|---|---|---|---|
| Ab 621 | 1241 | EVQLVESGPGLVKPSQTLSLTCAISGDSVSSNSAAWNWIRQSPSRGLERMGRTYYR SKWYDDYAVSVKSRIIINPDTSKNQFSLQLNSVTPEDTAVYYCARGISTFGGVIYA LEIWGQGTMVTVSS | ADI- 41308 | Heavy chain variable region ("HC") amino acid sequence |
| Ab 621 | 1242 | SYVLTQPASVSGSPGQSITISCTGLTSDVGGYNFVSWYQQHPGKAPKLIIYDVSHR PSGVSNRFSGSESGNTASLTISGLQAEDEAHYYCSSYTRTSIVVFGGGTKLTVL | ADI- 41308 | Light chain variable region ("LC") amino acid sequence |
| Ab 622 | 1243 | EVQLLESGPGLVKPSQTLSLTCTVSGGSISSGDYYWSWVRQPPGKGLEWIGNIYHS GSTYYKPSLKSRVSISLDTSKNQFSLKLSSVTAADTAIYYCARDGGENYVWGTFRF LDVWGQGTTVTVSS | ADI- 41309 | Heavy chain variable region ("HC") amino acid sequence |
| Ab 622 | 1244 | DIRLTQSPGTLSLSPGERATLSCRASQSVSSSYLAWYQQKPGQAPRLLIYGVSSRA TGIPDRFSGSGSGTDFTLTINRLEPEDFALYHCQQYGSSPHTFGQGTKVEIK | ADI- 41309 | Light chain variable region ("LC") amino acid sequence |
| Ab 623 | 1245 | QVQLVQSGVEVKKPGESLKISCRGSGYSFYNYWIAWVRQKPGKGLEYMGTIYLDDS DTIYSPSFQGEVTISADKSINTAYLQWNSLKASDTANYYCARQMDFYFDVWGRGTL VTVSS | ADI- 41310 | Heavy chain variable region ("HC") amino acid sequence |
| Ab 623 | 1246 | SYELTQPPSVSVSPGQTARITCSGDPLPRESAYWYQQKPGQAPVVVIFNDIERPLGI PGRFSGSRSGATATLTINGAQAEDEADYYCQSADSRKTFVFGAGTKLTVL | ADI- 41310 | Light chain variable region ("LC") amino acid sequence |
| Ab 624 | 1247 | QVTLKQSGPALVKPTQTLTLTCTFSGFSLSTKRMGVSWIRQPPGKALEWLARIDWD DDKYYSTSLRTRLTISKDTSKNQVVLTMTDMDPVDTATYYCARIQPYTSGGYYSYY FDYWGQGTLVTVSS | ADI- 41311 | Heavy chain variable region ("HC") amino acid sequence |
| Ab 624 | 1248 | DIQVTQSPSSLSASIGDRVTITCRASQTIASYLNWYQQKPGKAPKLLIYIASSLQS GVPSRFSGSGSGTDFTLTISTLQPEDFATYYCQQSYGTPWTFGQGTKVEIK | ADI- 41311 | Light chain variable region ("LC") amino acid sequence |
| Ab 625 | 1249 | QVQLQESGPGLVKPSGTLSLTCAVSGGSISSSNWWNWVRQPPGKGLEWIGEIYHS GRTNYNPSLKSRVSISIDKFKSQFSLNLNSVTAADTAVYYCARDLPGTPYDIVPGY YPGLRRHDAFDIWGQGTMVTVSS | ADI- 41312 | Heavy chain variable region ("HC") amino acid sequence |
| Ab 625 | 1250 | QSVLTQPPSASGTPGQRVTMSCSGSSSNIGSDTVNWYQQLPGTAPKLLIYSNNQR PSGVPDRFSGSKSGTSASLAISGLQSEDEADYYCAAWDDSLNGWVFGGGTKLTVL | ADI- 41312 | Light chain variable region ("LC") amino acid sequence |
| Ab 626 | 1251 | EVQLVESGAEVKKPGASVKVSCKASGYTFNNYDISWVRQAPGQGLEWMGWISTY NGNTNYAQKFQGRATMTTDTSTTTAYMELRSLRSDDSAIYYCARVYCGGDCHNPF FLYFDLWGRGTLVTVSS | ADI- 41313 | Heavy chain variable region ("HC") amino acid sequence |
| Ab 626 | 1252 | SYVLTQPLSVSVALGQTARITCGGNNIGSKSVHWYQQKPGQAPLLVIYRDNNRPSG IPERFSGSTSGNTATLTISRAQAGDEADYSCQVWDNSDWVFGGGTKLTVL | ADI- 41313 | Light chain variable region ("LC") amino acid sequence |
| Ab 627 | 1253 | QVQLVQSGAEVKKPGSSVKVSCKAFGGIFSSYAISWVRQAPGQGLEWMGGIIPIFG TTKYAQKFQGRVTITADKSTSTVYMEVSSLRFEESAVYFCARAYCSGGTWYGGADY WGQGTLVTVSS | ADI- 41314 | Heavy chain variable region ("HC") amino acid sequence |
| Ab 627 | 1254 | QSVLTQPPSVSVSPGQTARITCSGDVLPKQYAYWYQQKPGQAPLLVMYKDTERPS GIPERFSGSSSVTAVTLTISGVQAEDEADYYCQSADSTQELFGGGTKLTVL | ADI- 41314 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 628 | 1255 | EVQLLESGPGLVKPSETLSLTCAVSGGSISNYYWSWIRQPPGKGLEWIAYISYSGT TNYNPSLESRVTISVDTSKNQFSLKLNSVTAADTAVYYCARHEFLVLPDVWGQGTL VTVSS | ADI-41315 | Heavy chain variable region ("HC") amino acid sequence |
| Ab 628 | 1256 | ETTLTQSPGTLSLSPGERATLSCRASQSVSSTFLAWYQQKPGQAPRLLIYAASSRAT GIPDRFSGSGSGTDFTLIISRLEPEDFAVYYCQQYRSSPFSFGPGTKVEIK | ADI-41315 | Light chain variable region ("LC") amino acid sequence |
| Ab 629 | 1257 | QVQLVQSGGGVVQPGRSLRLSCAASGFTFNNYGMHWVRQAPGKGLEWVAVLSF DGINKYYADSARGRFTISRDNSKNTLYLQMNSLRAEDTALYYCAKDRQEYSSGWTH DACDIWGQGTMVTVSS | ADI-41316 | Heavy chain variable region ("HC") amino acid sequence |
| Ab 629 | 1258 | EIVMTQSPATLSVSPGERATLSCRASQNVNNNLAWYQQNPGQAPRLLIFGASTRA TGIPARFSGSGSGTEFTLTISSLQSEDFAVYYCQQYNNWPRTFGQGTKLEIK | ADI-41316 | Light chain variable region ("LC") amino acid sequence |
| Ab 630 | 1259 | EVQLVESGGGLVQPGGSLRLSCEASRFKFSTFWMAWVRQAPGKGLEWVANIKQD GSETYYLDSVKGRFTISRDNAKNSLFLQMKSLRAEDTAVYYCAGLWWGDLENWFD PWGQGTLVTVSS | ADI-41317 | Heavy chain variable region ("HC") amino acid sequence |
| Ab 630 | 1260 | QSVLTQPPSVSGAPGQRVTISCTGSSSNLGTGFDVHWYRQLPGTAPQLLIYGSTNR PSGVPDRFSGSKYGTSASLAITGLQAEDEADYYCQSYDSNLRAYVFGTVTKVTVL | ADI-41317 | Light chain variable region ("LC") amino acid sequence |
| Ab 631 | 1261 | EVQLLESGAEVKKPGSSVRVSCKAFGGTFSSYAFSWVRQAPGQGLEWMGGITPM FGTENYAPNFQGRVTITADKLTTTVYMELSRLRSEDSAVYYCAREGGRLGTTMGAF DMWGQGTMVTVSS | ADI-41318 | Heavy chain variable region ("HC") amino acid sequence |
| Ab 631 | 1262 | DIRLTQSPSSLSASVGDRVTITCRASHGISSALAWYQQRPGRVPQVLIFHASTLES GVPSRFSGSGSGTDFTLTISSLQPEDFATYYCQQFNSYPYTFGQGTKVEIK | ADI-41318 | Light chain variable region ("LC") amino acid sequence |
| Ab 632 | 1263 | QVQLQESGPGLVKPSQTLSLTCTVSGGSISSGDYYWSWIRQPPGKGLEWIGYIFYSG TTYYNPSLKSRVTISLDTSQNQFSLKLSSVTAADTAVYYCARDGDEVDYVWGTRRYL DSWGRGTLVTVSS | ADI-41319 | Heavy chain variable region ("HC") amino acid sequence |
| Ab 632 | 1264 | EIVLTQSPGTLSLSPGERATLSCRASQSVSSRYLAWYQQKPGQAPRLLIHGASSRAT GIPDRFSGSGSGTDFTLTISRLEPEDFAVYYCLQYGSLPKTFGQGTKVEIK | ADI-41319 | Light chain variable region ("LC") amino acid sequence |
| Ab 633 | 1265 | QVQLVQSGVEVKKPGESLKISCRGFGYSAYNYWIAWVRQKPGKGLEYMGTIYLDD SDTIYSPSFQGEVTISADRSINTAYLQWNSLKASDTANYYCARQMDFYFDVWGRGT LVTVSS | ADI-41320 | Heavy chain variable region ("HC") amino acid sequence |
| Ab 633 | 1266 | QSVLTQPPSVSVSPGQTARITCSGDPLPRESAYWYQQKPGQAPVVVIFNDIERPLGI PARFSGSRSGTTVTLTISGAQAEDEADYYCQSADSRKTFVFGPGTKLTVL | ADI-41320 | Light chain variable region ("LC") amino acid sequence |
| Ab 634 | 1267 | QVQLVQSGAEVKKPGSSVRVSCKASGGSFSSYATSWVRQAPGQGLEWMGGIIPM YDAVNYAQKFQGRVTITADESTTTAYMELSSLRSEDTAVYYCARSSGYTGTNFFDY WGQGTLVTVSS | ADI-41322 | Heavy chain variable region ("HC") amino acid sequence |
| Ab 634 | 1268 | DIQMTQSPSSVSASVGDRVTITCRASQDISSWLAWYQQKPGKAPKLLIYTASSLQSG VPSRFSGSGSGTDFTLTISRLQPEDFATYYCQQANSFPRVTFGGGTKVEIK | ADI-41322 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 635 | 1269 | EVQLLESGGGVVRPGGSLRLSCAASGFTFDDYAMGWVRQAPGKGLEWVSGITW NAGSTAYAGSVKGRFTISRDNAKNSLFLQMNSLRAEDTAFYLCARHVDSSGPVARH FDYWGQGTLVTVSS | ADI-41323 | Heavy chain variable region ("HC") amino acid sequence |
| Ab 635 | 1270 | NFMLTQPHSVSESPGKTVTISCTRSSGSIARNYVQWYQQRPGSAPTIVIYEDNQRPS GVPDRFSGSIDSSSNSASLTISGLKTEDEADYYCQSYDPSNVVFGGGTKLTVL | ADI-41323 | Light chain variable region ("LC") amino acid sequence |
| Ab 636 | 1271 | EVQLVESGGGLVQPGGSLRLSCAASGFTVSNNYMRWVRQAPGKGLEWVSVIYSS GSTDYADSVKGRFTISRDNSKNTLYLQMNSLRAEDTAVYYCARERTLFYYDSSGFFD YWGQGTLVTVSS | ADI-41324 | Heavy chain variable region ("HC") amino acid sequence |
| Ab 636 | 1272 | ETTLTQSPGTLSLSPGERATLSCRASQSVDSSYLAWYQQKPGQAPRLLIYGASNRAT GIPDRFSGSGSGTDFTLTISRLEPEDFAVYYCQQYGRSLTFGGGTKLEIK | ADI-41324 | Light chain variable region ("LC") amino acid sequence |
| Ab 637 | 1273 | QVQLVQSGAEVKTPGSSVKVSCKASGGTFRSYPITWVRQAPGQGLEWMGTVIPVF DTVNYAPKFQGRVSITADESTNTAYMELSSLRSDDSAVYYCARDLGWLRPMTTVTS PHFDYWGQGTLVTVSS | ADI-41340 | Heavy chain variable region ("HC") amino acid sequence |
| Ab 637 | 1274 | QSVLTQPASVSGSPGQSITISCTGTSSDVGGYDFVSWYQQHPGKAPKLMISEVTDR PSGVSNRFSGSKSGNTASLTISGLQAEDEADYYCTSYTSSRTYVFGTGTKLTVL | ADI-41340 | Light chain variable region ("LC") amino acid sequence |
| Ab 638 | 1275 | QVQLVQSGAEVKKPGSSVKVSCKASGGTFSSYATHWVRQAPGQGLEWMGGIIPIF GRATYAQKFQGRVTISADESTSTAYMELSSLRSEDTAVYYCARGRDDRSGDHIAFLY HYGMDVWGQGSTVTVSS | ADI-41341 | Heavy chain variable region ("HC") amino acid sequence |
| Ab 638 | 1276 | QSVLTQPPSVSAAPGQKVSISCSGSSSNIGINHASWYQHLPGTAPKLLIYDNNKRPS GIPDRFSGSKSGTSATLGISGLQTGDEAAYYCGTWDTGLSAVVFGGGTKLTVL | ADI-41341 | Light chain variable region ("LC") amino acid sequence |
| Ab 639 | 1277 | QVQLVQSGAEVKKPGSSVKVSCKASGGTLTSYGVSWVRQAPGQGLEWMGGIIPIF GTVDYAQKFQGRVTITADEPTSTAYMELSSLTSDDTAVYYCARDPWVSGPVEFYYY FDVWGRGTLVTVSS | ADI-41342 | Heavy chain variable region ("HC") amino acid sequence |
| Ab 639 | 1278 | DIVLTESPATLSLSPGERATLSCRASQSINNRYLAWYQQKPGQAPRLLIFGASSRAT GIPDRFSGSGSGTDFTLTISRLEPEDFAVYYCQQYGSTPPTFGQGTKVEIK | ADI-41342 | Light chain variable region ("LC") amino acid sequence |
| Ab 640 | 1279 | EVQLVESGGGLVKPGGSLRLSCAASGFTFSSYYMNWVRQAPGKGLEWVSSISGGS SYISYADSVKGRFTISRDNAKNSLYLQMNSLRAEDTAVYYCARVDTPMVRGYYFDY WGQGTLVTVSS | ADI-41343 | Heavy chain variable region ("HC") amino acid sequence |
| Ab 640 | 1280 | QSVLTQPPSVSGAPGRRVTISCTGSSSNIGAGYDVHWYQQLPGTAPKLLIFANSNRP SGVPDRFSGSKSGTSASLAITGLQAEDEADYYCQSYDSSLSGSVFGGGTKVTVL | ADI-41343 | Light chain variable region ("LC") amino acid sequence |
| Ab 641 | 1281 | EVQLVESGGGLVKPGGSLRLSCAASGSSFSSYYMNWVRQAPGKGLEWVSSISSSST YIDYADSVKGRFTISRDNAKNSLFLQMNSLRAEDTAVYYCARVSSPMIRGYYLDYW GQGTLVTVSS | ADI-41344 | Heavy chain variable region ("HC") amino acid sequence |
| Ab 641 | 1282 | QPVLTQPPSVSGAPGQRVTISCTGSSSNIGAGYDVHWYQQLPGTAPKLVIHGNSN RPSGVPDRFSGSKSGTSASLAITGLQGEDEADYYCQSYDSSLSGSVFGGGTKLTVL | ADI-41344 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 642 | 1283 | EVQLVQSGAEVRKPGESLKISCKGSGYNFASYWIAWVRQMPGKGLEWMGIIFPGD SDTRYSPSFQGQVTISVDKSISTAYLQWSSLKASDTAIYYCATSKYTFGYLDWGQ GTLVTVSS | ADI-41345 | Heavy chain variable region ("HC") amino acid sequence |
| Ab 642 | 1284 | NFMLTQPHSVSESPGKTVTISCTRSSGSIASNYVQWYQQRPGSAPTTVIYEDNQRP SGVPDRFSGSIDSSSNSASLTISGLKTEDEADYYCQSYDTSNQVFGTGTKVTVL | ADI-41345 | Light chain variable region ("LC") amino acid sequence |
| Ab 643 | 1285 | QVQLVQSGPEVKKPGESLKISCTLSASGLTTYWIGWVRQMPAKGLEWMGIIFPGD SDTRYSPSFQGQVTISADKSTNTAYLQWSGLKASDTAIYYCATLQTPVTGLDQWGQ GTLVTVSS | ADI-41346 | Heavy chain variable region ("HC") amino acid sequence |
| Ab 643 | 1286 | NFMLTQPHSVSESPGKTVTISCTRSSGNIARSYVQWYQQRPGSAPTTVIHEDDQRP SGVPDRFSGSIDTSSNSASLTISGLKTEDEADYYCQSYDPSNYVFGTGTKVTVL | ADI-41346 | Light chain variable region ("LC") amino acid sequence |
| Ab 644 | 1287 | EVQLVESGPGLVKPSGTLSLTCAVSGGSVSSDNWWSWVRQPPGKGIEWIGEIYPS GGTNYNPSLNSRVTISVDKSKNQFSLKLNSVTAADTAIYYCARAPFDSSGYHSNSV WGQGTLVTVSS | ADI-41347 | Heavy chain variable region ("HC") amino acid sequence |
| Ab 644 | 1288 | ETTLTQSPLSLPVTPGEPASISCRSSQSLLHSNGHNYLDWYVQKPGQSPQLLIYLS SNRASGVPDRFSGSGSGTDFTLRISRVEAEDVGVYYCMQPLQTPQTFGQGTKVEIK | ADI-41347 | Light chain variable region ("LC") amino acid sequence |
| Ab 645 | 1289 | QVQLQESGPGLVKPSQTLSLTCAVSGGSISSGGYYWSWIRQHPGKGLEWIGYIYYS GSTYYNPSLKSPVTISVDTSKNQFSLKLTSVTAADTAVYYCARGDYYFDGSGRTTA AFDIWGQGTMVTVSS | ADI-41348 | Heavy chain variable region ("HC") amino acid sequence |
| Ab 645 | 1290 | DIQVTQSPSSLSASVGDRVTITCRASQSISTFLNWYQQKPGRAPKLLIYDASNLQS GVPSRVSGSGSGTDFTLTISSLHPEDFATYYCQQSYTTPYTFGQGTKVDIK | ADI-41348 | Light chain variable region ("LC") amino acid sequence |
| Ab 646 | 1291 | EVQLLESGGGLVQPGRSLRLSCTGSGFTFGDYAMNWVRQAPGKGLEWVGLIRSKD YGGTTEFAASLKGRLTISRDDSKSIAYLQMHSLKTEDSAVYYCTRAHLTDYTDING YQYYFDYWGQGSPVTVSS | ADI-41349 | Heavy chain variable region ("HC") amino acid sequence |
| Ab 646 | 1292 | DIQMTQSPSSLSASVGDRVTITCQASQDISNFLNWYQQRPGKAPKLLIHDASNLET GVPSRFSGSGSGRTEFTFTISSLQPEDIGTYYCQHYDNFPYTFGQGTKVEIK | ADI-41349 | Light chain variable region ("LC") amino acid sequence |
| Ab 647 | 1293 | EVQLVESGAGLVQPGGSLRLSCAASGFTFSTYAVSWVRQAPGKGLEWVSAISGSG ASTYYFADSVKGRFTISRDNSKNTLYLQMNSLRAEDTAVYYCAKARLELRPYYYGMD VWGQGTTVTVSS | ADI-41350 | Heavy chain variable region ("HC") amino acid sequence |
| Ab 647 | 1294 | QPVLTQPASVSGSPGQSITISCTGTSSDVGGYNFVSWYQQHPGKAPKLIIYEVSNRP SGVSNRFSGSKSGNTASLTISGLQAEDEADYYCSSSTLSTTYVFGTGTKVTVL | ADI-41350 | Light chain variable region ("LC") amino acid sequence |
| Ab 648 | 1295 | QVQLVQSGGGLVQPGGSLRLSCSASGFTFSSKSMHWVRQAPGKGLEYVSAIRSDG VSTYYGDSVKGRFTVSRDNAKNTVYLRMSSLRREDTAVYYCVKGPYGDFQYNWFD TWGQGTLVTVSS | ADI-41351 | Heavy chain variable region ("HC") amino acid sequence |
| Ab 648 | 1296 | ETTLTQSPATLSVSPGERATLSCRASQSVSSNLAWYQQKPGQAPRLLIYGASIRAT GIPARFSGSGSGTEFTLTISSLQSEDFAVYYCQQYDNWPPGDTFGQGTKVEIK | ADI-41351 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 649 | 1297 | EVQLVESGGGLVQPGGSLRLSCAASGFTFSSYRMNWVRQAPGKGLEWVSYIDISSS TIYYADSVKGRFTISRDNAKNSLYLQMNSLRAEDTAVYYCARDQLVWEPLIRNHYYY AMDVWGQGTTVTVSS | ADI-41352 | Heavy chain variable region ("HC") amino acid sequence |
| Ab 649 | 1298 | EIVMTQSPDSLAVSLGERATINCKSSQSVLYSSNNKNYLAWYQQKPGQPPKLLIYW ASTRESGVPDRFSGSGSGTDFTLTISSLQAEDVAVYYCQQYYSSPPTFGQGTKVEIK | ADI-41352 | Light chain variable region ("LC") amino acid sequence |
| Ab 650 | 1299 | EVQLVESGVEVKKPGESLKISCRGSGYSFHNYWIAWVRQAPGKGLEYMGTIYVDDS DTIYSPSFQGEVTISADKSINTAYLQWNSLKASDTANYYCARQMDFYFDVWGRGTL VTVSS | ADI-41353 | Heavy chain variable region ("HC") amino acid sequence |
| Ab 650 | 1300 | SYELTQPPSVSVSPGQTARITCSGDPLPRESAYWYQQKPGQAPVVVIFNDIERPLGI PERFSGSRSGTTVTLTISGAQAEDEADYYCQSADSRKTFVFGSGTKLTVL | ADI-41353 | Light chain variable region ("LC") amino acid sequence |
| Ab 651 | 1301 | EVQLLESGGGLVQPGGSLRLSCAASGFTFSSYAMSWVRQAPGKGLEWVSGISGSG GTTYYADSVKGRFTISRDNSKNTLYLQMNSLRAEDTAVYYCAKDSPVNINCGGDCD VAYWGQGTLVTVSS | ADI-41354 | Heavy chain variable region ("HC") amino acid sequence |
| Ab 651 | 1302 | EIVMTQSPSSLSASVGDTVTITCQASQDISYSLNWYQQKPGKAPNLLIFDASHLQTG VPSRFSGGGDGKHFSFTISSLQPEDVATYYCQQYDSLMYTFGQGTKVEIK | ADI-41354 | Light chain variable region ("LC") amino acid sequence |
| Ab 652 | 1303 | EVQLVESGGGLVKPGGSLRLSCTASGFTFSDYYMNWIRQAPGKGLEWVSYISGDG NTIYYTDSVKGRFTISRDNAKNSLFLQMNSLRGEDSAVYYCAGPVRGYTYGIFDYW GQGALVTVSS | ADI-41355 | Heavy chain variable region ("HC") amino acid sequence |
| Ab 652 | 1304 | YYVLTQPPSVSVAPGQAARITCGGNNIGSRSVNWYQQKPGQAPVVVIYGDSVRPS GIPERFSGSNSGNTATLTFSRVEAGDEADYYCQVWETNSDHPVVFGGGTKVTVL | ADI-41355 | Light chain variable region ("LC") amino acid sequence |
| Ab 653 | 1305 | QVQLVQSGAEVKKPGASVKVSCKASGYTFTNYDINWVRQATGQGLEWMGWMN RNNGNTGYARKFQGRVTMTRNTSISTAYMELSSLRSEDTAVYYCARGGDFYAMDV WGQGTTVTVSS | ADI-41356 | Heavy chain variable region ("HC") amino acid sequence |
| Ab 653 | 1306 | SYELTQPPSVSVSPGQTASITCSGDKLGDKYASWYQQKPGQSPVLVIYQDTKRPSG VPERFSGSNSGNTATLTISGTQAVDEADYYCQVWDGSIAFGGGTKVTVL | ADI-41356 | Light chain variable region ("LC") amino acid sequence |
| Ab 654 | 1307 | EVQLVESGGGLVQPGGSLRLSCAASGFTFSTYGMNWVRQAPGKGLEWVSYIGGS GRIIYYADSVKGRFTISRDNAKNSLYLQMNSLRAEDTAVYYCARDQHIVLVTGSTP DYWGQGTLVTVSS | ADI-41357 | Heavy chain variable region ("HC") amino acid sequence |
| Ab 654 | 1308 | EIVLTQSPSSLSASVGDRVTITCRASHAISNYLAWFQQKPGKAPKSLIYAASTLQS GVPSKFSGSGSGTDFTLTISSLQPEDFATYYCQQYSSYPLTFGGGTKVEIK | ADI-41357 | Light chain variable region ("LC") amino acid sequence |
| Ab 655 | 1309 | EVQLVESGGGLVKPGGSLRLSCEASGFTLTSYSMNWVRQAPGKGLEWVSSISSSST YIHYADSVKGRFTISRDNAKNSLYLQMNSLRAEDTAVYYCARDKVMVTKYNGMDV WGQGTTVTVSS | ADI-41358 | Heavy chain variable region ("HC") amino acid sequence |
| Ab 655 | 1310 | QSVLTQPPAVSGAPGQRVTISCTGSSSNIGAGHDVHWYQQLPGTAPKLLIYGNSNR PSGVPDRFSGSKSGTSASLAITGLQAGDEADYYCQSYDSSLSGSLFGGGTKLTVL | ADI-41358 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 656 | 1311 | EVQLVESGGGLVKPGGSLRLSCAASGFTISGYSMDWVRQAPGKGLEWVSSISSSSS YIHYADSVKGRFTISRDNAKNSLYLQMNSLRAEDTAVYYCATNPREGGAFDIWGQ GTTVTVSS | ADI- 41359 | Heavy chain variable region ("HC") amino acid sequence |
| Ab 656 | 1312 | QSVLTQPPSMSGAPGQRVTISCTGSSSNIGAGYDVHWYQQLPGTAPKLLIYNNSNR PSGVPDRFSASKSGTSASLAITGLQAEDEADYYCQSYDSSLSGYVFGTGTRVTVP | ADI- 41359 | Light chain variable region ("LC") amino acid sequence |
| Ab 657 | 1313 | EVQLVESGGGLVQPGGSLRLSCAASGLTFSRYSMNWVRQAPGKGLEWVSYISSTG RRIQYADSVKGRFTISRDDGKNSLYLQMNSLRAEDTAVYYCARDPLNYHDNTAYW SYWGQGTLVTVSS | ADI- 41360 | Heavy chain variable region ("HC") amino acid sequence |
| Ab 657 | 1314 | NFMLTQPHSVSESPGKTVTISCTRSSGSIASNYVQWYQQRPGSAPTTVIYEDNQRP SGVPDRFSGSIDSSSNSASLTISGLKTEDEADYYCQSYDSSNPLVFGGGTKLTVL | ADI- 41360 | Light chain variable region ("LC") amino acid sequence |
| Ab 658 | 1315 | QVQLQESGGGVVQPGRSLRLSCAASGFAFSDYAMDWVRQAPGKGLEWVAVISFD GSNKFYADSVKGRFTISRDNSENTLFLQMNSLRAEDTAVYYCVRDFVPCSGATCYL PPVYWGRGTLVTVSS | ADI- 41361 | Heavy chain variable region ("HC") amino acid sequence |
| Ab 658 | 1316 | EIVLTQSPATLSVSPGERATLSCRASQSVSSDLAWYQQKPGQAPRLLIYGASTRAT GIPARFSGSGSGTEFTLTISRLQSEDFAVYFCQQYNNWPSWTFGQGTKVEIK | ADI- 41361 | Light chain variable region ("LC") amino acid sequence |
| Ab 659 | 1317 | EVQLVESGGGLVQPGGSLRLSCAASGFTFSDHWMNWVRQTPGKGLEWVANIKP DGRETYYVDSVKGRFTISRDNSKKSVYLQMNSLRAEDTAVYYCVRDGHIVVVTAVP PGFFDLWGRGTLVTVSS | ADI- 41362 | Heavy chain variable region ("HC") amino acid sequence |
| Ab 659 | 1318 | DIQVTQSPSSLSASVGDRVTITCQASQDLTKYLNWYQQKPGKAPKLLIYDISNLET GVPSRFSGSGFGTEFTLTISSLQPEDVATYYCQQYQNLPYTFGQGTKVEIK | ADI- 41362 | Light chain variable region ("LC") amino acid sequence |
| Ab 660 | 1319 | QVQLVQSGAEVKKPGSSVKVSCKASGGTFSSYAITWVRQAPGQGLEWMGGIIPLF GTAKYAQQFQGRVTITADESTSTAYMELSSLRSEDTAVYYCARDGEVCTNGFCWFL DWGLGTLVTVSS | ADI- 41363 | Heavy chain variable region ("HC") amino acid sequence |
| Ab 660 | 1320 | DIRVTQSPSSLSASVGDRVTITCQASQDISNYLNWYQQKPGKAPKLLIYDASKLETG VPSRFSGSGSGTDFTFTISSLQPEDIATYYCQNYGNFPHFGGGTKLEIK | ADI- 41363 | Light chain variable region ("LC") amino acid sequence |
| Ab 661 | 1321 | EVQLLESGAEVKKPGASVKVSCKASGYTFTDHSIHWVRQAPGRGLEWMGWFNPH TGVTDYAQKFQGWVTMTSDTSISTAYMELSSLKSDDTAIYFCARDQWETDGAYFL DYWGQGTLVTVSS | ADI- 41364 | Heavy chain variable region ("HC") amino acid sequence |
| Ab 661 | 1322 | QSALTQPASVSGSPGQSITISCTGTSSDVGNFKLVSWYQQHPGKAPKLMIYEGNKR PSGVSNRFSGSKSGNTASLTISGLQAEDEADYYCCSSAVSSTFFGTGTKLTVL | ADI- 41364 | Light chain variable region ("LC") amino acid sequence |
| Ab 662 | 1323 | EVQLVESGGGLVKPGGSLRLSCATSGFTFSDYYMTWIRQAPGKGLEWVSYISSSGG YTNYADSVRGRFTISRDNAKRSLYLQMNSLRAEDTAVYYCARVEFSSGDVPSLFDS WGQGTLVTVSS | ADI- 41365 | Heavy chain variable region ("HC") amino acid sequence |
| Ab 662 | 1324 | QSVLTQPPSVSGAPGQRVTISCTGSSSNLGAGYHVHWYQQFPGTAPKPLIYGNTN RPSGVPDRFSGSKSGTSASLAITGVQAEDEADYYCQSYDYSLSGWVFGGGTKLTVL | ADI- 41365 | Light chain variable region ("LC") amino acid sequence |

TABLE 5-continued

Informal Sequence Listing

| Anti- body No. | SEQ ID NO: | Sequence | Clone # (ADI) | Descriptors |
|---|---|---|---|---|
| Ab 663 | 1325 | QVQLVQSGAEVKKPGESLKISCKASGYSSTTYWIGWVRQISGKGLEWMGIIYPGDS DTRYSPSFQGQVTISADRSTKTAYLQWSSLKASDTAMYYCGTSGFGVATPFDYWG QGTLVTVSS | ADI- 41366 | Heavy chain variable region ("HC") amino acid sequence |
| Ab 663 | 1326 | NFMLTQPHSVSESPGKTVTISCTRTSGSIAGNYVHWYQQRPGSAPTTVIYEDNQRP SGVPDRFSGSIDRSSNSASLTISGLKTEDEADYYCQSYASGIHGVFGGGTKVTVL | ADI- 41366 | Light chain variable region ("LC") amino acid sequence |
| Ab 664 | 1327 | QVQLVQSGAAVKRPGASVKVSCKASGYTFSTNALHWVRQAPGQSLEWMGWINT DNGIPKYSERFHGRVTFTRDTSASTVYMDLSGLRSGDTAVYYCARDGSSGHWLGLS VLDNWGQGTLVTVSS | ADI- 41367 | Heavy chain variable region ("HC") amino acid sequence |
| Ab 664 | 1328 | QSALIQPASVSGSPGQSITISCTGTSDDVGAYNYVSWYQQYPNKAPKLVIYEVSHRP SGVSNRFSGSKSGNTASLTISGLQAEDEADYYCSSYTRSATPYVFGTGTKLTVL | ADI- 41367 | Light chain variable region ("LC") amino acid sequence |
| Ab 665 | 1329 | EVQLVESGGGVVQPGRSLRLSCAASGFIFRNYGMHWVRQAPGKGLEWVAGTSFE GRNKDYGHSVKGRFTISRDNSKDTLYLQMNSLRPEDTAVYSCAKGSSLQWSHLDW YFDLWGRGTLVTVSS | ADI- 41368 | Heavy chain variable region ("HC") amino acid sequence |
| Ab 665 | 1330 | DIVMTQSPSTLSASVGDRVTITCRASQSFSSWLAWYQQKPGKAPNLLIYDASTLESG VPSRFSGSGSGTEFTLTISSLQPDDFATYYCQQERTFGQGTKVEIK | ADI- 41368 | Light chain variable region ("LC") amino acid sequence |
| Ab 666 | 1331 | EVQLVQSGGGVVQPGRSLRLSCAASGFTFSSYGMHWVRQAPGKGLEWVAVISHD GNNKYYGDSVKGRFTISRDNSKNTLHLQMNSLRGDDTAVYYCGKDPLKGDCSGGS CYQRIDYWGQGTLVTVSS | ADI- 41369 | Heavy chain variable region ("HC") amino acid sequence |
| Ab 666 | 1332 | NFMLTQPHSVSESPGKTVTISCTGSSGRIASNYVQWYQQRPGSAPATVIYDDNQRP SGVPDRFSGSIDSSSNSASLTISGLKTEDEADYYCQSYDRSNHVIFGGGTKLTVL | ADI- 41369 | Light chain variable region ("LC") amino acid sequence |
| Ab 667 | 1333 | EVQLVESGGGLVKPGGSLRLSCAASGFTFSGFSMNWVRQAPGKGLEWVSSISSTSR YIYYADSVQGRFTISRDNAKNSLYLQMNSLRAEDTAVYYCARDPGGSASFVPYYYG MDVWGQGATVTVSS | ADI- 41370 | Heavy chain variable region ("HC") amino acid sequence |
| Ab 667 | 1334 | SYELIQPPSVSVSPGQTARITCSGDALPNQYVYWYQKKPGQAPVLVIYKDTEGPLGI PERFSGSSSGTTVTLTISGVQAEDEADYYCQSADSSGTYPYVVFGGGTKLTVL | ADI- 41370 | Light chain variable region ("LC") amino acid sequence |
| Ab 668 | 1335 | QVQLQESGPRLVKPSQTLSLTCTVSGGSITTGEHYWSWIRQSPGRGLEWIGYISYSG STYYNPSLKSRVTISVDTSKTRISLNLRSVTAADSAVYYCARDQEDSDYIWGSSRVF DIWGQGTMVTVSS | ADI- 41371 | Heavy chain variable region ("HC") amino acid sequence |
| Ab 668 | 1336 | ETTLTQSPGTLSLSPGERATLSCRASQNVGNNYLAWYQQKPGQAPRVLIQDASTRA TGIPDRFSGSGSGTDFTLTISRLEPEDFAVYHCQQYGSAPWTFGQGTKVEIK | ADI- 41371 | Light chain variable region ("LC") amino acid sequence |
| Ab 669 | 1337 | QVQLVQSGAEVKKPGSSVKVSCKASGGISSSYAISWVRQAPGQGLEWMGGIIPIFG TTNYAQKFQGRVTITADKSTSTVYMELSSLRSEDSAVYFCARAYCSGGTCYGGADY WGQGTLVTVSS | ADI- 41372 | Heavy chain variable region ("HC") amino acid sequence |
| Ab 669 | 1338 | SYELTQPPSVSVSPGQTARITCSGDVLPKQYAYWYQQKLGQAPLLVMYKDTERPSG IPERFSGSSSVTAVTLTISGVQAEDEADYYCQSADSTQELFGGGTKLTVL | ADI- 41372 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 670 | 1339 | QVTLKESGGGLVKPGGSLRLSCAASGFTFSDYFMTWIRQAPGKGLEWVSYISSNSG YTKYAEDVKGRFSISRDNAKKTLFLQLNSLSAEDTAVYYCARVEFSSGDVPSLFDLW GQGTLVTVSS | ADI-41373 | Heavy chain variable region ("HC") amino acid sequence |
| Ab 670 | 1340 | QSVLTQPPSVSGAPGQRVTISCTGSSSNIGAGYHVHWYQQLPGTAPKVLIHGNNN RPSGVPDRFSGSRSGTSASLAITGLQAEDEADYYCQSYDFSLSGWVFGGGTKLTVL | ADI-41373 | Light chain variable region ("LC") amino acid sequence |
| Ab 671 | 1341 | QVQLVQSGAEVKKPGSSVKVSCKASGGTFSNHAIDWVRQAPGQGLEWMGRIIPM VGLATYTRKFQGRVTISVDKSTSTAYMELSSLISDDTAVYYCARRTPEMAWGYWG QGTTVTVSS | ADI-41374 | Heavy chain variable region ("HC") amino acid sequence |
| Ab 671 | 1342 | DIVMTQTPSSLSASVGDRVTITCQASQDIRYYVNWYQQKPGKAPKLLIYDASTLETG VPSRFSGRGSGTDFTLIISSLQPEDIATYYCQQYGDLPTFGQGTRLEIK | ADI-41374 | Light chain variable region ("LC") amino acid sequence |
| Ab 672 | 1343 | QVQLVQSGGGVVQPGRSLRLSCATSGFTFSDYAIHWVRQAPGKGLEWVAVISYDG SHKYYGDSVKGRFTISRDNSKNTLYLQMNSLRPEDTAVYYCARSRSGSYYSSAIDNW GQGTLVTVSS | ADI-41375 | Heavy chain variable region ("HC") amino acid sequence |
| Ab 672 | 1344 | DIQMTQSPSSLSASVGDRVTIACRASQGISSALAWYRQRPGKAPELLIYDASTLESG VPSRFSGYGAGTDFTLTISSLQPEDFATYYCQQFNSYPSITFGQGTKVEIK | ADI-41375 | Light chain variable region ("LC") amino acid sequence |
| Ab 673 | 1345 | QVQLQESGGGVVQPGRSLRLSCAASGFTFSSYAMHWVRQAPGKGLEWVAVISFD GTANKYYADSVKGRFAISRDNSKNTLYLQMNSLRAEDTAVYYCAKDDAIYSGGWV GDAFDLWGQGTMVTVSS | ADI-41376 | Heavy chain variable region ("HC") amino acid sequence |
| Ab 673 | 1346 | EIVLTQSPATLSVSPGERATLSCRASQGVNSNLAWYQQKPGQAPRLLMYGASTRAT GIPARFSGSGSETEFTLTISSLQSEDFAVYYCQQYNNWPRTFGQGTKVDIK | ADI-41376 | Light chain variable region ("LC") amino acid sequence |
| Ab 674 | 1347 | QVQLQQSGPGLVKPSQTLSLTCAISGDSVSSDSATWNWIRQSPSRGLEWLGRAYY RSKWYYDYAPSVKSRLTINPDTSKNQFSLQLTSVTPQDTAVYFCARDLPPLEYFDGS GYYFLDHWGQGTLVTVSS | ADI-41377 | Heavy chain variable region ("HC") amino acid sequence |
| Ab 674 | 1348 | SYELTQPPSVSVAPGQTARLSCGGHNIGSKSVQWYQQKPDQAPVLVVYDDHDRPS GIPDRFSGSNSGDMATLTISRVEAGDEADYYCQVCESGRDPMVFGGGTKVTVL | ADI-41377 | Light chain variable region ("LC") amino acid sequence |
| Ab 675 | 1349 | EVQLVESGPGLVKPSGTLSLTCAVSGDSISSSNWWSWVRQPPGKGLEWIGEVSHS GNTDYNPSLKSRVTISVDKSKNQFSLKLSSVTAADTAVYYCARPSPCSGGSCYWFFD LWGRGTLVTVSS | ADI-41378 | Heavy chain variable region ("HC") amino acid sequence |
| Ab 675 | 1350 | DIRLTQSPSSLSASVGDRVTITCRASQTINAYLNWYQQRPGKAPNLLIYAASSLQSG VPSRFSGSGSGTDFTLTISSLQPEDFATYYCQQSYKTAYTFGQGTKVEIK | ADI-41378 | Light chain variable region ("LC") amino acid sequence |
| Ab 676 | 1351 | QVQLVQSGAEVKKPGESLKISCKGSGYSFSSFWIGWVRQMPGKGLEWMGIIYPGD SDTRYSPSFKGQVTISADTSISTAYLQWSSLKASDTAMYYCAKSIVGSTGSFDPWGQ GTLVTVSS | ADI-41379 | Heavy chain variable region ("HC") amino acid sequence |
| Ab 676 | 1352 | DIQMTQSPSSLSASVGDRVTITCQASQDISNFLNWYQQKPGKAPKLLIYDASNLRT GVPSRFSGSGSGTEFTFTISSLQPEDIATYYCQQYHDLPPLTFGGGTKVDIK | ADI-41379 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 677 | 1353 | QVQLVQSGAEVKKPGESLKISCKGSGYSFTSYWIGWVRQMPGKGLEWMGIIYPGD SDTRYSPSFQGQVTISADKSISTAYLQWSSLKASDTAMYYCASSRAYYDILTGYYV ASAETQTKAAFDIWGQGTTVTVSS | ADI-41380 | Heavy chain variable region ("HC") amino acid sequence |
| Ab 677 | 1354 | DIQVTQSPSSLSASVGDRVTITCQASQDISNYLNWYQQKPGKAPKLLIYDASNLETG VPSRFSGSGSGTDFSFTISSLQPEDIATYYCQQYDNLITFGQGTKVEIK | ADI-41380 | Light chain variable region ("LC") amino acid sequence |
| Ab 678 | 1355 | QVQLQESGPGLVKPSQTLSLTCTVSGDSISGGEHYWSWIRQPPGKGLEWIGSIYYS GTTYYNPSLKSRLTVSVDTFKNQFSLMLSYVTAADTAVYYCARDASPAYHDYIWGS CRYFDKWGQGTLVTVSS | ADI-41381 | Heavy chain variable region ("HC") amino acid sequence |
| Ab 678 | 1356 | EIVLTQSPGTLSLSPGERATLSCRASQSVSSNYLAWYQQKPGQAPRILIHGASSRAT GIPDRFSGSGSGTDFTLTVSRLEPEDFAVYYCQQYGSTPYTFGQGTKVEIK | ADI-41381 | Light chain variable region ("LC") amino acid sequence |
| Ab 679 | 1357 | EVQLVESGGGLVQPGRSLRLSCAASGFTFDDYAMHWVRQAPGKGLEWVSGISWS GDTRGYAESVKGRFTITRDNAKKYLYLQMNSLRAEDTAFYYCAKDAYYFGSGNEKF YYGMDVWGQGTTVTVSS | ADI-41382 | Heavy chain variable region ("HC") amino acid sequence |
| Ab 679 | 1358 | DIVLTQTPATLSVSPGERATLSCRASQNVISNLAWYQQKPGQAPRLLIYGASTRATG IPARFSGSGSGTEFTLTISSLQSEDFAVYYCQQYNNWPQTFGQGTKVEIK | ADI-41382 | Light chain variable region ("LC") amino acid sequence |
| Ab 680 | 1359 | QVQLVQSGAEVKKPGSSVRVSCKASGGTFSRYAISWVRQAPGQGLEWMGGVIPR FDKTNYAQKFQGRVMITADKSTSTAYMELSSLRSDDTAVYYCAGDRLDTKITHTWY GFGDFWGQGTTVTVSS | ADI-41384 | Heavy chain variable region ("HC") amino acid sequence |
| Ab 680 | 1360 | EIVLTQSPGTLSLSPGERATLSCRASQSVTSNFLAWYQQRPGQAPRLLIYGASVRAI DIPDRFSGSGSGTDFTLTISRLEPEDFAVYYCQQYGDPFRTFGQGTKVEIK | ADI-41384 | Light chain variable region ("LC") amino acid sequence |
| Ab 681 | 1361 | EVQLVESGGGVVQPGRSLRLSCAASGFTFSSYGMHWVRQAPGKGLEWVAVIWYD GNNEKYADSVKGRFTISRDNSKNTLYLQMNSLRAEDTAVYYCARPTQKYSSSWYW EDSIDYWGQGTLVTVSS | ADI-41385 | Heavy chain variable region ("HC") amino acid sequence |
| Ab 681 | 1362 | QSVLTQPPSVFGAPGQRVTISCTGSSSNIGAGYPVHWYQQLPGTAPKLLIYGNSR PSGVPDRFSGSKSGTSASLAITGLQAEDEADYYCQSYDSSLSGGVVFGGGTKLTVL | ADI-41385 | Light chain variable region ("LC") amino acid sequence |
| Ab 682 | 1363 | QVQLVQSGAEVKKPGASVKVSCKASGYTFTGNYIHWVRQAPGQGLEWMGGINP NSGATNYARKFQGRISMTRDTSINTAYMEVSSLRSDDTATYYCARDAPPVVIPAAIH WFDAWGQGTLVTVSS | ADI-41386 | Heavy chain variable region ("HC") amino acid sequence |
| Ab 682 | 1364 | SYELTQPPSASGTPGQRVTISCSGSSSNIGRNTVNWYQQFSGTAPRLLIYRTNQRPS GVPDRFSGSKSGTSASLVISGLQSEDEADYYCASWHDTLNDVVFGGGTKLTVL | ADI-41386 | Light chain variable region ("LC") amino acid sequence |
| Ab 683 | 1365 | EVQLVESGGGVVQPGRSLRLSCAASGFTFSNYAIHWVRQAPGKGLEWVAAISYDG GNKFYADSVKGRFTISRDNSRNTLYLQMNSLRPEDTAVYYCARDRWELNYGIDVW GQGTTVTVSS | ADI-41389 | Heavy chain variable region ("HC") amino acid sequence |
| Ab 683 | 1366 | SYELMQPPSVSVSPGQTARITCSGDALPKQYAYWYQQKPGQAPVLVIYKDSERPSG IPERFSGSTSGTTVTLTISGVQAEDEADYYCQSADSSSTFFYVFGTGTKLTVL | ADI-41389 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 684 | 1367 | EVQLVESGGGLVKPGGSLRLSCAASGFSSSSYFMNWVRQAPGKGPEWVSSISGSSS FINYADSVKGRFTISRDNAKNSLYLQMNSLRAEDTAVYYCARAVLPAGVGGYWFDS WGQGTLVTVSS | ADI-41390 | Heavy chain variable region ("HC") amino acid sequence |
| Ab 684 | 1368 | QSVVTQPPSVSGAPGQRVTISCTGSSSNIGAGYDVHWYQHLPGRAPKLLIYGNSNR PSGVPDRFSGSKSGTSASLVITGLQAEDEADYCCQSYDSSLSGAVFGGGTQLTVL | ADI-41390 | Light chain variable region ("LC") amino acid sequence |
| Ab 685 | 1369 | EVQLLESGPGLVKPSETLSLTCTVSGGSISGYYWSWIRQPPGKGLEWIGYIYHSGG STNYNPSLKSRVTISVDTSKNQFSLKVSSVTAADTAVYYCARLARVVTTFDFWGQG ALVTVSS | ADI-41391 | Heavy chain variable region ("HC") amino acid sequence |
| Ab 685 | 1370 | QPVLTQPASVSGSPGQSITISCTGTSSDVGGYNYVSWYQQKPGTAPKLMIFDVSNR PSGVSNRFSGSKSDNTASLTISGLQAEDEADYYCSSYTSSTNLVFGGGTKLTVL | ADI-41391 | Light chain variable region ("LC") amino acid sequence |
| Ab 686 | 1371 | EVQLVESGGGVVQPGGSLRLSCAASGFEFRDYAMHWVRQAPGKGLEWVALISYD GSKIHYADSVQGRFSISRDNSKNSLYLQMNSLRSEDSAKYYCVQDHWLVPAFWGQ GAQVTVSS | ADI-41392 | Heavy chain variable region ("HC") amino acid sequence |
| Ab 686 | 1372 | QPVLTQPASVSGSPGQWITISCTGTSSDIGYYDYVSWYQQYPGKAPKLIIYEVSHR PSGVSNRFSGSKSGNTASLSISGLQAEDEADYYCSSYTTSNAGVFGTGTKLTVL | ADI-41392 | Light chain variable region ("LC") amino acid sequence |
| Ab 687 | 1373 | QVQLVQSGAEVKKPGESLKISCKGSGYSFTSYWIGWVRQMPGKGLEWMGIIYPGD SDTRYSPSFQGQVTISADKSTSTAYLQWSSLKASDSAMYYCARSEFSSSFDFWGQG TLVTVSS | ADI-41393 | Heavy chain variable region ("HC") amino acid sequence |
| Ab 687 | 1374 | NFMLTQPHSVSESPGKTVTISCTGSSGSIASYYVQWYQLRPGSAPTTVIYEDNQRLS GVPDRFSGSIDSSSNSASLTISGLKTEDEADYYCQSYRSGIPWVFGGGTKLTVL | ADI-41393 | Light chain variable region ("LC") amino acid sequence |
| Ab 688 | 1375 | QVQLVQSGAEVKKPGSSVKVSCKASGGTFNTYAISWVRQAPGQGLEWMGGIIPIL GVSNYAQRFQGRVTFSADELTNTAYMELSSLRSEDTAVYFCARPVGAYTLGDAFEI WGRGTTVTVSS | ADI-41394 | Heavy chain variable region ("HC") amino acid sequence |
| Ab 688 | 1376 | QPVLTQSSSASASLGSSVKLTCTLSSGHSDFIIAWHQQQPGKAPRYLMKFEGNGRY SKGSGIPDRFSGSSSGADRCLTISNLQSEDEADYYCETWDSNTHVVFGGGTKLTVL | ADI-41394 | Light chain variable region ("LC") amino acid sequence |
| Ab 689 | 1377 | EVQLVESGGGLVNPGGSLRLSCVVSGFAFSSYGMNWVRQAPGKGLEWVSSISASS SYIDYADSVKGRFIISRDNAKNSLHLQMNSLRAEDTAVYYCARLGYDSSTYYTNWFD PWGRGTLVTVSS | ADI-41396 | Heavy chain variable region ("HC") amino acid sequence |
| Ab 689 | 1378 | QSVVTQEPSVSGAPGQRVTISCTGSSSNIGTGYDVHWYQQLPGAAPKLLIYGNSNR PSGVPDRISGSKSGTSASLAITGLQAEDEADYYCQSYDSSLSGYVFGTGTKVTVL | ADI-41396 | Light chain variable region ("LC") amino acid sequence |
| Ab 690 | 1379 | EVQLVESGGGLVKPGGSLRLSCAASGFKFSSYYLNWVRQAPGKGLEWVSSISGGSS YINYADSVKGRFTISRDNAKNTLDLQMSNLRAEDTAVYYCARVVGATGPLYFDLWG RGTLVTVSS | ADI-41397 | Heavy chain variable region ("HC") amino acid sequence |
| Ab 690 | 1380 | QSVLTQPPSVSGAPGQRVTISCTGSSSNIGAGYDVHWYQQFPGTAPKLLIYGNNNR PSGVPDRFSGSKSGTSASLAITGLQAEDEADYYCQSYDSSLSGYVFGAGTKVTVL | ADI-41397 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 691 | 1381 | EVQLLESGAEVKKPGASVKVSCKASGYTFTNYGISWVRQAPGQGLEWMGWISAY NGNTNYAQKLQGRVTMTTDTSTSTAYMELRSLRSDDTAVYYCARDGGVIAAATLG YWGQGTLVTVSS | ADI-41398 | Heavy chain variable region ("HC") amino acid sequence |
| Ab 691 | 1382 | EIVLTQSPLSLPVTLGQPASISCRSSQSLVYSDGNTYLSWFQQRPGQSPRRLIYKI SNRDSGVPNRFSGSGSGTDFTLKISRVEAEDVGIYYCMQGIYWPPTFGQGTKVEIK | ADI-41398 | Light chain variable region ("LC") amino acid sequence |
| Ab 692 | 1383 | QVQLVQSGAEVKKPGASVKVSCKASGYTFTTFAIHWVRQAPGQRLEWMGWINA GNGNTKYSQKFQGRVTITRDTSASTAYMELSSLRSEDTAVYYCARPEISSSSLNEK DDYWGQGTLVTVSS | ADI-41399 | Heavy chain variable region ("HC") amino acid sequence |
| Ab 692 | 1384 | QPVLTQPASVSGSPGQSITISCTGTSSDVGAYDFVSWYQQHPGKAPKFMIYEVSHR PSGVSNRFSGSKSGNTASLTISGLQAEDEADYYCSSYTTSNTLVFGGGTKLTVL | ADI-41399 | Light chain variable region ("LC") amino acid sequence |
| Ab 693 | 1385 | EVQLLESGGGLIQPGGSLRLSCAASKFTFSDYEMNWVRQAPGKGLEWLSYISSSGGI MYYADSVKGRFTISRDNAKNSLYLQMNSLRAEDTAVYFCARAGRLLSGLDVWGHG TTVTVSS | ADI-41400 | Heavy chain variable region ("HC") amino acid sequence |
| Ab 693 | 1386 | EIVLTQSPSTLSASVGDRVTITCRASQSISPWLAWYQQKPGKAPKLLIYRASSLETG VPPRFSGSGSGTEFTLTISSLQPDDFATYYCQHYNSYLYSFGQGTKVEIK | ADI-41400 | Light chain variable region ("LC") amino acid sequence |
| Ab 694 | 1387 | EVQLLESGGGLVHPGRSLRLSCAASGFTFGDYAMHWVRQAPGKGLEWVSGISWN SDTIEYADSVKGRFTISRDNAKNSLYLQMNSLRAEDTALYYCAKDFGSSWEAYFDY WGQGTLVTVSS | ADI-41401 | Heavy chain variable region ("HC") amino acid sequence |
| Ab 694 | 1388 | DIVLTQSPSYLSASVGDRVTITCRASQSISTYLNWYQQKPGKAPKLLISAASSLQS GVTSRFSGSGSGTDFSLTISSLQPEDFATYYCQQSYSTALTFGGGTKVEIK | ADI-41401 | Light chain variable region ("LC") amino acid sequence |
| Ab 695 | 1389 | EVQLVESGGGLVKPGGSLRLSCAASGFTFGTYTMNWVRQAPGKGLEWVSSISSSS HIYYADSVKGRFTISRDNARKALYLQMNSLRPEDTAVYFCARFLGDYGGDGNTYYY YYGMDVWGQGTTVTVSS | ADI-41403 | Heavy chain variable region ("HC") amino acid sequence |
| Ab 695 | 1390 | EIVMTQSPLSLPVTPGEPASISCRSSQSLLHSNGKNYLDWYLQKPGQSPQLLIHLGS NRASGVPDRFSGSGSGTDFTLQISRVEAEDVGVYYCMQALQTPTFGGGTKLEIK | ADI-41403 | Light chain variable region ("LC") amino acid sequence |
| Ab 696 | 1391 | QVQLVQSGAEVKKPGSSVKVSCKASGGTFSSYGISWVRQAPGQGLEWMGGIIPIF GTVSYAQKFRGRLTITAHEPTSTAYMDLSSLRSEDTAVYYCARINGRGWELSSLNYY YGMDVWGQGTTVTVSS | ADI-41404 | Heavy chain variable region ("HC") amino acid sequence |
| Ab 696 | 1392 | EIVLTQSPGTLSLSPGERGTLSCRASQSVASSYLAWYQQKPGQAPRLLIYGATSRAT GIPDRFSGSGSGTDFTLTISRLEPEDFAVYYCQQYGSSLFTFGGGTKVDIK | ADI-41404 | Light chain variable region ("LC") amino acid sequence |
| Ab 697 | 1393 | EVQLLESGGGLVQPGGSLRLSCAASGFSFSIYSMNWVRQAPGKGLEWISYITSTGSP TYYADSVKGRFTISRDNAKNSLYLQMSSLRAEDTAVYYCVTYCSSSSCPAEFDYWGQ GTLVTVSS | ADI-41405 | Heavy chain variable region ("HC") amino acid sequence |
| Ab 697 | 1394 | EIVLTQSPATLSLSPGERATLSCRASQSVNSYLAWYQQKPGQAPRLLIYDASNRATG IPARFSGSGSGTDFTLTISSLEAEDFAVYYCQHRNNWPALTFGGGTKVEIK | ADI-41405 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 698 | 1395 | EVQLVESGGNLVQPGGSLRLSCAASGFTFSSYVMNWVRQAPGKGLEWVSGISGS GGTSYYADSVKGRFTISRDNSNNTLYLQMKSLRAEDTAVYYCAKDPRFQKWLIEGT NWFDSWGQGTLVTVSS | ADI-41406 | Heavy chain variable region ("HC") amino acid sequence |
| Ab 698 | 1396 | DIQVTQSPSSLSASVGDRVTITCRASQDVSNYLAWFQQKPGTAPKSLIYAASILQSG VPSKFRGSGSGTDFSLTISSLQPEDFATYYCQQYRSFPPTFGGGTKVEIK | ADI-41406 | Light chain variable region ("LC") amino acid sequence |
| Ab 699 | 1397 | EVQLVESGGGLVQPGGSLRLSCAASGFTFSSNAMSWVRQAPGKGLEWVSYISGGS ATKSYADSVKGRFTISRDNSKNTLYLQMKSLRAEDTAVYYCVGGSAYYSGFDYWGQ GTLVTVSS | ADI-41407 | Heavy chain variable region ("HC") amino acid sequence |
| Ab 699 | 1398 | DIVMTQSPSSLSASVGDRVTISCRASQDIRNYLAWYQQKPGKVPNLLIYAASTLESG VPSRFSGSGYGTDFTLTISGLQPEDVATYYCQKYDSAPPFTFGPGTKVDIK | ADI-41407 | Light chain variable region ("LC") amino acid sequence |
| Ab 700 | 1399 | QVQLVESGAEVKKPGESLKISCRDSGYSFSSFWIGWVRQMPGKGLEWVGIIYPGDS DIRYSPSFQGRVTISADKSISTAYLQWRSLKASDSAMYYCARSEKLGSFDRWGQGTL VTVSS | ADI-41408 | Heavy chain variable region ("HC") amino acid sequence |
| Ab 700 | 1400 | DIQMTQSPSSLSASVGDRVTITCQANRDISNCLNWYQQRPGKAPELLIYDASYLETG VPSRFTGSGSGTDFTFTISSLQPEDIATYYCQQYDNLLFTFGPGTKVEIK | ADI-41408 | Light chain variable region ("LC") amino acid sequence |
| Ab 701 | 1401 | QVQLVQSGAEVKKPGASVKVSCKASGYTFTNYGISWVRQAPGQGLEWMGWISA YNGNTNYAQKFQDRVTMTTDTSTSTAYMELRSLRYDDTAVYYCARDTPGEYASA MFDHWGQGTLVTVSS | ADI-41409 | Heavy chain variable region ("HC") amino acid sequence |
| Ab 701 | 1402 | DIVMTQSPLSLPVTLGQPASISCRSSQSLVYSDGNTYLSWFQQRPGQSPRRLIYKVS NRDSGVPDRFSGSGSGTDFTLKISGVEAEDVGVYYCMQGTHWPPTFGQGTKLEIK | ADI-41409 | Light chain variable region ("LC") amino acid sequence |
| Ab 702 | 1403 | EVQLLESGGGLAQPGRSLKVSCAASGVTVTSTYMGWVRQAPGKGLQWVSVIYSD GTTYYADSVKGRFTISRDHYKNTLYLQMNSLRAEDTALYYCARGNRRTDFGYWGQ GTLVTVSS | ADI-41414 | Heavy chain variable region ("HC") amino acid sequence |
| Ab 702 | 1404 | EIVMTQSPSTLSASVGDRVTITCRASQTISNWLAWYQQKPGKAPKLLIYQASTLESG VPSRFSGSGSGTEFTLTISSLQPDDFATYYCQQYNTYYTFGPGTKVEIK | ADI-41414 | Light chain variable region ("LC") amino acid sequence |
| Ab 703 | 1405 | QVTLKESGPALVKPTQTLTLTCTFSGFSLSTSRTRVSWIRQPPGKALEWLARVDWD DDKFYNPVLKTRLSISKDPSKNQVVLTMTNVDPVDTATYYCVRMAHYGSGGYYVE YFQDWGQGTLVTVSS | ADI-41415 | Heavy chain variable region ("HC") amino acid sequence |
| Ab 703 | 1406 | DIQLTQSPASLSASAGDRVTITCRASQNINRYLNWYQQSGKAPKLLIYAASILQSG VPSRFSGSGSGTDFTLTITSLQPEDFAIYYCQQSYTTPKYTFGQGTKVEIK | ADI-41415 | Light chain variable region ("LC") amino acid sequence |
| Ab 704 | 1407 | EVQLVESGGGLVKPGGSLRLSCAASGFKFSSYTMNWVRQAPGKGLEWVSSITGGS SFINYADSVKGRFTISRDNAKNSLYLQMVSLRAEDTAVYYCARDLSSHITIFGAVSD YWGRGTTVTVSS | ADI-41416 | Heavy chain variable region ("HC") amino acid sequence |
| Ab 704 | 1408 | QSVLTQPPSVSGAPGQRVTISCTGSSSNIGAGYDAHWFQQLPGSAPKLLIYANTNR PSGVPDRFSGSKSGTSASLAITGLQAEDEADYYCQSYDSTLSVVFGGGTKLTVL | ADI-41416 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 705 | 1409 | QVQLVESGGGLVKPGGSLRLSCAASGFTFSSYSMNWVRQAPGKGLEWVSSISAGS SYIYYADSLKGRFTISRDNAKNSLYLQMNSLRAEDTAVYYCARVNTHYYDSSAYHNF DSWGQGTLVTVSS | ADI-41417 | Heavy chain variable region ("HC") amino acid sequence |
| Ab 705 | 1410 | QPVVTQPPSVSGAPGQRVTISCTGSSSNIGAGYDVHWYQQLPGTAPKLLIYGNTNR PSGVPERFSGSKSGTSASLAITGLQAEDEADYYCQSYDTNLSAPWVFGGGTKLTVL | ADI-41417 | Light chain variable region ("LC") amino acid sequence |
| Ab 706 | 1411 | EVQLVESGGGLVKPGGSLRLSCAASGLSFTDAWMGWVRQAPGKGLEWVGHIKKK TDYGPTAYAAPVRGRFTVSRDDSKNTLYLQMTSLKTEDTAVYYCITERGYNFGYND YFGVDVWGQGTLVTVSS | ADI-41418 | Heavy chain variable region ("HC") amino acid sequence |
| Ab 706 | 1412 | QPGLTQPPSVSVSPGQTARITCSGDALPKKYAYWYQQKSGQAPVMIIYEDNKRPSG IPERFSGSTSGTMATLTISGAQMEDEADYYCFSTDSGDDQSGVFGGGTRLTVL | ADI-41418 | Light chain variable region ("LC") amino acid sequence |
| Ab 707 | 1413 | EVQLVESGGGLVQPGRSLRLSCAASGFTFDDYAMHWVRQAPGKGLEWVSGISW NSGSVGYSDSVKGRFTISRDNAKSSLYLQMNNLRAEDTALYYCARDMAHTQDYFD TSEYDSWGQGTLVTVSS | ADI-41419 | Heavy chain variable region ("HC") amino acid sequence |
| Ab 707 | 1414 | QPVLTQPASVSGSPGQSITISCTGTSSDIGAYNYVSWYQQHPGKAPKLVVYEVNNR PSGISNRFSGSKSGNTASLTISGLQAEDEADYYCSSYTVSATLVFGGGTKLTVL | ADI-41419 | Light chain variable region ("LC") amino acid sequence |
| Ab 708 | 1415 | EVQLLESGGGVVQPGRSLRLSCAASGFTFSSYAMHWVRQAPGKGLEWVAVISYDG SNKYYADSVKGRFTISRDNSKNTLYLQMNSLRAEDTAVYYCARVPCSSTSCYTTDY WGQGTLVTVSS | ADI-41420 | Heavy chain variable region ("HC") amino acid sequence |
| Ab 708 | 1416 | QPVLTQPPSVSGSPGQSVTISCTGTSSDVGSYNRVSWYQQPPGTAPKLMIYEVSNR PSGVPDRFSGSKSGNTASLTISGLQAEDEADYYCSSYTSSSPVFGGGTKVTVL | ADI-41420 | Light chain variable region ("LC") amino acid sequence |
| Ab 709 | 1417 | QVQLVESAAEVKRPGASLKVSCKASGYTFIDYDISWVRQAPGQGLDWMGWISTY DGSAKYPENLQARVAMTTDTSTSTAYMELESLTSDDTAVYYCARARRGSSGWVST TGPTPFFDYWGRGTLVTVSS | ADI-41421 | Heavy chain variable region ("HC") amino acid sequence |
| Ab 709 | 1418 | SYELTQPPSVSVSPGQTARITCSGDALPKRYAYWYQQKSGQAPVLVIYEDNKRPSG IPERFSGSSSGTVATLTISGAQVEDEADYSCYSTDATGNHRGLFGGGTKLTVL | ADI-41421 | Light chain variable region ("LC") amino acid sequence |
| Ab 710 | 1419 | QVQLVESGGGLVKPGGSLRLSCAASGFTFSSYSMNWVRQAPGKGLEWVSSISSSSS YIYYADSVKGRFTISRDNAKNSLYLQMNSLRAEDTAVYYCARDPSSSWNRNDYWG QGTLVTVSS | ADI-41423 | Heavy chain variable region ("HC") amino acid sequence |
| Ab 710 | 1420 | QSVLIQPASVSGSPGQSITISCTGTSSDVGGYNYVSWYQQHPGKAPKLMIYDVSNR PSGVSNRFSGSKSGNTASLTISGLQAEDEADYYCSSYTSSSTLVVFGGGTKVTVL | ADI-41423 | Light chain variable region ("LC") amino acid sequence |
| Ab 711 | 1421 | QVQLVQSGAEVREPGASVKVSCKPSGYTFANYGISWVRQAPGQGLEWMAWISAY NGNTNYAPKVQGRVSVTTDSSTGIGYMELRSLRSDDTAVYYCVRDTPAIAGAATLD FWGQGTLVTVSS | ADI-41424 | Heavy chain variable region ("HC") amino acid sequence |
| Ab 711 | 1422 | DIVLTQSPLSLAVTPGQSASISCRSRQSHVFSDGNTYVSWFQQRPGRSPRRLIYRV SYRDSGVPDRFSGSGSGSDFTLRISRVEAEDVGVYYCMQGTHWPRTFGQGTKLEIK | ADI-41424 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 712 | 1423 | EVQLLESGPAVVKPTQTLTLTCTVSGLSLSSPRMSVSWIRQPPGKGLEWLARIDWD GDKYYGTSLKTRLSISKDTSKNQVVLTMTNMDPVDTGTYYCAQTSIYASNAYYLAR LDPWGQGMLVTVSS | ADI-41425 | Heavy chain variable region ("HC") amino acid sequence |
| Ab 712 | 1424 | EIVMTQSPSLLSASVGDRVTITCRASQNIATYLNWYQQKPGKAPRLLIYAASNLQS GVPSGFSGSGSGTVFTLTISSLQPEDFATYFCQQSYETSLTFGGGTKVEIK | ADI-41425 | Light chain variable region ("LC") amino acid sequence |
| Ab 713 | 1425 | QVQLVESGPGLVKPSETLSLTCTVSGGSIGGYYWSWIRQPPGKGLEWIGYMYYSGS TNYNPSLKSRVTMSVDTSKNQFSLKLTSVTAADTAVYYCARVLRFLVGGMDVWGQ GTTVTVSS | ADI-41427 | Heavy chain variable region ("HC") amino acid sequence |
| Ab 713 | 1426 | QSVLIQPASVSGSPGQSITISCTGTSSDVGGYNYVSWYQQHPGKAPKLIIYEVSNR PSGVSNRFSGSKSGNTASLTISGLQAEDEADYYCNSYTTIATLVFGTGTKVTVL | ADI-41427 | Light chain variable region ("LC") amino acid sequence |
| Ab 714 | 1427 | QVQLVQSGAEVKKPGSSVKVSCKASGGTFSSYAISWVRQAPGQGLEWMGGIIPIF GTVNYAQKFPGRVTITADESTSTAYMELSSLRSEDTAIYYCARDSPSYTGSLLFSQ YYYGMDVWGQGTTVTVSS | ADI-41429 | Heavy chain variable region ("HC") amino acid sequence |
| Ab 714 | 1428 | QPVLTQPASVSGSPGQSITISCTGTSSDVGGYDYVSWYQHHPGKAPKLMIYEVSNR PSGVSNRFSGSKSGNTASLTISGLQAEDEADYYCSSFTTSSPRVFGTGTKLTVL | ADI-41429 | Light chain variable region ("LC") amino acid sequence |
| Ab 715 | 1429 | QVQLVQSGAEVKKPGASVRVSCTASGYRFFTYGITWVRQAPGQGLEWMGWISAY NGNTKFAQKFQGRLTMTTDAPTSTADMELRGLRSDDTAVYYCAREEGGYHGTGS NNYWGQGTLVTVSS | ADI-41431 | Heavy chain variable region ("HC") amino acid sequence |
| Ab 715 | 1430 | QSVLTQPPSVSAAPGQKVTISCSGSGSNVGGNDVSWYQQFPGTAPKLLIYDNSKRP SGIPDRFSGSKSGTSATLVITGLQTGDEADYYCGTWDSSLSVGVFGTGTKLTVL | ADI-41431 | Light chain variable region ("LC") amino acid sequence |
| Ab 716 | 1431 | QVQLVQSGAEVKKPGYSVKVSCKASGGTFSTFGISWVRQAPGLGLEWMGGIIPLF GTADYSKKYQGRVTITADESTSTGYMELNSLTPEDTAVYYCARSPGHLWSRYDAFE VWGQGTTVTVSS | ADI-41432 | Heavy chain variable region ("HC") amino acid sequence |
| Ab 716 | 1432 | QPVLTQPRSVSGSPGQSVTISCSGTSSDVGGYNYVSWYQQYPGKAPKLIIYDVNKR PSGVPDRFSGSKSDNTASLTISGLQADDESDYFCCSYAGSHTFEVFGTGTKVTVL | ADI-41432 | Light chain variable region ("LC") amino acid sequence |
| Ab 717 | 1433 | EVQLLESGGGAVQPGRFLRLSCAASGFTFRSYGMHWVRQAPGKGLEWVAVISYD GSDKYYADSVKGRFTISRDNSKNTLFLLMNGLRAEDAAVYYCAKDIASAGTLRGSD VWGQGTMVTVSS | ADI-41433 | Heavy chain variable region ("HC") amino acid sequence |
| Ab 717 | 1434 | QPVLTQPRSVSGSPGQSVTISCTGTSSDVGGFNYVSWYQQHPGKAPKLMIYDVRV RPSGVPDRFSGSKSGNTASLTISGLQGEDEADYYCCSYTVTYTLVFGGGTKLTVL | ADI-41433 | Light chain variable region ("LC") amino acid sequence |
| Ab 718 | 1435 | EVQLVESGGGLVQPGRSLRLSCEASGFTFDDYAMHWVRQTPGKGLEWVSGISWN SGSIVYADSVKGRFTISRDNAKNSLYLQMHSLRPEDTALYYCAKDNYTFGNYYYY YGMDVWGQGTTVTVSS | ADI-41434 | Heavy chain variable region ("HC") amino acid sequence |
| Ab 718 | 1436 | EIVLTQSPVTLSVSPGERATLSCRASQNVISNLAWYQQKPGQAPRLLIYGASTRAT GIPARFSGSGSGTEFTLTISSLQSEDFAVYYCQQYNNWPLSFGGGTKVEIK | ADI-41434 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 719 | 1437 | EVQLLESGGGLVKPGGSLRLSCAASGFTFSSYSLNWVRQAPGKGLEWVSSISSSGTY IFYADSVKGRFTISRDNAKDSLFLQMNSLRAEDTAVYYCARARDMGNYDILTGYYR VDAFDIWGQGTMVTVSS | ADI-41435 | Heavy chain variable region ("HC") amino acid sequence |
| Ab 719 | 1438 | QSVLTQPPSASKTPGQRVTISCSGSSSNIGGNTVNWYQQLPGTAPKLLIYTNDQRPS GVPDRFSGSKSGTSASLAISGLQSEDEADYYCAAWDDSLNGWVFGGGTKLTVL | ADI-41435 | Light chain variable region ("LC") amino acid sequence |
| Ab 720 | 1439 | EVQLLESGGGVVQPGRSLRLSCAASGFTFSDYAMHWVRQAPGKGLEWVALISFDG SNEYYADSVKGRFTISRDNSRNTVYLQVNTLRPDDTAVFYCARDSHLRLTTRGWGS FDYWGQGTLVTVSS | ADI-41436 | Heavy chain variable region ("HC") amino acid sequence |
| Ab 720 | 1440 | NFMLTQPHSVSESPGKTVTIACTRSSGSIARNYVQWYQQRPGRSPTMVIYEDNQR PSGVPDRFSGSIDTSSNSASLTISGLKTEDEADYYCQPYDPDNLVFGGGTKLTVL | ADI-41436 | Light chain variable region ("LC") amino acid sequence |
| Ab 721 | 1441 | QVQLVQSGGEVKKPGASVKVSCKASGYTFTHYGISWARQAPGQGIEWMGWINV HNGNTEYAQRFQGRVTMTTDTSTNTAYMEMTSLTSDDTAVYYCARDKIVVVVVP NYHGMDVWGQGTLVTVSS | ADI-41437 | Heavy chain variable region ("HC") amino acid sequence |
| Ab 721 | 1442 | EIVLTQSPDSLAVSLGERATINCKSSQSVLYRANNRNYLAWYQQKPGQPPKLLIYWA STRESGVPDRFSGSGSGTDFTLTISSLQAEDVALYYCHQYHSSPRTFGQGTKVDIK | ADI-41437 | Light chain variable region ("LC") amino acid sequence |
| Ab 722 | 1443 | QVQLVQSGAEMRRPGSSVRLPCKASGYTFVSHTIVWVRQAPGQGLEWMGGIIPS LRTPNYAQNFQDRLTITADESARTAYMELSSLTSNDTAVYYCARETFQGGYYLDYW GQGTLVTVSS | ADI-41438 | Heavy chain variable region ("HC") amino acid sequence |
| Ab 722 | 1444 | EIVMTQSPGTLSVSPGDTAALSCRASQSVGRNLAWYQQKPGQAPRLLIFGASTRAA DIPGRFSGSGSGTEFTLTITSLQSEDFAVYYCQQYNKWPPYTFGQGTKVEIK | ADI-41438 | Light chain variable region ("LC") amino acid sequence |
| Ab 723 | 1445 | QVQLVQSGTEVKNPGASVKVSCKASGYTFSNYGITWVRQAPGQGLEWMAWISAY NGNILYAQNVQGRVTMTTDTSTSTGYMELRSLRSDDTAVYYCARDAPAGTLTLLDY WGQGTLVTVSS | ADI-41439 | Heavy chain variable region ("HC") amino acid sequence |
| Ab 723 | 1446 | DIVMTQTPLSLPVTLGQPASISCRPSQSLVYSDGNTYLNWFQQRPGQSPRRLIYKVS NRDSGVPDRFSGSGSGTDFTLRISRVEAEDVGVYYCMQGSHWPYAFGQGTKVEIK | ADI-41439 | Light chain variable region ("LC") amino acid sequence |
| Ab 724 | 1447 | EVQLVESGGGLVKPGGSLRLSCAVSGFTFSDYTMNWVRQAPGKGLEWVSSISGSG TYIYYGDSVKGQFTISRDNAKNSLYLQMNSLRAEDTAVYYCARELPAKTIFGVDFLG GTTAYDCWGQGTPVTVSS | ADI-41440 | Heavy chain variable region ("HC") amino acid sequence |
| Ab 724 | 1448 | EIVLTQSPATLSVSPGERATLSCRASQSVSSNLAWYQQKPGQAPRLLIYSATTRATG VPARFSGSGSGTEFTLTISSLRSEDFAVYYCQQYNNGGTFGPGTKVEIK | ADI-41440 | Light chain variable region ("LC") amino acid sequence |
| Ab 725 | 1449 | EVQLVQSGPGLVKPSETLSLTCSVSGASISRYHYYWGWIRQSPGKGLEWIGTIYYSG TTYYNPSLESRVTISADTSKNQVSLKLTSVTAADTAVYYCARGSGDTALDFSFEYWG QGALVTVSS | ADI-41441 | Heavy chain variable region ("HC") amino acid sequence |
| Ab 725 | 1450 | DIQLTQSPSFLSASVGDRITITCRASQGISNSLAWYQQKPGKAPKLLIYAASTLQFA VPSRFSGSGSGTEFTLTISSLQPEDFATYYCQQLDSYPLTFGGGTKLEIK | ADI-41441 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 726 | 1451 | EVQLLESGGGLVQPGRSLRLSCAASGFTFDDYAMHWVRQAPGKGLEWVSGISWH SGSIVYADSVKGRFTISRDNAKNSLYLQMSSLRAEDTALYYCVKDHYNWNDNPHFH YGLDVWGQGTTVTVSS | ADI-41442 | Heavy chain variable region ("HC") amino acid sequence |
| Ab 726 | 1452 | EIVLTQSPATLSVSPGERATLSCRASQSVISNLAWYQQKPGQAPRLFIYGASTRATG IPARFSGSGSGTEFTLTISSLQSEDFAVYFCQQYNNWPITFGQGTRLEIK | ADI-41442 | Light chain variable region ("LC") amino acid sequence |
| Ab 727 | 1453 | EVQLVESGGGVVQPGKSLRLSCAASGFTFSSYAMHWVRQAPGKGLEWVSVIWYE DSDKYYGDSVKGRFTISRDNSKNTLYLQMNSLRAEDTAVYYCARKSGGFGGLDYW GQGTLVTVSS | ADI-41443 | Heavy chain variable region ("HC") amino acid sequence |
| Ab 727 | 1454 | DIVMTQSPLSLPVTPGEPASISCKSSQSLLTANGYNYLDWYVQKPGQSPHVLISLGS NRASGVPDRFSGSGSGTDFTLKISRVEAEDVGVYYCMQAIETPITFGQGTRLEIK | ADI-41443 | Light chain variable region ("LC") amino acid sequence |
| Ab 728 | 1455 | EVQLVESGPRLVKPSQTLSLTCTVSGGSIGTGDYHWTWIRQSPGKGLEWIGNIYYN GRTFYNPSLKGRGSISRDASKNQFSLNLSSVSAADTAVYYCARDRAAKGFDHWGQ GTLVTVSS | ADI-41444 | Heavy chain variable region ("HC") amino acid sequence |
| Ab 728 | 1456 | DIQLTQSPSTLSASVGDRVTITCRASQNINGWLAWYQQKPGRVPKLLIYKASTLESG VPSRFSGSASGTEFTLTINNLLPDDFATYYCQQYNDYPYTFGQGTKVEIK | ADI-41444 | Light chain variable region ("LC") amino acid sequence |
| Ab 729 | 1457 | QVQLVQSGAEVKRPGSSVKVSCKAFGGSFSNYAINWVRQAPGQGLEWMGGISPV LGTAIYAKRFQGKVTITADKFANTAYMDLSSLRFEDTAVYYCARSPPHVEFPLTKWF DPWGQGTLVTVSS | ADI-41445 | Heavy chain variable region ("HC") amino acid sequence |
| Ab 729 | 1458 | EIVMTQSPGTLSLSPGERATLSCRASQSVNSGYLAWYQHKPGRAPRLLIYGASNRAT GVPDRFSGSGSGTDFTLTISRLEPEDFAVYYCQQYDNSLFTFGPGTKVDIK | ADI-41445 | Light chain variable region ("LC") amino acid sequence |
| Ab 730 | 1459 | EVQLLESGGGLVQPGGSLRLSCAASGFTYYSYAMNWVRQAPGKGLEWVSAISGG GDNTFYAESVKGRFTISRDNAKNTLYLQMDSLRAEDTAVYYCAKDLQGYTSLYCFDY WGQGTLVTVSS | ADI-41446 | Heavy chain variable region ("HC") amino acid sequence |
| Ab 730 | 1460 | EIVMTQSPATLSLSPGERAALSCRASQSVFNYVAWYQQKPGQAPRLLIYDTSKRAT GIPARFSGSGSGTDFTLTISSLEPEDFAVYYCQHRYNWPGLIFGGGTKVEIK | ADI-41446 | Light chain variable region ("LC") amino acid sequence |
| Ab 731 | 1461 | EVQLLESGGGLVQPGGSLRLSCAASGFTFSTYAMNWVRQAPGKGLEWVSTISGSG GSTYYGDSVKGRFTISRDNSKNTLYLQMNSLRAEDTAVYYCAKAPTPWCSGGSCYV SYWGQGTLVTVSS | ADI-41447 | Heavy chain variable region ("HC") amino acid sequence |
| Ab 731 | 1462 | DIVMTQTPGTLSLSPGERGTLSCRASQSVSSSYLAWYQQKPGQAPRLLIYGASSRAT GIPDRFGGSGSGTDFTLTISTLEPEDFAVYYCQQYQSSPWTFGQGTKLEIK | ADI-41447 | Light chain variable region ("LC") amino acid sequence |
| Ab 732 | 1463 | TVQLVESGAEVKSPGSSVRVSCQASGGSSNSYAISWVRQAPGQGLEWMGMISPLF GTTRFSQRFQGRVTITADKSTSTAYMELSSLNSEDTALYYCARGRFDFWSGPTRFY YTMDVWGQGTMVTVSS | ADI-41448 | Heavy chain variable region ("HC") amino acid sequence |
| Ab 732 | 1464 | QSVLIQPASVSGSPGQSITISCSGTSSDIGGYNYVSWYQQHPGKAPKLLISDVTDR PSGISDRFSGSKSGTSASLTISGLQADDEADYYCTSYTTSSTWVFGGGTKLTVL | ADI-41448 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 733 | 1465 | EVQLVESGGGLVKPGGSLRLSCAASGFSFSSYRVNWVRQAPGKGLEWVSSITGGSS FIDYADSVKGRFTISRDNAKNSLFLQMNSLRAEDTAVYFCARDSMTTVTNSLAFDI WGQGTMVTVSS | ADI-41449 | Heavy chain variable region ("HC") amino acid sequence |
| Ab 733 | 1466 | QSVLTQPPSVSGAPGQRVTISCTGSSSNIGVGYDVQWYQQLPGTAPKLLIYSNNKR PSGVPDRFSGSKSGTSASLAITGLQAEDEADYYCQSYDRSLSVVFGGGTKVTVL | ADI-41449 | Light chain variable region ("LC") amino acid sequence |
| Ab 734 | 1467 | EVQLVESGGGLVKPGGSLRLSCAASGFAFSSYGINWVRQVPGKRLEWVSSISGGSS FINYADSVKGRFTISRDNAGNSVYLQMNSLRAEDTAVYFCARESYGSGSSLNWFDP WGQGTLVTVSS | ADI-41450 | Heavy chain variable region ("HC") amino acid sequence |
| Ab 734 | 1468 | QSVLTQPPSVSGAPGQRVTISCTGSGSNIGAGYDVHWYQQLPGIAPRLVIFGNRNR PSGVPDRISGSKSDTSASLAITGLQAEDEGDYYCQSYDKRLSGWVFGGGTKLTVL | ADI-41450 | Light chain variable region ("LC") amino acid sequence |
| Ab 735 | 1469 | EVQLVESGGGLVQPGGSLRLSCAAAGFTFNNYEMHWVRQAPGKGLEWVSCVTSS GTATYYADSVKGRFTVSRDNAKKSLQLQMNSLRAEDTAVYYCARELYLGEDYYYGL DVWGQGTTVTVSS | ADI-41451 | Heavy chain variable region ("HC") amino acid sequence |
| Ab 735 | 1470 | SYELTQPPSVSVSPGQTASISCSGDKLRNKHTCWYQHKSGQSPVLLIYQDNRRPSGI PDRLSGSKSGTTATLTISWTQAMDEAEYYCQAWDSNSAVIFGGGTKLTVL | ADI-41451 | Light chain variable region ("LC") amino acid sequence |
| Ab 736 | 1471 | QVQLVQSGAELKKPGASVKVSCKASGHTFATYAIHWVRQAPGQSLEWLGWINTA NGDTKYSQKFRATVTIHGDTSANTVYLELSRLRSEDTAVYYCASPPLVGAINLEFWG PGTLVTVSS | ADI-41452 | Heavy chain variable region ("HC") amino acid sequence |
| Ab 736 | 1472 | QSVLTQPASVSGSVGQSITISCTGTSSDVGGYNSVSWYQHHPDKAPKLIIYEVSNRP SGVSHRFSGSKSGNTASLTISGLQAEDEADYYCSSYTTSDTLIFGGGTKVTVL | ADI-41452 | Light chain variable region ("LC") amino acid sequence |
| Ab 737 | 1473 | QVQLVQSGAEVRKPGASVKVSCKASGYTFSIYDMNWVRQAPGQGLEWMGWM NPNSGNTGYAQKFQGRVTMTGDTSISTAYMELSSLTSEDTAVYYCAVMYGDYPGY WGQGSLVTVSS | ADI-41453 | Heavy chain variable region ("HC") amino acid sequence |
| Ab 737 | 1474 | SYELTQPLSVSVALGQTARITCGGNNIGSKSVHWYQQKPGQAPVLVIYRDAKRPSGI PERFSGSNSGNTATLTISGAQAGDEADYYCQVWDSNAWIFGGRTKLTVL | ADI-41453 | Light chain variable region ("LC") amino acid sequence |
| Ab 738 | 1475 | QVQLVQSGAEVKKPGASVKVSCKASGYTFTHFGISWVRQAPGQGLEWMGWISIY NGNTNYAQKIQGRATMTTDASTSTAYMELRSLTSDDTAVYYCAREPPSTTAAATSD YWGQGTLVTVSS | ADI-41454 | Heavy chain variable region ("HC") amino acid sequence |
| Ab 738 | 1476 | DIVMTQSPLSLPVTLGQPASISCRSSQSLVYIEGNTYLSWFQQRPGQSPRRLIYKVS NRDSGVPDRFSGSGSGTDFTLKISRVEAEDVGLYYCMQGTHWPRTFGQGTKLEIK | ADI-41454 | Light chain variable region ("LC") amino acid sequence |
| Ab 739 | 1477 | QVQLQESGPGLVKPSQTLSLTCSVSEGSVISGDYYWSWIRQSPGKGLEWLGYIHYS GSTYYNPSLKSRVTISVDTSKKQFSLKLSSVTAADTAVYYCARDLGCIGGVCSAYGL EHNYYFGMDVWGQGTTVTVSS | ADI-41455 | Heavy chain variable region ("HC") amino acid sequence |
| Ab 739 | 1478 | EIVLTQSPATLSLSPGERATLSCRASQSVSSYLAWYQQKPGQAPRLLIYTASNRATG IPARFSGSGSGTDFTLTISSLEPEDFAVYYCQQRSSWPPYTFGQGTKLEIK | ADI-41455 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 740 | 1479 | EVQLLESGGGLFHPGGSLTLSCVASGFTLSTYYMHWVRQAPGKGLVWVARINSDG GYTTYADSVKGRFTVSRDNAKNTLYLQMNSLRVEDTAVYYCAREWVEFDSWGQG TLVTVSS | ADI-41456 | Heavy chain variable region ("HC") amino acid sequence |
| Ab 740 | 1480 | NFMLTQPHSVSASPGKTVTISCTRSSGNIASNYVQWYQQRPGSSPTTVITEDNQRP SGVPDRFSGSIDSSSNSASLTISGLKTEDEADYYCQSYDSSTYVFGTGTKLTVL | ADI-41456 | Light chain variable region ("LC") amino acid sequence |
| Ab 741 | 1481 | EVQLVESGGGLVRPGGSLRVSCAASGFTFIRYDMHWVRQAPGKGLEWVSGIGTA GDTYYAASVQGRFTISRENAKNSLYLQMSNLRPGDTAVYYCAGSMAATGIDQWG QGTLVTVSS | ADI-41457 | Heavy chain variable region ("HC") amino acid sequence |
| Ab 741 | 1482 | EIVMTQSPLTLPVTPGEPASISCRSSQSLLHSNGFTYLDWFLQKPGQSPQLLIFLG SNRASGVPDRFSGSGSGTDFTLKISRVEAEDVGIYYCMQALQTPYTFGQGTKVEIK | ADI-41457 | Light chain variable region ("LC") amino acid sequence |
| Ab 742 | 1483 | EVQLLESGSGLVKPSQTLSLTCAVSGDSLNSALYSWSWIRQPPGKGLEWIGYIYYSG STYYNSSLKSRVTISIDRSKNQFSLNLNSVTAADTAVYYCASLQTGYSSGWFFDFWG PGTLVTVSS | ADI-41458 | Heavy chain variable region ("HC") amino acid sequence |
| Ab 742 | 1484 | EIVLTQSPGTLSLSPGERATLSCRASQSVSRTYLTWYQQKPGQAPRLLIYGASNRAT GIPDRFSGSGSGTDFTLTISRLEPEDFAVYYCQQYGSTPLFGQGTKVEIK | ADI-41458 | Light chain variable region ("LC") amino acid sequence |
| Ab 743 | 1485 | QVQLVESGGGLVQPGGSLRLSCAASGFPFSAYGINWVRQAPGKGLEWVSYISSTST TIKYADSVKGRFTISRDDAKNSLYLQLRSLRPEDTAVYYCAGGVWSGYYIDFWGQG TPVTVSS | ADI-41459 | Heavy chain variable region ("HC") amino acid sequence |
| Ab 743 | 1486 | NFMLTQPQSVSESPGKTVTISCTRSSGSIGSNFVQWYQQRPGSSPTTVIYEDYQRPS GVPDRFSGSIDSSSNSASLTISGLKTEDEADYYCQSYDADMMVFGGGTKLTVL | ADI-41459 | Light chain variable region ("LC") amino acid sequence |
| Ab 744 | 1487 | QVTLKESGPALVKPTQTLTLTCTFSGFSLNTRGMCVSWVRQPPGKALEWLARIDW DDDKNYSTSLRTRLTISKDTSRNQVVLAMANMDPVDTATYYCARCARYDRSGYYV WYLDSWGQGTLVTVSS | ADI-41460 | Heavy chain variable region ("HC") amino acid sequence |
| Ab 744 | 1488 | DIQMTQSPSSLSASVGDRVTITCRASQTIASYLNWYQQKPGKAPKLLIYVASTLQSG VPSRFSGSGSGTDFTLTISSLQPEDFATYYCQQSYSLTQWTFGQGTKVEIK | ADI-41460 | Light chain variable region ("LC") amino acid sequence |
| Ab 745 | 1489 | QVQLVQSGAEVKKPGASVKVSCRASGYTFSSYDINWVRQATGQGLEWMGWMS PNSANTGYAQKFQGRVTMTRDTSINTAYMELSSLSSEDTAVYYCARFLGYCSGGSC YPGYGMDVWGQGTTVTVSS | ADI-41461 | Heavy chain variable region ("HC") amino acid sequence |
| Ab 745 | 1490 | EIVLTQSPDSLAVSLGERATINCKSSQNVLYSSNNKDYLSWYQQKPGQPPKLLIYWA STRESGVPDRFSGSGSGTDFTLTINSLQAEDVAVYYCQQYYGTPYTFGQGTKLEIK | ADI-41461 | Light chain variable region ("LC") amino acid sequence |
| Ab 746 | 1491 | QVQLQQWGAGLVKPSETLSLSCDVYGGSFSGYYWTWIRQPPGKGLEWIGEINHS GRTNYNPSLKNRVTISVDTSKKQFSLKLSSVTAADTAVYFCARAPYYDIVTDYNITT AYFYGMDVWGQGTTVTVSS | ADI-41462 | Heavy chain variable region ("HC") amino acid sequence |
| Ab 746 | 1492 | DIQMTQSPDSLAVSLGERATINCRSSQSVLYSSNNKNYLTWYQQKPGQPPKLLIYW ASTRESEVPDRFSGSGSGTDFSLTISSLQAEDVAVYYCQQYYNTPLTFGGGTKVEIK | ADI-41462 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 747 | 1493 | QVQLVQSGAEVKKPGASVKVSCTASGYSFTDYDISWVRQAPGQGLEWMGWISAY NGNTNYAQKFQDRVTMNTDTSTNTAYMELRGLRSDDTAVYYCARNCYYGSGTCYI EDYYFDYWGQGTLVTVSS | ADI-41463 | Heavy chain variable region ("HC") amino acid sequence |
| Ab 747 | 1494 | DIQMTQSPSSLSASVGDRVTITCRASQDIKNDLGWYQQKPGKPPKRLIYGASRSQS GVPSRFSGSGSGTDFTLTIYSLQPEDFATYYCLQHSDYPFTFGQGTRLEIK | ADI-41463 | Light chain variable region ("LC") amino acid sequence |
| Ab 748 | 1495 | QVQLVESGPGLVRPSGTLSLTCTVSGDSVNSYRWSWIRQSPGKGLEWIGYISYSGET NYNPSLKSRVSISVGTSRYQFFLKLSSVTAADTATYYCARDKTTIFGVSHYYFGVDV WGQGTTVTVSS | ADI-41464 | Heavy chain variable region ("HC") amino acid sequence |
| Ab 748 | 1496 | DIVMTQTPLSLPVTPGEPASISCRSSQSLLKSDGYNSLDWYLQRPGQSPQLLIYLGS NRASGVPARFSGSGSGTDFTLKISRVEAEDVGVYYCMQALQTPFTFGPGTKVEIK | ADI-41464 | Light chain variable region ("LC") amino acid sequence |
| Ab 749 | 1497 | QVQLVQSGGGVVQPGRSLRLSCAASGFTFTSYDMHWVRQAPGKGLEWVAIISHD GSKQFYADSVKGRFTISRDNSKNTLYLQMNSLRPEDTAMYYCAKDTPSWGLLAEFF RHWGQGTLVTVSS | ADI-41465 | Heavy chain variable region ("HC") amino acid sequence |
| Ab 749 | 1498 | EIVLTQSPDSLAVSLGERATINCKSSQSVLYSSNDKDYLAWYQHKPGQPPKLLIYWA STRESGVPDRFSGSGSGTDFTLTISSLQAEDVAVYYCQQYYGTPYTFGQGTKVEIK | ADI-41465 | Light chain variable region ("LC") amino acid sequence |
| Ab 750 | 1499 | QVQLVQSGAEVKKPGASVKVSCKASGYTFNFYYMHWVRQAPGQGLEWMGWIN PKSGGTSYAQKFQGRVIMTGDTSISTTYMELSRLRSDDTAVYYCARADTGLELDVW GQGTTVTVSS | ADI-41466 | Heavy chain variable region ("HC") amino acid sequence |
| Ab 750 | 1500 | QSALIQPASVSGSPGQSITISCTGTSSDVGGYNYVSWYQQHPGKAPKLILYDVSKRP SGVSNRFSGSKSGNTASLTISGLQAEDESDYFCSSYTRSNTVVFGGGTKVTVL | ADI-41466 | Light chain variable region ("LC") amino acid sequence |
| Ab 751 | 1501 | EVQLVESGGGLVKPGGSLRLSCAASGFSFSSYNMNWVRQAPGKGLEWVSSISGGS SFVNYADSVKGRFTISRDNAKNSLYLQMSSLKAEDTAIYYCARDPVYCSAASCSAYF DSWGQGSLVTVSS | ADI-41467 | Heavy chain variable region ("HC") amino acid sequence |
| Ab 751 | 1502 | QSVLTQPPSVSGAPGQRVTISCTGSSSNIGAGYDVHWYQQLPGTAPKLLIYGNNNR PSGVPDRFSGFKSGSSASLAITGLQAEDEADYYCQSYDIGLSDSHVVFGGGTQLTVL | ADI-41467 | Light chain variable region ("LC") amino acid sequence |
| Ab 752 | 1503 | QVQLQQWGAGPLKSSETLSLTCEVYGGPFSGYSWSWIRQPPGKGLEWIGEINHSG STNYNPSLKSRVSFSVDTSKNQFSLKLSSVTAADTAVYYCARGAGFCTSTSCPPGLY YYYGMDVWGHGTTVTVSS | ADI-41468 | Heavy chain variable region ("HC") amino acid sequence |
| Ab 752 | 1504 | SYELTQPLSVSVALGQTARITCGGNNIESKNVHWYQQMPGLAPVMVIYRDTNRPS GIPERFSGSNSGNTATLTISRAQAGDEADYYCQVWDSGTVIFGGGTKLTVL | ADI-41468 | Light chain variable region ("LC") amino acid sequence |
| Ab 753 | 1505 | EVQLVESGGGVVQPGRSLRLSCAASGFTFSSYGMHWVRQAPGKGLEWVAVISYD GSFIKYADSMMGRFTISRDNSKNTLYLQMSSLRPEDTATYYCAKDALIPEYWGQGT LVTVSS | ADI-41469 | Heavy chain variable region ("HC") amino acid sequence |
| Ab 753 | 1506 | QPVLTQPASVSGSPGQSITISCTGTSSDVGGYNYVSWYQKHPDKAPRVIIYEVSNRP SGVSNRFSGSKSGNTASLTISGLQAEDEADYYCCSYTSTSGVVFGGGTKLTVL | ADI-41469 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 754 | 1507 | QVQLVQSGADVKKPGSSVKISCKASGGSFITNSLSWVRRAPGQGLEWMGGIIPVS GTTTYAQKFLGRVTFTADESTSTAYMELNSLRSEDTAVYYCARFLGTPYPNVHYGM DVWGQGTTVTVSS | ADI-41471 | Heavy chain variable region ("HC") amino acid sequence |
| Ab 754 | 1508 | DIRVTQSPSSLSASVGARVTITCRASQSISTYLNWYQEKPGKAPKLLIYAASSLQR GVPSRFSGSGSETTFTLTISSLQPEDFATYYCQQSYTAAYNFGQGTKVEIK | ADI-41471 | Light chain variable region ("LC") amino acid sequence |
| Ab 755 | 1509 | QVQLVQSGAEVKKPGSSVKVSCKASGGTFSSYAISWVRQAPGQGLEWMGRIIPVL DITNYAQKFQGRVTIMADKSTSTAYMELSSLRSEDTAIYYCARETSNFYFYYNAMDV WGQGTTVTVSS | ADI-41472 | Heavy chain variable region ("HC") amino acid sequence |
| Ab 755 | 1510 | QPVLTQPPSASGSPGQSVTISCTGTSSDVGGDNYVSWYQQHPGKAPKLLIYEVSKR PSGVPDRFSGSRSGHTASLTVSGLQAEDEADYYCSSYAGRNNLGVFGGGTKLTVL | ADI-41472 | Light chain variable region ("LC") amino acid sequence |
| Ab 756 | 1511 | QVQLVQSGPGLVKPSQTLSLTCAISGDSVSSNSAAWSWIRQSPSRGLEWLGRTYYR SKWYYDHAVSVEGRITINADTSKNHFSLQLNSVTPEDTAVYYCARDPDSGNYFHYY GMDVWGQGTTVTVSS | ADI-41473 | Heavy chain variable region ("HC") amino acid sequence |
| Ab 756 | 1512 | ETTLTQSPATLSLSPGERATLSCRTSQSVSSYLAWYQQKPGQAPRLLIYDASRRAT GIPARFSGSGSGTHFTLTITSLEPEDFAVYYCQQRSKWPPYSFGQGTKVDIK | ADI-41473 | Light chain variable region ("LC") amino acid sequence |
| Ab 757 | 1513 | QVQLVQSGAEVKRPGASVKVSCKISGYTFTSHYIHWLRQAPGQGLEWMGWINPN TGDTKYEQKFQGRVTMTRDTSLSTAYMELRRLRSDDTAVYYCARDSFYAANGYYFV WFDPWGQGALVTVSS | ADI-41474 | Heavy chain variable region ("HC") amino acid sequence |
| Ab 757 | 1514 | DIQMTQSPTSLSASVGDRVTITCRASQSISSYLNWYQQKPGKAPRFLIYAASSLQS GVPSRFRGSGSGTDFTLTISSLQPEDFATYYCQQSYSSPYTFGQGTKVEIK | ADI-41474 | Light chain variable region ("LC") amino acid sequence |
| Ab 758 | 1515 | QVQLQESGPGLVKPSQTLSLTCAISGDSVSSNSAAWNWIRQSPSRGLEWLGRTYYR SKWWTDYAVSVKSRITINPDTSKNQFSLQLNSVTPEDTAVYYCARDPDSGNYFHYY GMDVWGQGTTVTVSS | ADI-41475 | Heavy chain variable region ("HC") amino acid sequence |
| Ab 758 | 1516 | ETTLTQSPATLSLSPGERATLSCRASQSASSYLAWYQQKPGQAPRLLIYDASKRAT GIPARFSGSGSGTDFSLTISSLEPEDFAVYYCQLRSKWPPYTFGQGTKVEIK | ADI-41475 | Light chain variable region ("LC") amino acid sequence |
| Ab 759 | 1517 | EVQLLESGGGLVQPGGSLRLSCATSGFRFTRYWMHWVRQAPGKGLEWVARINFD GTTTNYADSVKGRFTVSRDNAKNTLYLQINSLRAEDTAVYFCARDQTFLEWLPFES WGQGTLVTVSS | ADI-41476 | Heavy chain variable region ("HC") amino acid sequence |
| Ab 759 | 1518 | QTVVTQEPSFSVSPGGTVTLTCGLTSGSVSTSYYPSWYQQTPGQAPRTLIYNTKTR FSGVPDRFSGSILGNKAALTITGAQADDESDYYCVLYMSGGMVFGGGTKLTVL | ADI-41476 | Light chain variable region ("LC") amino acid sequence |
| Ab 760 | 1519 | QVQLVQSGAEVKKPGASVRVSCKASGYPFISYYIHWVRQAPGQGLEWMGMINTN GGSTHYAQKFQGRVTMTRDTSTTTIYMELSRLKSEDTAYYFCARDNTETVLHGFWS GYGSYLDYWGQGTLVTVSS | ADI-41477 | Heavy chain variable region ("HC") amino acid sequence |
| Ab 760 | 1520 | EIVLTQSPGTLSLSPGGRATLSCRASQSVTSSYLAWYQQRPGQAPRLLIYGASSR AAGIPDRFSGSGSGTDFTLTISRLEPEDFAVYYCQQYGSAPLTFGGGTKLEIK | ADI-41477 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 761 | 1521 | QVQLVQSGAEVKKPGESLKISCKGSGYSFISYWIGWVRQMPGKGLEWMGIIYPAD SDTRYSPSFQGQVTISVDKSISTAYLQWSSLKASDTGMYYCVRYGVGGTAPRYWG QGTTVTVSS | ADI-41479 | Heavy chain variable region ("HC") amino acid sequence |
| Ab 761 | 1522 | NFMLTQPHSVSESPGKTVTISCTGSSGSIASNYVHWYQQRPGSAPTTVIYEDNQR PSGVPDRFSGSIDSSSNSASLTISGLKTEDEADYYCQSYDISNLWVFGGGTKLTVL | ADI-41479 | Light chain variable region ("LC") amino acid sequence |
| Ab 762 | 1523 | EVQLLESGPGLVRPSGTLSLTCTVSGDSISGSNWWAWVRQPPGRRLEWIGEIYYRG ATDYNSSLKSRVIISVDNSKNQFSLNLRSVTAADTAIYYCARVEKFATSGYYISYF DYWGQGTLVTVSS | ADI-41480 | Heavy chain variable region ("HC") amino acid sequence |
| Ab 762 | 1524 | DIRVTQSPSSLSASVGDRVTITCRASQSISTYLNWYQHPGKAPKLLIYAASSLQS GVPSRFSGSGSGTHFTLTISSLQPADFSTYYCQQSYSSPWTFGQGTKVEIK | ADI-41480 | Light chain variable region ("LC") amino acid sequence |
| Ab 763 | 1525 | QVQLVESGPGLVKPSETLSLACSVSGVSISTYYWTWIRQPPGKGLEWIGYISYSGS TNYNPSLKSRVTISADTSKNQFSLRLNSVTAADTAVYYCARTYYDFWSTYYGEFDH WGHGTLVTVSS | ADI-41481 | Heavy chain variable region ("HC") amino acid sequence |
| Ab 763 | 1526 | SYELTQPLSVSVALGQTARITCGGNNIESKNVHWYQQKPGQAPVVVMYRDTNRPS GIPERFSGSNSGNTATLTISRAQAGDEADYYCQVWDSGTAGVVFGGGTKVTVL | ADI-41481 | Light chain variable region ("LC") amino acid sequence |
| Ab 764 | 1527 | QVQLVQSGAEVKKPGSSVKVSCKASGGTFGSYTINWVRQAPGQGLEWMGGIIPIF GATNYAQNFQGRVSITADKSTATAYMDLISLRSEDTAVYYCARLGRSSPLNSCTTTS CYFWGRGMDVWGQGTTVTVSS | ADI-41482 | Heavy chain variable region ("HC") amino acid sequence |
| Ab 764 | 1528 | QSVLIQPASVSGSPGQSITISCTGTISDVGIYNYVSWYQQHPGKAPKLIISDVSDRP SGVSNRFSGSKSGITASLTITGLQAEDEADYYCSSYSSSTLYVFGTGTKLTVL | ADI-41482 | Light chain variable region ("LC") amino acid sequence |
| Ab 765 | 1529 | EVQLVESGPGLVKPSEALSLTCTVSGASISSYYWTWIRQSPRKGLEWIGYIYHTGRT NYNPSLKRVTMSVDWSKNQFSLTLSSVTAADTAVYYCARLKVVPAALESAILEHHF GLDVWGQGTTVTVSS | ADI-41484 | Heavy chain variable region ("HC") amino acid sequence |
| Ab 765 | 1530 | DIVMTQTPSTLSASIGDRVTLTCRASQSINRWLAWYQQKPGKAPKLLIYKASTLESG VPSRFSGSGSGTEFTLTISGLQPDDFATYYCQQYNNFPYTFGPGTKVDIK | ADI-41484 | Light chain variable region ("LC") amino acid sequence |
| Ab 766 | 1531 | EVQLLESGPGLVRPSETLSLTCTVSGGSLDSGPHYWNWIRQPPGKGLEWIGYIYYSV STNYNPSLKSRVTISMDTSKNQFSLNLTSVTAADTAVYYCASFQLIYGPQIWGQGKK VTVSS | ADI-41485 | Heavy chain variable region ("HC") amino acid sequence |
| Ab 766 | 1532 | DIVLTQSPSSVSASVGDRVTITCRASQAISSWLIWSQHPGKAPKVLIYAASSLQSG VPSRFSGSGSGTDFTLTISSLQPEDFATYYCQQANNFPLTFGGGTKVEIK | ADI-41485 | Light chain variable region ("LC") amino acid sequence |
| Ab 767 | 1533 | QVQLQQWGAGLLKPSETLSLTCSVYGGSFSGYYWSWIRQPPGKGLEWIGEINHSG STNYNPSLKSRITISVDTSKNQFSLKLNSVTAADTAVYYCARGDYAFVTFDYWGQGT LVTVSS | ADI-41486 | Heavy chain variable region ("HC") amino acid sequence |
| Ab 767 | 1534 | QSVLTQPASVSGSPGQSITISCTGTSSDVGGYNYVSWYQQHPGKAPKLMIYEVSNR PSGVSNRFSGSKSGNTASLTISGLQAEDEADYYCSSYTSSSTPVFGGGTKLTVL | ADI-41486 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 768 | 1535 | QVQLVESGGGLVKPGGSLRLSCAASGFTFSTYTMNWVRQAPGKGLEWVSSISGSS AYIYYADSVKGRFTISRDNAKNSLFLQMNSLRAEDTAVYYCARLQGLVLPAVMPSYY YYSGMDVWGQGTTVTVSS | ADI-41487 | Heavy chain variable region ("HC") amino acid sequence |
| Ab 768 | 1536 | EIVMTQSPLSLPVTPGEPASISCRSSQSLLHSNGYNYLDWYLQKPGQSPQLLIYLAS NRASGVPDRFSGSGSGTDFTLKISRVEAEDVGVYYCMQALQTPQAFGQGTKVEIK | ADI-41487 | Light chain variable region ("LC") amino acid sequence |
| Ab 769 | 1537 | EVQLVESGPGLVKPSETLSLTCTVSGGSINSDYWNWIRQTPGKGLEWIGYIFYSGNT NYNPSLKSRVTISIDTSKKKFSLQVTSVTAADTAVYYCARMGTLKFDFDNWGQGTL VTVSS | ADI-41488 | Heavy chain variable region ("HC") amino acid sequence |
| Ab 769 | 1538 | QSALTQPRSVSGSPGQSVTIPCTGTSSDVGAYKYVSWYQQHPGKAPKLIIYDVTKRP SGVPNRFSGSKSGNTASLTISGLQAEDEADYYCCSYAGTHTYWVFGGGTKVTVL | ADI-41488 | Light chain variable region ("LC") amino acid sequence |
| Ab 770 | 1539 | EVQLVESGGGVVQPGRSLRLSCAASGFNFHNYAFHWVRQAPGKGLDWVAVTSYD GSSAFYADSVKGRFTISRDNSKKILYLQMTSLRAEDTALYYCARGSSSWSGDYFDYW GQGILVTVSS | ADI-41489 | Heavy chain variable region ("HC") amino acid sequence |
| Ab 770 | 1540 | DIVMTQSPVTLSVSPGERATLSCRASQSVGSNLAWYQQKHGQTPRLLIYDASTRAT SIPARFSGSGSGTEFTLTISSLQSEDFAVYYCQQYNKWPSYTFGQGTKVEIK | ADI-41489 | Light chain variable region ("LC") amino acid sequence |
| Ab 771 | 1541 | EVQLLESGGGLVQPGGSLRLSCAASGFTFSSYSMNWVRQAPGKGLEWVSYMSSD RSAIYYSDSVKDRFTISRDNAKNSLYLQMHSLRAEDTAVYYCARRYCSSTSCYRGLG YYYGMDVWGQGTTVTVSS | ADI-41491 | Heavy chain variable region ("HC") amino acid sequence |
| Ab 771 | 1542 | SYELTQPPSVSVAPGQTARITCGGSNIGNKDVHWYQQKPGQAPVLVVYDDSDRPS GIPERFAGSNSGNTATLTISRVEAGDEADYYCQVWHSAGDHVVFGGGTKLTVL | ADI-41491 | Light chain variable region ("LC") amino acid sequence |
| Ab 772 | 1543 | QVQLVQSGAEVRKPGSSVKVSCKASGGTFNSFVISWVRQAPGQGLEWMGRIIPIL ATVDYAQKFQGRVTITADKSTTTAYMELSGLTSEDTAVYYCARDPPRWDTTMADY YYQGMDVWGQGTTVTVSS | ADI-41492 | Heavy chain variable region ("HC") amino acid sequence |
| Ab 772 | 1544 | DIRVTQSPASLSAFVGDRVTISCRASQSIGSFLNWYQQKPGKAPKLLIYAASSLQS GVPSRFSGSGSGTDFTLAISSLQPEDFATYYCQQSYRSTPTFGGGTKVEIK | ADI-41492 | Light chain variable region ("LC") amino acid sequence |
| Ab 773 | 1545 | QVQLVQSGAEVKKPGESLKISCKGSGYSFTKYWIGWVRQLPGKGLEWMGIIYPGD SETIYSPSFQGQVTISADKSVSTAYLQWSSLKASDTAMYYCARQTFVFWGESHDAF DIWGQGTTVTVSS | ADI-41493 | Heavy chain variable region ("HC") amino acid sequence |
| Ab 773 | 1546 | QPVLTQPPSASGSPGQSVTISCTGTSSDVGAHNYVSWYQQHPGKAPKLMIYEVSK RPSGVPDRFSGSKSGNTASLTVSGLQAEDEADYYCSSYAGSNNWVFGGGTKLTVL | ADI-41493 | Light chain variable region ("LC") amino acid sequence |
| Ab 774 | 1547 | EVQLVESGGGLVQPGRSLRLSCTTSGFTFGDYAVTWVRQAPGKGLEWIGIMKSKTY RGTTDYAASLRGRFSISRDDSKSIAYLQMTSLKSEDTGVYYCVRGHDYGDPFDYWG QGTLVTVSS | ADI-41494 | Heavy chain variable region ("HC") amino acid sequence |
| Ab 774 | 1548 | QSVLTQPASVSGSPGQSITISCTGGSSDVGYYNYVSWYQQHPGKAPKLLIYDVNNR PSGVSDRFSGSKSGNTASLTISGLQPEDEADYYCSSYTRSRTWVFGGGTKLTVL | ADI-41494 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 775 | 1549 | QVQLVQSGGGLVEPGGSLRLSCAASGFTFSNTWMNWVRQAPGKGLTWVGRIKR KTDFGTSDYAAPVKGRFTISRDDSKNMVFLQMNSLKIEDTGVYYCTTHPRPYLDTT AVVYWGQGTLVTVSS | ADI-41495 | Heavy chain variable region ("HC") amino acid sequence |
| Ab 775 | 1550 | QPVLTQPHSVSESPGKTVTISCIGSSGSITSNYVQWFQQRPGSAPTTVIYEDDQRPS GVPDRFSGSIDSSSNSASLTISGLKTEDEADYYCQSYHHTNPWVFGGGTKLTVL | ADI-41495 | Light chain variable region ("LC") amino acid sequence |
| Ab 776 | 1551 | QVQLVQSGAEVKKPGASVKVSCKASGYTFTSDDINWVRQATGQGLEWMGWMN PNSGDTGYAQKFQGRVTMTRDTSISTAYMELSSLRSEDTAVYYCARVRIQCSGGRC SYWFFDLWGRGTLVTVSS | ADI-41496 | Heavy chain variable region ("HC") amino acid sequence |
| Ab 776 | 1552 | QSALTQPASVSGSPGQSITISCIGTSSDVGNYNLVSWYQHHPGKAPKVMIYEVNER PSGVSNRFSGSKSGNTASLTISGLQAEDEADYYCCSYAGRSTWVFGGGTKLTVL | ADI-41496 | Light chain variable region ("LC") amino acid sequence |
| Ab 777 | 1553 | QVQLVESGGGVVQPGRSLRLSCAASGFTFSNHAMHWVRQAPGKGLEWLSFISYD GGVNFYRDSVKGRFTISRDNSKNTLYLQMSSLRPEDTAVYYCARDRVGRVVGASYY LDYWGRGALVTVSS | ADI-41497 | Heavy chain variable region ("HC") amino acid sequence |
| Ab 777 | 1554 | QSVVTQPPSVSVAPGQTASITCGGKHIGSKSVHWYQQKPGQSPVLVVHDDSDRPS GILERFSGSNSGNTATLTINRVEAGDEADYYCQVWDNASDHPYVFGPGTKVTVL | ADI-41497 | Light chain variable region ("LC") amino acid sequence |
| Ab 778 | 1555 | EVQLLESGGGLVKPGGSLRLSCAASGFIFSDYAMNWVRQTPGKGLEWVSSISDSSA YKYYTGSVSGRFTISRDNAKNSLYLQMNDLRPEDTAVFYCARGQWRCSGASCYSPF DSWGQGTLVTVSS | ADI-41498 | Heavy chain variable region ("HC") amino acid sequence |
| Ab 778 | 1556 | SYELTQPPSVSVAPGQTARIPCGGNNIESKNVHWYQQKPGQAPVLVVYDDSDRPS GIPERFSGSNSGSTATLTISRVEAGDEADYYCHVWHRSGDLREVFGSGTKVTVL | ADI-41498 | Light chain variable region ("LC") amino acid sequence |
| Ab 779 | 1557 | EVQLVESGGGVVVQPGGSLRLSCAASGFSFDDYTMYWVRQAPEKGLEWISLISWNG GVTYYPDSVKGRFTVSRDNNKNSLYLQMDSLRPEDSAFYYCAKESLESSGHFLDYW GQGTLVTVSS | ADI-41499 | Heavy chain variable region ("HC") amino acid sequence |
| Ab 779 | 1558 | QPVLTQSRSVSGSPGQSVTISCIGTNSDVGGYHYVSWFQHHPGKAPKLMIYDVSRR PSGVPARFSGSKSGNTASLSISGLRAEDEADYYCCSFAGTYTPYVFGTGTKLTVL | ADI-41499 | Light chain variable region ("LC") amino acid sequence |
| Ab 780 | 1559 | QVQLVQSGAEVKKPGSSVKVSCKASGGIFSDFAISWVRQAPGQGLEWMGGIITIIG TPEYAQKFQGRVRITADESTTTVFMELSRLTSEDTAVYYCARDSRYGSGWYWDHW GQGTLVTVSS | ADI-41501 | Heavy chain variable region ("HC") amino acid sequence |
| Ab 780 | 1560 | DIVMTQTPDSLAVSLGERATINCKSSQSVLYISNNKNYLAWYQQKPGQPPKLLIYW ASTRDSGVPDRFSGSGSGTDFTLSISSLQPEDVAVYYCQQYYDTPRTFGQGTKLEIK | ADI-41501 | Light chain variable region ("LC") amino acid sequence |
| Ab 781 | 1561 | QVQLVQSGAEVKKPGSSVKVSCKASGGPFSSDAMSWVRQAPGQGLEWMGGIIPI LGSATYAQKFKGRVTIAADESTSTSYMELSGLKYEDTAVYYCARPFYDPLTGYFDT FNVWGQGTTVTVSS | ADI-41502 | Heavy chain variable region ("HC") amino acid sequence |
| Ab 781 | 1562 | QSVLTQPRSVPGSPGQSVTISCTGTSGDVGGYNYVSWYQQHPGKAPKLVIYDVTK RPSGVPDRFSGSKSGNRASLTISGLQAEDEADYYCCSYAGSQTGYVFGTGTKVTVL | ADI-41502 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 782 | 1563 | EVQLLESGGGLVQPGGSLRLSCAASGFTFSDFPLSWVRQAPGKGLVWVSAISSSGG DTYYADSVKGRFTISRDSSKNALYLQMNSLRAEDTAVYYCAKGQELLRPYYYGMDV WGQGTTVTVSS | ADI-41503 | Heavy chain variable region ("HC") amino acid sequence |
| Ab 782 | 1564 | QSALIQPASVSGSPGQSITISCTGTSSDVGGYNFVSWYQQHPGKAPKLMIFEVSNR PSGVSHRFSGSKSGNTASLTISGLQAEDEADYYCSSCTSRFTYVFGTGTKLTVL | ADI-41503 | Light chain variable region ("LC") amino acid sequence |
| Ab 783 | 1565 | EVQLLESGPGLLKTSETLSLTCTVSDGSISGYYWTWIRQPPGKGLECIGYISYSGS TNYSPSLKSRVTISVDTSKNQFSLKLSSVTAADTAVYYCAKIGGYCNPTKCYGWFD PWGQGTLVTVSS | ADI-41504 | Heavy chain variable region ("HC") amino acid sequence |
| Ab 783 | 1566 | QPVLTQPPSVSGAPGQRVTISCTGSSSNIGAGYDVHWYQQLPGTAPKLLIFGNTNR PSGVPDRFSGSKSGTSASLAITGLQAEDEAAYYCQSYDSSLFYVVLGGGTKLTVL | ADI-41504 | Light chain variable region ("LC") amino acid sequence |
| Ab 784 | 1567 | QVQLQQSGAGLLKPSETLSLTYVVYGGSFSGYYWSWIRQPPGKGLEWVGDINHST TTNYNPSLESRITISIDTSKNQFSLNLSSVTAADSAVYYCARGPKECTSSSCDRFG VDYFYYGMDVWGRGTTVTVSS | ADI-41505 | Heavy chain variable region ("HC") amino acid sequence |
| Ab 784 | 1568 | QSVLTQPPSVSGAPGQRVTISCTGSSANIGAGYDVHWYQQFPGTAPKLLIFGNSNR PSGVPDRFSGSKSGTSASLAITGLQAGDEADYYCQSYDGTLGGWVFGGGTQLTVL | ADI-41505 | Light chain variable region ("LC") amino acid sequence |
| Ab 785 | 1569 | QVTLKESGPTLVKPTQTLRLTCTFSGFSLNVISGVGVGWIRQPPGKALEWLALIYWD DDKRYSPSLKSRLTIAKDTSKNQVVLTMTNMDPVDTATYYCAHKGGSIEAAVGFDY WGQGTLVTVSS | ADI-41507 | Heavy chain variable region ("HC") amino acid sequence |
| Ab 785 | 1570 | QSVLTQPPSVSGAPGQRVIISCTGSSSNIGAGFAVHWYQQLPGTAPKLLIYANTNRP SGVPDRFSGSKSGTSASLAITGLQAEDEADYYCQSYDTSLSGFYVFGTGTKLTVL | ADI-41507 | Light chain variable region ("LC") amino acid sequence |
| Ab 786 | 1571 | QVQLVQSGAEVRKPGASVKVSCKASGYGFRSYDLTWVRQAPGKGLEWVGWISAY SGGTNYAQTLQGRVTMTTDTSTSTAYMELRSLGPDDTAVYYCARAGLYGSGSPDG FDSWGQGTLVTVSS | ADI-41508 | Heavy chain variable region ("HC") amino acid sequence |
| Ab 786 | 1572 | SYELTQPPSVSVSPGQTASITCSGDKLGDKYASWYQQRPGQSPVLVISQDTKRPSGI PERFSGSTSGNTAILTISGTQAMDEADYYCLAWDSSTAWVFGGGTKLTVL | ADI-41508 | Light chain variable region ("LC") amino acid sequence |
| Ab 787 | 1573 | QVQLVESGGGLVQPGGSLRLSCAASGFTFSDYAMSWVRQAPGKGLVWVSSISGS GKFTYYEDSLRGRVTISRDNSKNTVYLHMNSLRTEDTALYYCARLRIPVINEVDGAM DVWGQGTTVTVSS | ADI-41515 | Heavy chain variable region ("HC") amino acid sequence |
| Ab 787 | 1574 | SYELTQLPSVSVSPGQTARITCSGDALPKKFAYWYQQKSGQAPVLVIYEDTGRPSGI PERFSGSTSGTTATLTINGAQVEDEGDYYCYSADSSDNQGVFGGGTKVTVL | ADI-41515 | Light chain variable region ("LC") amino acid sequence |
| Ab 788 | 1575 | EVQLLESGPRLVKPSETLSLTCIVSGGFISYDYWSWIRQPAGKGLEWIGRIYAGGIP KYNPSLKSRVTMSLDMSNNQFSLRLKSVTAADSAVYYCARAEPCSGDCFLGENPFDS WGQGTLVTVSS | ADI-41516 | Heavy chain variable region ("HC") amino acid sequence |
| Ab 788 | 1576 | QSVLTQPPSASGTPGQRVTISCSGSSSSIGSNYVYWYQQLPGTAPKLLIHKDNERPS GVPDRFSGSKSGTSASLAISGLRSEDEGDYSCAAWDDSLSGWVFGGGTKLTVL | ADI-41516 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 789 | 1577 | QVQLVQSGGGLVQPGGSLRLACAASGFTLSGYAMNWVRQAPGKGLEWVSSISGS GGSTYYADSVKGRFTTSRDNSKNTVFLHMNSLRAEDTAIYYCATVPWETGPFDHW GQGTLVTVSS | ADI-41517 | Heavy chain variable region ("HC") amino acid sequence |
| Ab 789 | 1578 | QSVLTQPPSVSGAPGQRVTISCTGSSSNIGAGYAVHWYQQLPGTAPKLLIHGTTNR PSGVPDRFSGSKSGTSASLAITGLQAEDEADYYCQSYDSRLSGYVFGTGTKLTVL | ADI-41517 | Light chain variable region ("LC") amino acid sequence |
| Ab 790 | 1579 | EVQLVESGGGLVKPGGSLRLSCAASGFTFSSYSMNWVRQAPGKGLEWVSSISSSSS YINYADSVKGRFTISRDNAKNSLYLQMNSLRAEDTALYYCARDLGYCSDTSCTPGIG YWGQGTLVTVSS | ADI-41518 | Heavy chain variable region ("HC") amino acid sequence |
| Ab 790 | 1580 | QPVLTQPPSVSGAPGQRVTISCTGSSSNIGAGYDVHWYQQLPGTAPKLLIYGNSNR PSGVPDRFSGSKSGTSASLAITGLQAEDEADYYCQSYDSGLSPWVFGGGTKLTVL | ADI-41518 | Light chain variable region ("LC") amino acid sequence |
| Ab 791 | 1581 | QVQLVESGPGLVKPSETLSLTCNVSGGSIITSGSYWGWIRQPPGKGLTWIGSISYSG TTYYNPSLRSRLTISLDTSRNHFSLQLTSVSAADTAVYYCARAFYEVWTGSEIPGDF DRWGQGTLVTVSS | ADI-41519 | Heavy chain variable region ("HC") amino acid sequence |
| Ab 791 | 1582 | EIVLTQSPGTLSLSPGERATLSCRASQSVSSSYLAWYQQKPGQAPRLLIYGASSRAI DIPDRFSGSGSGTDFTLTISRLEPEDFAVYYCQQFRRSPWTFGQGTKVDIK | ADI-41519 | Light chain variable region ("LC") amino acid sequence |
| Ab 792 | 1583 | EVQLLESGGGVVRPGGSLRLSCAASGFSFDDYGMTWVRQAPGKGLEWVSGINW NGISTDYADSVKGRFTISRDNAKNSVYLQMNSLRAEDTALYYCARIGGVVVIASTAY YYGMDVWGQGTTVTVSS | ADI-41520 | Heavy chain variable region ("HC") amino acid sequence |
| Ab 792 | 1584 | DIQLTQSPSSLSAYVGDRVTITCRASQSIRNHLNWYQQKPGKAPQLLIYTASSLQDG VPSRFSGSGSGTDFTLAISSLQPEDFATYYCQQSHSMPPTFGQGTRLEIK | ADI-41520 | Light chain variable region ("LC") amino acid sequence |
| Ab 793 | 1585 | EVQLVESGGGLVQPGRSLRLSCAASGFTFDDFAMDWVRQVPGKGLEWVSGISWN GVSKDYAGSVKGRFTISRDNAKNSLYLQMNSLRAEDTALYFCAKARRDVYNWGDA FDIWGQGTMVTVSS | ADI-41521 | Heavy chain variable region ("HC") amino acid sequence |
| Ab 793 | 1586 | DIRLTQSPGTLSLSPGERATLSCRASQPLNSNYLAWYRQKPGQAPRLLIFDASSRAT GVPDRISGSGSGTDFTLTVSRLEPEDIAVYYCQQYASSPWTFGLGTKVEIK | ADI-41521 | Light chain variable region ("LC") amino acid sequence |
| Ab 794 | 1587 | QVQLVQSGAEVKKPGSSVKVSCKASGGTFNNFPISWVRQAPGQGLEWMGGIIPM FGRANYAQKFQGRVTITADESTTTVYMALRSLRSEDTAVYYCARPDYDVLTGFEGA FDIWGQGTMVTVSS | ADI-41522 | Heavy chain variable region ("HC") amino acid sequence |
| Ab 794 | 1588 | QSALTQPASVSGSPGQLITISCTGTSRDVGGYNYVSWYQQHPGKAPKLMIYDVTNR PSGVSNRFSGSKSGNTASLTISGLQSEDEADYYCSSYTSTTTWVFGGGTKLTVL | ADI-41522 | Light chain variable region ("LC") amino acid sequence |
| Ab 795 | 1589 | QVQLVQSGAEVKKPGESLRISCKGSGDTFSNYWIGWVRQMPGKGLEWMGIIYPG DSDTRYSPSFQGQVTFSADKSISTAYLQWSSLKASDTAMYYCVRQVGGVVVTDTD NYYYGMDVWGQGTTVTVSS | ADI-41523 | Heavy chain variable region ("HC") amino acid sequence |
| Ab 795 | 1590 | DIRLTQSPSSLSASVGDRVTITCRASQSIRSYLNWYQQKPGKAPKLLIYSASSLQS GVPSRFSGSGSGTDFTLTISSLQPEDFATYYCQQSHSTPLTFGPGTKVDIK | ADI-41523 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 796 | 1591 | EVQLVESGGGLVQPGRSLRLSCTGSGFTFGDYAISWFRQAPGKGLEWVGFIRSKPY GGTTEYAASVKGTFTISRDDSKSIAYLQMNSLKTGDTAVYFCTRGIWGITMIVPWS DPWGQGTLVTVSS | ADI-41524 | Heavy chain variable region ("HC") amino acid sequence |
| Ab 796 | 1592 | DIVMTQTPLSLPVTPGEPASISCRSSQSLLHSNGFNYLAWYLQKPGQSPQLLIYLN SNRASGVPDRFSGSGSGTDFTLKISRVEAEDVGVYYCMQALQTPLTFGPGTKLEIK | ADI-41524 | Light chain variable region ("LC") amino acid sequence |
| Ab 797 | 1593 | QVQLVQSGAEMKKPGSSVKVSCKASGRTFKYFALNWMRRAPGHGLEWIGGDIPIS GSTNYAQKFQGRVTITADESASTAYMEVSRLRSDDTAVYYCASLHYDVSTGFSDAF DIWGQGTMVTVSS | ADI-41525 | Heavy chain variable region ("HC") amino acid sequence |
| Ab 797 | 1594 | QSVLTQPASVSGSPGQSITISCTGTSSDVGAYNYVSWYQHHPGKAPKLMIFDVSNR PSGVSNRFSGSKSGNTASLTISGLQAEDEADYYCSSYRSTFSYVFGTGTKVTVL | ADI-41525 | Light chain variable region ("LC") amino acid sequence |
| Ab 798 | 1595 | QVQLVQSGAEVKKPGASVKVSCEASGYTFTDYYMHWVRQAPGQGLEWMGWIN PNSGVTKIAQNFQGRVTMTRDTSITTAYMDLSRLRSDDTAVYYCARVVDGDYDN WFDFWGQGTLVTVSS | ADI-41526 | Heavy chain variable region ("HC") amino acid sequence |
| Ab 798 | 1596 | SYVLTQPPSASGTPGQRVTISCSGSTSNIGTNTVNWYQQPPGMAPKLLIYANNQRP SGVPDRFSGSKSGTSASLAISGLQSEDEADYHCAVWDDSLPGWVFGGGTKLTVL | ADI-41526 | Light chain variable region ("LC") amino acid sequence |
| Ab 799 | 1597 | EVQLLESGGGLVQPGGSLRLSCAASGFTFTSYWMSWVRQAPGQGLEWVATIKQD GSEKYYVDSVKGRFTISRDNAKNSLYLQMNSLGAEDTAVYYCARDMYCSTTTCYFF ETYYYNGMDVWGQGTTVTVSS | ADI-41527 | Heavy chain variable region ("HC") amino acid sequence |
| Ab 799 | 1598 | DIRLTQSPSSVSASVGDRVTITCRASQVTSTWLAWYQQNPGKAPKLLIYAASRLQS GVPSRFSGSGSGTEFTLTISSLQPEDFATYYCQQANSFPLTFGGGTKVEIK | ADI-41527 | Light chain variable region ("LC") amino acid sequence |
| Ab 800 | 1599 | EVQLVESGGGVVQPGRSLRLSCAASGFTFSSYAMHWVRQAPGKGLEWVAVISFD GSSDYYADSVKGRFTISRDSSKNTLYLRMNSLRAEDTAVYYCARRAVEYSIYNNDA FDVWGQGTTVTVSS | ADI-41528 | Heavy chain variable region ("HC") amino acid sequence |
| Ab 800 | 1600 | SYELTQPPSVSVSPGQTASITCSGDKLGNKFTFWYQQKSGQSPVLVIYQETKRPSG IPERFSGSNSGNTATLTISGTQSMDEADYYCQAWDSSTAFFGGGTKLTVL | ADI-41528 | Light chain variable region ("LC") amino acid sequence |
| Ab 801 | 1601 | EVQLVQSGAEVRRPGSSVKVSCKASGGTLDTDSISWVRQVPGQGLVWVGGVIPIL GSVVYARKFQGRVTITADGSTSTAYMELRSLRSEDTAMYYCASQFYDFRRGYFDAF DIWGQGTTVTVSS | ADI-41529 | Heavy chain variable region ("HC") amino acid sequence |
| Ab 801 | 1602 | ETTLTQSPGILSLSPGERATLSCRATQTVISNYINWYQQKPGQAPRLLIYGASSRAT GIPDRFSGSGSGTDFTLTISRLEPEDFAVYYCQRYDSSPPGFTFGPGTKVDIK | ADI-41529 | Light chain variable region ("LC") amino acid sequence |
| Ab 802 | 1603 | QVQLVESGAEVKKPGASVKVSCRASGYTFSAYDINWVRQAPGQGLEWVGWMNP NSGNTGYALRFQGRVTMTRDTSINTAYMELSSLRSDDTAVYYCAAQLWYPNWGQ GTLVTVSS | ADI-41530 | Heavy chain variable region ("HC") amino acid sequence |
| Ab 802 | 1604 | SYELTQPPSVSVGLGQTASITCGGNNIGSKSVHWYQQKPGQAPTLVIYRDTNRPSGI PERFSGSNSENTATLTISRAQAGDEADFYCQVSDNYSWVFGGGTKLTVL | ADI-41530 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 803 | 1605 | EVQLLESGGDLVQPGGSLRLSCAASGFTFFSYALNWVRRTPGKGLEWVSGISGSGG STYYADSVKGRFTISRDNSKSTLYLQMNSLKVDDTAVYFCAKDFQHDYGDPYRSYYF DHWGQGTLVTVSS | ADI-41531 | Heavy chain variable region ("HC") amino acid sequence |
| Ab 803 | 1606 | DIQLTQSPSSLAASVGDRVTITCQASRDIRKSLNWYQVKPGKAPKLLISDASYLETG VPPRFSGSGFGTHFTFTISSLQPEDIATYYCQQYDNLPPPTFGGGTKVDIK | ADI-41531 | Light chain variable region ("LC") amino acid sequence |
| Ab 804 | 1607 | QVQLVQSGAEVKKPGESLKISCKGSGYSFTSSWIGWVRQMPGKGLEWMGIIYPGD SDTRYSPSIQGRVTISADKSITTAYLQWSSLKASDTATYYCAKFGGYADAYFYHGMD VWGQGTTVTVSS | ADI-41532 | Heavy chain variable region ("HC") amino acid sequence |
| Ab 804 | 1608 | SYVLTQPPSASGTPGQRVTISCSGSSSNVGSNTVNWYQQLPGTAPKLLIHFNNQRP SGVPDRFSGSKSGTSASLAISGLQSEDEADYYCAAWDDSLNTWVFGGGTKVTVL | ADI-41532 | Light chain variable region ("LC") amino acid sequence |
| Ab 805 | 1609 | QVQLVESGGGVVQPGRSLRLSCAASGFTFSSYAMHWVRQAPGKGLEWLAVISFD GSSEFYGDSVRGRFTISRDNSKNTLYLRVNSLRAEDTALYYCARRSLKYSMYNNDAF DVWGQGTTVTVSS | ADI-41533 | Heavy chain variable region ("HC") amino acid sequence |
| Ab 805 | 1610 | QPVLTQPPSVSVSPGQTASITCSGDKLGNKFTFWYQQKSGQSPVLVIYQESQRPSGI PERFSGSNSGNTATLTIRGAQAMDEADYYCQAWDSSTAFFGGGTKLTVL | ADI-41533 | Light chain variable region ("LC") amino acid sequence |
| Ab 806 | 1611 | QVQLVQSGGGVVQPGRSLRLSCAASGFTFSNYAMHWVRQAPGKGLEWVTLISYD GSAQDYADSVKGRITISRDNSKNTLYLQMSSLRPEDTAVYYCARYYCTNDVCSSSAL DIWGQGTTVTVSS | ADI-41534 | Heavy chain variable region ("HC") amino acid sequence |
| Ab 806 | 1612 | SYELIQPPSVSVSPGQTASITCSGDKLGNKFTCWYQQKPGQSPVLVIYQDSKRPSGI PERFSGSNSGNTATLTISGTQAMDEADYYCQAWDSSTVVFGGRTKLTVL | ADI-41534 | Light chain variable region ("LC") amino acid sequence |
| Ab 807 | 1613 | QVTLKESGPALVKPTQTLTLTCTFSGFSLSTSRMCVSWIRQSPGKALEWLARIDWD DDKFFSTSLKTRLTISKDTSRNQVVLTMTNMDPVDTATYYCARTTVYASGGYYLYYF DYWGQGTLVTVSS | ADI-41535 | Heavy chain variable region ("HC") amino acid sequence |
| Ab 807 | 1614 | DIQLTQSPSSLPASVGDRVTITCRASQRIASYLNWYQQKPGKAPKVLIYAASNLQSG VPSRFSGSGSGTDFTLTINSLQPEDFATYYCQQSYTTPWTFGQGTKVEIK | ADI-41535 | Light chain variable region ("LC") amino acid sequence |
| Ab 808 | 1615 | EVQLVESGAGLLKPSETLSLTCVVYGGSFSGYYWSWIRQPPGKGLEWVGDINHSTT TNYNPSLESRITISIDTSKNQFSLNLSSVTAADSAVYYCARGPKECTSSSCDRFGVD YFYYGMDVWGRGTTVTVSS | ADI-41536 | Heavy chain variable region ("HC") amino acid sequence |
| Ab 808 | 1616 | QSVLTQPPSVSGAPGQRVTISCTGSSANIGAGYDVHWYQQFPGTAPKLLIFGNSNR PSGVPDRFSGSKSGTSASLAITGLQAEDEADYYCQSYDGTLGGWVFGGGTQLTVL | ADI-41536 | Light chain variable region ("LC") amino acid sequence |
| Ab 809 | 1617 | EVQLLESGGGLVQPGGSLRLSCAASEFTFSRYPMSWVRQAPGKGLEWVSGISVSG DSTYYADSVKGRLTISRDNSKNTLYLQMNSLRAEDTAVYYCAIDHYDTSGYYGMDV WGQGTTVTVSS | ADI-41537 | Heavy chain variable region ("HC") amino acid sequence |
| Ab 809 | 1618 | DIRLTQSPLSLPVTPGEPASISCRSSRSLLRSNGYNYLDWYLQKPGQSPQLLIYLG SNRASGVPDRFSGSGSGTDFTLKISRVEAEDVGVYYCMQALQSSYTFGQGTKLEIK | ADI-41537 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 810 | 1619 | EVQLVESGGGLVKPGGSLRLSCAASGFTLSTYGVNWVRQAPGKGLEWVSSISSSGN NIHYADSVKGRFTVFRDNAKHSMYLQMNSLRAEDTAVYYCARSLDYSNYYYYGLD VWGQGTTVTVSS | ADI-41538 | Heavy chain variable region ("HC") amino acid sequence |
| Ab 810 | 1620 | EIVLTQSPDSLAVSLGERATINCKSSQSIFYSSNNMNYLAWYQQKAGQPPKLLIYWA STRESGVPDRFSGSGSGTDFTLTISSLQAEDVAVYYCHQYYSIPLTFGGGTKVEIK | ADI-41538 | Light chain variable region ("LC") amino acid sequence |
| Ab 811 | 1621 | QVQLVESGAEVKKPGASVKVSCKASGYNFIDYGISWVRQAPGQGLEWVGWISAY NGNTNYAQKLQGRVTMTTDTSTNTAYMELRSLRSDDTALYYCARDSSSLHPTYYYY YPMDVWGQGTTVTVSS | ADI-41539 | Heavy chain variable region ("HC") amino acid sequence |
| Ab 811 | 1622 | DIVMTQSPATLSVSPGERATLSCRASQSVSSRLAWYQQKPGQAPRLLIYGASTRAT DVPARFSGSGSGTEFTLTISSLQSEDFAVYYCQQYNNWPPERTFGQGTKVEIK | ADI-41539 | Light chain variable region ("LC") amino acid sequence |
| Ab 812 | 1623 | QVQLQQWGAGLLKPSETLSLTCGVYGGSFTGYQWSWIRQSPGKGLEWIGDIDHG GNTNYRPSLKSRIITSVNMSKKEFSLKLASVTAADTAVYYCARGVGFLEFSGGPTG RRRNWFDSWGQGTLVTVSS | ADI-41540 | Heavy chain variable region ("HC") amino acid sequence |
| Ab 812 | 1624 | DIQLTQSPGTLSLSPGEGATLSCRASQSVGGSYLAWYQQRPGQAPRLLIYGASNRA ADSPDRFSGSGSATDFTLTISRLEPEDFAVYYCQQYGSSPWTFGQGTKVEIK | ADI-41540 | Light chain variable region ("LC") amino acid sequence |
| Ab 813 | 1625 | QITLKESGPTLVKPTQTLTLTCTFSGFSLSSSGVGVGWIRQPPGKALEWLALIYWDD DKRYSPSLKSRLTITKDTSKNQVVLTMTNMDPVDTATYYCAHRGPYYYDMSGYYYE AFDIWGQGTTVTVSS | ADI-41541 | Heavy chain variable region ("HC") amino acid sequence |
| Ab 813 | 1626 | SYELMQPPSVSVAPGQTARITCGGNNIGSKGVHWYQQKPGQAPVLVVYDDNDRP SGIPERFSGSNSGNTATLTISRVEAGDEADYYCQVWDSSSDHHYVFGTGTKVTVL | ADI-41541 | Light chain variable region ("LC") amino acid sequence |
| Ab 814 | 1627 | EVQLVESGVAVKKPGESLKISCKGSGYNFDSFWIGWVRQLPGKGLEWMGIIFPGDS DTRYGPSFQGQVTISADKSINTAYLQWRSLKASDTAMYYCARHGLGGYDNSGYNL WGHGTMVTVSS | ADI-41542 | Heavy chain variable region ("HC") amino acid sequence |
| Ab 814 | 1628 | DIVMTQSPSSLSASVGDRVTITCQASHDISTSLNWYQQKPGKAPNLLISDASTLERG VPSRFSGGGSGTEFTFTISSLQPEDIATYYCQQFENLPITFGQGTRLEIK | ADI-41542 | Light chain variable region ("LC") amino acid sequence |
| Ab 815 | 1629 | QVQLVQSGAEVKKPGASVRVSCKASGYTLTGYYIHWLRQAPGQGLEWVGRINPNT GETSYSQKFQGRVIMTRDTSVSTAYVDLSRLRSRDTAVYFCARSDVMITVTAEGDFS YYYYRFDVWGQGTTVTVSS | ADI-41543 | Heavy chain variable region ("HC") amino acid sequence |
| Ab 815 | 1630 | DIVMTQTPLSLPVTPGEPASISCRSSQSLLHSNGHNYLDWYLQKPGQSPQLLIYLGS IRASGVSDRFSGSGSGTDFTLKISRVEAEDVGIYYCMQALQTPHFGGGTKVEIK | ADI-41543 | Light chain variable region ("LC") amino acid sequence |
| Ab 816 | 1631 | QVQLVQSGAEVKKPGESLKISCKGSGYSFTNYWIGWVRQMPGKGLEWMGIIFPA DSDTRYSPSFQGQVTISADKSVSTAYLQWTSLKASDTAIYYCARLGVAAAGGYWGQ GTLVTVSS | ADI-41544 | Heavy chain variable region ("HC") amino acid sequence |
| Ab 816 | 1632 | DIQVTQSPSSLSASVGDRVTITCQASQDISNYLNWYQQKPGKAPKLLIHDASTLETG VPSRFSGRGSGTDFTFTISSLQPEDIATYYCQQYDNLPPTFGGGTKVEIK | ADI-41544 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 817 | 1633 | QVQLVESGPGLVKPSETLSLTCTVSGGSISRYYWSWIRQSPGKGLEWIGYIYHSVIT NYNPSLKSRVTISIDMSKNQFSLKLSSVTAADTAVYYCASRPLINGYGPDNYFDYWG QGTLVTVSS | ADI-41545 | Heavy chain variable region ("HC") amino acid sequence |
| Ab 817 | 1634 | SYVLTQPPSVSVAPGQTARITCGGNNIGSKSVHWYQRKPGQAPVLVVYDDSDRPS GIPERFSGSNSGNTATLTIIRVEAGDEADYYCQVWDNSSDHPVFGGGTKLTVL | ADI-41545 | Light chain variable region ("LC") amino acid sequence |
| Ab 818 | 1635 | QVQLVQSGAEVKKPGESLKISCKGSGYSFTNYWIGWVRQMPGKGLEWMGIIFSAD SDTRYSPSFQGQVTISADKSISTAYLQWSSLKASDTAMYYCARQWGITGDAFDIWG QGTMVTVSS | ADI-41546 | Heavy chain variable region ("HC") amino acid sequence |
| Ab 818 | 1636 | DIQVTQSPSFLSASVGDRVTITCRASQGISGYLAWYQQKPGKAPKLLIYAASTLQS GVPSRFSGSGSGTEFTLTISSLQPEDFATYYCQQLNSYPYTFGQGTKVEIK | ADI-41546 | Light chain variable region ("LC") amino acid sequence |
| Ab 819 | 1637 | QVQLVQSGAEVKKPGSSVKVSCKASGGSFSSNTINWVRQAPGQGLEWMGGIIPVF ETPNYAQKFQGRVSFTADESTRTAYMELSSLRSEDTAVYFCARQGMSYYDTNGNY YVGWFDTWGQGTLVTVSS | ADI-41547 | Heavy chain variable region ("HC") amino acid sequence |
| Ab 819 | 1638 | EIVLTQSPGTLSLSPGERATLSCRASQSLNNNYLAWYQRKPGQAPRLLIYGAGAFS RATGIPDRFSGSGSGTDFTLTISRLEPEDFALYYCQQYGSSPLTFGQGTRLEIK | ADI-41547 | Light chain variable region ("LC") amino acid sequence |
| Ab 820 | 1639 | QVQLQQWGPGLVKPSETLSLTCTVSGASITSHYWSWLRQPAGKGLEWIGRFYPSG TTEKTPSLKSRVTLSVDTSKNHFSLKLTSVTAADTAVYYCARDSYDDIAGSYEYYF ADWGQGTLVTVSS | ADI-41548 | Heavy chain variable region ("HC") amino acid sequence |
| Ab 820 | 1640 | EIVLTQSPATLSVSPGERATLSCRASQSVSSNLAWYQQKPGQAPRLLIYDISTRAT PGVARFSGSGSGTEFTLTITSLQSEDFTVYYCQQYNNWPPTFGQGTKLEIK | ADI-41548 | Light chain variable region ("LC") amino acid sequence |
| Ab 821 | 1641 | EVQLLESGGGVVQPGGSLRLSCAASGFTFSGYGMHWVRQAPGKGLEWVAFIQYN GSNKYYADSVKGRFTISRDNSKNTLYVQLNSLRAEDTAVYYCATDILVVPAATPLI SYYFGMDVWGQGTTVTVSS | ADI-41549 | Heavy chain variable region ("HC") amino acid sequence |
| Ab 821 | 1642 | QSALTQPASVSGSPGQSITISCTGTSSDVGGYNYVSWYQQYPGKAPKLMIYEVTNR PSGVSNRFSGSKSGNTASLTISGLQAEDEADYYCCSYTSTNTRVFGTGTKVTVL | ADI-41549 | Light chain variable region ("LC") amino acid sequence |
| Ab 822 | 1643 | QVQLVQSGAEVKMPGASVRVSCKASGYTLGSHGITWVRQAPGQGLEWMGWISA NNFNTHYAQKFQGRVTMTTDTSTSTAYMELRSLRSDDTAVYYCAREVMGHMVET ISFDYWGQGTLVTVSS | ADI-41550 | Heavy chain variable region ("HC") amino acid sequence |
| Ab 822 | 1644 | QPVLTQPPSVSVAPGQTARITCGGNNIGSESVHWYQQKPGQAPVLVVHDDSDRP SGIPERFSGSNSGNTATLTISRVEAGDEADYYCQVWDFTPDHPVFGGGTKVTVL | ADI-41550 | Light chain variable region ("LC") amino acid sequence |
| Ab 823 | 1645 | QVQLQESGGGVVQPGGSLRLSCAASGFTFSRHWMHWVRQVPGKGLVWVSRINS DESTIDYADSVKGRFTISRDNAKNTLYLQMNSLRAEDTAVYYCVRDMVAVPGTTG GDYWGQGTLVTVSS | ADI-41551 | Heavy chain variable region ("HC") amino acid sequence |
| Ab 823 | 1646 | SYELTQPPSVSVSPGQTADITCSGDKLGDKYACWYQQRAGQSPILVLYQDTRRPSGI PERFSGSNSGDTATLTISGTQAMDEADYYCQAWDSSTAWVFGGGTKLTVL | ADI-41551 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 824 | 1647 | QVQLVQSGGGLVKPGGSLRLSCAASGFTFSSYSMNWVRQAPGKGLEWVSSISSSS SYIYYADSVKGRFTISRDNAKNSLYLQMNSLRAEDTAVYYCARVLSGYSYGYDYWG QGTLVTVSS | ADI-43643 | Heavy chain variable region ("HC") amino acid sequence |
| Ab 824 | 1648 | QSVLTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGSVFGTGTKVTVL | ADI-43643 | Light chain variable region ("LC") amino acid sequence |
| Ab 825 | 1649 | EVQLVESGGGLVQPGGSLRLSCAASGFTFSSYAMSWVRQAPGKGLEWVSAISGSG GSTYYADSVKGRFTISRDNSKNTLYLQMNSLRAEDTAVYYCAKDFTVVHPLQQLT YYYFDYWGQGTLVTVSS | ADI-43644 | Heavy chain variable region ("HC") amino acid sequence |
| Ab 825 | 1650 | DIVLTQSPATLSLSPGERATLSCRASQSVSSYLAWYQQKPGQAPRLLIYDASNRAT GIPARFSGSGSGTDFTLTISSLEPEDFAVYYCQQRSNWPPGFTFGGGTKVEIK | ADI-43644 | Light chain variable region ("LC") amino acid sequence |
| Ab 826 | 1651 | QVQLVQSGAEVKKPGSSVKVSCKASGGTFSSYAISWVRQAPGQGLEWMGGIIPIF GTANYAQKFQGRVTITADESTSTAYMELSSLRSEDTAVYYCARGWRGGGMTGSYY YYGMDVWGQGTTVTVSS | ADI-43645 | Heavy chain variable region ("HC") amino acid sequence |
| Ab 826 | 1652 | DIQVTQTPSTLSASVGDRVTITCRASQSISSWLAWYQQKPGKAPKLLIYKASSLES GVPSRFSGSGSGTEFTLTISSLQPDDFATYYCQQHRGTFGQGTKVDIK | ADI-43645 | Light chain variable region ("LC") amino acid sequence |
| Ab 827 | 1653 | EMQLMQSGGVVVQPGGSLRLSCAASGFTFDDYAMHWVRQAPGKGLEWVSLIS WDGGSTYYADSVKGRFTISRDNSKNSLYLQMNSLRAEDTALYYCAKDFDPLVVPAA MCFDYWGQGTLVTVSS | ADI-43646 | Heavy chain variable region ("HC") amino acid sequence |
| Ab 827 | 1654 | QSVLIQPASVSGSPGQSITISCTGTSSDVGGYNYVSWYQQHPGKAPKLMIYDVSNR PSGVSNRFSGSKSGNTASLTISGLQAEDEADYYCSSYTSSSTLYVFGTGTKLTVL | ADI-43646 | Light chain variable region ("LC") amino acid sequence |
| Ab 828 | 1655 | EVQLVESGGGLVQLGGPLRLSCAASGFTFSSYAMSWVRQAPGKGLEWVSAISGSG GSTYYADSVKGRFTISRDNSKNTLYLQMNSLRAEDTAVYYCAKGFERDYADAFDIW GQGTTVTVSS | ADI-43647 | Heavy chain variable region ("HC") amino acid sequence |
| Ab 828 | 1656 | DIRMTQSPSSVSASVGDRVTITCRASQGISSWLAWYQQKPGKAPKLLIYAASSLQS GVPSRFSGSGSGTDFTLTISSLQPEDFATYYCQQANSFPITFGQGTRLEIK | ADI-43647 | Light chain variable region ("LC") amino acid sequence |
| Ab 829 | 1657 | EVQLVQSGAEVKKPGASVKVSCKASGYTFTSYDINWVRQATGQGLEWMGWMN PNSGNTGYAQKFQGRVTMTRNTSISTAYMELSSLRSEDTAVYYCATRPAALDYWG QGTLVTVSS | ADI-43648 | Heavy chain variable region ("HC") amino acid sequence |
| Ab 829 | 1658 | QPVLTQPLSVSVALGQTARITCGGNNIGSKNVHWYQQKPGQAPVLIIYRDSNRPSG IPERFSGSNSGNTATLTISRAQAGDEADYYCQVWDSSTWVFGGGTKLTVL | ADI-43648 | Light chain variable region ("LC") amino acid sequence |
| Ab 830 | 1659 | QVQLVQSGGGLVKPGGSLRLSCAASGFTFRDFYMSWIRQAPGKGLEWVSNISPSS TYTNYADSVKGRFTISRDNAKNSLYLQMNSLRAEDTAVYYCVKSEGYSSGWYDYW GQGTLVTVSS | ADI-36673 | Heavy chain variable region ("HC") amino acid sequence |
| Ab 830 | 1660 | QPVLTQPPSVSGAPGQRVTISCTGSSSNIGAGYDVNWYHQLPGAAPKLLIYTNSNR PSGVPDRFSGSKSGTSASLAITGLQAEDEADYYCQSYDSSLSGYVFGTGTKLTVL | ADI-36673 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 831 | 1661 | EVQLVESGGGLVQPGGSLRLSCAASGFTFNRFAMSWVRQAPGKGLEWVSGISGS GGSTLYADSVKGRFTISRDNSKNTLYLQINSLRVEDTAVYYCASRSSYDDVWNGYV DWDWGFDFYYYGMDVWGQGTTVTVSS | ADI-36675 | Heavy chain variable region ("HC") amino acid sequence |
| Ab 831 | 1662 | QAVVTQEPSMSAAPGQKVTISCSGGDSNIRNNYVFWYQQLPGTAPKLLIYDNTKR PSGIPGRFSGSKSGASATLDITGLQTGDEADYYCGTWDSSLSALVFGGGTQLTVL | ADI-36675 | Light chain variable region ("LC") amino acid sequence |
| Ab 832 | 1663 | EVQLLESGGGVVQPGRSLRLSCAASGFSFRNYDMHWVRQAPGKGLEWVAIISYDG SNKYADSVKGRFTISRDTSKNTLYLQMNSLRVEDTAVYYCARADSSGYYKGSEYFQ HWGQGTLVTVSS | ADI-36676 | Heavy chain variable region ("HC") amino acid sequence |
| Ab 832 | 1664 | SYELTQLPSVSVAPGQTARITCGGNNIGTKSVQWYQHKPGQAPVLVVYDDSDRPS DIPERFSGSNSGNTATLTISRVEAGDEADYYCQVWDSSSDHYVFGTGTKLTVL | ADI-36676 | Light chain variable region ("LC") amino acid sequence |
| Ab 833 | 1665 | EVQLVQSGGGLVQPGGSLRVSCAASGLTVSTNYMSWVRQLPGKGLEWVSVIYSG GNTYYADSVKGRFTISRDNSKNIVYLEMNSLRIEDTAVYYCARAHLNNWFVSVTDT KDYYFDYWGQGTLVTVSS | ADI-36678 | Heavy chain variable region ("HC") amino acid sequence |
| Ab 833 | 1666 | SYELTQPPSVSVLPGQTASITCSGDKLGDKYASWYQQKPGQSPILVVFQDDKRPSG IPERFSGSNSGNTATLTISGTQATDEADYYCQACDRNTGVFGTGTKLTVL | ADI-36678 | Light chain variable region ("LC") amino acid sequence |
| Ab 834 | 1667 | EVQLLESGGGLVQPGGSLRLSCAASGFTFSPYSMNWVRQAPGKGLEWVSYISRSG SFKYYADSVKGRFTISRDDAKNSLYLHMNSLRDDDTAVYYCVSYCSSATCHQRFDY WGQGTLVTVSS | ADI-41552 | Heavy chain variable region ("HC") amino acid sequence |
| Ab 834 | 1668 | EIVLTQSPATLSLSPGERATLSCRASQSVNSYLAWYQQKPGQAPRLLIYDASNRAT GIPARFSGSGSGTDFTLTISSLEPEDFAVYYCQERNSWPKLTFGGGTKVEIK | ADI-41552 | Light chain variable region ("LC") amino acid sequence |
| Ab 835 | 1669 | EVQLVESETEVKKPGASVKVSCKASGYTFTKYGISWVRQAPGQGLEWMGWISAYN GNTMYPHKLLGRVTMTTDTSTSTAYMELRSLRSDDTAVYYCARDQTYYDFWSGYY TYWGQGTLVTVSS | ADI-41553 | Heavy chain variable region ("HC") amino acid sequence |
| Ab 835 | 1670 | DIVMTQTPSTLSASVGDRVTITCRASQSISSWLAWYQQKPGKAPKLLIYKASSLES GVPSRFSGSGSGTEFTLTISSLQPDDSATYYCQQYNSYSRTFGQGTKVEIK | ADI-41553 | Light chain variable region ("LC") amino acid sequence |
| Ab 836 | 1671 | EVQLVESGGGLVQPGGSLRLSCAASGFTFSSYPMNWVRQGPGKGLEWVSSISSSG ASPYYADSVKGRFTISRDNSKNTLYLQMNSLRADDTAVYYCAREDYYYYMDVWG KGTTVTVSS | ADI-41554 | Heavy chain variable region ("HC") amino acid sequence |
| Ab 836 | 1672 | ETTLTQSPSTLSASVGDRVTITCRASESISSWLAWYQQKPGKAPKLLIFKASTVQS GVPSRFSGSGSGTEFTLTISSLQPDDFATYYCQQYNSYLLTFGGGTKVEIK | ADI-41554 | Light chain variable region ("LC") amino acid sequence |
| Ab 837 | 1673 | EVQLVESGPGLVKPSQTLSLTCSVSGGSISSGIHYWSWIRQHPGKGLEWIGYIYYS GSTYYNPSLESRITISVDTSKNQFSLKVSSVTAADTAVYYCARVNRASRMTTFGVA NERSIYYFMDVWGKGTTVTVSS | ADI-41555 | Heavy chain variable region ("HC") amino acid sequence |
| Ab 837 | 1674 | ETTLTQSPATLSLSPGERATLSCRATQSVGNYLAWYQQKPGQAPRLLIHDASNRAT GIPARFSGSGSGTDFTLTISSLEPEDFAVYYCQLRINWLFTFGPGTKVEIK | ADI-41555 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 838 | 1675 | EVQLLESGGGLVKPGGSLRLSCAASGFSFSSYSMHWVRQAPGKGLEWVSSISSSST YIYYADSVKGRFTISRDNAKTSLFLQMNSLRAEDTAVYYCARDPYSSGWYWDWGQG TTVTVSS | ADI-41556 | Heavy chain variable region ("HC") amino acid sequence |
| Ab 838 | 1676 | EIVMTQSPATLSVSPGERATLSCRASQSVSGNLAWYQQKPGQAPRLLIYGASTRAT GIPARFSGSGSGTEFTLTISSLQSEDFAVYYCHQYNNRPATFGQGTKVDIK | ADI-41556 | Light chain variable region ("LC") amino acid sequence |
| Ab 839 | 1677 | EVQLLESGPGLVKPSETLSLTCNVSGGSISSYYWSWIRQSPGKGLEWIGHIYDTGYT NYNPSLKSRVTMSVDTSKNRFSLKLDSVTAADTAVYYCARGRGWRNLYNWFDPW GQGTLVTVSS | ADI-41557 | Heavy chain variable region ("HC") amino acid sequence |
| Ab 839 | 1678 | DIVMTQSPATLSVSPGERATLSCRTSQSFSSMLAWYQQKPGQAPRLLIYGASTRAT GIPARFSGSGSATEFTLTISNLQSEDVAVYYCQQYNSWPLTFGGGTKVEIK | ADI-41557 | Light chain variable region ("LC") amino acid sequence |
| Ab 840 | 1679 | EVQLLESGGGLVKPGGSLRLSCEVSGFPFSDYYVSWIRQAPGKGLEWLSYSSRGGIY TNYADSVKGRFTISRDNDKNSLFLQMNSLRAEDTAVYYCARDRSDIWSGRVGFDY WGQGTLVTVSS | ADI-41558 | Heavy chain variable region ("HC") amino acid sequence |
| Ab 840 | 1680 | DIVMTQSPATLSLSPGERATLSCRASQSVSSSYLAWYQQKPGQAPRLLIYGASSRAT GIPDRFSGSGSGTDFTLTISRLEPEDFAVYYCQQYNKSPPGYIFGPGTKVDIK | ADI-41558 | Light chain variable region ("LC") amino acid sequence |
| Ab 841 | 1681 | QVQLVQSGPTLVKPTQTLTLTCSFSGFSLTNTGVGVGWIRQPPGKALEWLALIYWD DDKRYRPSLKSRLTITKDTSKSQVVLTMTNMDPLDTATYYCAHRRSAYDPIYFDYW GQGALVTVSS | ADI-41561 | Heavy chain variable region ("HC") amino acid sequence |
| Ab 841 | 1682 | DIRVTQSPSSVSASVGDRVTITCRASRSINNWLAWYQQKPGKAPKLLIYAASSLQSG VPSRFSGSGYGTDFTLTISSLQPEDFATYYCQQAHSFPSITFGQGTRLEIK | ADI-41561 | Light chain variable region ("LC") amino acid sequence |
| Ab 842 | 1683 | QVQLVQSGAEVKKPGASVRVSCKTSGYAFSKYGISWVRQAPGQGLEWIGWISAYN ENTHFSHKFLGRVTMTTDTSTGIAYMDLRSLKSDDTAVYYCARDWYSLGSDWYFG PMFDYWGQGTLVTVSS | ADI-41562 | Heavy chain variable region ("HC") amino acid sequence |
| Ab 842 | 1684 | EIVLTQSPDTLSVSPGERATLSCRASQSVTTNLAWYQQKPGHAPRLLIYGASTRATG IPARFSGSGSGTEFTLTISSLQSEDFAIYYCQQYTNWPRTFGQGTKVEIK | ADI-41562 | Light chain variable region ("LC") amino acid sequence |
| Ab 843 | 1685 | QVQLVESGPGLVKPSETLSLTCTVSDDSITNNFWTWIRQPPGKGLEWIGYIYYSGST NYNPSLKSRITMSVDLSKNQFSLKLSSVTAADTAVYYCARLTSGGVDYWGQGTLVT VSS | ADI-41563 | Heavy chain variable region ("HC") amino acid sequence |
| Ab 843 | 1686 | QSVLTQPPSLSGAPGQRVTISCTGSSSNIGADYHVHWYQQLPGTAPKLLIYQNTNR PSGVPDRFSASKSGTSVSLAITGLQAEDEADYYCQSYDSSLSAWVFGGGTKLTVL | ADI-41563 | Light chain variable region ("LC") amino acid sequence |
| Ab 844 | 1687 | QVQLVQSGAEVKKPGSSVKVSCKAFGGTLRRYALSWVRQAPGQGLEWMGGIIPV FGTRRYAQKFQGRITITADGSTSTASMEVSSLRFEDTAIYYCATVYFDFVSGPPPT YYYYYMDVWGKGTTVTVSS | ADI-41564 | Heavy chain variable region ("HC") amino acid sequence |
| Ab 844 | 1688 | DIVMTQSPGTLSLSPGERATLSCRASQSVSSSYLAWYQQKPGQAPRLLIYGASSRAT GIPDRFSGSGSGTDFTLTISRLEPEDFAVYYCQQYDSSLRVLTFGGGTKVDIK | ADI-41564 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 845 | 1689 | QVQLQQWGAGLLKPSETLSLTCEVYGGSFSGYYWTWFRQPPGEGLEWIGEINHSG GTNYNPSLKSRVTMSVDASINQFSLQLSSVTAADTSVYYCARGHYYNTNDFYGLFD YWGQGTLVTVSS | ADI-41567 | Heavy chain variable region ("HC") amino acid sequence |
| Ab 845 | 1690 | DIRLTQSPSFLSASVGDRVTITCRASQGISTYLAWYQQKPGKAPKLLLYAASTLHS GVPSRFSGSGSGTEFTLTISSLQPEDFATYYCQQLNRYPPSTFGPGTKLEIK | ADI-41567 | Light chain variable region ("LC") amino acid sequence |
| Ab 846 | 1691 | QVQLQQWGARLLKPSETLSLTCAVYGGSFSGYYWSWIRQSPGKGLEWIGEINHSG STNYNPSLKSRVTISRDTSKKQFSLKVSSVTAADTAVYYCARDPPIRCNGDSCKSD QYRYGMDVWGQGTTVTVSS | ADI-41568 | Heavy chain variable region ("HC") amino acid sequence |
| Ab 846 | 1692 | QPGLTQPPSVSVSPGQTARITCSGDALPKQYAYWYQQKPGQAPVLVIHKDNERPS GIPERFSGSSSGTTVTLTISGVQAEDEADYYCQSADTSGSYRLFGGGTKLTVL | ADI-41568 | Light chain variable region ("LC") amino acid sequence |
| Ab 847 | 1693 | EVQLLESGAEVKKPGSSVKVSCKASGGTFSTYAISWVRQAPGQGLEWMGGIIPVLG TTKYAQKFQDRVTITADESTSTAYMDLSGLRSDDTAVYYCARGVWGDCGRASCLF DWYFDLWGRGTLVTVSS | ADI-41569 | Heavy chain variable region ("HC") amino acid sequence |
| Ab 847 | 1694 | EIVMTQSPATLSVSPGERVTLSCSASQTVSSNLAWYQQKPGQAPRLLIYGASIRAT DIPARFSGSGSRTEFTLTISSLQSEDFAVYYCQQYNNRPPLTFGGGTKVEIK | ADI-41569 | Light chain variable region ("LC") amino acid sequence |
| Ab 848 | 1695 | QVQLVQSGAEVKKPGSSVKVSCMASGGTFSNSAINWVRQAPGQGLEWMGGTIPI FGAANYAQRFQARVTITADKSTSTAYMELTSLRSDDTAVYYCVRTPHRSSDHIWGS YRYFDSWGQGTLVTVSS | ADI-41570 | Heavy chain variable region ("HC") amino acid sequence |
| Ab 848 | 1696 | QSVVTQEPSVSAAPGQKITISCSGSTSNIGINYVSWYQQFPGTAPKLLIYDNDKRP SGIPDRFSGSKSGTSATLGITGLQAGDEADYYCGTWDSSLSAGHIFGGGTKVTVL | ADI-41570 | Light chain variable region ("LC") amino acid sequence |
| Ab 849 | 1697 | EVQLLESGGGLVKPGGSLRLSCEASGFPFNSYHMNWIRQSPGKGLEWVSYITGGSS FSNYADSVKGRFTISRDNAKNSLYLQMNSLRAEDTAVYYCARTTLDCTSTSCHYRF DYWGQGTLVTVSS | ADI-41571 | Heavy chain variable region ("HC") amino acid sequence |
| Ab 849 | 1698 | QSVLTQPPSVSGAPGQRITISCNGSNSNIGAGYDVHWYQQLPGKAPKLLIYSNNNR PSGVPDRFSGSKSGTSASLAITGLQGEDEADYYCQSHDTRLSGNVVFGGGTKLTVL | ADI-41571 | Light chain variable region ("LC") amino acid sequence |
| Ab 850 | 1699 | QITLKESGPTLVKPTQTLTLTCTFSGFSLSTSGVGVAWIRQPPGKALEWLALIYWD DDKRYSPSLKSRLTITKDTSKNQVVLTMTNMDPVDTATYYCAHSSVYTTPFDYWGQ GSLVTVSS | ADI-41574 | Heavy chain variable region ("HC") amino acid sequence |
| Ab 850 | 1700 | DIQLTQSPSTLSASVGDRVTITCRASQSISDWLAWYQQKPGKAPKLLIYKAFTLES GVPSRFSGSGSGTEFTLTISSLQPDDFATYYCQQYTSYWTFGQGTKVEIK | ADI-41574 | Light chain variable region ("LC") amino acid sequence |
| Ab 851 | 1701 | QVTLKESGPTLVKPTQTLTLSCSFSGFSLSAYAVGVGWIRQPPGKALEWLALIYWD DDKRYSPSLETRLTITKDTSKNQVVLTMTKMDPVDTATYYCVYSYNGYYEYMDVWG NGTTVTVSS | ADI-41576 | Heavy chain variable region ("HC") amino acid sequence |
| Ab 851 | 1702 | DIVMTQSPATLSLSPGERATLSCRASQSVSNYLAWYQQKPGQAPRLLISGASNRAT GIPDRFSGSGSGTDFTLTITTPEPEDFAVYYCQQRNAWPRTFGQGTKVEIK | ADI-41576 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 852 | 1703 | EVQLVESGGGVVQPGRSLRLSCAASGFTLSSYVMDWVRQAPGKGLEWVAVISYD GSSKYYADSVKGRFTVSRDNSNNAMYLQMNSLRAEDTAVYYCARDPYYDILTGYSY FDYWGHGTTVTVSS | ADI-41578 | Heavy chain variable region ("HC") amino acid sequence |
| Ab 852 | 1704 | SYVLTQPPSVSGAPRQTATITCGGNNIGSKSVNWYQQKPGQAPVLVVYDDSARPS GIPERFSGSNSGNTATLTVSSVEAGDEADYFCQVWDTSSAPYPWVFGGGTKLTVL | ADI-41578 | Light chain variable region ("LC") amino acid sequence |
| Ab 853 | 1705 | QVQLVESGAEARKPGSSVKVSCKLSGGTFSTDPISWVRQAPGQGLEWMGRIIPLLG IANYAQKFQGRVTIIADKSTSTVYMELRNLRFEDTAVYFCARRGDGYYGMDVWGQ GTTVTVSS | ADI-41579 | Heavy chain variable region ("HC") amino acid sequence |
| Ab 853 | 1706 | QSVLTQPASVSGSPGQSITISCTGTSNDIGGYDYVSWYQQHPGKAPKLMIYDVHNR PSGVSNRFSGSKSGNTASLTISGLQAEDEADYYCSSFSDSGNLYVFGTGTKLTVL | ADI-41579 | Light chain variable region ("LC") amino acid sequence |
| Ab 854 | 1707 | QVQLQQWGAGLLKPSETLSLTCAVYGGSFSGYYWSWIRQPPGKGLEWIGEMNHS GGSNYNPSFKSRVTISVDTSKKYFSLNLSSVTAADTAIYYCARTPFYYESTGYYYY YYGMDVWGQGTTVTVSS | ADI-41580 | Heavy chain variable region ("HC") amino acid sequence |
| Ab 854 | 1708 | DIVMTQTPDSLAVSLGERATINCKSSQSVSHSSNNKNYLSWYQQKPGQPPKLLIYW ASIRESEAPDRFTGSGSGTDFTLTISSLQAEDVAVYYCQQYYTAPITFGQGTRLEI K | ADI-41580 | Light chain variable region ("LC") amino acid sequence |
| Ab 855 | 1709 | EVQLLESGSELKKPGASVKISCKTSGYTFTNYLMNWVRQAPGQGLEWMGWINTH TGNPTYAQDFTGRFVFSLDTSVNTAYLQISSLKAEDTAIYYCARDGLEAFSGYNG VDYWGQGTLVTVSS | ADI-41581 | Heavy chain variable region ("HC") amino acid sequence |
| Ab 855 | 1710 | DIVMTQTPLSLPVTPGEPASISCRSSPSLLHSNGYNYLDWYLQKPGQSPQLLIYL GSTRASGVPDRFSGSGSGTDFTLRISRVEAEDVGVYYCMQALQIPLTFGQGTKLE IK | ADI-41581 | Light chain variable region ("LC") amino acid sequence |
| Ab 856 | 1711 | EVQLVESGPGLVKPSQTLSLTCTVSGGPISSGVYYWSWIRQHPGKGLESIGYIYYS GSTHYNPSLKTRVTISLDTSKNQFSLKLSSVTAADTAVYYCARGCSGGSCYLYAFD IWGQGTTVTVSS | ADI-41582 | Heavy chain variable region ("HC") amino acid sequence |
| Ab 856 | 1712 | QPVLTQPPSVSVAPGQTARITCGGNNIGTKSVHWYQQKPGQAPLLVVYDDSDRPS GIPERFSGSNSGNTATLTISRVEAGDEADFYCQVWDYATDHVVFGGGTKLTVL | ADI-41582 | Light chain variable region ("LC") amino acid sequence |
| Ab 857 | 1713 | QVQLVQSGAEVKKPGSSVKVSCKASGGTFSRHTITWVRQAPGQGLEWMGRIAPIV GFANYAQKFQGRVTITADKSTSTAYMELRSLRSEDTAVYYCARRSEDYYGLDVWG QGTTVTVSS | ADI-41583 | Heavy chain variable region ("HC") amino acid sequence |
| Ab 857 | 1714 | DIVMTQSPSSLSASVGDRVTITCQASQDISNYLNWYQQKPGKAPKLLIYEASNLET GVPSRFSGSGSGTDFTFTISSLQPEDIATYYCQQYDNLFGGGTKLEIK | ADI-41583 | Light chain variable region ("LC") amino acid sequence |
| Ab 858 | 1715 | QVQLVESGAEVKKPGASVKVSCKASGYTFTDYYIHWVRQAPGQGLEWVGRINPNS GYINYAQKFQGRLTMTRDTSISTAYLELSSLRSDDTAVYYCTRLPLLEPLNFFDYW GQGTLVTVSS | ADI-41584 | Heavy chain variable region ("HC") amino acid sequence |
| Ab 858 | 1716 | QSVVTQPPSVSGAPGQRVTISCTGSSSNIGAGYDVHWYQQLPGTAPKVLIYGNNN RPSGVPDRFSGSKSGTSASLAITGLQAEDEADYYCQSFDSSLSSSYVFGTGTKLTV L | ADI-41584 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 859 | 1717 | EVQLLESGGGLVKPGGSLRLSCAASGFTFADYYMSWIRQAPGKGLEWVSYISGGSS FTNYADSVKGRFTISRDNAKNSLYLQMNSLRADDTAVYYCARGISPALGGGEYFQD WGQGTLVTVSS | ADI-41585 | Heavy chain variable region ("HC") amino acid sequence |
| Ab 859 | 1718 | QPVLTQPPSVSGAPGQRVTISCTGSSSNIGAGYDVHWYQHLPGTAPKLLIYGNSNR PSGVPDRFSGSKSSTSASLAITGLQAEDEADYYCQSYDSSLGGYVFGTGTKVTVL | ADI-41585 | Light chain variable region ("LC") amino acid sequence |
| Ab 860 | 1719 | QVQLQQWGAGLLKPSETLSLTCAVYGGSFSGYSWSWIRQPPGKGLEWIGDIDHD GSTYYNSSLKSRVTMSIDTSKNQFSLKLSSVTAADTAVYYCARVGGNSGYWGQGTL VTVSS | ADI-41586 | Heavy chain variable region ("HC") amino acid sequence |
| Ab 860 | 1720 | DIVMTQTPLSLPVTPGEPASISCRSSQSLLHSNGFNYLDWYLQKPGQSPQLLIYLG SNRASGVPDRFSGSGSGTDFTLKISRVEAEDVGVYYCMQALQTLTFGPGTKVEIK | ADI-41586 | Light chain variable region ("LC") amino acid sequence |
| Ab 861 | 1721 | QVQLVQSGAGLLKPSETLSLTCAVYGGSFSGYSWSWIRQPPGKGLEWIGEINYSVS TSYNSSLKSRVSISVDTSKNQFSLKLTSVTAADTAVYYCARVGGAVADWGQGTLVT VSS | ADI-41587 | Heavy chain variable region ("HC") amino acid sequence |
| Ab 861 | 1722 | EIVLTQSPLSLPVTPGEPASISCRSSQRLLHSNGYNYLDWYLQKPGQSPQLLIYLG SNRASGVPDRFSGSGSGTDFTLKISRVEAEDVGVYYCMQNLQTLTFGGGTKVDIK | ADI-41587 | Light chain variable region ("LC") amino acid sequence |
| Ab 862 | 1723 | QVQLVESGPTLVKPTQTLTLTCTFSGFSLSTNGVGVAWIRQPPGKALEWLAIIYWD DDKRYSPSLKSRLTITKDTSKNQVVLTVTDMDPVDTATYYCAHTIGVPAATRFDYW GQGTLVTVSS | ADI-41588 | Heavy chain variable region ("HC") amino acid sequence |
| Ab 862 | 1724 | SYELTQPPSVSVSPGQTASITCSGDKLGDKFACWYQQKPGQSPVLVIYQDNKRPSG IPERFSGSNSGNTATLTISGTQAMDEADYYCQAWDSSTASYVFGTGTKLTVL | ADI-41588 | Light chain variable region ("LC") amino acid sequence |
| Ab 863 | 1725 | EVQLLESGGGLVQPGGSLRLSCAASGFTFNFFALTWVRQAPGKGLEWVSAISGSGE STYYADSVKGRFTISRDNSKNTLYLQMNSLRAEDTAVYYCAKFARSGDYASFFDYW GQGTLVTVSS | ADI-41589 | Heavy chain variable region ("HC") amino acid sequence |
| Ab 863 | 1726 | DIRVTQSPDSLAVSLGERATINCKSSQNVFYSSNNKNFLAWYQQKPGQPPKLLIYW ASTRESGIPDRFSGSGSGTDFTLTISSLQAEDVAVYYCQQYYSTKFTFGPGTKVEI K | ADI-41589 | Light chain variable region ("LC") amino acid sequence |
| Ab 864 | 1727 | EVQLVQSGGGLVKPGGSLRLSCTASGFTFSDHYMSWIRQAPGKGLEWISYISSTSS FTNYANSVKGRFTISRDNAKNSLYLQMNSLRAEDTAVYYCARDRSILYSGYSLDYW GQGTLVTVSS | ADI-41590 | Heavy chain variable region ("HC") amino acid sequence |
| Ab 864 | 1728 | DIQMTQSPSSLSASVGDRVTISCRASQSILNYLNWYQHKPGKAPKLLIYAASSLQS GVPSRFSGSGSGTDFTLTISGLQPEDFATYYCQQSDSTRTFGQGTKVEIK | ADI-41590 | Light chain variable region ("LC") amino acid sequence |
| Ab 865 | 1729 | QVTLKESGGGLVKPGGSLRLSCAASGFTFSDYYMSWIRQAPGKGLEWVSYISSSSS YTNYADSVKGRFTISRDNAKNSLYLQMNSLRAEDTAVYYCAREAVAAAGTDYFDYW GQGTLVTVSS | ADI-41591 | Heavy chain variable region ("HC") amino acid sequence |
| Ab 865 | 1730 | QSVLTQPPSVSGAPGQRVTISCTGSSSNIGAGYDVHWYQQPPRTAPKLLIYGNSNR PSGVPDRFSGSKSGTSASLAITGLQAEDEADYYCQSYDSSLSGYVFGTGTKLTVL | ADI-41591 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 866 | 1731 | EVQLVESGSELKKPGASVKVSCKASGYTFRTYVMNWVRQAPGQGLEWMGWINT NTGNPTYAQGFTGRFVFSLDTSVSTAYLQISSLKAEDTAVYYCARESIDDYDSSGY GRTFDYWGQGTLVTVSS | ADI-41592 | Heavy chain variable region ("HC") amino acid sequence |
| Ab 866 | 1732 | SYELTQPPSVSVSPGQTASIPCSGDKVGKTYVYWYQQTPGQSPGLVIYQDTKRPS GIPERFSGSSSGNTATLTISGTQTMDEADYYCQAWDTSTASYVFGTGTKLTVL | ADI-41592 | Light chain variable region ("LC") amino acid sequence |
| Ab 867 | 1733 | QVQLVQSGVEVKKPGESLKISCKGSGYSFTNYWIAWVRQMPGKGLEWMGIIYPG DSDTRYSPSFQGQVTISADKSISTAYVQWSSLKASDTAIYYCARGDILTNSGPDA FDIWGQGTMVTVSS | ADI-41593 | Heavy chain variable region ("HC") amino acid sequence |
| Ab 867 | 1734 | DIQMTQSPSSFSASTGDRVTITCRASQAISSYLAWFQQKPGKAPKLLIYAASTLQS GVPSRFSGSGSGTDFTLTISCLQSEDFATYYCQQYYSYPLTFGGGTKVEIK | ADI-41593 | Light chain variable region ("LC") amino acid sequence |
| Ab 868 | 1735 | EVQLVESGGGLVKPGGSLRLSCAASGFSFSSYYMNWVRQAPGKGLEWVSSISPSSS YTNYADSVKGRFTISRDNAKDSLYLQMNSLRAEDTAVYYCARDGLLGITIFGVVQD YWGQGTLVTVSS | ADI-41594 | Heavy chain variable region ("HC") amino acid sequence |
| Ab 868 | 1736 | QSVVTQPPSVSGAPGQRVTISCTGSSSNIGAGYDVHWYQQLPGTAPKLLIYGNTNR PSGVPDRFSASKSGTSASLAITGLQAEDEADYYCQSYDSSLSVVFGGGTKLTVL | ADI-41594 | Light chain variable region ("LC") amino acid sequence |
| Ab 869 | 1737 | QVQLVQSGGGVVQPGGSLRLSCAASGFTFSDYGMHWVRQAPGKGLEWVAVISD GGSNQYSADSVRGRFTISRDNSKNTLYLQMNSLRPEDTAVYYCAKARIAARAIFDY WGQGTLVTVSS | ADI-41595 | Heavy chain variable region ("HC") amino acid sequence |
| Ab 869 | 1738 | DIQLTQSPSSLSASVGERITITCQASRDVRIYLNWYQHKPGKAPKLLIYDASNLET GVPSRYSGSGSGTDFTFTISSLQPEDIATYFCQQYDLLPPTFGVGTKVEIK | ADI-41595 | Light chain variable region ("LC") amino acid sequence |
| Ab 870 | 1739 | QVQLQQWGAGLLKPSETLSLTCAVYGDSFSGYFWTWIRQPPGKGLEWIGEINLSG STNYNPSLKSRVTILVDTSKNQFSLKLSSVTAADTAVYYCARGLHVSDDQDSSGYY FHPGSFDYWGQGTLVTVSS | ADI-41596 | Heavy chain variable region ("HC") amino acid sequence |
| Ab 870 | 1740 | DIRMTQSPDSLAVSLGERATINCKSSQSVLYSSNNKNYLAWYQQKPGQPPKLLINW ASTRESGVPDRFSGSGSGTDFTLAISSLQAEDVAVYYCQQYYSTPLTFGGGTKVEI K | ADI-41596 | Light chain variable region ("LC") amino acid sequence |
| Ab 871 | 1741 | QVQLQESGPGLVKPSETLSLTCTVSGASVSSNNYYWSWIRQPPGKGLEWIGYIYYS GSTNYNASLKSRVTISVDTSKNQFSLKLSSVTAADTALYYCAGEHIFGVASPFEAP FDYWGQGTMVTVSS | ADI-41597 | Heavy chain variable region ("HC") amino acid sequence |
| Ab 871 | 1742 | SSELSQPPSVSVAPGKTARITCGGNNIGIKSVHWYQQKPGQAPVLVIYSDSDRPS GIPERFSGSNSGNTATLTITRVEAGDEADYYCQVWDSSSDHFVFGIGTKVTVL | ADI-41597 | Light chain variable region ("LC") amino acid sequence |
| Ab 872 | 1743 | EVQLVESGPGLVKPSETLSLTCTVSGGSITPYYWSWIRQPPGKGLEWIGNISYSGS TTYNPSLKSRVTISVDRSKDQFSLRLRSVTAADTAVYYCARVVTLVLGVSLNDAFD IWGQGTMVTVSS | ADI-41598 | Heavy chain variable region ("HC") amino acid sequence |
| Ab 872 | 1744 | DIQMTQSPSSLSASVGDRVTITCRASQSISRYLNWYQHKPGKAPILLIYAATTLES GVPPRFSGSGSGTDFSLTISSLQPEDFATYYCQQSYSVPLTFGGGTKLEIK | ADI-41598 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 873 | 1745 | EVQLLESGGGLVQPGGSLRLSCAASGFIFSNYEMNWVRQAPGKGLEWISHITPTGN SIYYADSVKGRFTISRDNAKNAQYLQMHSLRPDDTAIYYCARGEDPIAATGGFDSW GQGTLVTVSS | ADI-41599 | Heavy chain variable region ("HC") amino acid sequence |
| Ab 873 | 1746 | EIVLTQSPSSLSASVGDRVTIPRRSSQNVDKFLHWYQQRPGKAPKLLIYAAFSLQS GVPSRFSGSGSGTDFTLTISSLQPEDFATYYCQQSYSTPFTFGQGTKVEIK | ADI-41599 | Light chain variable region ("LC") amino acid sequence |
| Ab 874 | 1747 | EVQLLESGGNMVQPGKSLRLSCAASGFTFSNYGMHWVRQAPGKGLEWVAVISKD GNNEHYADSVRARFTVSRDNSKNTLFLQMNSLRPEDTAVYYCAIGGLSGSYFGEYF QHWGRGTLVTVSS | ADI-41600 | Heavy chain variable region ("HC") amino acid sequence |
| Ab 874 | 1748 | DIQMTQSPSSMSASLGDRVTITCRASQGISTWLAWYQQKPGEAPKLLIYAAFGLQS GVPSRFSGSGSGTDFTLTINNLQPEDFATYYCQQAISFPPFTFGGGTKVEIK | ADI-41600 | Light chain variable region ("LC") amino acid sequence |
| Ab 875 | 1749 | EVQLLESGGGLVKPGGSLRLSCAGSGFRFSDYYMTWIRQAPGKGLEWVSYISSSST YTYYTDSVKGRFTVSRDNAKNSLYLQMNTLRAEDTAIYYCAISNRYDSRTFYYDYW GQGTLVTVSS | ADI-41601 | Heavy chain variable region ("HC") amino acid sequence |
| Ab 875 | 1750 | QSVLTQPPSVSGAPGQRVIISCTGSSSNIGAGYDVHWYQQFPGTAPKLLIYGNNNR PSGVPERFSGSKSGTSASLAITGLQADDEADYYCQSYDSLSEVVFGGGTKVTVL | ADI-41601 | Light chain variable region ("LC") amino acid sequence |
| Ab 876 | 1751 | EVQLQESGPGLVKPSETLSLTCTVSGGSLSGYYWSWIRQPPGKGLEWIGYIYHSGS TNYNPSLESRVTISVDTSKNQFSLKVNAVTAADTAVYYCAKVERLLRFDPWGQGTL VTVSS | ADI-41602 | Heavy chain variable region ("HC") amino acid sequence |
| Ab 876 | 1752 | QSVLIQPASVSGSPGQSITISCIGSSSDVGGYNYVSWYQHYPGKAPKLMIYDVSNR PSGVSNRFSGSKSGNTASLTISGLQAEDEADYYCSSYTSSTSYVFGTGTKVTVL | ADI-41602 | Light chain variable region ("LC") amino acid sequence |
| Ab 877 | 1753 | EVQLVESGGGLVKPGRSLRLSCTTSGFTFGDYAMSWFRQAPGKGLEWVGFIRSKPY GGATAYAASVRGRFTISNDDSKSIAYLQMESLKIEDTAVYYCARDYDDFFFYDYWG QGTLVTVSS | ADI-41603 | Heavy chain variable region ("HC") amino acid sequence |
| Ab 877 | 1754 | DIRMTQSPATLSVSPGERATLSCRASENIYSNLAWYQQKPGQAPRLLIYGASTRAT GLPARFSGSGSGTEFTLTISSLQSEDFAVYYCQQYNNWPAFGGGTKVEIK | ADI-41603 | Light chain variable region ("LC") amino acid sequence |
| Ab 878 | 1755 | QVTLKESGAEVKKPGASVKVSCKASGYTFTGYYMHWVRQAPGQGLEWMGRINP NSGGTNYAQKFQGRVTMTRDTSISTAYMELSRLRSDDTAVYYCAREASRFGGFDY WGQGTLVTVSS | ADI-41604 | Heavy chain variable region ("HC") amino acid sequence |
| Ab 878 | 1756 | DIVLTQSPSSLSASVGDRVTITCQASQDISNYLNWYQQKPGKAPKLLIYDASNLET GVPSRFSGSGSGTDFTFTISSLQPEDIATYYCQQYDNLLGYTFGQGTKVEIK | ADI-41604 | Light chain variable region ("LC") amino acid sequence |
| Ab 879 | 1757 | QVQLVESGPGLVKPSQTLSLTCSVSGGSISSDDHYWSWIRQHPGKGLEWIGYIYYS GYTNYNPSLKSRVTISVDTSKNQFSLRLSSVTAADTAVYYCARETDITIFGVVPVG YFDYWGQGTLVTVSS | ADI-41605 | Heavy chain variable region ("HC") amino acid sequence |
| Ab 879 | 1758 | DIQVTQSPDSLAVSLGERATINCKSSQSILSSTNNKNFLAWYQQKPGQPPKLLLHW ASTREFGVPDRFSGSGSGTEFTLTISSLQAEDVAVYYCQQYYTTPYTFGQGTKVEIK | ADI-41605 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 880 | 1759 | EVQLLESGPGLVKPSETLSLTCTVSGGSVSSGGYYYTWIRQPPGKGLEWIGYAFYSG<br>DTNYNPSLKSRVTISVDTSKNQFSLKLTSVTAADTAVYYCASTYTFGASGFDFWGQG<br>TLVTVSS | ADI-41606 | Heavy chain variable region ("HC") amino acid sequence |
| Ab 880 | 1760 | DIVMTQSPSFMSASVGDRVTITCRASQGISNWLLWYQQKPGKAPKLLIYAASSLQS<br>GVPSRFSGSRSGTDFTLTISSLQPEDFAIYYCQQANSFPLTFGQGTRLEIK | ADI-41606 | Light chain variable region ("LC") amino acid sequence |
| Ab 881 | 1761 | EVQLVESGPGLVKPSQTLSLTCTVSGGSINIGGYYWSWIRQHPEKGLEWIGYIYYSG<br>TTYYNPSLESRVTISIDTSKNQFSLNLSSVTAADTAVYYCASVDQIGATRFDYWGQG<br>TLVTVSS | ADI-41607 | Heavy chain variable region ("HC") amino acid sequence |
| Ab 881 | 1762 | QPVLTQPRSVSGSPGQSVTLSCTGTSSDVGTYNYVSWYQHHPGKAPKLIIYDVNKR<br>PSGVPDRFSGSKSGNTASLTISGLQAEDEADYYCCSYAGSYTLNVFGTGTKLTVL | ADI-41607 | Light chain variable region ("LC") amino acid sequence |
| Ab 882 | 1763 | QVQLVQSGDEVKKPGESLKISCKGSEHTFTNYWIAWVRQMPGKGLECMGVIWPD<br>DSDTKYSPSFQGQVTISADKSINTAYLHLSSLRASDTAMYYCATSKFRTGFDFWGQ<br>GTLVTVSS | ADI-41608 | Heavy chain variable region ("HC") amino acid sequence |
| Ab 882 | 1764 | NFMLTQPHSVSESPGKTVIISCTRSSGNIASNYVQWYQQRPGSSPTTVVYEDNQRP<br>SGVPDRFSGSIDSSSNSASLTISGLKTEDEADYYCQSYDSSNPWVFGGGTKLTVL | ADI-41608 | Light chain variable region ("LC") amino acid sequence |
| Ab 883 | 1765 | QVQLVESGAEVKKPGASVKVSCKASGYSFTSYYMHWVRQAPGQGLEWMGVISTN<br>GGTASYSQNFRGRVTLTRDTSTSTAYMELSSLTSEDTAVYYCVREGYCNGGSCSYF<br>DSWGQGTLVTVSS | ADI-41609 | Heavy chain variable region ("HC") amino acid sequence |
| Ab 883 | 1766 | QSVLTQPPSVSGAPGQRVSISCTGSSSNIGAGYDVHWYQQLPGTAPKVLIYGNNYR<br>PSGVPDRFSGSKSGTSASLAITGLQTEDEADYYCQSYDSRLSVVFGGGTKLTVL | ADI-41609 | Light chain variable region ("LC") amino acid sequence |
| Ab 884 | 1767 | EVQLLESGGGVVQPGRSLRLSCAASELSFRNYGMHWVRQAPGKGLEWVAVISYD<br>GNDKYYADSVKGRFTISRDNSKKTLYLQMDSLRAEDTAVYYCAKEGAYCGGDCFSS<br>WGQGTLVTVSS | ADI-41610 | Heavy chain variable region ("HC") amino acid sequence |
| Ab 884 | 1768 | GIQLTQSPSSLSASVGDRVTITCRASQSSSSYLNWYQQKPGKAPKLLIYAASSLQS<br>GVPSRFSGSGSGTDFTLTISSLQPEDFATYYCQQSYSFGGGTKVEIK | ADI-41610 | Light chain variable region ("LC") amino acid sequence |
| Ab 885 | 1769 | EVQLVESGGGLVKPGGSLRLSCAASGFTFSDYSMNWVRQAPGKGLEWVSSTSSGS<br>TYIYYADSVKGRFTISRDNGKNSLYLQMNSLRAEDTAVYYCARAFRLGYDALDIWG<br>QGTMVTVSS | ADI-41611 | Heavy chain variable region ("HC") amino acid sequence |
| Ab 885 | 1770 | DIRMTQSPSSLSASVGDRVTIICRASQSISNYLNWYQQKPGKAPKLLIYVASNLQS<br>GVPSRFSGSGSGTDFTLTISSLQPEDFATYYCQQTYSPPPTFGGGTKLEIK | ADI-41611 | Light chain variable region ("LC") amino acid sequence |
| Ab 886 | 1771 | EVQLQESGPGLVKPSGTLSLTCAVAGGFISSGNWWSWIRQPPGKGLEWIGEVYHS<br>GRTSYNPSLKSRVTISVDNSKNQFSLKMSSVTAADTAVYYCARVESYSSSGYYIAY<br>FDNWGQGNLVTVSS | ADI-41626 | Heavy chain variable region ("HC") amino acid sequence |
| Ab 886 | 1772 | DIVLTQSPSSLSASVGDRVTITCRASQSISRYLSWYQQKPGKAPKLLIYAAFSLQT<br>GVPSRFSGSGSGTDFTLTISSFQTEDSATYYCQQSYSAPVTFGGGTKVEIK | ADI-41626 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 887 | 1773 | QVQLQQWGPGLVKPSETLSLSCAVSGGSLRGHFWSWIRQPPGKGLEWIGEINHG GRTNFNPSLKSRLTISEDSSKNQFSLKLSSVTAADTAVYYCARRWGYDSSGYYFFD YWGQGTLVTVSS | ADI-41644 | Heavy chain variable region ("HC") amino acid sequence |
| Ab 887 | 1774 | EIQMTQSPATLSVSPGERATLSCRASQTLGFNLAWYQQKPGQSPRLLIYGASTRAT GIPARFSGSGAGTEFTLTISSLQSEDFAVYFCQQYSNYYTFGQGTKVEIK | ADI-41644 | Light chain variable region ("LC") amino acid sequence |
| Ab 888 | 1775 | EVQLVQSGAEVKKPGSSVKVSCKASGGTFSRNAISWVRQAPGQGLEWMGGIIPIF GAANYPQKFQGRVTITADKSTSTAYMELSSLRSEDTALYYCARTMGEMTTTPVSIY YYGMDVWGQGTTVTVSS | ADI-41660 | Heavy chain variable region ("HC") amino acid sequence |
| Ab 888 | 1776 | QSVLTQPPSVSAAPGQKVTISCSGSSSNIGINYVSWYQQLPGTAPKLLIYDNNKRP SGIPDRFSGSKSGTSATLGITGLQTGDEADYYCGTWDSSLSAGYVFGSGTKLTVL | ADI-41660 | Light chain variable region ("LC") amino acid sequence |
| Ab 889 | 1777 | QVQLVQSGAEVKKAGESLKISCKGPRHSFTSYWIGWVRQMPGKGLEWMASIYPG DSDSRYSPSFEGQVTISADKSIDTAFLQWSSLKASDTAMYFCARYVGAVPGGNWYF DLWGRGTLVTVSS | ADI-41662 | Heavy chain variable region ("HC") amino acid sequence |
| Ab 889 | 1778 | SYELIQLPSVSVSPGQTARITCSGDALPKKYAYWYQQKSGQAPVLVIYDDNKRPSG IPARFSGSSSGTMATLTISGAQVEDEGDYYCYSTDSTGDHRGVFGGGTKLTVL | ADI-41662 | Light chain variable region ("LC") amino acid sequence |
| Ab 890 | 1779 | EVQLVQSGDEVKKPGASVKVSCKASGYPFSTYGISWVRQAPGQGLEWMGWIGVY TGGTNYAQKFQGRVTLTTDTSTSTAYMELRSLRSDDTAVYYCARGTGSYMTATYFD YWGQGTLVTVSS | ADI-41664 | Heavy chain variable region ("HC") amino acid sequence |
| Ab 890 | 1780 | SYELTQPPSVSVAPGQTARITCGGNNIGSKAVHWYQQKPGQAPVLVVYDDYDRPS GIPERFSGSNSGNTATLTISRVEAGDEADYYCQVWDSSSDYVFGTGTKLTVL | ADI-41664 | Light chain variable region ("LC") amino acid sequence |
| Ab 891 | 1781 | QVTLKESGPALVKPTQTLTLTCTFSGFSLSTSRMCVSWIRQPPGKALEWLARIDWD GDIYYSTSLRTRLTISKDTSKNQVVLTMTNMDPVDTATYYCARTSIYATGGYYLYY SDYWGQGTLVTVSS | ADI-41677 | Heavy chain variable region ("HC") amino acid sequence |
| Ab 891 | 1782 | EIVMTQSPSSLSASVGDRVTITCRASQSIASYVNWFQQKPGKAPKLLIYAASNVHS GVPSRFSGSGSGTGFTLTISSLQPEDSAIYYCQQSYTTPWTFGQGTKLEIK | ADI-41677 | Light chain variable region ("LC") amino acid sequence |
| Ab 892 | 1783 | EVQLVESGGGVVQPGGSLRLSCAASGFTFRTYGMHWVRQAPGKGLEWVAVISYD GSNKYYADSLMGRFTISRDNSKNTLYLQMNSLRAEDTAVYYCAKCFVPGSGGWYE YYFDYWGQGTLVTVSS | ADI-41678 | Heavy chain variable region ("HC") amino acid sequence |
| Ab 892 | 1784 | QSVLTQPPSASGSPGQSVTISCTGTSSDVGGYNYVSWYQQHPGKAPKLMIYEVSKR PSGVPDRFSGSKSGNTASLTVSGLQAEDEADYYCSSYAGINNSVLFGGGTKLTVL | ADI-41678 | Light chain variable region ("LC") amino acid sequence |
| Ab 893 | 1785 | QVQLVQSGAEVKKPGESLRISCKGSGYSFSSHWIGWVRQKPGKGLEWMGIIYPGD SDTRYSPSFQGHVTISADKSISTAYLRWSSLKASDTAIYYCAKRMVGDYYGMNLWG QGTTVTVSS | ADI-41690 | Heavy chain variable region ("HC") amino acid sequence |
| Ab 893 | 1786 | EIVMTQSPSSLSASVGDRVTITCQASQDISNRLNWYQQKPGKAPKLLIYDASNLETG VPSRFSGSGSGTDFTFTISSLQPEDIATYFCQQYDYLLWFTFGPGTKVDIK | ADI-41690 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 894 | 1787 | QVQLVQSGAEVKKPGESLKISCQASGYSFTTYWIGWVRQTPGKGLEWMGIIYPGD SDTRYTPSFQGQVTISADKSISTAYLHWSSLKASDTAMYYCARLSGGYTFGFDYWGL GTLVTVSS | ADI-41701 | Heavy chain variable region ("HC") amino acid sequence |
| Ab 894 | 1788 | NFMLTQPHSVSESPGKTVTISCTRSSGNIARYYVQWYQQRPGRAPTTVIYEDDQRP SGVPDRFSGSIDRSSNSASLTISGLKTEDEADYYCQSYDASNYVFATGTKVTVL | ADI-41701 | Light chain variable region ("LC") amino acid sequence |
| Ab 895 | 1789 | EVQLLESGSGLVKPLQTLSLTCAVSGGSISSGGYSWSWIRQPPGKGLEWIGYIYPS GSTYYNPSLKSRVTMSIDRSKNQFSLRLTSVTAADTAVYYCARGDGNDFWSADSSH AFAIWGQGTMVTVSS | ADI-41703 | Heavy chain variable region ("HC") amino acid sequence |
| Ab 895 | 1790 | EIVMTQSPGTLSLSPGERATLSCRASQIVGNSYLAWYQQKPGQAPRLLIYGASSRAT GIPERFSGSGSGTDFTLTISRLEPEDFAVYHCQQYGSSPWTFGQGTKVEIK | ADI-41703 | Light chain variable region ("LC") amino acid sequence |
| Ab 896 | 1791 | QVQLVESGGGVVQPGRSLRLSCAASGFTFSSYGMHWVRQAPGKGLEWVSVIWFD GSKKYYEDSVKGRFTISRDNSKNTLYLEMNSLRAEDTAVYYCAREAPVRLGELSLYG YFDYWGQGTLVTVSS | ADI-41720 | Heavy chain variable region ("HC") amino acid sequence |
| Ab 896 | 1792 | DIQMTQSPSTLSASVGDRVTITCRASQSFSSWLAWYQQKPGKAPKLLIYDASTLESG VPSRFSGSGSGTEFTLTISSLQPDDFATYYCQQYNSYSWTFGQGTKLEIK | ADI-41720 | Light chain variable region ("LC") amino acid sequence |
| Ab 897 | 1793 | QVQLQESGPGLVKPSQTLSLTCTVSGGSMISGDFYWSWIRQPPGKGLEWIGYIYYS GTTYYSPSLKSRVSMSIDTSKSQFSLKLSSVTAADTAVYYCARKYSYGEKAYHYWGQ GTLVTVSS | ADI-41737 | Heavy chain variable region ("HC") amino acid sequence |
| Ab 897 | 1794 | EIVLTQSPGTLSLSPGERATLSCRASQTVGNNYLAWYQQKPGQAPRLLIYGASSRAT GIPDRFSGSGSGTDFTLTISRLESEDFAVYHCHQYGTSPQTFGQGTKVEIK | ADI-41737 | Light chain variable region ("LC") amino acid sequence |
| Ab 898 | 1795 | EVQLVESGSGLVKPSQTLSLTCSVSGGSISSGGYSWSWIRQPPGKGLEWIGFIYNTG STYSNPSLKSRLTLSVDRSNNRFSLKLNSVTAADTGVYFCARSGNVRQCDATGHCST NYYFEYWGLGTLVTVSS | ADI-41743 | Heavy chain variable region ("HC") amino acid sequence |
| Ab 898 | 1796 | EIVMTQSPATLSVSPGERATLSCRASQSVSSNLAWYQQKPGQAPRLLIYGASTRAT GIPARFSGSGSGTEFTLTISSLQSEDFAVYYCQQHDDWPPLTFGGGTKVEIK | ADI-41743 | Light chain variable region ("LC") amino acid sequence |
| Ab 899 | 1797 | EVQLLESGGGVVQPGRSLRLSCAASGLSFNSFGMHWVRQAPGKGLEWVAVIAYD GSNKYYADSVKGRFSISRDNSKNTLYLQMDSLRAEDTAVYYCAKAEAPNFSWSGYL SAFDIWGQGTTVTVSS | ADI-41756 | Heavy chain variable region ("HC") amino acid sequence |
| Ab 899 | 1798 | QPVLTQPASVSGSPGQSVTVSCTGTSDDVGDYNYVSWYQQHPGKAPKLLIFEVSD RPSGVSTRFSGSKSGNTASLTISGLQTEDEADYYCSSYTSRNLYVFGTGTKVTVL | ADI-41756 | Light chain variable region ("LC") amino acid sequence |
| Ab 900 | 1799 | EVQLVESGGGLVQPGRSLRLSCAASGFTFGDYAMHWVRQAPGKGLEWVSGITW NSGRVVYADSVKGRFTISRDNAKNSLYLQINSLRAEDTALYYCVKGSCNGGICYS ADYWGQGTLVTVSS | ADI-41768 | Heavy chain variable region ("HC") amino acid sequence |
| Ab 900 | 1800 | NFMLTQPHSVSESPGKTVTISCTRSSGSIARNFVHWYQQRPGSSPTTVIYEDNQR PSGVPGRFSGSIDSSSNSASLTISGLRSEDEADYYCQSYDSDNWVFGGGTKLTVL | ADI-41768 | Light chain variable region ("LC") amino acid sequence |

TABLE 5-continued

| | | | | |
|---|---|---|---|---|

Informal Sequence Listing

| Antibody No. | SEQ ID NO: | Sequence | Clone # (ADI) | Descriptors |
|---|---|---|---|---|
| Ab 901 | 1801 | EVQLLESGGGLVEPGTSLRLSCEASGFTFSDYYMSWIRQAPGKGPEWVADISSRGV VTYYADSVKGRFTISRDNAKNSLYLQLNSLGAEDTAVYYCARLREVTYIMPTIDYF DYWGQGTLVTVSS | ADI-41772 | Heavy chain variable region ("HC") amino acid sequence |
| Ab 901 | 1802 | SYELTQPPSVSVSPGQTARITCSGDAFVKKYAYWYHQKSGQAPVVVIYEDTKRPSG IPERFSGSSSGTTATLTISGAQVEDEGDYYCYSRDFSGDHGVFGGGTKLTVL | ADI-41772 | Light chain variable region ("LC") amino acid sequence |
| Ab 902 | 1803 | QVQLVESGGGQGQPGRSLRLSCAASGFTFDDYAMHWVRQVPGKGLEWVSGIN WNSGYIGYADSVKGRFTISRDNAKNSLYLQMNSLRAEDTALYYCAKANNPIDSSGY NRGFDTWGQGTLVTVSS | ADI-41778 | Heavy chain variable region ("HC") amino acid sequence |
| Ab 902 | 1804 | QSALTQPRSVSGSPGQSVTISCTGTSSDVGGYNYVSWYQQHPGKAPKLMIYDVNK RPSGVPDRFSGSKSDNTASLTISGLQAEDESDYFCCSYAGTYTWVFGGGTKVTVL | ADI-41778 | Light chain variable region ("LC") amino acid sequence |
| Ab 903 | 1805 | QVQLVQSGAEVRKPGASVKVSCKAFGYTFTNFAISWVRQAPGQGLEWMGWIGP YNGDTDYEQKFQGRVTMTADTSSSTVFMELRSLRFDDTAVYYCARGKGSTIPLGYY IGMDVWGQGTTVTVSS | ADI-41781 | Heavy chain variable region ("HC") amino acid sequence |
| Ab 903 | 1806 | ETTLTQSPSSLSASVGDRVTMTCRASQGISNYLAWYQQKPGKPPKLLIYLASSLQS GVPSRFSGSGSGTDFTLTISSLQPEDVATYYCQKYNSAPLTFGGGTKLEIK | ADI-41781 | Light chain variable region ("LC") amino acid sequence |
| Ab 904 | 1807 | QVQLVQSGDEVKKPGASVKVSCKSSGYTFTHFGVSWVRQAPGQGLEWMGWISG YNGNTNYAQKLQGRVTMTTDTSTTTAYMELTSLRSDDTAVYYCARDSPAGTVTLD FWGQGTTVTVSS | ADI-41783 | Heavy chain variable region ("HC") amino acid sequence |
| Ab 904 | 1808 | DIVMTQSPLSLPVTLGQPASISCRSSQSLVYSDGNTYLNWFQQRPGQSPRRLIYKV SNRDSGVPDRFSGSGSGTDFTLKISRVEAEDVGVYYCMHGTHWPPEYTFGQGTKVE IK | ADI-41783 | Light chain variable region ("LC") amino acid sequence |
| Ab 905 | 1809 | EVQLLESGGGVVQPGRSLRLSCAASGFTFSSSGMHWVRQAPGKGLEWVAIISSDG SKHYYADSVKGRFTISRDNSKNTLYLEMNSLRAEDSAVYYCAREGVWSGFFVDTGT DFRHHGMDVWGQGTTVTVSS | ADI-41787 | Heavy chain variable region ("HC") amino acid sequence |
| Ab 905 | 1810 | SYELTQPPSVSVSPGQTARITCSGDALPKKFAFWYQQKSGQAPLLVIHEDNKRPSGI PERFSGSSSGTLATLTISGAQVEDEADYYCYSIDTSANLGVFGGGTKLTVL | ADI-41787 | Light chain variable region ("LC") amino acid sequence |
| Ab 906 | 1811 | QVQLVQSGAEVKKPGASVKVSCQASGYTLTTYDINWVRQAPGQGLEWMGWMN ANSGNTGYAQKFQGRVTMTRNISISTAYMELSSLGPEDTAVYYCARGFYKWNDW SFDYWGQGTLVTVSS | ADI-41788 | Heavy chain variable region ("HC") amino acid sequence |
| Ab 906 | 1812 | QSVLTQPPSVSVAPGQTARITCGGNNIGSKSVHWYQQKPGQAPVLVVYDDSDRPS GIPERFSGSNSGNTAPLTISRVEAGDEADYYCQVWDGDSAHHAVFGGGTQLTVL | ADI-41788 | Light chain variable region ("LC") amino acid sequence |
| Ab 907 | 1813 | QVQLVQSGAEVKKPGSSVKVSCKASGGTFSNYGISWVRQAPGQGLERLGGIIPIYG TANHAQNFQGRVTITADESTSTAYMELSSLRSEDTAVYYCARDGTFVRYYGMDVW GQGTTVTVSS | ADI-41790 | Heavy chain variable region ("HC") amino acid sequence |
| Ab 907 | 1814 | EIVLTQSPATLFLSPGERATLSCRASQSVSNYLAWFQQKPGQAPRLLIYDTSIRAT GIPARFSGSGSGTDFTLTISSLEPEDFAFYYCQQRSNWPPTFGGGTKLEIK | ADI-41790 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 908 | 1815 | QVQLVQSGGGLVKHGGSLRLSCAASGFTFSSYSMNWVRQAPGKGLEWASSISSSS SYIYYADSVKGRFTISRDNAKNSLYLQMNSLRAEDTAVYYCARTEYSSSSPIFDYW GQGTLVTVSS | ADI-41792 | Heavy chain variable region ("HC") amino acid sequence |
| Ab 908 | 1816 | QSVLTQPPSVSGAPGQRVTISCTGSSSNIGAGYDVHWYQQLPGTAPKLLTYGNSNR PSGVPDRFSGSKSGTSASLAITGLQAEDEADYYCQSYDSSLSGSVFGGGTKVTVL | ADI-41792 | Light chain variable region ("LC") amino acid sequence |
| Ab 909 | 1817 | EVQLQQWGAGLLKPSETLSLTCAVYGGSFSGYYWSWIRQPPGKGLEWIGEINHSG STNYNPSLKSRVTISVDTSKNQFSLKLSSVTAADTAVYYCARGTRTIVYCDGDCYQ PWAYHYYGMDVWGQGTTVTVSS | ADI-41794 | Heavy chain variable region ("HC") amino acid sequence |
| Ab 909 | 1818 | QSVVTQEPSVSAAPGQKVTISCSGGSSNIGNNYVSWYQHLPGTAPKLLIYDNDKRP SGIPDRFSGSKSGTSATLGITGLQTGDEADYYCGTWDSSLSAVVFGGGTKLTVL | ADI-41794 | Light chain variable region ("LC") amino acid sequence |
| Ab 910 | 1819 | QVQLVQSGAEVKKPGSSVKVSCQASGGTFSTHALSWVRQTPGHGLEWVGGVLPV FGATKYPRKFQGRVTITADKSTNTAYMELSSLRSDDTAVYYCARVVVHSTITTAKD FFSGVHDIWGQGTMVTVSS | ADI-41799 | Heavy chain variable region ("HC") amino acid sequence |
| Ab 910 | 1820 | DIRMTQSPSTLSASVGDRVTITCRASQTVSSWLAWYQQKPGKAPKLLIYQASSLES GVPSRFSGSGSGTEFTLTISGLQPDDFATYFCQHYNSYSPVTFGGGTKVEIK | ADI-41799 | Light chain variable region ("LC") amino acid sequence |
| Ab 911 | 1821 | QVQLVQSGAEVKKPGASVKVSCKASGYTFTDYYMHWVRQAPGQGLEWLAWINP YTGGTNYAQKFQGRVTLTRDTSVSTTYMEVTRLRSDDTAVYYCARGESFHHWGQ GTLVTVSS | ADI-41800 | Heavy chain variable region ("HC") amino acid sequence |
| Ab 911 | 1822 | QSALTQPASVSGSPGQSITISCTGTSSDIGGYDYVSWYQQHPGKVPKLMIYEVSTR PSGVSIRFSGSKSGNTASLTISGLQAEDEADYYCSSYTRSTITSVVFGGGTKLTVL | ADI-41800 | Light chain variable region ("LC") amino acid sequence |
| Ab 912 | 1823 | RCTLQQWGAGRVKPSETLSLTCAVYRGPFSGYYWSWIRQPPGKGLEWIGEINLGE TNPGGSTHYNPSLRSRLSMSIDTSKKQFSLRVNSVTAADTAVYYCTRGPVSRIYDT SGSYSLNYYGMDVWGQGTTVTVSS | ADI-41803 | Heavy chain variable region ("HC") amino acid sequence |
| Ab 912 | 1824 | DIRMTQSPSSLSASVGDRVTITCRASQGIRNDLGWYQQKPGRAPERLIYPASSLQG GVPSRFIASGSGTEFTLTISNLQPEDFATYYCLQHNSYPRTFGQGTKVEIK | ADI-41803 | Light chain variable region ("LC") amino acid sequence |
| Ab 913 | 1825 | QVQLQQWGAGLLKPSETLSLTCSVLGGSFSGYYWTWIRQPPGKGLEWIGEITHDG SSNYNPSLNSRVTISVDTSNYQFSLKMRSVTAADTAVYYCARSPDLTIFGGLYFYY GISVWGQGTTVTVSS | ADI-41804 | Heavy chain variable region ("HC") amino acid sequence |
| Ab 913 | 1826 | DIQMTQSPSSLSASMGDRVTITCRASQDISNYLAWYQQKPGKVPNLLIYAASTLQG GVPSRFSGSGSGTDFTLTISSLQPEDVAIYYCQKYKSAPRTFGQGTKVEIK | ADI-41804 | Light chain variable region ("LC") amino acid sequence |
| Ab 914 | 1827 | QVQLVQSGAEVKKPGESLKISCKASGYSFTSYWIAWVRQMPGKGLEWMGIIFPGD SDTRYSPSFQGQVTISADKSISTAYLQWSSLEASDTAMYYCAKSTTYYYYGLDVWG QGTTVTVSS | ADI-41805 | Heavy chain variable region ("HC") amino acid sequence |
| Ab 914 | 1828 | QPVLTQPASVSGSPGQSITISCTGTSSDVGGYDYVSWYQQYPGKAPKLMIYEVSNR PLGVSNRFSGSRSGYTASLTISGLQAEDETNYYCSSYTSSRTWVFGGGTKLTVL | ADI-41805 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 915 | 1829 | EVQLLESGPALVKPTQTLTLTCTFSGFSLTTTRMSVSWIRQPPGKALEWLARIDWD DDKYYSTSLKTRLTISKDTSKNQVVLTMTNMDPVDTATYFCARVNVYAANGYYSYY LDYWGQGTLVTVSS | ADI-41807 | Heavy chain variable region ("HC") amino acid sequence |
| Ab 915 | 1830 | DIVMTQTPSSLSASVGDRVTITCRTSQSSSRYLNWYQKEPGKAPRLLIYLASALRSGV PSRFSGSGSGTDFTLTISSLQSEDFATYYCQQTYSIPWTFGQGTKVEIK | ADI-41807 | Light chain variable region ("LC") amino acid sequence |
| Ab 916 | 1831 | QVQLVQSGAELKKPGSSVRISCKVSGVTSDNYAITWVRQAPGQGLEWMGRVIPIF PVPQYAQKFQGRVTLSADKSTRTAYLELHSLRSEDTATYYCATHRPSDSWGQGTLV TVSS | ADI-41808 | Heavy chain variable region ("HC") amino acid sequence |
| Ab 916 | 1832 | DIRVTQSPSTLSASVGDRVTITCRASQNINSWLAWYQQKPGKAPKLLIFKASSLESG VPARFSGSGFGTEFTLTITSLQPDDFASYYCQQYDTYPYPFGQGTKVEIK | ADI-41808 | Light chain variable region ("LC") amino acid sequence |
| Ab 917 | 1833 | QVTLKESGGGLVQPGGSLRLSCAASGFTFSNYAMSWVRQAPGKGLEWVSAISHSD SRTFYADSVKGRFTISRDNSKNTLFLQMDSLRAHDTAVYYCANVDPSSVTYYGYYYG MDVWGQGTTVTVSS | ADI-41809 | Heavy chain variable region ("HC") amino acid sequence |
| Ab 917 | 1834 | QSVLTQPPSASGTPGQRVTISCSGSSSNIGKNFVYWYQQFPGTAPKRLIYRNNQRP SGVPDRFSGSRSGTSASLAISGLRSEDEADYYCATWDDSLSGWVFGGGTKLTVL | ADI-41809 | Light chain variable region ("LC") amino acid sequence |
| Ab 918 | 1835 | QVQLVQSGGGVVQPGRSLRLSCAASGFNFHNYAMHWVRQAPGKGLEWVAVISY DGGNKHYADSVKGRFTISRDNSKNTLYLQMNSLRPDDTAVYYCARGHSDWRGDY FDFWGQGTLVTVSS | ADI-41810 | Heavy chain variable region ("HC") amino acid sequence |
| Ab 918 | 1836 | DIQLTQSPATLSVSPGERAILSCRASQNVGTNLAWYQQKPGQAPRLLIYDASTRATG IPARFSGSGAGTDFTLTISGLQSEDFAVYYCQQYINWPPYTFGQGTKLEIK | ADI-41810 | Light chain variable region ("LC") amino acid sequence |
| Ab 919 | 1837 | QVQLQQSGPRLVKPSHTLSLTCVISGDSVSSGSAAWSWIRQSPSRGLEWLGRTYYR SKWYYDYAVSVKGRIIIQPDTSKNQFSLQLNSVSPEDTAVYYCARDPDSGNYFHYYG MDVWGQGTTVTVSS | ADI-41811 | Heavy chain variable region ("HC") amino acid sequence |
| Ab 919 | 1838 | DIVMTQSPATLSLSPGERATLSCRASQSVDVYFAWYQQKPGQAPRLLIYDASKRAS GVPARFSGSASGTDFTLTISSLEPEDFAVYYCQQRAKWPPYTFGQGTKLEIK | ADI-41811 | Light chain variable region ("LC") amino acid sequence |
| Ab 920 | 1839 | EVQLVESGGGLVKPGGSLRLSCAASGFTFSSYSMNWVRQAPGKGLEWVSSISAGSS YTDYAESVKGRFTISRDNAKNSLYLKMNSLRAEDTAVYYCARDPGYCSSNSCTVAM DVWGQGTTVTVSS | ADI-41812 | Heavy chain variable region ("HC") amino acid sequence |
| Ab 920 | 1840 | SYELTQPPSVSGAPGQRVTISCTGSSSNIGAGYDVHWYQQLPGTAPKLLIYGNNNR PSGVPDRFSGSKSGTSASLAITGLQAEDEADYYCQSYDRTLVIFGGGTKLTVL | ADI-41812 | Light chain variable region ("LC") amino acid sequence |
| Ab 921 | 1841 | EVQLLESGPTLVKPTQTLTLTCTFSGFSLSTFGVGVGWIRQPPGKALECLALIYWDD DKRYSPSLKSRLTITRDTSKNQVVLTMTNMDPVDTATYYCAHRRSSTVTTGFFDYW GRGTLVTVSS | ADI-41814 | Heavy chain variable region ("HC") amino acid sequence |
| Ab 921 | 1842 | QPVLTQPPSVSGAPGQRVTVSCTGNSSNIGAGHGAHWYQQLPGTAPKLLIYGSTD RPSGVPDRFFGSQSGTSASLVITELRAEDEADYYCQSFDSSLSIWVFGGGTKLTVL | ADI-41814 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 922 | 1843 | EVQLLESGGGLVKPGGSLRLSCGASGFTFSTSSFNWVRQAPGKGLEWVSSISSTSSY VFYADSVKGRFTVSRDNAQNSLYLQMNSLRAEDTAVYYCARARGVGATIGFDYW GQGTLVTVSS | ADI-41815 | Heavy chain variable region ("HC") amino acid sequence |
| Ab 922 | 1844 | DIVMTQSPLSLPVTPGEPASISCRSSQSLLHSNGYNYLDWYLQKPGQSPQLLIYLG SNRASGVPDRFSGSGSGTDFTLKISRVEAEDVGVYYCMQALQTPYTFGQGTKVEIK | ADI-41815 | Light chain variable region ("LC") amino acid sequence |
| Ab 923 | 1845 | QVQLVQSGAEVKKPGASVKVSCEASGYTFTDSYIHWVRQAPGQGLEWMGWINP NSGGTNYAQKFQGRVTMTRDTSTSTAFIELSRLRSDDTAVYYSARGVRQQWLVNT GDPDYYFDFWGQGTLVTVSS | ADI-41816 | Heavy chain variable region ("HC") amino acid sequence |
| Ab 923 | 1846 | SYVLTQPPSVSVSPGQTASITCSGDKLGDKYSCWYQQKPGQSPVLVIYQDYKRPSG IPERFSGSNSGNTATLTISGTQAMDEADYYCQAWDRNAGVFGTGTKLTVL | ADI-41816 | Light chain variable region ("LC") amino acid sequence |
| Ab 924 | 1847 | QVQLVQSGAEVKKPGESLKISCKGPGYSFTTYWIGWVRQMPGKGLEWMGIIYPG DSDTKYSPSFQGQVTITADKSIATAYLQWSRLKASDTAVYYCATVVTYADNIRWFD SWGQGTLVTVSS | ADI-41817 | Heavy chain variable region ("HC") amino acid sequence |
| Ab 924 | 1848 | QSALTQPASVSGSPGQSITISCTGTSGDVGGYKFVSWYQHHPGKAPKLVIYDVANR PSGVSDRFSGSKSGTTASLTISGLQAEDEADYYCSSYTSSSTYVFGTGTKVTAL | ADI-41817 | Light chain variable region ("LC") amino acid sequence |
| Ab 925 | 1849 | EVQLVESGGGLVQPGGSLRLSCAASGFTVNTNYMSWVRQAPGKGLEWVSIIYSSG STSYADSVKGRFTISRDNSENTLYLQMHTLRAEDTAVYYCVRERTPFYYVSSGYWD SWGQGTLVTVSS | ADI-41818 | Heavy chain variable region ("HC") amino acid sequence |
| Ab 925 | 1850 | EIVLTQSPGTLSLSPGERATLSCRASQSVDSSYLAWYQQKPGQAPRLLIFGASSRA TGIPDRFSGSGSGTDFTLTISRLEPEDFAVYYCQQYGFSYTFGQGTKVEIK | ADI-41818 | Light chain variable region ("LC") amino acid sequence |
| Ab 926 | 1851 | EVQLVESGGGVVQPGRSLRLSCAVSGFTFSTYGMHWVRQTPGRGLEWVAVISYD GNHKYYADSVMGRFTISRDNSKDTLYLQVNSLRPEDSAVYYCAKDRIHCPNGVCYV HSSFYGLDVWGQGTTVTVSS | ADI-41820 | Heavy chain variable region ("HC") amino acid sequence |
| Ab 926 | 1852 | QTVVTQEPSLTVSPGGTVTLTCGSSTGAVTSGHYPYWLQQKPGQAPRTLIYDTTNK DSWTPARFSGSLLGGKAALTLSGAQPEDEAQYYCLLSFNGPYWVFGGGTKVTVL | ADI-41820 | Light chain variable region ("LC") amino acid sequence |
| Ab 927 | 1853 | EVQLSESAGGVVQPGGSLRLTCAASGFSFSTNGMHWVRQAPGKGLEWVAFIRYD GSKKYYAESVKGRFTISREDSNNTLYLQMNSLRPEDTAVYYCAKEDCSGGTCYHER NYYYYGMDVWGQGTTVTVSS | ADI-41827 | Heavy chain variable region ("HC") amino acid sequence |
| Ab 927 | 1854 | QPVLTQPPSLPVSPGQTASITCSGDKLEYKYACWYQHKPGQSPVLVIYQDNKRPSG IPERFSGSNSGNTATLTISGTQPMDEADYYCQAWDSSTVVFGGGTKVTVL | ADI-41827 | Light chain variable region ("LC") amino acid sequence |
| Ab 928 | 1855 | EVQLVESGGGLVQPGGSLRLSCADSDFTFSTYSMNWVRQAPGKGLEWISYITGRSS AIYYADSVKGRFTISRDNAKNSLFLQMNSLRAEDTAVYYCTTFMAGYSFGHGDAFD IWGQGTTVTVSS | ADI-41828 | Heavy chain variable region ("HC") amino acid sequence |
| Ab 928 | 1856 | SYELTQPPSVSVAPGQTARITCGGNNIGSKSVHWYQQKPGQAPVLVVYDDSDRPS GIPERFSGSNSGNTATLTISRVEAGDEADYYCQVWNSNSDHPHWVFGGGTQLTVL | ADI-41828 | Light chain variable region ("LC") amino acid sequence |

TABLE 5-continued

Informal Sequence Listing

| Anti-body No. | SEQ ID NO: | Sequence | Clone # (ADI) | Descriptors |
|---|---|---|---|---|
| Ab 929 | 1857 | EVQLVESGGGLVKPGGSLRLSCAASGFTSSGYNMNWVRQAPGKGLEWVSSISGSS SYIHYADSVKGRFTISRDNAKNSLYLQMNSLRAEDTAVYYCATVGALPGHFDNWG QGTLVTVSS | ADI-41829 | Heavy chain variable region ("HC") amino acid sequence |
| Ab 929 | 1858 | QAVVTQEPSVSGAPGQRVTISCTGSSSNIGAGYDVHWYQQLPGTAPKLLIYDNTNR PSGVPDRFSGSKSGTSASLAITGLQAEDEADYYCQSYDSRLTYVFGTGTKVTVL | ADI-41829 | Light chain variable region ("LC") amino acid sequence |
| Ab 930 | 1859 | QVQLVQSGPAVKKPGASVKVSCKASGYIFTSYGVSWVRQAPGQGLEWMGWISGY NGNTDYAQKFQGRVTLTVDSSTGTVYMDLRSLRSDDTAIYYCARAPPLPGQVYDG AGSYLLHGYWGQGTLVTVSS | ADI-41830 | Heavy chain variable region ("HC") amino acid sequence |
| Ab 930 | 1860 | DIVMTQSPLSLPVTPGEPASISCRSSQSLLHSNGYNYLDWYLQKPGQSPQLLIYLG SNRASGVPDRFSGSGSGTDFTLKISRVEAEDVGVYYCMQALQTPRTFGQGTKVEIK | ADI-41830 | Light chain variable region ("LC") amino acid sequence |
| Ab 931 | 1861 | EVQLLESGGGLVKPGGSLRLSCAASGFTFSSYAMHWVRQPPGKGLEWVSSISASSS FINYADSVKGRFTISRDGARNSLYLQMNSLRAEDTAVYYCVREDYDSSGYGLHWFD PWGQGTTVTVSS | ADI-41831 | Heavy chain variable region ("HC") amino acid sequence |
| Ab 931 | 1862 | SYVLTQPPSVSGAPGQRVTISCTGSSSNIGAGYDVHWYQQFPGTAPKLLMYGNTN RPSGVPDRFSGSKSGTSASLAITGLQAEDEADYYCQSYDRSLSGWVFGGGTKLTVL | ADI-41831 | Light chain variable region ("LC") amino acid sequence |
| Ab 932 | 1863 | EVQLVESGGGLVQPGGSLRLSCAASGFTFSKYAMNWVRQAPGKGLEWVSSISDSG DSRYYADSVKGRFTISRDSSKNTLNLQMNSLRAEDTAVYYCAKAGWELFSPQGAFD LWGQGTMVTVSS | ADI-41832 | Heavy chain variable region ("HC") amino acid sequence |
| Ab 932 | 1864 | EIVMTQSPGTLSLSPGERATLSCRASQSVSSSHLAWYQQKPGQAPRLLIYGASSRDS GIPDRFSGSGSGTDFTLSISRLEPEDFAVYYCQHYGNSPYTFGQGTKVDIK | ADI-41832 | Light chain variable region ("LC") amino acid sequence |
| Ab 933 | 1865 | EVQLLESGGGLVQPGGSLRLSCAASRFTFSTYAMSWVRQAPGKGLEWVSSISGSG DKTFYTDSVKGRFTISRDNSKNTLYLQMNSLRAEDTAVYYCARESYYELWTGTYPG WELDYWGQGTLVTVSS | ADI-41833 | Heavy chain variable region ("HC") amino acid sequence |
| Ab 933 | 1866 | DIQLTQSPSSLSASVGDRVTITCRASQDISNYLAWYQQKPGKPPKLLIYAASILES GAPSRFSGSGSGTDFTLTISSLQPEDVGTYYCQKSNSAPRPFGQGTKVEIK | ADI-41833 | Light chain variable region ("LC") amino acid sequence |
| Ab 934 | 1867 | EVQLLESGGRLVQPGRSLRLSCAASGFTVSGSYMSWVRQAPGKGLEWVSVIYIDG GTKYADSVKGRFTISRDNSKNTVYLQMNSLRAEDTAVYYCARDSSLWYRGGDYWG QGTLVTVSS | ADI-41834 | Heavy chain variable region ("HC") amino acid sequence |
| Ab 934 | 1868 | DIQMTQSPSSLSASVGDRVTITCQANHDISNYLNWYQQKPGKAPKLLIYDASILEAG VPSRFSGSGSGTHFTFTISSLQPEDIATYYCQQFDFRALTFGGGTKVEIK | ADI-41834 | Light chain variable region ("LC") amino acid sequence |
| Ab 935 | 1869 | EVQLLESGGGLVQPGGSLRLSCAASGFTFSSYAMNWVRQAPGKGLEWVSIISDSG GSTYYADSVKGRFTISRDNSKNTLYLQMNSLRAEDTAVYYCAKATPLKWELLIGSTP GYYFDYWGQGTTVTVSS | ADI-41835 | Heavy chain variable region ("HC") amino acid sequence |
| Ab 935 | 1870 | SYELTQLPSVSVSPGQTASITCSGDKLGDKYACWYQQKPGQSPVVIMYQDNKRPS GIPERFSGSNSGNTATLTISGTQAMDEADYYCQAWDSSTGVFGGGTKVTVL | ADI-41835 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 936 | 1871 | EVQLLESGAEVKKPGASVKVSCRASGYTFTSNTLHWVRQAPGQGLEWMGWINAD NGNTRYSQKFQGRVTITRDTSANTAYMELSSLISEDTAVYYCAREWSGFWSGLNW FEPWGQGTLVTVSS | ADI-41836 | Heavy chain variable region ("HC") amino acid sequence |
| Ab 936 | 1872 | QSVLTQPPSVSGAPGQRVTISCTGSSSNIGSGNDVHWYQQFPGTAPKVLIYVNSIRP SGVSDRFSGSKSGTSASLAITGLRAEDEADYYCQSYDSSLNGVAFGGGTKLTVL | ADI-41836 | Light chain variable region ("LC") amino acid sequence |
| Ab 937 | 1873 | QVQLVQSGAEVKKPGASVKVSCKASGYTFTSYGISWVRQAPGQGLEWMGWISAY SGDTDYAQKLQGRVTMTTDTATSTAYMELRSLRSDDTAVYYCARDAHCSSTNCYID LGGAPVDYWGQGTLVTVSS | ADI-41837 | Heavy chain variable region ("HC") amino acid sequence |
| Ab 937 | 1874 | DIVLTQTPLSLSVTLGQPASISCRSSQSLVYIDGYTYLNWFQQRPGQSPRRLIYKV SNRDSGVPDRFSGSGSGTDFTLKISRVEAEDVGVYYCMQGAHWPWTFGQGTKVEIK | ADI-41837 | Light chain variable region ("LC") amino acid sequence |
| Ab 938 | 1875 | EVQLLESGGGVVQPGRSLRLSCAASEFTFRSYAMHWVRQAPGMGLEWVAVTPYD GISKYYADSVKGRFTISRDNSKNTLYLQMNSLRPEDTAVYYCARGFPEPITSWPGYF YAMDVWGQGTTVTVSS | ADI-41838 | Heavy chain variable region ("HC") amino acid sequence |
| Ab 938 | 1876 | QSALTQPASVSGSPGQSITISCTGTTSDVGVYNYVSWYQQHPGKAPKLMIYDVSNR PSGVSNRFSGSKSGNTASLTISGLQAEDEADYYCSSYTNSDTPVVFGGGTKLTVL | ADI-41838 | Light chain variable region ("LC") amino acid sequence |
| Ab 939 | 1877 | EVQLLESGGGVVQPGGSLRLSCVASGFTFSAYGMHWVRQAPGKGPEWVAMTRS DGNKIYYADSVKGRFTISRDDSKNTLYLEMNSLRPDDTAVYFCAKEVGYGGNSLHY WGQGTLVTVSS | ADI-41839 | Heavy chain variable region ("HC") amino acid sequence |
| Ab 939 | 1878 | SYELIQPPSVSVAPGQTAKITCGGNNIGSKSVHWYQQKPGQAPVLVVFDDSDRPSG IPERFSGSNSGNTATLTISRVEAGDEADYYCQVWDFSSDLWVFGGGTKLTVL | ADI-41839 | Light chain variable region ("LC") amino acid sequence |
| Ab 940 | 1879 | QVQLVQSGAEVKKPGSSVKVSCKASGDTFSGYAIYWVRQAPGRGLELMGGIIPILG TSSYAQRFLGRTSFTADESTSTAYMDLSSLTSADTAMYYCARKRVTVPVPFDSWGQ GTLVTVSS | ADI-41840 | Heavy chain variable region ("HC") amino acid sequence |
| Ab 940 | 1880 | EIVMTQSPATLSVSPGERATLSCRASQSVSSNLAWYQQKLGQAPRLLIYGASTRATD IPARFSGSGSGTEFTLTISSLQSEDFVVYYCQQYNNWPWTFGQGTKVEIK | ADI-41840 | Light chain variable region ("LC") amino acid sequence |
| Ab 941 | 1881 | EVQLLESGGGLVKPGGSLRLSCAASGFSFSYYSMNWVRQTPGKGLEWVSSISDRSS YISYADSVKGRFTISRDNAKNSLYLQMNSLRAEDTAVYYCARDQYESYAFDIWGQG TTVTVSS | ADI-41841 | Heavy chain variable region ("HC") amino acid sequence |
| Ab 941 | 1882 | DIQVTQSPSSLSASVGDRITITCQASQDVGNYLNWYQQKVGKAPKLLIHDASDLET GVPSRFSGSGSGTYFTFTISSLQPEDFATYYCQPYDNLRPVTFGQGTRLEIK | ADI-41841 | Light chain variable region ("LC") amino acid sequence |
| Ab 942 | 1883 | QVQLVQSGAEVKKPGASVRVSCKASGYTFTHYDINWVRQAPGQGLEWMGWINP NSGDTDYAQKFQGRVTMTVDTSISTAYLDLRSLTSADAAVYYCARGGAYATNGYYII WFDPWGQGTLVTVSS | ADI-41842 | Heavy chain variable region ("HC") amino acid sequence |
| Ab 942 | 1884 | DIVVTQSPSSLSASVGDRVTITCRASQSISRYLNWFQKKPGKAPHLLIYAASILQSE VPSRFSGSGSGTDFTLTISSLQPEDFATYYCQQSYNSPYTFGPGTKVDIK | ADI-41842 | Light chain variable region ("LC") amino acid sequence |

TABLE 5-continued

Informal Sequence Listing

| Antibody No. | SEQ ID NO: | Sequence | Clone # (ADI) | Descriptors |
|---|---|---|---|---|
| Ab 943 | 1885 | QVQLQQWGAGLLKPSETLSLTCAVYGGSFSGYYWSWIRQPPGKGLEWIGEINHSG STNYNPSLKSRVTISVDTSKNQFSLKLSSVTAADTAVYYCARGVPVLRYFDWLRFGY GMDVWGQGTTVTVSS | ADI- 43638 | Heavy chain variable region ("HC") amino acid sequence |
| Ab 943 | 1886 | EIVMTQSPDSLAVSLGERATINCKSSQSVLYSSNNKNYLAWYQQKPGQPPKLLIYW ASTRESGVPDRFSGSGSGTDFTLTISSLQAEDVAVYYCQQYYSTPPLTFGGGTKLE IK | ADI- 43638 | Light chain variable region ("LC") amino acid sequence |
| Ab 944 | 1887 | QVQLVQSGSELKKPGASVKVSCKASGYTFTSYAMNWVRQAPGQGLEWMGWINT NTGNPTYAQGFTGRFVFSLDTSVSTAYLQISSLKAEDTAVYYCAAYGIHDAFDIWG QGTMVTVSS | ADI- 43639 | Heavy chain variable region ("HC") amino acid sequence |
| Ab 944 | 1888 | DIRLTQSPSSLSASVGDRVTITCRASQSISSYLNWYQQKPGKAPKLLIYAASSLQS GVPSRFSGSGSGTDFTLTISSLQPEDFATYYCQQSYSTPRTFGQGTKVEIK | ADI- 43639 | Light chain variable region ("LC") amino acid sequence |
| Ab 945 | 1889 | QVQLVQSGGGLVKPGGSLRLSCAASGFTFSSYSMNWVRQAPGKGLEWVSSISSSS SYIYYADSVKGRFTISRDNAKNSLYLQMNSLRAEDTAVYYCAREGRDGYNYNFDYW GQGTLVTVSS | ADI- 43640 | Heavy chain variable region ("HC") amino acid sequence |
| Ab 945 | 1890 | QSVVTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGVVFGGGTKLTVL | ADI- 43640 | Light chain variable region ("LC") amino acid sequence |
| Ab 946 | 1891 | EVQLVESGGGLVKPGGSLRLSCAASGFTFSDYYMSWIRQAPGKGLEWVSYISSSSS YTNYADSVKGRFTISRDNAKNSLYLQMNSLRAEDTAVYYCARDFSGQWLVLGYGM DVWGQGTTVTVSS | ADI- 43641 | Heavy chain variable region ("HC") amino acid sequence |
| Ab 946 | 1892 | QSVVTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGPVFGGGTKLTVL | ADI- 43641 | Light chain variable region ("LC") amino acid sequence |
| Ab 947 | 1893 | EVQLLESGGGLVKPGGSLRLSCAASGFTFSSYSMNWVRQAPGKGLEWVSSISSSSS YIYYADSVKGRFTISRDNAKNSLYLQMNSLRAEDTAVYYCARDGADSSYYYYMDVW GKGTTVTVSS | ADI- 43642 | Heavy chain variable region ("HC") amino acid sequence |
| Ab 947 | 1894 | QAVVTQPPSVSGAPGQRVTISCTGSSSNIGAGYDVHWYQQLPGTAPKLLIYGNSNR PSGVPDRFSGSKSGTSASLAITGLQAEDEADYYCQSYDSSLSGSVFGGGTKLTVL | ADI- 43642 | Light chain variable region ("LC") amino acid sequence |

Exemplary Embodiments

1. An isolated antibody or antigen-binding fragment thereof that cross-competes for binding or specifically binds to the same epitope(s) of a Respiratory Syncytial Virus (RSV) fusion glycoprotein (F) ("an anti-RSV F antibody") as an antibody or antigen-binding fragment thereof comprising a CDRH3 amino acid sequence that is at least 80%, 85%, 90%, 95%, 96%, 97%, 98%, or 99% identical to a CDRH3 amino acid sequence of an antibody selected from Antibody Number 1 through Antibody Number 465 as disclosed in Table 5.

2. An isolated antibody or antigen-binding fragment thereof that cross-competes for binding or specifically binds to the same epitope(s) of a Respiratory Syncytial Virus (RSV) fusion glycoprotein (F) ("an anti-RSV F antibody") as an antibody or antigen-binding fragment thereof comprising a CDRH2 amino acid sequence that is at least 80%, 85%, 90%, 95%, 96%, 97%, 98%, or 99% identical to a CDRH2 amino acid sequence of an antibody selected from Antibody Number 1 through Antibody Number 947 as disclosed in Table 5.

3. An isolated antibody or antigen-binding fragment thereof that cross-competes for binding or specifically binds to the same epitope(s) of a Respiratory Syncytial Virus (RSV) fusion glycoprotein (F) ("an anti-RSV F antibody") as an antibody or antigen-binding fragment thereof comprising a CDRH1 amino acid sequence that is at least 80%, 85%, 90%, 95%, 96%, 97%, 98%, or 99% identical to a CDRH1 amino acid sequence of an antibody selected from Antibody Number 1 through Antibody Number 947 as disclosed in Table 5.

4. An isolated antibody or antigen-binding fragment thereof that cross-competes for binding or specifically binds to the same epitope(s) of a Respiratory Syncytial Virus (RSV) fusion glycoprotein (F) ("an anti-RSV F antibody") as an antibody or antigen-binding fragment thereof comprising a CDRL3 amino acid sequence that is at least 80%, 85%, 90%, 95%, 96%, 97%, 98%, or 99% identical to a CDRL3 amino acid sequence of an antibody selected from Antibody Number 1 through Antibody Number 947 as disclosed in Table 5.

5. An isolated antibody or antigen-binding fragment thereof that cross-competes for binding or specifically binds to the same epitope(s) of a Respiratory Syncytial Virus (RSV) fusion glycoprotein (F) ("an anti-RSV F antibody") as an antibody or antigen-binding fragment thereof comprising a CDRL2 amino acid sequence that is at least 80%, 85%, 90%, 95%, 96%, 97%, 98%, or 99% identical to a CDRL2 amino acid sequence of an antibody selected from Antibody Number 1 through Antibody Number 947 as disclosed in Table 5.

6. An isolated antibody or antigen-binding fragment thereof that cross-competes for binding or specifically binds to the same epitope(s) of a Respiratory Syncytial Virus (RSV) fusion glycoprotein (F) ("an anti-RSV F antibody") as an antibody or antigen-binding fragment thereof comprising a CDRL1 amino acid sequence that is at least 80%, 85%, 90%, 95%, 96%, 97%, 98%, or 99% identical to a CDRL1 amino acid sequence of an antibody selected from Antibody Number 1 through Antibody Number 947 as disclosed in Table 5.

7. The isolated anti-RSV F antibody of any one of embodiments 1 to 6, comprising (i) the CDRH3 amino acid sequence of an antibody selected from Antibody Number 1 through Antibody Number 947 as disclosed in Table 5; (ii) the CDRH2 amino acid sequence of an antibody selected from Antibody Number 1 through Antibody Number 947 as disclosed in Table 5; (iii) the CDRH1 amino acid sequence of an antibody selected from Antibody Number 1 through Antibody Number 947 as disclosed in Table 5; (iv) the CDRL3 amino acid sequence of an antibody selected from Antibody Number 1 through Antibody Number 947 as disclosed in Table 5; (v) the CDRL2 amino acid sequence of an antibody selected from Antibody Number 1 through Antibody Number 947 as disclosed in Table 5; (vi) the CDRL1 amino acid sequence of an antibody selected from Antibody Number 1 through Antibody Number 947 as disclosed in Table 5; or (vii) any combination of two or more of (i), (ii), (iii), (iv), (v), and (vi).

8. An isolated antibody or antigen-binding fragment thereof that cross-competes for binding or specifically binds to the same epitope(s) of a Respiratory Syncytial Virus (RSV) fusion glycoprotein (F) ("an anti-RSV F antibody") as an antibody or antigen-binding fragment thereof comprising (i) a heavy chain variable region ($V_H$) that is at least 80%, 85%, 90%, 95%, 96%, 97%, 98%, or 99% identical to a VHamino acid sequence of an antibody selected from Antibody Number 1 through Antibody Number 947 as disclosed in Table 5, and/or (ii) a light chain variable region ($V_L$) that is at least 80%, 85%, 90%, 95%, 96%, 97%, 98%, or 99% identical to a $V_L$ amino acid sequence of an antibody selected from Antibody Number 1 through Antibody Number 947 as disclosed in Table 5.

9. The isolated anti-RSV F antibody of embodiment 8, comprising (i) the $V_H$ amino acid sequence of an antibody selected from Antibody Number 1 through Antibody Number 947 as disclosed in Table 5; and/or (ii) the $V_L$ amino acid sequence of an antibody selected from Antibody Number 1 through Antibody Number 947 as disclosed in Table 5.

10. The isolated anti-RSV F antibody of any one of embodiments 1 to 9, which is selected from the group consisting of Antibody Number 1 through Antibody Number 947 as disclosed in Table 5.

11. The isolated anti-RSV F antibody of any one of embodiments 1 to 10, which binds to an epitope comprising site Ø, site I, site II, site III, site IV, or site V of RSVF.

12. The isolated anti-RSV F antibody of any one of embodiments 1 to 11, which binds to an epitope on prefusion F (preF), preferably antigenic site III.

13. The isolated anti-RSV F antibody of any one of embodiments 1 to 12, which binds to prefusion F (preF) with high affinity but does not bind to or binds with low affinity to postfusion F (postF).

14. The isolated anti-RSV F antibody of any one of embodiments 1 to 12, which binds to an epitope on postfusion F (post F), preferably antigenic site I.

15. The isolated anti-RSV F antibody of any one of embodiments 1 to 14, which does not compete with D25 for binding to RSV F.

16. The isolated anti-RSV F antibody of any one of embodiments 1 to 15, which competes with MPE8 and/or motavizumab for binding to RSV F.

17. The isolated anti-RSV F antibody of any one of embodiments 1 to 16, which is a neutralizing antibody.

18. The isolated anti-RSV F antibody of embodiment 17, which has a neutralizing activity ($IC_{50}$) of less than 100 µg/ml, 50 µg/ml, 25 µg/ml, 10 µg/ml, 5 µg/ml, 1 µg/ml, 0.5 µg/ml, 0.1 µg/ml, or 0.05 µg/ml.

19. The isolated anti-RSV F antibody of any one of embodiments 1 to 18, which binds to RSV prefusion F with a $K_D$ value of less than 50 nM, 25 nM, 10 nM, 5 nM, 1 nM, 0.5 nM, or 0.1 nM as measured by surface plasmon resonance.

20. The isolated anti-RSV F antibody of any one of embodiments 1 to 19, which binds to RSV prefusion F through one or both of the following interactions:
a) Tyr33 in CDRL1 and Tyr93 in CDRL3 both contact the α6-α7 loop of RSV prefusion F; and
b) five consecutive serine residues, preferably followed by a tyrosine residue (Tyr56), in CDRH2 form a network of hydrogen bonds with Asp310 on β6 of RSV prefusion F.

21. The isolated anti-RSV F antibody of any one of embodiments 1 to 20, which has a clean or low polyreactivity profile.

22. The isolated anti-RSV F antibody of any one of embodiments 1 to 21, which is a full-length IgG1 monoclonal antibody.

23. The isolated anti-RSV F antibody of any one of embodiments 1 to 22, which comprises a Fc region that has been modified to alter effector function, half-life, proteolysis, and/or glycosylation.

24. The isolated anti-RSV F antibody of any one of embodiments 1 to 23, which is derivatized.

25. An isolated nucleic acid sequence or nucleic acid sequences encoding an antibody or antigen-binding fragment thereof according to any one of embodiments 1 to 24.

26. An expression vector or vectors comprising the isolated nucleic acid sequence according to embodiment 25.

27. A host cell comprising the isolated nucleic acid sequence(s) according to embodiment 25 or the expression vector(s) according to embodiment 26.

28. The host cell of embodiment 27, which is a mammalian cell, a bacterial cell, a fungal cell, a yeast cell, or an insect cell.

29. A method for producing an isolated antibody or antigen-binding fragment thereof that specifically binds to Respiratory Syncytial Virus (RSV) fusion glycoprotein (F) ("an anti-RSV F antibody") comprising expressing the nucleic acid sequence(s) of embodiment 25 or culturing the host cell of embodiment 27 or 28 under conditions that provide for expression of the anti-RSV F antibody and optionally recovering the anti-RSV F antibody from the host cell and/or culture medium.

30. The method of embodiment 29, wherein the host cell is a yeast cell or a mammalian cell.

31. A pharmaceutical composition comprising (i) the anti-RSV F antibody of any one of embodiments 1 to 24, the nucleic acid sequence(s) of embodiment 25, the expression vector(s) of embodiment 26, or the host cell of embodiments 27 or 28; and (ii) a pharmaceutically acceptable carrier and/or excipient.

32. The pharmaceutical composition of embodiment 31 for use in preventing or treating a RSV infection in a subject.

33. The pharmaceutical composition of embodiment 32, wherein the subject is a human, preferably an infant.

34. A method of preventing or treating a Respiratory Syncytial Virus (RSV) infection in a subject, comprising administering to the subject in need thereof an effective amount of the anti-RSV F antibody of any one of embodiments 1 to 24, the isolated nucleic acid sequence(s) of embodiment 25, the expression vector(s) of embodiment 26, or the host cell(s) of embodiment 27 or 28, optionally in association with a further prophylactic and/or therapeutic agent.

35. The method of embodiment 34, wherein the further prophylactic and/or therapeutic agent is selected from an antiviral agent; a vaccine specific for RSV; a vaccine specific for influenza virus; a vaccine specific for metapneumovirus (MPV); an siRNA specific for a RSV antigen; an siRNA specific for a MPV antigen; a second anti-RSV antibody; an anti-MPV antibody; an anti-IL4R antibody; an anti-influenza antibody; and a NSAID.

36. The method of embodiment 34 or 35, wherein the subject is human, preferably an infant.

37. A method of preventing or treating a Respiratory Syncytial Virus (RSV) infection in a human subject, comprising administering to the subject in need thereof an effective amount of the pharmaceutical composition of any one of embodiments 31 to 33.

38. The method of embodiment 37, wherein the human subject is an infant.

39. A method for detecting a Respiratory Syncytial Virus (RSV) infection in a subject, comprising obtaining a sample from the subject; contacting the sample with the anti-RSV F antibody of any one of embodiments 1 to 24; and detecting the presence of a complex between the anti-RSV F antibody and the RSV fusion glycoprotein (F), wherein detection of the complex indicates the presence of RSV.

40. The method of embodiment 39, wherein the subject is a human, preferably an infant.

41. An isolated antibody or antigen-binding polypeptide comprising a $V_H$ CDR3 having an amino acid sequence according to an antibody number in Table 9B.

42. An isolated antibody or antigen-binding polypeptide comprising a $V_H$ CDR3 having an amino acid sequence according to an ADI listed in Table 8.

43. An isolated antibody or antigen binding polypeptide characterized by ability to neutralize respiratory syncytial virus (RSV).

44. An isolated antibody or antigen binding polypeptide characterized by high affinity binding to RSV F.

45. An isolated antibody or antigen binding polypeptide characterized by high affinity binding to RSV prefusion F (preF).

46 An isolated antibody having an amino acid sequence according to:
(i) Antibody Number 2, 71, 112, 217, 227, 228, 249, 466, 467, 469, 470, 832, 471, 516, 527, 532, 543, 544, 551, 554, 571, 578, 581, 592, 615, 641, 843, 868, or 870;
(ii) an Antibody Number of (i) with no more than 3 amino acid substitutions, additions, or deletions;
(iii) an Antibody Number of (i) with no more than 3, 2, or 1 amino acid substitution(s), addition(s), or deletion(s) in a CDR; or
(iv) an Antibody Number of (i) with no more than 3, 2, or 1 amino acid substitution(s), addition(s), or deletion(s) in CDRH3.

47. An antibody or antigen-binding polypeptide according to any preceding embodiment having an $IC_{50}$ of less than 300 pM for neutralization of RSV.

48. An antibody or antigen-binding polypeptide according to any preceding embodiment having an $IC_{50}$ of less than 200 pM for neutralization of RSV.

49. An antibody or antigen-binding polypeptide according to any preceding embodiment having an $IC_{50}$ of less than 100 pM for neutralization of RSV.

50. An antibody or antigen-binding polypeptide according to any preceding embodiment characterized by binding affinity to pre-F with a kD of less than 10 nM.

51. An antibody or antigen-binding polypeptide according to any preceding embodiment characterized by a binding affinity to pre-F that is at least 10, 100, or 1000 fold greater than binding affinity to post-F.

52. An antibody or antigen-binding polypeptide according to any preceding embodiment characterized by high affinity binding to RSV F site III.

53. A nucleic acid molecule encoding an antibody or antigen binding protein according to any preceding embodiment.

54 A vector comprising a nucleic acid molecule encoding an antibody or antigen binding protein according to any preceding embodiment.

55. A cell comprising a vector according to embodiment 54.

SEQUENCE LISTING

The patent contains a lengthy sequence listing. A copy of the sequence listing is available in electronic form from the USPTO web site (https://seqdata.uspto.gov/docdetail?docId=US12630611B2). An electronic copy of the sequence listing will also be available from the USPTO upon request and payment of the fee set forth in 37 CFR 1.19(b)(3).

What is claimed is:

1. A composition comprising an antibody component, wherein:

the antibody component consists of:

a first antibody, or antigen binding fragment thereof, that has heavy and light chain CDRs found in antibody number 554; and a second antibody, or antigen binding fragment thereof, that has heavy and light chain CDRs found in an antibody that is selected from the group consisting of antibody numbers 843, 466, 2, 71, 112, 217, 227, 228, 249, 467, 469, 470, 832, 471, 516, 527, 532, 543, 544, 551, 571, 578, 581, 592, 615, 641, 868, and 870;

wherein each of the first and second antibodies, or antigen binding fragments thereof, specifically binds to and neutralizes RSV F; and further wherein the composition does not include any antibodies other than the antibody component.

2. The composition of claim 1, wherein either the first and/or second antibody has an IC50 of less than 300 pM for neutralization of RSV.

3. The composition of claim 1, wherein either the first and/or second antibody has an IC50 of less than 200 pM for neutralization of RSV.

4. The composition of claim 1, wherein either the first and/or second antibody has an $IC_{50}$ of less than 100 pM for neutralization of RSV.

5. The composition of claim 1, wherein each of the first and second antibody is characterized by binding affinity to pre-F with a $k_D$ of less than 10 nM.

6. A method of treating an RSV infection in a mammal, comprising administering the composition of claim 1.

7. The method according to claim 6, wherein the method further comprises administering to the mammal an additional prophylactic or therapeutic agent.

8. The method according to claim 7, wherein the additional prophylactic or therapeutic agent is one or more of: an antiviral agent; a vaccine specific for RSV; a vaccine specific for influenza virus; a vaccine specific for metapneumovirus (MPV); an siRNA specific for a RSV antigen; an siRNA specific for a MPV antigen; a further anti-RSV antibody; an anti-MPV antibody; an anti-ILAR antibody; an anti-influenza antibody; and a NSAID.

9. The method according to claim 6, wherein the mammal is a human.

10. The composition of claim 1, wherein the first antibody has framework regions with at least 90% sequence identity to those of antibody number 554, and/or the second antibody has framework regions with at least 90% sequence identity to the framework regions of the antibody in which its heavy and light chain CDRs are found.

11. The composition of claim 1, wherein the first antibody and/or second antibody comprise a heavy chain IgG Fc region.

12. The composition of claim 11, wherein the heavy chain IgG Fc region is a variant associated with increased antibody serum half-life, improved stability, modified effector function, or a combination thereof.

13. The composition of claim 1, which composition consists of:

the antibody component; and a carrier for parenteral administration.

14. The composition of claim 1, which composition is formulated for parenteral administration.

15. The composition of claim 13, which composition is in powder form.

16. The composition of claim 1, which composition is formulated for intravenous-, intramuscular-, intradermal-, transdermal-, intraperitoneal, intranasal-, inhalation, and/or subcutaneous-administration and/or intramuscular administration.

17. The composition of claim 14, disposed within a syringe.

18. The composition of claim 1, wherein the second antibody, or antigen binding fragment thereof, has heavy and light chain CDRs found in antibody number 466.

19. The composition of claim 1, wherein the second antibody, or antigen binding fragment thereof, has heavy and light chain CDRs found in antibody number 2.

20. The composition of claim 1, wherein the second antibody, or antigen binding fragment thereof, has heavy and light chain CDRs found in antibody number 71.

21. The composition of claim 1, wherein the second antibody, or antigen binding fragment thereof, has heavy and light chain CDRs found in antibody number 112.

22. The composition of claim 1, wherein the second antibody, or antigen binding fragment thereof, has heavy and light chain CDRs found in antibody number 217.

23. The composition of claim 1, wherein the second antibody, or antigen binding fragment thereof, has heavy and light chain CDRs found in antibody number 227.

24. The composition of claim 1, wherein the second antibody, or antigen binding fragment thereof, has heavy and light chain CDRs found in antibody number 228.

25. The composition of claim 1, wherein the second antibody, or antigen binding fragment thereof, has heavy and light chain CDRs found in antibody number 249.

26. The composition of claim 1, wherein the second antibody, or antigen binding fragment thereof, has heavy and light chain CDRs found in antibody number 467.

27. The composition of claim 1, wherein the second antibody, or antigen binding fragment thereof, has heavy and light chain CDRs found in antibody number 469.

28. The composition of claim 1, wherein the second antibody, or antigen binding fragment thereof, has heavy and light chain CDRs found in antibody number 470.

29. The composition of claim 1, wherein the second antibody, or antigen binding fragment thereof, has heavy and light chain CDRs found in antibody number 832.

30. The composition of claim 1, wherein the second antibody, or antigen binding fragment thereof, has heavy and light chain CDRs found in antibody number 471.

31. The composition of claim 1, wherein the second antibody, or antigen binding fragment thereof, has heavy and light chain CDRs found in antibody number 516.

32. The composition of claim 1, wherein the second antibody, or antigen binding fragment thereof, has heavy and light chain CDRs found in antibody number 527.

33. The composition of claim 1, wherein the second antibody, or antigen binding fragment thereof, has heavy and light chain CDRs found in antibody number 532.

34. The composition of claim 1, wherein the second antibody, or antigen binding fragment thereof, has heavy and light chain CDRs found in antibody number 543.

35. The composition of claim 1, wherein the second antibody, or antigen binding fragment thereof, has heavy and light chain CDRs found in antibody number 544.

36. The composition of claim 1, wherein the second antibody, or antigen binding fragment thereof, has heavy and light chain CDRs found in antibody number 551.

37. The composition of claim 1, wherein the second antibody, or antigen binding fragment thereof, has heavy and light chain CDRs found in antibody number 571.

38. The composition of claim 1, wherein the second antibody, or antigen binding fragment thereof, has heavy and light chain CDRs found in antibody number 578.

39. The composition of claim 1, wherein the second antibody, or antigen binding fragment thereof, has heavy and light chain CDRs found in antibody number 581.

40. The composition of claim 1, wherein the second antibody, or antigen binding fragment thereof, has heavy and light chain CDRs found in antibody number 592.

41. The composition of claim 1, wherein the second antibody, or antigen binding fragment thereof, has heavy and light chain CDRs found in antibody number 615.

42. The composition of claim 1, wherein the second antibody, or antigen binding fragment thereof, has heavy and light chain CDRs found in antibody number 641.

43. The composition of claim 1, wherein the second antibody, or antigen binding fragment thereof, has heavy and light chain CDRs found in antibody number 868.

44. The composition of claim 1, wherein the second antibody, or antigen binding fragment thereof, has heavy and light chain CDRs found in antibody number 870.

\* \* \* \* \*